United States Patent
Lee et al.

(10) Patent No.: US 10,961,242 B2
(45) Date of Patent: Mar. 30, 2021

(54) COMPOUNDS AS AUTOTAXIN INHIBITORS AND PHARMACEUTICAL COMPOSITIONS COMPRISING THE SAME

(71) Applicant: LegoChem Biosciences, Inc., Daejeon (KR)

(72) Inventors: Dae Yon Lee, Daejeon (KR); Sang Eun Chae, Daejeon (KR); Eun Mi Jung, Daejeon (KR); Eun Hye Yang, Daejeon (KR); Yoon Jeong Choi, Daejeon (KR); Chul-Woong Chung, Daejeon (KR); Ju Hyun Shin, Daejeon (KR); Yun Ki Kim, Daejeon (KR); Hyun Jin Kwon, Daejeon (KR); Jeong Hee Ryu, Daejeon (KR); Eun Hye Ban, Daejeon (KR); Yong Zu Kim, Daejeon (KR); Yeong Soo Oh, Daejeon (KR); Jeiwook Chae, Daejeon (KR)

(73) Assignee: LegoChem Biosciences, Inc., Daejeon (KR)

( * ) Notice: Subject to any disclaimer, the term of this patent is extended or adjusted under 35 U.S.C. 154(b) by 0 days.

(21) Appl. No.: 16/783,893

(22) Filed: Feb. 6, 2020

(65) Prior Publication Data

US 2020/0172542 A1 Jun. 4, 2020

Related U.S. Application Data

(63) Continuation of application No. 16/098,748, filed as application No. PCT/KR2018/005516 on May 15, 2018.

(51) Int. Cl.
| | |
|---|---|
| *C07D 471/04* | (2006.01) |
| *C07D 498/10* | (2006.01) |
| *C07D 519/00* | (2006.01) |
| *C07D 471/10* | (2006.01) |
| *C07D 413/14* | (2006.01) |
| *C07D 413/12* | (2006.01) |
| *C07D 403/14* | (2006.01) |
| *C07D 401/14* | (2006.01) |
| *C07D 513/04* | (2006.01) |

(52) U.S. Cl.
CPC ......... *C07D 471/04* (2013.01); *C07D 401/14* (2013.01); *C07D 403/14* (2013.01); *C07D 413/12* (2013.01); *C07D 413/14* (2013.01); *C07D 471/10* (2013.01); *C07D 498/10* (2013.01); *C07D 513/04* (2013.01); *C07D 519/00* (2013.01)

(58) Field of Classification Search
CPC .. C07D 471/10; C07D 513/04; C07D 413/14; C07D 471/04; C07D 519/00; C07D 498/10; C07D 413/12; C07D 403/14; C07D 401/12

See application file for complete search history.

(56) References Cited

U.S. PATENT DOCUMENTS

| | | |
|---|---|---|
| 2010/0222341 A1 | 9/2010 | Schiemann et al. |
| 2011/0105527 A1 | 5/2011 | Connolly et al. |
| 2013/0012505 A1 | 1/2013 | Staehle et al. |
| 2014/0200231 A1 | 7/2014 | Beauchamp et al. |
| 2015/0368273 A1 | 12/2015 | Jones et al. |
| 2017/0044133 A1 | 2/2017 | Takahashi et al. |
| 2017/0166568 A1 | 6/2017 | Babiss et al. |
| 2018/0022742 A1 | 1/2018 | Blum et al. |

FOREIGN PATENT DOCUMENTS

| | | |
|---|---|---|
| EP | 2352732 A1 | 8/2011 |
| EP | 2483253 A2 | 8/2012 |
| EP | 2496556 A1 | 9/2012 |
| EP | 2606031 A2 | 6/2013 |
| JP | 2017/078039 A | 4/2017 |
| KR | 101798840 B1 | 11/2017 |
| WO | WO-96/22293 A1 | 7/1996 |
| WO | WO-2007/113276 A1 | 10/2007 |
| WO | WO-2008/063504 A2 | 5/2008 |
| WO | WO-2008/064255 A2 | 5/2008 |

(Continued)

OTHER PUBLICATIONS

Leblanc et al., "Interaction of platelet-derived autotaxin with tumor integrin $\alpha_v\beta_3$ controls metastasis of breast cancer cells to bone," Blood, 124(20):3141-3150 (2014).

Allanore et al., "Double-blind, randomized, 8-week placebo-controlled followed by a 16-week open label extension study, with the LPA1 receptor antagonist SAR100842 for patients with diffuse cutaneous systemic sclerosis," 1-29. Frst published as an accepted manuscript on Aug. 12, 2017, Later published as Arthritis & Rheumatology (2018) 70(10)1634-1643 doi: 10.1002/art.40547.

Aoki et al., "Two pathways for lysophosphatidic acid production," Biochimica et Biophysica Acta, 1781:513-518 (2008).

Bain et al., "Selective inhibition of autotaxin is efficacious in mouse models of liver fibrosis," JPET Fast Forward, 1-62 (2016).

Bain et al., "Selective inhibition of autotaxin is efficacious in mouse models of liver fibrosis," The Journal of Pharmacology and Experimental Therapeutics, 360:1-13 (2017).

(Continued)

*Primary Examiner* — Mark L Shibuya
*Assistant Examiner* — Ebenezer O Sackey
(74) *Attorney, Agent, or Firm* — David P. Halstead; Foley Hoag LLP

(57) ABSTRACT

The present invention relates to novel compounds as autotoxin inhibitors for treatment and prophylaxis of conditions or a disorder caused by autotaxin activation or increased concentration of lysophosphatidic acid, and also a pharmaceutical composition containing the same.

The novel compounds of the present invention are autotaxin inhibitors, and by inhibiting the production of lysophosphatidic acid, they are useful for treatment or prophylaxis of cardiovascular disorder, cancer, metabolic disorder, kidney disorder, liver disorder, inflammatory disorder, nervous system disorder, respiratory system disorder, fibrotic disease, ocular disorder, cholestatic and other forms of chronic pruritus, or acute or chronic organ transplant rejection.

28 Claims, No Drawings

(56) References Cited

FOREIGN PATENT DOCUMENTS

| WO | WO-2008/138889 A2 | 11/2008 |
| --- | --- | --- |
| WO | 2010-112116 A1 * | 10/2010 |
| WO | WO-2010/112116 A1 | 10/2010 |
| WO | WO-2010/115491 A2 | 10/2010 |
| WO | WO-2011/065800 A2 | 6/2011 |
| WO | WO-2011/089400 A1 | 7/2011 |
| WO | WO-2011/133888 A1 | 10/2011 |
| WO | WO-2013054185 A1 | 4/2013 |
| WO | WO-2013186159 A1 | 12/2013 |
| WO | WO-2014/110000 A1 | 7/2014 |
| WO | WO-2014143583 A1 | 9/2014 |
| WO | WO-2014/168824 A1 | 10/2014 |
| WO | WO-2015/163435 A1 | 10/2015 |
| WO | WO-2016/138472 A1 | 9/2016 |
| WO | WO-2016/193844 A1 | 12/2016 |

OTHER PUBLICATIONS

Balupuri et al., "Design, synthesis, docking and biological evaluation of 4-phenyl-thiasole derivatives as autotaxin (ATX) inhibitors," Bioorganic & Medicinal Chemistry Letters, 1-12 (2017).
Banerjee et al., "Highly potent non-carboxylic acid autotaxin inhibitors reduce melanoma metastasis and chemotherapeutic resistance of breast cancer stem cells," J Med Chem, 1-69 (2017).
Barbayianni et al., "Autotaxin, a secreted lysophospholipase D, as a promising therapeutic target in chronic inflammation and cancer," Progress in Lipid Research, (2015).
Bekele et al., "Role of autotaxin and lysophosphatidate in cancer progression and resistance to chemotherapy and radiotherapy," Clin Lipidol, 7(3):313-328 (2012).
Benesch et al., "Autotaxin is an inflammatory mediator and therapeutic target in thyroid cancer," Endocrine-Related Cancer, 22(4):593-607 (2015).
Benesch et al., "Coming of Age for Autotaxin and Lysophosphatidate Signaling: Clinical Applications for Preventing, Detecting and Targeting Tumor-Promoting Inflammation," Cancers, 10(73):1-25 (2018).
Benesch et al., "Inhibition of autotaxin delays breast tumor growth and lung metastasis in mice," The FASEB Journal, 28(6):2655-2666 (2014).
Benesch et al., "Recent advances in targeting the autotaxin-lysophosphatidate-lipid phosphate phosphatase axis in vivo," The Journal of Biomedical Research, 30(4):272-284 (2016).
Black et al., "Autotaxin activity increases locally following lung injury, but is not required for pulmonary lysophosphatidic acid production or fibrosis," The FASEB Journal, 30:2435-2450 (2016).
Bouchareb et al., "Activated platelets promote an osteogenic programme and the progression of calcific aortic valve stenosis," European Heart Journal, 0:1-13 (2018).
Bouchareb et al., "Autotaxin derived from lipoprotein(a) and valve interstitial cells promotes inflammation and mineralization of the aortic valve," Circulation, 132:677-690 (2015).
Brooks et al., "Limited fibrosis accompanies triple-negative breast cancer metastasis in multiple model systems and is not a preventive target," Oncotarget, 9(34):23462-23481 (2018).
Cao et al., "Autocrine lysophosphatidic acid signaling activates β-catenin and promotes lung allograft fibrosis," J Clin Invest, 127(4):1517-1530 (2017).
Castelino et al., "Amelioration of dermal fibrosis by genetic deletion or pharmacologic antagonism of lysophosphatidic acid receptor 1 in a mouse model of scleroderma," Arthritis & Rehumatism, 63(5):1405-1415 (2011).
Castelino et al., "An autotaxin/lysophosphatidic acid/interleukin-6 amplification loop drives scleroderma fibrosis," Arthritis & Rheumatology, 68(12):2964-2974 (2016).
Chu et al., "Autotaxin-LPA receptor axis in the pathogenesis of lung diseases," Int J Clin Exp Med, 8(10):17117-17122 (2015).
D'Souza et al., "Autotaxin-lysophosphatidic acid signaling contributes to obesity-induced insulin resistance in muscle and impairs mitochondrial metabolism," Journal of Lipid Research, 1-38 (2018).
Deng et al., "Knowledge-Based Design of Target-focused Libraries Using Protein-Ligand Interaction Constraints," Journal of Medicinal Chemistry, 49:490-500 (2006).
Dusaulcy et al., "Adipose-specific disruption of autotaxin enhances nutritional fattening and reduces plasma lysophosphatidic acid," Journal of Lipid Research, 52:1247-1255 (2011).
Extended European Search Report for EP Application No. EP 18785796 dated Dec. 19, 2019.
Farquhar et al., "Autotaxin-lysophosphatidic acid receptor signalling regulates hepatitis C virus replication," Journal of Hepatology, 1-26 (2017).
Federico et al., "Autotaxin, a lysophospholipase D with pleomorphic effects in oncogenesis and cancer progression," Journal of Lipid Research, 57:25-35 (2016).
Fotopoulou et al., "ATX expression and LPA signalling are vital for the development of the nervous system," Developmental Biology, 339:451-464 (2010).
Gan et al., "Blockade of lysophosphatidic acid receptors LPAR1/3 ameliorates lung fibrosis induced by irradiation," Biochemical and Biophysical Research Communications, 409:7-13 (2011).
Gierse et al., "A Novel Autotaxin Inhibitor Reduces Lysophosphatidic Acid Levels in Plasma and the Site of Inflammation," The Journal of Pharmacology and Experimental Therapeutics, 334(1):310-317 (2010).
Hashimoto et al., "Lysophosphatidic acid activates Arf6 to promote the mesenchymal malignancy of renal cancer," Nature Communications, 7(10656):1-11 (2016).
He et al., "Inhibition of autotaxin alleviates inflammation and increases the expression of sodium-dependent glucose cotransporter 1 and Na+/H+ exchanger 3 in SAMP1/Fc mice," Physiology.org, 1-32 (2018).
Huang et al., "Lysophosphatidic Acid Receptor-2 Deficiency Confers Protection against Bleomycin-Induced Lung Injury and Fibrosis in Mice," Am J Respir Cell Mol Biol, 49(6):912922 (2013).
International Search Report and Written Opinion for International Application No. PCT/KR2018/005516 dated Aug. 10, 2018.
Kaffe et al., "Hepatocyte autotaxin expression promotes liver fibrosis and cancer," Hepatology, 65(4):1369-1383 (2017).
Katsifa et al., "The Bulk of Autotaxin Activity is Dispensable for Adult Mouse Life," PLOS One, 10(11):e0143083 (2015).
King Jr et al., "Effect of interferon gamma-1b on survival in patients with idiopathic pulmonary fibrosis (Inspire): a multicentre, randomised, placeno-controlled trial," The Lancet, 374:222-228 (2009).
Kritikou et al., "Inhibition of lysophosphatidic acid receptors 1 and 3 attenuates atherosclerosis development in LDL-receptor deficient mice," Scientific Reports, 6:1-10 (2016).
Kuttruff et al., "Discovery of BI-2545: A novel autotaxin inhibitor that significantly reduces LPA levels in vivo," ACS Med Chem Lett, 1-8 (2017).
Leblanc et al., "Autotaxin-β interaction with the cell surface via syndecan-4 impacts on cancer cell proliferation and metastasis," Oncotarget, 9(69):33170-33185 (2018).
Leblanc et al., "Interaction of platelet-derived autotaxin with tumor integrin α vβcontrols metastasis of breast cancer cells to bone," Blood, 124(20):3141-3150 (2014).
Lee et al., "Autotaxin and LPA1 and LPA5 receptors exert disparate functions in tumor cells versus the host tissue microenviroment in melanoma invasion and metastasis," Mol Cancer Res, 13(1):174-185 (2015).
Li et al., "Blocking lysophosphatidic acid receptor 1 signaling inhibits diabetic nephropathy in db/db mice," Kidney International, 91:1362-1373 (2017).
Lin et al., "Lysophosphatidic acid receptor 1 is important for intestinal epithelial barrier function and susceptibility to colitis," The American Journal of Pathology, 188(2):353-366 (2018).
Maher et al., "Safety, tolerability, pharmacokinetics, and pharmacodynamics of GLPG1690, a novel autotaxin inhibitor, to treat idiopathic pulmonary fibrosis (FLORA): a phase 2a randomised placebo-controlled trial," Lancet Respir Med, (2018).

(56) References Cited

OTHER PUBLICATIONS

Maher et al., "Safety, tolerability, pharmacokinetics, and pharmacodynamics of GLPG1690, a novel autotaxin inhibitor, to treat idiopathic pulmonary fibrosis (FLORA): a phase 2a randomized placebo-controlled trial," Lancet Respir Med, 1-9 (2018).
Mathieu et al., "Pathobiology of Lp(a) in calcific aortic valve disease," Expert Review of Cardiovascular Therapy, 15(10):797-807 (2017).
Mazzocca et al., "Lysophosphatidic acid receptor LPAR6 supports the tumorigenicity of hepatocellular carcinoma," Cancer Res, 75(3):532-543 (2015).
Miyasaka et al., "Syntheses of 6-Aminonicotinamide Derivatives and Their Biological Activities," Yakugaku Zasshi, 95(5):547-551 (1975).
Murai et al., "Analgesic effects of novel lysophosphatidic acid receptor 5 antagonist AS2717638 in rodents," Neuropharmacology, 1-50 (2017).
Nam et al., "Autotaxin (NPP-2), a metastasis-enhancing motogen, is an angiogenic factor," Cancer Res, 61:6938-6944 (2001).
Nam et al., "Autotaxin (NPP-2), a Metastasis-enhancing Motogen, Is an Angiogenic Factor," Cancer Research, 61:6938-6944 (2001).
Nikolaou et al., "Hydroxamic acids constitute a novel class of autotaxin inhibitors that exhibit in vivo efficacy in a pulmonary fibrosis model," J Med Chem, 61:3697-3711 (2018).
Noble et al., "Pirfenidone in patients with idiopathic pulmonary fibrosis (Capacity): two randomised trials," The Lancet, 337:1760-1769 (2011).
Noth et al., "A Placebo-Controlled Randomized Trial of Warfarin in Idiopathic Pulmonary Fibrosis," Am J Respir Crit Care Med, 186(1):88-95 (2012).
Nsaibia et al., "Autotaxin interacts with lipoprotein(a) and oxidized phospholipids in predicting the risk of calcific aortic valve stenosis in patients with coronary artery disease," Journal of Internal Medicine, 280:509-517 (2016).
Nsaibia et al., "OxLDL-derived lysophosphatidic acid promotes the progression of aortic valve stenosis through a LPAR1-RhoA-NF-kB pathway," Cardiovascular Research, 113:1351-1363 (2017).
Ohashi et al., "Anti-fibrotic effect of lysophosphatidic acid receptors LPA1 and LPA3 antagonist on experimental murine scleroderma induced by bleomycin," Fukushima Medical University, 1-28. First published as an accepted manuscript. May 6, 2015. Later published as Experimenlal Dermatology (2015) 24:698-702 doi: 10.1111/exd.12752.
Orosa et al., "The Autotaxin-Lysophosphatidic acid pathway in pathogenesis of rheumatoid arthritis," European Journal of Pharmacology, (2015). http://dx.doi.org/10.1016/j.ejphar.2015.08.028.
Park et al., "Inhibition of lysophosphatidic acid receptor ameliorates Sjorgen's syndrome in NOD mice," Oncotarget, 8(16):27240-27251 (2017).
Quan et al., "The critical role and potential target of the autotaxin/lyphosphatidate axis in pancreatic cancer," Tumor Biology, 1-11 (Mar. 2017).
Raghu et al., "An Official ATS/ERS/JRS/ALAT Clinical Practice Guideline: Treatment of Idiopathic Pulmonary Fibrosis," Am J Respir Crit Care Med, 192(2):e3-e19 (2015).
Raghu et al., "Treatment of Idiopathic Pulmonary Fibrosis with Ambrisentan," Annals of Internal Medicine, 158(9):641-649 and W-262-W-272 (2013).
Richeldi et al., "Efficacy and Safety of Nintedanib in Idiopathic Pulmonary Fibrosis," The New England Journal of Medicine, 360(22):2071-2082 (2014).
Richeldi et al., "Efficacy of a Tyrosine Kinase Inhibitor in Idiopathic Pulmonary Fibrosis," The New England Journal of Medicine, 365(12):1079-1087 (2011).
Saga et al., "A Novel Highly Potent Autotaxin/ENPP2 Inhibitor Produces Prolonged Decreases in Plasma Lysophosphatidic Acid Formation in Vivo and Regulates Urethral Tension," PLOS One, 9(4):e93230 (2014).
Samadi et al., "Regulation of lysophosphatidate signaling by autotaxin and lipid phosphate phosphates with respect to tumor progression, angiogenesis, metastasis and chemo-resistance," Biochimie, 93:61-70 (2011).
Sanchez-Marin et al., "Systemic blockade of LPA1/3 lysophosphatidic acid receptors by ki16425 modulates the effects of ethanol on the brain and behavior," Neuropharmacology, 1-26 (2018). doi: 10.1016/j.neuropharm.2018.01.033.
Schneider et al., "Bioactive lipids, LPC and LPA, are novel prometastatic factors and their tissue levels increase in response to radio/chemotherapy," Mol Cancer Res, 12(11):1560-1573 (2014).
Servusova et al., "Alkylamino derivatives of pyrazinamide: Synthesis and antimycobacterial evaluation," Bioorganic & Medicinal Chemistry Letters, 24:450-453 (2014).
Srikanth et al., "Lysophosphatidic acid and its receptor LPA1 mediate carrageenan induced inflammatory pain in mice," European Journal of Pharmacology, 1-34 (2018). https://doi.org/10.1016/j.ejphar.2018.10.005.
Stracke et al., "Identification, Purification, and Partial Sequence Analysis of Autotaxin, a Novel Motility-stimulating Protein," The Journal of Biological Chemistry, 267(4):2524-2529 (1992).
Swaney et al., "A novel, orally active LPA1 receptor antagonist inhibits lung fibrosis in the mouse bleomycin model," British Journal of Pharmacology, 160:1699-1713 (2010).
Szepanowski et al., "Fingolimod promotes peripheral nerve regeneration via modulation of lysophospholipid signaling," Journal of Neuroinflammation, 13(143):1-11 (2016).
Tabibian et al., "Absence of the intestinal microbiota exacerbates hepatobiliary disease in a murine model of primary sclerosing cholangitis," Hepatology, 63(1):185-196 (2016).
Tabuchi, "The autotaxin-lysophosphatidic acid-lysophosphatidic acid receptor cascade: proposal of a novel potential therapeutic target for treating glioblastoma multiforme," Lipids in Health and Disease, 14(56):1-9 (2015).
Tager et al., "The lysophosphatidic acid receptor LPA1 links pulmonary fibrosis to lung injury by mediating fibroblast recruitment and vascular leak," Nature Medicine, 14(1):45-54 (2008).
Tager, "Autotaxin Emerges as a Therapeutic Target for Idiopathic Pulmonary Fibrosis," Am J Respir Cell Mol Biol, 47(5):563-565 (2012).
Taghavi et al., "In vitro genetic screen identifies a cooperative role for LPA signaling and c-Myc in cell transformation," Oncogene, 27:6806-6816 (2008).
Tando et al., "The role of lysophosphatidic acid on airway epithelial cell denudation in a murine heterotopic tracheal transplant model," Transplantation Direct, 1-11 (2015).
Thalman et al., "Synaptic phospholipids as a new target for cortical hyperexcitability and E/I balance in psychiatric disorders," Molecular Psychiatry, 23:1699-1710 (2018).
Thirunavukkarasu et al., "Pharmacological characterization of a potent inhibitor of autotaxin in animal models of inflammatory bowel disease and multiple sclerosis," J Pharmacol Exp Ther, 359:207-214 (2016).
Tigyi, "Aiming drug discovery at lysophosphatidic acid targets," British Journal of Pharmacology, 161:241-270 (2010).
Toews et al., "Lysophosphatidic acid in airway function and disease," Biochimica et Biophysica Acta, 1582:240-250 (2002).
Tokumura et al., "Identification of Human Plasma Lysophospholipase D, a Lysophosphatidic Acid-producing Enzyme, as Autotaxin, a Multifunctional Phosphodiesterase," The Journal of Biological Chemistry, 277(42):39436-39442 (2002).
Torzewski et al., "Lipoprotein(a)-associated molecules are prominent components in plasma and valve leaflets in calcific aortic valve stenosis," JACC: Basic to Translational Science, 2(3):229-240 (2017).
Umezu-Goto et al., "Autotaxin has lysopholipase D activity leading to tumor cell growth and motility by lysophosphatidic acid production," The Journal of Cell Biology, 158(2):227-233 (2002).
Valdes-Rives et al., "Autotaxin-Lysophosphatidic Acid: From Inflammation to Cancer Developmen," Mediators of Inflammation, (2017), 15 pages. https://doi.org/10.1155/2017/9173090.

(56) References Cited

OTHER PUBLICATIONS

Van Meeteren et al., "Regulation and biological activities of the autotaxin—LPA axis," Progress in Lipid Research, 46:145-160 (2007).
Weng et al., "Autotaxin/lysophosphatidic acid signaling mediates obesity-related cardiomyopathy in mice and human subjects," J Cell Mol Med, 1-9 (2018).
Wunsch et al., "Serum autotaxin is a marker of the severity of liver injury and overall survival in patients with cholestatic liver diseases," Scientific Reports, 6(30847):1-12 (2016).
Yang et al., "Expression of autotaxin (NPP-2) is closely linked to invasiveness of breast cancer cells," Clinical & Experimental Metasis, 19:603-608 (2002).
Yun et al., "Diverse roles of LPA signaling in the intestinal epithelium," Exp Cell Res, 333(2):201-207 (2015).
Zhang et al., "Lysophosphatidic acid receptor antagonism protects against diabetic nephropathy in a type 2 diabetic model," J Am Soc Nephrol, 28:3300-3311 (2017).
Zhao et al., "Lysophosphatidic acid signaling in airway epithelium: Role in airway inflammation and remodeling," Cellular Signalling, 21:367-377 (2009).

\* cited by examiner

COMPOUNDS AS AUTOTAXIN INHIBITORS AND PHARMACEUTICAL COMPOSITIONS COMPRISING THE SAME

CROSS-REFERENCE TO RELATED APPLICATIONS

This application is a continuation of U.S. patent application Ser. No. 16/098,748 filed on Nov. 2, 2018, which is a National Stage Entry of International Application No. PCT/KR2018/05516, filed May 15, 2018, which claims priority to Korean Patent Application 10-2017-0060940, filed on May 17, 2017. The contents of U.S. patent application Ser. No. 16/098,748 and International Application No. PCT/KR2018/005516 are incorporated herein by reference in their entirety.

TECHNICAL FIELD

The present invention relates to novel compounds as autotoxin inhibitors for treatment and prophylaxis of conditions or a disorder caused by autotoxin activation or increased concentration of lysophosphatidic acid, and also a pharmaceutical composition containing the same.

BACKGROUND ART

Autotaxin (hereinbelow, abbreviated as ATX) is an enzyme which is responsible for the increase in lysophosphatidic acid in ascites and plasma, and it is a secretory enzyme important for converting lysophosphatidylchloine (hereinbelow, abbreviated as LPC) into lysophosphatidic acid (hereinbelow, abbreviated as LPA) as a bioactive signaling molecule. ATX is also referred to as an ectonucleotide pyrophosphatase/phosphodiesterase 2 or lysophospholipase D. ATX plays a role in causing pathological conditions including fibrosis, arthritis inflammation, neurodegeneration, neuropathic pain, and cancer.

LPA is a physiologically active lipid having an influence on the migration, proliferation, and survival of various types of cells. Since the LPA level in plasma is highly related to the activity of ATX, it is believed that ATX is an important supply source of extracellular LPA.

It has been shown that, in pathological conditions, inhibition of ATX reduces the LPA level. LPA reduction may provide therapeutic benefit for a disorder with unsatisfied medical needs, including cancer, lymphocyte homing, chronic inflammation, neuropathic pain, fibrotic disorder like idiopathic pulmonary fibrosis (IPF), thrombosis, cholestatic pruritus, or the like that are induced, mediated, and/or propagated by increased LPA level and/or ATX activation.

Furthermore, it has been found that LPA is present in increased concentrations in plasma and ascites fluid from ovarian cancer patients in the early and late phase. Increased LPA level and altered expression and altered response of a receptor for LPA can be one of the causes of having an onset, a progress, or a result of ovarian cancer. LPA is also related to prostate cancer, breast cancer, melanoma cancer, head and neck cancer, bowel cancer, brain cancer, and thyroid cancer. LPA plays a role in tumor cell proliferation and invasion thereof into neighboring tissue, which can result in metastasization. These biological and pathobiological processes are switched on by activation by LPA of G-protein coupled receptors.

For the treatment of tumor patients, it is desirable to lower the LPA level. This can be achieved by the inhibition of enzymes which are involved with LPA biosynthesis, for example, ATX. Autotaxin belongs to the enzyme family of the nucleotide pyrophosphatases and phosphodiesterases representing an important starting point in anti-tumor therapy. That is because ATX is expressed to an increased extent in tumors to exhibit an influence on tumor cell proliferation and invasion into neighboring tissue, which can result in metastases formation.

Namely, as ATX is expressed in tumors and has an influence on tumor cell proliferation and infiltration to neighboring tissue, both of them can result in metastases formation, ATX is a target for anti-tumor therapy. Furthermore, during the course of angiogenesis, ATX together with other angiogenic factors causes blood vessel formation. Angiogenesis supplies the tumor with nutrients during tumor growth. As such, it can be said that inhibition of angiogenesis is an important starting point in cancer and tumor therapy.

CITATION LIST

Patent Literature

WO2010-112116 A1 (2010 Oct. 7)
WO1995-035284 A1 (1995 Nov. 28)
WO2015-144605 A1 (2015 Oct. 1)

SUMMARY OF INVENTION

Problem to be Solved by the Invention

Under the circumstances, the inventors of the present invention found that compounds having novel structure, which have not been studied until now, not only exhibit an excellent inhibitory activity for ATX but also can lower LPA concentration, and thus completed the present invention accordingly.

One Object of the present invention is to provide novel compounds as autotoxin inhibitors for treatment and prophylaxis of conditions or a disorder caused by autotaxin activation or increased concentration of LPA, or a prodrug thereof, a hydrate thereof, a solvate thereof, an isomer thereof, or a pharmaceutically acceptable salt thereof.

Another object of the present invention is to provide an autotoxin inhibitor composition containing, as an effective ingredient, the aforementioned novel compounds, or a prodrug thereof, a hydrate thereof, a solvate thereof, an isomer thereof, or a pharmaceutically acceptable salt thereof Still another object of the present invention is to provide a pharmaceutical composition for prophylaxis or treatment of a disorder related to autotoxin activity containing, as an effective ingredient, the aforementioned novel compounds, or a prodrug thereof, a hydrate thereof, a solvate thereof, an isomer thereof, or a pharmaceutically acceptable salt thereof.

Means for Solving Problem

To achieve the aforementioned object, the present invention provides a novel compound of the following chemical formula 1 which can effectively inhibit the activity of ATX, and a prodrug thereof, a solvate thereof, a stereoisomer thereof, or a pharmaceutically acceptable salt thereof.

[Chemical formula 1]

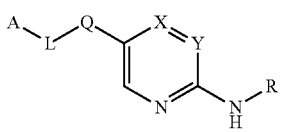

wherein A, L, Q, X, Y, and R are defined herein. In some embodiments, in the chemical formula 1, X and Y are each independently CR' or N, with the exclusion of cases in which both of them are N;

R' is hydrogen, C1-C10 alkyl, or C6-C12 aryl;

R is indanyl (e.g., 2-indanyl), C6-C12arC1-C10 alkyl, or C6-C12arC3-C10 cycloalkenyl;

said aralkyl and arcycloalkenyl of above R may be further substituted with one or more (e.g., 1, 2, or 3) substituents that are each independently selected from halogen, C1-C10 alkoxy, and halo substituted C1-C10 alkoxy;

A is C2-C12 heteroaryl, carboxyl-substituted C1-C10 alkyl, C6-C12 aryl, C6-C12arC1-C10 alkyl, C2-C12 heterocycloalkyl, or $NR_1R_2$;

said heteroaryl, aryl, aralkyl, and heterocycloalkyl of above A may be further substituted with one or more (e.g., 1, 2, or 3) substituents that are each independently selected from hydroxy, carboxyl, carbamoyl, aminosulfonyl, C1-C10 alkylsulfonylamino, C6-C12 arylsulfonylamino, aminosulfonylamino ($-NHSO_2NH_2$), $-C(=O)CH_2OH$ and amino, $R_1$ and $R_2$ are each independently hydrogen or carboxyl-substituted C1-C10 alkyl, or $R_1$ and $R_2$ may be linked to each other to form a monocycle, a polycycle, or a spriro ring that are either saturated or unsaturated;

said ring formed as above may contain one or more hetero atoms that are selected from nitrogen, oxygen, and sulfur and may contain C=C, C=N, or N=N double bond, and $CH_2$ in said ring formed as above may be substituted with C(=O) and also may be further substituted with one or more substituents that are selected from hydroxy, carboxyl, carbamoyl, aminosulfonyl, C1-C10 alkylsulfonylamino, C6-C12 arylsulfonylamino, aminosulfonylamino ($-NHSO_2NH_2$), hydrazide and amino;

L is a single bond, $-(CR_3R_4)_aC(=O)-$, $-C(=O)-(CR_3R_4)_a-$, $-C(=O)-(CR_5R_6)_b-NH-(CR_7R_8)_c-$, $-NH-(CR_7R_8)_c-C(=O)-(CR_5R_6)_b-$, $-C(=NR_9)-(CR_3R_4)_a-$, C2-C12 heteroarylene, $-(CR_3R_4)_a-$C2-C12 heterocycloalkylene-, $-$C2-C12 heterocycloalkenylene-$(CR_3R_4)_a-$, $-$C2-C12 heterocycloalkylene-$(CR_3R_4)_a-$(NH)$_d-$,

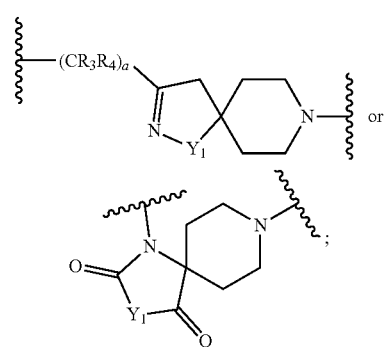

$R_3$ to $R_8$ are each independently hydrogen or C1-C10 alkyl;

$R_9$ is hydroxy, C1-C10 alkoxy, or mono- or di-C1-C10 alkylamino;

Y1 is $NR_{10}$, O, or S;

each $R_{10}$ is independently hydrogen or C1-C10 alkyl;

a is an integer of from 1 to 5;

b and c are each independently an integer of from 0 to 5;

d is an integer of 0 or 1;

Q is carbonyl, C2-C12 heterocycloalkylene, or C2-C12 heteroarylene;

said heteroarylene of above Q may be further substituted with one or more (e.g., 1, 2, or 3) substituents that are selected from C1-C10 alkyl, halo-substituted C1-C10 alkyl, hydroxy C1-C10 alkyl, C3-C10 cycloalkyl, C6-C12 aryl, C2-C12 heteroaryl, carboxyl, $NR_{11}R_{12}$, $-O(CH_2)_eR_{13}$, $-(CH_2)_fR_{14}$, and $-C(=O)R_{15}$, in which said alkyl, cycloalkyl, aryl, and heteroaryl may be further substituted with $NR_{11}R_{12}$, halogen or carboxyl;

$R_{11}$ and $R_{12}$ are each independently hydrogen, C1-C10 alkyl, C6-C12 aryl, C2-C12 heteroaryl, or C3-C10 cycloalkyl;

e and f are each independently an integer of from 0 to 5;

$R_{13}$ is hydrogen, C1-C10 alkyl, C6-C12 aryl, C2-C12 heterocycloalkyl, or carboxyl, in which said aryl and heterocycloalkyl of above $R_{13}$ may be further substituted with one or more (e.g., 1, 2, or 3) substituents that are selected from C1-C10 alkyl, halo-substituted C1-C10 alkyl, and carboxy;

$R_{14}$ and $R_{15}$ are each independently C2-C12 heterocycloalkyl, in which said heterocycloalkyl of $R_{14}$ and $R_{15}$ may be a single ring, a fused ring, or a spriro ring that are either saturated or unsaturated and also may be further substituted with $-C(=O)CH_2OH$, or $CH_2$ in the ring may be substituted with C(=O) and also may be further substituted with one or more (e.g., 1, 2, or 3) substituents that are selected from halogen, C1-C10 alkyl, halo-substituted C1-C10 alkyl, and C6-C12 aryl; and said heteroaryl, heteroarylene, heterocycloalkylene, heterocycloalkenylene, and heterocycloalkyl contain at least one hetero atom that is selected from nitrogen, oxygen, and sulfur.

In addition, according to confirmation of an excellent ATX inhibiting activity of the compound represented by the above chemical formula 1, the present invention further provides an autotoxin inhibitor composition containing, as an effective ingredient, the compound of the above chemical formula 1, or a prodrug thereof, a solvate thereof, a stereoisomer thereof, or a pharmaceutically acceptable salt thereof.

In addition, the present invention still further provides a pharmaceutical composition for prophylaxis or treatment of a disorder related to autotoxin activity containing, as an effective ingredient, the compound of the above chemical formula 1, or a prodrug thereof, a hydrate thereof, a solvate thereof, an isomer thereof, or a pharmaceutically acceptable salt thereof.

Effects of the Invention

Because the compounds of the present invention as a novel compound exhibit a very high inhibiting activity on ATX and also inhibits simultaneously the production of LPA, they can be used advantageously as an effective agent for prophylaxis and treatment of a disorder mediated by ATX, for example, cardiovascular disorder, cancer, metabolic disorder, kidney disorder, liver disorder, inflammatory disorder, nervous system disorder, respiratory system disorder, fibrotic disease, ocular disorder, cholestatic and other forms of chronic pruritus, or acute or chronic organ transplant rejection.

EMBODIMENTS FOR CARRYING OUT THE INVENTION

Hereinbelow, the present invention is explained more specifically. With regard to the technical terms and scientific terms that are used therefor, if there is no other definition available, they have a meaning that is commonly understood by a person who has common knowledge in the technical field to which the present invention pertains, and explanations of well-known functions and constitutions, which may unnecessarily obscure the gist of the present invention, are omitted in the descriptions that are given below.

The present invention provides a compound that is represented by the following chemical formula 1, and a prodrug thereof, a solvate thereof, a stereoisomer thereof, or a pharmaceutically acceptable salt thereof.

[Chemical formula 1]

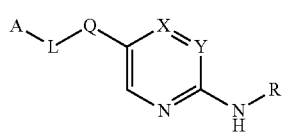

wherein A, L, Q, X, Y, and R are defined herein. In some embodiments, in the chemical formula 1, X and Y are each independently CR' or N, with the exclusion of cases in which both of them are N;

R' is hydrogen, C1-C10 alkyl, or C6-C12 aryl;

R is indanyl (e.g., 2-indanyl), C6-C12arC1-C10 alkyl, or C6-C12arC3-C10 cycloalkenyl;

said aralkyl and arcycloalkenyl of above R may be further substituted with one or more (e.g., 1, 2, or 3) substituents that are selected from halogen, C1-C10 alkoxy, and halo-substituted C1-C10 alkoxy;

A is C2-C12 heteroaryl, carboxyl-substituted C1-C10 alkyl, C6-C12 aryl, C6-C12arC1-C10 alkyl, C2-C12 heterocycloalkyl, or $NR_1R_2$;

said heteroaryl, aryl, aralkyl, and heterocycloalkyl of above A may be further substituted with one or more (e.g., 1, 2, or 3) substituents that are selected from hydroxy, carboxyl, carbamoyl, aminosulfonyl, C1-C10 alkylsulfonylamino, C6-C12 arylsulfonylamino, aminosulfonylamino (—$NHSO_2NH_2$), —C(=O)$CH_2OH$ and amino, $R_1$ and $R_2$ are each independently hydrogen or carboxyl-substituted C1-C10 alkyl, or $R_1$ and $R_2$ may be linked to each other to form a monocycle, a polycycle, or a spriro ring that are either saturated or unsaturated;

said ring formed as above may contain one or more (e.g., 1, 2, or 3) hetero atoms that are selected from nitrogen, oxygen, and sulfur and may contain C=C, C=N, or N=N double bond, and $CH_2$ in said ring formed as above may be substituted with C(=O) and also may be further substituted with one or more (e.g., 1, 2, or 3) substituents that are selected from hydroxy, carboxyl, carbamoyl, aminosulfonyl, C1-C10 alkylsulfonylamino, C6-C12 arylsulfonylamino, aminosulfonylamino (—$NHSO_2NH_2$), hydrazide and amino;

L is a single bond, —$(CR_3R_4)_aC(=O)$—, —C(=O)—$(CR_3R_4)_a$—, —C(=O)—$(CR_5R_6)_b$—NH—$(CR_7R_8)_c$—, —NH—$(CR_7R_8)_c$—C(=O)—$(CR_5R_6)_b$—, —C(=$NR_9$)—$(CR_3R_4)_a$—, C2-C12 heteroarylene, —$(CR_3R_4)_a$—C2-C12 heterocycloalkylene-, —C2-C12 heterocycloalkenylene-$(CR_3R_4)_a$—, —C2-C12 heterocycloalkylene-$(CR_3R_4)_a$—$(NH)_d$—,

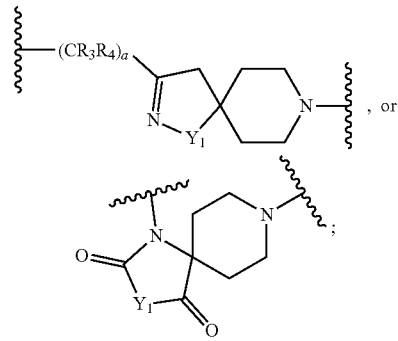

$R_3$ to $R_8$ are each independently hydrogen or C1-C10 alkyl;

$R_9$ is hydroxy, C1-C10 alkoxy, or mono- or di-C1-C10 alkylamino;

Y1 is $NR_{10}$, O, or S;

each $R_{10}$ is independently hydrogen or C1-C10 alkyl;

a is an integer of from 1 to 5;

b and c are each independently an integer of from 0 to 5;

d is an integer of 0 or 1;

Q is carbonyl, C2-C12 heterocycloalkylene, or C2-C12 heteroarylene;

said heteroarylene of above Q may be further substituted with one or more (e.g., 1, 2, or 3) substituents that are selected from C1-C10 alkyl, halo-substituted C1-C10 alkyl, hydroxy C1-C10 alkyl, C3-C10 cycloalkyl, C6-C12 aryl, C2-C12 heteroaryl, carboxyl, $NR_{11}R_{12}$, —O($CH_2$)$_eR_{13}$, —($CH_2$)$_fR_{14}$, and —C(=O)$R_{15}$, in which said alkyl, cycloalkyl, aryl, and heteroaryl may be further substituted with $NR_{11}R_{12}$, halogen or carboxyl;

$R_{11}$ and $R_{12}$ are each independently hydrogen, C1-C10 alkyl, C6-12 aryl, C2-C12 heteroaryl, or C3-C10 cycloalkyl;

e and f are each independently an integer of from 0 to 5;

$R_{13}$ is hydrogen, C1-C10 alkyl, C6-C12 aryl, C2-C12 heterocycloalkyl, or carboxyl, in which said aryl and heterocycloalkyl of above $R_{13}$ may be further substituted with one or more (e.g., 1, 2, or 3) substituents that are selected from C1-C10 alkyl, halo-substituted C1-C10 alkyl, and carboxy;

$R_{14}$ and $R_{15}$ are each independently C2-C12 heterocycloalkyl, in which said heterocycloalkyl of $R_{14}$ and $R_{15}$ may be a single ring, a fused ring, or a spriro ring that are either saturated or unsaturated and also may be further substituted with —C(=O)$CH_2OH$, or $CH_2$ in the ring may be substituted with C(=O) and also may be further substituted with one or more (e.g., 1, 2, or 3) substituents that are selected from halogen, C1-C10 alkyl, halo-substituted C1-C10 alkyl, and C6-C12 aryl; and said heteroaryl, heteroarylene, heterocycloalkylene, heterocycloalkenylene, and heterocycloalkyl contain at least one hetero atom that is selected from nitrogen, oxygen, and sulfur).

The compound of the chemical formula 1 according to the present invention inhibits LPA production based on very high inhibiting activity on ATX. As such, it is useful as a therapeutic agent and a prophylactic agent for a disorder mediated by ATX, for example, kidney disorder, liver disorder, inflammatory disorder, nervous system disorder, fibrotic disease, and acute or chronic organ transplant rejection.

Some of the variables in Formula 1 herein are divalent radicals. For example, "L" is linked to both A and Q in Formula 1; and "Q" is linked to both L and the core aromatic ring. For the avoidance of doubt, as used herein, unless otherwise specified, a divalent radical can be attached to the remaining of the molecule through either attaching points. To illustrate, for example, when L is said to be "—$(CR_3R_4)_aC(=O)$—", the as written left attaching point of L, i.e., a $CR_3R_4$ unit, can be linked to either A or Q, whereas the carbon atom of the $C(=O)$ unit can be linked to the remaining Q or A accordingly. However, in any of the embodiments described herein, the as drawn or written left attaching point of a divalent radical of L can be linked to the variable "A" in any of the formulae herein, and the as drawn or written right attaching point of the divalent radical of L can be linked to the variable "Q" in any of the formulae herein. And in any of the embodiments described herein, the as drawn or written left attaching point of a divalent radical of Q can be linked to the variable "L" in any of the formulae herein.

In various definitions herein, the symbol "-" may be used preceding and after a divalent radical, indicating its connection points. For example, a divalent radical "C2-C12 heterocycloalkylene" can be used in a definition such as "—$(CR_3R_4)_a$—C2-C12 heterocycloalkylene-", which should be understood such that one of the two C2-C12 heterocycloalkylene connecting points is connected to a CR3R4 unit, whereas the other connecting point is connected to the remaining of the structure. Other similar expressions should be understood similarly. Also, those skilled in the art would understand that a divalent radical will have two attaching points regardless whether the symbol "-" is used or not.

In various embodiments herein, the expression "Cx-Cy" or "Cx-y" can be used to designate the number of carbon atoms in the definition. For example, a C1-C10 (or C1-10) alkyl means an alkyl that has 1-10 carbon atoms. Also, C0 means no carbon atom, C1 means one carbon, and so on.

In various embodiments herein, an alkyl, alkoxy, cycloalkyl, cycloalkenyl, cycloalkylene, cycloalkenylene, heterocycloalkyl, heterocycloalkylene, heterocycloalkenyl, heterocycloalkenylene, aryl, arylene, heteroaryl or heteralene, etc. can be described as "optionally substituted," which refers to the respective group being unsubstituted or further substituted with one or more (e.g., 1, 2, 3, or 4) independently selected substituents. If substituted, unless otherwise specified, the substituents can be selected from the group that includes, but is not limited to, halo, $C_1$-$C_{20}$alkyl, —$CF_3$, —$NH_2$, —$N(C_1$-$C_6$ alkyl$)_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$ ($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C (O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_1$-$C_6$ alkyl) OC(O)NH—, aryl, aralkyl, heteroaryl, heterocycloalkyl, halo-aryl, halo-aralkyl, halo-heterocycle and halo-heterocycloalkyl.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, $R^h$) occurs more than one time in any constituent or in formula 1 or in any other formula depicting and describing compounds of the invention, its definition on each occurrence is independent of its definition at every other occurrence. Combinations of substituents and/or variables are permissible if such combinations result in stable compounds.

Unless expressly stated to the contrary, substitution by a named substituent is permitted on any atom provided such substitution is chemically allowed and results in a stable compound. A "stable" compound is a compound that can be prepared and isolated and that has a structure and properties that remain or can be caused to remain essentially unchanged for a period of time sufficient to allow use of the compound for the purposes described herein (e.g., therapeutic or prophylactic administration to a subject).

The term "alkyl" in the present invention means a monovalent linear or branched saturated hydrocarbon radical which consists of carbon and hydrogen atoms only, and 1 to 10 carbon atoms, and preferably 1 to 7 carbon atoms (e.g., 1 to 4 carbons) may be contained therein. Examples of the alkyl radical include methyl, ethyl, propyl, isopropyl, butyl, isobutyl, t-butyl, pentyl, and hexyl, but it is not limited thereto.

The term "aryl" in the present invention means an organic radical that is derived from aromatic hydrocarbons according to removal of one hydrogen, and it includes a mono- or fused-ring system containing suitably 4 to 7, preferably 5 or 6 ring atoms in each ring, and also a type in which several aryls are connected to one another via a single bond. Specific examples thereof include phenyl, naphthyl, biphenyl, anthryl, indenyl and fluorenyl, but it is not limited thereto.

Carboxyl-substituted alkyl as used herein refers to an alkyl group defined herein substituted with one or more carboxyl group, for example, 1 carboxyl group.

Hydroxy-substituted alkyl as used herein refers to an alkyl group defined herein substituted with one or more hydroxyl group, for example, 1 or 2 hydroxyl groups.

The term "heteroaryl" in the present invention means an aryl group which includes, as an aromatic ring skeleton atom, 1 to 4 hetero atoms that are selected from N, O, and S in which the rest of the aromatic ring skeleton atoms are carbons. It is 5- to 6-membered monocyclic heteroaryl or a polycyclic heteroaryl fused to one or more benzene rings, and can be partially saturated. Furthermore, also included in the heteroaryl in the present invention is a type in which one or more heteroaryls are linked to one another via a single bond. Examples of the heteroaryl group include pyrrole, quinoline, isoquinoline, pyridine, pyrimidine, oxazole, thiazole, thiadiazole, triazole, imidazole, benzimidazole, isoxazole, benzisoxazole, thiophene, benzothiophene, furan, and benzofuran, but it is not limited thereto.

The term "halo" in the present invention represents an element of the halogen group, and examples thereof include fluoro, chloro, bromo, and iodo.

Halo-substituted group refers to the respective group being substituted with one or more halogen, for example, substituted with 1, 2, or 3 fluorine. For example, halo-substituted alkyl (or halo alkyl) as used herein refers to an alkyl group defined herein substituted with one or more halogen, for example, substituted with 1, 2, or 3 fluorine. Similarly, halo-substituted alkoxy as used herein refers to an alkoxy group defined herein substituted with one or more halogen, for example, substituted with 1, 2, or 3 fluorine.

The term "cycloalkyl" in the present invention means a monovalent saturated carbocyclic radical consisting of one or more rings, and it may have 3 to 10 carbon atoms, and preferably 3 to 7 carbon atoms. Specific examples thereof include cyclopropyl, cyclobutyl, cyclopentyl, and cyclohexyl, but it is not limited thereto.

The term "alkoxy" in the present invention means a —O-alkyl radical, and it may have 1 to 10 carbon atoms, and preferably 1 to 7 carbon atoms. Herein, the 'alkyl' is as defined in the above. Specific examples thereof include methoxy, ethoxy, isopropoxy, butoxy, isobutoxy, and t-butoxy, but it is not limited thereto.

The term "heterocycloalkyl" in the present invention means a monovalent radical of a non-aromatic heterocycle which includes 1 to 4 hetero atoms that are selected from N, O, and S, in which the non-aromatic heterocycle includes all types of ring structures such as a monocyclic ring and polycyclic ring, including a single ring, a fused ring (e.g., a fused bicyclic ring), and a spiro ring (e.g., a bicyclic ring including a spiro ring) that are either saturated or unsaturated, and in the case of a polycyclic structure, the rings can bind to each other via one or more hetero atom(s) and/or carbon atom(s). Examples of the heterocycloalkyl radical may include a monovalent radical of non-aromatic heterocycle such as aziridine, pyrrolidine, azetidine, piperidine, tetrahydropyridine, piperazine, morpholine, thiomorpholine, 3-azabicyclo[3.1.0]hexane, octahydropyrrolo[3,4-c]pyrrole. 2,7-diazaspiro[4.4]nonane, or 2-azaspiro[4.4]nonane.

The term "heterocycloalkenyl" in the present invention means a monovalent radical of a non-aromatic heterocycle which includes 1 to 4 hetero atoms that are selected from N, O, and S, and includes one or more double bonds, and it includes all types of ring structures such as a monocyclic ring and polycyclic ring, including a single ring, a fused ring, and a spiro ring that are unsaturated, and in the case of a polycyclic structure, the rings can bind to each other via one or more hetero atom(s) and/or carbon atom(s).

The term "cycloalkenyl" in the present invention means an unsaturated monovalent carbocyclic radical consisting of one or more rings, and it may have 3 to 10 carbon atoms, and preferably 3 to 7 carbon atoms. Specific examples thereof include cyclopropenyl, cyclobutenyl, cyclopentenyl, and cyclohexenyl.

The terms "arylene" and "heteroarylene" in the present invention mean a divalent radical of an aromatic ring and a divalent radical of a heteroaromatic ring, respectively.

The terms "heterocycloalkylene" and "heterocycloalkenylene" in the present invention mean a divalent radical of a saturated heterocycle and a divalent radical of an unsaturated heterocycle, respectively.

In some embodiments, A is $NR_1R_2$. In some embodiments, $R_1$, $R_2$, and the nitrogen atom to which they are attached, form an optionally substituted monocyclic or polycyclic heterocyclic ring (e.g., a 5-14 membered ring). As used herein, a polycyclic ring can include a ring system containing two rings fused together via two shared atoms, and a ring system containing two rings sharing only one single carbon atom, i.e., forming a spiro ring. With regard to the compounds according to one example of the present invention, the ring formed as $R_1$ and $R_2$ are linked to each other is a monocycle, a polycycle, or a spiro ring that are either saturated or unsaturated, and it can be preferably a ring selected from the following structures:

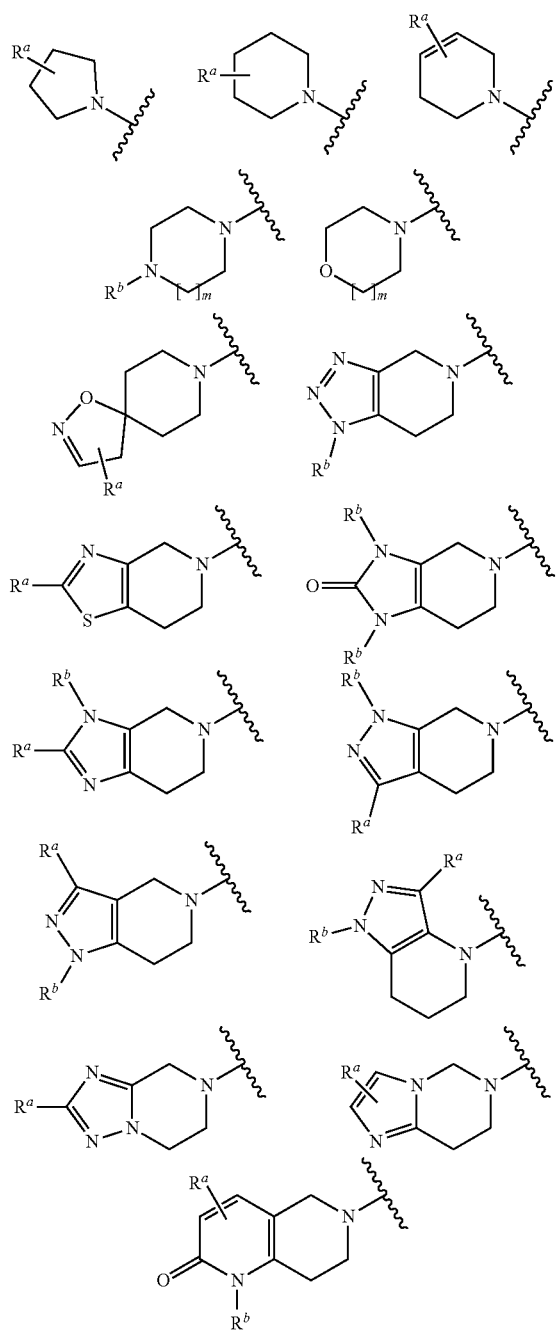

wherein $R^a$ is hydrogen, hydroxy, carboxyl, carbamoyl, C1-C10 alkylsulfonylamino, aminosulfonylamino (—$NHSO_2NH_2$), or amino;
$R^b$ is hydrogen, carboxyl, or aminosulfonyl; and
m is an integer of 0, 1, or 2.

With regard to the compounds according to one example of the present invention, the above A can be selected from the following structures.

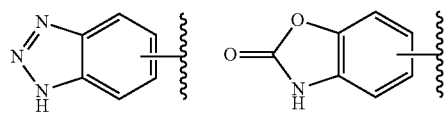

-continued

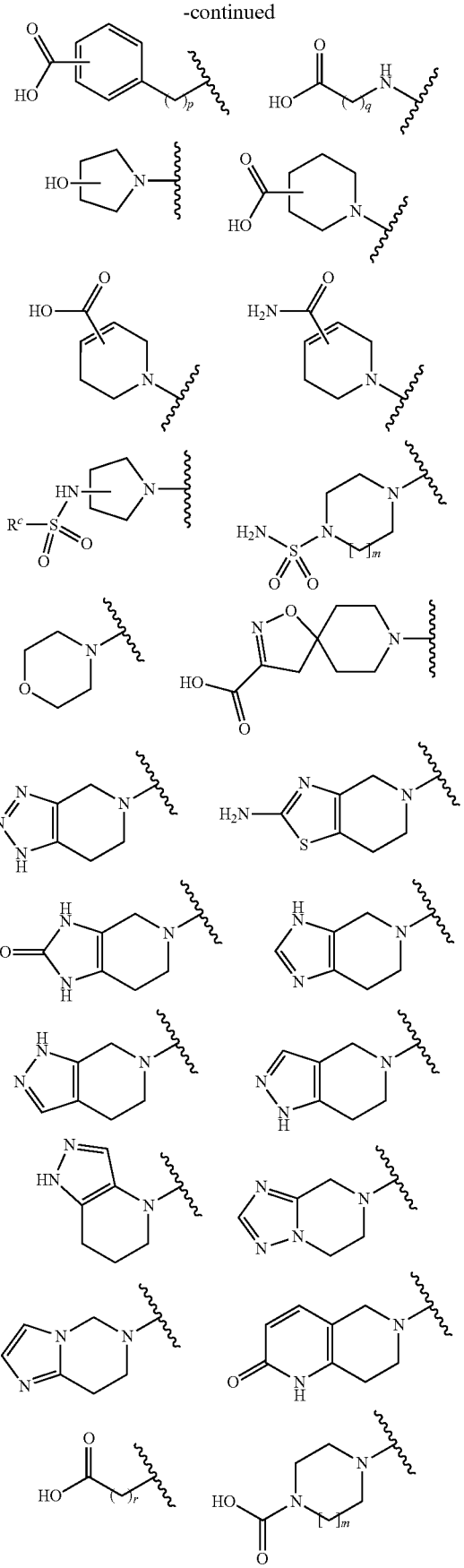

-continued

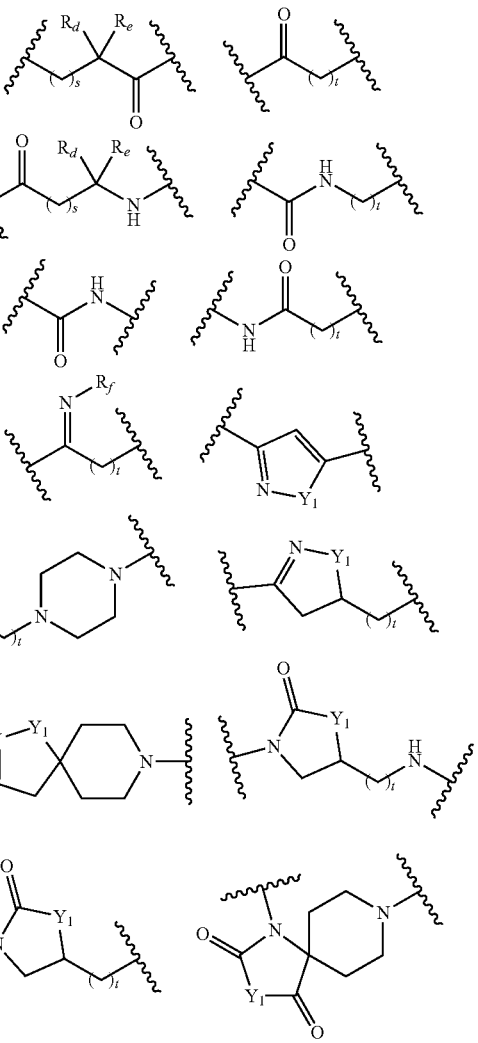

wherein $R^c$ is C1-C7 alkyl or amino;
p is an integer of from 0 to 5;
q and r are each independently an integer of from 1 to 5; and
m is an integer of 0, 1, or 2 (e.g., 1).

With regard to the compounds according to one example of the present invention, the above L may be either a single bond or selected from the following structures.

wherein $R^d$ and $R^e$ are each independently hydrogen or C1-C7 alkyl;
$R^f$ is hydroxy, C1-C7 alkoxy, or mono- or di-C1-C7 alkylamino;
Y1 is $NR_{10}$, O, or S;
each $R_{10}$ is independently hydrogen or C1-C7 alkyl;

s is an integer of from 0 to 3; and t is an integer of from 1 to 3.

With regard to the compounds according to one example of the present invention, the above Q may be selected from the following structures.

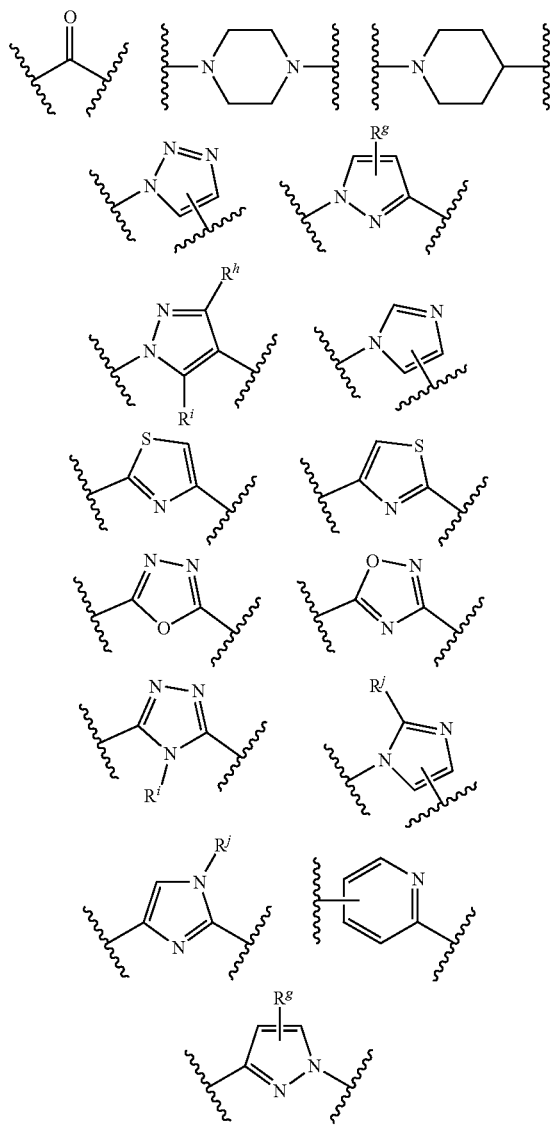

wherein $R^y$ is hydrogen or C1-C7 alkyl;

$R^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, carboxyl, —O(CH$_2$)$_e$R$_{13}$, —(CH$_2$)$_f$R$_{14}$, or —C(=O)R$_{15}$, in which said alkyl, cycloalkyl, aryl, and heteroaryl of $R^h$ may be further substituted with $NR_{11}R_{12}$ or carboxyl;

$R_{11}$ and $R_{12}$ are each independently hydrogen, C1-C7 alkyl, C6-C12 aryl, C2-C12 heteroaryl, or C3-C7 cycloalkyl;

$R_{13}$ is C6-C12 aryl, C3-C9 heterocycloalkyl, or carboxyl, in which said aryl and heterocycloalkyl of $R_{13}$ may be further substituted with one or more substituents that are selected from C1-C7 alkyl, halo-substituted C1-C7 alkyl, and carboxyl;

$R_{14}$ and $R_{15}$ are each independently C3-C9 heterocycloalkyl, in which said heterocycloalkyl of $R_{14}$ and $R_{15}$ may be a single ring, a fused ring, or a spriro ring that are either saturated or unsaturated, or CH$_2$ in the ring may be substituted with C(=O), and said heterocycloalkyl of $R_{14}$ and $R_{15}$ may be further substituted with one or more substituents that are selected from halogen, C1-C10 alkyl, halo-substituted C1-C10 alkyl, and C6-C12 aryl;

$R^i$ is hydrogen, C1-C7 alkyl, or halo-substituted C1-C7 alkyl;

$R^j$ is hydrogen, C1-C7 alkyl, halo-substituted C1-C7 alkyl, C3-C7 cycloalkyl, or C6-C12 aryl;

e is an integer of from 0 to 3; and f is an integer of from 0 to 3.

With regard to the compounds according to one example of the present invention, the above $R^h$ may be more preferably hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from the following structures.

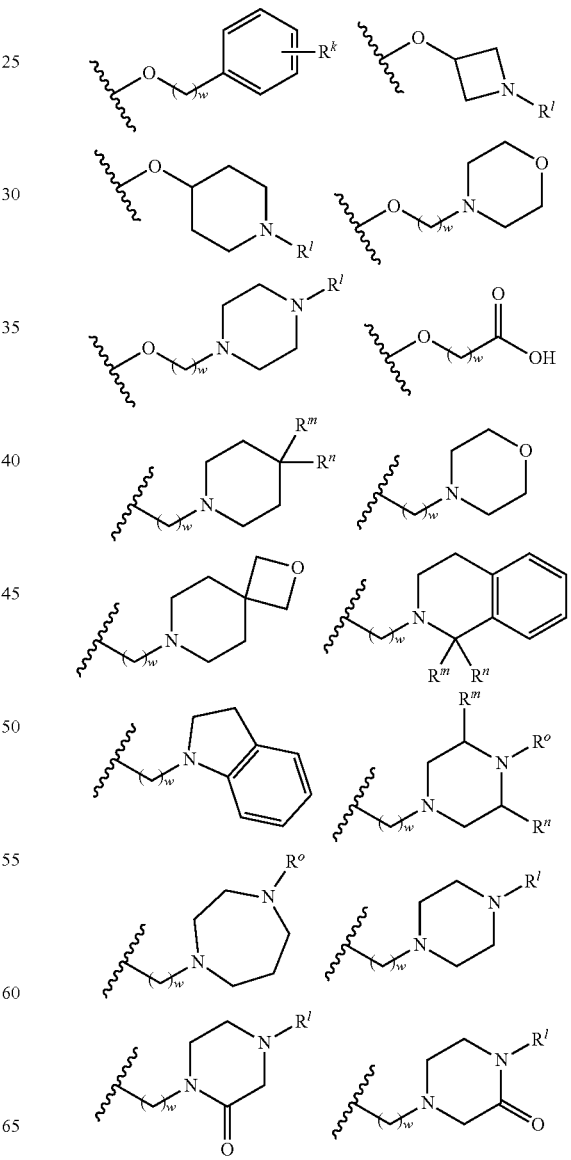

-continued

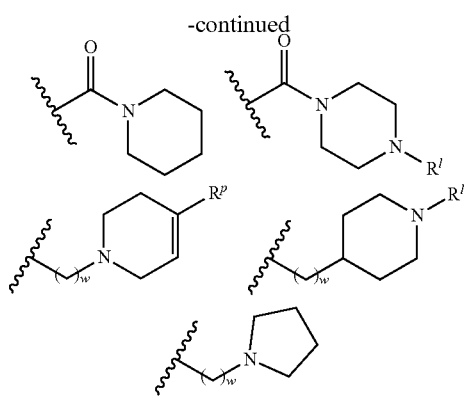

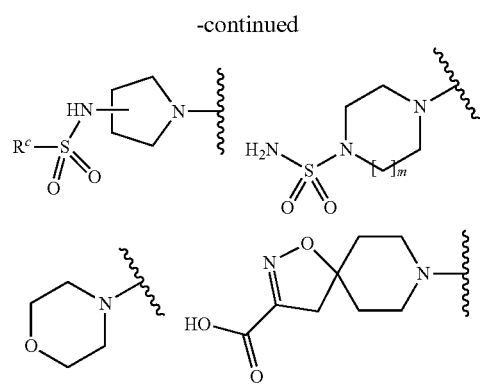

wherein $R_{11}$ and $R_{12}$ are each independently hydrogen, C1-C7 alkyl, C6-C12 aryl, or C3-C7 cycloalkyl;

$R^k$ is hydrogen or carboxyl;

$R^l$ is hydrogen, C1-C7 alkyl, halo-substituted C1-C7 alkyl, or carboxyl;

$R^m$ and $R^n$ are each independently hydrogen, C1-C7 alkyl, halogen, or carboxyl;

$R^o$ is hydrogen or C1-C7 alkyl;

$R^p$ is C6-C12 aryl; and w is an integer of from 0 to 3.

With regard to the compounds according to one example of the present invention, the compounds can be more preferably represented by the chemical formula 2:

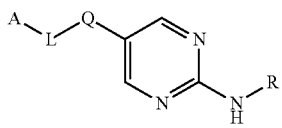

[Chemical formula 2]

wherein A, L, Q, and R are defined herein. In some embodiments, in the chemical formula 2, R is indanyl (e.g., 2-indanyl), halo-substituted C1-C7 alkoxybenzyl, or halo-substituted C6-C12 aryl C5-C7 cycloalkenyl;

A is selected from the following structures;

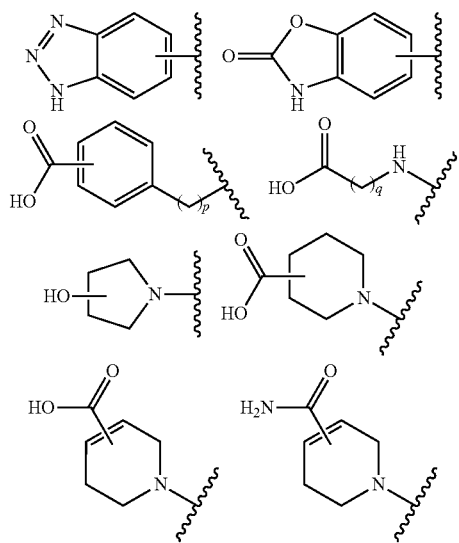

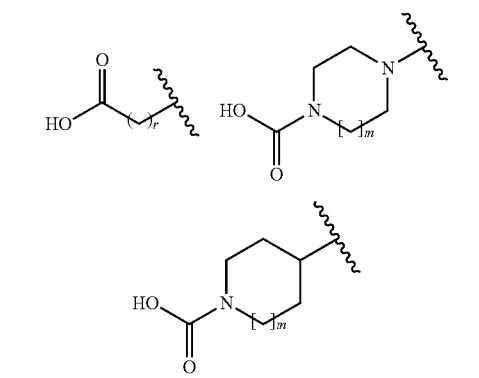

$R^c$ is C1-C7 alkyl or amino;

p is an integer of from 0 to 5;

q and r are each independently an integer of from 1 to 5;

m is an integer of 0, 1, or 2;

L is either a single bond or selected from the following structures;

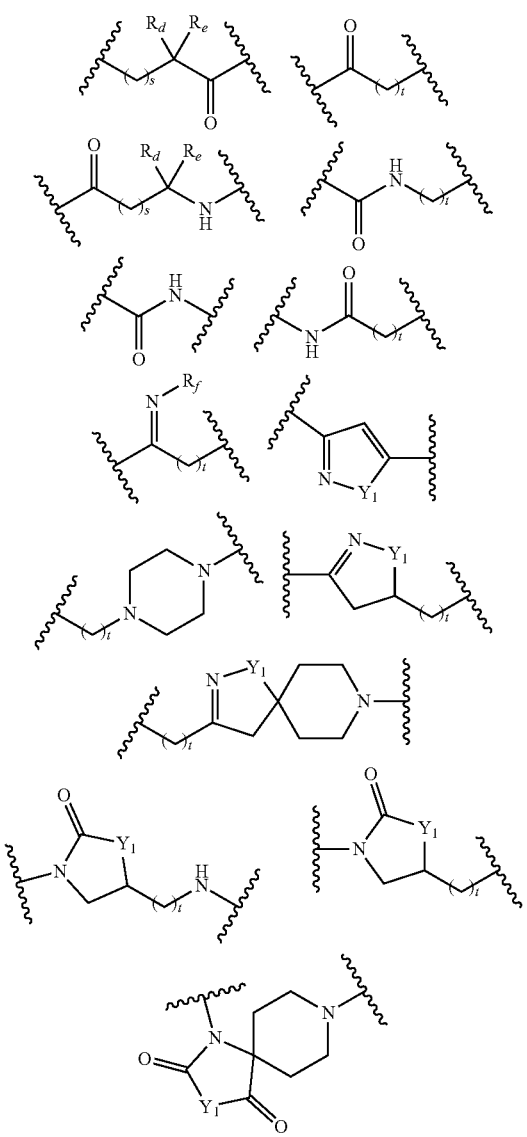

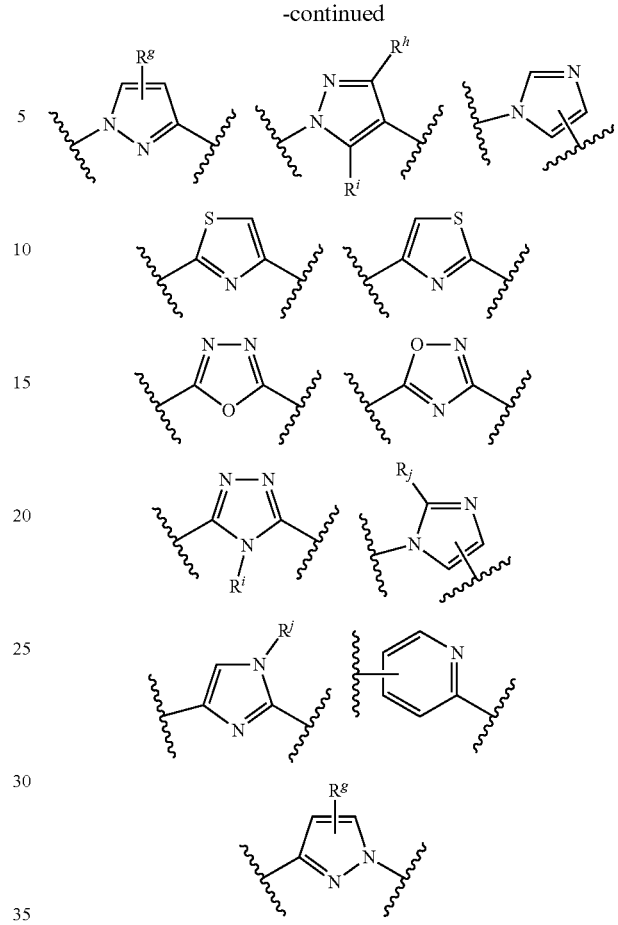

$R^d$ and $R^e$ are each independently hydrogen or C1-C7 alkyl;

$R^f$ is hydroxy, C1-C7 alkoxy, or mono- or di-C1-C7 alkylamino;

Y1 is $NR_{10}$, O, or S;

each $R_{10}$ is independently hydrogen or C1-C7 alkyl;

s is an integer of from 0 to 3;

t is an integer of from 1 to 3;

Q is selected from the following structures;

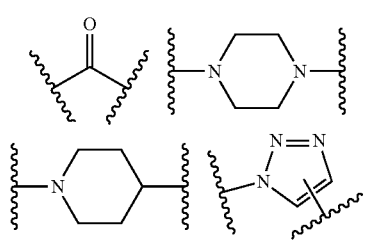

$R^g$ is hydrogen or C1-C7 alkyl;

$R^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from the following structures;

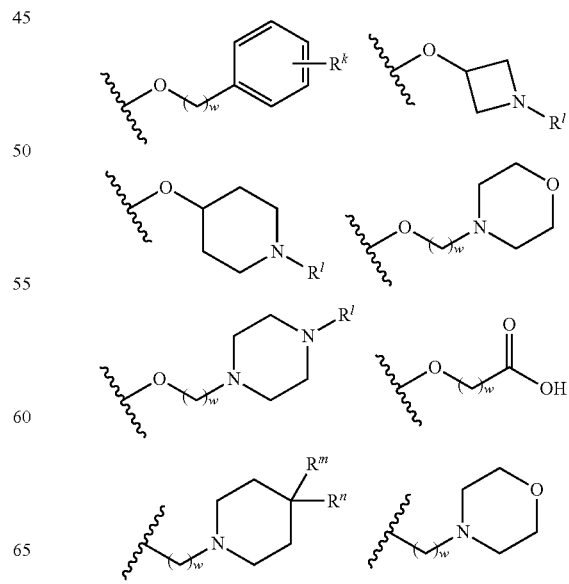

-continued

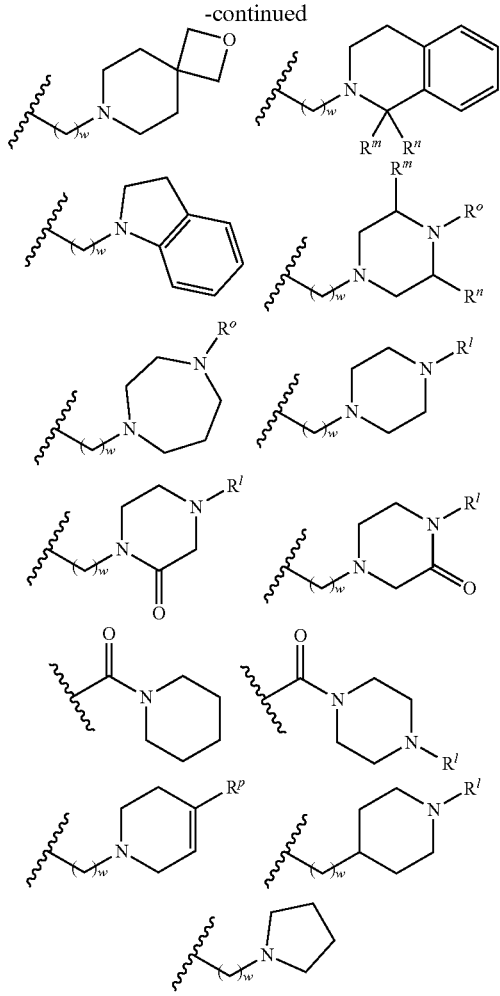

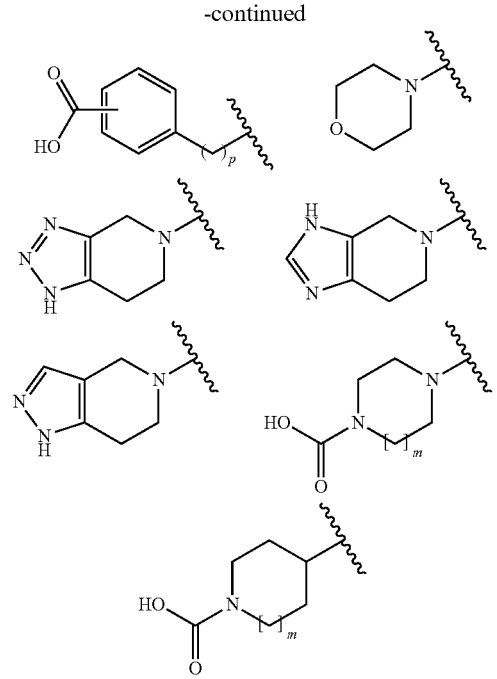

said alkyl, cycloalkyl, aryl, and heteroaryl of $R^h$ may be further substituted with $NR_{11}R_{12}$ or carboxyl;

$R^i$ is hydrogen, C1-C2 alkyl, or halo-substituted C1-C7 alkyl; $R^j$ is hydrogen, C1-C7 alkyl, halo-substituted C1-C7 alkyl, C3-C7 cycloalkyl, or C6-C12 aryl;

$R_{11}$ and $R_{12}$ are each independently hydrogen, C1-C7 alkyl, C6-C12 aryl, or C3-C7 cycloalkyl;

$R^k$ is hydrogen or carboxyl;

$R^l$ is hydrogen, C1-C7 alkyl, halo-substituted C1-C7 alkyl, or carboxyl;

$R^m$ and $R^n$ are each independently hydrogen, C1-C7 alkyl, halogen, or carboxyl;

$R^o$ is hydrogen or C1-C7 alkyl;

$R^p$ is C6-C12 aryl; and w is an integer of from 0 to 3).

With regard to the compounds according to one example of the present invention, it is more preferable that said R is indanyl (e.g., 2-indanyl) or halo-substituted C1-C7 alkoxybenzyl;

A is selected from the following structures;

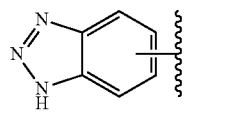 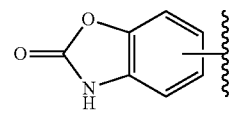

p is an integer of from 1 to 5;

m is an integer of 0, 1, or 2;

L is either a single bond or selected from the following structures;

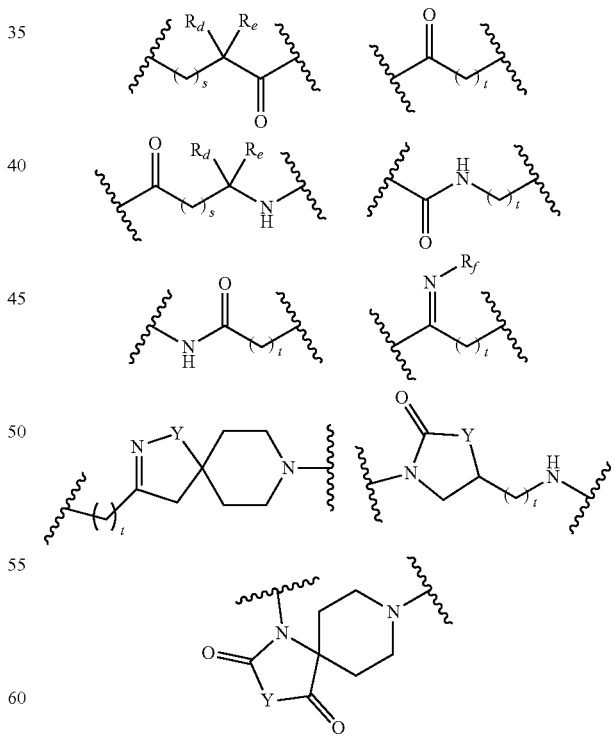

$R^d$ and $R^e$ are each independently hydrogen or C1-C7 alkyl;

s is an integer of from 0 to 3;

t is an integer of from 1 to 3;

Q is selected from the following structures;

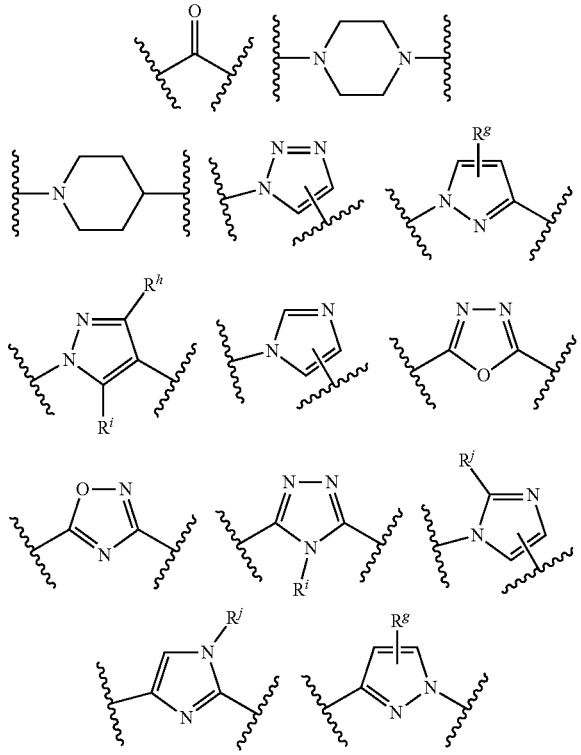

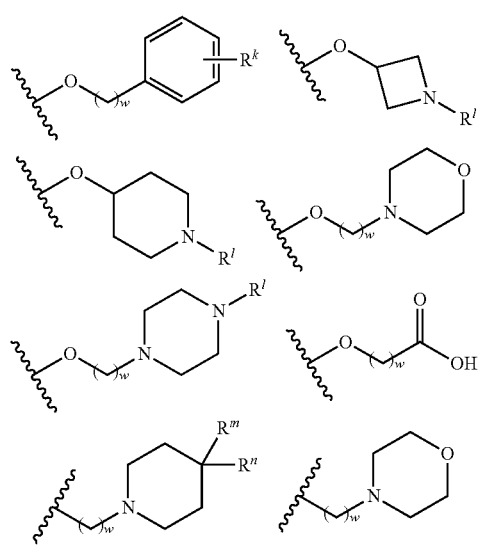

$R^g$ is hydrogen or C1-C7 alkyl;

$R^i$ is hydrogen, C1-C7 alkyl, or halo-substituted C1-C7 alkyl;

$R^j$ is hydrogen, C1-C7 alkyl, halo-substituted C1-C7 alkyl, C3-C7 cycloalkyl, or C6-C12 aryl;

$R^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from the following structures;

$R_{11}$ and $R_{12}$ are each independently hydrogen, C1-C7 alkyl, C6-C12 aryl, or C3-C7 cycloalkyl;

$R^k$ is hydrogen or carboxyl;

$R^l$ is hydrogen, C1-C7 alkyl, halo-substituted C1-C7 alkyl, or carboxyl;

$R^m$ and $R^n$ are each independently hydrogen, C1-C7 alkyl, or halogen;

$R^o$ is hydrogen or C1-C7 alkyl;

$R^p$ is C6-C12 aryl; and w may be an integer of from 0 to 3.

With regard to the compounds according to one example of the present invention, it is more preferable that said R is indanyl, more preferably, 2-indanyl, i.e.,

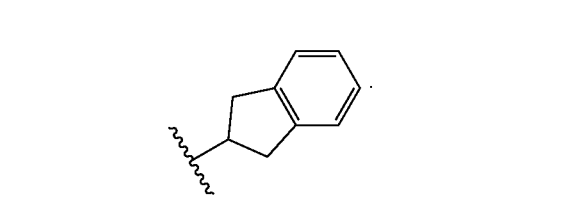 [SMILES: *C1Cc2ccccc2C1]

With regard to the compounds according to one example of the present invention, the compounds can be selected specifically from the following structures, but they are not limited thereto.

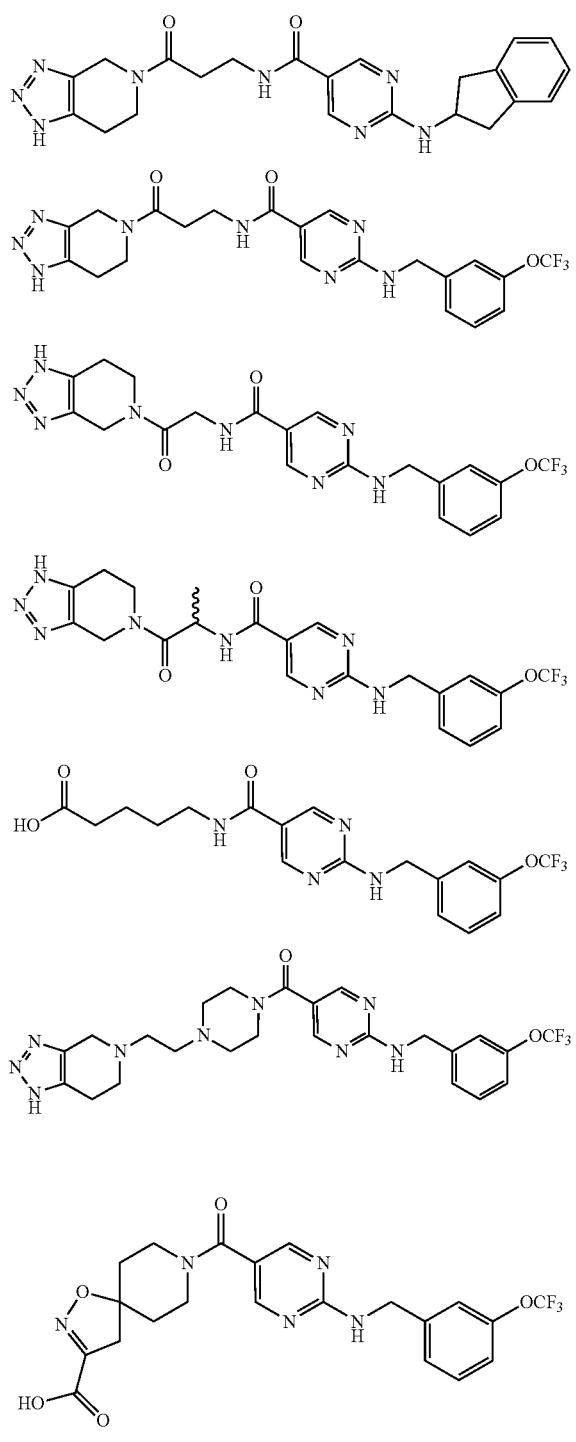
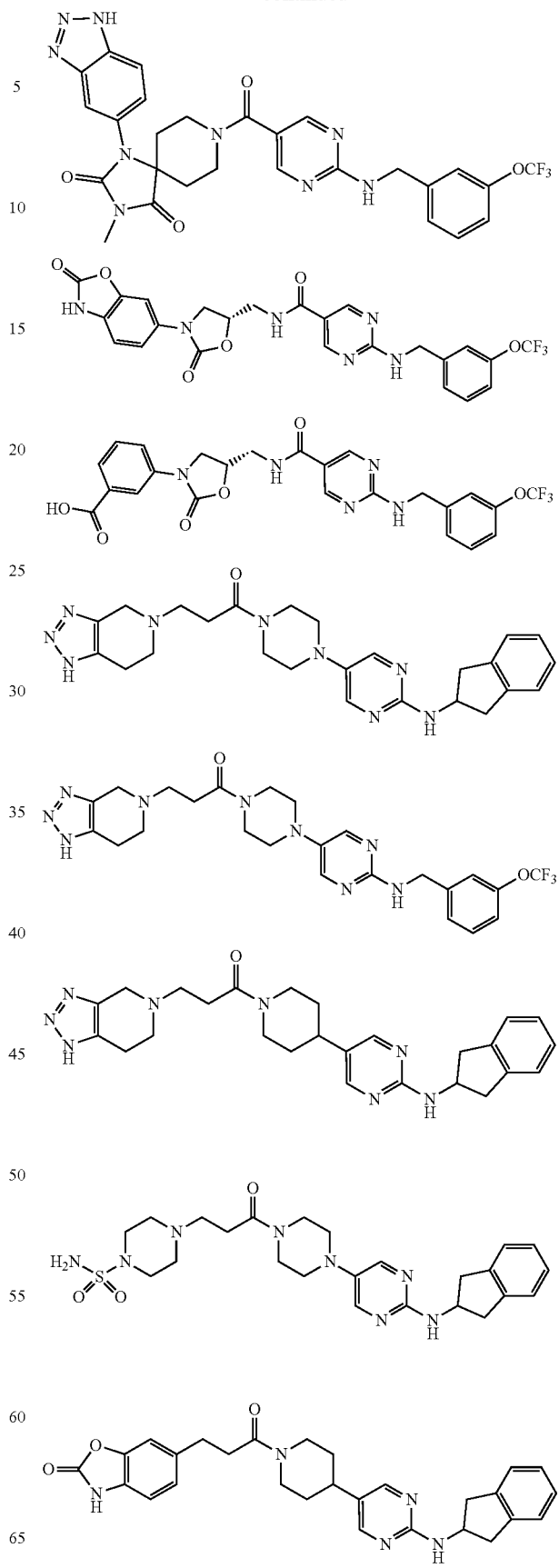

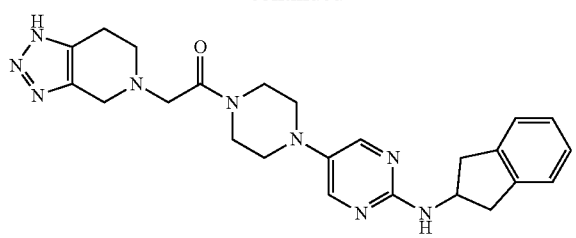
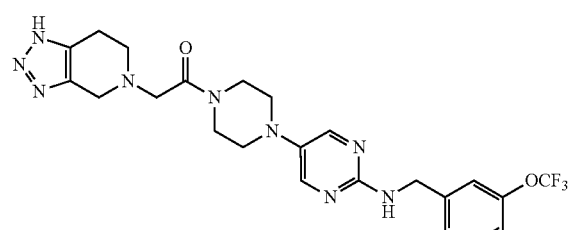
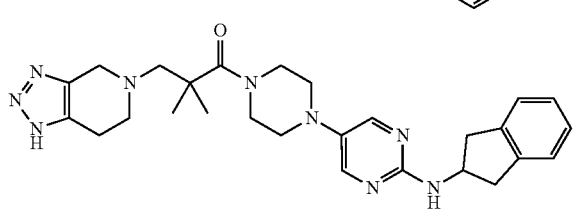
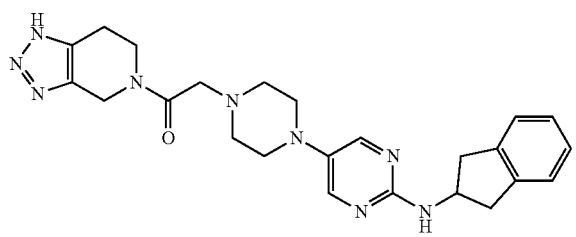
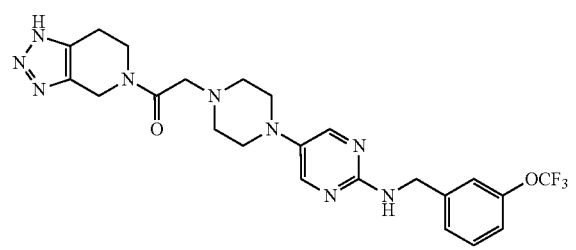
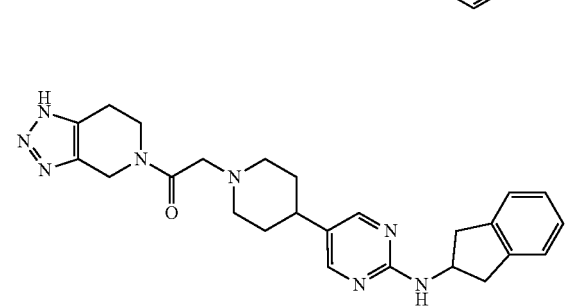
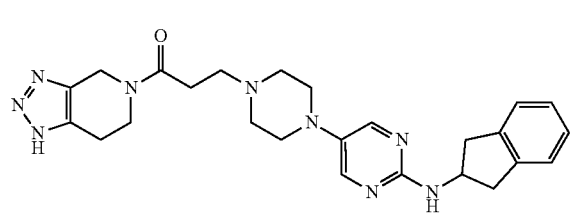
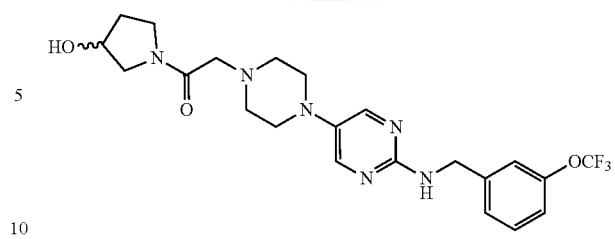
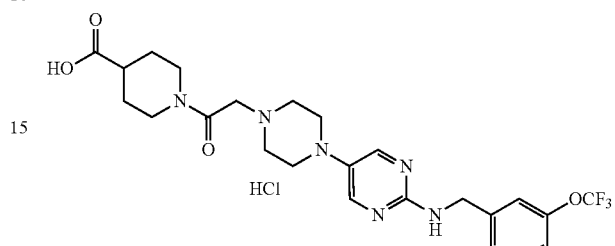
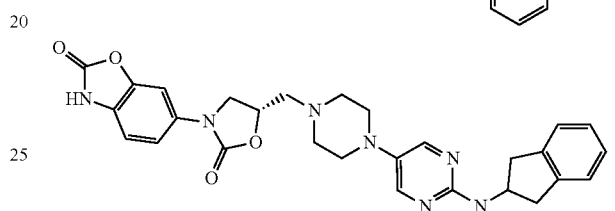
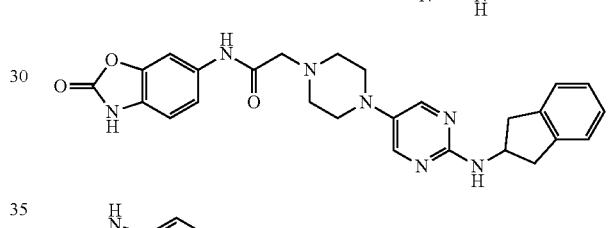
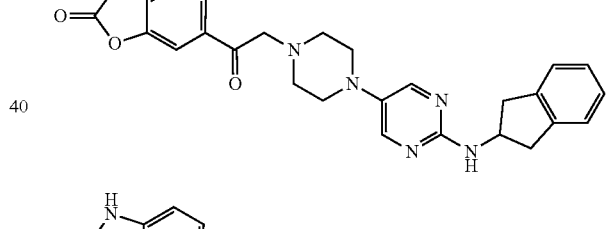
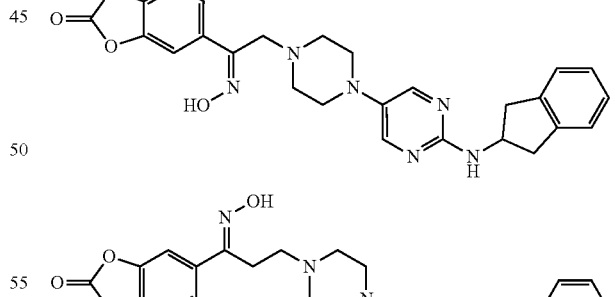
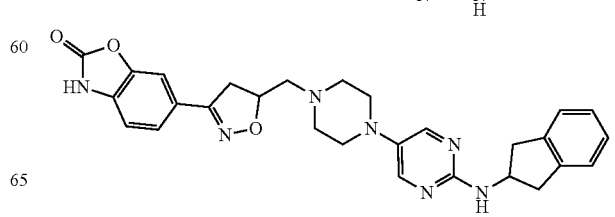

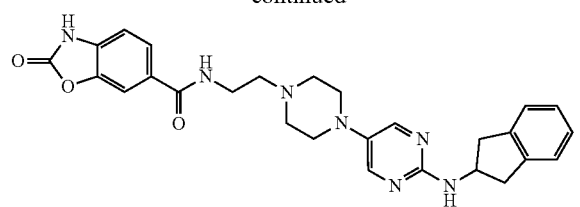
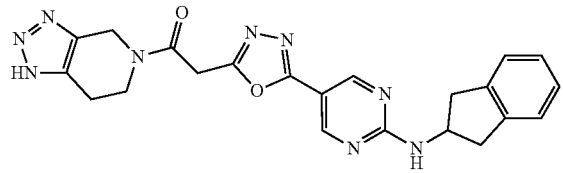
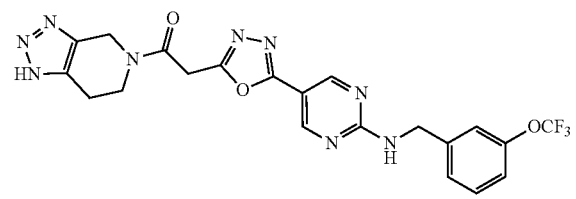
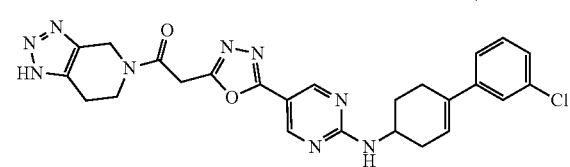
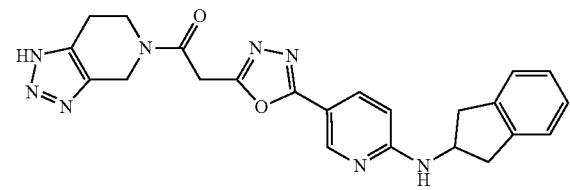
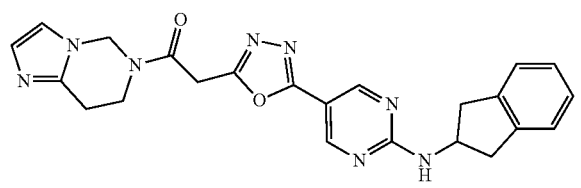
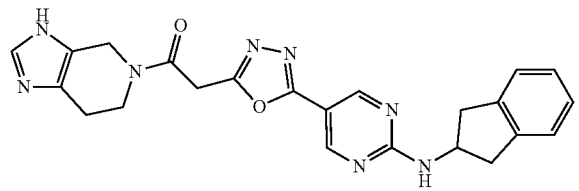
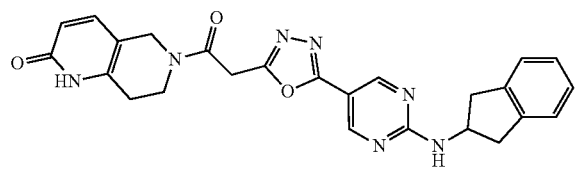
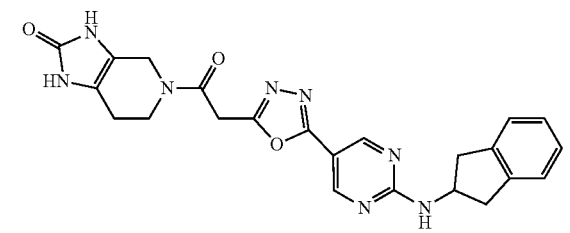
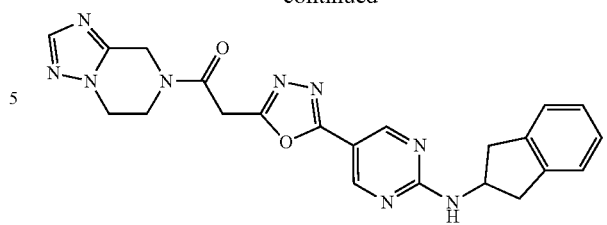
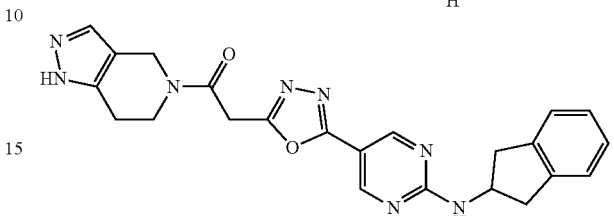
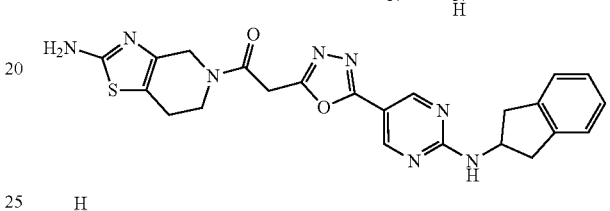
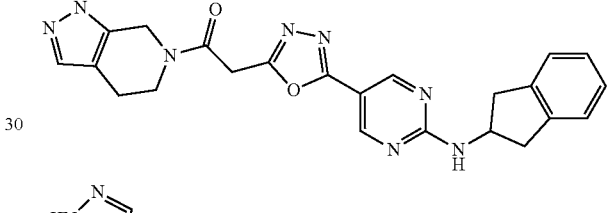

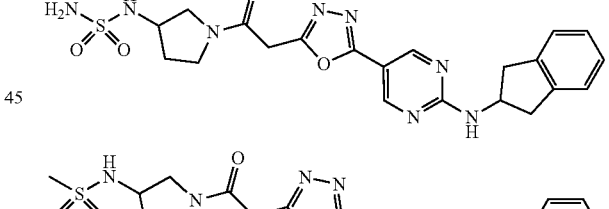
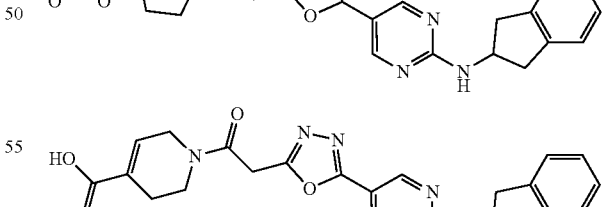
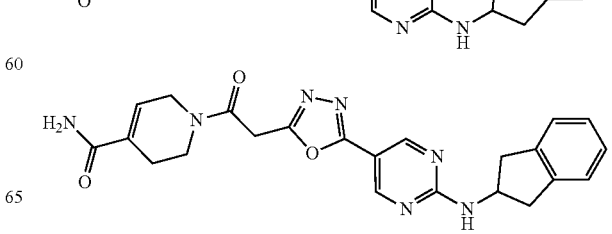

-continued
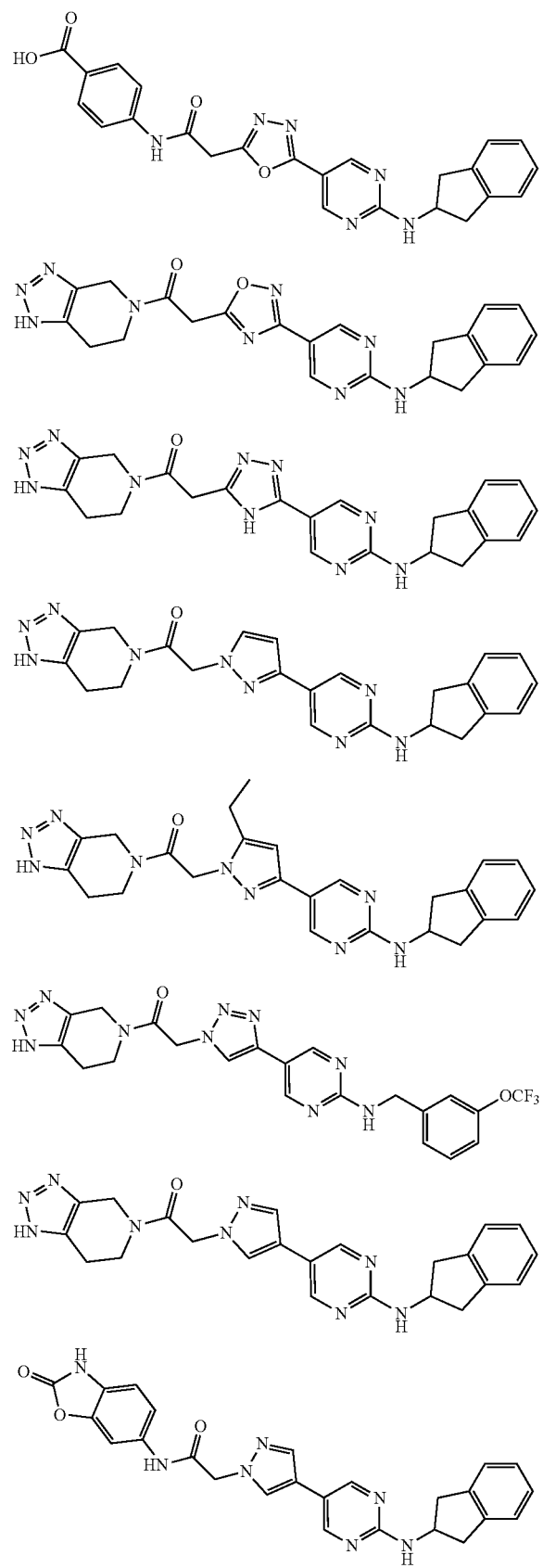
-continued
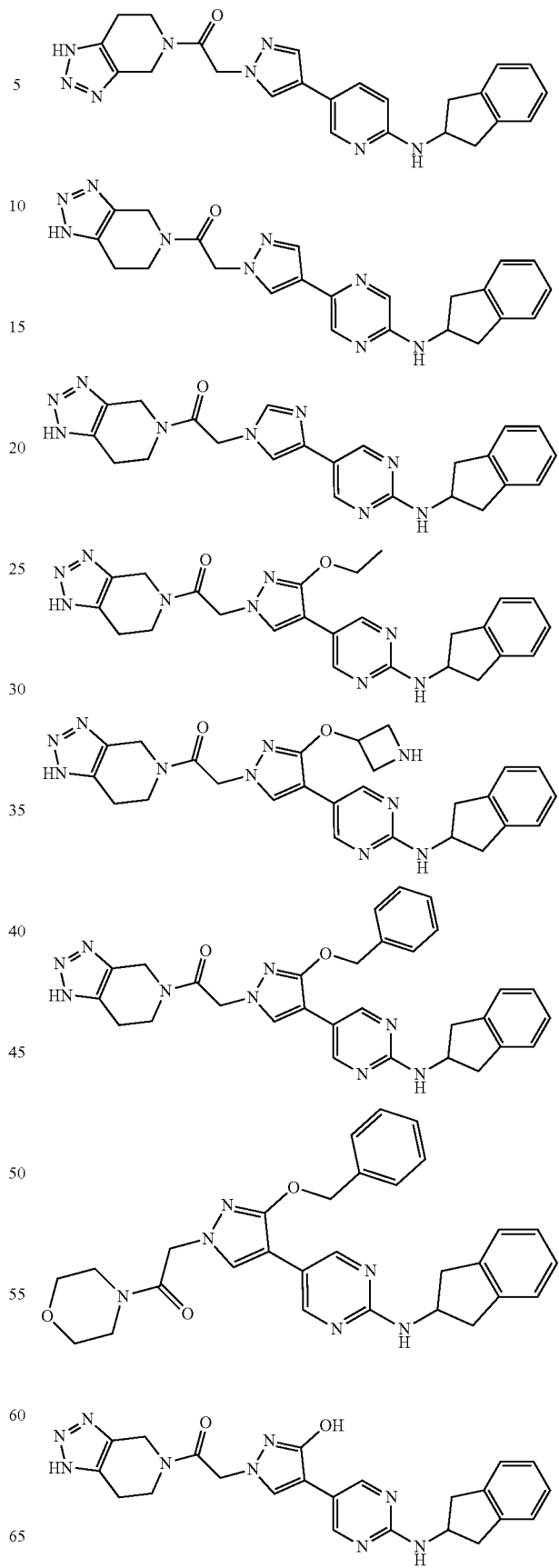

31
-continued
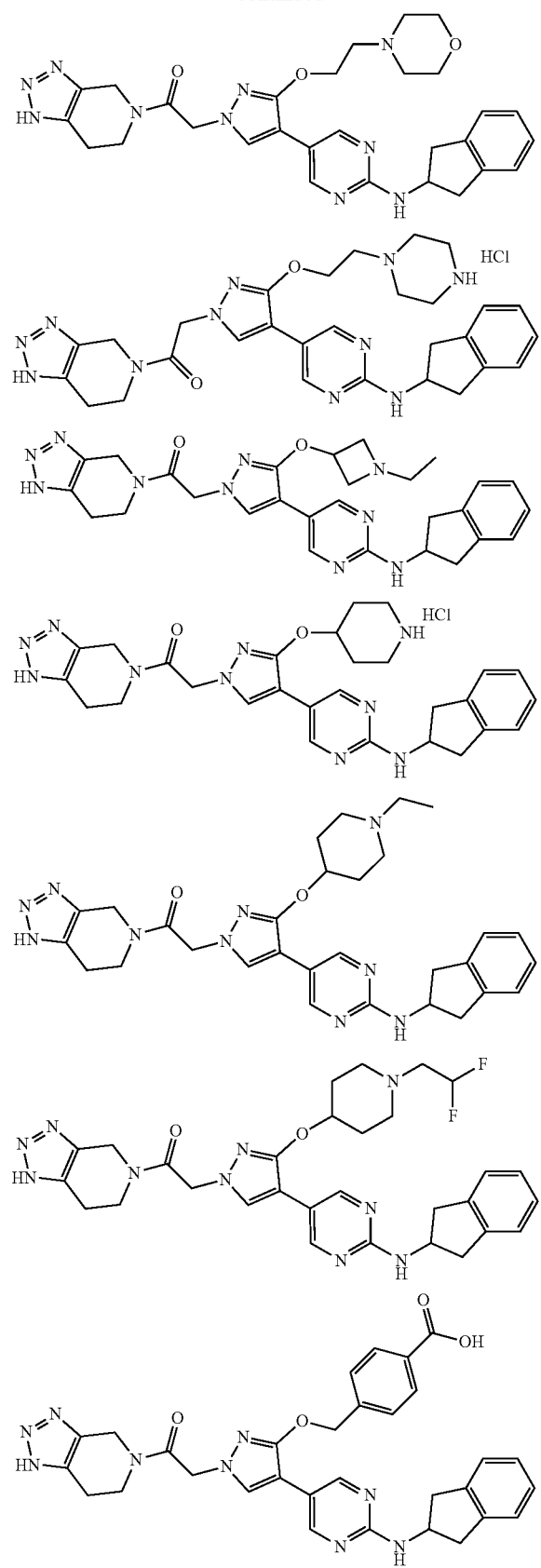
32
-continued
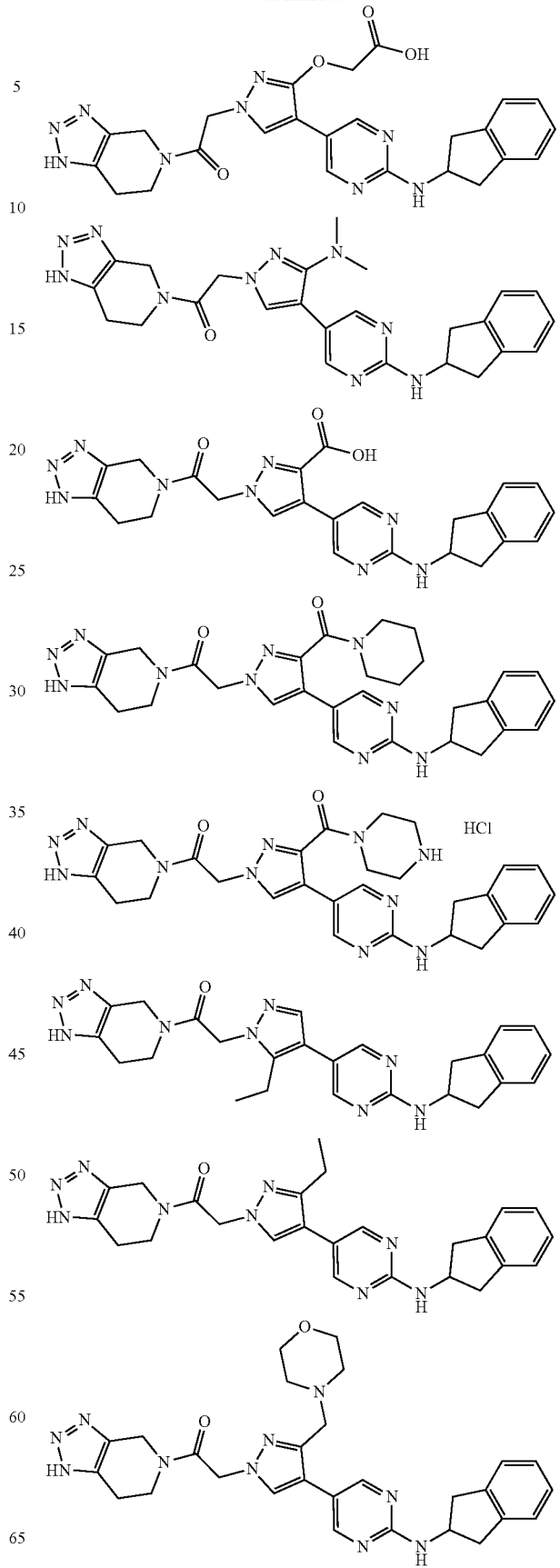

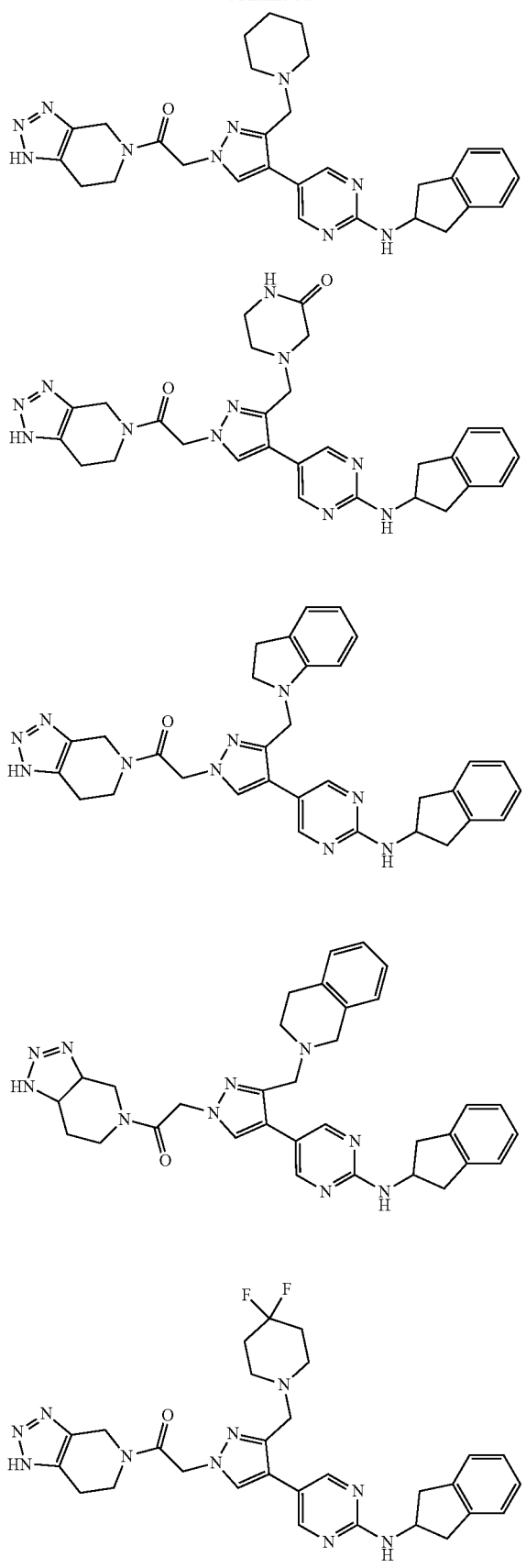
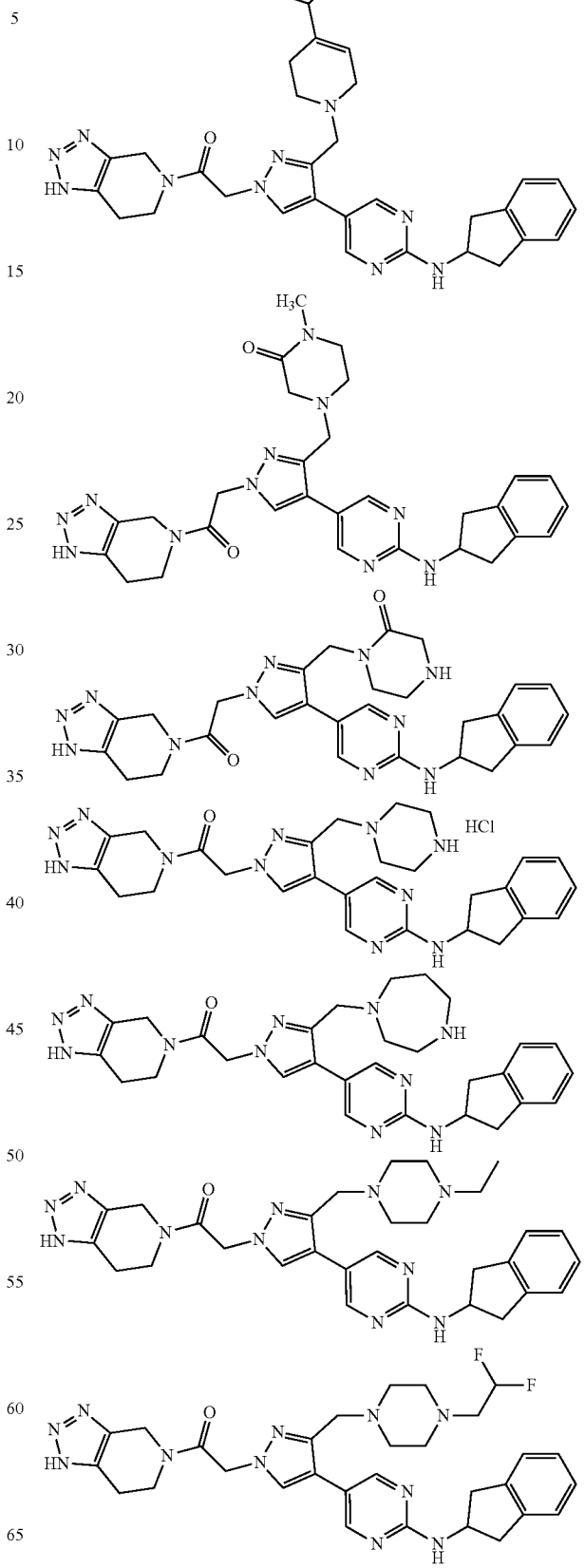

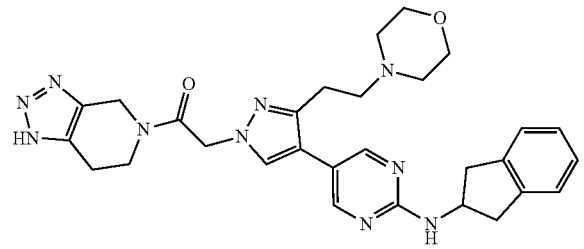
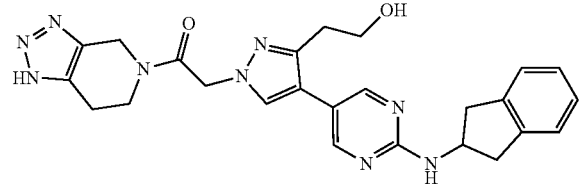
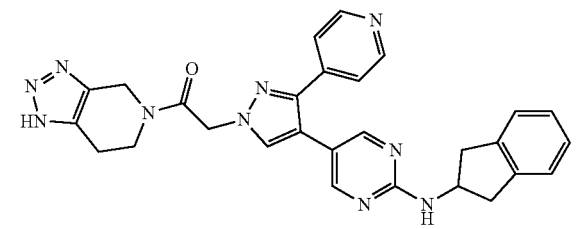
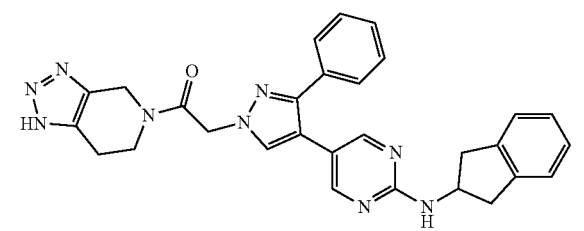
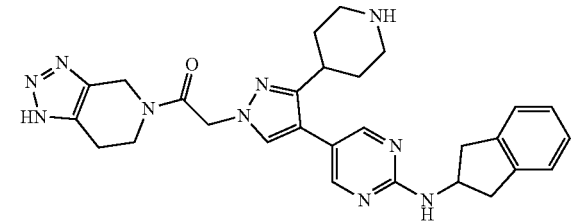
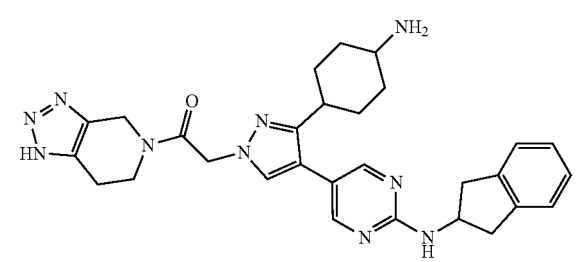
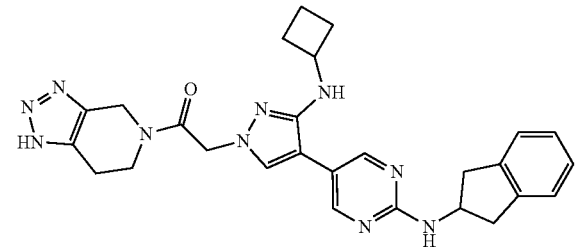
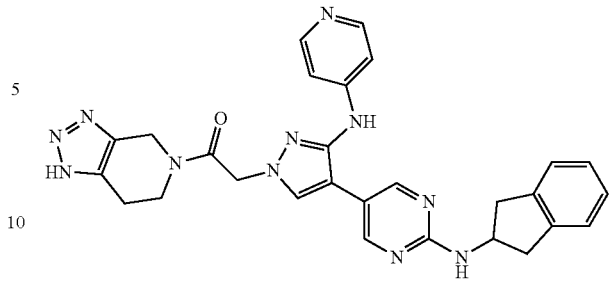

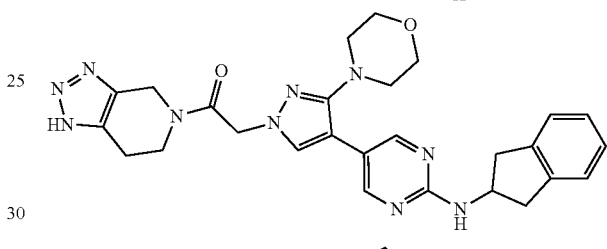
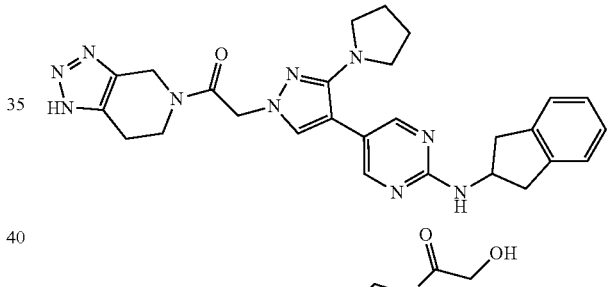
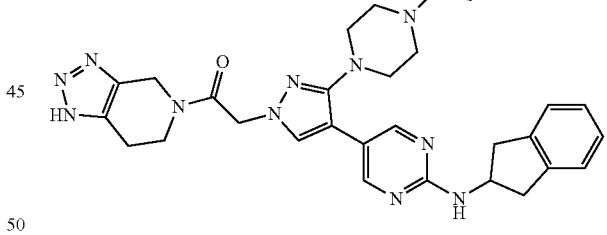
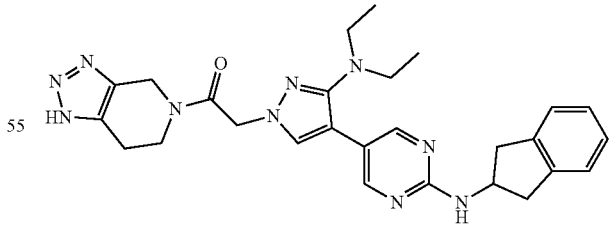
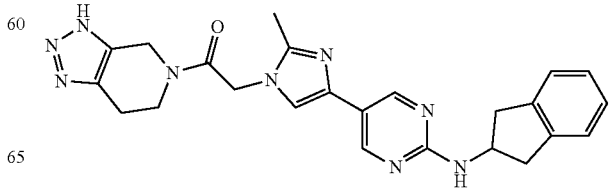

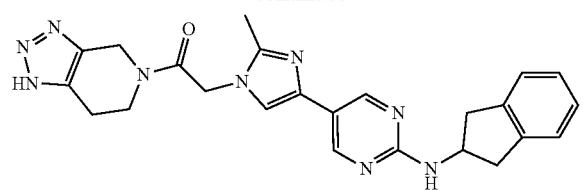
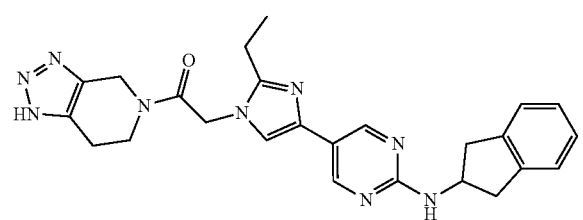
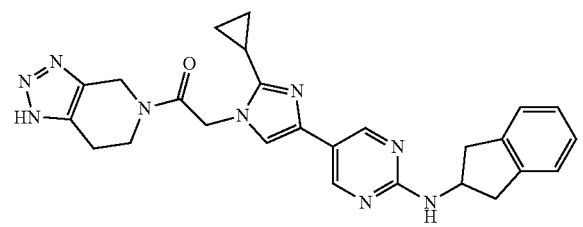
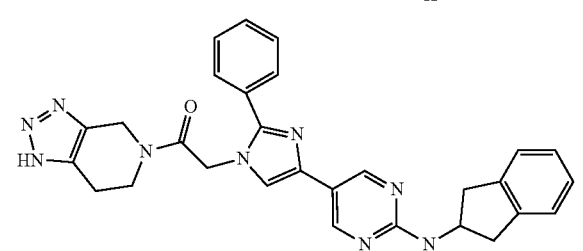
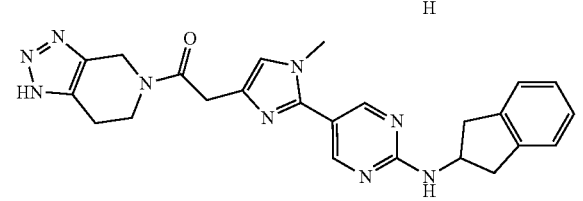
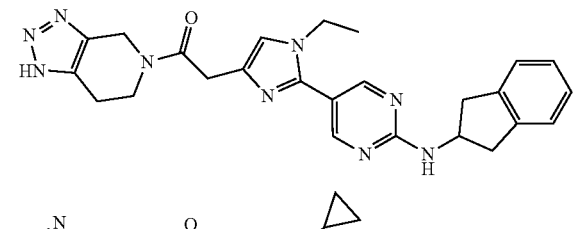
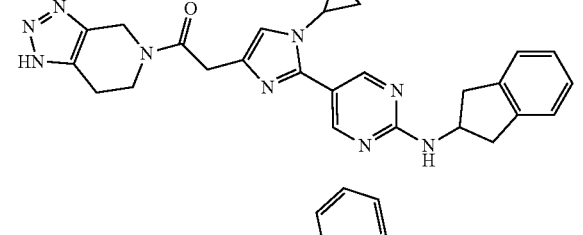
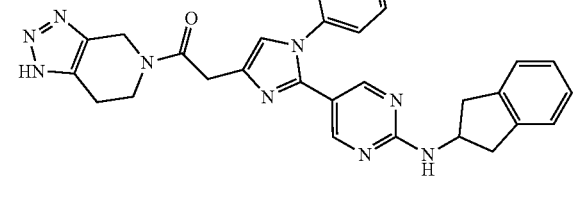
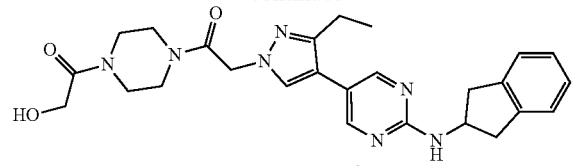
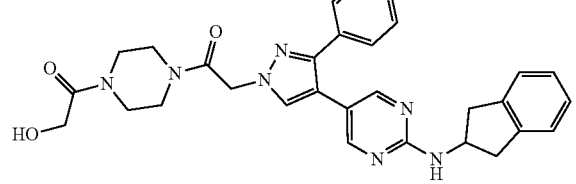
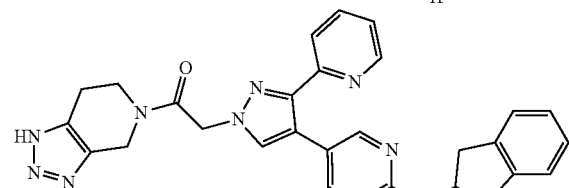
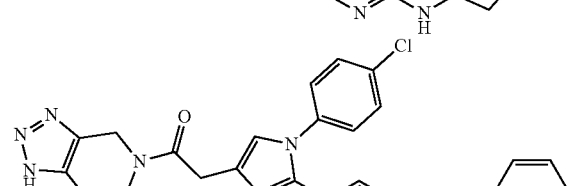
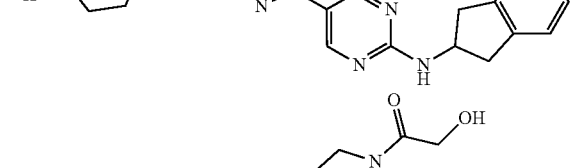
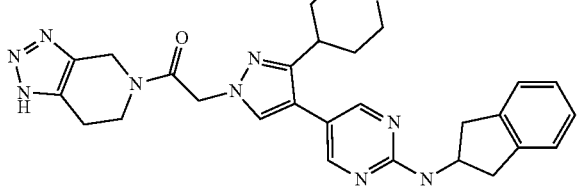
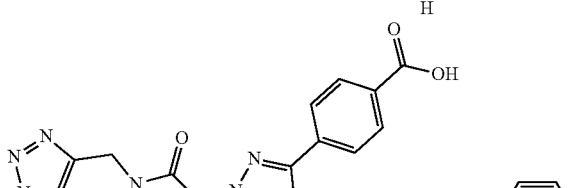
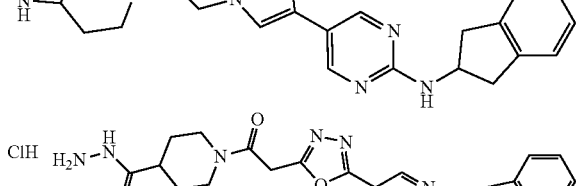
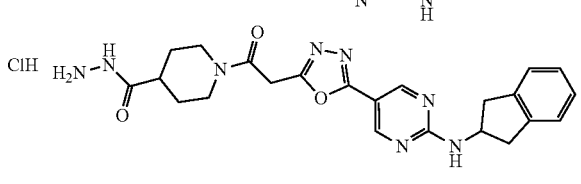
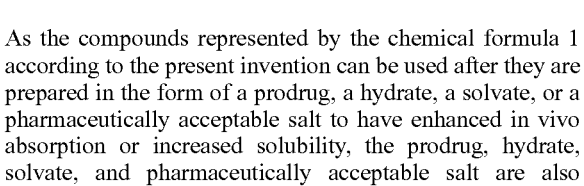
As the compounds represented by the chemical formula 1 according to the present invention can be used after they are prepared in the form of a prodrug, a hydrate, a solvate, or a pharmaceutically acceptable salt to have enhanced in vivo absorption or increased solubility, the prodrug, hydrate, solvate, and pharmaceutically acceptable salt are also encompassed within the scope of the present invention. Furthermore, as the compounds represented by the chemical formula 1 can have a chiral carbon, stereoisomers thereof are also present and those stereoisomers are also encompassed within the scope of the present invention.

In the compounds of generic formula 1, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula 1. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula 1 can be prepared without undue experimentation by conventional techniques well known to those skilled in the art or by processes analogous to those described in the Schemes and Examples herein using appropriate isotopically-enriched reagents and/or intermediates.

As would be recognized by one of ordinary skill in the art, certain of the compounds of the present invention can exist as tautomers. For the purposes of the present invention a reference to a compound of formula 1 is a reference to the compound per se, or to any one of its tautomers per se, or to mixtures of two or more tautomers.

The present invention also provides a method for producing the compounds of the chemical formula 1.

As a method for producing the compounds of the chemical formula 1, the reaction schemes 1 to 11 are exemplified, but the method for producing the compounds of the chemical formula 1 according to the present invention is not limited by the following production methods. The following reaction schemes 1 to 11 are only exemplifications, and it is evident that, depending on a specific substituent, they can be easily modified by a person skilled in the pertinent art.

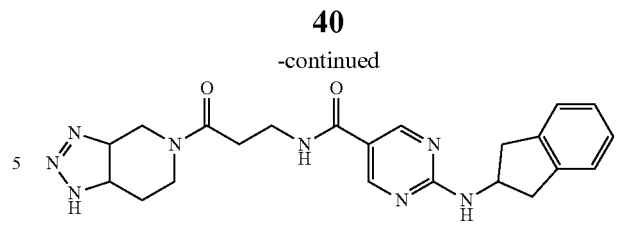

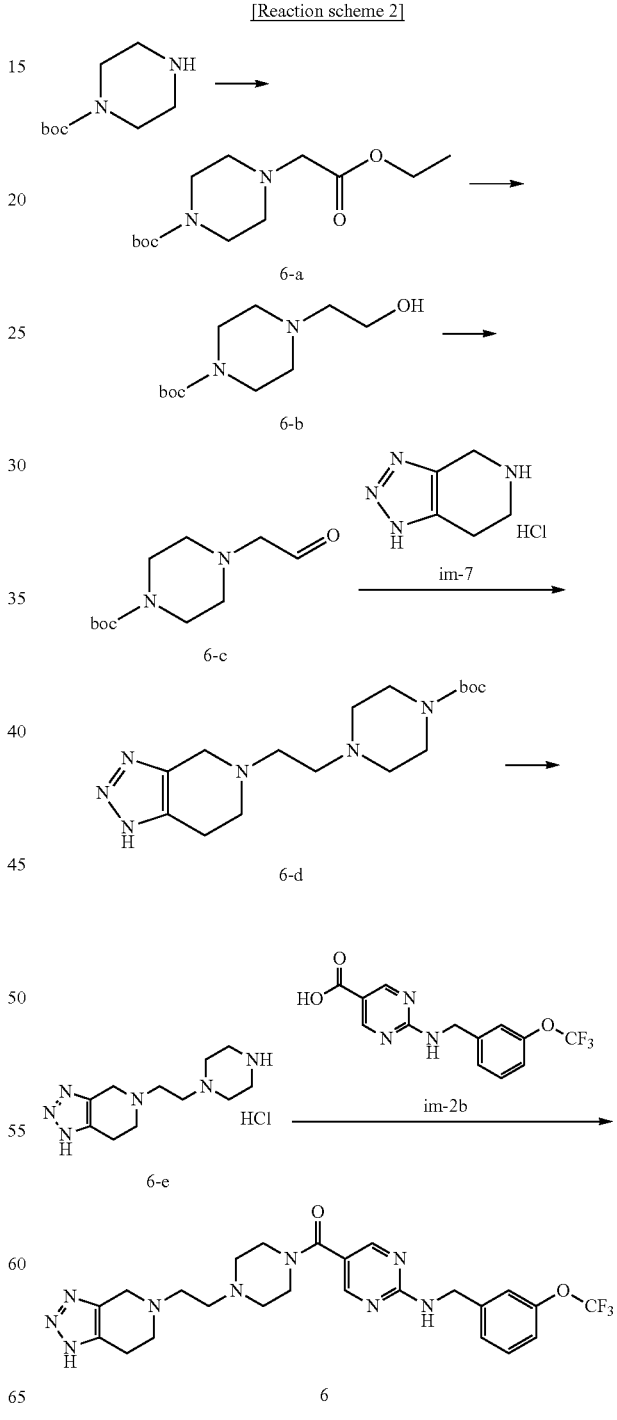

[Reaction scheme 3]
[Reaction scheme 5]
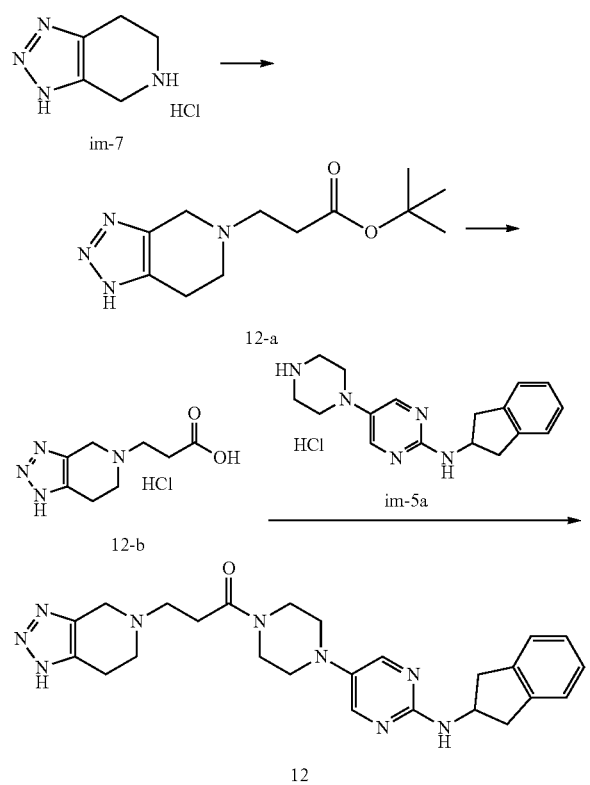
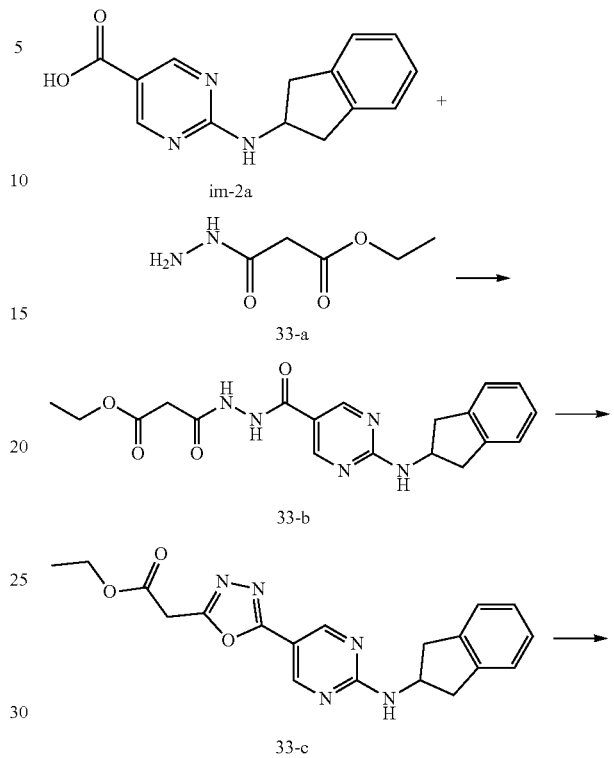
[Reaction scheme 4]
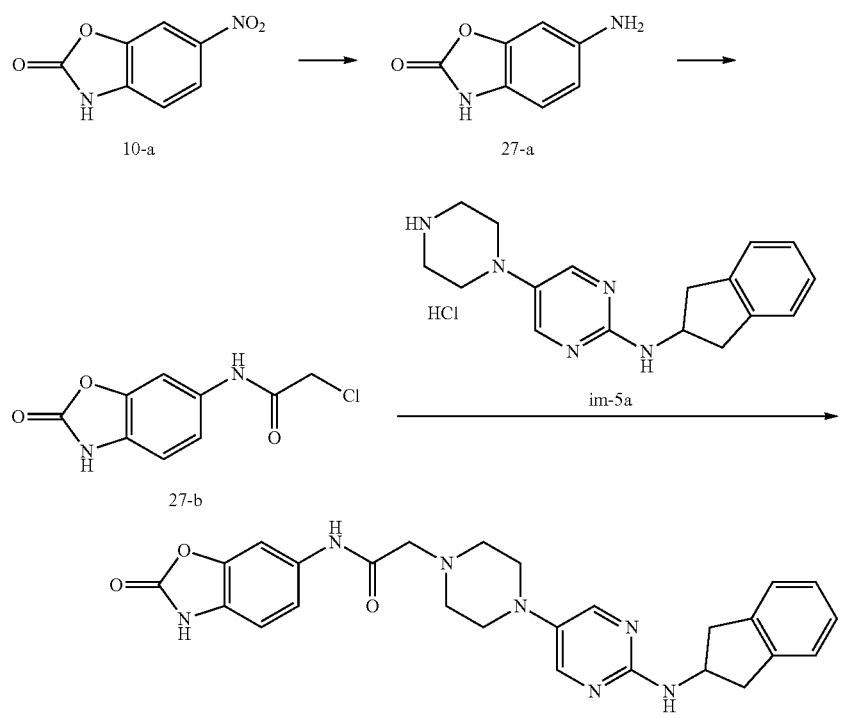

[Reaction scheme 7]
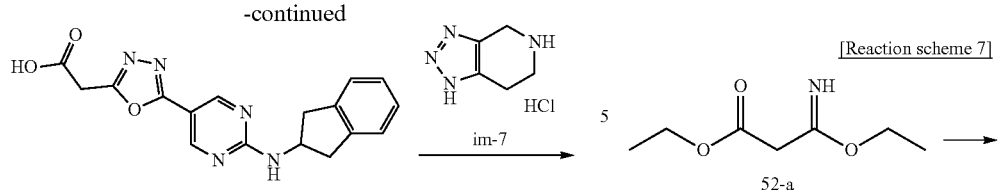
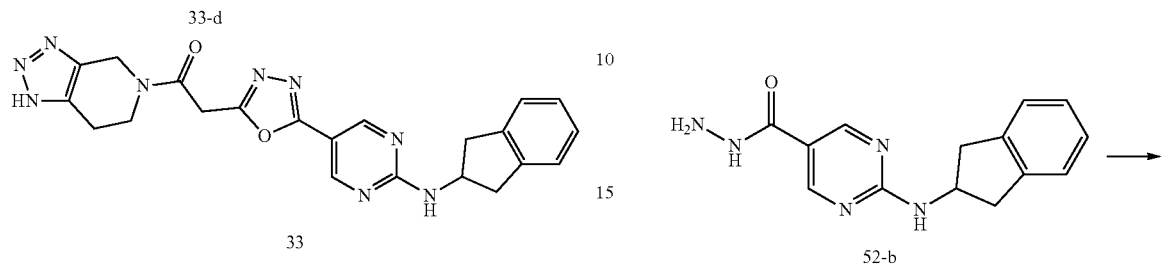
[Reaction scheme 6]
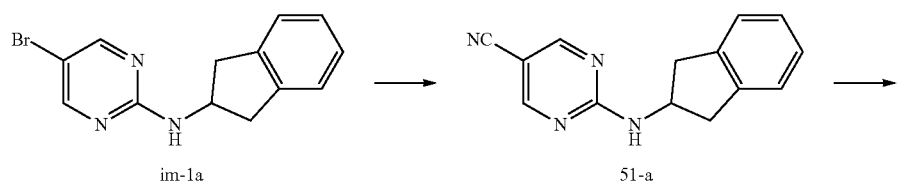
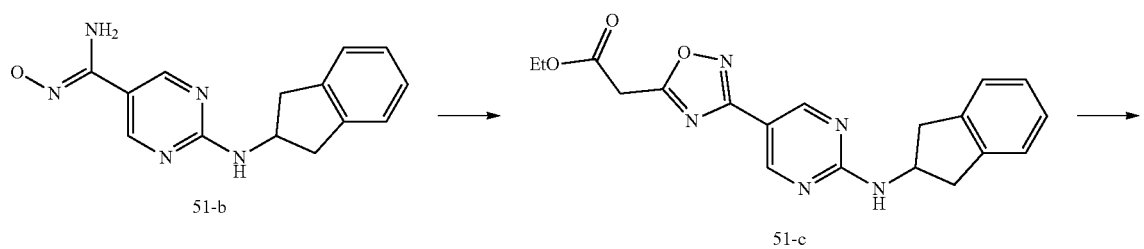
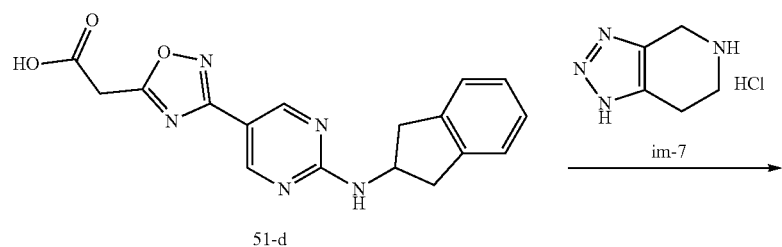
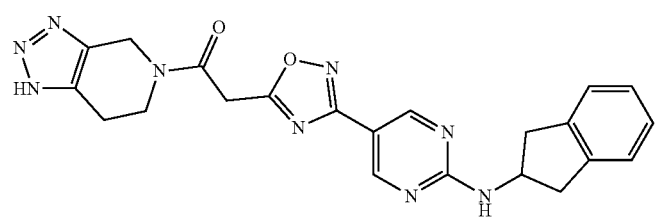

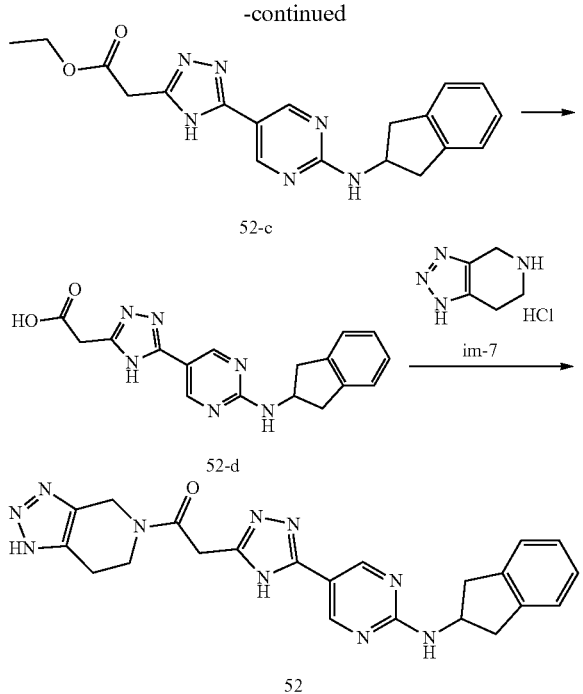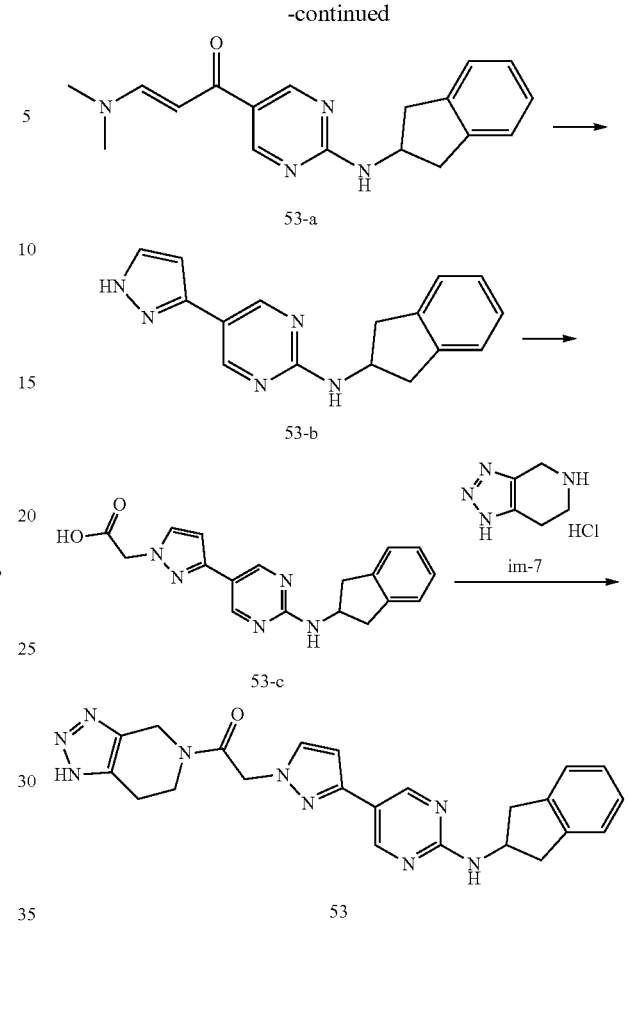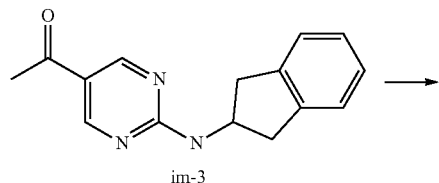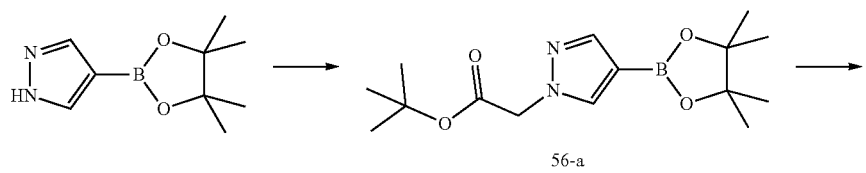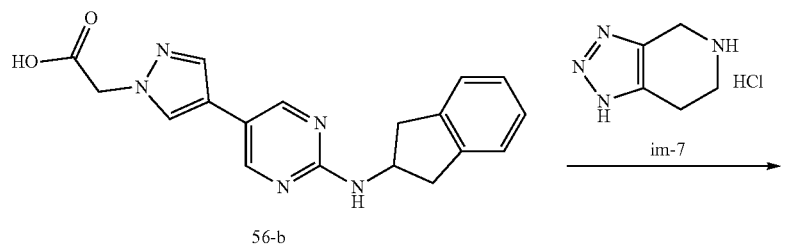

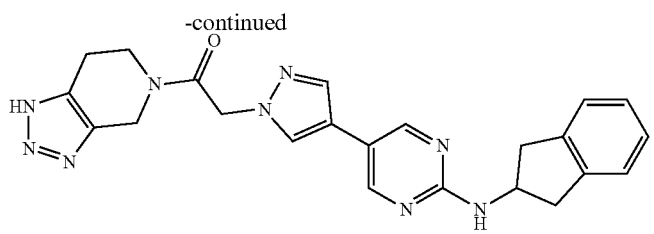
56
[Reaction scheme 10]
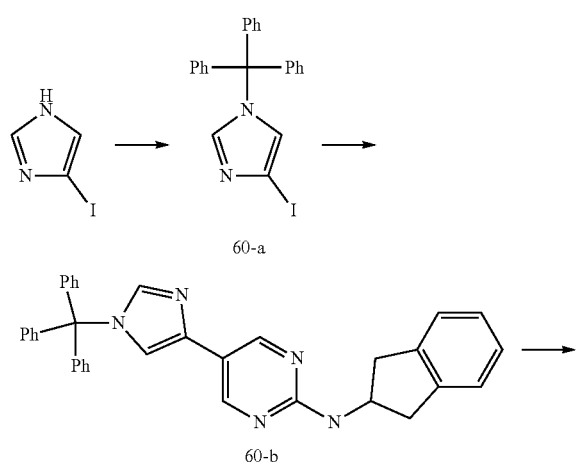
[Reaction scheme 11]
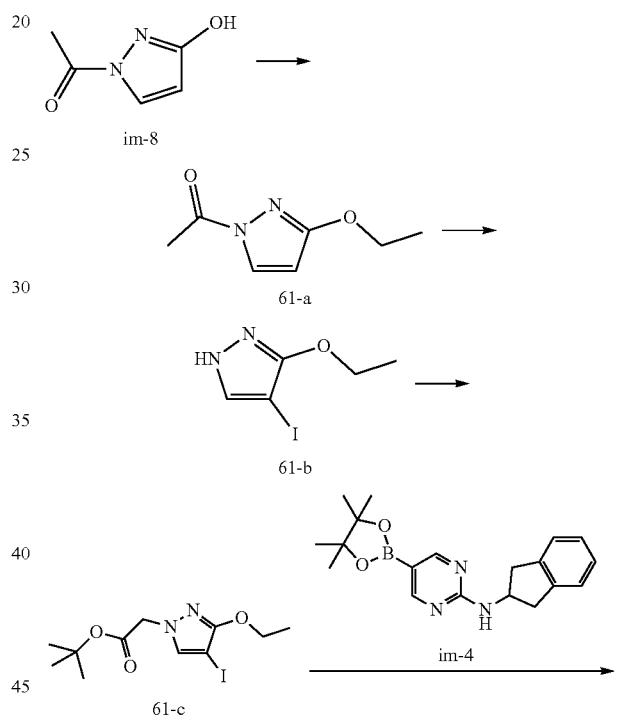

-continued

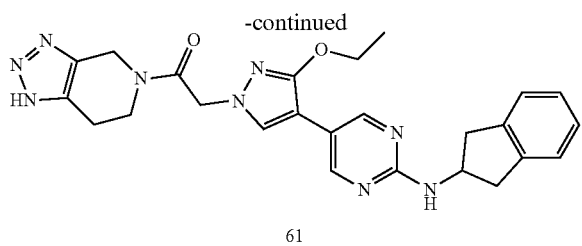

61

As a result of biochemical and pharmacological tests, the compounds of the chemical formula 1 according to the present invention are found to exhibit an excellent inhibiting activity on ATX and also simultaneously lower the LPA concentration, and thus they can exhibit a therapeutic and prophylactic effect for conditions or a disorder caused by ATX activation or increased LPA concentration.

The term "pharmaceutically acceptable salt" means a salt of a compound that does not cause severe irritation to an organism into which the compound is administered and does not deteriorate biological activity and physical properties of the compound. The terms "hydrate," "solvate," "isomer," and "prodrug" also mean the same as defined here. The pharmaceutically acceptable salt includes pharmaceutically acceptable, anion-containing, non-toxic acid addition salts formed by acids, for example, inorganic acids such as hydrochloric acid, sulfuric acid, nitric acid, phosphoric acid, hydrobromic acid, hydriodic acid, and the like, organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and the like, and sulfonic acids such as methane sulfonic acid, ethane sulfonic acid, benzene sulfonic acid, p-toluene sulfonic acid, and the like. Examples of the pharmaceutically acceptable salt for a carboxylic acid include metallic salts or alkaline earth metal salts of lithium, sodium, potassium, calcium, magnesium, and the like, amino acid salts such as lysine, arginine, guanidine, and the like, and organic salts such as dicyclohexylamine, N-methyl-D-glucamine, tris(hydroxymethyl)methylamine, diethanolamine, choline, triethylamine, and the like. The compound of the chemical formula 1 may be converted into a salt thereof by using a conventional method.

The term "hydrate" refers to the compound according to the present invention or a salt thereof that contains stoichiometric or non-stoichiometric amount of water bound thereto by non-covalent intermolecular force.

The term "solvate" refers to the compound according to the present invention or a salt thereof that contains stoichiometric or non-stoichiometric amount of solvent bound thereto by non-covalent intermolecular force. In this regard, preferable solvents may be volatile solvents, nontoxic solvents, and/or solvents that are suitable for administration to humans.

The term "isomer" refers to the compound according to the present invention or a salt thereof which has the same chemical or molecular formula but is structurally or stereochemically different. Such isomers include structural isomers such as tautomers and the like, R or S isomers having an asymmetric carbon center, and stereoisomers such as geometric isomers (trans and cis) and the like. All the isomers and mixtures thereof are also encompassed within the scope of the present invention.

The term "prodrug" refers to a substance that is converted into a parent drug in a living organism. In some cases, prodrugs are often used because of easier administration than parent drugs. For example, prodrugs have bioavailability when orally administered, whereas parent drugs may not. In addition, a prodrug may have improved solubility in a pharmaceutical composition when compared to a parent drug. For example, in a living organism, the prodrug may be a hydrolyzable ester of the compound according to the present invention or a pharmaceutically acceptable salt thereof. As another example, the prodrug may be a short peptide (polyamino acid) with an acid group linked thereto that is metabolized such that the peptide exposes an active site.

Other terms as used herein may be interpreted as commonly understood in the pertinent art to which the present invention pertains.

Various types of prodrugs are known in the pertinent art, and reference can be made to the following literatures, for example: a) Literature [Design of Prodrugs, edited by H. Bundgaard, (Elsevier, 1985) and Methods in Enzymology, Vol. 42, p. 309-396, edited by K. Widder, et al. (Academic press, 1985)]; b) Literature [A Textbook of Drug Design and Development, edited by Krogsgaard-Larsen and H. Bundgaard, Chapter 5 "Design and Application of Prodrugs", by H. Bundgaard p. 113-191 (1991)]; c) Literature [H. Bundgaard, Advanced Drug Delivery Reviews, 8, 1-38 (1992)]; d) Literature [H. Bundgaard, et al., Journal of Pharmaceutical Sciences, 77, 285 (1988)]; and e) Literature [N. Kakeya, et al., Chem Pharm Bull, 32, 692 (1984)].

Such prodrug is mainly used when solubility is relatively low or absorptivity is low. Conversion into prodrugs may lead to improvement of absorption, distribution, metabolism and excretion (ADME) and PK profile, in addition to increase in solubility and absorption.

Furthermore, the present invention provides an ATX inhibitor composition containing, as an effective ingredient, the compound of the above chemical formula 1, or a prodrug thereof, a hydrate thereof, a solvate thereof, an isomer thereof, or a pharmaceutically acceptable salt thereof.

Furthermore, the present invention provides a pharmaceutical composition for prophylaxis or treatment of a disorder related to autotoxin activity containing, as an effective ingredient, the compound of the above chemical formula 1, or a prodrug thereof, a hydrate thereof, a solvate thereof, an isomer thereof, or a pharmaceutically acceptable salt thereof, and also containing additionally a pharmaceutically acceptable carrier, a diluent, an excipient, or a combination thereof.

As described above, the compound of the above chemical formula 1, a prodrug thereof, a solvate thereof, a stereoisomer thereof, or a pharmaceutically acceptable salt thereof exhibits a very high inhibiting activity on ATX and also inhibits simultaneously the LPA production, and thus the pharmaceutical composition containing them as an effective ingredient can be used, without any side effects, as an efficient therapeutic agent and a prophylactic agent for a disorder mediated by ATX, for example, kidney disorder, liver disorder, inflammatory disorder, nervous system disorder, respiratory system disorder, vascular and cardiovascular disorder, fibrotic disease, cancer, ocular disorder, metabolic conditions, cholestatic and other forms of chronic pruritus, or acute or chronic organ transplant rejection.

Cardiovascular disorder includes, but not limited thereto, acute coronary syndrome, coronary heart disease, myocardial infarction, arterial and pulmonary hypertension, cardiac arrhythmia such as atrial fibrillation, stroke and other vascular damage.

Cancer includes, but not limited thereto, breast cancer, ovarian cancer, lung cancer, prostate cancer, mesothelioma, glioma, hepatic carcinoma, and stomach cancer.

Kidney disorder includes, but not limited thereto, acute kidney failure and chronic kidney disease with or without proteinuria (including end stage renal disease (ESRD)). In greater detail, the kidney disorder includes decreased creatinine clearance and decreased glomerular filtration rate, microalbuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

According to one example of the present invention, the kindey disorder is selected from a group consisting of acute kidney failure, chronic kidney disease, diabetic nephropathy, acute kidney transplant rejection, and chronic allograft nephropathy.

Liver disorder includes, but not limited thereto, liver cirrhosis, hepatic congestion, cholestatic liver disease including pruritus, nonalcoholic steatohepatitis and acute and chronic liver transplant rejection.

According to one example of the present invention, the liver disorder is acute and chronic liver transplant rejection.

Inflammatory disorder includes, but not limited thereto, atopic dermatitis, arthritis, osteoarthritis, multiple sclerosis, systemic lupus erythematodes as well as inflammatory airway diseases such as idiopathic pulmonary fibrosis (IPF), chronic obstructive pulmonary disease (COPD), or chronic asthma bronchiale.

According to one example of the present invention, the inflammatory disorder is selected from arthritis, atopic dermatitis, and asthma.

Disorder of the nervous system includes, but not limited thereto, neuropathic pain, schizophrenia, neuro-inflammation (e.g. astrogliosis), peripheral and/or autonomic (diabetic) neuropathies and the like.

According to one example of the present invention, the disorder of the nervous system is neuropathic pain.

Respiratory system disorder includes, but not limited thereto, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Fibrotic disease includes, but not limited thereto, myocardial and vascular fibrosis, kidney fibrosis, liver fibrosis, pulmonary fibrosis, skin fibrosis, scleroderma and encapsulating peritonitis. Furthermore, the fibrotic disease is renal tubulo-interstitial fibrosis or glomerulosclerosis, or non-alcoholic liver steatosis, liver fibrosis, liver cirrhosis, or idiopathic pulmonary fibrosis.

According to one example of the present invention, the fibrotic disease is selected from encapsulating peritonitis, idiopathic pulmonary fibrosis. is non-alcoholic liver steatosis, liver fibrosis, and liver cirrhosis.

Ocular disorder includes, but not limited thereto, proliferative and non-proliferative (diabetic) retinopathy, dry and wet age-related macular degeneration (AND), macular edema, central arterial/venous occlusion, traumatic injury, glaucoma and the like.

The term "pharmaceutical composition" means a mixture of the compound according to the present invention and other chemical components such as a diluent or a carrier. The pharmaceutical composition facilitates administration of the compound to a living organism. Various techniques are present for the administration of the compounds. Examples of the various administration techniques include, but not limited thereto, oral administration, injection, aerosol administration, parenteral administration, and local administration. The pharmaceutical composition may be obtained through a reaction with an acid such as hydrochloric acid, bromic acid, sulfuric acid, nitric acid, phosphoric acid, methanesulfonic acid, p-toluenesulfonic acid, salicylic acid, or the like.

The term "therapeutically effective amount" means an effective amount of an active ingredient of a compound for administration to alleviate or reduce one or more symptoms of disorders treated by the composition or to delay initiation of clinical markers or symptoms of diseases needed for prevention. Thus, the therapeutically effective amount means an amount that has the effect of: (1) reversing progression rate of disorders, (2) inhibiting further progression of disorders to some extent, and/or (3) alleviating (preferably, eliminating) one or more symptoms related to disorders to some extent. The therapeutically effective amount may be experimentally determined through experiment of a compound in a known in vivo and in vitro model system for disorders needed for treatment.

The term "carrier" is defined as a compound that facilitates delivery of a compound into cells or tissues. For example, dimethyl sulfoxide (DMSO) is a commonly used carrier that facilitates introduction of many organic compounds into cells or tissues of a living organism.

The term "diluent" is defined as a compound that stabilizes a biologically active form of a target compound and is diluted in water used for dissolving the compound. Salts dissolved in buffer solutions are used as diluents in the art. A commonly used buffer solution is phosphate buffered saline because it mimics the salt state of a human solution. Buffer salts can control pH of a solution at low concentrations and thus a buffered diluent rarely modifies the biological activity of a compound.

The compounds used herein may be administered alone to a patient, or be administered to a patient as a pharmaceutical composition prepared by mixing the compound with other active ingredients or with an appropriate carrier or excipient as in combination therapy. Techniques for formulation and administration of the compound of the present application can be found in "Remington's Pharmaceutical Sciences," Mack Publishing Co., Easton, Pa., 18$^{th}$ edition, 1990.

The pharmaceutical composition of the present invention may be prepared in a known manner by methods such as conventional mixing, dissolution, granulation, dragee making, levigating, emulsification, encapsulation, trapping, or lyophilization.

Accordingly, pharmaceutical compositions for use in accordance with the present invention may be prepared in a conventional manner using one or more pharmaceutically acceptable carriers including excipients or auxiliary agents which facilitate processing of active compounds into formulations for pharmaceutical use. Proper formulation is dependent upon route of administration selected. Any suitable well-known techniques, carriers, and excipients may be used as understood in the pertinent art, e.g., Remington's Pharmaceutical Sciences described above. The compound of the chemical formula 1 according to the present invention may be formulated into a preparation for injection, a preparation for oral administration, or the like according to intended application.

For injection, the ingredients of the present invention may be formulated with a liquid solution, preferably with a physiologically acceptable buffer such as Hank's solution, Ringer's solution, or physiological saline buffer. For transmucosal administration, non-invasive agents suitable for a barrier through which the ingredients pass are used in formulation. Such non-invasive agents are generally known in the pertinent art.

For oral administration, the compounds may be formulated by combining active compounds with therapeutically acceptable carriers known in the pertinent art. Such carriers enable the compounds of the present invention to be formulated as tablets, pills, powders, granules, dragees, capsules, liquids, gels, syrups, slurries, suspensions, and the like. Capsules, tablets, pills, powders, and granules are preferable and, in particular, capsules and tablets may be used. Tablets and pills may be preferably prepared with enteric coatings. Pharmaceutical preparations for oral use may be obtained by mixing one or more excipients with one or more compounds of the invention, optionally grinding the resulting mixture, and processing the mixture of granules, after adding suitable auxiliary agents, if desired, to obtain tablets or dragee cores. Suitable excipients include, in particular, fillers such as lactose, sucrose, mannitol, or sorbitol; cellulose-based materials such as corn starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, disintegrating agents such as cross-linked polyvinyl pyrrolidone, agar, or alginic acid or a salt thereof such as sodium alginate, lubricants such as magnesium stearate, and carriers such as binders and the like may be added.

Pharmaceutical preparations which can be orally administered include push-fit capsules made of gelatin, as well as soft, sealed capsules made of gelatin and a plasticizer, such as glycol or sorbitol. The push-fit capsules may contain active ingredients in admixture with a filler such as lactose, a binder such as starch, and/or a lubricant such as talc or magnesium stearate. In soft capsules, the active compounds may be dissolved or dispersed in suitable liquids, such as fatty oils, liquid paraffin, or liquid polyethylene glycol. In addition, stabilizers may be included. All formulations for oral administration should be in dosages that are suitable for such administration.

The compounds may be formulated for parenteral administration by injection, e.g., by bolus injection or continuous infusion. Formulations for injection may be provided in unit dosage form, e.g., in ampoules or in multi-dose containers, with an added preservative. The compositions may take such forms as suspensions, solutions or emulsions in oily or aqueous vehicles, and may contain agents for formulation such as suspending agent, stabilizing agent, and/or dispersing agent.

In addition, they may be in the form of dried powder that is used after being dissolved in sterile pyrogen-free water.

The compounds may be formulated as suppositories including conventional suppository bases such as cacao butter or other glycerides, or as compositions for rectal administration, such as retention enema.

Pharmaceutical compositions that are suitable for use in the present invention include compositions in which the active ingredients are contained in an amount effective to achieve its intended purpose. More specifically, a therapeutically effective amount means an amount of compound effective to extend the survival of a subject to be treated or to prevent, alleviate or ameliorate symptoms of disorders. Determination of the therapeutically effective amount may be within the capacity of one of ordinary skill in the pertinent art, in particular, in terms of the detailed description provided herein.

When formulated in a unit dosage form, the compound of the chemical formula 1 as an active ingredient is preferably contained in a unit dosage of approximately 0.1 to 1,000 mg. The dose of the compound of the chemical formula 1 is determined in accordance with the prescription of doctors depending upon factors, such as body weights and ages of patients and particular properties and severity of diseases. However, the dose required for treatment of adults may be administered once to three times per day depending on frequency and intensity of administration and a dose thereof per administration is generally in the range of about 1 to about 1,000 mg. When administered to an adult either intramuscularly or intravenously, the administration can be separately made once to three times per day and it would be sufficient that a single dose thereof is about 1 to about 1,000 mg in general. However, for some patients, a higher daily dose may be preferable.

The pharmaceutical composition of the present invention inhibits the activity of ATX. According to the present invention, the compounds of the above chemical formula 1 can inhibit the activity of ATX, which is a basic regulator for the conversion of LPC to LPA.

A method of treating a disease or disorder in a subject in need thereof, comprising administering to the subject a therapeutically effective amount of the compound of the present invention, or a pharmaceutically acceptable salt thereof.

A method of treating idiopathic pulmonary fibrosis (IPF) in a subject in need thereof, comprising administering to the subject a therapeutically effective amount of any one of the compound of the present invention, or a pharmaceutically acceptable salt thereof.

A method of treating a disease or disorder in a subject in need thereof, comprising administering to the subject a therapeutically effective amount of any one of the compound of the present invention, or a pharmaceutically acceptable salt thereof.

A method of inhibiting autotaxin in a subject in need thereof, comprising administering to the subject an effective amount of any one of the compound of the present invention, or a pharmaceutically acceptable salt thereof.

The subject is a human subject.

Hereinbelow, the present invention is described in greater detail with reference to preferred examples. However, those examples are provided only for exemplification of the present invention and should not be construed as limiting the scope of the present invention in any sense, and the scope of the present invention is defined only by the claims that will be described later.

[Preparation Example 1-1] Preparation of 5-bromo-N-(2,3-dihydro-1H-inden-2-yl)pyrimidin-2-amine (Compound im-1a)

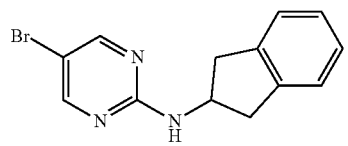

im-1a

5-Bromo-2-chloropyrimidine (2.0 g, 10.3 mmol), 2-aminoindane (1.6 mL, 12.4 mmol), and N,N-diisopropylethylamine (4.5 mL, 25.8 mmol) were dissolved in ethanol (10 mL) and stirred at 90° C. for 2 hours. Upon the completion of the reaction, the mixture was cooled to room temperature, and the resulting solid was filtered, washed with ethanol (20 mL), and dried to obtain the title compound im-1a as a beige solid (2.2 g, 72%).

MS m/z: 291 [M+1]$^+$ $^1$H NMR (DMSO-d$_6$, 400 MHz), δ ppm: 8.40 (s, 2H), 7.81 (d, 1H), 7.22-7.13 (m, 4H), 4.56-4.51 (m, 1H), 3.23 (dd, 2H), 2.88 (dd, 2H)

[Preparation Example 1-2] Preparation of 5-bromo-N-{[3-(trifluoromethoxy)phenyl]methyl}pyrimidin-2-amine (Compound im-1b)

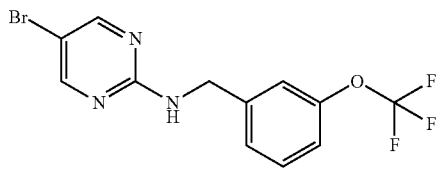

im-1b

Except that 3-trifluoromethoxy benzylamine is used instead of 2-aminoindane, the reaction was carried out in the same manner as Preparation example 1-1 to obtain the title compound im-1b as a light brown liquid.

MS m/z: 349 [M+1]$^+$ $^1$H NMR (DMSO-do, 400 MHz), δ ppm: 8.39 (s, 2H), 8.11 (t, 1H), 7.44 (t, 1H), 7.33 (d, 1H), 7.25 (s, 1H), 7.22 (d, 1H), 4.52 (d, 2H)

[Preparation Example 1-3] Preparation of 5-bromo-N-[4-(3-chlorophenyl)cyclohex-3-en-1-yl]pyrimidine-2-amine (Compound im-1c)

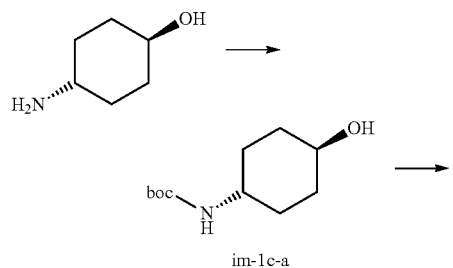

im-1c-a

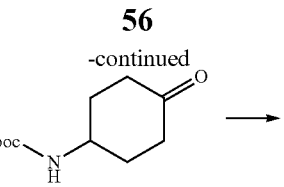

im-1c-b

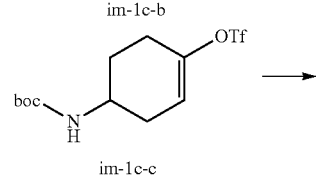

im-1c-c

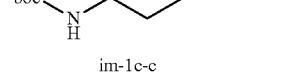

im-1c-d

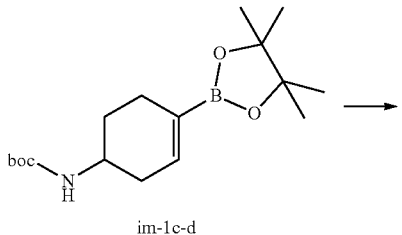

im-1c-e

im-1c-f

im-1c (Step 1) Preparation of tert-butyl N-(4-hydroxycyclohexyl) carbamate (compound im-1c-a)

After dissolving (1R,4R)-4-aminocyclohexan-1-ol (15.0 g, 0.13 mol) in methylene chloride (250 mL), di-tert-butyl dicarbonate (25.6 g, 0.12 mol) diluted in methylene chloride (100 mL) and triethylamine (45.4 mL, 0.33 mol) were slowly added dropwise thereto in order under stirring at 0° C., followed by stirring for 14 hours at room temperature. The reaction mixture was diluted with distilled water (300 mL) and stirred for 10 minutes to terminate the reaction, followed by extraction with methylene chloride. The organic layer was washed with distilled water and saturated brine, dried over anhydrous sodium sulfate, and concentrated to obtain the title compound im-1c-a as a pink solid (24.5 g, 97%).

MS m/z: 216 [M+1]$^+$

¹H NMR (CDCl₃, 400 MHz), δ ppm: 4.35 (br, 1H), 3.61 (m, 1H), 3.42 (m, 1H), 1.99 (t, 4H), 1.48-1.31 (m, 12H), 1.21-1.10 (m, 2H).

(Step 2) Preparation of tert-butyl N-(4-oxocyclohexyl)carbamate (Compound im-1c-b)

To a solution of oxalyl chloride (11.8 mL, 0.14 mol) in methylene chloride (100 mL) at −78° C. dimethyl sulfoxide (19.8 mL, 0.28 mol) diluted in methylene chloride (100 mL) and the compound im-1c-a (20 g, 0.093 mol) diluted in methylene chloride (300 mL) was added dropwise in order under nitrogen stream. After adding additional methylene chloride (300 mL), the reaction mixture was stirred for 1 hour. After dropwise adding triethylamine (64.7 mL, 0.46 mol), the reaction mixture was stirred for 1 hour. After stirring for additional 2 hours while the temperature was gradually increased to room temperature, the reaction was terminated by adding distilled water (100 mL). The reaction mixture was extracted with methylene chloride, and the organic layer was washed with distilled water and saturated brine, dried over anhydrous sodium sulfate, and concentrated. The residue was treated with n-hexane to produce a solid. The solid was filtered and washed with n-hexane to obtain the title compound im-1c-b as a light brown solid quantitatively (20.5 g).

MS m/z: 214 [M+1]⁺
¹H NMR (CDCl₃, 400 MHz), δ ppm: 4.51 (br, 1H), 3.93 (m, 1H), 3.36-2.48 (m, 2H), 2.28-2.21 (m, 2H), 1.72-1.64 (m, 2H), 1.46 (s, 9H).

(Step 3) Preparation of tert-butyl N-[4-(trifluoromethanesulfonyloxy)cyclohex-3-en-1-yl]carbamate (Compound im-1c-c)

The compound im-1c-b (5.0 g, 0.023 mol) which has been prepared in the above (Step 2) was dissolved in 250 mL of anhydrous tetrahydrofuran. After cooling to −78° C. and under stirring nitrogen stream, 1 M potassium bis(trimethylsilyl)amide tetrahydrofuran solution (35 mL, 0.035 mmol) was added dropwise thereto. After 20 minutes, a diluted solution of N-phenyl bis(trifluoromethanesulfonamide) (16.7 g, 0.047 mol) in anhydrous tetrahydrofuran (50 mL) was added dropwise thereto followed by stirring for 2 hours. After raising the temperature to room temperature, the reaction was terminated by adding distilled water (200 mL) followed by extraction with ethyl acetate. The organic layer was washed with distilled water and saturated brine, dried over anhydrous sodium sulfate, and concentrated. The residue was purified by silica gel column chromatography (ethyl acetate:n-hexane=1:9) to obtain the title compound im-1c-c (4.5 g, 56%).

MS m/z: 346 [M+1]⁺
¹H NMR (CDCl₃, 400 MHz), δ ppm: 5.70 (s, 1H), 4.51 (br, 1H), 3.84 (m, 1H), 2.60-2.34 (m, 2H), 2.12-1.96 (m, 2H), 1.84-1.73 (m, 1H), 1.45 (s, 9H).

(Step 4) Preparation of tert-butyl N-[4-(tetramethyl-1,3,2-dioxaborolan-2-yl)cyclohex-3-en-1-yl]carbamate (Compound im-1c-d)

A mixture of the compound im-1c-c (6.5 g, 0.019 mol), bis(pinacolato)diboron (5.7 g, 0.023 mol), potassium acetate (5.5 g, 0.056 mol), and [1,1'-bis(diphenylphosphino)ferrocene]dichloropalladium (II) (4.6 g, 5.6 mmol) in N,N-dimethylformamide (120 mL) was stirred for 9 hours at 90° C. under nitrogen stream. Upon the completion of the reaction, the mixture was cooled to room temperature. Insoluble mass was removed by filtration through a Celite pad, and the filtrate was extracted with ethyl acetate and distilled water. The organic layer was washed with distilled water and saturated brine, dried over anhydrous sodium sulfate, and concentrated. The residue was purified by silica gel column chromatography (ethyl acetate:n-hexane=5:95) to obtain the title compound im-1c-d as a white solid (4.9 g, 81%).

MS m/z: 324 [M+1]⁺
¹H NMR (CDCl₃, 400 MHz), δ ppm: 6.46 (s, 1H), 4.52 (br, 1H), 3.77 (m, 1H), 2.54-2.43 (m, 2H), 2.26-2.18 (m, 2H), 1.98-1.81 (m, 2H), 1.54-1.41 (m, 10H), 1.26 (s, 12H)

(Step 5) Preparation of tert-butyl N-[4-(3-chlorophenyl)cyclohex-3-en-1-yl]carbamate (Compound im-1c-e)

To a solution of the compound im-1c-d (4.9 g, 0.015 mol) in 1,4-dioxane (100 mL) was added 3-chloroiodobenzene (3.3 g, 0.014 mmol), cesium carbonate (13.6 g, 0.042 mol), and tetrakis(triphenylphosphine)palladium (0) (1.61 g, 1.39 mmol) in order. Distilled water (15 mL) and 1,4-dioxane (50 mL) were further added and the resultant was stirred for 5 hours at 100° C. under nitrogen stream. Upon the completion of the reaction, the temperature was lowered to room temperature. Insoluble mass was removed by filtration through a Celite pad, and the filtrate was extracted with ethyl acetate and distilled water. The organic layer was washed with distilled water and saturated brine, dried over anhydrous sodium sulfate, and concentrated. The residue was purified by silica gel column chromatography (ethyl acetate: n-hexane=5:95) to obtain the title compound im-1c-e as a yellow solid (4.1 g, 98%).

MS m/z: 308 [M+1]⁺
¹H NMR (CDCl₃, 400 MHz), δ ppm: 7.35 (s, 1H), 7.28-7.18 (m, 3H), 6.04 (m, 1H), 4.57 (m, 1H), 3.85 (m, 1H), 2.64-2.45 (m, 3H), 2.12-1.98 (m, 2H), 1.74-1.66 (m, 1H), 1.46 (s, 9H)

(Step 6) 4-(3-Chlorophenyl)cyclohex-3-en-1-amine hydrochloride Salt (Compound im-1c-f)

To a solution of the compound im-1c-e (4.1 g, 0.013 mmol) in methylene chloride (30 mL) at 0° C. was added 4 N hydrogen chloride dioxane solution (30 mL), and the reaction mixture was stirred for 15 hours at room temperature. Upon the completion of the reaction, the solvent was removed under reduced pressure, and diethyl ether was added to produce a solid. The solid was filtered, washed with n-hexane, and dried to obtain the title compound im-1c-f as a yellow solid (3.2 g, 96%).

MS m/z: 208 [M+1]⁺
¹H NMR (DMSO-d₆, 400 MHz), δ ppm: 8.07 (br, 3H), 7.45-7.30 (m, 4H), 6.14 (m, 1H), 3.32-3.28 (m, 1H), 2.60-2.56 (m, 1H), 2.32-2.18 (m, 4H), 1.80-1.68 (m, 1H)

(Step 7) Preparation of 5-bromo-N-[4-(3-chlorophenyl)cyclohex-3-en-1-yl]pyrimidin-2-amine (Compound im-1c)

Except that the compound im-1c-f (3.2 g, 0.013 mol) is used instead of 2-aminoindane, the reaction was carried out in the same manner as Preparation example 1-1 to obtain the title compound im-1c as a beige solid (3.6 g, 77%).

MS m/z: 365 [M+1]⁺

$^1$H NMR (CDCl$_3$, 400 MHz), δ ppm: 8.28 (s, 2H), 7.36 (s, 1H), 7.28-7.18 (m, 3H), 6.08 (m, 1H), 5.21-5.19 (d, 1H), 4.17 (m, 1H), 2.78-2.46 (m, 3H), 2.26-2.24 (m, 2H), 1.89-1.78 (m, 1H)

[Preparation Example 1-4] Preparation of 5-bromo-N-(2,3-dihydro-1H-inden-2-yl)pyridine-2-amine (Compound im-1d)

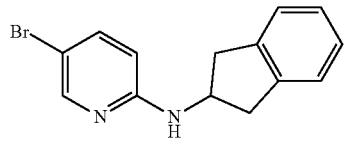

A mixture of 5-bromo-2-fluoropyridine (1.3 g, 7.5 mmol), 2-aminoindane (1.0 g, 7.5 mmol), and potassium carbonate (1.3 g, 9.0 mmol) in N,N-dimethylformamide (10 mL) was stirred for 10 hours at 140° C. Upon the completion of the reaction, the mixture was lowered to room temperature, diluted with 20 mL of distilled water, and extracted with ethyl acetate. The organic layer was washed with distilled water and saturated brine, dried over anhydrous sodium sulfate, and concentrated. The residue was recrystallized by using methylene chloride and n-hexane to obtain the title compound im-1d as a brown solid (0.8 g, 38%).

MS m/z: 290 [M+1]$^+$

[Preparation Example 1-5] Preparation of 5-bromo-N-(2,3-dihydro-1H-inden-2-yl) pyrazin-2-amine (Compound im-1e)

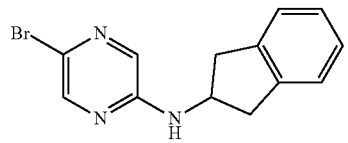

2,5-Dibromopyrazine (1.0 g, 4.3 mmol), 2-aminoindane (0.6 g, 4.5 mmol), and cesium carbonate (2.2 g, 6.7 mmol) were dissolved in N,N-dimethylformamide (5 mL), and the mixture was stirred for 2 hours at 80° C. Upon the completion of the reaction, the mixture was cooled to room temperature, diluted with distilled water (60 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=1:9→3:7) to obtain the title compound im-1e as a brown solid (124 mg, 10%).

MS m/z: 291 [M+1]$^+$

[Preparation Example 2-1] Preparation of 2-[(2,3-dihydro-1H-inden-2-yl)amino]pyrimidine-5-carboxylic Acid (Compound im-2a)

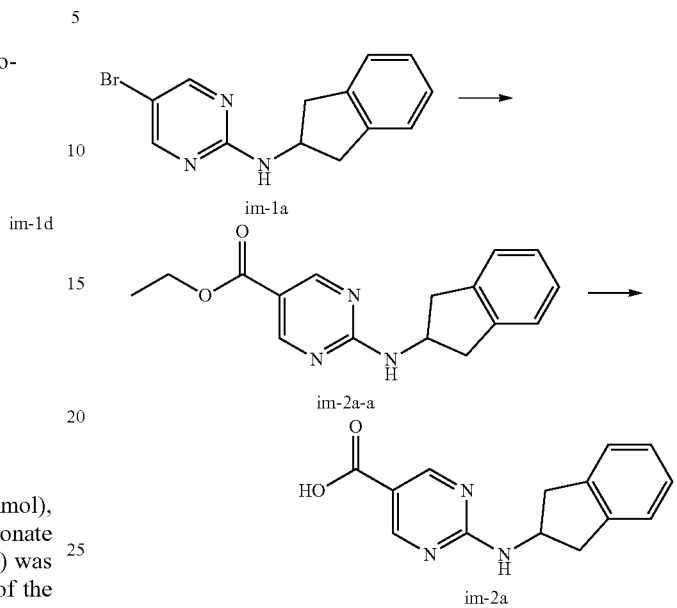

(Step 1) Preparation of ethyl 2-[(2,3-dihydro-1H-inden-2-yl)amino]pyrimidine-5-carboxylate (Compound im-2a-a)

To a solution of the intermediate im-1a (5.0 g, 17.2 mmol) in ethanol (30 mL) and N,N-dimethylformamide (3 mL) was added palladium (II) acetate (386 mg, 1.72 mmol) 1,1'-bis(diphenylphosphino)ferrocene (1.43 g, 2.58 mmol), and triethylamine (7.2 mL, 0.052 mol) in order, and the reaction mixture was stirred for 16 hours at 75° C. under one atmosphere of CO. Upon the completion of the reaction, the mixture was cooled to room temperature, diluted with distilled water (100 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=2:8→5:5) to obtain the title compound im-2a-a as a yellow solid (4.1 g, 84%)

MS m/z: 284 [M+1]$^+$ $^1$H NMR (DMSO-d$_6$, 400 MHz), δ ppm: 8.80 (d, 2H), 8.46 (d, 1H), 7.23-7.14 (m, 4H), 4.70 (q, 1H), 4.27 (q, 2H), 3.28 (dd, 2H), 2.92 (dd, 2H), 1.29 (t, 3H)

(Step 2) Preparation of 2-[(2,3-dihydro-1H-inden-2-yl)amino]pyrimidine-5-carboxylic Acid (Compound im-2a)

To a solution of the compound im-2a-a (2.5 g, 8.6 mmol) in tetrahydrofuran (30 mL) and distilled water (10 mL) was added with lithium hydroxide (1.8 g, 0.043 mmol), and the reaction mixture was stirred for 15 hours at room temperature. Upon the completion of the reaction, 2 N aqueous hydrochloric acid solution was added thereto to adjust pH of 2 or lower, followed by extraction with ethyl acetate. The organic layer was washed with distilled water and saturated brine, dried over anhydrous sodium sulfate, and concentrated to obtain the title compound im-2a as a white solid quantitatively (2.2 g).

MS m/z: 256 [M+1]⁺

¹H NMR (DMSO-$d_6$, 400 MHz), δ ppm: 8.77 (d, 2H), 8.36 (d, 1H), 7.23-7.14 (m, 4H), 4.73-4.67 (m, 1H), 3.27 (dd, 2H), 2.92 (dd, 2H)

[Preparation Example 2-2] Preparation of 2-({[3-(trifluoromethoxy)phenyl]methyl}amino)pyrimidine-5-carboxylic Acid (Compound im-2b)

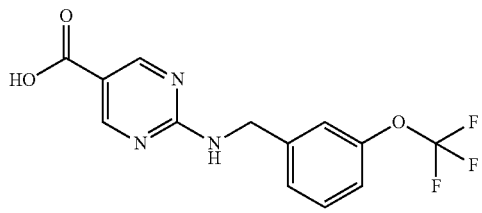

im-2b

Except that the compound im-1b is used instead of the compound im-1a, the reaction was carried out in the same manner as Preparation example 2-1 to obtain the title compound im-2b.

MS m/z: 314 [M+1]⁺

¹H NMR (DMSO-$d_6$, 400 MHz), δ ppm: 8.72 (s, 2H), 8.59 (m, 1H), 7.45 (t, 1H), 7.34 (d, 1H), 7.27 (s, 1H), 7.24 (d, 1H), 4.62 (d, 2H)

[Preparation Example 2-3] Preparation of 2-{[4-(3-chlorophenyl)cyclohex-3-en-1-yl]amino}pyrimidine-5-carboxylic Acid (Compound im-2c)

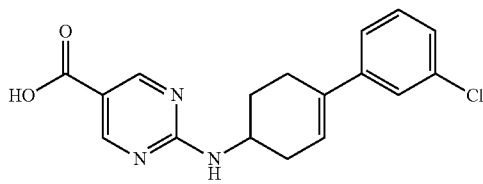

im-2c

Except that the corresponding compound im-1c is used instead of the compound im-1a, the reaction was carried out in the same manner as Preparation example 2-1 to obtain the title compound im-2c as a white solid.

MS m/z: 330 [M+1]⁺

¹H NMR (DMSO-$d_6$, 400 MHz) δ 12.73 (br-s, 1H), 8.72 (d, 2H), 8.07 (d, 1H), 7.46-7.28 (m, 4H), 6.18 (s, 1H), 4.10 (m, 1H), 2.60-2.43 (m, 3H), 2.28-2.18 (m, 1H), 2.30-2.21 (m, 1H), 1.78-1.64 (m, 1H)

[Preparation Example 2-4] Preparation of 6-[(2,3-dihydro-1H-inden-2-yl)amino]pyridine-3-carboxylic Acid (Compound im-2d)

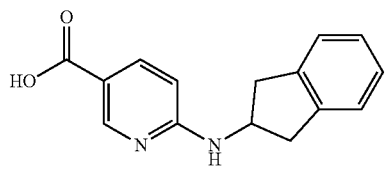

im-2d

Except that the corresponding compound im-1d is used instead of the compound im-1a, the reaction was carried out in the same manner as Preparation example 2-1 to obtain the title compound im-2d as a brown solid.

MS m/z: 255 [M+1]⁺

¹H NMR (CDCl₃, 400 MHz), δ ppm: 8.71 (m, 1H), 8.01 (m, 1H), 7.25-7.19 (m, 4H), 6.44-6.42 (m, 1H), 4.69 (m, 1H), 3.44-3.39 (m, 2H), 2.93-2.88 (m, 2H),

[Preparation Example 3] Preparation of 1-{2-[(2,3-dihydro-1H-inden-2-yl)amino]pyrimidin-5-yl}ethan-1-one (Compound im-3)

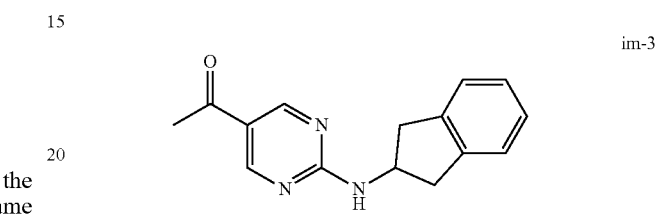

im-3

To a solution of the compound im-1a (0.2 g, 0.68 mmol) and bis(triphenylphosphine)dichloropalladium (II) (30 mg, 0.043 mmol) in tetrahydrofuran (2 mL) under nitrogen atmosphere was added with tributyl(ethoxyvinyl)tin (0.25 mL, 0.74 mmol), and the mixture was stirred for 16 hours at 75° C. After adding 2 N aqueous solution of potassium fluoride to terminate the reaction, the reaction mixture was extracted with ethyl acetate. The organic layer was washed with distilled water and saturated brine, dried over anhydrous sodium sulfate, and concentrated. The residue was dispersed in methanol (10 mL) and was treated with 2 N aqueous hydrochloric acid (5 mL). After stirring for 4 hours at room temperature, a saturated aqueous solution of sodium hydrogen carbonate was added thereto to adjust pH 7, followed by extraction with ethyl acetate. The organic layer was washed with distilled water and saturated brine, dried over anhydrous sodium sulfate, and concentrated. The residue was purified by silica gel column chromatography (ethyl acetate:n-hexane=1:9→3:7) to obtain the title compound im-3 as a white solid (0.11 g, 63%).

¹H NMR (CDCl₃, 400 MHz), δ ppm: 8.87 (s, 1H), 8.60 (s, 1H), 7.27-7.16 (m, 4H), 6.85 (m, 1H), 4.90 (m, 1H), 3.40 (dd, 2H), 2.90 (m, 2H), 2.44 (s, 3H)

[Preparation Example 4] Preparation of N-(2,3-dihydro-1H-inden-2-yl)-5-(tetramethyl-1,3,2-dioxaborolan-2-yl)pyrimidin-2-amine (Compound im-4)

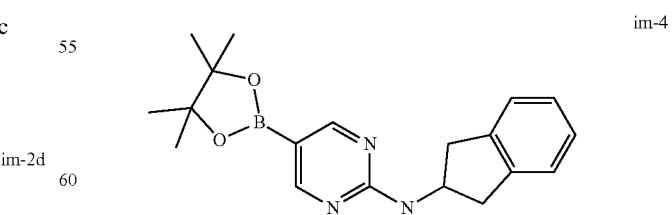

im-4

A mixture of the compound im-1a (4.5 g, 0.015 mol), bis(pinacolato)diboron (5.1 g, 0.020 mol), [1,1'-bis(diphenylphosphino)ferrocene]dichloropalladium (II) (1.27 g, 1.55 mmol) and potassium acetate (4.6 g, 0.046 mol) in 1,4- dioxane (36 mL) was stirred for 18 hours at 100° C. under nitrogen stream. Upon the completion of the reaction, the mixture was cooled to room temperature and insoluble mass was filtered out by through a Celite pad. The filtrate was diluted with distilled water (100 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=15:85) to obtain the title compound im-4 as a white solid (3.7 g, 71%).

MS m/z: 338 [M+1]$^+$ $^1$H NMR (CDCl$_3$, 400 MHz), δ ppm: 8.58 (s, 2H), 7.24-7.16 (m, 4H), 5.50 (d, 1H), 4.90-4.82 (m, 1H), 3.42-3.37 (m, 2H), 2.90-2.85 (m, 2H), 1.33 (s, 12H).

[Preparation Example 5-1] Preparation of N-(2,3-dihydro-1H-inden-2-yl)-5-(piperazin-1-yl)pyrimidin-2-amine hydrochloride (Compound im-5a)

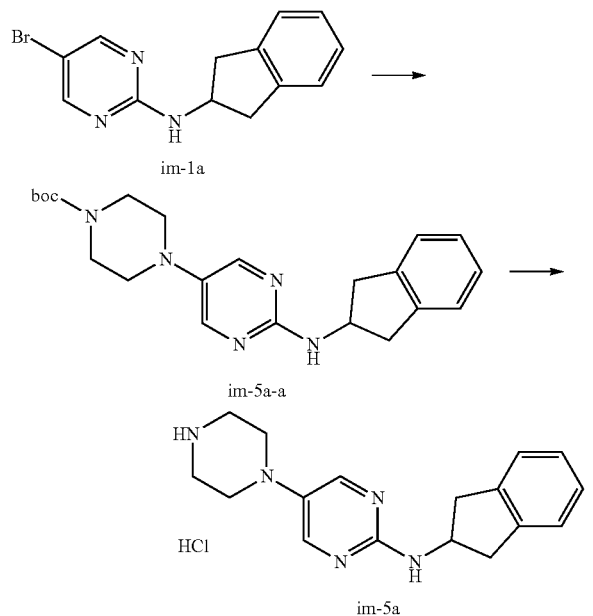

(Step 1) Preparation of tert-butyl 4-{2-[(2,3-dihydro-1H-inden-2-yl)amino]pyrimidin-5-yl}piperazine-1-carboxylate (Compound im-5a-a)

A mixture of the compound im-1a (0.9 g, 3.1 mmol), 1-tert-butoxycarbonyl piperazine (1.3 g, 6.9 mmol), 2-dicyclohexylphosphino-2',4',6'-triisopropylbiphenyl (0.22 g, 0.461 mmol), palladium (II) acetate (0.070 g, 0.31 mmol), and sodium tert-butoxide (0.92 g, 9.6 mmol) in toluene (18 mL) was flushed with nitrogen gas, and stirred for 48 hours at 110° C. Upon the completion of the reaction, the mixture was cooled to room temperature, and insoluble mass was filtered out through a Celite pad. The filtrate was diluted with distilled water, and extracted with ethyl acetate. The organic layer was washed with distilled water and saturated brine, dried over anhydrous sodium sulfate, and concentrated. The residue was purified by silica gel column chromatography (ethyl acetate:n-hexane=1:9→1:1) to obtain the title compound im-5a-a as a yellow solid (0.60 g, 49%).

MS m/z: 396 [M+1]$^+$ $^1$H NMR (CDCl$_3$, 400 MHz), δ ppm: 8.08 (s, 2H), 7.22-7.17 (m, 4H), 5.24 (s, 1H), 4.73 (m, 1H), 3.58 (br, 4H), 3.40-3.36 (m, 2H), 2.94 (br, 4H), 2.88-2.84 (m, 2H), 1.48 (s, 9H)

(Step 2) Preparation of N-(2,3-dihydro-1H-inden-2-yl)-5-(piperazin-1-yl)pyrimidin-2-amine Hydrochloride (Compound im-5a)

To a solution of the compound im-5a-a (0.60 g, 1.51 mmol) in methylene chloride (2 mL) was added 4 N hydrogen chloride dioxane solution (1 mL) at room temperature, and the mixture was stirred for 1.5 hours. The solvent was removed by concentration under reduced pressure to obtain the title compound im-5a as a yellow solid quantitatively (0.44 g).

MS m/z: 296 [M+1]$^+$ $^1$H NMR (DMSO-d$_6$, 400 MHz), δ ppm: 8.95 (s, 2H), 7.21-7.13 (m, 4H), 4.56 (m, 1H), 3.57 (br, 4H), 3.25 (m, 2H), 3.22 (br, 4H) 2.87 (m, 2H)

[Preparation Example 5-2] Preparation of 5-(piperazin-1-yl)-N-{[3-(fluoromethoxy)phenyl]methyl}pyrimidin-2-amine hydrochloride (Compound im-5b)

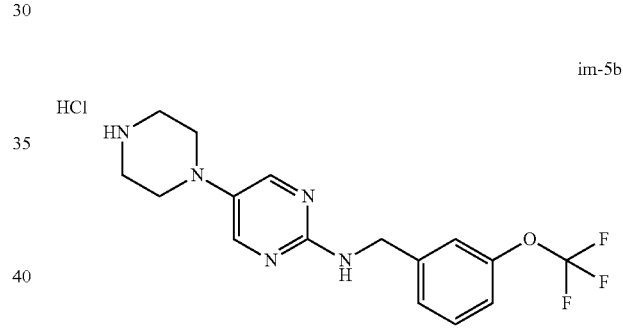

Except that the corresponding compound im-1b is used instead of the compound im-1a, the reaction was carried out in the same manner as Preparation example 5-1 to obtain the title compound im-5b as a yellow solid.

MS m/z: 354 [M+1]$^+$ $^1$H NMR (DMSO-d$_6$, 400 MHz), δ ppm: 8.79 (s, 2H), 8.26 (s, 2H), 7.66 (s, 1H), 7.40 (t, 1H), 7.30 (d, 1H), 7.22 (s, 1H), 7.17 (d, 1H), 4.46 (s, 2H), 3.15 (br, 8H)

[Preparation Example 6] Preparation of N-(2,3-dihydro-1H-inden-2-yl)-5-(piperidin-4-yl)pyrimidin-2-amine hydrochloride (Compound im-6)

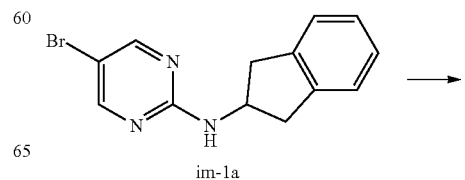

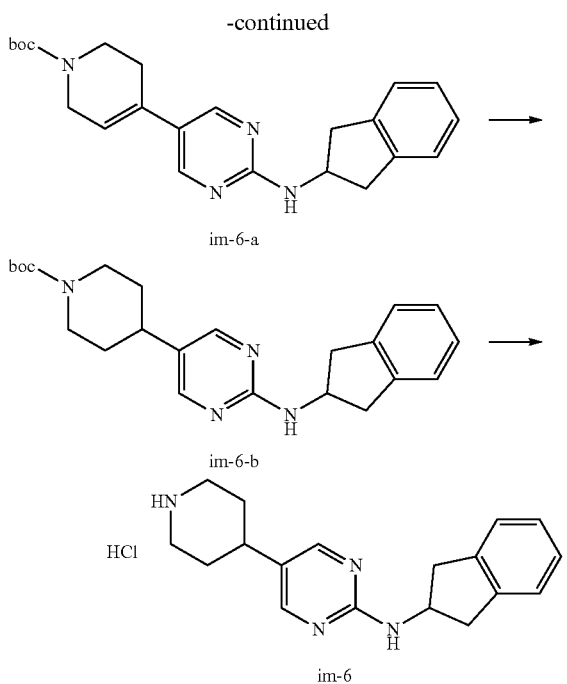

(Step 1) Preparation of tert-butyl 4-{2-[(2,3-dihydro-1H-inden-2-yl)amino]pyrimidin-5-yl}-1,2,3,6-tetrahydropyridine-1-carboxylate (Compound im-6-a)

The compound im-1a (0.93 g, 3.19 mmol) and N-tert-butoxycarbonyl-1,2,3,5-tetrahydropyridine-4-boric acid pinacol ester (0.99 g, 3.19 mmol) were dissolved in a mixture solvent of 1,4-dioxane (6 mL)/distilled water (2 mL). To the reaction mixture was then added sodium carbonate (1.0 g, 9.6 mmol) and tetrakis(triphenylphosphine) palladium (0) (0.37 g, 0.32 mmol). The reaction mixture was flushed with nitrogen gas, and stirred for 7 hours at 80° C. The mixture was cooled to room temperature, and insoluble mass was then removed by filtration through a Celite pad. Thereafter, the filtrate was diluted with distilled water and extracted with ethyl acetate. The organic layer was washed with distilled water and saturated brine, dried over anhydrous sodium sulfate, and concentrated. The residue was purified by silica gel column chromatography (ethyl acetate:n-hexane=3:7) to obtain the title compound im-6-a as a yellow solid (0.83 g, 98%).

MS m/z: 393 [M+1]$^+$ $^1$H NMR (CDCl$_3$, 400 MHz), δ ppm: 8.32 (s, 2H), 7.26-7.19 (m, 4H), 5.91 (s, 1H), 5.37 (d, 1H), 4.81-4.79 (m, 1H), 4.06 (s, 2H), 3.63 (s, 2H), 3.43-3.37 (m, 2H), 2.91-2.87 (m, 2H), 2.44 (s, 2H), 1.49 (s, 9H)

(Step 2) Preparation of tert-butyl 4-{2-[(2,3-dihydro-1H-inden-2-yl)amino]pyrimidin-5-yl}piperidine-1-carboxylate (Compound im-6-b)

To a solution of the compound im-6-a (0.30 g, 0.76 mmol) in methanol (5 mL) was added Pd/C (10% by weight, 0.2 g) and the reaction mixture was stirred for 15 hours under hydrogen pressure (1 atm). Upon the completion of the reaction, the catalyst was removed by filtration through a Celite pad. The filtrate was concentrated under reduced pressure, and the residue was purified by silica gel column chromatography (ethyl acetate:n-hexane=3:7→5:5) to obtain the title compound im-6-b as a yellow solid (0.17 g, 57%).

MS m/z: 395 [M+1]$^+$ $^1$H NMR (CDCl$_3$, 400 MHz), δ ppm: 8.14 (s, 2H), 7.23-7.17 (m, 4H), 5.33 (d, 1H), 4.79-4.77 (m, 1H), 4.24 (s, 2H), 3.39 (dd, 2H), 2.90-2.79 (m, 4H), 2.49 (t, 1H), 1.80 (d, 2H), 1.58 (d, 2H), 1.48 (s, 9H).

(Step 3) Preparation of N-(2,3-dihydro-1H-inden-2-yl)-5-(piperidin-4-yl)pyrimidin-2-amine Hydrochloride (Compound im-6)

To a solution of the compound im-6-b (0.17 g, 0.43 mmol) in methylene chloride (1 mL) was added with 4 N hydrogen chloride dioxane solution (1 mL), and the reaction mixture was stirred for 3 hours at room temperature. Upon the completion of the reaction, the solvent was concentrated under reduced pressure to obtain the title compound im-6 as a yellow solid quantitatively (0.14 g).

MS m/z: 295 [M+1]$^+$ $^1$H NMR (DMSO-d$_6$, 400 MHz), δ ppm: 8.81-8.63 (m, 2H), 8.27 (s, 2H), 7.77 (s, 1H), 7.14-7.23 (m, 4H), 4.63-4.60 (m, H), 3.22-3.37 (m, 4H), 2.77-3.01 (m, 4H), 2.68-2.74 (m, 1H), 1.99 (d, 2H), 1.73-1.83 (m, 2H)

[Preparation Example 7] Preparation of 4H,5H,6H,7H-tetrahydro-1H-[1,2,3]triazolo[4,5-c]pyridine Hydrochloride (Compound im-7)

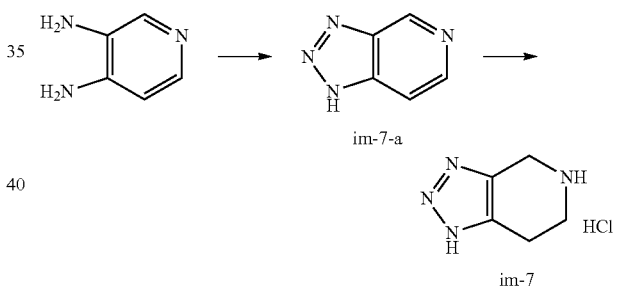

(Step 1) Preparation of 1H-[1,2,3]triazolo[4,5-c]pyridine (Compound im-7-a)

To a solution of 3,4-diaminopyridine (2.0 g, 0.048 mol) in 2 N aqueous hydrochloric acid (25 mL) was slowly added a solution of sodium nitrite (1.9 g, 0.027 mol) in distilled water (3 mL) at 0° C., and the mixture was stirred for 1 hour. The precipitate was filtered and washed with distilled water to obtain the title compound im-7-a as a yellow solid (1.96 g, 89%).

MS m/z: 121 [M+1]$^+$ $^1$H NMR (DMSO-d$_6$, 400 MHz), δ ppm: 9.47 (s, 1H), 8.49 (d, 1H), 7.89 (d, 1H)

(Step 2) Preparation of 4H,5H,6H,7H-tetrahydro-1H-[1,2,3]triazolo[4,5-c]pyridine Hydrochloride (Compound im-7)

To a solution of the compound im-7-a (1.0 g, 8.3 mmol) in methanol (60 mL) was added Pd/C (10% by weight, 2.0 g) and conc. hydrogen chloric acid (1 mL), the mixture was reacted for 7 hours under hydrogen pressure (75 psi). After removing the catalyst through a Celite pad, the filtrate was concentrated and dried under reduced pressure to obtain the title compound im-7 as a yellow solid quantitatively (1.38 g).

MS m/z: 125 [M+1]+
1H NMR (DMSO-d6, 400 MHz), δ ppm: 15.04 (S, 1H), 9.78 (s, 2H), 4.32 (s, 2H), 3.42 (t, 2H), 2.99 (t, 2H)

[Preparation Example 8] Preparation of 1-(3-hydroxy-1H-pyrazol-1-yl)ethan-1-one (Compound im-8)

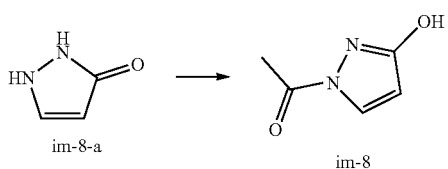

(Step 1) Preparation of 2,3-dihydro-1H-pyrazol-3-one (Compound im-8-a)

The title compound im-8-a was synthesized according to a well-known method (Tetrahedron, 2012, 68(27-28), 5434-5444).

MS m/z: 85 [M+1]+
1H NMR (DMSO-d6, 400 MHz), δ ppm: 9.61 (brs, 1H), 7.35 (s, 1H), 5.43 (s, 1H)

(Step 2) Preparation of 1-(3-hydroxy-1H-pyrazol-1-yl)ethan-1-one (Compound im-8)

To a solution of the compound im-8-a (2.85 g, 0.034 mol) in pyridine (6 mL) at 0° C. was added acetic anhydride (3.36 mL, 0.036 mol), and the reaction mixture was stirred for 1 hour at room temperature. Upon the completion of the reaction, the solvent was removed. Diethyl ether (30 mL) was added to the residue and the mixture was stirred for 16 hours at room temperature. The precipitate was collected and dried to obtain the title compound im-8 as a yellow solid (3.24 g, 76%)

MS m/z: 127 [M+1]+
1H NMR (DMSO-d6, 400 MHz), δ ppm: 10.99 (brs, 1H), 8.13 (d, 1H), 6.01 (d, 1H), 2.48 (s, 3H)

[Preparation Example 9-1] Preparation of tert-butyl 2-(4-{2-[(2,3-dihydro-1H-inden-2-yl)amino]pyrimidin-5-yl}-3-formyl-1H-pyrazol-1-yl)acetate (Compound im-9a)

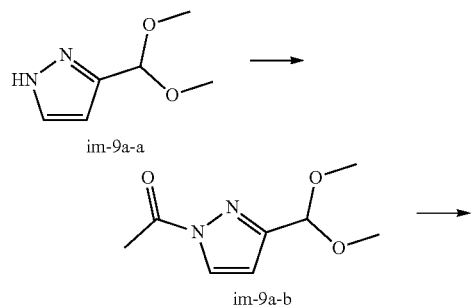

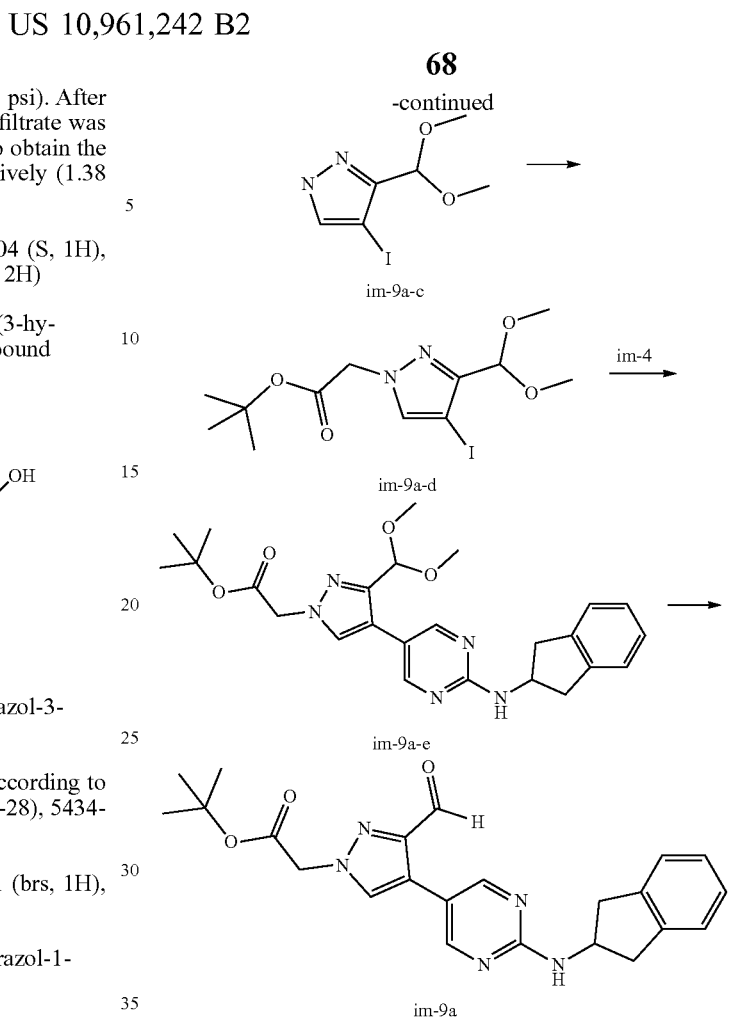

(Step 1) Preparation of 3-(dimethoxymethyl)-1H-pyrazole (Compound im-9a-a)

According to a well-known method (WO 2007043677), the title compound im-9a-a was synthesized.

MS m/z: 143 [M+1]+
1H NMR (CDCl3, 400 MHz), δ ppm: 7.59 (d, 1H), 3.35 (d, 1H), 5.58 (s, 1H), 3.37 (s, 6H)

(Step 2) Preparation of 1-[3-(dimethoxymethyl)-1H-pyrazol-1-yl]ethan-1-one (Compound im-9a-b)

By using the compound im-9a-a (7.6 g, 0.053 mol) instead of the compound im-8-a, the reaction was carried out in the same manner as the Step 2 of Preparation example 8 to obtain the title compound im-9a-b as a yellow liquid (6.6 g, 67%).

MS m/z: 185 [M+1]+
1H NMR (CDCl3, 400 MHz), δ ppm: 8.22 (d, 1H), 6.52 (d, 1H), 5.45 (s, 1H), 3.42 (s, 6H), 2.72 (s, 3H)

(Step 3) Preparation of 3-(dimethoxymethyl)-4-iodo-1H-pyrazole (Compound im-9a-c)

By using the compound im-9a-b (1.0 g, 5.4 mol) instead of the compound 61-a, the reaction was carried out in the same manner as the Step 2 of Example 10-1 to obtain the title compound im-9a-c as a light yellow liquid (1.4 g, 99%).

MS m/z: 269 [M+1]+

¹H NMR (CDCl₃, 400 MHz), δ ppm: 7.62 (s, 1H), 5.52 (s, 1H), 3.37 (s, 6H)

(Step 4) Preparation of tert-butyl 2-[3-(dimethoxymethyl)-4-iodo-1H-pyrazol-1-yl]acetate (Compound im-9a-d)

By using the compound im-9a-c (1.4 g, 5.2 mmol) instead of the compound 61-b, the reaction was carried out in the same manner as the Step 3 of Example 10-1 to obtain the title compound im-9a-d as a white solid (1.3 g, 64%).
MS m/z: 383 [M+1]⁺
¹H NMR (CDCl₃, 400 MHz), δ ppm: 7.55 (s, 1H), 5.50 (s, 1H), 4.83 (s, 2H), 3.38 (s, 6H), 1.46 (s, 9H)

(Step 5) Preparation of tert-butyl 2-(4-{2-[(2,3-dihydro-1H-inden-2-yl)amino]pyrimidin-5-yl}-3-(dimethoxymethyl)-1H-pyrazol-1-yl)acetate (Compound im-9a-e)

By using the compound im-9a-d (0.2 g, 0.52 mmol) instead of the compound 61-c, the reaction was carried out in the same manner as the Step 4 of Example 10-1 to obtain the title compound im-9a-e as a white solid (0.2 g, 84%).
MS m/z: 466 [M+1]⁺
¹H NMR (CDCl₃, 400 MHz), δ ppm: 8.45 (s, 2H), 7.53 (s, 1H), 7.25-7.16 (m, 4H), 5.53 (d, 1H), 5.49 (s, 1H), 4.87-4.79 (m, 3H), 3.43 (dd, 2H), 3.37 (s, 6H), 2.91 (dd, 2H), 1.48 (s, 9H)

(Step 6) Preparation of tert-butyl 2-(4-{2-[(2,3-dihydro-1H-inden-2-yl)amino]pyrimidin-5-yl}-3-formyl-1H-pyrazol-1-yl)acetate (Compound im-9a)

A mixture of the compound im-9a-e (0.2 g, 0.44 mmol) in a mixture solvent of distilled water (1.5 mL) and acetic acid (1.5 mL) was stirred for 2 hours at room temperature. Upon the completion of the reaction, the reaction mixture was concentrated under reduced pressure. The residue was diluted with ethyl acetate and washed with a saturated aqueous sodium hydrogen carbonate and distilled water in order. The organic layer was dried over anhydrous sodium sulfate and concentrated to obtain the title compound im-9a as a yellow solid quantitatively (0.19 g).
MS m/z: 420 [M+1]⁺
¹H NMR (CDCl₃, 400 MHz), δ ppm: 10.05 (s, 1H), 8.51 (br, 2H), 7.60 (s, 1H), 7.24-7.15 (m, 4H), 6.05 (d, 1H), 4.93 (s, 2H), 4.83 (m, 1H), 3.41 (dd, 2H), 2.92 (dd, 2H), 1.51 (s, 9H)

[Preparation Example 9-2] Preparation of ethyl 2-(4-(2-(2,3-dihydro-1H-inden-2-ylamino)pyrimidin-5-yl)-3-formyl-1H-pyrazol-1-yl)acetate (Compound im-9b)

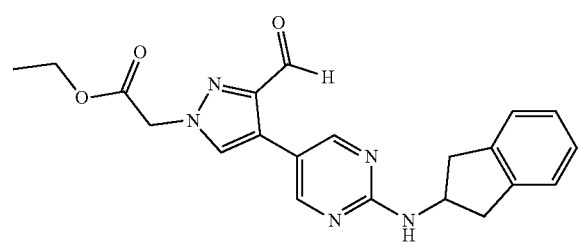

im-9b

By using ethyl bromoacetate instead of tert-butyl bromoacetate, the reaction was carried out in the same manner as the Step 4 to the Step 6 of Preparation example 9-1 to obtain the title compound im-9b as a yellow solid.
MS m/z: 392 [M+1]⁺
¹H NMR (CDCl₃, 400 MHz), δ ppm: 9.82 (s, 1H), 8.41 (d, 2H), 7.67 (s, 1H), 7.25-7.08 (m, 4H), 5.56 (d, 1H), 4.89-4.82 (m, 1H), 4.29-4.12 (m, 2H), 3.44 (dd, 2H), 2.93 (dd, 2H), 1.30 (t, 3H)

EXAMPLES

[Example 1-1] Preparation of 2-[(2,3-dihydro-1H-inden-2-yl)amino]-N-(3-oxo-3-{1H,4H,5H,6H,7H-[1,2,3]triazolo[4,5-c]pyridin-5-yl}propyl)pyrimidine-5-carboxamide (Compound 1)

(Step 1) Preparation of ethyl 3-({2-[(2,3-dihydro-1H-inden-2-yl)amino]pyrimidin-5-yl}formamido)propanoate (Compound 1-a)

To a solution of the intermediate im-2a (0.10 g, 0.39 mmol) in N,N-dimethylformamide (1 mL) was added ethyl 3-aminopropanoate hydrochloride (54 mg, 0.35 mmol) and N,N-diisopropylethylamine (0.24 mL, 1.37 mmol) in order. To a reaction mixture was slowly added benzotriazol-1-yl oxy-tripyrrolidinophosphonium hexafluorophosphate (0.30 g, 0.58 mmol) at 0° C., and the mixture was stirred for 15 hours at room temperature under nitrogen stream. Upon the completion of the reaction, the mixture was diluted with distilled water (50 mL) and extracted with ethyl acetate. The organic layer was washed with distilled water and saturated brine, dried over anhydrous sodium sulfate, and concentrated. The residue was purified by silica gel column chromatography (ethyl acetate:n-hexane=8:2→ethyl acetate) to obtain the title compound 1-a as a white solid (82 mg, 65%).

MS m/z: 355 [M+1]$^+$ $^1$H NMR (CDCl$_3$, 400 MHz), δ ppm: 8.65 (br, 2H), 7.24-7.18 (m, 4H), 6.66 (br, 1H), 5.77 (d, 1H), 4.87-4.85 (m, 1H), 4.17 (q, 2H), 3.70 (q, 2H), 3.40 (dd, 2H), 2.89 (dd, 2H), 2.63 (t, 2H), 1.28 (t, 3H)

(Step 2) Preparation of 3-({2-[(2,3-dihydro-1H-inden-2-yl)amino]pyrimidin-5-yl}formamido)propanoic Acid (Compound 1-b)

To a solution of the compound 1-a (82 mg, 0.23 mmol) in a mixture solvent of tetrahydrofuran (2 mL) and distilled water (1 mL) was added lithium hydroxide (48 mg, 1.16 mmol), and the reaction mixture was stirred for 1.5 hours at room temperature. Upon the completion of the reaction, 2 N aqueous hydrochloric acid solution was added thereto to adjust pH 2 or lower, followed by extraction with ethyl acetate. The organic layer was washed with distilled water and saturated brine, dried over anhydrous sodium sulfate, and concentrated to obtain the title compound 1-b as a white solid (70 mg, 93%).

MS m/z: 327 [M+1]$^+$ $^1$H NMR (DMSO-d$_6$, 400 MHz), δ ppm: 8.72 (br, 2H), 8.42 (s, 1H), 8.13 (s, 1H), 7.22-7.13 (m, 4H), 4.66 (q, 1H) 3.48-3.40 (m, 2H), 3.25 (dd, 2H), 2.89 (dd, 2H)

(Step 3) Preparation of 2-[(2,3-dihydro-1H-inden-2-yl)amino]-N-(3-oxo-3-{1H,4H,5H,6H,7H-[1,2,3]triazolo[4,5-c]pyridin-5-yl}propyl)pyrimidine-5-carboxamide (Compound 1)

To a mixture of the compound 1-b (70 mg, 0.21 mmol), the compound im-7 (27 mg, 0.17 mmol), N,N-diisopropylethylamine (0.14 mL, 0.78 mmol), and N,N-dimethylaminopyridine (5 mg, 0.04 mmol) in N,N-dimethylformamide (2 mL) was slowly added 1-ethyl-3-(3-dimethylaminopropyl)carbodiimide (61 mg, 0.32 mmol) at 0° C. Then, the mixture was stirred for 15 hours at room temperature under nitrogen stream. Upon the completion of the reaction, the mixture was diluted with distilled water (50 mL) and extracted with ethyl acetate. The organic layer was washed with distilled water and saturated brine, dried over anhydrous sodium sulfate, and concentrated. The residue was purified by silica gel column chromatography (methanol:methylene chloride=5: 95-7:93) to obtain the title compound 1 as a white solid (4 mg, 5%).

MS m/z: 433 [M+1]$^+$ $^1$H NMR (DMSO-d$_6$, 400 MHz), δ ppm: 8.69 (br, 2H), 8.40-8.36 (m, 1H) 8.11-8.09 (m, 1H), 7.21-7.14 (m, 4H), 4.67-4.65 (m, 3H), 3.79-3.76 (m, 2H), 3.46-3.34 (m, 2H), 2.28-3.22 (m, 2H), 2.90 (dd, 2H), 2.80 (s, 2H), 2.74-2.68 (m, 2H)

Example 1-2 to Example 1-5

Except that, instead of the compound im-2a and ethyl 3-aminopropanoate, the compound im-2b and the corresponding amino acid ester for the title compound are used, the reaction was carried out in the same manner as Example 1-1 to obtain the following compounds.

[Example 1-2] Preparation of N-(3-oxo-3-{1H,4H,5H,6H,7H-[1,2,3]triazolo[4,5-c]pyridin-5-yl}propyl)-2-({[3-(trifluoromethoxy)phenyl]methyl}amino)pyrimidine-5-carboxamide (Compound 2)

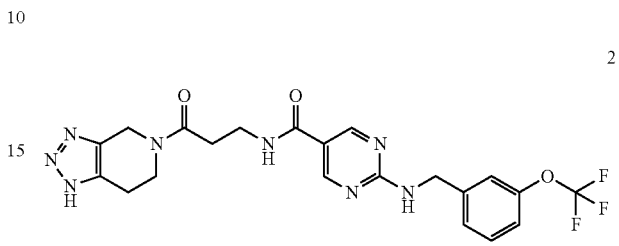

2

MS m/z: 491 [M+1]$^+$ $^1$H NMR (CDCl$_3$, 400 MHz), δ ppm: 11.64 (m, 1H), 8.69 (s, 2H), 7.35 (t, 1H), 7.26 (d, 1H), 7.18 (s, 1H), 7.12 (d, 1H), 7.02 (m, 1H), 5.86 (m, 1H), 4.71 (d, 2H), 3.96 (t, 1H), 3.77 (q, 3H), 3.47 (m, 2H), 2.89 (m, 2H), 2.72 (m, 2H)

[Example 1-3] Preparation of N-(2-oxo-2-{1H,4H,5H,6H,7H-[1,2,3]triazolo[4,5-c]pyridin-5-yl}ethyl)-2-({[3-(trifluoromethoxy)phenyl]methyl}amino)pyrimidine-5-carboxamide (Compound 3)

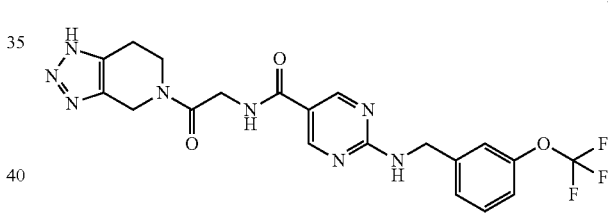

3

MS m/z 477 [M+1]$^+$ $^1$H NMR (DMSO-d$_6$, 400 MHz), δ ppm: 8.73 (s, 2H), 8.57-8.54 (m, 1H), 8.39 (t, 1H), 7.45 (t, 1H), 7.34 (d, 1H), 7.27 (s, 1H), 7.23 (d, 1H), 4.67 (m, 4H), 4.23-4.17 (m, 2H), 3.80 (s, 2H), 2.84-2.71 (m, 2H)

[Example 1-4] Preparation of N-(1-oxo-1-{1H,4H,5H,6H,7H-[1,2,3]triazolo[4,5-c]pyridin-5-yl}propan-2-yl)-2-({[3-(trifluoromethoxy)phenyl]methyl}amino)pyrimidine-5-carboxamide (Compound 4)

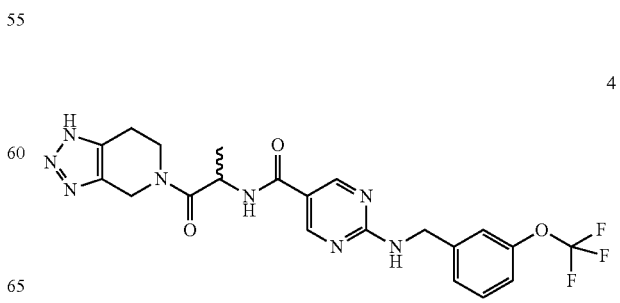

4

MS m/z 491 [M+1]$^+$ $^1$H NMR (DMSO-d$_6$, 400 MHz), δ ppm: 8.74-8.56 (m, 3H), 8.39-8.38 (m, 1H), 7.44 (t, 1H), 7.34 (d, 1H), 7.27 (s, 1H), 7.23 (d, 1H), 5.04-4.98 (m, 1H), 4.86-4.74 (m, 2H), 4.60 (d, 2H), 4.50 (d, 1H), 3.94-3.72 (m, 2H), 2.82-2.67 (m, 2H), 1.32-1.23 (m, 3H)

[Example 1-5] Preparation of 5-{[2-({[3-(fluoromethoxy)phenyl]methyl}amino)pyridin-5-yl]formamido}pentanoic Acid (Compound 5)

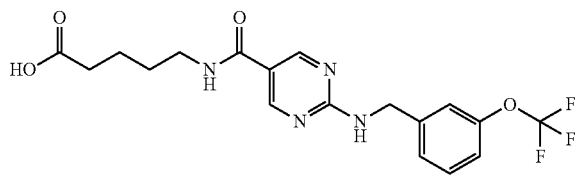

MS m/z: 413 [M+1]$^+$ $^1$H NMR (CDCl$_3$, 400 MHz), δ ppm: 8.76 (s, 2H), 7.34 (t, 1H), 7.27 (d, 1H), 7.19 (s, 1H), 7.12 (d, 1H), 4.69 (d, 2H), 3.40 (s, 2H), 2.53 (s, 4H), 2.37 (m, 2H), 1.67 (m, 4H)

[Example 1-6] Preparation of 5-[4-(2-{1H,4H,5H,6H,7H-[1,2,3]triazolo[4,5-c]pyridin-5-yl}ethyl)piperazine-1-carbonyl]-N-{[3-(trifluoromethoxy)phenyl]methyl}pyrimidin-2-amine (Compound 6)

(Step 1) Preparation of tert-butyl 4-(2-ethoxy-2-oxoethyl)piperazine-1-carboxylate (Compound 6-a)

To a solution of 1-(tert-Butoxycarbonyl)piperazine (1.0 g, 5.37 mmol) in acetonitrile (15 mL) under nitrogen atmosphere was slowly added triethylamine (1.1 g, 0.011 mmol) and ethyl bromoacetate (1.3 g, 8.05 mmol) successively at 0° C., and the mixture was stirred for 3 hours at room temperature. Upon the completion of the reaction, the precipitate was collected, washed with diethyl ether, and dried to obtain the title compound 6-a as a white solid (1.35 g, 92%).

MS m/z: 273 [M+1]$^+$ $^1$H NMR (CDCl$_3$, 400 MHz), δ ppm: 4.19 (q, 2H), 3.48 (t, 4H), 3.22 (s, 2H), 2.52 (t, 2H), 1.45 (s, 9H), 1.27 (t, 3H)

(Step 2) Preparation of tert-butyl 4-(2-hydroxyethyl)piperazine-1-carboxylate (Compound 6-b)

To a solution of the compound 6-a (1.35 g, 4.96 mmol) in anhydrous tetrahydrofuran (15 mL) under nitrogen atmosphere was slowly added lithium aluminum hydride (3.2 g, 0.084 mmol) at 0° C., and the mixture was stirred for 24 hours at room temperature. The reaction was terminated by adding distilled water (5 mL). After adding 15% aqueous sodium hydroxide (3.2 mL) and methylene chloride (50 mL) thereto, the mixture was stirred for 30 minutes. Insoluble mass was removed by filtration through a Celite pad, and the filtrate was concentrated under reduced pressure and extracted with ethyl acetate. The organic layer was washed with distilled water and saturated brine, dried over anhydrous sodium sulfate, and concentrated to obtain the title compound 6-b as a colorless liquid (0.94 g, 82%).

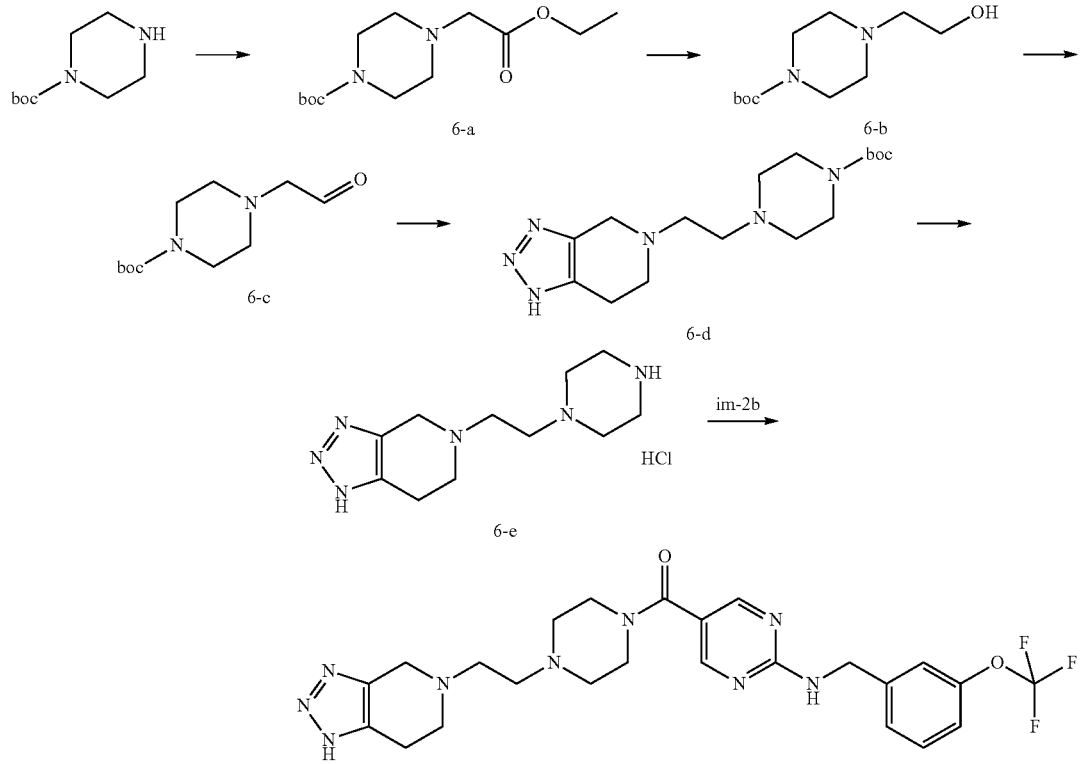

MS m/z: 231 [M+1]$^+$
$^1$H NMR (CDCl$_3$, 400 MHz), δ ppm: 3.62 (t, 2H), 3.44 (t, 4H), 2.65 (brs, 1H), 2.55 (t, 2H), 2.45 (t, 4H), 1.46 (s, 9H)

(Step 3) Preparation of tert-butyl 4-(2-oxoethyl) piperazine-1-carboxylate (Compound 6-c)

To a solution of oxalyl chloride (165 mg, 1.30 mmol) in anhydrous methylene chloride (4 mL) under nitrogen atmosphere was slowly added a solution of dimethyl sulfoxide (0.20 g, 2.60 mmol) in methylene chloride (1 mL) at −78° C. After stirring for 10 minutes, a solution of the compound 6-b (0.2 g, 0.87 mmol) in methylene chloride (2 mL) was slowly added to the reaction mixture. After stirring for 1 hour, triethylamine (0.44 g, 4.34 mmol) was slowly added thereto. Temperature was raised to room temperature, and stirring was continued for 3 hours. Upon the completion of the reaction, the mixture was diluted with distilled water (30 mL), and extracted with methylene chloride. The organic layer was washed with distilled water and saturated brine, dried over anhydrous sodium sulfate, and concentrated to obtain the title compound 6-c as a yellow liquid quantitatively (0.216 g).
MS m/z: 229 [M+1]$^+$
$^1$H NMR (CDCl$_3$, 400 MHz), δ ppm: 9.71 (s, 1H), 3.48 (m, 4H), 2.61 (s, 2H), 2.54 (m, 4H), 1.45 (s, 9H)

(Step 4) Preparation of tert-butyl 4-(2-{1H,4H,5H, 6H,7H-[1,2,3]triazolo[4,5-c]pyridin-5yl}ethyl)piperazine-1-carboxylate (Compound 6-d)

To a solution of the compound 6-c (0.2 g, 0.87 mmol) in methylene chloride (10 mL) under nitrogen atmosphere was added with the intermediate im-7 (0.14 g, 0.87 mmol). After stirring for 1 hour at room temperature, sodium acetoxyborohydride (0.46 g, 2.17 mmol) was added and the mixture was stirred for 48 hours. The reaction was terminated by adding a saturated aqueous solution of sodium hydrogen carbonate, and the mixture was extracted with ethyl acetate. The organic layer was washed with distilled water and saturated brine, dried over anhydrous sodium sulfate, and concentrated. The residue was purified by silica gel column chromatography (methanol:methylene chloride=3:97→15: 85) to obtain the title compound 6-d as a yellow solid (91 mg, 31%).
MS m/z: 337 [M+1]$^+$
$^1$H NMR (CDCl$_3$, 400 MHz), δ ppm: 3.68 (s, 2H), 3.46 (t, 4H), 2.85 (d, 2H), 2.82 (d, 2H), 2.77 (t, 2H), 2.64 (t, 2H), 2.51 (t, 4H), 1.44 (s, 9H)

(Step 5) Preparation of 1-(2-{1H,4H,5H,6H,7H-[1, 2,3]triazolo[4,5-c]pyridin-5yl}ethyl)piperazine hydrochloride (Compound 6-e)

To a solution of the compound 6-d (90 mg, 0.27 mmol) in methylene chloride (3 mL) was added 4 N hydrogen chloride dioxane solution (1 mL), and the reaction mixture was stirred for 14 hours at room temperature. Upon the completion of the reaction, the solvent was removed by concentration under reduced pressure to obtain the title compound 6-e as a white solid quantitatively (98 mg).
MS m/z: 237 [M+1]$^+$
$^1$H NMR (DMSO-d$_6$, 400 MHz), δ ppm: 8.79 (s, 1H), 4.52 (s, 1H), 3.60 (m, 4H), 3.56 (s, 2H), 3.14 (m, 4H), 3.08 (t, 2H), 2.86 (m, 2H), 2.74 (m, 4H)

(Step 6) Preparation of 5-[4-(2-{1H,4H,5H,6H,7H-[1,2,3]triazolo[4,5-c]pyridin-5-yl}ethyl)piperazine-1-carbonyl]-N-{[3-(trifluoromethoxy)phenyl] methyl}pyrimidin-2-amine (Compound 6)

Except that, the compound 6-e and the compound im-2b are used instead of the compound im-7 and the compound 1-b described in Example 1-1 respectively, the reaction was carried out in the same manner as the Step 3 of Example 1-1 to obtain the title compound 6.
MS m/z: 532 [M+1]$^+$
$^1$H NMR (CDCl$_3$, 400 MHz), δ ppm: 8.44 (s, 2H), 7.36 (t, 1H), 7.27 (d, 1H), 7.19 (s, 1H), 7.13 (d, 1H), 5.77 (m, 1H), 4.87 (m, 1H), 4.71 (d, 2H), 3.66 (m, 6H), 2.61 (t, 2H), 2.56 (s, 4H), 2.02 (d, 2H), 1.50 (m, 4H)

[Example 1-7] Preparation of 8-[2-({[3-(trifluoromethoxy)phenyl]methyl}amino)pyrimidine-5-carbonyl]-1-oxa-2,8-diazaspiro[4.5]dec-2-ene-3-carboxylic acid (Compound 7)

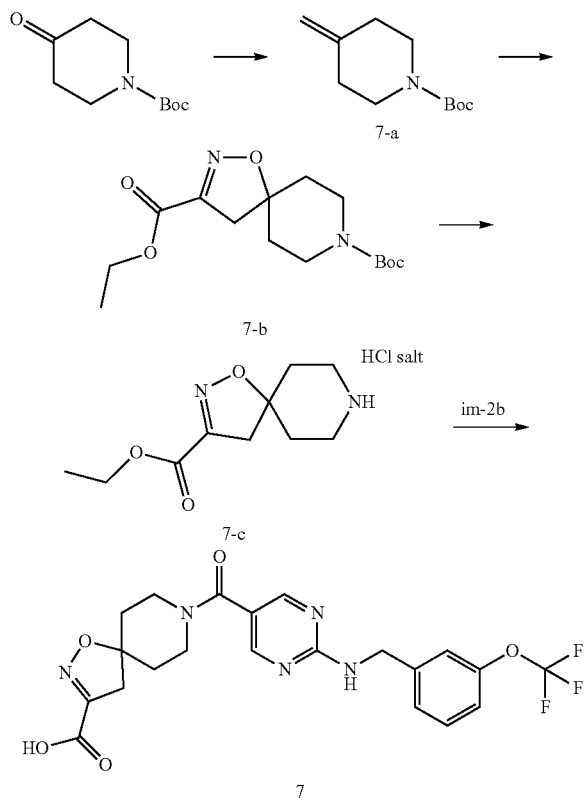

(Step 1) Preparation of tert-butyl-4-methylidenepiperidine-1-carboxylate (Compound 7-a)

To a solution of methyltriphenyl phosphonium bromide (13.0 g, 0.037 mol) in anhydrous tetrahydrofuran (100 mL) was slowly added potassium tert-butoxide (4.2 g, 0.037 mol) at 0° C., and the mixture was stirred for 30 minutes at room temperature under nitrogen atmosphere. After cooling to 0° C. again, 1-(tert-butoxycarbonyl)-4-piperidone (5.0 g, 0.025 mol) diluted in anhydrous tetrahydrofuran (55 mL) was slowly added thereto and stirred for 14 hours at room temperature. Upon the completion of the reaction, the mixture was diluted with distilled water (50 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=1:9) to obtain the title compound 7-a as a colorless liquid (4.5 g, 90%).

$^1$H NMR (CDCl$_3$, 400 MHz), δ ppm: 4.74 (s, 2H), 3.42 (t, 4H), 2.17 (t, 4H), 1.46 (s, 9H)

(Step 2) Preparation of 8-tert-butyl-3-ethyl-1-oxa-2,8-diazaspiro[4.5]dec-2-ene-3,8-dicarboxylate (Compound 7-b)

To a suspension of the compound 7-a (1.0 g, 5.1 mmol) and sodium hydrogen carbonate (2.1 g, 0.025 mol) in ethyl acetate (10 mL) at 0° C. was added ethyl (2Z)-2-chloro-2-(hydroxyimino)acetate (1.2 g, 7.6 mmol), which has been synthesized according to a known method (Tetrahedron Letters, 2011, 52(43), 5656-5658), and the mixture was stirred for 48 hours at room temperature. Upon the completion of the reaction, the reaction mixture was diluted with distilled water (100 mL) and extracted with ethyl acetate. The organic layer was washed with distilled water and saturated brine, dried over anhydrous sodium sulfate, and concentrated. The residue was purified by silica gel column chromatography (ethyl acetate:n-hexane 5:95→3:7) to obtain the title compound 7-b as a yellow solid (1.4 g, 93%).

MS m/z: 313 [M+1]$^+$ (Step 3) Preparation of ethyl 1-oxa-2,8-diazaspiro[4.5]dec-2-ene-3-carboxylate hydrochloride (Compound 7-c)

To a solution of the compound 7-b (0.10 g, 0.32 mmol) in methylene chloride (2 mL) was added 4 N hydrogen chloride dioxane solution (2 mL) and the reaction mixture was stirred for 1 hour at room temperature. Upon the completion of the reaction, the solvent was removed to obtain the title compound 7-c as a beige solid (80 mg), which was then used for the next reaction without further purification.

MS m/z: 213 [M+1]$^+$ $^1$H NMR (CDCl$_3$, 400 MHz), δ ppm: 9.79 (br, 2H), 4.37 (m, 2H), 3.52-3.24 (m, 4H), 3.07 (s, 2H), 2.38-2.21 (m, 2H), 2.18-2.08 (m, 1H), 1.39 (t, 3H)

(Step 4) Preparation of 8-[2-({[3-(trifluoromethoxy)phenyl]methyl}amino)pyrimidine-5-carbonyl]-1-oxa-2,8-diazaspiro[4.5]dec-2-ene-3-carboxylic Acid (7)

Except that, the compound 7-c and the compound im-2b is used instead of the compound im-7 and the compound 1-b described in Example 1-1 respectively, the reaction was carried out in the same manner as the Step 3 of Example 1-1 to obtain the title compound 7.

MS m/z: 480 [M+1]$^+$ $^1$H NMR (DMSO-d$_6$, 400 MHz), δ ppm: 13.50 (br, 1H), 8.39 (s, 2H), 8.28 (t, 1H), 7.44 (t, 1H), 7.32-7.18 (m, 3H), 4.57 (d, 2H), 3.68-3.48 (m, 4H), 3.00 (s, 2H), 1.82-1.72 (m, 4H)

[Example 1-8] Preparation of 5-(3-{1H,4H,5H,6H,7H-[1,2,3]triazolo[4,5-c]pyridin-5-ylmethyl}-1-oxa-2,8-diazaspiro[4.5]dec-2-ene-8-carbonyl)-N-{[3-(trifluoromethoxy)phenyl]methyl}pyrimidin-2-amine (Compound 8)

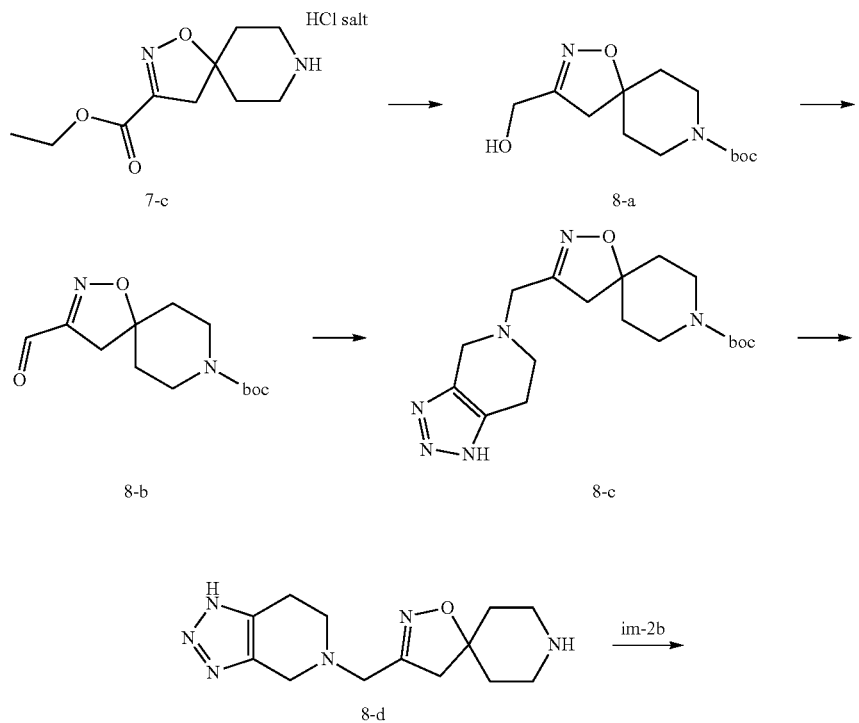

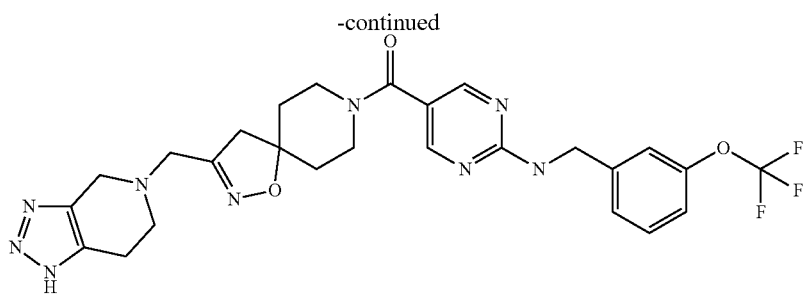

8

(Step 1) Preparation of tert-butyl-3-(hydroxymethyl)-1-oxa-2,8-diazaspiro[4.5]dec-2-ene-8-carboxylate (Compound 8-a)

To a solution of the compound 7-c (1.47 g, 4.70 mmol) in ethanol (10 mL) was added sodium borohydride (0.46 g, 0.012 mol) at 0° C., and the reaction mixture was stirred for 1 hour at room temperature under nitrogen atmosphere. The reaction was quenched by adding distilled water (30 mL), and the mixture was extracted with ethyl acetate. The organic layer was washed with distilled water and saturated brine, dried over anhydrous sodium sulfate, and concentrated to obtain the title compound 8-a as a white solid (1.25 g, 98%).

MS m/z: 271[M+1]$^+$ (Step 2) Preparation of tert-butyl-3-formyl-1-oxa-2,8-diazaspiro[4.5]dec-2-ene-8-carboxylate (Compound 8-b)

To a solution of the compound 8-a (1.25 g, 4.62 mmol) in methylene chloride (70 mL) was added manganese oxide (II) (8.75 g), and the reaction mixture was stirred for 23 hours at room temperature. Upon the completion of the reaction, insoluble mass was removed by filtration through a Celite pad, and the filtrate was concentrated under reduced pressure to obtain the title compound 8-b as a grey solid (0.55 g, 44%).

MS m/z: 269[M+1]$^+$ (Step 3) Preparation of tert-butyl-3-{1H,4H,5H,6H,7H-[1,2,3]triazolo[4,5-c]pyridin-5-ylmethyl}1-oxa-2,8-diazaspiro[4.5]dec-2-ene-8-carboxylate (Compound 8-c)

By using the compound 8-b (0.4 g, 1.5 mmol) instead of 6-C, the reaction was carried out in the same manner as the Step 4 of Example 1-6 to obtain the title compound 8-c as a white solid (0.31 g, 55%).

MS m/z: 377 [M+1]$^+$ $^1$H NMR (CDCl$_3$, 400 MHz), δ ppm: 11.29 (s, 1H), 3.73 (s, 2H), 3.65 (m, 2H), 3.49 (s, 2H), 3.39 (t, 2H), 2.87 (s, 4H), 2.79 (s, 2H), 1.83 (d, 2H), 1.65 (t, 2H), 1.46 (s, 9H)

(Step 4) Preparation of 3-{1H,4H,5H,6H,7H-[1,2,3]triazolo[4,5-c]pyridin-5-ylmethyl}1-oxa-2,8-diazaspiro[4.5]dec-2-ene hydrochloride (Compound 8-d)

By using the compound 8-c (0.31 g, 0.82 mmol) instead of 6-d, the reaction was carried out in the same manner as the Step 5 of Example 1-6 to obtain the title compound 8-d as a white solid quantitatively (0.27 g).

MS m/z: 313 [M+1]$^+$ (Step 5) Preparation of 5-(3-{1H,4H,5H,6H,7H-[1,2,3]triazolo[4,5-c]pyridin-5-ylmethyl}-1-oxa-2,8-diazaspiro[4.5]dec-2-ene-8-carbonyl)-N-{[3-(trifluoromethoxy)phenyl]methyl}pyrimidin-2-amine (Compound 8)

Except that, instead of the compound im-7 and the compound 1-b described in Example 1-1, the compound 8-d and the compound im-2b are used respectively, the reaction was carried out in the same manner as the Step 3 of Example 1-1 to obtain the title compound 8.

MS m/z: 572 [M+1]$^+$ $^1$H NMR (CDCl$_3$, 400 MHz), δ ppm: 11.57 (s, 1H), 8.45 (s, 2H), 7.36 (t, 1H), 7.27 (d, 1H), 7.19 (s, 1H), 7.13 (d, 1H), 5.85 (t, 1H), 4.71 (d, 2H), 3.73 (s, 2H), 3.58 (m, 2H), 3.50 (s, 2H), 2.87 (s, 4H), 2.84 (s, 2H), 1.94 (m, 2H), 1.74 (m, 2H), 1.59 (s, 2H)

[Example 1-9] Preparation of 1-(1H-1,2,3-benzotriazol-5-yl)-3-methyl-8[2-({[3-(trifluoromethoxy)phenyl]methyl}amino)pyrimidine-5-carbonyl]-1,3,8-triazaspiro[4,5]-decane-2,4-dione (Compound 9)

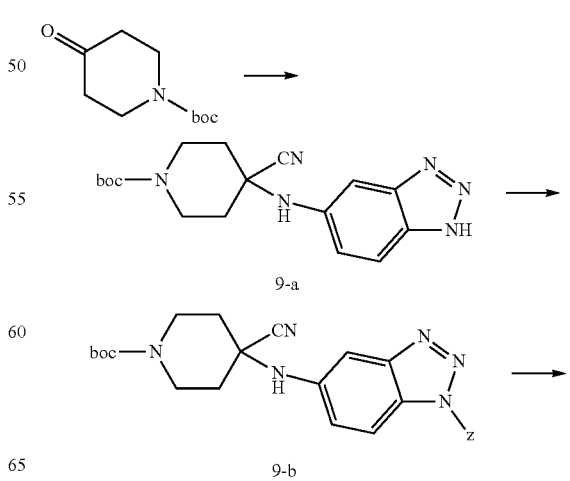

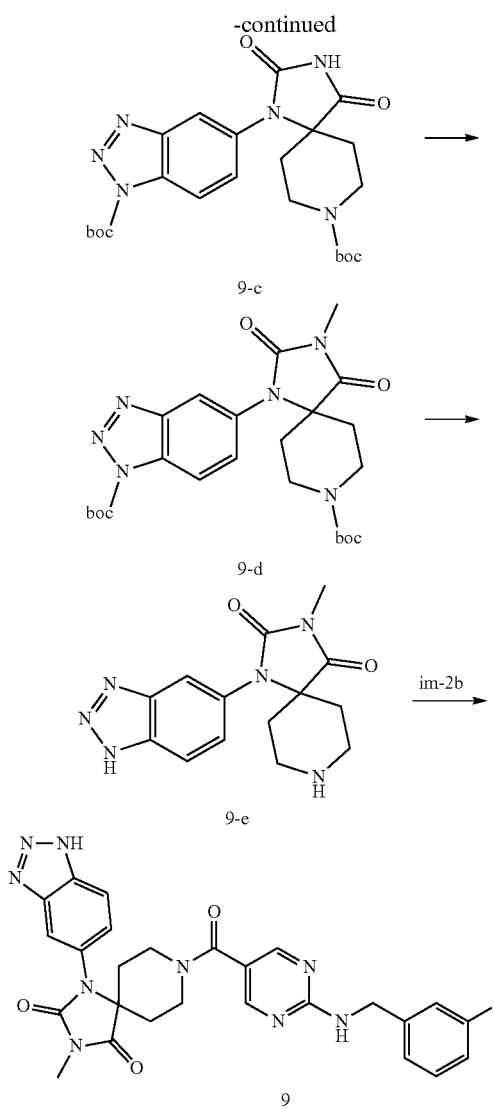

-continued 9-c 9-d im-2b 9-e

9

(Step 1) Preparation of tert-butyl 4-[(1H-1,2,3-benzotriazol-5-yl)amino]-4-cyanopiperidine-1-carboxylate (Compound 9-a)

To a solution of 4-(tert-Butoxycarbonyl)piperidone (0.59 g, 2.96 mmol) and 5-amino-1H-benzotriazole (0.34 g, 2.56 mmol) in acetic acid (3 mL) was added trimethylsilyl cyanide (0.51 g, 5.12 mmol) at 0° C. Then, after flushing with nitrogen gas, the reaction mixture was stirred for 15 hours at room temperature. Upon the completion of the reaction, the mixture was diluted with a saturated aqueous solution of ammonium chloride and extracted with ethyl acetate. The organic layer was washed with distilled water and saturated brine, dried over anhydrous sodium sulfate, and concentrated. The residue was purified by silica gel column chromatography (ethyl acetate:n-hexane=1:1→8:2) to obtain the title compound 9-a as a light brown solid quantitatively (0.9 g).

MS m/z: 343 [M+1]$^+$ $^1$H NMR (CDCl$_3$, 400 MHz), δ ppm: 7.84 (d, 1H), 7.22 (s, 1H), 6.83 (d, 1H), 4.34 (s, 1H), 4.00 (s, 2H), 3.33 (t, 2H), 2.40 (d, 2H), 1.92-1.85 (m, 2H), 1.48 (s, 9H)

(Step 2) Preparation of benzyl 5-({1-[(tert-butoxy)carbonyl]-4-cyanopiperidin-4-yl}amino)-1H-1,2,3-benzotriazole-1-carboxylate (Compound 9-b)

To a solution of the compound 9-a (0.9 g, 2.6 mmol) in a mixture solvent of tetrahydrofuran (5 mL) and distilled water (5 mL) was added potassium carbonate (0.84 g, 6.05 mmol) and benzyl chloroformate (0.64 mL, 4.46 mmol) at 0° C., and the mixture was stirred for 1 hour at room temperature. Upon the completion of the reaction, the mixture was diluted with distilled water (30 mL) and extracted with ethyl acetate. The organic layer was washed with distilled water and saturated brine, dried over anhydrous sodium sulfate, and then concentrated. The residue was purified by silica gel column chromatography (ethyl acetate:n-hexane=4:6) to obtain the title compound 9-b as a yellow solid (1.12 g, 92%).

MS m/z: 477 [M+1]$^+$ $^1$H NMR (CDCl$_3$, 400 MHz), δ ppm: 7.97 (d, 1H), 7.64 (d, 1H), 7.56 (d, 1H), 7.46-7.37 (m, 3H), 7.21-7.18 (dd, 1H), 4.04 (br, 2H), 3.29 (t, 2H), 2.38 (d, 2H), 1.87-1.81 (m, 2H), 1.47 (s, 9H)

(Step 3) Preparation of tert-butyl 1-{1-[(tert-butoxy)carbonyl]-1H-1,2,3-benzotriazol-5-yl}-2,4-dioxo-1,3,8-triazaspiro[4.5]decane-8-carboxylate (Compound 9-c)

To a solution of the compound 9-b (315 mg, 0.64 mmol) in methylene chloride (4 mL) was added chlorosulfonyl isocyanate (10 mg, 0.70 mmol) at 0° C., and the reaction mixture was stirred for 1 hour. To the reaction mixture was added 2 N aqueous hydrochloric acid solution (1 mL) and ethanol (5 mL), and the mixture was stirred at 80° C. for 1 hour. After cooling to room temperature, the solvent was removed and a solution of di-tert-butyl dicarbonate (0.37 mL, 1.6 mmol) in tetrahydrofuran (3 mL) was added to the mixture. After adjusting pH 9 by adding 1 N aqueous solution of sodium hydroxide, the mixture was stirred for 4 hours at room temperature. Upon the completion of the reaction, the mixture was dilute with distilled water (80 mL) and extracted with ethyl acetate. The organic layer was washed with distilled water and saturated brine, dried over anhydrous sodium sulfate, and then concentrated. The residue was purified by silica gel column chromatography (ethyl acetate:n-hexane=1:1) to obtain the title compound 9-c as a white solid (240 mg, 75%).

MS m/z: 487 [M+1]$^+$ $^1$H NMR (CDCl$_3$, 400 MHz), δ ppm: 8.26-8.17 (m, 2H), 8.00 (d, 1H), 4.66 (bs, 2H), 4.10 (br, 1H), 3.50 (br, 2H), 2.03 (d, 2H), 1.78 (m, 11H), 1.37 (s, 9H)

(Step 4) Preparation of tert-butyl 1-{1-[(tert-butoxy)carbonyl]-1H-1,2,3-benzotriazol-5-yl}-3-methyl-2,4-dioxo-1,3,8-triazaspiro[4.5]decane-8-carboxylate (Compound 9-d)

To a solution of the compound 9-c (93 mg, 0.19 mmol) in N,N-dimethylformamide (1.5 mL) was added sodium hydride (11 mg, 0.29 mmol) at 0° C., and the mixture was stirred for 20 minutes at room temperature. After cooling again to 0° C., iodomethane (0.014 mL, 0.23 mmol) was added thereto, and the mixture was stirred for 30 minutes at room temperature. Upon the completion of the reaction, the mixture was diluted with distilled water (30 mL) and extracted with ethyl acetate. The organic layer was washed with distilled water and saturated brine, dried over anhydrous sodium sulfate, and then concentrated. The residue was purified by silica gel column chromatography (ethyl acetate:n-hexane=1:1) to obtain the title compound 9-d as a white solid (73 mg, 77%).

MS m/z: 501 [M+1]$^+$ $^1$H NMR (CDCl$_3$, 400 MHz), δ ppm: 8.22-8.17 (m, 1H), 7.99 (d, 1H), 7.26 (d, 1H), 4.08 (br, 2H), 3.56 (br, 2H), 3.15 (s, 3H), 1.96 (d, 2H), 1.79 (m, 11H), 1.38 (s, 9H)

(Step 5) Preparation of 1-(1H-1,2,3-benzotriazol-5-yl)-3-methyl-1,3,8-triazaspiro[4.5]decane-2,4-dione (Compound 9-e)

By using the compound 9-d (73 mg, 0.14 mmol) instead of the compound 6-d, the reaction was carried out in the same manner as the Step 5 of Example 1-6 to obtain the title compound 9-e as a yellow solid quantitatively (38 mg, 75%).

MS m/z: 315 [M+1]$^+$ $^1$H NMR (DMSO-d$_6$, 400 MHz), δ ppm: 8.97 (s, 1H), 8.15-7.98 (m, 2H), 7.39 (d, 1H), 3.39-3.26 (m, 4H), 2.99 (s, 3H), 2.35 (d, 2H), 1.96-1.88 (m, 2H)

(Step 6) Preparation of 1-(1H-1,2,3-benzotrizol-5-yl)-3-methyl-8 [2-({[3-(trifluoromethoxy)phenyl]methyl}amino)pyrimidine-5-carbonyl]-1,3,8-triazaspiro[4,5]-decane-2,4-dione (Compound 9)

Except that, instead of the compound im-7 and the compound 1-b described in Example 1-1, the compound 9-e and the compound im-2b are used respectively, the reaction was carried out in the same manner as the Step 3 of Example 1-1 to obtain the title compound 9.

MS m/z: 596[M+1]$^+$ $^1$H NMR (CDCl$_3$, 400 MHz), δ ppm: 8.33 (s, 2H), 7.72 (br, 2H), 7.34 (t, 1H), 7.26-7.22 (m, 1H), 7.16-7.11 (m, 3H), 5.85 (s, 1H), 4.67 (d, 2H), 3.89 (br, 4H), 3.17 (s, 3H), 2.05-1.83 (m, 4H)

[Example 1-10] Preparation of N-{[(5S)-2-oxo-3-(2-oxo-2,3-dihydro-1,3-benzoxazol-6-yl)-1,3-oxazolidin-5-yl]methyl}-2-({[3-(trifluoromethoxy)phenyl]methyl}amino)pyrimidine-5-carboxamide (Compound 10)

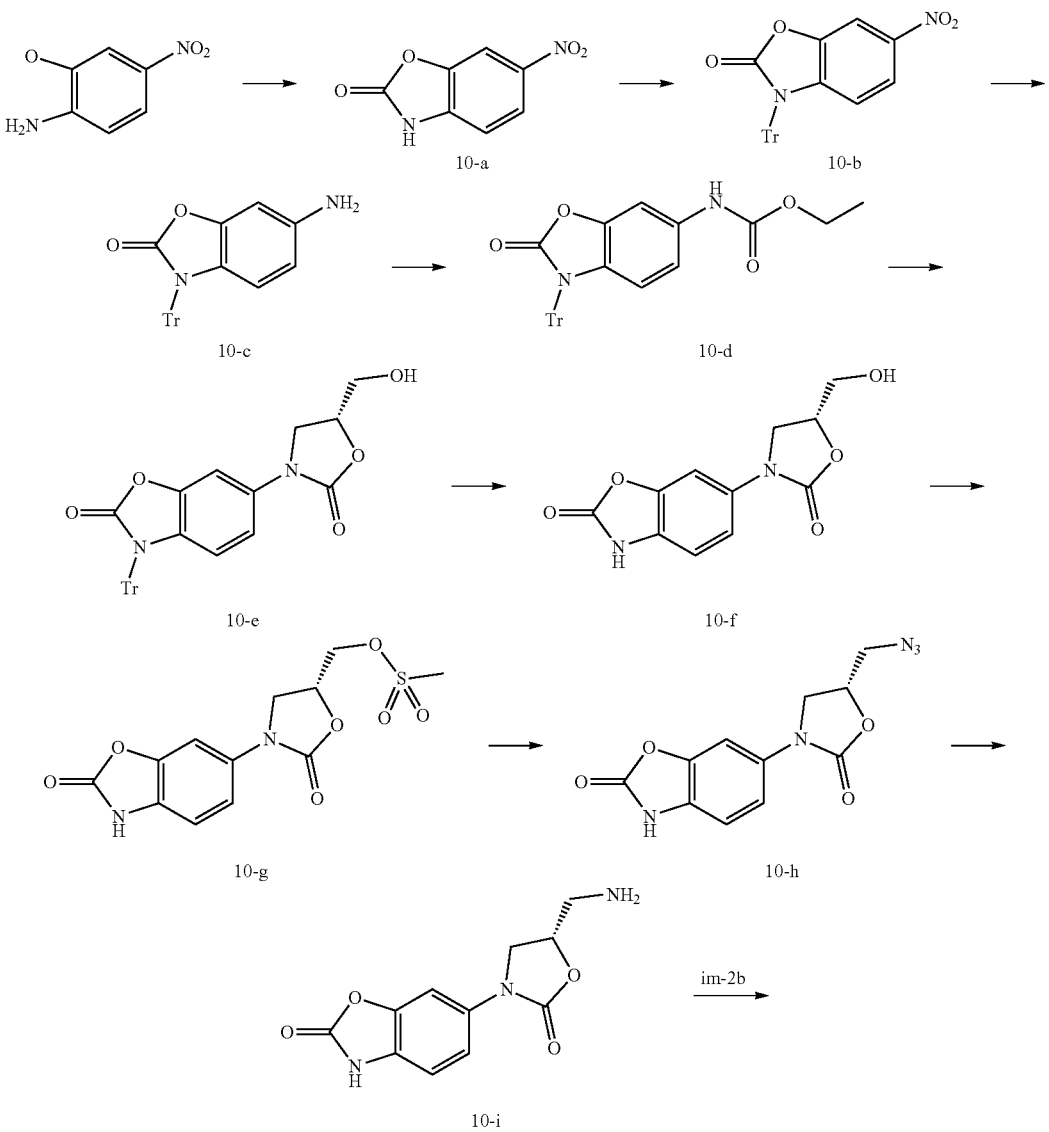

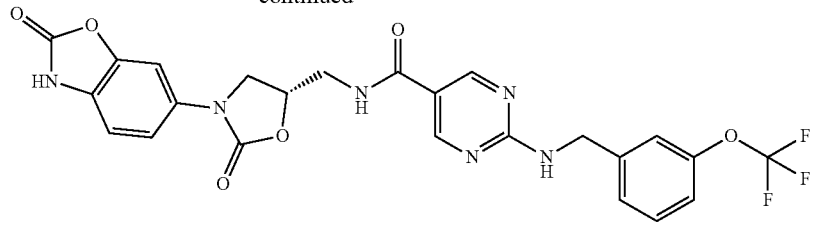

10

(Step 1) Preparation of 6-nitro-2,3-dihydro-1,3-benzoxazol-2-one (Compound 10-a)

To a solution of 2-amino-5-nitrophenol (3.0 g, 0.013 mol) in tetrahydrofuran (50 mL) was added 1,1'-carbonyldiimidazole (3.79 g, 23.35 mmol). After stirring for 4 hours at 100° C., the mixture was cooled to room temperature and stirred for 9 hours. Upon the completion of the reaction, the solvent was removed by concentration under reduced pressure, and the residue was diluted with 2 N aqueous hydrochloric acid and extracted with ethyl acetate and. The organic layer was washed with distilled water and saturated brine, dried over anhydrous sodium sulfate, and concentrated to obtain the title compound 10-a as a light-brown solid (3.49 g, 99%).

MS m/z: 181 [M+1]$^+$ $^1$H NMR (DMSO-d$_6$, 400 MHz), δ ppm: 12.42 (br, 1H), 8.21 (d, 1H), 8.14 (dd, 2H), 7.29 (d, 1H)

(Step 2) Preparation of 6-nitro-3-(triphenylmethyl)-2,3-dihydro-1,3-benzoxazol-2-one (Compound 10-b)

To a solution of the compound 10-a (0.50 g, 2.8 mmol) in methylene chloride (20 mL) was added triethylamine (1.1 mL) and triphenylmethyl chloride (TrCl, 930 mg, 3.33 mmol) in order at 0° C., and the mixture was stirred for 9 hours at room temperature. Upon the completion of the reaction, the mixture was diluted with distilled water, and extracted with ethyl acetate. The organic layer was dried over anhydrous sodium sulfate and concentrated. The residue was treated with diethyl ether, and the precipitated was collected, washed with n-hexane to obtain the title compound 10-b as a beige solid quantitatively (1.26 g).

MS m/z: 423 [M+1]$^+$ $^1$H NMR (CDCl$_3$, 400 MHz), δ ppm: 8.01 (d, 1H), 7.82 (dd, 1H), 7.45-7.29 (m, 15H), 6.15 (d, 1H)

(Step 3) Preparation of 6-amino-3-(triphenylmethyl)-2,3-dihydro-1,3-benzoxazol-2-one (Compound 10-c)

To a solution of the compound 10-b (1.26 g, 2.78 mmol) in methanol (20 mL) was added with Pd/C (10% by weight, 0.63 g), and it was stirred for 3 hours at room temperature under hydrogen (1 atm). The catalyst was removed by filtration through a Celite pad. After washing with methanol, the filtrate was concentrated under reduced pressure to obtain the title compound 10-c as a beige solid quantitatively (1.21 g).

MS m/z: 393 [M+1]$^+$ $^1$H NMR (CDCl$_3$, 400 MHz), δ ppm: 7.47-7.21 (m, 15H), 7.12 (d, 1H), 6.50 (d, 1H), 6.13 (dd, 1H), 5.81 (d, 1H), 3.55 (br, 2H)

(Step 4) Preparation of ethyl N-[2-oxo-3-(triphenylmethyl)-2,3-dihydro-1,3-benzoxazol-6-yl]carbamate (Compound 10-d)

To a solution of the compound 10-c (1.21 g, 2.78 mmol) in methylene chloride (10 mL) was added 1 N aqueous solution of sodium carbonate (4.2 mL) and ethyl chloroformate (0.32 mL, 3.33 mmol) at 0° C. The reaction mixture was stirred for 2 hours at room temperature. Upon the completion of the reaction, the mixture was diluted with distilled water, and extracted with methylene chloride. The organic layer was dried over anhydrous sodium sulfate, and concentrated. The residue was purified by silica gel column chromatography (ethyl acetate:n-hexane=1:9) to obtain the title compound 10-d as a white solid (0.84 g, 65%).

MS m/z: 465 [M+1]$^+$ $^1$H NMR (DMSO-d$_6$, 400 MHz), δ ppm: 9.64 (s, 1H), 7.49-7.24 (m, 15H), 6.83 (d, 1H), 5.94 (d, 1H), 5.72 (s, 1H), 4.09 (m, 2H), 1.21 (t, 3H)

(Step 5) Preparation of 6-[5-(hydroxymethyl)-2-oxo-1,3-oxazolidin-3-yl]-3-(triphenylmethyl)-2,3-dihydro-1,3-benzoxazol-2-one (Compound 10-e)

To a solution of the compound 10-d (840 mg, 1.81 mmol) in a mixture solvent of tetrahydrofuran (4 mL) and N,N-dimethylformamide (2 mL) was dropwise added 2.2 M lithium tert-butoxide (1.54 mL, 3.08 mmol) at 0° C. After stirring for 30 minutes at 0° C., R-(−)-glycine butyrate (0.4 mL, 2.8 mmol) and methanol (0.08 mL) was added in order, and the reaction mixture was stirred for 4 hours at room temperature. After adding a saturated aqueous solution of ammonia chloride to quench the reaction, the mixture was extracted with ethyl acetate. The organic layer was washed with distilled water, dried over anhydrous sodium sulfate, and concentrated. The residue was then purified by silica gel column chromatography (ethyl acetate:n-hexane=55:45) to obtain the title compound 10-e as a pink solid (563 mg, 63%).

MS m/z: 493 [M+1]$^+$ $^1$H NMR (CDCl$_3$, 400 MHz), δ ppm: 7.49-7.22 (m, 16H), 6.93 (dd, 1H), 5.99 (d, 1H), 4.72 (m, 1H), 3.99-3.88 (m, 3H), 3.76-3.71 (m, 1H), 1.86 (t, 1H).

(Step 6) Preparation of 6-[5-(hydroxymethyl)-2-oxo-1,3-oxazolidin-3-yl]-2,3-dihydro-1,3-benzoxazol-2-one (Compound 10-f)

To a solution of the compound 10-e (0.35 g, 0.71 mmol) in methylene chloride (2 mL) was added anisole (0.2 mL)

and trifluoroacetic acid (1.5 mL) in order, and the reaction mixture was stirred for 14 hours at room temperature. Upon the completion of the reaction, the solvent was removed by concentration under reduced pressure and diethyl ether was added to the residue. The precipitate was collected and washed with diethyl ether to obtain the title compound 10-f as a pink solid quantitatively (0.18 g).

MS m/z: 251 [M+1]$^+$
$^1$H NMR (DMSO-d$_6$, 400 MHz), δ ppm: 11.66 (br, 1H), 7.57 (s, 1H), 7.26 (dd, 1H), 7.12 (d, 1H), 5.05 (m, 1H), 4.70-4.62 (m, 2H), 4.21 (t, 1H), 3.91 (dd, 1H)

(Step 7) Preparation of [2-oxo-3-(2-oxo-2,3-dihydro-1,3-benzoxazol-6-yl)-1,3-oxazolidin-5-yl] methyl methanesulfonate (Compound 10-g)

To a solution of the compound 10-f (0.18 g, 0.71 mmol) in methylene chloride (3 mL) was added triethylamine (0.15 mL, 1.06 mmol) and methanesulfonyl chloride (0.07 mL, 0.85 mmol) in order at 0° C., and the mixture was stirred for 1 hour. Upon the completion of the reaction, the mixture was diluted with distilled water (20 mL) and extracted with methylene chloride. The organic layer was washed with distilled water, dried over anhydrous sodium sulfate, and concentrated. The residue was treated with diethyl ether so as to produce a solid. The precipitate was collected and washed with diethyl ether to obtain the title compound 10-g as a beige solid (0.21 g, 90%).

MS m/z: 329 [M+1]$^+$
$^1$H NMR (DMSO-d$_6$, 400 MHz), δ ppm: 7.79-7.74 (m, 1H), 7.57-7.52 (m, 1H), 7.42-7.36 (m, 1H), 5.08 (m, 1H), 4.72-4.49 (m, 2H), 4.23 (t, 1H), 3.94 (dd, 1H), 3.67 (s, 3H)

(Step 8) Preparation of 6-[5-(azidomethyl)-2-oxo-1,3-oxazolidin-3-yl]-2,3-dihydro-1,3-benzoxazol-2-one (Compound 10-h)

To a solution of the compound 10-g (0.21 g, 0.64 mmol) in N,N-dimethylformamide (3 mL) was added with sodium azide (0.10 g, 1.60 mmol), and the mixture was stirred for 3 hours at 90° C. Upon the completion of the reaction, the mixture was cooled to room temperature, diluted with distilled water, and extracted with ethyl acetate. The organic layer was washed with distilled water, dried over anhydrous sodium sulfate, and concentrated. The residue was purified by silica gel column chromatography (ethyl acetate:n-hexane=1:1) to obtain the title compound 10-h as a beige solid (33 mg, 18%).

MS m/z: 276 [M+1]$^+$
$^1$H NMR (DMSO-d$_6$, 400 MHz), δ ppm: 11.65 (br, 1H), 7.60 (s, 1H), 7.27 (d, 1H), 7.11 (d, 1H), 4.88 (m, 1H), 4.14 (t, 1H), 3.82-3.64 (m, 3H)

(Step 9) Preparation of 6-[5-(aminomethyl)-2-oxo-1,3-oxazolidin-3-yl]-2,3-dihydro-1,3-benzoxazol-2-one (Compound 10-i)

To a solution of the compound 10-h (82 mg, 0.30 mmol) in methanol (5 mL) was added Pd/C (10% by weight, 50 mg), and the mixture was stirred for 5 hours at room temperature under hydrogen (1 atm). The catalyst was removed by filtration through a Celite pad. After washing with methanol, the filtrate was concentrated under reduced pressure to obtain the title compound 10-i as a beige solid (45 mg, 60%).

MS m/z: 250 [M+1]$^+$
$^1$H NMR (DMSO-d$_6$, 400 MHz), δ ppm: 7.53 (s, 1H), 7.20 (d, 1H), 7.03 (d, 1H), 4.56 (m, 1H), 4.01 (t, 1H), 3.82 (t, 1H), 2.83-2.73 (m, 2H)

(Step 10) Preparation of N-{[(5S)-2-oxo-3-(2-oxo-2,3-dihydro-1,3-benzoxazol-6-yl)-1,3-oxazolidin-5-yl]methyl}-2-({[3-(trifluoromethoxy)phenyl]methyl}amino)pyrimidine-5-carboxamide (Compound 10)

Except that, instead of the compound im-7 and the compound 1-b described in Example 1-1, the compound 10-i and the compound im-2b are used respectively, the reaction was carried out in the same manner as the Step 3 of Example 1-1 to obtain the title compound 10.

MS m/z: 545 [M+1]$^+$
$^1$H NMR (DMSO-d$_6$, 400 MHz), δ ppm: 11.62 (m, 1H), 8.67-8.67 (m, 3H), 8.40 (t, 1H), 7.58-7.02 (m, 7H), 4.81 (m, 1H), 4.59 (d, 2H), 4.15 (t, 1H), 3.86-3.81 (m, 1H), 3.64-3.52 (m, 2H)

[Example 1-11] Preparation of 3-[2-oxo-5-({[2-({[3-(trifluoromethoxy)phenyl]methyl}amino)pyrimidin-5-yl]formamido}methyl)-1,3-oxazolidin-3-yl] benzoic Acid (Compound 11)

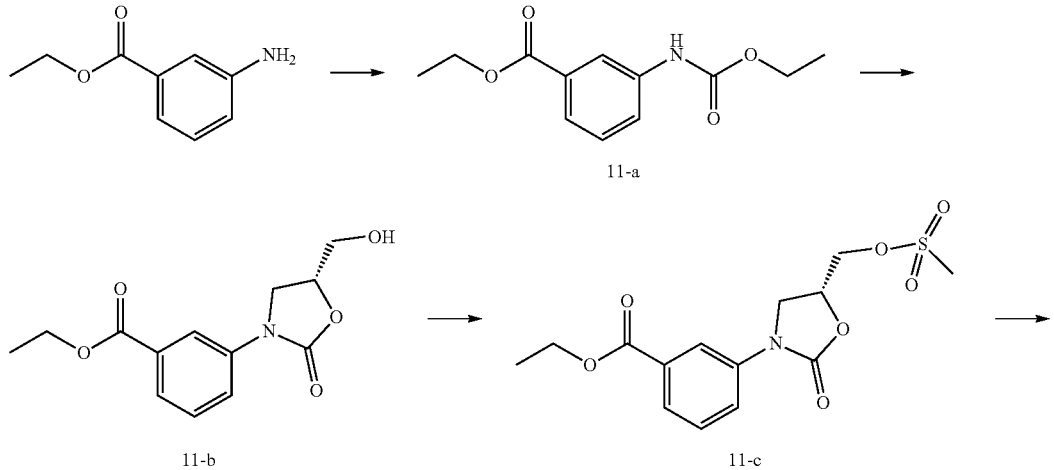

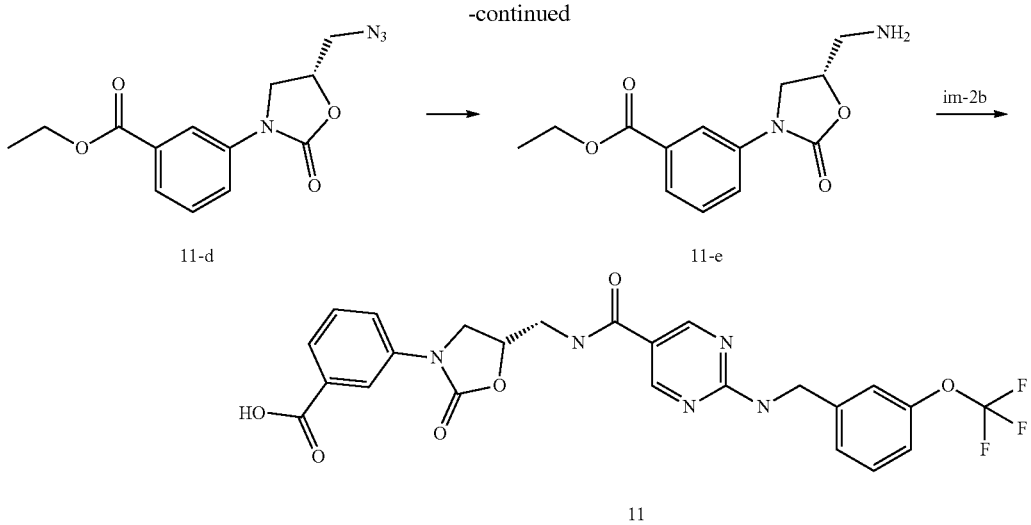

(Step 1) Preparation of ethyl 3-[(ethoxycarbonyl)amino]benzoate (Compound 11-a)

By using ethyl 3-aminobenzoate (1.0 g, 6.05 mmol) instead of the compound 10-c, the reaction was carried out in the same manner as the Step 4 of Example 1-10 to obtain the title compound 11-a as a pink solid (1.4 g, 98%).

MS m/z: 238 [M+1]$^+$ $^1$H NMR (CDCl$_3$, 400 MHz), δ ppm: 7.92 (s, 1H), 7.78-7.72 (m, 2H), 7.39 (t, 1H), 6.67 (br, 1H), 4.37 (m, 2H), 4.24 (m, 2H), 1.39 (t, 3H), 1.32 (t, 3H)

(Step 2) Preparation of ethyl 3-[(5R)-5-(hydroxymethyl)-2-oxo-1,3-oxazolidin-3-yl]benzoate (Compound 11-b)

By using the compound 11-a (1.0 g, 4.2 mmol), which has been prepared in the above (Step 1), instead of the compound 10-d, the reaction was carried out in the same manner as the Step 5 of Example 1-10 to obtain the title compound 11-b as a light pink solid (0.9 g, 83%).

MS m/z: 266 [M+1]$^+$ $^1$H NMR (CDCl$_3$, 400 MHz), δ ppm: 8.30-8.15 (m, 2H), 8.05 (d, 1H), 7.69 (t, 1H), 5.02 (m, 1H), 4.61 (m, 2H), 4.38-4.20 (m, 3H), 4.08-3.39 (m, 1H), 2.29 (t, 1H), 1.63 (t, 3H)

(Step 3) Preparation of ethyl 3-[(5R)-5-[(methanesulfonyloxy)methyl]-2-oxo-1,3-oxazolidin-3-yl]benzoate (Compound 11-c)

By using the compound 11-b (0.4 g, 1.5 mmol), which has been prepared in the above (Step 2), instead of the compound 10-f, the reaction was carried out in the same manner as the Step 7 of Example 1-10 to obtain the title compound 11-c as a pink liquid quantitatively (0.6 g).

MS m/z: 344 [M+1]$^+$ $^1$H NMR (CDCl$_3$, 400 MHz), δ ppm: 8.02-7.94 (m, 2H), 7.84 (d, 1H), 7.47 (t, 1H), 4.97 (m, 1H), 4.56-4.36 (m, 4H), 4.23 (t, 1H), 4.02 (m, 1H), 3.93 (s, 2H), 3.11 (s, 3H), 1.40 (t, 3H)

(Step 4) Preparation of ethyl 3-[(5R)-5-(azidomethyl)-2-oxo-1,3-oxazolidin-3-yl]benzoate (Compound 11-d)

By using the compound 11-c (0.6 g, 1.5 mmol), which has been prepared in the above (Step 3), instead of the compound 10-g, the reaction was carried out in the same manner as the Step 8 of Example 1-10 to obtain the title compound 11-d as a beige solid (0.2 g, 47%).

MS m/z: 291 [M+1]$^+$ $^1$H NMR (CDCl$_3$, 400 MHz), δ ppm: 8.07-8.04 (m, 1H), 7.92 (s, 1H), 7.84 (d, 1H), 7.47 (t, 1H), 4.82 (m, 1H), 4.39 (m, 2H), 4.16 (t, 1H), 3.93 (m, 1H), 3.74 (dd, 1H), 3.62 (dd, 1H), 1.41 (t, 3H)

(Step 5) Preparation of ethyl 3-[(5S)-5-(aminomethyl)-2-oxo-1,3-oxazolidin-3-yl]benzoate (Compound 11-e)

By using the compound 11-d (0.2 g, 0.7 mmol), which has been prepared in the above (Step 4), instead of the compound 10-h, the reaction was carried out in the same manner as the Step 9 of Example 1-10 to obtain the title compound 11-e as a yellow liquid (0.18 g, 95%).

MS m/z: 265 [M+1]$^+$ $^1$H NMR (CDCl$_3$, 400 MHz), δ ppm: 8.08-8.06 (m, 1H), 7.94 (s, 1H), 7.81 (d, 1H), 7.45 (t, 1H), 4.71 (m, 1H), 4.38 (m, 2H), 4.11 (t, 1H), 3.94 (m, 1H), 3.18-2.92 (m, 2H), 1.40 (t, 3H)

(Step 6) Preparation of 3-[2-oxo-5-({[2-({[3-(trifluoromethoxy)phenyl]methyl}amino)pyrimidin-5-yl]formamido}methyl)-1,3-oxazolidin-3-yl]benzoic Acid (Compound 11)

Except that, instead of the compound im-7 and the compound 1-b described in Example 1-1, the compound 11-e and the compound im-2b are used respectively, the reaction was carried out in the same manner as the Step 3 of Example 1-1 to obtain the title compound 11.

MS m/z: 532 [M+1]$^+$ $^1$H NMR (DMSO-d$_6$, 400 MHz), δ ppm: 13.10 (br, 1H), 8.75-8.66 (m, 3H), 8.39 (t, 1H), 8.14 (s, 1H), 7.78-7.66 (m, 2H), 7.54-7.41 (m, 2H), 7.35-7.19 (m, 3H), 4.84 (m, 1H), 4.59 (d, 2H), 4.21 (t, 1H), 3.92 (dd, 1H), 3.64-3.59 (m, 2H)

Example 2

[Example 2-1] Preparation of 1-(4-{2-[(2,3-dihydro-1H-inden-2-yl)amino]pyrimidin-5-yl}piperazin-1-yl)-3-{1H,4H,5H,6H,7H-[1,2,3]triazolo[4,5-c]pyridin-5-yl}propan-1-one (Compound 12)

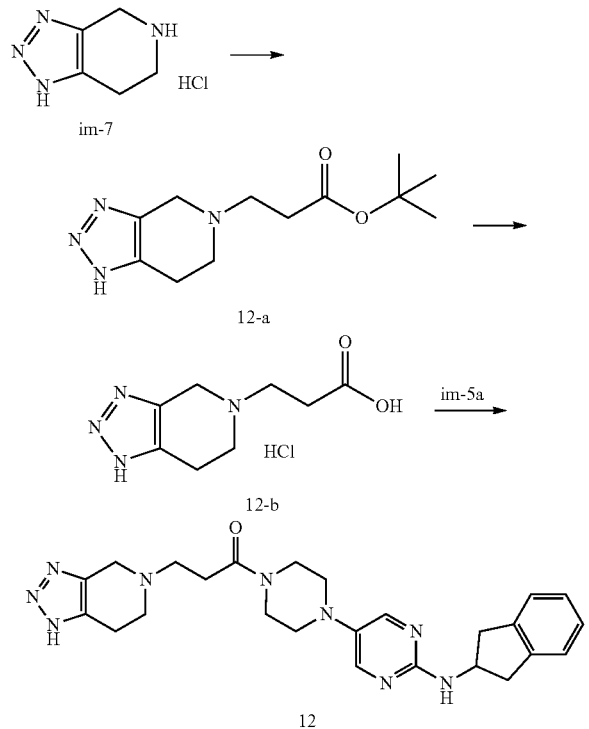

(Step 1) Preparation of tert-butyl 3-{1H,4H,5H,6H,7H-[1,2,3]triazolo[4,5-c]pyridin-5-yl}propanoate (Compound 12-a)

To a solution of the compound im-7 (0.1 g, 0.62 mmol) in methylene chloride (1 mL) was added tert-butyl acrylate (0.1 mL, 0.68 mmol) and triethylamine (0.2 mL, 1.6 mmol) at 0° C. under nitrogen atmosphere, and the mixture was stirred for 6 hours at room temperature. After cooling the reaction mixture to room temperature, the solvent was concentrated under reduced pressure. The residue was purified by silica gel column chromatography (methanol methylene chloride=3:97) to obtain the title compound 12-a as colorless liquid (99 mg, 67%).

MS m/z: 253 [M+1]$^+$ $^1$H NMR (CDCl$_3$, 400 MHz), δ ppm: 3.89 (s, 2H), 3.41 (s, 2H), 3.01 (t, 2H), 2.91-2.88 (m, 2H), 1.49 (s, 9H)

(Step 2) Preparation of 3-{1H,4H,5H,6H,7H-[1,2,3]triazolo[4,5-c]pyridin-5-yl}propanoic Acid (Compound 12-b)

To a solution of the compound 12-a (99 mg, 0.42 mmol) in methylene chloride (1 mL) was slowly added 4 N hydrogen chloride dioxane solution (1 mL) at 0° C., and the mixture was stirred for 2 hours at room temperature. The solvent was removed by concentration under reduce pressure to obtain the title compound 12-b as a white liquid quantitatively (90 mg).

MS m/z: 197 [M+1]$^+$ (Step 3) 1-(4-{2-[(2,3-dihydro-1H-inden-2-yl)amino]pyrimidin-5-yl}piperazin-1-yl)-3-{1H,4H,5H,6H,7H-[1,2,3]triazolo[4,5-c]pyridin-5-yl}propan-1-one (Compound 12)

To a solution of the compound 12-b (49 mg, 0.21 mmol) and the compound im-5a (60 mg, 0.16 mmol) in N,N-dimethylformamide (2 mL) was added N,N-diisopropylethylamine (0.14 mL, 0.80 mmol) and benzotriazol-1-yl oxytripyrrolidinophosphonium hexafluorophosphate (0.13 g, 0.24 mmol) in order at 0° C., and the mixture was stirred for 3 hours at room temperature under nitrogen stream. Upon the completion of the reaction, the mixture was diluted with distilled water (30 mL) and extracted with ethyl acetate. The organic layer was washed with distilled water and saturated brine, dried over anhydrous sodium sulfate, and then concentrated. The residue was purified by silica gel column chromatography (methanol methylene chloride=5:95) to obtain the title compound 12 as an ivory solid (27 mg, 36%).

MS m/z: 474 [M+1]$^+$ $^1$H NMR (CDCl$_3$, 400 MHz), δ ppm: 8.07 (s, 2H), 7.24-7.18 (m, 4H), 5.16 (m, 1H), 4.74 (m, 1H), 3.84-3.62 (m, 6H), 3.42-3.34 (m, 2H), 3.04-2.82 (m, 12H), 2.82-2.62 (m, 2H)

[Example 2-2] Preparation of 3-{1H,4H,5H,6H,7H-[1,2,3]triazolo[4,5-c]pyridin-5-yl}-1-{4-[2-({[3(trifluoromethoxy)phenyl]methyl}amino)pyrimidin-5-yl]piperazin-1-yl}propan-1-one (Compound 13)

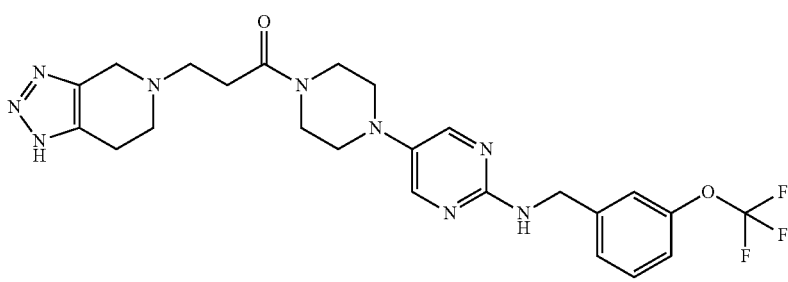

Except that the compound im-5b is used instead of the compound im-5a, the reaction was carried out in the same manner as Example 2-1 to obtain the title compound 13 as a yellow solid.

MS m/z: 532 [M+1]+

$^1$H NMR (CDCl$_3$, 400 MHz), δ ppm: 8.06 (s, 2H), 7.34 (t, 1H), 7.28 (d, 1H), 7.20 (s, 1H), 7.12 (d, 1H), 5.43 (t, 1H), 4.64 (d, 2H), 3.79 (br, 2H), 3.75 (s, 2H), 3.65 (br, 2H), 3.03-2.97 (m, 6H), 2.91-2.87 (m, 4H), 2.67 (t, 2H)

[Example 2-3] Preparation of 1-(4-{2-[(2,3-dihydro-1H-inden-2-yl)amino]pyrimidin-5-yl}piperidin-1-yl)-3-{1H,4H,5H,6H,7H-[1,2,3]triazolo[4,5-c]pyridin-5-yl}propan-1-one (Compound 14)

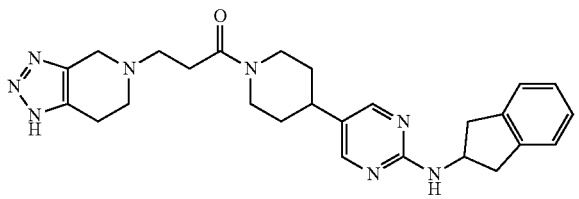

14

Except that the compound im-6 is used instead of the compound im-5a, the reaction was carried out in the same manner as Example 2-1 to obtain the title compound 14.

MS m/z: 473 [M+1]+

$^1$H NMR (DMSO-d$_6$, 400 MHz), δ ppm: 8.20 (s, 2H), 7.29 (d, 1H), 7.29-7.13 (m, 4H), 5.76 (s, 1H), 4.58-4.52 (m, 2H), 4.06-4.03 (m, 1H), 3.60 (s, 2H), 3.25-3.04 (m, 3H), 2.89-2.56 (m, 12H), 1.75-1.39 (m, 4H)

[Example 2-4] Preparation of 4-[3-(4-{2-[(2,3-dihydro-1H-inden-2-yl)amino]pyrimidin-5-yl}piperazin-1-yl)-3-oxopropyl]piperazine-1-sulfonamide (Compound 15)

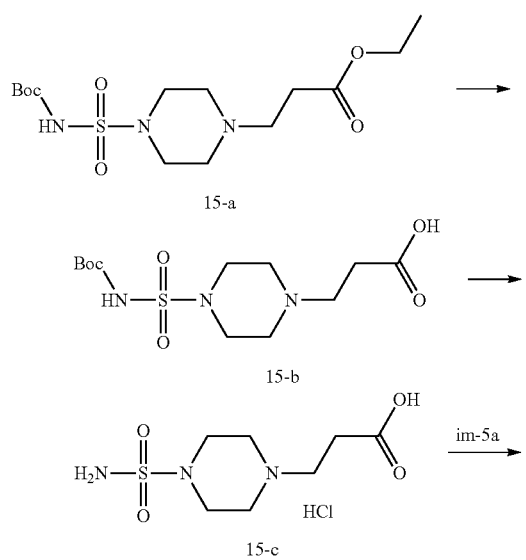

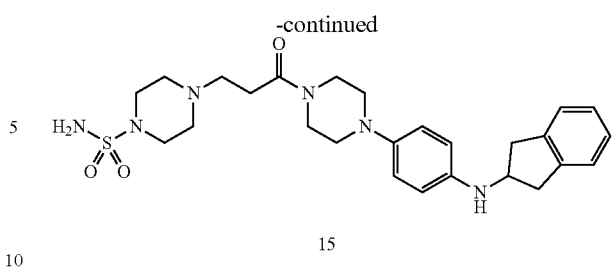

15

(Step 1) Preparation of ethyl 3-[4-({[(tert-butoxy)carbonyl]amino}sulfonyl)piperazin-1-yl]propanoate (Compound 15-a)

Chlorosulfonyl isocyanate (0.11 mL, 1.30 mmol) and tert-butanol (0.12 mL, 1.30 mmol) was added successively to methylene chloride (2 mL) at 0° C., and the mixture was stirred for 30 minutes at room temperature under nitrogen stream, and cooled again to 0° C. To a reaction mixture a solution of ethyl ester of 3-(piperazin-1-yl)propionic acid (240 mg, 1.082 mmol) in methylene chloride (3 mL) and triethylamine (0.75 mL, 5.41 mol) was slowly added successively, and the mixture was stirred for 14 hours at room temperature. Upon the completion of the reaction, 2 N aqueous hydrochloric acid solution (20 mL) was added and the mixture was extracted with ethyl acetate. The organic layer was washed with distilled water and saturated brine, dried over anhydrous sodium sulfate, and then concentrated. The residue was purified by silica gel column chromatography (ethyl acetate n-hexane=5:5→methanol:methylene chloride=1:9) to obtain the title compound 15-a as a yellow solid (174 mg, 44%).

MS m/z: 366 [M+1]+.

$^1$H NMR (DMSO-d$_6$, 400 MHz), δ ppm: 4.72-4.09 (m, 2H), 3.43 (s, 4H), 2.79-2.52 (m, 8H), 1.49 (s, 9H), 1.28-1.24 (m, 3H)

(Step 2) Preparation of 3-[4-({[(tert-butoxy)carbonyl]amino}sulfonyl)piperazin-1-yl]propanoic Acid (Compound 15-b)

To a solution of the compound 15-a (174 mg, 0.476 mmol) in a mixture solvent of tetrahydrofuran (2 mL) and distilled water (1 mL) was added lithium hydroxide (110 mg, 2.63 mmol), and the mixture was stirred for 5 hours at room temperature. Upon the completion of the reaction, the solvent was removed by concentration under reduced pressure, and the residue was purified by silica gel column chromatography (methanol:methylene chloride=1:9→2:8) to obtain the title compound 15-b as a white solid (95 mg, 59%).

MS m/z: 338 [M+1]+

$^1$H NMR (DMSO-d$_6$, 400 MHz), δ ppm: 3.17-3.14 (m, 4H), 2.57 (t, 2H), 2.43 (s, 4H), 2.37 (t, 2H)

(Step 3) Preparation of 3-(4-sulfamoylpiperazin-1-yl)propanoic Acid Hydrochloride (Compound 15-c)

To a solution of the compound 15-b (95 mg, 0.28 mmol) in methylene chloride (1 mL) was added 4 N hydrogen chloride dioxane solution (1 mL) and the mixture was stirred for 15 hours at room temperature. Upon the completion of the reaction, the solvent was concentrated under reduced pressure to obtain the title compound 15-c as a white solid quantitatively (72 mg).

MS m/z: 238 [M+1]+

¹H NMR (DMSO-d₆, 400 MHz), δ ppm: 7.11 (s, 2H), 3.65-3.12 (m, H), 2.80 (t, 2H)

(Step 4) Preparation of 4-[3-(4-{2-[(2,3-dihydro-1H-inden-2-yl)amino]pyrimidin-5-yl}piperazin-1-yl)-3-oxopropyl]piperazine-1-sulfonamide (Compound 15)

Except that, instead of the compound 12-b of Example 2-1, the compound 15-c is used, the reaction was carried out in the same manner as the Step 3 of Example 2-1 to obtain the title compound 15.
MS m/z: 514 [M+1]⁺
¹H NMR (DMSO-d₆, 400 MHz), δ ppm: 8.15 (s, 2H), 7.21-7.12 (m, 4H), 7.05 (d, 1H), 6.79 (s, 2H), 4.54-4.52 (m, 1H), 3.59-3.58 (m, 4H), 3.22 (dd, 2H), 2.97-2.82 (m, 12H), 2.58-2.53 (m, 4H)

[Example 2-5] Preparation of 6-[3-(4-{2-[(2,3-dihydro-1H-inden-2-yl)amino]pyrimidin-5-yl}piperidin-1-yl)-3-oxopropyl]-2,3-dihydro-1,3-benzoxazol-2-one (Compound 16)

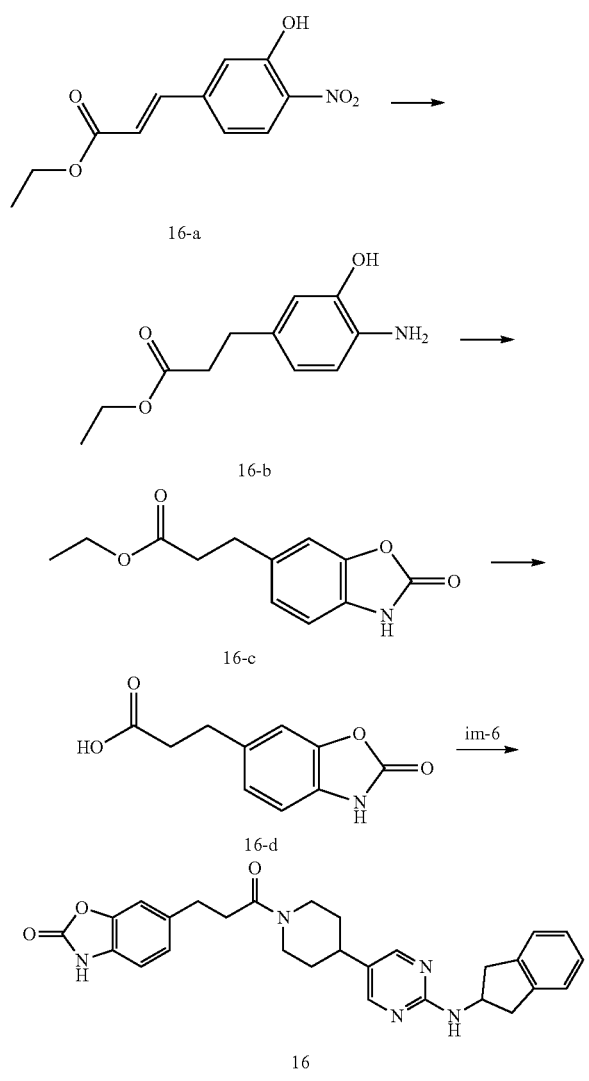

(Step 1) Preparation of ethyl (2E)-3-(3-hydroxy-4-nitrophenyl)prop-2-enoate (Compound 16-a)

To a solution of 3-hydroxy-4-nitrobenzaldehyde (0.50 g, 2.99 mmol) in N,N-dimethylformamide (5 mL) was added triethyl phosphonoacetate (1.32 mL, 6.59 mmol) and sodium ethoxide (0.45 g, 6.59 mmol) in order, and the mixture was stirred for 14 hours at room temperature. The reaction was terminated by adding 2 N aqueous hydrochloric acid (8 mL), and the precipitate was collected, washed with distilled water and n-hexane, and dried under reduced pressure to obtain the title compound 16-a as a yellow solid. (0.52 g, 74%).
MS m/z: 238 [M+1]⁺
¹H NMR (CDCl₃, 400 MHz), δ ppm: 10.61 (s, 1H), 8.14-8.12 (d, 1H), 7.63-7.59 (d, 1H), 7.15-7.13 (d, 1H), 6.56-6.52 (d, 1H), 4.29 (m, 2H), 1.35 (t, 3H)

(Step 2) Preparation of ethyl 3-(4-amino-3-hydroxyphenyl)propanoate (Compound 16-b)

To a solution of the compound 16-a (0.77 g, 3.25 mmol) in methanol (50 mL) was added Pd/C (10% by weight, 1.4 g) and the mixture was stirred for 15 hours under hydrogen pressure (1 atm). Upon the completion of the reaction, the catalyst was removed by filtration through a Celite pad. The filtrate was concentrated under reduced pressure to obtain the title compound 16-b as a grey solid (0.62 g, 91%).
MS m/z: 210 [M+1]⁺
¹H NMR (DMSO-d₆, 400 MHz), δ ppm: 8.87 (br, 1H), 6.51-6.36 (m, 3H), 4.36 (br, 2H), 4.02 (m, 2H), 2.62 (t, 2H), 2.46 (t, 2H), 1.15 (t, 3H)

(Step 3) Preparation of ethyl 3-(2-oxo-2,3-dihydro-1,3-benzoxazol-6-yl)propanoate (Compound 16-c)

To a solution of the compound 16-b (0.70 g, 3.34 mmol) in tetrahydrofuran (16 mL) was added 1,1'-carbonyldiimidazole (0.91 g, 5.61 mmol) under stirring, and the mixture was stirred under reflux for 15 hours. Upon the completion of the reaction, the mixture was cooled to room temperature, diluted with distilled water and extracted with ethyl acetate. The organic layer was washed with distilled water and saturated brine, dried over anhydrous sodium sulfate, and concentrated to obtain the title compound 16-c as a pink solid (0.74 g, 94%).
MS m/z: 236 [M+1]⁺
¹H NMR (DMSO-d₆, 400 MHz), δ ppm: 11.56 (br, 1H), 7.18 (s, 1H), 7.01-6.96 (m, 2H), 4.03 (m, 2H), 2.85 (t, 2H), 2.62 (t, 2H), 1.15 (t, 3H)

(Step 4) Preparation of 3-(2-oxo-2,3-dihydro-1,3-benzoxazol-6-yl)propanoic Acid (Compound 16-d)

The compound 16-c (0.74 g, 3.14 mmol) was dissolved in tetrahydrofuran (16 mL), and after adding 1 N aqueous solution of lithium hydroxide (15 mL) thereto, the mixture was stirred for 5 hours at room temperature. Upon the completion of the reaction, 2 N aqueous hydrochloric acid solution was added to adjust pH 2 or less. Half amount of the solvent was removed by concentration under reduced pressure, and the solid was filtered out. The filtrate was extracted with methylene chloride, and the organic layer was washed with distilled water and saturated brine, dried over anhydrous sodium sulfate, and then concentrated under reduced pressure to obtain the title compound 16-d as a yellow solid (0.63 g, 97%).

MS m/z: 208 [M+1]+

¹H NMR (DMSO-d₆, 400 MHz), δ ppm: 12.88-11.02 (m, 2H), 7.18 (s, 1H), 7.12-6.94 (m, 2H), 2.82 (t, 2H), 2.58-2.50 (m, 2H), (Step 5) Preparation of 6-[3-(4-{2-[(2,3-dihydro-1H-inden-2-yl)amino]pyrimidin-5-yl}piperidin-1-yl)-3-oxopropyl]-2,3-dihydro-1,3-benzoxazol-2-one (Compound 16)

Except that, instead of the compound 12-b and im-5a described in Example 2-1, the compound 16-d and the compound in-6 are used respectively, the reaction was carried out in the same manner as the Step 3 of Example 2-1 to obtain the title compound 16.

MS m/z: 484 [M+1]+

¹H NMR (DMSO-d₆, 400 MHz), δ ppm: 9.73 (br, 1H), 8.08 (s, 2H), 7.27 (s, 1H), 7.22-7.15 (m, 4H), 7.07 (s, 1H), 6.94 (d, 1H), 6.88 (d, 1H), 5.45 (d, 1H), 7.83-4.47 (m, 2H), 3.93 (d, 1H), 3.49 (s, 2H), 3.38 (dd, 2H), 3.12-2.94 (m, 3H), 2.87 (dd, 2H), 2.78-2.52 (m, 4H), 2.12-1.74 (m, 4H), 1.54-1.41 (m, 1H), 1.34-1.21 (m, 1H)

Example 3

[Example 3-1] Preparation of 1-(4-{2-[(2,3-dihydro-1H-inden-2-yl)amino]pyrimidin-5-yl}piperazin-1-yl)-2-{1H,4H,5H,6H,7H-[1,2,3]triazolo[4,5-c]pyridin-5-yl}ethan-1-one (Compound 17)

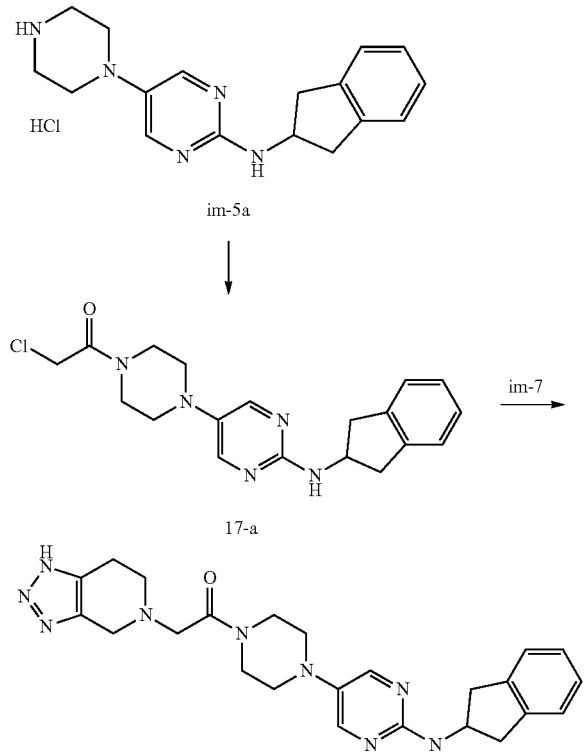

(Step 1) Preparation of 2-chloro-1-(4-{2-[(2,3-dihydro-1H-inden-2-yl)amino]pyrimidin-5-yl}piperazin-1-yl)ethan-1-one (Compound 17-a)

The compound im-5a (80 mg, 0.22 mmol) was dissolved in methylene chloride (3 mL). Under stirring at 0° C., triethylamine (0.1 mL) and chloroacetyl chloride (0.02 mL, 0.24 mmol) was added dropwise thereto in order followed by stirring for 20 minutes at 0° C. Upon the completion of the reaction, the mixture was diluted with 10 mL of methanol and concentrated under reduced pressure. The residue was purified by silica gel column chromatography (ethyl acetate:n-hexane=7:3) to obtain the title compound 17-a as a brown solid (74 mg, 91%).

MS m/z: 460 [M+1]+

¹H NMR (CDCl₃, 400 MHz), δ ppm: 8.09 (s, 2H), 7.24-7.14 (m, 4H), 5.22-5.19 (m, 1H), 4.74 (m, 1H), 4.11 (s, 2H), 3.82-3.65 (m, 4H), 3.42-3.34 (m, 2H), 3.08-2.98 (m, 4H), 2.90-2.82 (m, 2H).

(Step 2) Preparation of 1-(4-{2-[(2,3-dihydro-1H-inden-2-yl)amino]pyrimidin-5-yl}piperazin-1-yl)-2-{1H,4H,5H,6H,7H-[1,2,3]triazolo[4,5-c]pyridin-5-yl}ethan-1-one (Compound 17)

To a solution of the compound 17-a (73 mg, 0.20 mmol) in N,N-dimethylformamide (2 mL) was added dropwise a solution of the compound im-7 (70 mg, 0.44 mmol) and N,N-diisopropylethylamine (0.17 mL, 0.98 mmol) in N,N-dimethylformamide (1 mL), and the mixture was stirred for 14 hours at room temperature. Upon the completion of the reaction, the mixture was diluted with distilled water (20 mL) and extracted with ethyl acetate. The organic layer was washed with distilled water and saturated brine, dried over anhydrous sodium sulfate, and then concentrated. The residue was purified by silica gel column chromatography (methanol<methylene chloride=6:94) to obtain the title compound 17 as a yellow solid (36 mg, 40%).

MS m/z: 460 [M+1]+

¹H NMR (DMSO-d₆, 400 MHz), δ ppm: 11.39 (br, 1H), 8.07 (s, 2H), 7.24-7.17 (m, 4H), 5.20-5.16 (m, 2H), 4.74 (m, 1H), 3.82-3.74 (m, 6H), 3.50 (s, 2H), 3.37 (dd, 2H), 3.00-2.82 (m, 12H)

[Example 3-2] Preparation of 2-{1H,4H,5H,6H,7H-[1,2,3]triazolo[4,5-c]pyridin-5-yl}-1-{4-[2-({[3 trifluoromethoxy)phenyl]methyl}amino)pyrimidin-5-yl]piperazin-1-yl}ethan-1-one (Compound 18)

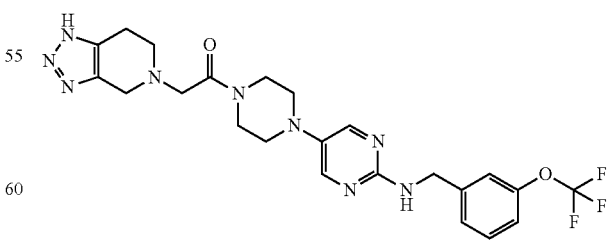

Except that the compound im-5b is used instead of the compound im-5a, the reaction was carried out in the same manner as the Example 3-1 to obtain the title compound 18.

MS m/z: 518 [M+1]+

¹H NMR (DMSO-d₆, 400 MHz), δ ppm: 8.10 (s, 2H), 7.44-7.39 (m, 2H), 7.32 (d, 1H), 7.24 (s, 1H), 7.19 (d, 1H), 4.48 (d, 2H), 3.65-3.58 (m, 6H), 3.45 (s, 2H), 2.93 (br, 4H), 2.81-2.67 (m, 4H)

[Example 3-3] Preparation of 1-(4-{2-[(2,3-dihydro-1H-inden-2-yl)amino]pyrimidin-5-yl}piperazin-1-yl)-2,2-dimethyl-3-{1H,4H,5H,6H,7H-[1,2,3]triazolo[4,5-c]pyridin-5-yl}propan-1-one (Compound 19)

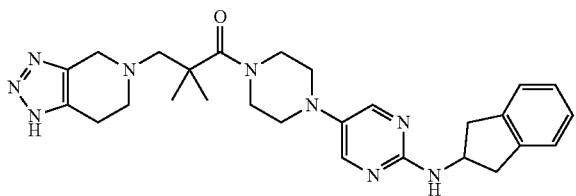

19

Except that 3-chloropivaloyl chloride is used instead of chloroacetyl chloride, the reaction was carried out in the same manner as the Example 3-1 to obtain the title compound 19 as a yellow solid.

MS m/z: 502 [M+1]⁺

¹H NMR (CDCl₃, 400 MHz), δ ppm: 7.99 (s, 2H), 7.26-7.15 (m, 4H), 5.39-5.37 (d, 1H), 4.73 (m, 1H), 3.84-3.76 (m, 6H), 3.41-3.35 (dd, 2H), 2.98-2.78 (m, 12H), 1.36 (s, 6H)

[Example 4-1] Preparation of 2-(4-{2-[(2,3-dihydro-1H-inden-2-yl)amino]pyrimidin-5-yl}piperazin-1-yl)-1-{1H,4H,5H,6H,7H-[1,2,3]triazolo[4,5-c]pyridin-5-yl}ethan-1-one (Compound 20)

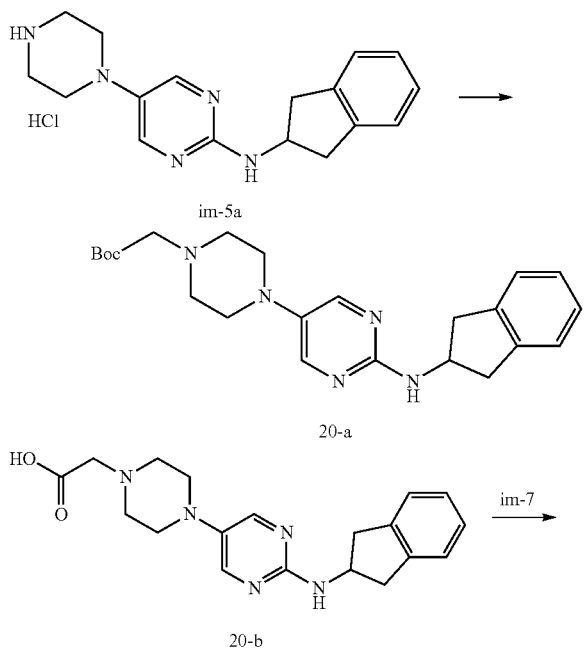

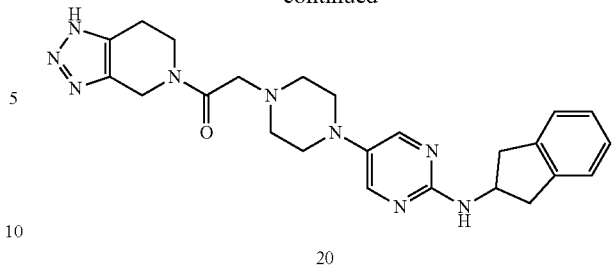

20

(Step 1) Preparation of tert-butyl 2-(4-{2-[(2,3-dihydro-1H-inden-2-yl)amino]pyrimidin-5-yl}piperazin-1-yl)acetate (Compound 20-a)

To a solution of the compound im-5a (0.10 g, 0.27 mmol) in methylene chloride (3 mL) was added dropwise triethylamine (0.19 mL, 1.35 mmol) and tert-butyl bromoacetate (0.06 mL, 0.40 mmol) in order, and the mixture was stirred for 14 hours at room temperature. Upon the completion of the reaction, the mixture was diluted with distilled water (20 mL) and extracted with methylene chloride. The organic layer was washed with distilled water and saturated brine, dried over anhydrous sodium sulfate, and then concentrated. The residue was purified by silica gel column chromatography (ethyl acetate:n-hexane=4:6) to obtain the title compound 20-a as a beige solid (93 mg, 84%).

MS m/z: 410 [M+1]⁺

¹H NMR (CDCl₃, 400 MHz), δ ppm: 8.08 (s, 2H), 7.24-7.15 (m, 4H), 5.11 (d, 1H), 4.72 (m, 1H), 3.38 (dd, 2H), 3.18 (s, 2H), 3.08 (t, 4H), 2.86 (dd, 2H), 2.75 (t, 4H), 1.48 (s, 9H)

(Step 2) Preparation of 2-(4-{2-[(2,3-dihydro-1H-inden-2-yl)amino]pyrimidin-5-yl}piperazin-1-yl)acetic acid (Compound 20-b)

To a solution of the compound 20-a (93 mg, 0.22 mmol) in methylene chloride (2 mL) was added trifluoroacetic acid (2 mL), and the mixture was stirred for 2 hours at room temperature. Upon the completion of the reaction, the solvent was concentrated under reduced pressure to obtain the title compound 20-b as a yellow solid quantitatively (130 mg).

MS m/z: 354 [M+1]⁺

¹H NMR (DMSO-d₆, 400 MHz), δ ppm: 8.18 (s, 2H), 7.20-7.11 (m, 4H), 4.84-3.92 (m, 7H), 3.59-3.29 (m, 4H), 3.21 (dd, 2H), 2.84 (dd, 2H)

(Step 3) Preparation of 2-(4-{2-[(2,3-dihydro-1H-inden-2-yl)amino]pyrimidin-5-yl}piperazin-1-yl)-1-{1H,4H,5H,6H,7H-[1,2,3]triazolo[4,5-c]pyridin-5-yl}ethan-1-one (Compound 20)

To a solution of the compound 20-b (130 mg, 0.22 mmol) and the compound im-7 (71 mg, 0.44 mmol) in N,N-dimethylformamide (3 mL) was slowly added N,N-diisopropylethylamine (0.19 mL, 1.10 mmol) and benzotriazol-1-yl oxy-tripyrrolidinophosphonium hexafluorophosphate (172 mg, 0.33 mmol) in order, and the reaction mixture was stirred for 15 hours at room temperature under nitrogen stream. Upon the completion of the reaction, the mixture was diluted with distilled water (50 mL) and extracted with ethyl acetate. The organic layer was washed with distilled water and saturated brine, dried over anhydrous sodium sulfate, and then concentrated. The residue was purified by silica gel column chromatography (methanol:methylene chloride=5:95) to obtain the title compound 20 as a white solid (12 mg, 12%).

MS m/z: 460 [M+1]$^+$ $^1$H NMR (CDCl$_3$, 400 MHz), δ ppm: 8.07 (d, 2H), 7.23-7.15 (m, 4H), 5.28-5.26 (m, 1H), 4.86 (d, 2H), 4.72 (m, 1H), 3.92 (m, 2H), 3.41-3.34 (m, 4H), 3.08-3.02 (m, 2H), 3.00-2.82 (m, 6H), 2.74-2.62 (m, 4H)

[Example 4-2] Preparation of 1-{1H,4H,5H,6H,7H-[1,2,3]triazolo[4,5-c]pyridin-5-yl}-2-{4-[2-({[3-(trifluoromethoxy)phenyl]methyl}amino)pyrimidin-5-yl]piperazin-1-yl}ethan-1-one (Compound 21)

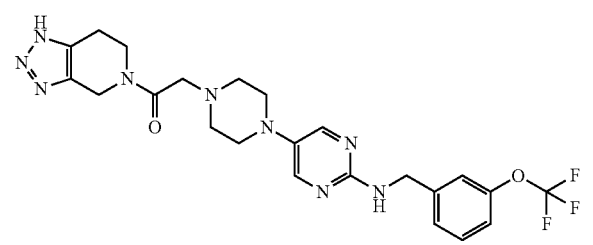

21

Except that the compound im-5b is used instead of the compound im-5a of Example 4-1, the reaction was carried out in the same manner as the Example 4-1 to obtain the title compound 21.

MS m/z: 518 [M+1]$^+$ $^1$H NMR (CDCl$_3$, 400 MHz), δ ppm: 11.49 (s, 1H), 8.08 (d, 2H), 7.33 (t, 1H), 7.20 (s, 1H), 7.11 (d, 1H), 5.24 (br, 1H), 4.89 (d, 2H), 4.64 (d, 2H), 3.96-3.90 (m, 2H), 3.40 (d, 2H), 3.06-2.88 (m, 6H), 2.70-2.66 (m, 4H)

[Example 4-3] Preparation of 2-(4-{2-[(2,3-dihydro-1H-inden-2-yl)amino]pyrimidin-5-yl}piperidin-1-yl)-1-{1H,4H,5H,6H,7H-[1,2,3]triazolo[4,5-c]pyridin-5-yl}ethan-1-one (Compound 22)

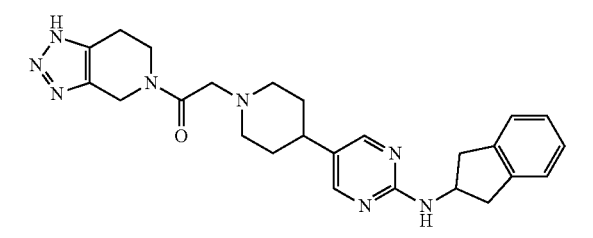

22

Except that the compound im-6 is used instead of the compound im-5a of Example 4-1, the reaction was carried out in the same manner as the Example 4-1 to obtain the title compound 22.

MS m/z: 459 [M+1]$^+$ $^1$H NMR (DMSO-d$_6$, 400 MHz), δ ppm: 8.21 (d, 2H), 7.29-7.27 (m, 1H), 7.14-7.12 (m, 4H), 4.83-4.54 (m, 3H), 3.85-3.78 (m, 2H), 3.28-3.19 (m, 4H), 2.83-2.82 (m, 5H), 2.70-2.67 (m, 1H), 2.13-2.08 (m, 2H), 1.74-1.45 (m, 4H)

[Example 4-4] Preparation of 3-(4-{2-[(2,3-dihydro-1H-inden-2-yl)amino]pyrimidin-5-yl}piperidin-1-yl)-1-{3H,4H,5H,6H,7H-[1,2,3]triazolo[4,5-c]pyridin-5-yl}propan-1-one (Compound 23)

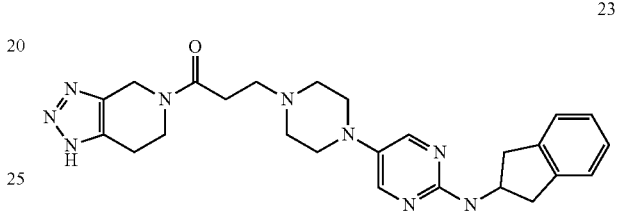

23

Except that ethyl bromopropionate is used instead of tert-butyl bromoacetate of Example 4-1, the reaction was carried out in the same manner as the Example 4-1 to obtain the title compound 23.

MS m/z: 474 [M+1]$^+$ $^1$H NMR (DMSO-d$_6$, 400 MHz), δ ppm: 8.07 (s, 2H), 7.22-7.15 (m, 4H), 5.19 (m, 1H), 4.80-4.71 (m, 3H), 3.95-3.77 (m, 2H), 3.41-3.35 (m, 2H), 3.06-3.02 (m, 4H), 2.89-2.83 (m, 6H), 2.73-2.71 (m, 6H)

[Example 475] Preparation of 1-(3-hydroxypyrrolidin-1-yl)-2-{4-[2-({[3-(trifluoromethoxy)phenyl]methyl}amino)pyrimidin-5-yl]piperazin-1-yl}ethan-1-one hydrochloride (Compound 24)

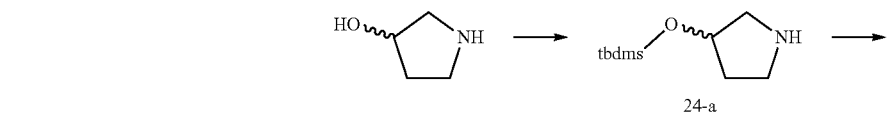

24-a

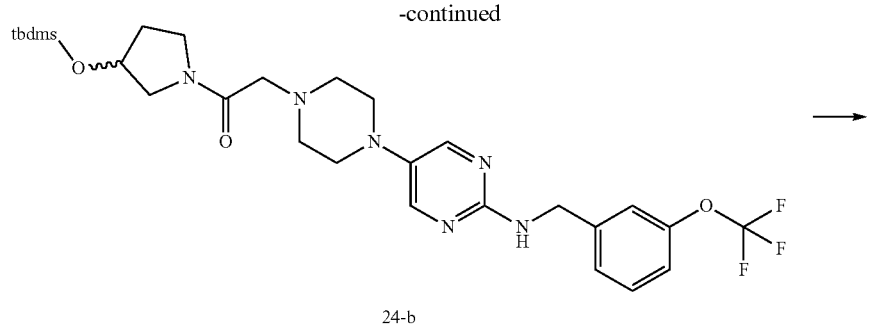

24-b

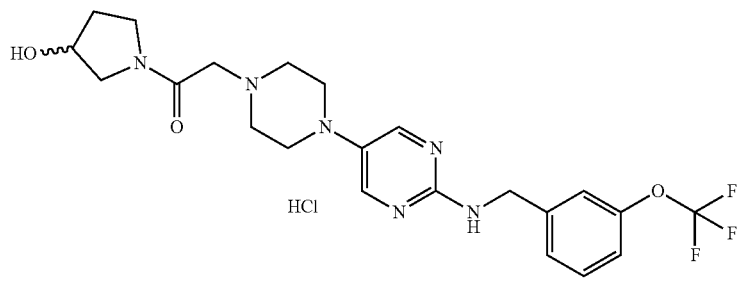

24

(Step 1) Preparation of 3-[(tert-butyldimethylsilyl)oxy]pyrrolidine (Compound 24-a)

To a solution of DL-3-Pyrrolidinol (0.10 g, 1.15 mmol) in methylene chloride (1 mL) was added imidazole (0.23 g, 3.45 mmol) and tert-butyldimethylsilyl chloride (0.26 g, 1.72 mmol) in order, and the mixture was stirred for 15 hours at room temperature under nitrogen stream. Upon the completion of the reaction, a saturated aqueous solution of sodium hydrogen carbonate was added and the mixture was extracted with ethyl acetate. The organic layer was washed with distilled water and saturated brine, dried over anhydrous sodium sulfate, and then concentrated to obtain the title compound 24-a as a crude brown liquid (0.25 g, crude).

MS m/z: 202 [M+1]$^+$ $^1$H NMR (CDCl$_3$, 400 MHz), δ ppm: 4.34 (s, 1H), 3.14-3.08 (m, 1H), 2.84-2.77 (m, 3H), 1.91-1.82 (m, 1H), 1.67-1.65 (m, 1H), 0.88 (s, 9H), 0.06 (s, 6H)

(Step 2) Preparation of 1-{3-[(tert-butyldimethylsilyl)oxy]pyrrolidin-1-yl}-2-{4-[2-({[3-(trifluoromethoxy)phenyl]methyl}amino)pyrimidin-5-yl]piperazin-1-yl}ethan-1-one (Compound 24-b)

Except that the compound 24-a (36 mg, 0.18 mmol) is used instead of the compound im-7 of Example 4-2, the reaction was carried out in the same manner as the Example 4-2 to obtain the title compound 24-b as a yellow solid (45 mg).

MS m/z: 595 [M+1]$^+$ $^1$H NMR (CDCl$_3$, 400 MHz), δ ppm: 8.07 (s, 2H), 7.34 (t, 1H), 2.28 (d, 1H), 7.20 (s, 1H), 7.11 (d, 1H), 5.32 (t, 1H), 4.64 (d, 2H), 4.45-4.39 (m, 2H), 3.71-3.41 (m, 4H), 3.21 (d, 2H), 3.07 (s, 4H), 2.72 (s, 4H), 1.99-1.86 (m, 2H), 0.88 (s, 9H), 0.08 (s, 6H)

(Step 3) Preparation of 1-(3-hydroxypyrrolidin-1-yl)-2-{4-[2-({[3-(trifluoromethoxy)phenyl]methyl}amino)pyrimidin-5-yl]piperazin-1-yl}ethan-1-one hydrochloride (Compound 24)

To a solution of the compound 24-b (45 mg, mmol) in methylene chloride (1 mL) was added 4 N hydrogen chloride dioxane solution (1 mL), and the mixture was stirred for 1 hour at room temperature. Upon the completion of the reaction, the reaction was quenched by adding ethyl acetate. The precipitate was collected and washed to obtain the title compound 24 as a yellow solid (20 mg, yield of the two-step reaction: 43%).

MS m/z: 481 [M+1]$^+$ $^1$H NMR (CDCl$_3$, 400 MHz), δ ppm: 10.02 (s, 1H), 8.14 (s, 2H), 7.56 (s, 1H), 7.40 (t, 1H), 7.30 (d, 1H), 7.22 (s, 1H), 7.18 (s, 1H), 4.47 (s, 2H), 4.35-4.13 (m, 4H), 3.22-2.99 (m, 4H), 1.92-1.70 (m, 2H)

[Example 4-6] Preparation of 1-(2-{4-[2-({[3-(trifluoromethoxy)phenyl]methyl}amino)pyrimidin-5-yl]piperazin-1-yl}acetyl)piperidine-4-carboxylic acid hydrochloride (Compound 25)

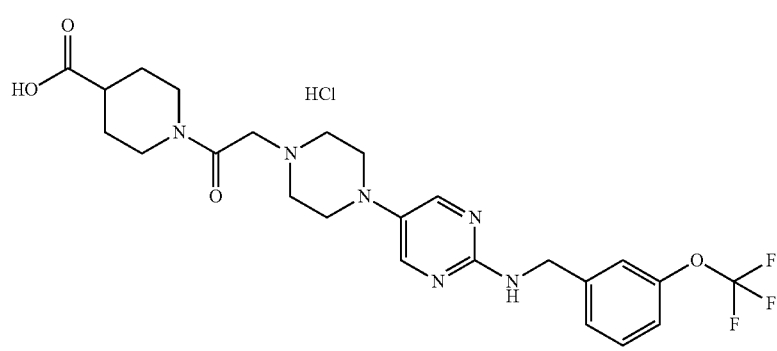

Except that methyl isonipecotate is used instead of the compound im-7, the reaction was carried out in the same manner as the Example 4-2, followed by the reaction as the Example 1-1 (Step 2) to obtain the title compound 25 as a yellow solid.

MS m/z: 523 [M+1]+

$^1$H NMR (CDCl$_3$, 400 MHz), δ ppm: 8.08 (s, 2H), 7.41 (t, 1H), 7.35-7.30 (m, 2H), 7.24 (s, 1H), 7.18 (d, 1H), 4.48 (d, 2H), 4.18 (d, 1H), 3.97 (d, 1H), 3.37-3.03 (m, 7H) 2.96 (s, 4H), 2.71 (t, 1H), 2.42-2.33 (m, 1H), 1.80 (s, 2H), 1.52-1.49 (m, 1H), 1.35-1.32 (m, 1H).

[Example 5-1] Preparation of 6-[(5S)-5-[(4-{2-[(2,3-dihydro-1H-inden-2-yl)amino]pyrimidin-5-yl}piperazin-1-yl)methyl]-2-oxo-1,3-oxazolidin-3-yl]-2,3-dihydro-1,3-benzoxazol-2-one (Compound 26)

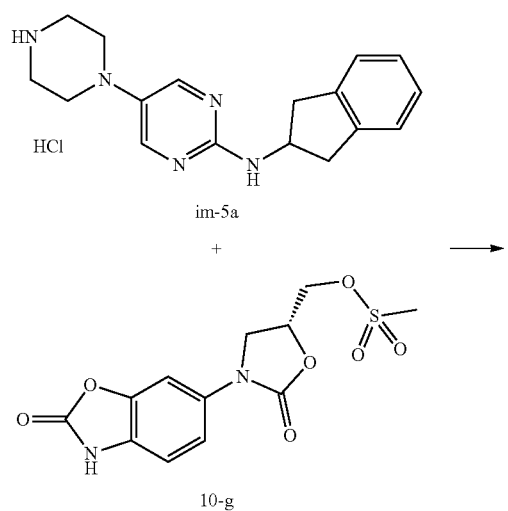

-continued

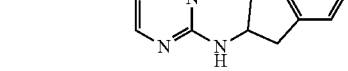

26

To a solution of the compound im-5a (0.14 g, 0.38 mmol) and the compound 10-g (63 mg, 0.19 mmol) in N,N-dimethylformamide (1 mL) was added N,N-diisopropylethylamine (0.17 mL, 0.94 mmol), and the mixture was stirred for 15 hours at 80° C. Upon the completion of the reaction, the mixture was cooled to room temperature, diluted with distilled water (20 mL), and then extracted with ethyl acetate. The organic layer was washed with distilled water and saturated brine, dried over anhydrous sodium sulfate, and then concentrated. The residue was purified by silica gel column chromatography (methanol methylene chloride=7:93) to obtain the title compound as a beige solid (5 mg, 5<).

MS m/z: 528 [M+1]+

$^1$H NMR (DMSO-d$_6$, 400 MHz), δ ppm: 11.69 (s, 1H), 10.21 (s, 1H), 8.20 (S, 2H), 7.61 (s, 1H), 7.31-7.28 (m, 1H), 7.22-7.12 (m, 4H), 5.24 (m, 1H), 4.54 (m, 1H), 4.24 (m, 1H), 3.83 (m, 2H), 3.78-3.48 (m, 4H), 3.25-3.20 (m, 3H), 3.16-2.91 (m, 4H), 2.86 (dd, 2H)

[Example 5-2] Preparation of 2-(4-{2-[(2,3-dihydro-1H-inden-2-yl)amino]pyrimidin-5-yl}piperazin-1-yl)-N-(2-oxo-2,3-dihydro-1,3-benzoxazol-6-yl)acetamide (Compound 27)

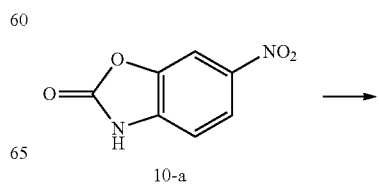

10-a

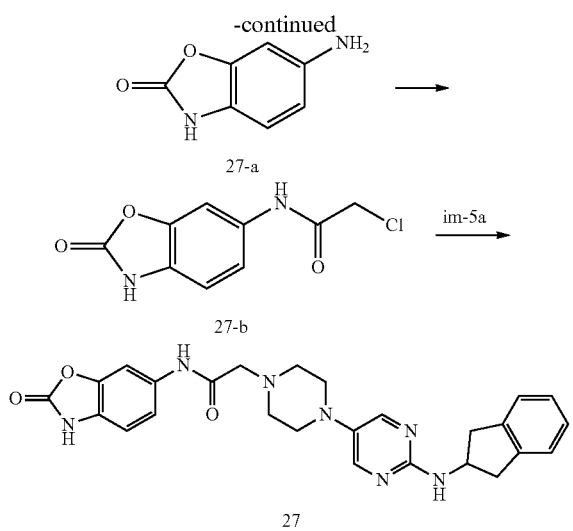

(Step 1) Preparation of 6-amino-2,3-dihydro-1,3-benzoxazol-2-one (Compound 27-a)

Except that the compound 10-a (3.4 g, 0.019 mol) is used instead of the compound 10-b, the reaction was carried out in the same manner as the Step 3 of Example 1-10 to obtain the title compound as a beige solid (2.68 g, 95%).

MS m/z: 151 [M+1]$^+$ $^1$H NMR (DMSO-d$_6$, 400 MHz), δ ppm: 10.98 (br, 1H), 6.69-6.67 (m, 1H), 6.44 (d, 1H), 6.30 (dd, 1H), 4.89 (br, 2H)

(Step 2) Preparation of 2-chloro-N-(2-oxo-2,3-dihydro-1,3-benzoxazol-6-yl)acetamide (Compound 27-b)

To a solution of the compound 27-a (0.50 g, 3.33 mmol) in methylene chloride (16 mL) was slowly added a solution of chloroacetyl chloride (0.3 mL, 3.7 mmol) in methylene chloride (5 mL) at 0° C., and the mixture was stirred at room temperature for 14 hours. Upon the completion of the reaction, the solvent was concentrated to ½ under reduced pressure. After adding distilled water (15 mL), the mixture was stirred for 30 minutes at room temperature. The precipitate was collected, washed with methanol, and dried to obtain the title compound 27-b as a brown solid (0.27 g, 36%).

MS m/z: 227 [M+1]$^+$ $^1$H NMR (DMSO-d$_6$, 400 MHz), δ ppm: 11.57 (br, 1H), 10.3 (s, 1H), 7.65 (d, 1H), 7.24 (dd, 1H), 7.05 (d, 1H), 4.24 (s, 2H)

(Step 3) Preparation of 2-(4-{2-[(2,3-dihydro-1H-inden-2-yl)amino]pyrimidin-5-yl}piperazin-1-yl)-N-(2-oxo-2,3-dihydro-1,3-benzoxazol-6-yl)acetamide (Compound 27)

Except that the compound 27-b (40 mg, 0.16 mmol) is used instead of the compound 10-g, the reaction was carried out in the same manner as Example 5-1 to obtain the title compound 27 as a brown solid (32 mg, 62%).

MS m/z: 486 [M+1]$^+$ $^1$H NMR (DMSO-d$_6$, 400 MHz), δ ppm: 11.69 (br, 1H), 10.21 (br, 1H), 8.20 (s, 2H), 7.61 (d, 1H), 7.26-7.12 (m, 6H), 5.24 (br, 1H), 4.54 (m, 1H), 4.24 (m, 1H), 3.83 (t, 2H), 3.61 (m, 4H), 3.42-3.32 (m, 1H), 3.22 (dd, 2H), 3.04 (m, 4H), 2.86 (dd, 2H)

[Example 5-3] Preparation of 6-[2-(4-{2-[(2,3-dihydro-1H-inden-2-yl)amino]pyrimidin-5-yl}piperazin-1-yl)acetyl]-2,3-dihydro-1,3-benzoxazol-2-one (Compound 28)

28

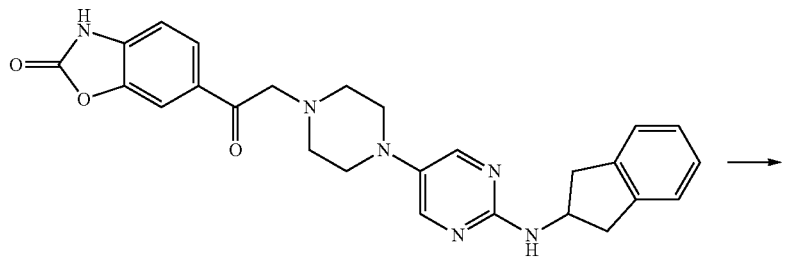

By using 6-(2-chloroacetyl)-2,3-dihydro-1,3-benzoxazol-2-one (50 mg, 0.24 mmol) instead of the compound 10-g, the reaction was carried out in the same manner as Example 5-1 to obtain the title compound 28 as a yellow solid (21 mg, 19%)

MS m/z: 471 [M+1]$^+$ $^1$H NMR (DMSO-d$_6$, 400 MHz), δ ppm: 12.07 (br, 1H), 8.12 (s, 2H), 7.90 (t, 1H), 7.21-7.11 (m, 5H), 6.96 (d, 1H), 4.52 (m, 1H), 3.87 (s, 2H), 3.22 (dd, 2H), 2.99 (m, 4H), 2.84 (dd, 2H), 2.66 (m, 4H)

[Example 5-4] Preparation of 6-[(1E)-2-(4-{2-[(2,3-dihydro-1H-inden-2-yl)amino]pyrimidin-5-yl}piperazin-1-yl)-1-(hydroxyimino)ethyl]-2,3-dihydro-1,3-benzoxazol-2-one (Compound 29)

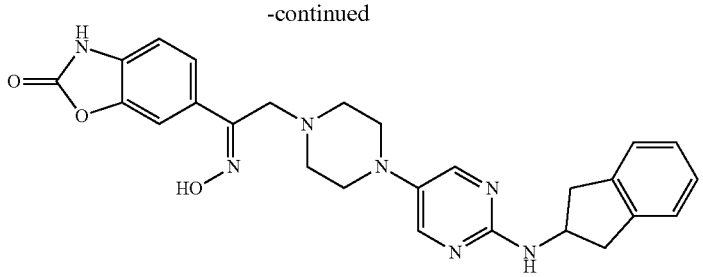

29

To a solution of the compound 28 (15 mg, 0.032 mmol) in a mixture solvent of methylene chloride (1 mL) and ethanol (4 mL) was added hydroxylamine hydrochloride (18 mg, 0.22 mmol) and sodium acetate (44 mg, 0.63 mmol) in order, and the mixture was stirred for 7 hours at 80° C. The mixture was cooled again to room temperature, and stirred for 14 hours. Upon the completion of the reaction, the solvent was concentrated under reduced pressure, and the residue was purified by silica gel column chromatography (methanol:methylene chloride=5:95) to obtain the title compound 29 as a yellow solid (7 mg, 44%).

MS m/z: 486 [M+1]$^+$ $^1$H NMR (DMSO-d$_6$, 400 MHz), δ ppm: 11.39 (s, 1H), 8.09 (s, 2H), 7.62 (s, 1H), 7.58 (d, 1H), 7.11-7.20 (m, 4H), 7.06 (d, 1H), 6.93 (d, 1H), 4.50 (m, 1H), 3.68 (s, 2H), 3.20 (dd, 2H), 2.91 (m, 4H), 2.83 (dd, 2H), 2.56 (m, 4H)

[Example 5-5] Preparation of 6-[(1E)-3-(4-{2-[(2,3-dihydro-1H-inden-2-yl)amino]pyrimidin-5-yl}piperazin-1-yl)-1-(hydroxyimino)propyl]-2,3-dihydro-1,3-benzoxazol-2-one (Compound 30)

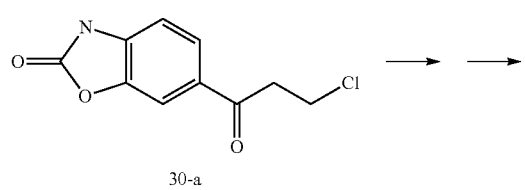

30-a

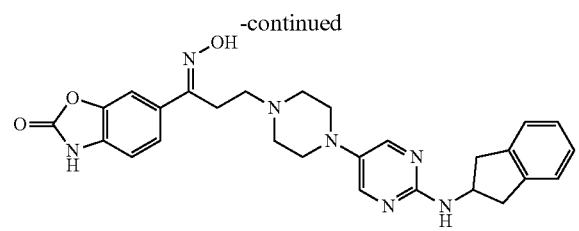

30

(Step 1) Preparation of 6-(3-chloropropanoyl)-2,3-dihydro-1,3-benzoxazol-2-one (Compound 30-a)

The title compound 30-a was synthesized according to a well-known method (WO 2008148449).

MS m/z: 226 [M+1]$^+$ $^1$H NMR (CDCl$_3$, 400 MHz), δ ppm: 12.10 (s, 1H), 7.86-7.93 (m, 2H), 7.24 (d, 1H), 4.00 (t, 2H), 3.54 (t, 2H).

(Step 2) Preparation of 6-[(1E)-3-(4-{2-[(2,3-dihydro-1H-inden-2-yl)amino]pyrimidin-5-yl}piperazin-1-yl)-1-(hydroxyimino)propyl]-2,3-dihydro-1,3-benzoxazol-2-one (Compound 30)

By using the compound 30-a (81 mg, 0.36 mmol), the reaction was carried out in the same manner as Example 5-3 followed by Example 5-4 to obtain the title compound 30 (3 mg, 2%).

MS m/z: 500 [M+1]$^+$

[Example 5-6] Preparation of 6-{5-[(4-{2-[(2,3-dihydro-1H-inden-2-yl)amino]pyrimidin-5-yl}piperazin-1-yl)methyl]-4,5-dihydro-1,2-oxazol-3-yl}-2,3-dihydro-1,3-benzoxazol-2-one (Compound 31)

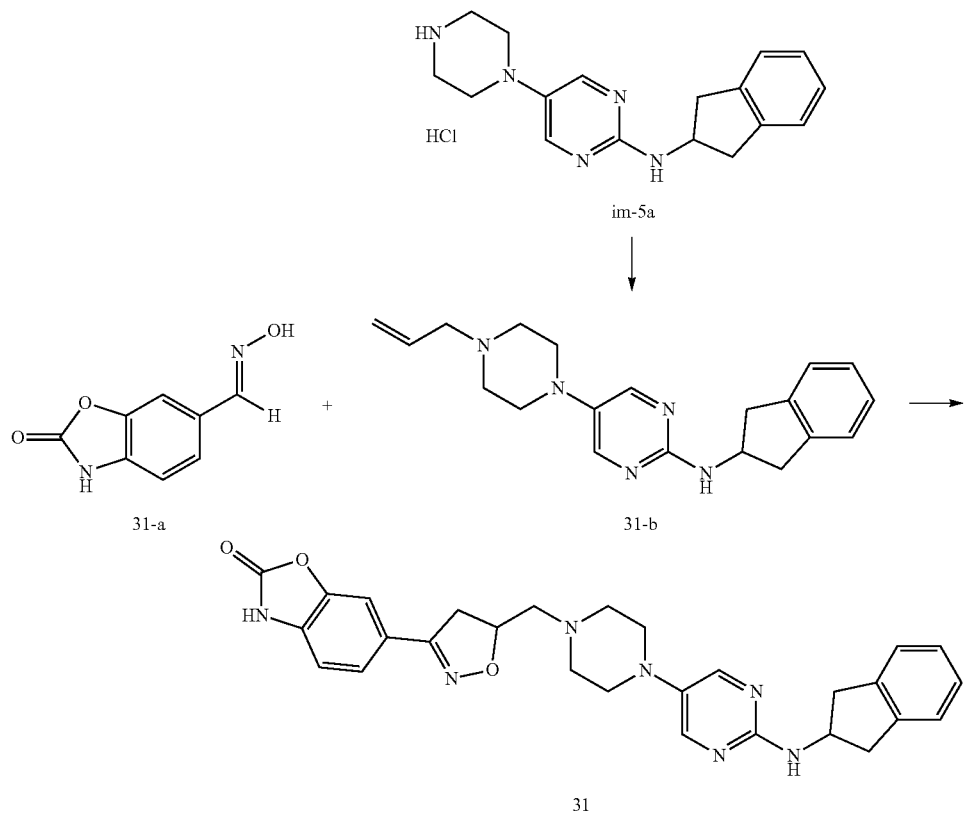

(Step 1) Preparation of 6-[(1E)-(hydroxyimino)methyl]-2,3-dihydro-1,3-benzoxazol-2-one (Compound 31-a)

The title compound 31-a was synthesized according to a well-known method (WO 2002050070).
MS m/z: 179 [M+1]$^+$
$^1$H NMR (DMSO-d$_6$, 400 MHz), δ ppm: 11.79 (br, 1H), 11.34 (s, 1H), 8.13 (s, 1H), 7.48 (s, 1H), 7.37 (d, 1H), 7.10 (d, 1H)

(Step 2) Preparation of N-(2,3-dihydro-1H-inden-2-yl)-5-[4-(prop-2-en-1-yl)piperazin-1-yl]pyrimidin-2-amine (Compound 31-b)

To a solution of the compound im-5a (00.15 g, 0.41 mmol) in N,N-dimethylformamide (4 mL) was slowly added N,N-diisopropylethylamine (0.35 mL, 2.03 mmol) and allyl bromide (0.05 mL, 0.6 mmol), and the mixture was stirred for 14 hours at room temperature. Upon the completion of the reaction, the mixture was cooled to room temperature, diluted with distilled water (20 mL), and then extracted with ethyl acetate. The organic layer was washed with distilled water and saturated brine, dried over anhydrous sodium sulfate, and then concentrated. The residue was purified by silica gel column chromatography (methanol methylene chloride=7:93) to obtain the title compound 31-b as a dark brown solid (41 mg, 30%).

MS m/z: 336 [M+1]$^+$
$^1$H NMR (CDCl$_3$, 400 MHz), δ ppm: 8.09 (s, 2H), 7.22-7.15 (m, 4H), 5.88 (m, 1H), 5.27-5.10 (m, 3H), 4.73 (m, 1H), 3.38 (dd, 2H), 3.09-3.02 (m, 6H), 2.86 (dd, 2H), 2.68-2.59 (m, 4H)

(Step 3) 6-{5-[(4-{2-[(2,3-dihydro-1H-inden-2-yl)amino]pyrimidin-5-yl}piperazin-1-yl)methyl]-4,5-dihydro-1,2-oxazol-3-yl}-2,3-dihydro-1,3-benzoxazol-2-one (Compound 31)

To a solution of the compound 31-a (0.10 g, 0.56 mmol) in N,N-dimethylformamide (1.5 mL) was added N-chlorosuccinimide (0.083 g, 0.62 mmol), and the mixture was stirred for 1 hour at room temperature. After adding the compound 31-b (40 mg, 0.12 mmol) and sodium hydrogen carbonate (50 mg, 0.60 mmol) in order, the reaction mixture was stirred for 9 hours at room temperature. Upon the completion of the reaction, the mixture was cooled to room temperature, diluted with distilled water (50 mL), and then extracted with ethyl acetate. The organic layer was washed with distilled water and saturated brine, dried over anhydrous sodium sulfate, and then concentrated. The residue was purified by silica gel column chromatography (methanol:methylene chloride=5:95) to obtain the title compound 31 as a dark brown solid (17 mg, 28%).

MS m/z: 512 [M+1]$^+$ $^1$H NMR (DMSO-d$_6$, 400 MHz), δ ppm: 11.06 (br, 1H), 8.12 (s, 2H), 7.57 (s, 1H), 7.47 (d, 1H), 7.22-7.11 (m, 5H), 6.83 (d, 1H), 4.89 (m, 1H), 4.52 (m, 1H), 3.53-3.46 (m, 1H), 3.28-3.17 (m, 3H), 2.98 (m, 4H), 2.85 (dd, 2H), 2.70-2.54 (m, 6H)

[Example 5-7] Preparation of N-[2-(4-{2-[(2,3-di-hydro-1H-inden-2-yl)amino]pyrimidin-5-yl}piperazin-1-yl)-2-oxo-2,3-dihydro-1,3-benzoxazole-6-carboxamide (Compound 32)

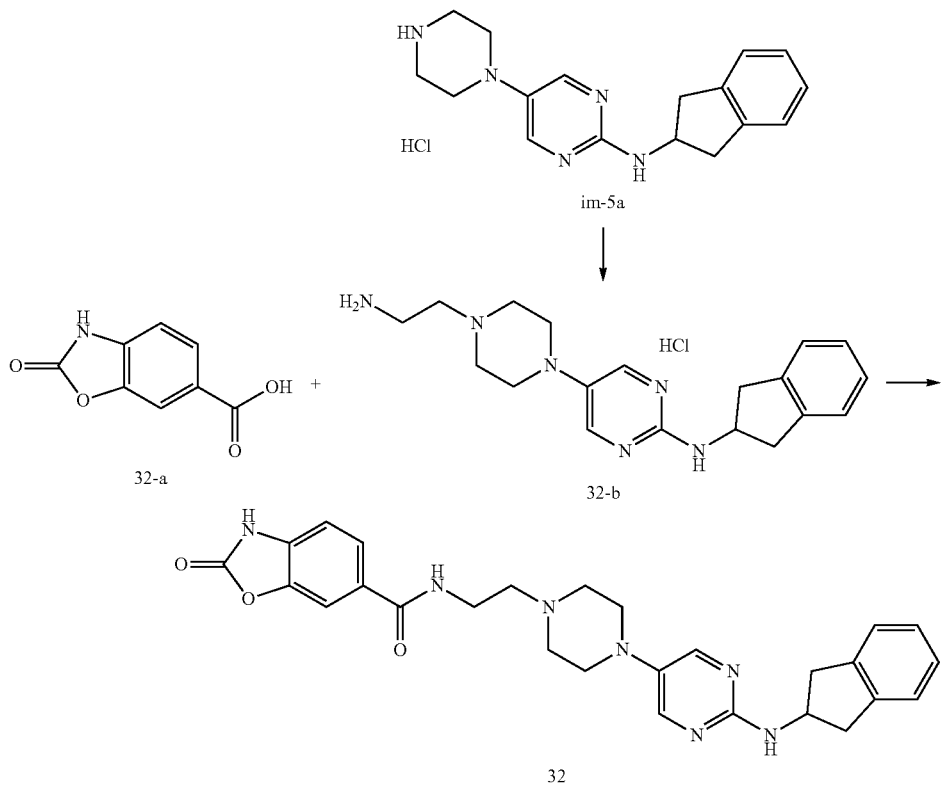

(Step 1) Preparation of 2-oxo-2,3-dihydro-1,3-benzoxazole-6-carboxylic Acid (Compound 32-a)

To a solution of 4-amino-3-hydroxybenzoic acid (1 g, 6.5 mmol) and potassium carbonate (1.4 g, 10.5 mmol) in distilled water (8 mL) was dropwise added methyl chloroformate (0.8 mL, 9.8 mmol) at 40° C., and the temperature was increased to 80° C. followed by stirring for 12 hours. Upon the completion of the reaction, the mixture was cooled to room temperature, and then treated with 2 N aqueous hydrochloric acid to adjust pH 2 or lower. The precipitate was collected, washed with cold water, and dried to obtain the title compound 32-a as a brown solid (0.66 mg, 57%).

MS m/z: 180.1, [M+1]$^+$ $^1$H NMR (DMSO-d$_6$, 400 MHz), δ ppm: 7.63 (d, 1H), 7.53 (s, 1H), 6.93 (d, 1H)

(Step 2) Preparation of 5-[4-(2-aminoethyl)piperazin-1-yl]-N-(2,3-dihydro-1H-inden-2-yl)pyrimidin-2-amine (Compound 32-b)

To a solution of the compound im-5a (40.46 g, 1.4 mmol) and tert-butyl N-(2-oxoethyl)carbamate (0.2 g, 1.3 mmol) in N,N-dimethylformamide (5 mL), and the mixture was stirred for 30 minutes at room temperature. Thereafter, sodium triacetoxy borohydride (0.53 g, 2.5 mmol) was added thereto, and the mixture was stirred for 12 hours at room temperature under nitrogen atmosphere. After adding distilled water (50 mL) to quench the reaction, the mixture was extracted with ethyl acetate. The organic layer was washed with distilled water and saturated brine, dried over anhydrous sodium sulfate, and concentrated. The residue was purified by silica gel column chromatography (methanol:methylene chloride=1:9) to obtain yellow solid. Thereafter, the reaction was carried out in the same manner as Example 1-3 (Step 6) to obtain the title compound 32-b as a light brown solid (0.1 g, 23%).

MS m/z: 339 [M+1]$^+$ $^1$H NMR (D$_2$O, 400 MHz), δ ppm: 8.31 (s, 2H), 7.34-7.25 (m, 4H), 4.65 (m, 1H), 3.58-3.36 (m, 14H), 3.01-2.96 (m, 2H)

(Step 3) Preparation of N-[2-(4-{2-[(2,3-dihydro-1H-inden-2-yl)amino]pyrimidin-5-yl}piperazin-1-yl)-2-oxo-2,3-dihydro-1,3-benzoxazole-6-carboxamide (Compound 32)

Except that the compound 32-a (0.1 g, 0.6 mmol) and the compound 32-b (0.11 g, 0.30 mmol) are used instead of the compound 12-b and the compound im-5a respectively, the reaction was carried out in the same manner as the Step 3 of Example 2-1 to obtain the title compound 32 as a yellow solid (64 mg, 44%)

MS m/z: 500 [M+1]$^+$ $^1$H NMR (DMSO-de, 400 MHz), δ ppm: 8.38 (m, 1H), 8.12 (s, 2H), 7.72-7.68 (m, 2H), 7.19-7.12 (m, 4H), 6.95 (d, 1H), 4.55-4.49 (m, 1H), 3.41-3.38 (m, 2H), 3.24-3.18 (m, 2H), 2.98 (br, 4H), 2.87-2.82 (m, 2H), 2.57 (br, 4H), 2.54 (m, 2H)

[Example 6-1] Preparation of 2-(5-(2-((2,3-dihydro-1H-inden-2-yl)amino)pyrimidin-5-yl)-1,3,4-oxadiazol-2-yl)-1-(1,4,6,7-tetrahydro-5H-[1,2,3]triazolo[4,5-c]pyridin-5-yl) ethan-1-one (Compound 33)

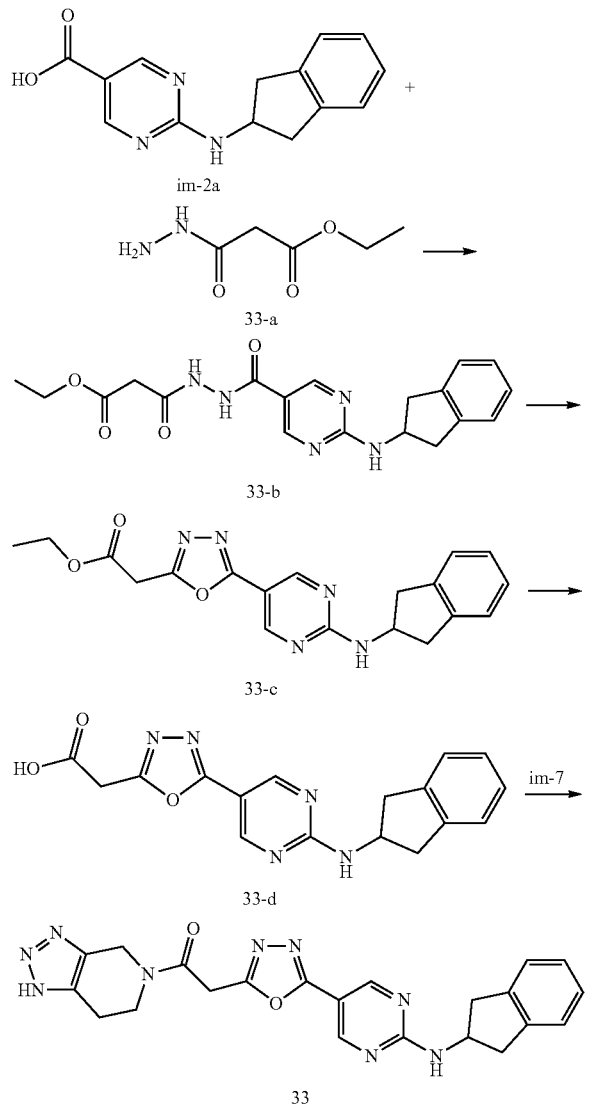

(Step 1) Preparation of ethyl 2-(hydrazinecarbonyl)acetate (Compound 33-a)

The title compound 33-a was synthesized according to a well-known method (European Journal of Medicinal Chemistry, 2008, 43(3), 584-594).

MS m/z: 147 [M+1]$^+$ $^1$H NMR (CDCl$_3$, 400 MHz), δ ppm: 8.14 (br, 1H), 4.21 (m, 2H), 3.35 (s, 2H), 1.30 (t, 3H)

(Step 2) Preparation of ethyl 3-({2-[(2,3-dihydro-1H-inden-2-yl)amino]pyrimidin-5-yl}formohydrazido)-3-oxopropanoate (Compound 33-b)

To a solution of the compound im-2a (2.2 g, 8.7 mmol) in N,N-dimethylformamide (30 mL) was slowly added the compound 33-a (1.9 g, 13.1 mmol), N,N-diisopropylethylamine (4.6 mL, 26.2 mmol), and benzotriazol-1-yl-oxy-tripyrrolidinophosphonium hexafluorophosphate (6.8 g, 13.1 mmol) in order at 0° C., and the mixture was stirred for 14 hours at room temperature under nitrogen stream. Upon the completion of the reaction, the reaction mixture was cooled to room temperature, diluted with distilled water (30 mL) and extracted with ethyl acetate. The organic layer was washed with distilled water and saturated brine, dried over anhydrous sodium sulfate, and concentrated. The residue was treated with methylene chloride to form solid, which was then filtered and dried to obtain the title compound 33-b as a white solid (1.4 g, 43%).

MS m/z: 384 [M+1]$^+$ $^1$H NMR (DMSO-d$_6$, 400 MHz), δ ppm: 10.47 (s, 1H), 10.17 (s, 1H), 8.79 (d, 2H), 8.26 (d, 2H), 7.23-7.14 (m, 4H), 4.42 (q, 1H), 3.35 (s, 2H), 3.27 (dd, 1H), 2.91 (dd, 2H), 1.18 (t, 3H)

(Step 3) Preparation of ethyl 2-(5-{2-[(2,3-dihydro-1H-inden-2-yl)amino]pyrimidin-5-yl}-1,3,4-oxadiazol-2-yl)acetate (Compound 33-c)

To a solution of the compound 33-b (0.17 g, 0.46 mmol) in anhydrous tetrahydrofuran (50 mL) was added methyl N-(triethylammoniumsulfonyl)carbamate (0.16 g, 0.55 mmol) at 0° C., and the mixture was stirred for 2 hours at 70° C. under nitrogen atmosphere. Upon the completion of the reaction, the mixture was cooled to room temperature, diluted with distilled water (80 mL), and extracted with ethyl acetate. The organic layer was washed with distilled water and saturated brine, dried over anhydrous sodium sulfate, and concentrated. The residue was purified by silica gel column chromatography (methanol:ethyl acetate=3:7) to obtain the title compound 33-c as a yellow solid (0.12 g, 75%)

MS m/z: 366[M+1]$^+$ $^1$H NMR (CDCl$_3$, 400 MHz), δ ppm: 8.94 (d, 2H), 7.25-7.19 (m, 4H), 5.80 (d, 1H), 4.90 (q, 1H), 4.02 (s, 1H), 3.44 (dd, 2H), 2.93 (dd, 2H), 1.28 (t, 3H)

(Step 4) Preparation of 2-(5-{2-[(2,3-dihydro-1H-inden-2-yl)amino]pyrimidin-5-yl}-1,3,4-oxadiazol-2-yl)acetic Acid (Compound 33-d)

To a solution of the compound 33-c (0.12 g, 0.35 mmol) in a mixture solvent of tetrahydrofuran (4 mL) and distilled water (2 mL) was added lithium hydroxide (0.072 g, 1.72 mmol), and the mixture was stirred for 1 hour at room temperature. Upon the completion of the reaction, the mixture was treated with 2 N aqueous hydrochloric acid to adjust pH 2 or lower followed by extraction with ethyl acetate. The organic layer was washed with distilled water and saturated brine, dried over anhydrous sodium sulfate, and concentrated to obtain the title compound 33-d as a yellow solid (0.11 g, 95%).

MS m/z: 338 [M+1]$^+$ $^1$H NMR (DMSO-d$_6$, 400 MHz), δ ppm: 8.87 (d, 2H), 8.45 (d, 2H), 7.24-7.14 (m, 4H), 4.71 (q, 1H), 4.12 (s, 1H), 3.29 (dd, 2H), 2.96 (dd, 2H)

(Step 5) Preparation of 2-(5-(2-((2,3-dihydro-1H-inden-2-yl)amino)pyrimidin-5-yl)-1,3,4-oxadiazol-2-yl)-1-(1,4,6,7-tetrahydro-5H-[1,2,3]triazolo[4,5-c]pyridin-5-yl)ethan-1-one (Compound 33)

To a solution of the compound 33-d (0.19 g, 0.55 mmol) and the compound im-7 (0.18 g, 1.09 mmol) in N,N-dimethylformamide (5 mL) was slowly added N,N-diisopropylethylamine (0.33 mL, 1.9 mmol) and benzotriazol-1-yl-oxy-tripyrrolidinophosphonium hexafluorophosphate (0.43 g, 0.82 mmol) at 0° C., and the mixture was stirred for 2 hours at room temperature under nitrogen atmosphere.

Upon the completion of the reaction, the mixture was diluted with distilled water (20 mL) and extracted with ethyl acetate. The organic layer was washed with distilled water and saturated brine, dried over anhydrous sodium sulfate, and concentrated. The residue was purified by silica gel column chromatography (methanol:methylene chloride=5:95) to obtain the title compound 33 as a white solid (0.065 g, 27%).

MS m/z: 444 [M+1]+
1H NMR (DMSO-d6, 400 MHz), δ ppm: 8.85-8.79 (m, 2H), 8.43 (d, 1H), 7.24-7.14 (m, 4H), 4.81-4.68 (m, 3H), 4.44 (d, 2H), 3.85-3.83 (m, 2H), 3.28 (m, 2H), 3.00-2.91 (m, 3H), 2.76-2.73 (m, 1H)

[Example 6-2] Preparation of 1-{1H,4H,5H,6H,7H-[1,2,3]triazolo[4,5-c]pyridin-5-yl}-2-{5-[2-({[3-(trifluoromethoxy)phenyl]methyl}amino)pyrimidin-5-yl]-1,3,4-oxadiazol-2-yl}ethan-1-one (Compound 34)

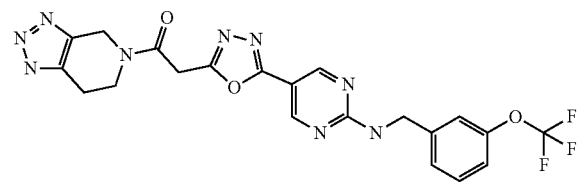

34

By using the compound im-2b instead of the compound im-2a, the reaction was carried out in the same manner as Example 6-1 to obtain the title compound 34.
MS m/z: 502 [M+1]+
1H NMR (DMSO-d6, 400 MHz), δ ppm: 8.85-8.78 (m, 2H), 8.65 (t, 1H), 7.48-7.21 (m, 4H), 4.82-4.62 (m, 4H), 4.42 (d, 2H), 3.88-3.79 (m, 2H), 2.84-2.72 (m, 2H)

[Example 6-3] Preparation of 2-[5-(2-{[4-(3-chlorophenyl)cyclohex-3-en-1-yl]amino}pyrimidin-5-yl)-1,3,4-oxadiazol-2-yl]-1-{1H,4H,5H,6H,7H-[1,2,3]triazolo[4,5-c]pyridin-5-yl}ethan-1-one (Compound 35)

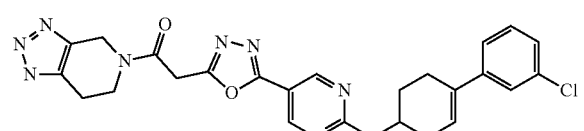

35

By using the compound im-2c instead of the compound im-2a, the reaction was carried out in the same manner as Example 6-1 to obtain the title compound 35.
MS m/z: 518 [M+1]+
1H NMR (DMSO-d6, 400 MHz), δ ppm: 8.84-8.78 (m, 2H), 8.13 (d, 1H), 7.46-7.26 (m, 4H), 6.19 (m, 1H), 4.69 (d, 2H), 4.42 (d, 2H), 4.11 (m, 1H), 3.88-3.80 (m, 2H), 2.92-2.72 (m, 2H), 2.62-2.51 (m, 3H), 2.32-2.22 (m, 1H), 2.12-2.02 (m, 1H), 1.80-1.68 (m, 1H)

[Example 6-4] Preparation of 2-(5-{6-[(2,3-dihydro-1H-inden-2-yl)amino]pyridin-3-yl}-1,3,4-oxadiazol-2-yl)-1-{1H,4H,5H,6H,7H-[1,2,3]triazolo[4,5-c]pyridin-5-yl}ethan-1-one (Compound 36)

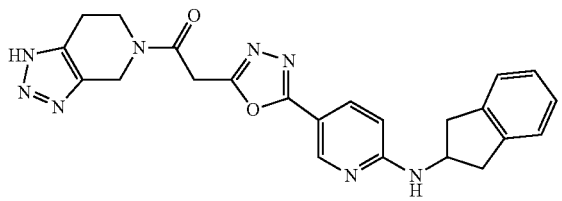

36

By using the compound im-2d instead of the compound im-2a, the reaction was carried out in the same manner as Example 6-1 to obtain the title compound 38.
MS m/z: 443 [M+1]+
1H NMR (DMSO-d6, 400 MHz), δ ppm: 8.54 (d, 1H), 7.84-7.79 (m, 1H), 7.67 (d, 1H), 7.21-7.12 (m, 4H), 6.60 (d, 1H), 4.78 (s, 1H), 4.65 (s, 2H), 4.38-4.34 (m, 2H), 3.82-3.81 (m, 2H), 3.29-3.25 (m, 2H), 2.87-2.71 (m, 4H)

[Example 6-5] Preparation of 2-(5-{2-[(2,3-dihydro-1H-inden-2-yl)amino]pyrimidin-5-yl}-1,3,4-oxadiazol-2-yl)-1-{5H,6H,7H,8H-imidazo[1,2-c]pyrimidin-6-yl}ethan-1-one (Compound 37)

37-a 33-d

37

(Step 1) Preparation of 5H,6H,7H,8H-imidazo[1,2-a]pyrazine (Compound 37-a)

According to a well-known method (US2004/220189 A1 and US2008/153843 A1), the intermediate 5H,6H,7H,8H-imidazo[1,2-a]pyrazine (compound 37-a) was synthesized.
MS m/z: 124 [M+1]$^+$ (Step 2) Preparation of 2-(5-{2-[(2,3-dihydro-1H-inden-2-yl)amino]pyrimidin-5-yl}-1,3,4-oxadiazol-2-yl)-1-{5H,6H,7H,8H-imidazo[1,2-c]pyrimidin-6-yl}ethan-1-one (Compound 37)

By using the compound 37-a instead of the compound im-7, the reaction was carried out in the same manner as Example 6-1 to obtain the title compound 37.
MS m/z: 443 [M+1]$^+$
$^1$H NMR (CDCl$_3$, 400 MHz), δ ppm: 8.91 (d, 2H), 7.25-7.18 (m, 4H), 7.07 (d, 2H), 6.91 (d, 2H), 5.89-5.87 (m, 1H), 4.92-4.88 (m 3H), 4.17-4.07 (m, 4H), 3.42 (dd, 2H), 2.92 (dd, 2H)

[Example 6-6] Preparation of 2-(5-{2-[(2,3-dihydro-1H-inden-2-yl)amino]pyrimidin-5-yl}-1,3,4-oxadiazol-2-yl)-1-{3H,4H,5H,6H,7H-imidazo[4,5-c]pyridin-5-yl}ethan-1-one (Compound 38)

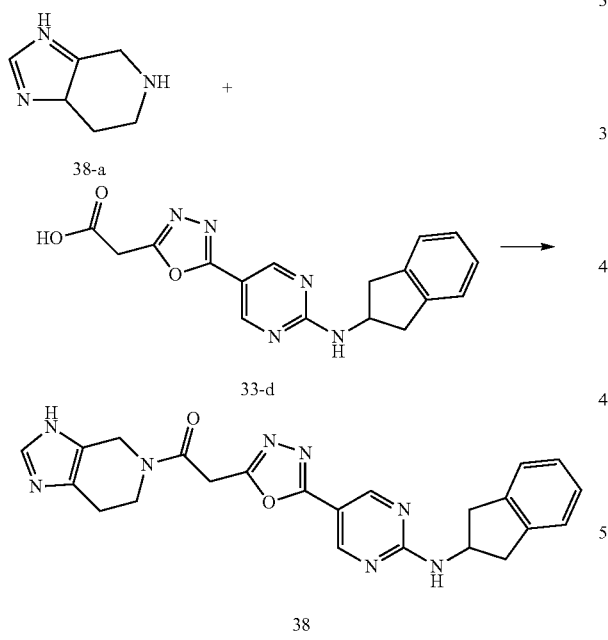

(Step 1) Preparation of 3H,4H,5H,6H,7H-imidazo[4,5-c]pyridine (Compound 38-a)

According to a well-known method (Bioorganic & Medicinal Chemistry, 2008, 18(11), 3359-3363), the intermediate 3H,4H,5H,6H,7H-imidazo[4,5-c]pyridine (compound 38-a) was synthesized.
MS m/z: 124 [M+1]$^+$
$^1$H NMR (DMSO-d$_6$, 400 MHz), δ ppm: 10.10 (br, 2H), 9.01 (s, 1H), 4.27 (s, 2H), 3.43-3.40 (m, 2H), 2.92 (s, 2H)

(Step 2) Preparation of 2-(5-{2-[(2,3-dihydro-1H-inden-2-yl)amino]pyrimidin-5-yl}-1,3,4-oxadiazol-2-yl)-1-{3H,4H,5H,6H,7H-imidazo[4,5-c]pyridin-5-yl}ethan-1-one (Compound 38)

By using the compound 38-a instead of the compound im-7, the reaction was carried out in the same manner as Example 6-1 to obtain the title compound 38.
MS m/z: 443 [M+1]$^+$
$^1$H NMR (DMSO-d$_6$, 400 MHz), δ ppm: 8.90 (d, 2H), 7.54 (d, 1H), 7.25-7.17 (m, 4H), 5.92 (t, 1H), 4.90-4.84 (m, 1H), 4.69-4.63 (m, 2H), 4.16 (d, 2H), 3.97-3.86 (m, 2H), 3.49 (s, 2H), 3.41 (dd, 2H), 2.92 (dd, 2H), 2.80-2.74 (m, 2H)

[Example 6-7] Preparation of 6-[2-(5-{2-[(2,3-dihydro-1H-inden-2-yl)amino]pyrimidin-5-yl}-1,3,4-oxadiazol-2-yl)acetyl]-1,2,5,6,7,8-hexahydro-1,6-naphthyridin-2-one (Compound 39)

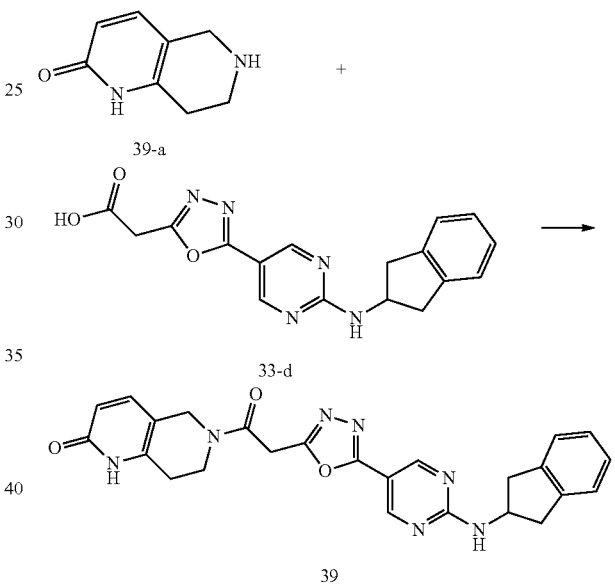

(Step 1) Preparation of 3H,4H,5H,6H,7H-imidazo[4,5-c]pyridine (Compound 39-a)

According to a well-known method (WO 2009121812), the intermediate 1,2,5,6,7,8-hexahydro-1,6-naphthiridin-2-one (compound 39-a) was synthesized.
MS m/z: 15 [M+1]$^+$ 6-[2-(5-{2-[(2,3-dihydro-1H-inden-2-yl)amino]pyrimidin-5-yl}-1,3,4-oxadiazol-2-yl)acetyl]-1,2,5,6,7,8-hexahydro-1,6-naphthyridin-2-one (Compound 39)

By using the compound 39-a instead of the compound im-7, the reaction was carried out in the same manner as Example 6-4 to obtain the title compound 39.
MS m/z: 470 [M+1]$^+$
$^1$H NMR (DMSO-d$_6$, 400 MHz), δ ppm: 11.57 (s, 1H), 8.85-8.79 (m, 2H), 8.44-8.42 (m, 1H), 7.30-7.14 (m, 5H), 6.23-6.18 (m, 1H) 4.73-4.68 (m, 1H), 4.47-4.33 (m, 4H), 3.75-3.70 (m, 2H), 3.29-3.22 (m, 2H), 2.93 (dd, 2H), 2.71-2.60 (m, 1H), 2.50 (m, 1H)

[Example 6-8] Preparation of 5-[2-(5-{2-[(2,3-dihydro-1H-inden-2-yl)amino]pyrimidin-5-yl}-1,3,4-oxadiazol-2-yl)acetyl]-1H,2H,3H,4H,5H,6H,7H-imidazo[4,5-c]pyridin-2-one (Compound 40)

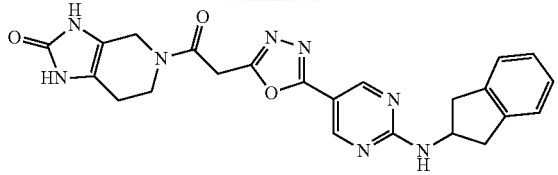

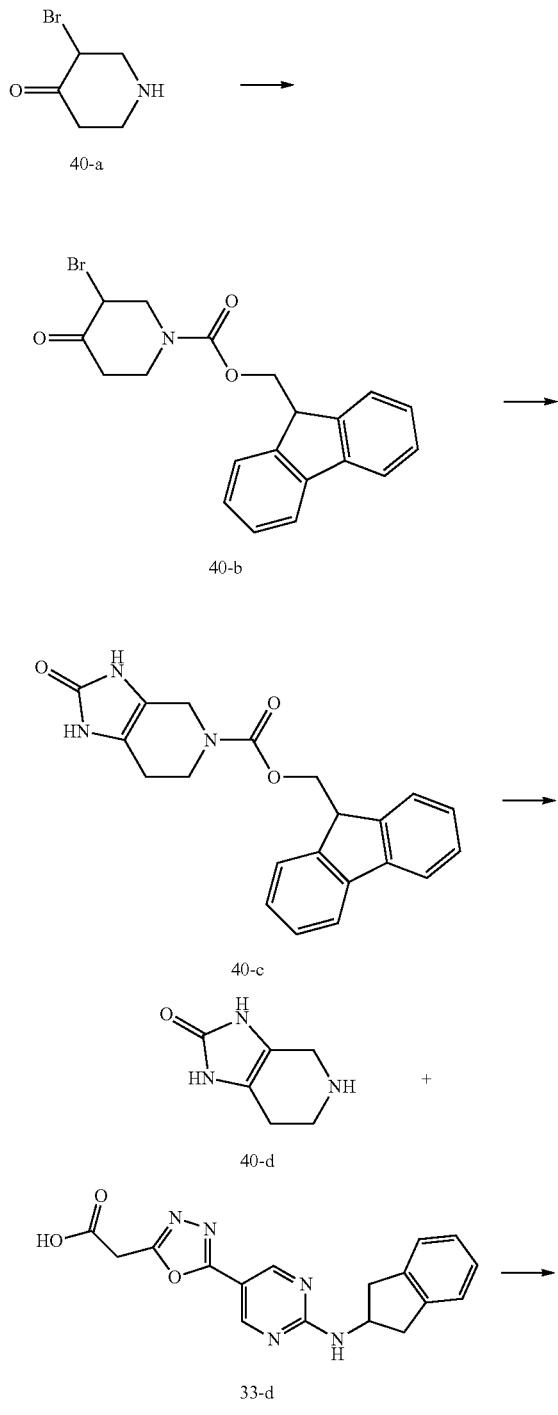

(Step 1) Preparation of 3-Bromo-piperidin-4-one hydrobromide (Compound 40-a)

According to a well-known method (Journal of Medicinal Chemistry, 2010, 53(19), 7107-7118), the title compound (40-a) was synthesized.

MS m/z: 179 [M+1]$^+$ $^1$H NMR (DMSO-d$_6$, 400 MHz), δ ppm: 9.23 (br, 2H), 5.06-5.03 (m, 1H), 4.00-3.95 (m, 1H), 3.71-3.49 (m, 3H), 2.84-2.76 (m, 2H)

(Step 2) Preparation of 9H-fluoren-9-ylmethyl 3-bromo-4-oxopiperidine-1-carboxylate (Compound 40-b)

To a solution of the compound 40-a (2.6 g, 0.010 mol) in a mixture solvent of distilled water (3 mL) and 1,4-dioxane (20 mL) was slowly added sodium carbonate (3.2 g, 0.030 mol) and 9-fluorenylmethoxycarbonyl chloride (2.6 g, 0.010 mmol) in order at 0° C., and the mixture was stirred for 15 hours at room temperature. Upon the completion of the reaction, the mixture was cooled to room temperature, diluted with distilled water (30 mL), and then extracted with ethyl acetate. The organic layer was washed with distilled water and saturated brine, dried over anhydrous sodium sulfate, and concentrated. The residue was purified by silica gel column chromatography (ethyl acetate:n-hexane=1:95) to obtain the title compound 40-b as a white solid (2.7 g, 69%).

MS m/z: 401 [M+1]$^+$ $^1$H NMR (CDCl$_3$, 400 MHz), δ ppm: 7.78 (d, 2H), 7.59 (d, 2H), 7.42-7.30 (m, 4H), 4.79-4.54 (m, 2H), 4.26 (t, 1H), 3.96-3.52 (m, 4H), 2.96-2.74 (m, 1H), 2.39-2.18 (m, 1H)

(Step 3) Preparation of 9H-fluoren-9-ylmethyl 2-oxo-1H,2H,3H,4H,5H,6H,7H-imidazo[4,5-c]pyridine-5-carboxylate (Compound 40-c)

To a solution of the compound 40-b (0.60 g, 1.50 mmol) and urea (0.55 mg, 8.99 mmol) in acetic acid (2.6 mL) was added 30% ammonia water (0.64 mL) at 0° C., and the mixture was stirred for 4 hours at 100° C. Upon the completion of the reaction, the mixture was cooled to room temperature, diluted with distilled water (50 mL) and extracted with ethyl acetate. The organic layer was washed with distilled water and saturated brine, dried over anhydrous sodium sulfate, and concentrated. The residue was purified by silica gel column chromatography (methanol:methylene chloride=5:95) to obtain the title compound 40-c as a yellow solid (0.22 g, 40%).

MS m/z: 362 [M+1]$^+$ $^1$H NMR (CDCl$_3$, 400 MHz), δ ppm: 9.86-9.64 (m, 2H), 7.78-7.64 (m, 2H), 7.54-7.24 (m, 6H), 4.51-4.36 (m, 2H), 4.30-4.12 (m, 3H), 3.72-3.56 (m, 2H), 2.42-2.30 (m, 2H)

(Step 4) Preparation of 1H,2H,3H,4H,5H,6H,7H-imidazo[4,5-c]pyridin-2-one (Compound 40-d)

The compound 40-c (0.22 g, 0.60 mmol) was dissolved in tetrahydrofuran (25 mL). After adding piperidine (5 mL) slowly, the mixture was stirred for 1 hour at room temperature. Upon the completion of the reaction, the mixture was concentrated under reduced pressure, and the residue was treated with diethyl ether to form a solid. The precipitate was collected, washed with diethyl ether, and then dried to obtain the title compound 40-d as a beige solid (77 mg).
MS m/z: 140 [M+1]$^+$
$^1$H NMR (DMSO-d$_6$, 400 MHz), δ ppm: 9.43 (d, 2H), 3.42-3.33 (m, 2H), 2.83 (t, 2H), 2.17 (m, 2H)

(Step 5) Preparation of 5-[2-(5-{2-[(2,3-dihydro-1H-inden-2-yl)amino]pyrimidin-5-yl}-1,3,4-oxadiazol-2-yl)acetyl]-1H,2H,3H,4H,5H,6H,7H-imidazo[4,5-c]pyridin-2-one (Compound 40)

By using the compound 40-d instead of the compound im-7, the reaction was carried out in the same manner as Example 6-1 to obtain the title compound 40.
MS m/z: 459 [M+1]$^+$
$^1$H NMR (DMSO-d$_6$, 400 MHz), δ ppm: 9.78-9.61 (m, 2H), 8.89-8.76 (m, 2H), 8.42 (d, 2H), 7.26-7.12 (m, 4H), 4.71 (m, 1H), 4.38-4.32 (m, 2H), 4.24 (d, 2H), 3.76-3.71 (m, 2H), 3.27 (m, 2H), 2.94 (dd, 2H), 2.44-2.28 (m, 2H)

[Example 6-9] Preparation of 2-(5-{2-[(2,3-dihydro-1H-inden-2-yl)amino]pyrimidin-5-yl}-1,3,4-oxadiazol-2-yl)-1-{5H,6H,7H,8H-[1,2,4]triazolo[1,5-a]pyrazin-7-yl}ethan-1-one (Compound 41)

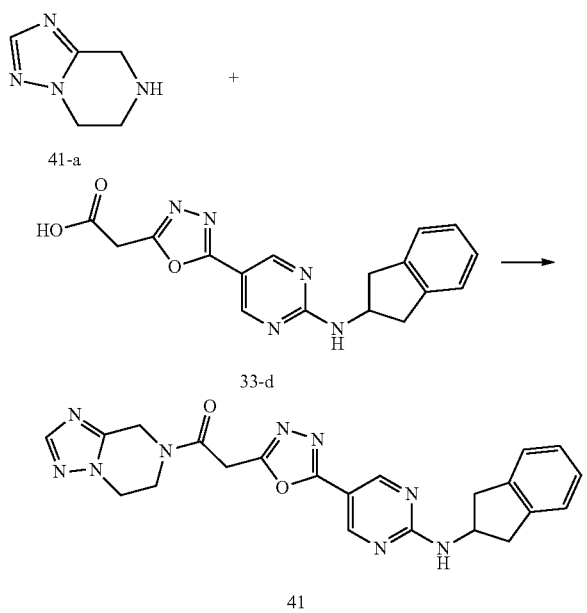

(Step 1) Preparation of 3H,4H,5H,6H,7H-imidazo[4,5-c]pyridine (Compound 41-a)

According to a well-known method (Journal of Medicinal Chemistry, 2014, 57(9), 3687-3706), the intermediate 5,6,7,8-tetrahydro-[1,2,4]triazolo[1,5-a]pyrazine (Compound 41-a) was synthesized.

MS m/z: 125 [M+1]$^+$
$^1$H NMR (DMSO-d$_6$, 400 MHz), δ ppm: 7.86 (s, 1H), 4.02 (t, 2H), 3.90 (s, 2H), 3.11 (m, 2H), 2.82 (br, 1H)

(Step 2) Preparation of 2-(5-{2-[(2,3-dihydro-1H-inden-2-yl)amino]pyrimidin-5-yl}-1,3,4-oxadiazol-2-yl)-1-{5H,6H,7H,8H-[1,2,4]triazolo[1,5-a]pyrazin-7-yl}ethan-1-one (Compound 41)

By using the compound 41-a instead of the compound im-7, the reaction was carried out in the same manner as Example 6-1 to obtain the title compound 41.
MS m/z: 444 [M+1]$^+$
$^1$H NMR (CDCl$_3$, 400 MHz), δ ppm: 8.88-8.81 (m, 2H), 7.95 (d, 1H), 7.28-7.20 (m, 4H), 5.84-5.79 (m, 1H), 4.98 (s, 2H), 4.91 (m, 1H), 4.39-4.29 (m, 2H), 4.24-4.14 (m, 4H), 3.44 (dd, 2H), 2.94 (dd, 2H)

[Example 6-10] Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-c]pyridin-5-yl}ethan-1-one (Compound 42)

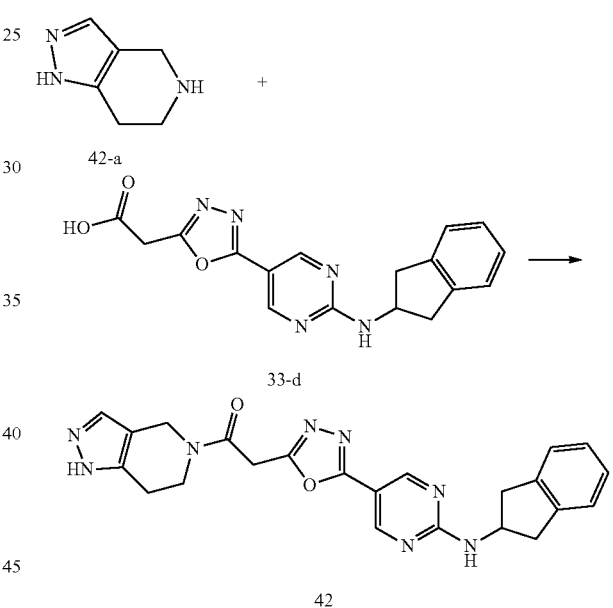

(Step 1) Preparation of 1H,4H,5H,6H,7H-pyrazolo[4,3-c]pyridine Hydrogen Chloride Salt (Compound 42-a)

According to a well-known method (US 20070232600887), 1H,4H,5H,6H,7H-pyrazolo[4,3-c]pyridine hydrogen chloride salt (compound 42-a) was synthesized.
$^1$H NMR (DMSO-d$_6$, 400 MHz), δ ppm: 9.39 (br, 2H), 7.57 (s, 1H), 4.10 (m, 2H), 3.35 (m, 2H), 2.90 (t, 2H).

(Step 2) Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-c]pyridin-5-yl}ethan-1-one (Compound 42)

By using the compound 42-a instead of the compound im-7, the reaction was carried out in the same manner as Example 6-1 to obtain the title compound 42.

MS m/z: 443 [M+1]+

¹H NMR (DMSO-d₆, 400 MHz), δ ppm: 12.54 (br, 1H), 8.86-8.78 (m, 2H), 8.42 (d, 2H), 7.24-7.14 (m, 4H), 4.70 (m, 1H), 4.64-4.46 (m, 2H), 4.36 (d, 2H), 3.82-3.74 (m, 2H), 3.29 (dd, 2H), 2.94 (dd, 2H), 2.84-2.62 (m, 2H)

[Example 6-11] Preparation of 1-{2-amino-4H,5H,6H,7H-[1,3]thiazolo[4,5-c]pyridin-5-yl}-2-(5-{2-[(2,3-dihydro-1H-inden-2-yl)amino]pyrimidin-5-yl}-1,3,4-oxadiazol-2-yl)ethan-1-one (Compound 43)

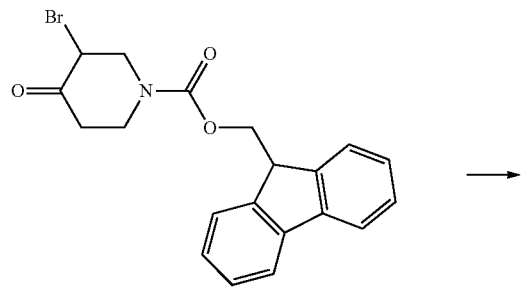

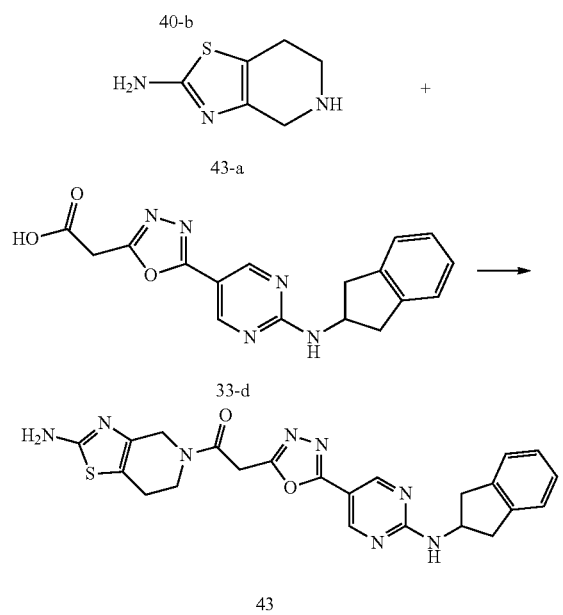

(Step 1) Synthesis of 4H,5H,6H,7H-[1,3]thiazolo[4,5-c]pyridin-2-amine dihydrobromide (Compound 43-a)

To a solution of the compound 40-b (0.7 g, 2.7 mmol) in ethanol (7 mL) was added thiourea (0.21 g, 2.7 mmol), and the mixture was stirred under reflux for 9 hours. Upon the completion of the reaction, the solid was filtered out and washed with ethanol. The filtrate was concentrated, and the resulting solid was filtered again. The solid was collected and dried to obtain the title compound 43-a as a pink solid (0.46 g, 53%), which was then used for the next reaction without further purification.

MS m/z: 155.9 [M+1]+

(Step 2) Preparation of 1-{2-amino-4H,5H,6H,7H-[1,3]thiazolo[4,5-c]pyridin-5-yl}-2-(5-{2-[(2,3-dihydro-1H-inden-2-yl)amino]pyrimidin-5-yl}-1,3,4-oxadiazol-2-yl)ethan-1-one (Compound 43)

By using the compound 43-a instead of the compound im-7, the reaction was carried out in the same manner as Example 6-1 to obtain the title compound 43.

MS m/z: 475 [M+1]+

¹H NMR (DMSO-d₆, 400 MHz), δ ppm: 8.86 (d, 2H), 8.41 (d, 1H), 7.23-7.14 (m, 4H), 6.85 (d, 2H), 4.74-4.69 (m, 1H), 4.57-4.31 (m, 4H), 3.79-3.76 (m, 2H), 3.31-3.26 (m, 2H), 2.97-2.91 (m, 3H), 2.62 (s, 1H)

[Example 6-12] Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[3,4-c]pyridin-6-yl}ethan-1-one (Compound 44) and 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-b]pyridin-4-yl}ethan-1-one (Compound 45)

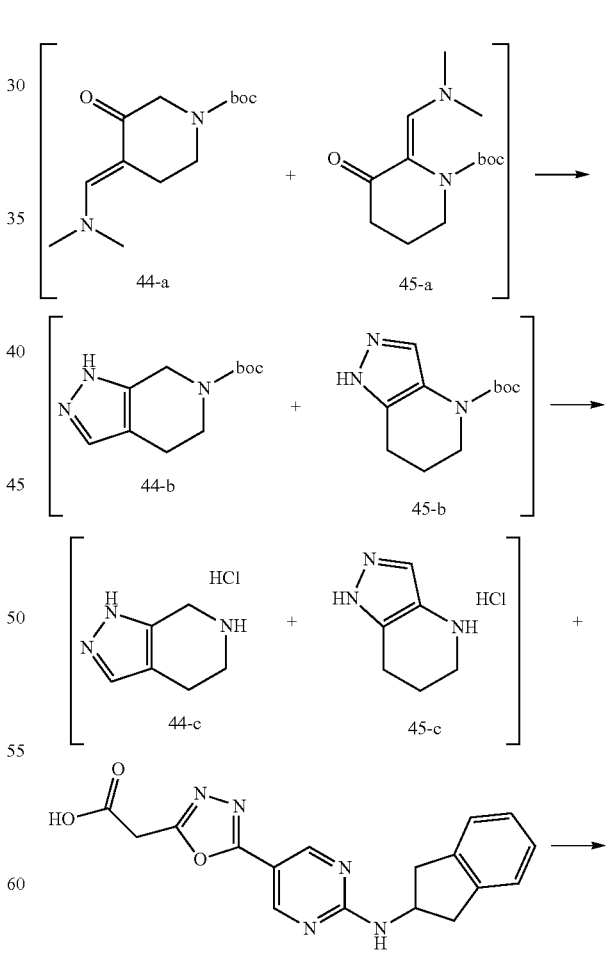

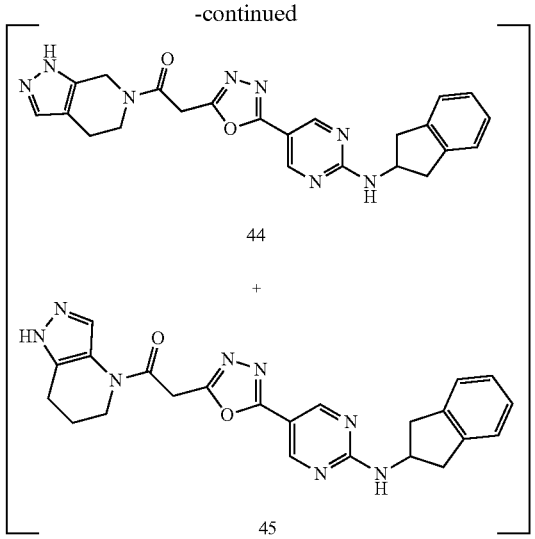

(Step 1) Preparation of tert-butyl (4E)-4-[(dimethylamino)methylidene]-3-oxopiperidine-1-carboxylate (44-a) and tert-butyl (2Z)-2-[(dimethylamino)methylidene]-3-oxopiperidine-1-carboxylate (Compound 45-a)

A solution of tert-butyl 3-oxopiperidine-1-carboxylate (1.0 g, 5.02 mmol) in N,N-dimethylformamide dimethyl acetal (1 mL) was stirred under reflux for 1 hour. Upon the completion of the reaction, the solvent was removed and the residue was purified by silica gel column chromatography (ethyl acetate) to obtain a mixture of the title compounds (44-a and 45-a) (0.89 g, 70%).
MS m/z: 255 [M+1]$^+$
$^1$H NMR (CDCl$_3$, 400 MHz), δ ppm: 4.24-4.01 (m, 1H), 3.20-2.80 (m, 8H), 2.39-2.08 (m, 3H), 1.73 (m, 1H), 1.43 (s, 1H)

(Step 2) Preparation of tert-butyl 1H,4H,5H,6H,7H-pyrazolo[3,4-c] pyridine-6-carboxylate (44-b) and tert-butyl 1H,4H,5H,6H,7H-pyrazolo[4,3-b]pyridine-4-carboxylate (Compound 45-b)

To a solution of the mixture (0.89 g, 3.50 mmol) of the compounds 44-a and 45-a in ethanol (10 mL) was added hydrazine hydrate (0.35 g, 6.99 mmol), and the mixture was stirred under reflux for 2 hours. Upon the completion of the reaction, the mixture was cooled to room temperature, and the solvent was removed to obtain a mixture of the title compounds (44-b and 45-b) (0.64 g, 81%), which was then used for the next reaction without further purification.

(Step 3) Preparation of 1H,4H,5H,6H,7H-pyrazolo[3,4-c]pyridine (44-c) and 1H,4H,5H,6H,7H-pyrazolo[4,3-b]pyridine (45-c)

To a solution of the mixture (0.64 g, 2.86 mmol) of the title compounds (44-b and 45-b) in methylene chloride (5 mL) was added 4 N hydrogen chloride dioxane solution (5 mL) at 0° C., and the mixture was stirred for 15 hours. Upon the completion of the reaction, the solvent was removed and thus the residue was treated with diethyl ether to form a solid. The precipitate was filtered, and washed with diethyl ether to obtain a mixture of the title compounds quantitatively (44-c and 45-c) (0.55 g).
MS m/z: 124 [M+1]$^+$ (Step 4) Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[3,4-c]pyridin-6-yl}ethan-1-one (Compound 44) and 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-b]pyridin-4-yl}ethan-1-one (Compound 45)

By using the mixture of the compounds 44-c and 45-c instead of the intermediate im-7, the reaction was carried out in the same manner as Example 6-1 to obtain a mixture of the title compounds 44 and 45.

(Compound 44)
MS m/z: 443 [M+1]$^+$
$^1$H NMR (CDCl$_3$, 400 MHz), δ ppm: 8.98-8.76 (m, 2H), 7.38 (s, 1H), 7.28-7.18 (m, 4H), 5.84-5.81 (m, 1H), 5.30 (d, 1H), 4.89 (m, 1H), 4.79 (d, 2H), 4.16 (d, 2H), 3.86 (m, 2H), 3.42 (dd, 2H), 2.92 (dd, 2H), 2.74 (m, 2H)

(Compound 45)
MS m/z: 443 [M+1]$^+$
$^1$H NMR (DMSO-d$_6$, 400 MHz), δ ppm: 8.85 (d, 2H), 8.42 (m, 1H), 7.99 (m, 1H), 7.24-7.14 (m, 4H), 4.72 (m, 1H), 4.67 (s, 2H), 3.27 (dd, 2H), 2.94 (dd, 2H), 2.74-2.66 (m, 2H), 2.04-1.94 (m, 2H)

[Example 6-13] Preparation of N-{1-[2-(5-{2-[(2,3-dihydro-1H-inden-2-yl)amino]pyrimidin-5-yl}-1,3,4-oxadiazol-2-yl)acetyl]pyrrolidin-3-yl}aminosulfonamide (Compound 46)

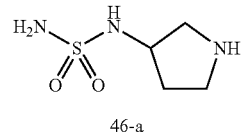

46-a

+

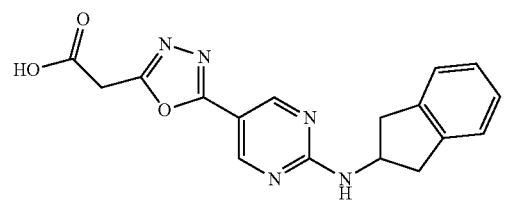

33-d

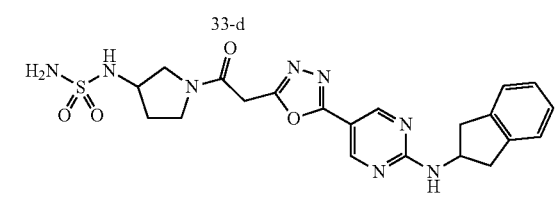

46

(Step 1) Preparation of
N-(pyrrolidin-3-yl)aminosulfonamide hydrochloride
salt (Compound 46-a)

According to a well-known method (WO 2011160020), the intermediate N-(pyrrolidin-3-yl)aminosulfonamide hydrochloride salt (Compound 46-a) was synthesized.
MS m/z: 166 [M+1]$^+$
$^1$H NMR (DMSO-d$_6$, 400 MHz), δ ppm: 9.30 (s, 2H), 6.99 (s, 1H), 6.77 (s, 1H), 3.92 (s, 2H), 3.33-3.04 (m, 4H), 2.17-1.89 (m, 2H)

(Step 2) Preparation of
N-(pyrrolidin-3-yl)aminosulfonamide Hydrochloride
Salt (Compound 46-a)

By using the compound 46-a instead of the compound im-7, the reaction was carried out in the same manner as Example 6-1 to obtain the compound 46.
MS m/z: 485 [M+1]$^+$
$^1$H NMR (DMSO-d$_6$, 400 MHz), δ ppm: 8.86 (s, 2H), 8.43 (d, 2H), 7.23-7.14 (m, 4H), 6.95 (dd, 1H), 6.70 (d, 2H), 4.74-4.69 (m, 1H), 4.19-4.12 (m, 2H), 3.94-3.43 (m, 4H), 3.33-3.26 (m, 2H), 2.97-2.91 (m, 2H), 2.16-1.87 (m, 2H)

[Example 6-14] Preparation of N-{1-[2-(5-{2-[(2,3-dihydro-1H-inden-2-yl)amino]pyrimidin-5-yl}-1,3,4-oxadiazol-2-yl)acetyl]pyrrolidin-3-yl}methanesulfonamide (Compound 47)

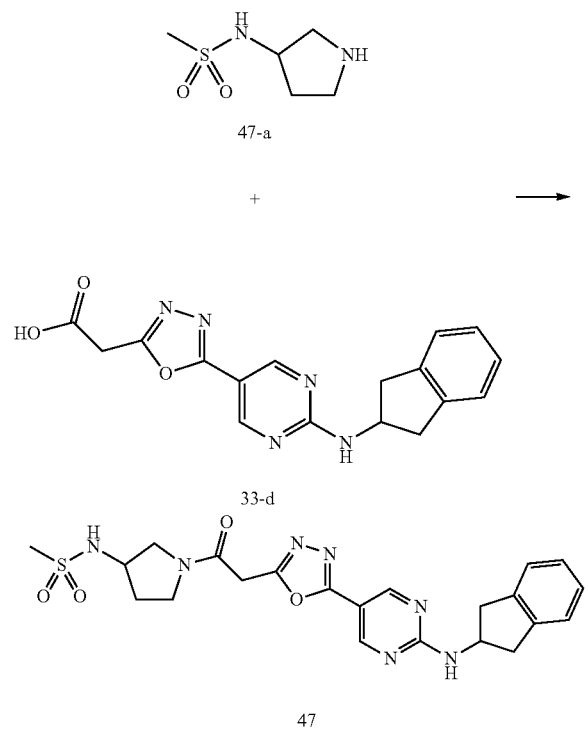

(Step 1) Preparation of N-(pyrrolidin-3-yl)methane sulfonamide (Compound 47-a)

According to a well-known method (US 20110183985), the intermediate N-(pyrrolidin-3-yl)methanesulfonamide (Compound 47-a) was synthesized.
MS m/z: 166 [M+1]$^+$ (Step 2) N-{1-[2-(5-{2-[(2,3-dihydro-1H-inden-2-yl)amino]pyrimidin-5-yl}-1,3,4-oxadiazol-2-yl)acetyl]pyrrolidin-3-yl}methanesulfonamide (Compound 47)

By using the compound 47-a instead of the compound im-7, the reaction was carried out in the same manner as Example 6-1 to obtain the compound 47.
MS m/z: 484 [M+1]$^+$
$^1$H NMR (DMSO-d$_6$, 400 MHz), δ ppm 8.85 (d, 2H), 5.41 (d, 2H), 7.45 (dd, 1H), 7.23-7.14 (m, 4H), 4.74-4.69 (m, 1H), 4.15 (s, 2H), 4.00-3.38 (m, 4H), 3.31-3.26 (m, 2H), 2.99-2.92 (m, 5H), 2.21-1.80 (m, 2H)

[Example 6-15] Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxylic Acid (Compound 48)

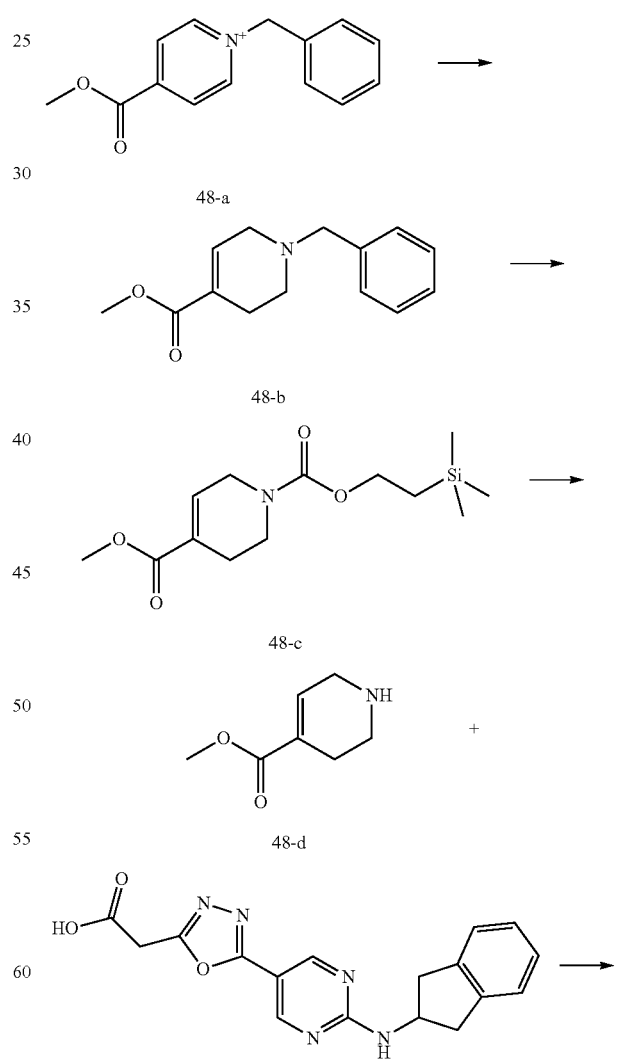

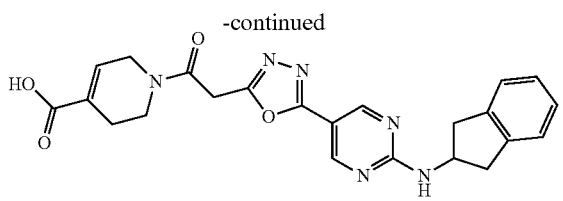

48

(Step 1) Preparation of 1-benzyl-4-(methoxycarbonyl)pyridin-1-ium (Compound 48-a)

To a solution of methyl isonicotinate (1.0 g, 7.3 mmol) in methanol (10 mL) was added benzyl bromide (0.95 mL, 8.75 mmol), and the mixture was stirred for 2 hours at 80° C. under nitrogen atmosphere. Upon the completion of the reaction, the reaction mixture was cooled to room temperature, and concentrated to remove the solvent. The residue was treated with n-hexane to form a solid. The formed solid was filtered and washed with n-hexane to obtain the title compound 48-a as a yellow solid quantitatively (1.7 g).

MS m/z: 229 [M+1]$^+$ $^1$H NMR (DMSO-d$_6$, 400 MHz), δ ppm: 8.39 (d, 2H), 8.54 (d, 2H), 7.56-7.45 (m, 5H), 3.98 (s, 3H)

(Step 2) Preparation of methyl 1-benzyl-1,2,3,6-tetrahydropyridine-4-carboxylate (Compound 48-b)

To a solution of the compound 48-a (2.1 g, 9.2 mmol) in ethanol (20 mL) was added sodium borohydride (0.38 g, 0.010 mol) and distilled water (4 mL) 0° C., and the mixture was stirred for 1 hour at room temperature. Upon the completion of the reaction, the mixture was diluted with distilled water (20 mL) and extracted with methylene chloride. The organic layer was washed with distilled water and saturated brine, dried over anhydrous sodium sulfate, and concentrated to obtain a crude product of the title compound 48-b as a yellow liquid (1.84 g) which was used for the next step without further purification.

MS m/z: 232 [M+1]$^+$ $^1$H NMR (CDCl$_3$, 400 MHz), δ ppm: 7.33-7.24 (m, 5H), 6.88-6.87 (m, 1H), 3.73 (s, 3H), 3.61 (s, 2H), 3.14-3.12 (m, 2H), 2.61 (t, 2H), 2.41-2.41 (m, 2H)

(Step 3) Preparation of 4-methyl 1-[2-(trimethylsilyl)ethyl] 1,2,3,6-tetrahydropyridine-1,4-dicarboxylate (Compound 48-c)

To a solution of the compound 48-b (1.8 g, 7.9 mmol) in methylene chloride (5 mL) was added 2-(trimethylsilyl)ethyl chloroformate (2.8 g, 0.016 mol) at 0° C., and the mixture was stirred for 1 hour at room temperature. Upon the completion of the reaction, the mixture was diluted with distilled water (20 mL) and extracted with ethyl acetate. The organic layer was washed with saturated solution of sodium hydrogen carbonate and saturated brine, dried over anhydrous sodium sulfate, and concentrate. The residue was then purified by silica gel column chromatography (ethyl acetate: n-hexane=1:9) to obtain the title compound 48-c as a colorless liquid (1.34 g, 59%).

MS m/z: 286 [M+1]$^+$ $^1$H NMR (CDCl$_3$, 400 MHz), δ ppm: 6.89 (s, 1H), 4.21 (t, 2H), 4.15-4.11 (m, 2H), 3.76 (s, 3H), 3.56 (s, 2H), 2.41 (s, 2H), 1.02 (t, 2H), 0.05 (s, 9H)

(Step 4) Preparation of methyl 1,2,3,6-tetrahydropyridine-4-carboxylate (Compound 48-d)

To a solution of the compound 48-c (0.50 g, 1.75 mmol) in methylene chloride (5 mL) was added trifluoroacetic acid (3 mL), and the mixture was stirred for 3 hours at room temperature. Upon the completion of the reaction, saturated solution of sodium hydrogen carbonate was added and the mixture was extracted with methylene chloride. The organic layer was washed with water and saturated brine, dried over anhydrous sodium sulfate, and concentrated to obtain the title compound 48-d as a brown liquid (0.22 g, 89%).

MS m/z: 142 [M+1]$^+$ $^1$H NMR (CDCl$_3$, 400 MHz), δ ppm: 6.95 (s, 1H), 3.75 (s, 3H), 3.53 (s, 2H), 2.99 (t, 2H), 2.32 (s, 3H)

(Step 5) Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxylic Acid (Compound 48)

By using the compound 48-d instead of the compound im-7, the reaction was carried out in the same manner as Example 6-1 to obtain the compound 48.

MS m/z: 447 [M+1]$^+$ $^1$H NMR (DMSO-d$_6$, 400 MHz), δ ppm: 8.86-8.63 (m, 2H), 8.43-8.42 (m, 1H), 7.23-7.14 (m, 4H), 7.00-6.69 (m, 1H), 4.74-4.62 (m, 1H), 4.40-4.28 (m, 2H), 4.24-4.09 (m, 1H), 3.70-3.59 (m, 2H), 3.23-3.22 (m, 3H), 2.97-2.87 (m, 3H), 2.38-2.18 (m, 1H)

[Example 6-16] Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxamide (Compound 49)

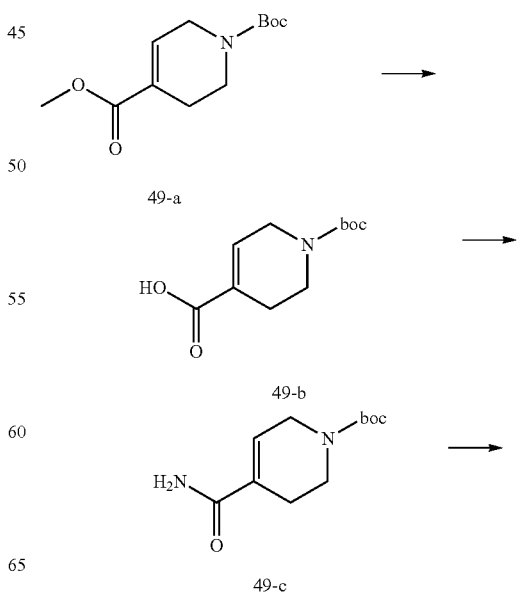

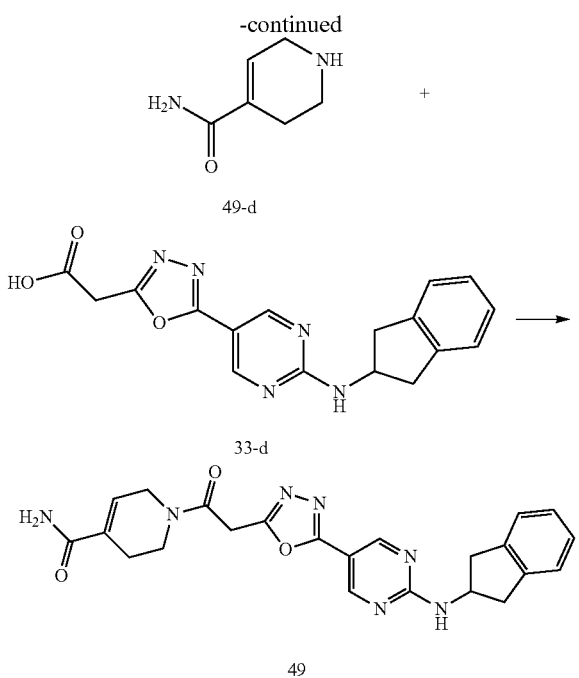

(Step 1) Preparation of 1-tert-butyl 4-methyl 1,2,3, 6-tetrahydropyridine-1,4-dicarboxylate (Compound 49-a)

To a solution of the compound 48-d (0.33 g, 2.36 mmol) in methylene chloride (15 mL) was slowly added di-tert-butyl dicarbonate (0.76 g, 3.49 mmol) and triethylamine (0.6 mL, 4.4 mmol) in order, and the mixture was stirred for 15 hours at room temperature. The reaction mixture was treated with 2 N aqueous hydrochloric acid (2 mL) and stirred for 10 minutes. After adding additionally distilled water (20 mL), the reaction mixture was extracted with methylene chloride. The organic layer was washed with distilled water and saturated brine, dried over anhydrous sodium sulfate, and concentrated. The residue was purified by silica gel column chromatography (ethyl acetate:n-hexane=1:9) to obtain the title compound 49-a as a colorless liquid (0.15 g, 27%).

MS m/z: 242 [M+1]$^+$ $^1$H NMR (CDCl$_3$, 400 MHz), δ ppm: 6.89 (br, 1H), 4.07 (m, 2H), 3.76 (s, 3H), 3.51 (m, 2H), 2.40 (m, 2H), 1.47 (s, 9H)

(Step 2) Preparation of 1-[(tert-butoxy)carbonyl]-1, 2,3,6-tetrahydropyridine-4-carboxylic Acid (Compound 49-b)

To a solution of the compound 49-a (0.15 g, 0.63 mmol) in tetrahydrofuran (3 mL) was added 1 N aqueous solution of lithium hydroxide (3 mL), and the mixture was stirred for 2 hours at room temperature. Upon the completion of the reaction, the mixture was treated with 2 N aqueous solution of hydrochloric acid to adjust pH 2 or lower followed by extraction with methylene chloride. The organic layer was washed with distilled water and saturated brine, dried over anhydrous sodium sulfate, and concentrated to obtain the title compound 49-b as a white solid (0.13 g, 92%).

MS m/z: 228 [M+1]$^+$ $^1$H NMR (CDCl$_3$, 400 MHz), δ ppm: 7.02 (br, 12H), 4.11 (m, 2H), 3.53 (m, 2H), 2.40 (m, 2H), 1.48 (s, 9H)

(Step 3) Preparation of tert-butyl 4-carbamoyl-1,2, 3,6-tetrahydropyridine-1-carboxylate (Compound 49-c)

To a solution of the compound 49-b (0.13 g, 0.59 mmol) and ammonium chloride (0.16 g, 2.93 mmol) in N,N-dimethylformamide (7 mL) was dropwise added to N,N-diisopropylethylamine (0.51 mL, 2.93 mmol) and benzotriazol-1-yl oxy-tripyrrolidinophosphonium hexafluorophosphate (0.46 g, 0.89 mmol) in order 0° C., and the mixture was stirred for 15 hours at room temperature. Upon the completion of the reaction, the mixture was diluted with distilled water (50 mL), and extracted with ethyl acetate. The organic layer was washed with distilled water and saturated brine, dried over anhydrous sodium sulfate, and concentrated. The residue was then purified by silica gel column chromatography (methanol:methylene chloride=5: 95) to obtain the title compound 49-c as a white solid quantitatively (0.14 g).

MS m/z: 227 [M+1]$^+$ $^1$H NMR (CDCl$_3$, 400 MHz), δ ppm: 6.62 (s, 1H), 6.21-5.54 (m 2H), 4.19 (m, 2H), 3.54 (m, 2H), 2.39 (m, 2H), 1.47 (s, 9H)

(Step 4) Preparation of 1,2,3,6-tetrahydropyridine-4-carboxamide (Compound 49-d)

To a solution of the compound 49-c (0.14 g, 0.59 mmol) in methylene chloride (2 mL) was added 4 N hydrogen chloride dioxane solution (2 mL) at 0° C., and the mixture was stirred for 9 hours at room temperature. Upon the completion of the reaction, the mixture was concentrated under reduced pressure. The residue was treated with methylene chloride to form a solid. The formed solid was filtered and washed with methylene chloride to obtain the title compound 49-d as a white solid (41 mg, 43%).

MS m/z: 127 [M+1]$^+$ $^1$H NMR (DMSO-d$_6$, 400 MHz), δ ppm: 9.12 (m, 2H), 7.54 (br, 1H), 7.18 (br, 1H), 6.54 (s, 1H), 3.70 (m, 2H), 3.17 (m, 2H), 2.43 (m, 2H)

(Step 5) Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxamide (Compound 49)

By using the compound 49-d instead of the compound im-7, the reaction was carried out in the same manner as Example 6-1 to obtain the compound 49.

MS m/z: 446 [M+1]$^+$ $^1$H NMR (DMSO-d$_6$, 400 MHz), δ ppm: 8.83 (d, 2H), 8.42 (d, 1H), 7.43 (br, 1H), 7.26-7.12 (m, 4H), 7.08-7.02 (m, 1H), 6.58-6.52 (m, 1H), 4.71 (m, 1H), 4.38-4.04 (m, 4H), 3.64-3.54 (m, 2H), 3.32-3.24 (m, 2H), 2.94 (dd, 2H), 2.42-2.21 (m, 2H)

[Example 6-17] Preparation of 4-[2-(5-{2-[(2,3-dihydro-1H-inden-2-yl)amino]pyrimidin-5-yl}-1,3,4-oxadiazol-2-yl)acetamido]benzoic Acid (Compound 50)

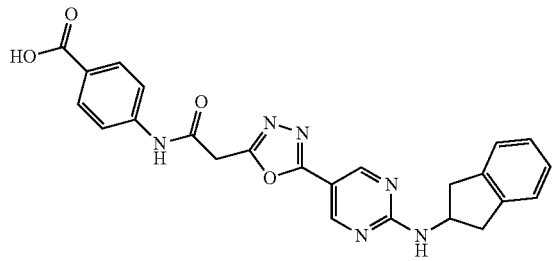

By using tert-butyl 4-aminobenzoate instead of the compound im-7, the reaction was carried out in the same manner as Example 6-1 to obtain the compound 50.

MS m/z: 457 [M+1]$^+$ $^1$H NMR (DMSO-d$_6$, 400 MHz), δ ppm: 10.72 (s, 1H), 8.85 (d, 2H), 8.43 (d, 1H), 7.92-7.90 (m, 4H), 7.24-7.14 (m, 4H), 4.74-4.68 (m, 1H), 3.27-3.25 (m, 2H), 2.97-2.91 (m, 2H)

Example 7

As explained in the following Example 7-1 to Example 7-5, the compound 51 to the compound 55 were prepared from the intermediate im-7 and the compounds that are produced in the following Examples, instead of the compound produced in Example 6-1 (Step 4) according to the similar manner as Example 6-1.

[Example 7-1] Preparation of 2-(3-{2-[(2,3-dihydro-1H-inden-2-yl)amino]pyrimidin-5-yl}-1,2,4-oxadiazol-5-yl)-1-{1H,4H,5H,6H,7H-[1,2,3]triazolo[4,5-c]pyridin-5-yl}ethan-1-one (Compound 51)

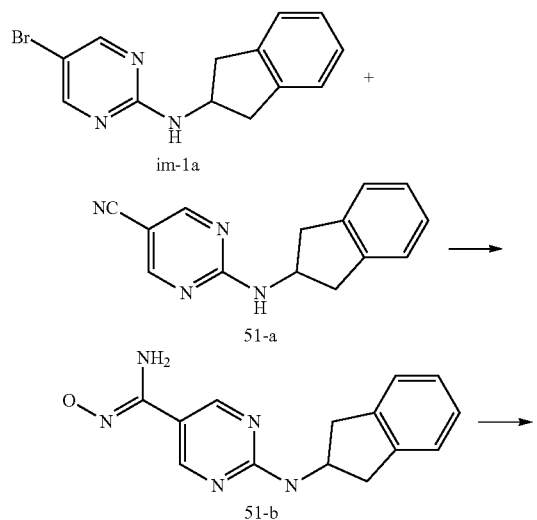

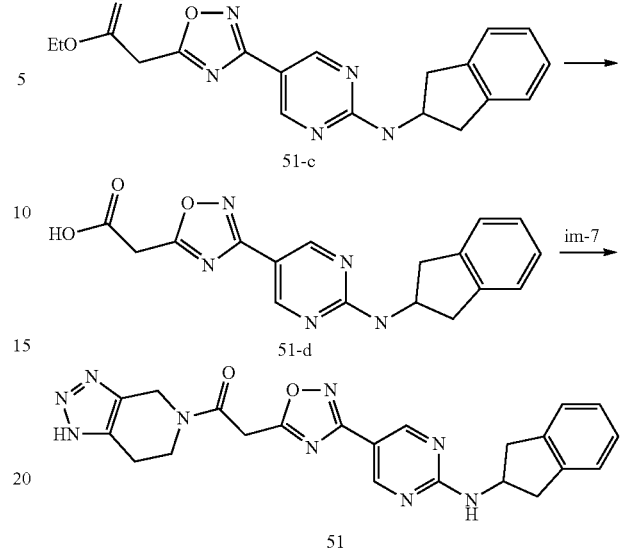

(Step 1) Preparation of 2-[(2,3-dihydro-1H-inden-2-yl)amino]pyrimidine-5-carbonitrile (Compound 51-a)

A mixture of the compound im-1a (2.5 g, 8.6 mmol) and copper (I) cyanide (1.0 g, 11.2 mmol) in N,N-dimethylformamide (41 mL) was stirred for 18 hours at 180° C. Upon the completion of the reaction, the reaction mixture was diluted with ethyl acetate (50 mL) and washed twice with an aqueous solution of sodium cyanide (50 mL). The organic layer was washed with distilled water and saturated brine, dried over anhydrous sodium sulfate, and concentrated. The residue was then purified by silica gel column chromatography (ethyl acetate:n-hexane=15:85) to obtain the title compound 51-a as a white solid (1.48 g, 73%).

MS m/z: 237 [M+1]$^+$ $^1$H NMR (CDCl$_3$, 400 MHz), δ ppm: 8.556 (s, 1H), 8.249 (s, 1H), 7.252-7.134 (m, 4H), 6.189 (d, 1H), 4.900-4.796 (m, 1H), 3.432-3.375 (m, 2H), 2.920-2.852 (m, 2H)

(Step 2) Preparation of (Z)-2-[(2,3-dihydro-1H-inden-2-yl)amino]-N-hydroxypyrimidine-5-carboximidamide (Compound 51-b)

The compound 51-a (0.30 g, 1.27 mmol), hydroxylamine hydrochloride (0.21 g, 3.02 mmol), and potassium carbonate (0.36 g, 2.59 mmol) were dissolved in a mixture solvent of methanol (9 mL) and distilled water (1 mL), and the mixture was stirred under reflux at 100° C. for 2 hours. The reaction mixture was diluted with distilled water (50 mL), and then the precipitate was filtered, washed with distilled water, and dried to obtain the title compound 51-b as a white solid (0.2 g, 59%).

MS m/z: 270 [M+1]$^+$ $^1$H NMR (DMSO-d$_6$, 400 MHz), δ ppm: 8.76 (m, 2H), 8.53 (s, 2H), 7.72 (d, 1H), 7.13-7.22 (m, 4H), 5.82 (br, 1H), 4.58-4.70 (m, 1H), 3.22-3.29 (m, 2H), 2.86-2.93 (m, 2H)

(Step 3) Preparation of ethyl 2-(3-{2-[(2,3-dihydro-1H-inden-2-yl)amino]pyrimidin-5-yl}-1,2,4-oxadiazol-5-yl)acetate (Compound 51-c)

To a solution of the compound 51-b (0.37 g, 1.37 mmol) in toluene (18 mL) was added sodium hydride (41 mg, 1.70 mmol) at 0° C., and the mixture was stirred for 30 minutes at room temperature. The mixture was cooled to 0° C. again, and after adding ethyl malonyl chloride (0.21 mL, 1.64 mmol) thereto, the mixture was stirred for 9 hours at 80° C. Upon the completion of the reaction, insoluble mass was removed by using Celite, and the filtrate was concentrated. The residue was then purified by silica gel column chromatography (ethyl acetate:n-hexane=1:1) to obtain the title compound 51-c as a yellow solid (0.29 mg, 58%).

MS m/z: 366 [M+1]$^+$ $^1$H NMR (CDCl$_3$, 400 MHz), δ ppm: δ 8.92 (m, 2H), 7.18-7.25 (m, 4H), 5.83 (d, 1H), 4.87-4.93 (m, 1H), 4.27 (q, 2H), 3.43 (dd, 2H), 2.92 (dd, 2H), 1.31 (t, 3H)

(Step 4) Preparation of 2-(3-{2-[(2,3-dihydro-1H-inden-2-yl)amino]pyrimidin-5-yl}-1,2,4-oxadiazol-5-yl)acetic acid (Compound 51-d)

By using the compound 51-c (0.29, 0.79 mmol) instead of the compound 33-c, the reaction was carried out in the same manner as the Step 4 of Example 6-1 to obtain the title compound 51-d (0.19 g, 73%).

MS m/z: 338 [M+1]$^+$ $^1$H NMR (DMSO-d$_6$, 400 MHz), δ ppm: 8.869 (d, 2H), 8.312 (d, 1H), 7.142-7.240 (m, 4H), 4.678-4.732 (m, 1H), 4.226 (s, 2H), 3.167-3.295 (m, 2H), 2.910-2.966 (dd, 2H)

(Step 5) Preparation of 2-(3-{2-[(2,3-dihydro-1H-inden-2-yl)amino]pyrimidin-5-yl}-1,2,4-oxadiazol-5-yl)-1-{1H,4H,5H,6H,7H-[1,2,3]triazolo[4,5-c]pyridin-5-yl}ethan-1-one (Compound 51)

By using the compound 51-d instead of the compound 33-d, the reaction was carried out in the same manner as the Step 5 of Example 6-1 to obtain the title compound 51.

MS m/z: 444 [M+1]$^+$ $^1$H NMR (DMSO-d$_6$, 400 MHz), δ ppm: 8.81-8.86 (m, 2H), 8.30 (d, 1H), 7.24-7.14 (m, 4H), 4.80-4.51 (m, 5H), 3.85-3.83 (m, 2H), 3.31-3.25 (m, 2H), 2.97-2.67 (m, 4H)

[Example 7-2] Preparation of 2-(5-{2-[(2,3-dihydro-1H-inden-2-yl)amino]pyrimidin-5-yl}-4H-1,2,4-triazol-3-yl)-1-{1H,4H,5H,6H,7H-[1,2,3]triazolo[4,5-c]pyridin-5-yl}ethan-1-one (Compound 52)

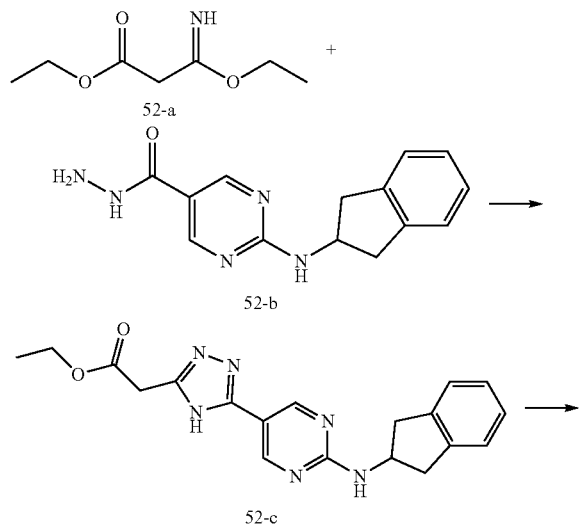

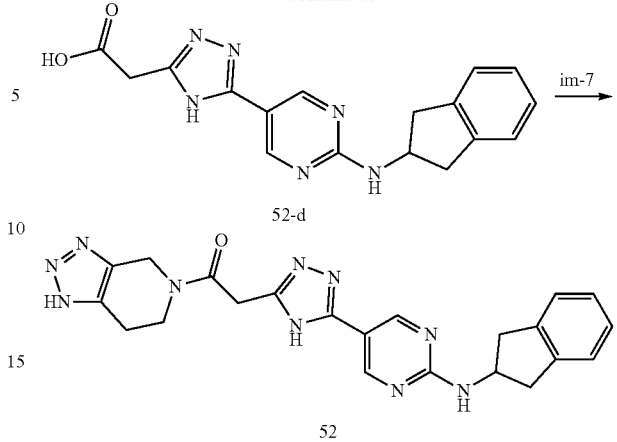

(Step 1) Preparation of ethyl 3-ethoxy-3-iminopropanoate Hydrochloride (Compound 52-a)

According to a well-known method (Synthesis, 2016, 48(17), 2851-2862), the title compound 52-a was prepared.

MS m/z: 160 [M+1]$^+$ $^1$H NMR (DMSO-d$_6$, 400 MHz), δ ppm: δ 4.13-4.09 (m, 4H), 3.45 (s, 2H), 1.20-1.18 (m, 6H)

(Step 2) Preparation of 2-[(2,3-dihydro-1H-inden-2-yl)amino]pyrimidine-5-carbohydrazide (Compound 52-b)

To a solution of the compound im-2a (6.0 g, 0.02 mol) in ethanol (50 mL) was added hydrazine hydrate (10 mL, 0.21 mol), and the mixture was stirred for 15 hours at 80° C. Upon the completion of the reaction, the reaction mixture was cooled to room temperature to form a solid, which was then filtered, washed with ethanol, and dried to obtain the title compound 52-b as a white solid (5.3 g, 83%).

MS m/z: 270[M+1]$^+$ $^1$H NMR (DMSO-d$_6$, 400 MHz), δ ppm: 9.58 (s, 1H), 8.71 (d, 2H), 8.08 (d, 2H), 7.23-7.13 (m, 4H), 4.69-4.63 (m, 1H) 4.41 (s, 2H), 3.26 (dd, 2H), 2.9 (dd, 2H)

(Step 3) Preparation of ethyl 2-(5-{2-[(2,3-dihydro-1H-inden-2-yl)amino]pyrimidin-5-yl}-4H-1,2,4-triazol-3-yl)acetate (Compound 52-c)

To a solution of the compound 52-a (0.88 g, 4.53 mmol) and the compound 52-b (0.61 g, 2.26 mmol) in ethanol (10 mL) was added triethylamine (0.95 mL, 6.80 mmol), and the mixture was stirred for 24 hours at 90° C. under nitrogen atmosphere. Upon the completion of the reaction, the reaction mixture was cooled to room temperature, diluted with distilled water (20 mL) and then extracted with ethyl acetate. The organic layer was washed with distilled water and saturated brine, dried over anhydrous sodium sulfate, and concentrated. The residue was then purified by silica gel column chromatography (ethyl acetate:n-hexane=6:4→7:3) to obtain the title compound 52-c as a yellow solid (0.27 g, 33%).

MS m/z: 365 [M+1]$^+$

¹H NMR (CDCl₃, 400 MHz), δ ppm: 8.93 (s, 2H), 7.26-7.16 (m, 4H), 5.77 (d, 1H), 4.90-4.85 (m, 1H), 4.30-4.21 (m, 2H), 3.99 (s, 2H), 3.42 (dd, 2H), 2.91 (dd, 2H), 1.42-1.35 (m, 3H)

(Step 4) Preparation of 2-(5-{2-[(2,3-dihydro-1H-inden-2-yl)amino]pyrimidin-5-yl}-4H-1,2,4-triazol-3-yl)acetic Acid (Compound 52-d)

By using the compound 52-c (73 mg, 0.20 mmol) instead of the compound 33-c, the reaction was carried out in the same manner as the Step 4 of Example 6-1 to obtain the title compound 52-d (52 mg, 77%).

MS m/z: 337 [M+1]⁺

¹H NMR (DMSO-d₆, 400 MHz), δ ppm: 8.82 (s, 2H), 7.96 (s, 1H), 7.23-7.15 (m, 4H), 4.69-4.67 (m, 1H), 3.79 (s, 2H), 3.29-3.25 (m, 2H), 2.92 (dd, 2H)

(Step 5) Preparation of 2-(5-{2-[(2,3-dihydro-1H-inden-2-yl)amino]pyrimidin-5-yl}-4H-1,2,4-triazol-3-yl)-1-{1H,4H,5H,6H,7H-[1,2,3]triazolo[4,5-c]pyridin-5-yl}ethan-1-one (Compound 52)

By using the compound 52-d (52 mg, 0.154 mmol) instead of the compound 33-d, the reaction was carried out in the same manner as the Step 5 of Example 6-1 to obtain the title compound 52 (10 mg, 15%).

MS m/z: 443 [M+1]⁺

¹H NMR (DMSO-d₆, 400 MHz), δ ppm: 8.80 (d, 2H), 8.08-7.82 (m, 1H), 7.22-7.15 (m, 4H), 4.84-4.68 (m, 3H), 4.13-3.83 (m, 4H), 3.31-3.24 (m, 2H), 2.95-2.73 (m, 4H)

[Example 7-3] Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-c]pyridin-5-yl}ethan-1-one (Compound 63)

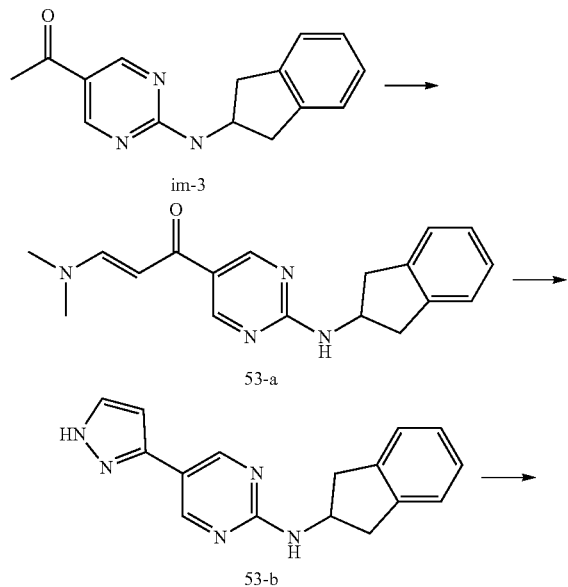

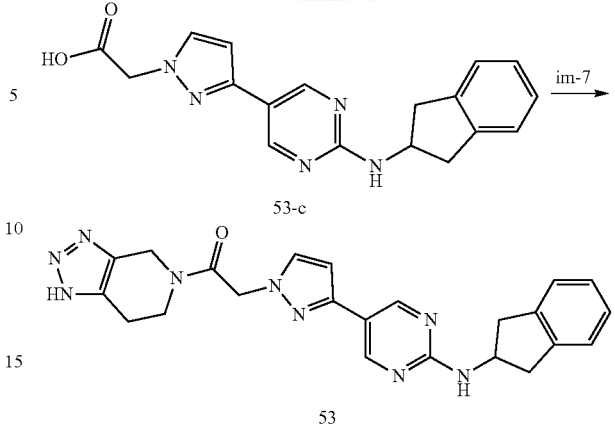

(Step 1) Preparation of (2E)-1-{2-[(2,3-dihydro-1H-inden-2-yl)amino]pyrimidin-5-yl}-3-(dimethylamino)prop-2-en-1-one (Compound 53-a)

To a solution of the compound im-3 (0.10 g, 0.39 mmol) in toluene (3 mL) was added N,N-dimethylformamide dimethyl acetal (0.06 mL, 0.45 mmol), and the mixture was stirred for 16 hours at 120° C. Upon the completion of the reaction, the reaction mixture was cooled to room temperature, diluted with distilled water (20 mL), and then extracted with ethyl acetate. The organic layer was washed with distilled water and saturated brine, dried over anhydrous sodium sulfate, and concentrated to obtain the title compound 53-a (0.11 g, 92%).

MS m/z: 309 [M+1]⁺

¹H NMR (CDCl₃, 400 MHz), δ ppm: 8.84 (br, 2H), 7.81 (d, 1H), 7.25-7.17 (m, 4H), 5.64 (d, 1H), 5.55 (d, 1H), 4.90-4.86 (m, 1H), 4.27 (q, 2H), 3.41 (dd, 2H), 3.16 (br, 3H), 2.92 (br, 3H), 2.90 (dd, 2H)

(Step 2) Preparation of N-(2,3-dihydro-1H-inden-2-yl)-5-(1H-pyrazol-3-yl)pyrimidin-2-amine (Compound 53-b)

To a solution of the compound 53-a (0.11 g, 0.36 mmol) in ethanol (15 mL) was added hydrazine hydrate (0.19 g, 3.71 mmol), and the mixture was stirred for 2 hours at 80° C. Upon the completion of the reaction, the mixture was cooled to room temperature, diluted with distilled water (50 mL), and then extracted with ethyl acetate. The organic layer was washed with distilled water and saturated brine, dried over anhydrous sodium sulfate, and concentrated to obtain the title compound 53-b as a red solid (97 mg, 98%).

MS m/z: 309 [M+1]⁺

¹H NMR (CDCl₃, 400 MHz), δ ppm: δ 8.73 (br, 2H), 7.63 (d, 1H), 7.25-7.17 (m, 4H), 6.54 (d, 1H), 5.50 (d, 1H), 4.90-4.84 (m, 1H), 3.43 (dd, 2H), 2.91 (dd, 2H)

(Step 3) Preparation of 2-(3-{2-[(2,3-dihydro-1H-inden-2-yl)amino]pyrimidin-5-yl}-1H-pyrazol-1-yl)acetic Acid (Compound 53-c)

To a solution of the compound 53-b (97 mg, 0.35 mmol) in acetone (12 mL) was added potassium carbonate (0.2 g, 1.4 mmol) and tert-butyl bromoacetate (0.06 mL, 0.64 mmol), and the mixture was stirred under reflux for 13 hours. Upon the completion of the reaction, the mixture was cooled to room temperature, diluted with distilled water (30 mL) and extracted with ethyl acetate. The organic layer was washed with distilled water and saturated brine, dried over anhydrous sodium sulfate, and concentrated. The residue was then dissolved in methylene chloride (2 mL) and trifluoroacetic acid (1.5 mL) was added thereto followed by stirring for 3 hours at room temperature. Upon the completion of the reaction, the solvent was concentrated and the residue was treated with diethyl ether to form a solid. The formed solid was filtered and washed with diethyl ether to obtain the title compound 53-c as a beige solid (94 mg, 80%)

MS m/z: 336 [M+1]$^+$ $^1$H NMR (DMSO-d$_6$, 400 MHz), δ ppm: 8.70 (s, 2H), 7.77 (d, 1H), 7.74-7.61 (m, 1H), 7.25-7.12 (m, 4H), 6.69-6.68 (d, 1H), 4.98 (s, 2H), 4.65 (m, 1H), 3.27 (dd, 2H), 2.91 (dd, 2H)

(Step 4) Preparation of 2-(5-{2-[(2,3-dihydro-1H-inden-2-yl)amino]pyrimidin-5-yl}-1,3,4-oxadiazol-2-yl)-1-{1H,4H,5H,6H,7H-pyrazolo[4,3-c]pyridin-5-yl}ethan-1-one (Compound 53)

By using the compound 53-c instead of the compound 33-d, the reaction was carried out in the same manner as the Step 5 of Example 6-1 to obtain the title compound 53.

MS m/z: 442 [M+1]$^+$ $^1$H NMR (CDCl$_3$, 400 MHz), δ ppm: 8.64 (d, 2H), 7.56 (dd, 1H), 7.21 (m, 4H), 6.51 (dd, 1H), 5.69 (dd, 1H), 5.13 (d, 1H), 4.87-4.83 (m, 3H), 3.93 (m, 2H), 3.43-3.38 (m, 2H), 2.93-2.83 (m, 4H)

[Example 7-4] Preparation of 2-(3-{2-[(2,3-dihydro-1H-inden-2-yl)amino]pyrimidin-5-yl}-5-ethyl-1H-pyrazol-1-yl)-1-{1H,4H,5H,6H,7H-[1,2,3]triazolo[4,5-c]pyridin-5-yl}ethan-1-one (Compound 54)

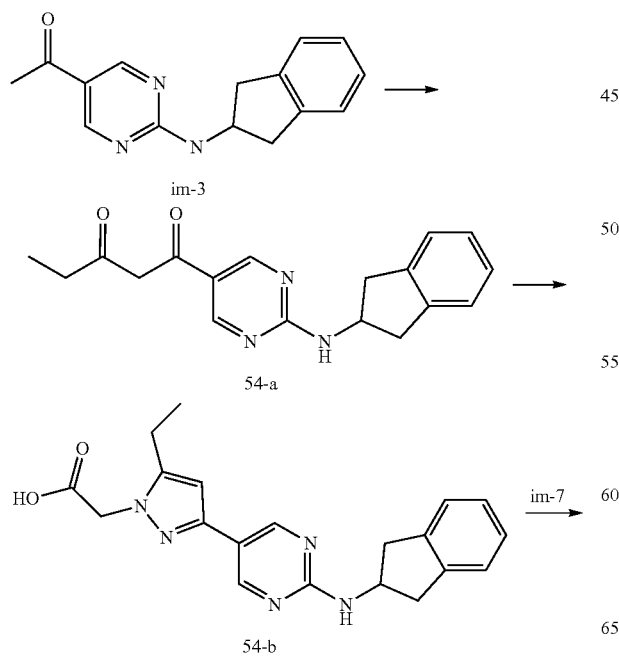

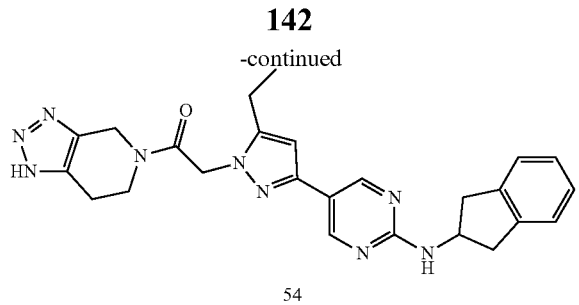

(Step 1) Preparation of 1-{2-[(2,3-dihydro-1H-inden-2-yl)amino]pyrimidin-5-yl}pentane-1,3-dione (Compound 54-a)

To a solution of the compound im-3 (80 mg, 0.32 mmol) in anhydrous tetrahydrofuran (1.5 mL) was added sodium hydride (20 mg, 0.63 mmol) under stirring at 0° C., and the mixture was stirred for 1 hour. Then, a solution of ethyl propionate (50 mg, 0.5 mmol) in anhydrous tetrahydrofuran (1 mL) was slowly added thereto. After stirring for 1.5 hours, N,N-dimethylformamide (0.3 mL) was added. After stirring for 1 hour, the reaction temperature was raised to 50° C. followed by stirring for 15 hours. Upon the completion of the reaction, the mixture was cooled to room temperature, diluted with distilled water (40 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=2:8) to obtain the title compound 54-a as a brown solid (26 mg, 27%).

MS m/z: 310 [M+1]$^+$ $^1$H NMR (CDCl$_3$, 400 MHz), δ ppm: 8.92-8.64 (m, 2H), 7.28-7.16 (m, 4H), 5.98 (s, 1H), 5.93 (d, 1H), 4.89 (m, 1H), 3.42 (dd, 2H), 2.91 (dd, 2H), 2.43 (m, 2H), 1.21 (t, 3H)

(Step 2) Preparation of 2-(3-{2-[(2,3-dihydro-1H-inden-2-yl)amino] pyrimidin-5-yl}-5-ethyl-1H-pyrazol-1-yl) acetic Acid (Compound 54-b)

From the compound 54-a (115 mg, 0.37 mmol) which has been prepared in the above (Step 1), the similar method of (Step 2) and (Step 3) of Example 7-3 was carried out to obtain the title compound 54-b as a beige solid (100 mg, 3-step yield of 57%).

MS m/z: 364 [M+1]$^+$ $^1$H NMR (CDCl$_3$, 400 MHz), δ ppm: 9.96 (m, 1H), 9.07 (m, 1H), 8.44 (1n, 1H), 7.25-7.18 (m, 4H), 6.27 (s, 1H), 4.92-4.84 (m, 3H), 3.42 (dd, 2H), 3.07 (dd, 2H), 2.63 (m, 2H), 1.33 (t, 3H)

(Step 3) Preparation of 2-(3-{2-[(2,3-dihydro-1H-inden-2-yl)amino]pyrimidin-5-yl}-5-ethyl-1H-pyrazol-1-yl)-1-{1H,4H,5H,6H,7H-[1,2,3]triazolo[4,5-c]pyridin-5-yl}ethan-1-one (Compound 54)

By using the compound 54-b instead of the compound 33-d, the reaction was carried out in the same manner as the Step 5 of Example 6-1 to obtain the title compound 54.

MS m/z: 470 [M+1]$^+$ $^1$H NMR (CDCl$_3$, 400 MHz), δ ppm: 8.63 (d, 2H), 7.24-7.12 (m, 4H), 6.29 (d, 1H), 5.74 (dd, 1H), 5.08-5.06 (m, 2H), 4.86-4.76 (m, 3H), 3.96-3.84 (m, 2H), 3.44-3.34 (m, 2H), 2.94-2.74 (m, 4H), 2.69-2.59 (m, 2H), 1.38-1.30 (m, 3H)

[Example 7-5] Preparation of 2-{4-[2-({[3-(trifluoromethoxy)phenyl]methyl}amino)pyrimidin-5-yl]-1H-1,2,3-triazol-1-yl}acetic Acid (Compound 55)

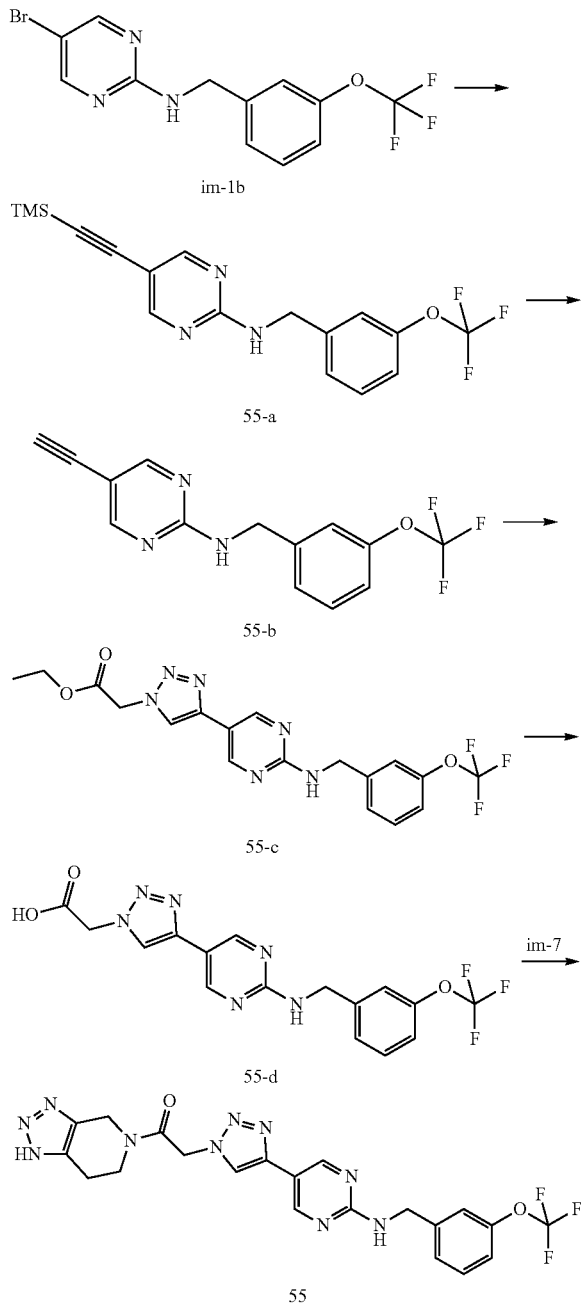

(Step 1) Preparation of N-{[3-(trifluoromethoxy)phenyl]methyl}-5-[2-(trimethylsilyl)ethynyl]pyrimidin-2-amine (Compound 55-a)

To a mixture of the compound im-1b (0.5 g, 1.44 mmol), bis(triphenylphosphine)dichloropalladium (II) (20 mg, 0.03 mmol), and copper iodide (CuI) (11 mg, 0.06 mmol) in N,N-dimethylformamide (3 mL) was added triethylamine (3 mL, 0.02 mol) and trimethylsilylacetylene (0.24 mL, 1.72 mmol), and the mixture was stirred at 90° C. Upon the completion of the reaction, insoluble mass was removed by filtration using a Celite pad. The filtrate was washed with water three times. The organic layer was washed with distilled water and saturated brine, dried over anhydrous sodium sulfate, and concentrated. The residue was purified by silica gel column chromatography (ethyl acetate:n-hexane=1:9) to obtain the title compound 55-a as a brown solid (0.55 g, 87%).

MS m/z: 366 [M+1]$^+$ $^1$H NMR (CDCl$_3$, 400 MHz), δ ppm: 8.34 (s, 2H), 7.36-7.11 (m, 4H), 6.03 (br, 1H), 4.66 (d, 2H), 0.24 (s, 9H)

(Step 2) Preparation of 5-ethynyl-N-{[3-(trifluoromethoxy)phenyl]methyl}pyrimidin-2-amine (Compound 55-b)

To a solution of the compound 55-a (0.25 g, 0.68 mmol) in methanol (3 mL) was added potassium carbonate (0.28 g, 2.05 mmol), and the mixture was stirred for 2 hours at room temperature. Upon the completion of the reaction, the mixture was cooled to room temperature, diluted with distilled water (10 mL), and then extracted with ethyl acetate. The organic layer was washed with distilled water and saturated brine, dried over anhydrous sodium sulfate, and concentrated. The residue was purified by silica gel column chromatography (ethyl acetate:n-hexane=1:9) to obtain the title compound 55-b as a beige solid (0.16 g, 80%).

MS m/z: 294 [M+1]$^+$ $^1$H NMR (CDCl$_3$, 400 MHz), δ ppm: 8.41 (s, 2H), 7.38-7.11 (m, 4H), 5.69 (br, 1H), 4.68 (d, 2H), 3.19 (s, 1H)

(Step 3) Preparation of ethyl 2-{4-[2-({[3-(trifluoromethoxy)phenyl]methyl}amino)pyrimidin-5-yl]-1H-1,2,3-triazol-1-yl}acetate (Compound 55-c)

To a solution of the compound 55-b (0.16 g, 0.54 mmol) in a mixture solvent of ethanol (3 mL) and distilled water (1 mL) was added ethyl 2-azidoacetate (85 mg, 0.65 mmol), copper sulfonate (8.7 mg, 0.05 mmol), and sodium ascorbate (0.11 g, 0.54 mmol) in order, and the mixture was stirred for 16 hours at room temperature. Upon the completion of the reaction, the mixture was diluted with distilled water (20 mL), and extracted with ethyl acetate. The organic layer was washed with distilled water and saturated brine, dried over anhydrous sodium sulfate, and concentrated to obtain the title compound 55-c as a beige solid quantitatively (0.24 g).

MS m/z: 423 [M+1]$^+$ $^1$H NMR (CDCl$_3$, 400 MHz), δ ppm: 8.77 (s, 2H), 7.87 (s, 1H), 7.41-7.13 (m, 4H), 5.67 (t, 1H), 5.23 (s, 2H), 4.74 (d, 2H), 4.34-4.28 (m, 2H), 1.36-1.32 (m, 3H)

(Step 4) Preparation of 2-{4-[2-({[3-(trifluoromethoxy)phenyl]methyl}amino)pyrimidin-5-yl]-1H-1,2,3-triazol-1-yl}acetic Acid] (Compound 55-d)

By using the compound 55-c (0.24 g, 0.54 mmol) instead of the compound 33-c, the reaction was carried out in the same manner as the Step 4 of Example 6-1 to obtain the title compound 55-d as a beige solid (0.21 g, 95%).

MS m/z: 395 [M+1]$^+$ $^1$H NMR (DMSO-d$_6$, 400 MHz), δ ppm: 8.75 (s, 2H), 8.45 (s, 1H), 8.08 (br, 1H), 7.47-7.21 (m, 4H), 5.34 (s, 2H), 4.60 (s, 2H)

(Step 5) Preparation of 2-{4-[2-({[3-(trifluoromethoxy)phenyl]methyl}amino)pyrimidin-5-yl]-1H-1,2,3-triazol-1-yl}acetic Acid (Compound 55)

By using the compound 55-d instead of the compound 33-d, the reaction was carried out in the same manner as the Step 5 of Example 6-1 to obtain the title compound 55.

MS m/z: 501 [M+1]$^+$ $^1$H NMR (DMSO-d$_6$, 400 MHz), δ ppm: 8.74 (br, 2H), 8.38-8.33 (m, 1H), 8.03 (t, 1H), 7.47-7.19 (m, 4H), 5.68 (d, 2H), 4.75 (d, 2H), 4.59 (d, 2H), 3.84-3.80 (m, 2H), 2.96-2.66 (m, 2H)

[Example 8-1] Preparation of 2-(4-{2-[(2,3-dihydro-1H-inden-2-yl)amino]pyrimidin-5-yl}-1H-pyrazol-1-yl)-1-{1H,4H,5H,6H,7H-[1,2,3]triazolo[4,5-c]pyridin-5-yl}ethan-1-one (Compound 56)

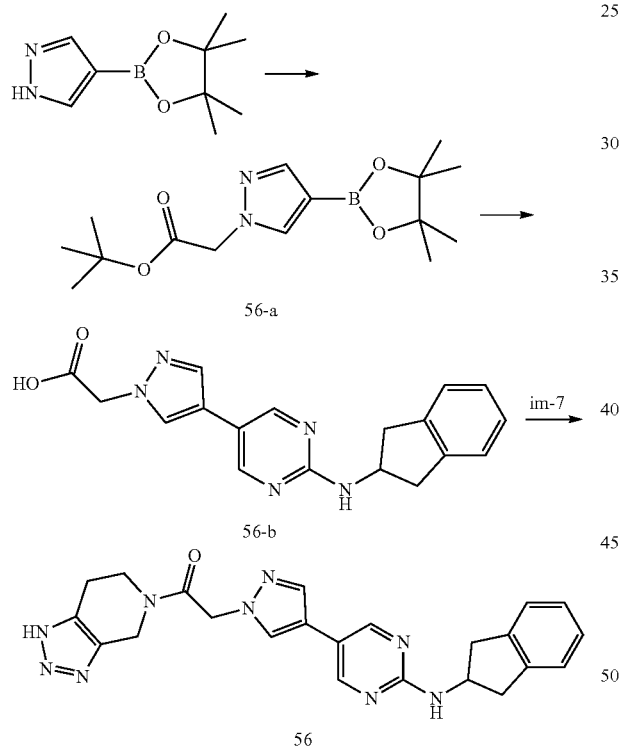

(Step 1) Preparation of tert-butyl 2-[4-(tetramethyl-1,3,2-dioxaboroalan-2-yl)-1H-pyrazol-1-yl]acetate (Compound 56-a)

To a mixture of 4-(4,4,5,5-Tetramethyl-1,3,2-dioxabororan-2-yl)-1H-pyrazole (0.5 g, 2.6 mmol) and cesium carbonate (1.3 g, 3.9 mmol) in N,N-dimethylformamide (10 mL) was added tert-butyl bromoacetate (0.6 mL, 3.9 mmol), and the mixture was stirred for 8 hours at room temperature. Upon the completion of the reaction, the mixture was cooled to room temperature, diluted with distilled water (50 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=1:3) to obtain the title compound 56-a as a yellow solid (1.1 g, 63%).

MS m/z: 309 [M+1]$^+$ $^1$H NMR (CDCl$_3$, 400 MHz), δ ppm: 7.82 (s, 1H), 7.75 (s, 1H), 4.82 (s, 2H), 1.47 (s, 9H), 1.31 (s, 12H)

(Step 2) Preparation of 2-(4-{2-[(2,3-dihydro-1H-inden-2-yl)amino]pyrimidin-5-yl}-1H-pyrazol-1-yl) acetic Acid (Compound 56-b)

The compound 56-a (0.2 mg, 0.7 mmol), the compound im-1a (0.2 g, 0.6 mmol), tetrakis(triphenylphosphine)palladium (0) (35 mg, 0.03 mmol), and potassium carbonate (0.2 mg, 1.2 mmol) were dissolved in a mixture solvent of acetonitrile and distilled water (4:1, 10 mL). After flushing with nitrogen gas, the mixture was stirred for 12 hours at 110° C. Upon the completion of the reaction, the mixture was cooled to room temperature, diluted with ethyl acetate (20 mL), and extracted with distilled water. Aqueous layer was diluted with saturated solution of sodium hydrogen carbonate and extracted with ethyl acetate. The organic layer was washed with distilled water and saturated brine, dried over anhydrous sodium sulfate, and concentrated to obtain the title compound 56-b as a light yellow solid (110 mg, 55%).

MS m/z: 336 [M+1]$^+$ (Step 3) Preparation of 2-(4-{2-[(2,3-dihydro-1H-inden-2-yl)amino]pyrimidin-5-yl}-1H-pyrazol-1-yl)-1-{1H,4H,5H,6H,7H-[1,2,3]triazolo[4,5-c]pyridin-5-yl}ethan-1-one (Compound 56)

By using the compound 56-b (97 mg, 0.3 mmol) instead of the compound 33-d, the reaction was carried out in the same manner as the Step 5 of Example 6-1 to obtain the title compound 56 as a white solid (44 mg, 34%).

MS m/z: 442 [M+1]$^+$ $^1$H NMR (CD$_3$OD, 400 MHz) δ (ppm) 8.632 (s, 2H), 8.028 (d, 1H), 7.870 (d, 1H), 7.232-7.147 (m, 4H), 5.334-5.297 (m, 2H), 4.825-4.739 (m, 3H), 3.946-3.916 (m, 2H), 3.397-3.341 (m, 2H), 2.993-2.835 (m, 4H)

[Example 8-2] Preparation of 2-(4-{2-[(2,3-dihydro-1H-inden-2-yl)amino]pyrimidin-5-yl}-1H-pyrazol-1-yl)-N-(2-oxo-2,3-dihydro-1,3-benzoxazol-6-yl)acetamide (Compound 57)

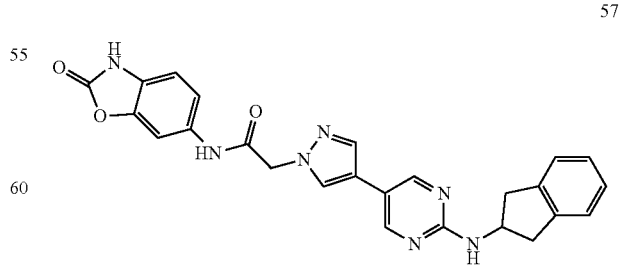

Except that the compound 27-a (54 mg, 0.40 mmol) which has been prepared in Example 5-2 (Step 1) and the compound 56-b (60 mg, 0.20 mmol) which has been prepared in Example 8-1 (Step 2) are used, instead of the compound im-7 and the compound 33-d respectively, the reaction was carried out in the same manner as the Step 5 of Example 6-1 to obtain the title compound 57 as a white solid (6 mg, 7%).

MS m/z: 468 [M+1]⁺

¹H NMR (400 MHz, DMSO-d₆), δ ppm: 10.349 (s, 1H), 8.540 (s, 2H), 8.099 (s, 1H), 7.840 (s, 1H), 7.588 (s, 1H), 7.435 (d, 1H), 7.183-7.091 (m, 5H), 6.981 (d, 1H), 4.972 (s, 2H), 4.613-4.560 (m, 1H), 3.249-3.191 (m, 2H), 2.891-2.834 (m, 2H)

[Example 8-3] Preparation of 2-(4-{6-[(2,3-dihydro-1H-inden-2-yl)amino]pyridin-3-yl}-1H-pyrazol-1-yl)-1-{1H,4H,5H,6H,7H-[1,2,3]triazolo[4,5-c]pyridin-5-yl}ethan-1-one (Compound 58)

58

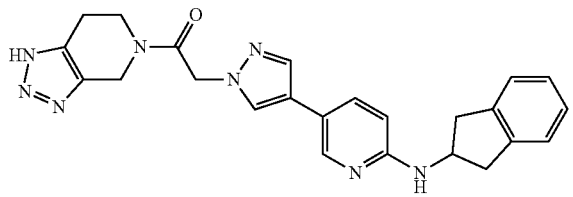

By using the compound im-1d instead of the compound im-1a, the reaction was carried out in the same manner as the Step 2 and the Step 3 of Example 8-1 to obtain the title compound 58 having white color (33 mg, 27%).

MS m/z: 441 [M+1]⁺

1H NMR (400 MHz, CD₃OD) δ (ppm) 8.116-8.033 (m, 3H), 7.891 (d, 1H), 7.286-7.179 (m, 4H), 7.068 (d, 1H), 5.348-5.307 (m, 2H), 4.793 (s, 2H), 4.575-4.518 (m, 1H), 3.976-3.917 (m, 2H), 3.496-3.438 (m, 2H), 3.039-2.987 (m, 2H), 2.977-2.832 (m, 2H)

[Example 8-4] Preparation of 2-(4-{5-[(2,3-dihydro-1H-inden-2-yl)amino]pyrazin-2-yl}-1H-pyrazol-1-yl)-1-{1H,4H,5H,6H,7H-[1,2,3]triazolo[4,5-c]pyridin-5-yl}ethan-1-one (Compound 59)

59

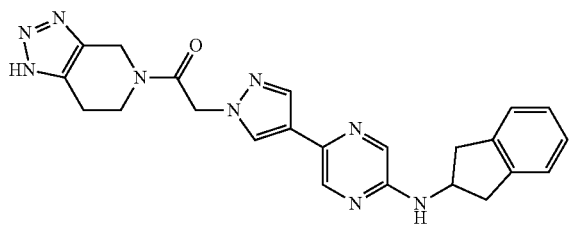

By using the compound im-1e instead of the compound im-1a, the reaction was carried out in the same manner as the Step 2 and the Step 3 of Example 8-1 to obtain the title compound 59 having white color (25 mg, 12%).

MS m/z: 442 [M+1]⁺

1H NMR (400 MHz, CD₃OD) δ (ppm) 8.273 (s, 1H), 8.042-8.013 (d, 1H), 7.927-7.914 (d, 1H), 7.866 (s, 1H), 7.230-7.125 (m, 4H), 5.328-5.291 (m, 2H), 4.833-4.796 (m, 2H), 4.690-4.657 (m, 1H), 3.974-3.910 (m, 2H), 3.391-3.333 (m, 2H), 2.956-2.848 (m, 4H)

[Example 9] Preparation of 2-(4-{2-[(2,3-dihydro-1H-inden-2-yl)amino]pyrimidin-5-yl}-1H-imidazol-1-yl)-1-{1H,4H,5H,6H,7H-[1,2,3]triazolo[4,5-c]pyridin-5-yl}ethan-1-one (Compound 60)

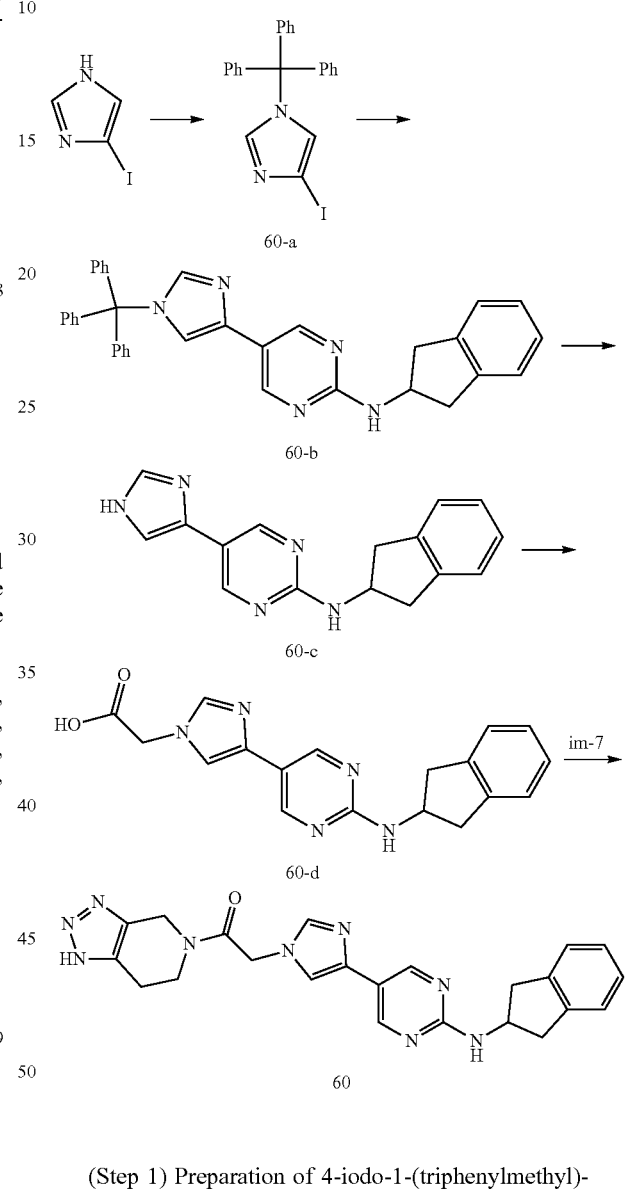

(Step 1) Preparation of 4-iodo-1-(triphenylmethyl)-1H-imidazole (Compound 60-a)

To a solution of 4-iodoimidazole (4-iodo-1H-imidazole) (3.0 g, 0.015 mol) and chlorotriphenylmethyl (6.0 g, 0.021 mol) in anhydrous N,N-dimethylformamide (50 mL) was slowly added triethylamine (7.2 mL, 0.052 mol) at 0° C., and the mixture was stirred for 14 hours at room temperature. The reaction mixture was concentrated, diluted with distilled water (100 mL), and stirred for 20 minutes at room temperature. Thereafter, the precipitate was filtered, and the filtrate was washed with distilled water and diethyl ether to obtain the title compound 60-a as a white solid (4.4 g, 66%).

MS m/z: 437 [M+1]⁺

¹H NMR (CDCl₃, 400 MHz), δ ppm: 7.34-7.36 (m, 9H), 7.32 (s, 1H), 7.10-7.12 (m, 6H), 6.91 (s, 1H)

(Step 2) Preparation of N-(2,3-dihydro-1H-inden-2-yl)-5-[1-(triphenylmethyl)-1H-imidazol-4-yl]pyrimidin-2-amine (Compound 60-b)

A mixture of the compound im-4 (0.69 g, 2.03 mmol), the compound 60-a (0.68 g, 1.56 mmol), tetrakis(triphenylphosphine)palladium (0)(0.18 g, 0.16 mmol), and 2 N aqueous solution of sodium carbonate (2.5 mL) in 1,4-dioxane (10 mL) was flushed with nitrogen gas, and stirred for 9 hours at 100° C. Upon the completion of the reaction, the mixture was cooled to room temperature, diluted with distilled water (50 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=3:7) to obtain the title compound 60-b as a red solid (0.65 g, 80%).

MS m/z: 520 [M+1]⁺

¹H NMR (CDCl₃, 400 MHz), δ ppm: 8.61 (br, 2H), 8.41 (s, 1H), 7.50 (s, 1H), 7.29-7.37 (m, 11H), 7.15-7.24 (m, 8H), 7.00 (s, 1H), 5.40 (d, 1H), 4.79-4.83 (m, 1H), 3.39 (dd, 2H), 2.86 (dd, 2H)

(Step 3) Preparation of N-(2,3-dihydro-1H-inden-2-yl)-5-(1H-imidazol-4-yl)pyrimidin-2-amine (Compound 60-c)

To a of the compound 60-b (0.68 g, 1.31 mmol) in methylene chloride (20 mL) was added trifluoroacetic acid (3 mL) and anisole (0.5 mL), and the mixture was stirred for 16 hours at room temperature. Upon the completion of the reaction, 2 N aqueous solution of hydrogen chloric acid was added to adjust pH 2 or lower, followed by washing with methylene chloride. The aqueous solution layer was treated with 2 N aqueous solution of sodium hydroxide to adjust pH 10 or higher, then extracted again with methylene chloride and ethyl acetate. The organic layer was washed with distilled water and saturated brine, dried over anhydrous sodium sulfate, and concentrated. The residue was purified by silica gel column chromatography (methanol:methylene chloride=1:9) to obtain the title compound 60-c as a dark brown solid (0.27 g, 73%).

MS m/z: 278 [M+1]⁺

¹H NMR (CDCl₃, 400 MHz), δ ppm: 8.68 (s, 2H), 7.73 (s, 1H), 7.16-7.25 (m, 4H), 7.19 (s, 1H), 5.47 (d, 1H), 4.83-4.85 (m, 1H), 3.41 (dd, 2H), 2.90 (dd, 2H)

(Step 4) Preparation of 2-(4-{2[(2,3-dihydro-1H-inden-2-yl)amino]pyrimidin-5-yl}-1H-imidazo-1-yl)acetic Acid (Compound 60-d)

To a solution of the compound 60-c (0.22 g, 0.79 mmol) in anhydrous N,N-dimethylformamide (15 mL) was added sodium hydride (29 mg, 1.2 mmol) at 0° C., and the mixture was stirred for 30 minutes. Then, the mixture was cooled again to 0° C. After adding tert-butyl bromoacetate (0.13 mL, 0.87 mmol) thereto, the mixture was stirred for 9 hours at 80° C. Upon the completion of the reaction, the mixture was cooled to room temperature, diluted with distilled water (50 mL), and extracted with ethyl acetate. The organic layer was washed with distilled water, dried over anhydrous sodium sulfate, and concentrated. The residue was then dissolved in methylene chloride (2 mL). After adding trifluoroacetic acid (1.5 mL) the mixture was stirred for 3 hours at room temperature. Upon the completion of the reaction, the solvent was removed and the residue was washed with diethyl ether to form a solid. The formed solid was filtered and washed with diethyl ether to obtain the title compound 60-d as a beige solid (0.16 g, 2-step yield of 60%).

MS m/z: 336 [M+1]⁺

¹H NMR (DMSO-d₆, 400 MHz), δ ppm: 8.67 (s, 2H), 7.55 (s, 1H), 7.16-7.25 (m, 4H), 7.13 (s, 1H), 5.68 (d, 1H), 4.81-4.85 (m, 1H), 3.41 (dd, 2H), 2.89 (dd, 2H)

(Step 5) Preparation of 2-(4-{2-[(2,3-dihydro-1H-inden-2-yl)amino]pyrimidin-5-yl}-1H-imidazol-1-yl)-1-{1H,4H,5H,6H,7H-[1,2,3]triazolo[4,5-c]pyridin-5-yl}ethan-1-one (Compound 60)

By using the compound 60-d (50 mg, 0.14 mmol) instead of the compound 33-d, the reaction was carried out in the same manner as the Step 5 of Example 6-1 to obtain the title compound 60 as a pink solid (17 mg, 28%).

MS m/z: 442[M+1]⁺

¹H NMR (DMSO-d₆, 400 MHz), δ ppm: 8.64 (s, 2H), 7.61 (d, 1H), 7.46-7.42 (m, 2H), 7.22-7.14 (m, 4H), 5.20 (d, 2H), 4.76-4.60 (m, 3H), 3.83-3.82 (m, 2H), 3.26 (dd, 2H), 2.93-2.67 (m, 4H)

[Example 10-1] Preparation of 2-(4-{2-[(2,3-dihydro-1H-inden-2-yl)amino]pyrimidin-5-yl}-3-ethoxy-1H-pyrazol-1-yl)-1-{1H,4H,5H,6H,7H-[1,2,3]triazolo[4,5-c]pyridin-5-yl}ethan-1-one (Compound 61)

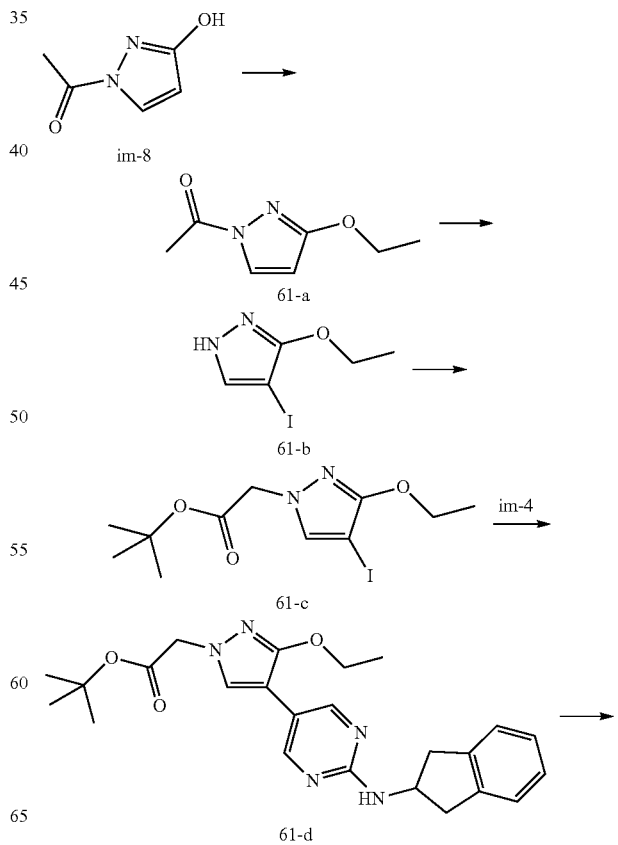

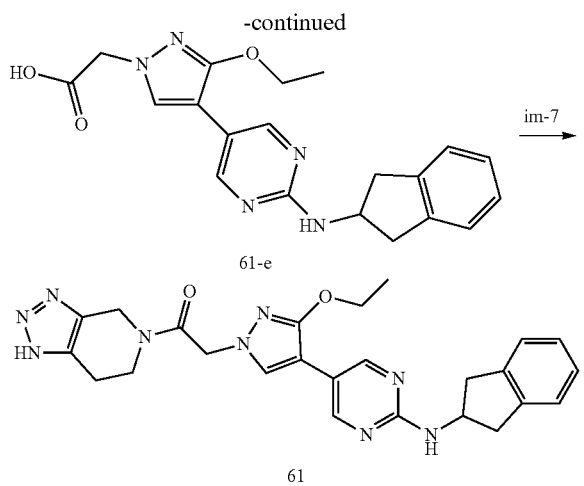

(Step 1) Preparation of 1-(3-ethoxy-1H-pyrazol-1-yl)ethan-1-one (Compound 61-a)

To a solution of the compound im-8 (3.24 g, 0.026 mol) in N,N-dimethylformamide (30 mL) was added potassium carbonate (7.10 g, 0.051 mol) and bromoethane (3.83 mL, 0.051 mol) in order, and the mixture was stirred for 15 hours at room temperature. Upon the completion of the reaction, the mixture was diluted with distilled water (20 mL) and extracted with ethyl acetate. The organic layer was washed with distilled water and saturated brine, dried over anhydrous sodium sulfate, and concentrated. The residue was purified by silica gel column chromatography (ethyl acetate:n-hexane=3:7) to obtain the title compound 61-a as a light brown solid (3.74 g, 76%).

MS m/z: 155 [M+1]$^+$
$^1$H NMR (CDCl$_3$, 400 MHz), δ ppm: 8.06 (d, 1H), 5.96 (d, 1H), 4.32-4.27 (m, 2H), 2.58 (s, 3H), 1.41 (t, 2H)

(Step 2) Preparation of 3-ethoxy-4-iodo-1H-pyrazole (Compound 61-b)

To a solution of the compound 61-a (3.2 g, 0.021 mol) in a mixture solvent of distilled water (100 mL) and ethanol (50 mL) was added sodium iodide (3.4 g, 0.022 mmol), iodine (7.9 g, 31.134 mmol), and potassium carbonate (11.5 g, 83.024 mmol) in order, and the mixture was stirred for 1.5 hours at room temperature. Upon the completion of the reaction, the mixture was diluted with saturated solution of sodium hydrogen carbonate to form a solid, which was then filtered and washed with distilled water to obtain the title compound 61-b as a yellow solid (4.1 g, 83%).

MS m/z: 239 [M+1]$^+$
$^1$H NMR (DMSO-d$_6$, 400 MHz), δ ppm: 12.27 (s, 1H), 7.69 (s, 1H), 4.18-4.12 (m, 2H), 1.30 (t, 3H)

(Step 3) Preparation of tert-butyl 2-(3-ethoxy-4-iodo-1H-pyrazol-1-yl)acetate (Compound 61-c)

To a solution of the compound 61-b (0.36 g, 1.59 mmol) in N,N-dimethylformamide (3 mL) was added cesium carbonate (0.73 g, 2.25 mmol) and tert-butyl bromoacetate (0.3 mL, 2.2 mmol) in order, and the mixture was stirred for 3 hours at room temperature. Upon the completion of the reaction, the mixture was diluted with distilled water (30 mL) and extracted with ethyl acetate. The organic layer was washed with distilled water and saturated brine, dried over anhydrous sodium sulfate, and concentrated. The residue was purified by silica gel column chromatography (ethyl acetate:n-hexane=1:9→3:7) to obtain the title compound 61-c as a light brown liquid (0.39 g, 82%).

MS m/z: 353 [M+1]$^+$
$^1$H NMR (DMSO-d$_6$, 400 MHz), δ ppm: 7.29 (d, 1H), 4.60 (s, 2H), 4.28-4.23 (m, 2H), 1.47 (s, 9H), 1.40 (t, 3H)

(Step 4) Preparation of tert-butyl 2-(4-{2-[(2,3-dihydro-1H-inden-2-yl)amino]pyrimidin-5-yl}-3-ethoxy-1H-pyrazol-1-yl)acetate (Compound 61-d)

To a mixture of the compound 61-c (0.46 g, 1.58 mmol) and the compound im-4 (0.58 g, 1.70 mmol) in a mixture solvent of 1,4-dioxane (6 mL) and distilled water (2 mL) was added tetrakis(triphenylphosphine)palladium (0) (0.15 g, 0.13 mmol) and sodium carbonate (0.42 mg, 3.93 mmol), and the mixture was stirred for 2 hours at 80° C. under nitrogen atmosphere. Upon the completion of the reaction, the mixture was cooled to room temperature, diluted with distilled water (50 mL) was added, and extraction with ethyl acetate was carried out. The organic layer was washed with distilled water and saturated brine, dried over anhydrous sodium sulfate, and concentrated. The residue was purified by silica gel column chromatography (ethyl acetate:n-hexane=3:7) to obtain the title compound 61-d as a yellow solid (0.37 g, 65%).

MS m/z: 436 [M+1]$^+$
$^1$H NMR (CDCl$_3$, 400 MHz), δ ppm: 8.56 (s, 2H), 7.44 (s, 1H), 7.25-7.16 (m, 4H), 5.34 (d, 1H), 4.85-4.77 (m, 1H), 4.63 (s, 2H), 4.33-4.28 (m, 2H), 3.41 (dd, 2H), 2.90 (dd, 2H), 1.98 (s, 1H), 1.48 (s, 9H), 1.40 (t, 3H)

(Step 5) Preparation of 2-(4-{2-[(2,3-dihydro-1H-inden-2-yl)amino]pyrimidin-5-yl}-3-ethoxy-1H-pyrazol-1-yl)acetic Acid (Compound 61-e)

To a solution of the compound 61-d (0.37 g, 0.85 mmol) in methylene chloride (3 mL) was added 4 N hydrogen chloride dioxane solution (3 mL), and the mixture was stirred for 15 hours at room temperature. Upon the completion of the reaction, the solvent was removed, the resulting solid was filtered, washed with diethyl ether, and dried to afford the title compound 61-e as a light brown solid (0.29 g, 89%).

MS m/z: 380 [M+1]$^+$
$^1$H NMR (DMSO-d$_6$, 400 MHz), δ ppm: 8.60 (s, 2H), 7.84 (s, 1H), 7.24-7.14 (m, 4H), 4.79 (s, 2H), 4.71-4.62 (m, 1H), 4.25-4.14 (m, 2H), 3.28 (dd, 2H), 2.92 (dd, 2H), 1.35 (t, 3H)

(Step 6) Preparation of 2-(4-{2-[(2,3-dihydro-1H-inden-2-yl)amino]pyrimidin-5-yl}-3-ethoxy-H-pyrazol-1-yl)-1-{1H,4H,5H,6H,7H-[1,2,3]triazolo[4,5-c]pyridin-5-yl}ethan-1-one (Compound 61)

By using the compound 61-e (30 mg, 0.08 mmol) instead of the compound 33-d, the reaction was carried out in the same manner as the Step 5 of Example 6-1 to obtain the title compound 61 as a white solid (11 mg, 41%).

MS m/z: 486[M+1]$^+$
$^1$H NMR (DMSO-de, 400 MHz), δ ppm: 8.54 (s, 2H), 7.89 (d, 1H), 7.41 (d, 1H), 7.22-7.13 (m, 4H), 5.13 (d, 2H), 4.76-4.58 (m, 3H), 4.22-4.08 (m, 4H), 3.81 (s, 2H), 3.28-3.22 (m, 2H), 2.92-2.73 (m, 4H), 1.35-1.31 (m, 3H)

153

[Example 10-2] Preparation of 2-[3-(azetidin-3-yloxy)-4-{2-[(2,3-dihydro-1H-inden-2-yl)amino]pyrimidin-5-yl}-1H-pyrazol-1yl]-1-{1H,4H,5H,6H,7H-[1,2,3]triazolo[4,5-c]pyridin-5-yl}ethan-1-one hydrochloride (Compound 62)

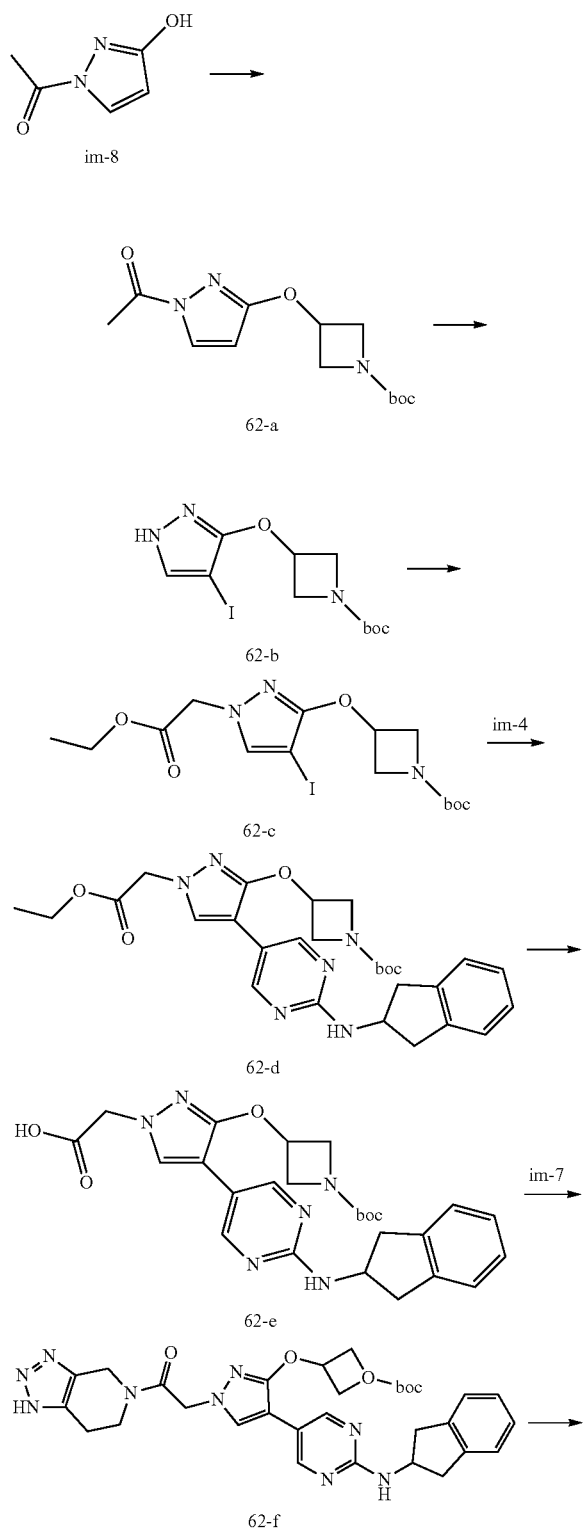

154

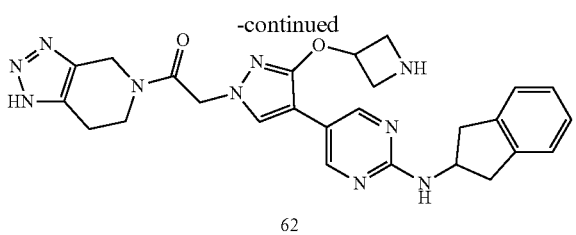

62

(Step 1) Preparation of tert-butyl 3-[(1-acetyl-1H-pyrazol-3-yl)oxy]azetidine-1-carboxylate (Compound 62-a)

To a mixture of the compound im-8 (0.50 g, 3.96 mmol) and 1-N-tert-butoxy carbonyl-3-hydroxyazetidine (0.89 g, 5.15 mmol) in anhydrous tetrahydrofuran (10 mL) was added triphenylphosphine (1.56 g, 5.94 mmol) and diisopropyl azodicarboxylate (1.17 mL, 5.95 mmol) in order at 0° C., and the mixture was stirred for 15 hours at 50° C. under nitrogen atmosphere-. Upon the completion of the reaction, the mixture was cooled to room temperature, diluted with distilled water (20 mL), and extracted with ethyl acetate. The organic layer was washed with distilled water and saturated brine, dried over anhydrous sodium sulfate, and concentrated. The residue was purified by silica gel column chromatography (ethyl acetate:n-hexane=1:9) to obtain the title compound 62-a as a light yellow liquid (0.86 g, 77%).

MS m/z: 282 [M+1]$^+$ $^1$H NMR (CDCl$_3$, 400 MHz), δ ppm: 8.07 (d, 1H), 5.98 (d, 1H), 5.21-5.16 (m, 1H), 4.32-4.28 (m, 2H), 4.03-4.00 (m, 2H), 2.56 (s, 3H)

(Step 2) Preparation of tert-butyl 3-[(4-iodo-1H-pyrazol-3-yl)oxy]azetidine-1-carboxylate (Compound 62-b)

By using the compound 62-a (0.86 g, 3.05 mmol) instead of the compound 61-a, the reaction was carried out in the same manner as the Step 2 of Example 10-1 to obtain the title compound 62-b as a white solid (0.71 g, 64%).

MS m/z: 366 [M+1]$^+$ $^1$H NMR (CDCl$_3$, 400 MHz), δ ppm: 10.89 (s, 1H), 7.39 (s, 1H), 5.12-5.07 (m, 1H), 4.34-4.05 (m, 4H), 1.46 (s, 9H)

(Step 3) Preparation of tert-butyl 3-{[1-(2-ethoxy-2-oxoethyl)-4-iodo-1H-pyrazol-3-yl]oxy}azetidine-1-carboxylate (Compound 62-c)

By using the compound 62-b (0.30 g, 0.82 mmol) and ethyl bromoacetate (0.18 mL, 1.23 mmol) instead of the compound 61-b and tert-butyl bromoacetate respectively, the reaction was carried out in the same manner as the Step 3 of Example 10-1 to obtain the title compound 62-c as a white solid (0.39 g, 99%).

MS m/z: 452 [M+1]$^+$ $^1$H NMR (CDCl$_3$, 400 MHz), δ ppm: 7.31 (s, 1H), 5.11-5.06 (m, 1H), 4.67 (s, 2H), 4.26-4.20 (m, 4H), 4.01 (dd, 2H), 1.45 (s, 9H), 1.32-1.24 (m, 3H)

(Step 4) Preparation of tert-butyl 3-[(4-{2-[(2,3-dihydro-1H-inden-2-yl)amino]pyrimidin-5-yl}-1-(2-ethoxy-2-oxoethyl)-1H-pyrazol-3-yl)oxy]azetidine-1-carboxylate (Compound 62-d)

By using the compound 62-c (0.39 g, 0.81 mmol) instead of the compound 61-c, the reaction was carried out in the same manner as the Step 4 of Example 10-1 to obtain the title compound 62-d as a yellow solid (0.32 g, 71%).

MS m/z: 535 [M+1]+

¹H NMR (CDCl₃, 400 MHz), δ ppm: 8.52 (s, 2H), 7.40 (s, 1H), 7.25-7.14 (m, 4H) 5.51 (d, H), 5.21-5.15 (m, 1H), 4.85-4.77 (m, 1H), 4.70 (s, 2H), 4.30-4.22 (m, 4H) 4.01 (dd, 2H), 3.45-3.38 (m, 2H), 2.95-2.87 (m, 2H), 1.45 (s, 9H), 1.33-1.23 (m, 3H)

(Step 5) Preparation of 2-[3-({1-[(tert-butoxy)carbonyl]azetidin-3-yl}oxy)-4-{2-[(2,3-dihydro-1H-inden-2-yl)amino]pyrimidin-5-yl}-1H-pyrazol-1-yl] acetic Acid (Compound 62-e)

To a solution of the compound 62-d (0.10 g, 0.19 mmol) in a mixture solvent of tetrahydrofuran (2 mL) and distilled water (1 mL) was added lithium hydroxide (40 mg, 0.94 mmol), and the mixture was stirred for 1.5 hours at room temperature. Upon the completion of the reaction, 2 N aqueous solution of hydrogen chloric acid was added to adjust pH 2 or lower, followed by extraction with ethyl acetate. The organic layer was washed with distilled water and saturated brine, dried over anhydrous sodium sulfate, and concentrated to obtain the title compound 62-e as a yellow solid (80 mg, 84%).

MS m/z: 507 [M+1]+

¹H NMR (DM*O-d₆, 400 MHz), δ ppm: 8.58 (s, 2H), 7.99 (s, 1H), 7.66 (brs, 1H), 7.22-7.14 (m, 4H), 5.15-5.10 (m, 1H), 4.79 (s, 2H), 4.65-4.60 (m, 1H), 4.23-4.19 (m, 2H), 3.87-3.85 (m, 2H), 3.27 (dd, 2H), 2.89 (dd, 2H), 1.38 (s, 9H)

(Step 6) Preparation of tert-butyl 3-[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)oxy]azetidine-1-carboxylate (Compound 62-f)

By using the compound 62-e (80 mg, 0.16 mmol) instead of the compound 61-e, the reaction was carried out in the same manner as the Step 6 of Example 10-1 to obtain the title compound 62-f as a light yellow solid (82 mg).

MS m/z: 613 [M+1]+

¹H NMR (DMSO-d₆, 400 MHz), δ ppm: 8.52 (s, 2H), 7.54 (d, 1H), 7.25-7.16 (m, 4H), 5.49 (d, 1H), 5.17-5.11 (m, 1H), 4.92-4.29 (m, 5H), 4.28-4.21 (m, 2H), 4.04-3.95 (m, 3H), 3.86-3.83 (m, 1H), 3.41 (dd, 2H), 2.93-2.85 (m, 4H), 1.45 (s, 9H)

(Step 7) Preparation of 2-[3-(azetidin-3-yloxy)-4-{2-[(2,3-dihydro-1H-inden-2-yl)amino]pyrimidin-5-yl}-1H-pyrazol-1yl]-1-{1H,4H,5H,6H,7H-[1,2,3]triazolo[4,5-c]pyridin-5-yl}ethan-1-one Hydrochloride (Compound 62)

To a solution of the compound 62-f in methylene chloride (1 mL) was added 4 N hydrogen chloride dioxane solution (2 mL), and the mixture was stirred for 15 hours at room temperature. Upon the completion of the reaction, the solvent was removed, the resulting solid was filtered, washed with methylene chloride, and dried to provide the title compound 62 as a light yellow solid (42 mg, 2-step yield of 48%).

MS m/z: 513 [M+1]+

¹H NMR (DMSO-d₆, 400 MHz), δ ppm: 9.03-8.73 (m, 2H), 8.61 (s, 2H), 7.96 (d, 1H), 7.52 (s, 1H) 7.23-7.14 (m, 4H), 5.18-5.10 (m, 3H), 4.75-4.62 (m, 3H), 4.34-4.32 (m, 2H), 4.07-4.00 (m, 2H), 3.80 (t, 2H), 3.29-3.23 (m, 2H), 2.94-2.74 (m, 4H)

[Example 10-3] Preparation of 2-[3-(benzyloxy)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one (Compound 63)

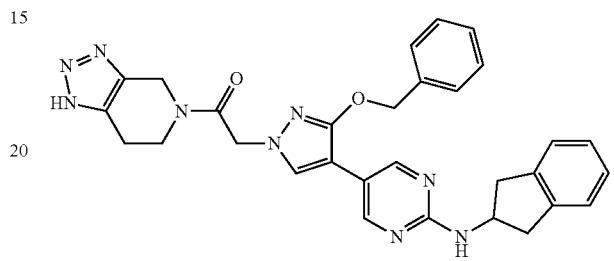

63

By using benzyl bromide instead of bromoethane, the reaction was carried out in the same manner as Example 10-1 to obtain the title compound 63.

MS m/z: 548 [M+1]+

¹H NMR (CDCl₃, 400 MHz), δ ppm: 12.58 (br, 1H), 8.54 (d, 2H), 7.54 (d, 1H), 7.33-7.28 (m, 5H), 7.23-7.14 (m, 4H), 5.45 (d, 1H), 5.27 (d, 2H), 4.96 (br, 2H), 4.84-4.74 (m, 3H), 3.89 (dt, 2H), 3.39 (dd, 2H), 2.92-2.80 (m, 4H)

[Example 10-4] Preparation of 2-[3-(benzyloxy)-4-{2-[(2,3-dihydro-1H-inden-2-yl)amino]pyrimidin-5-yl}-1H-pyrazol-1-yl]-1-(morpholin-4-yl)ethan-1-one (Compound 64)

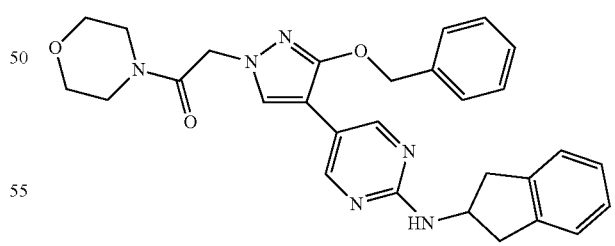

64

By using morpholine instead of the compound im-7, the reaction was carried out in the same manner as Example 10-3 to obtain the title compound.

MS m/z: 511 [M+1]+

¹H NMR (CDCl₃, 400 MHz), δ ppm: 8.54 (s, 2H), 7.53 (s, 1H), 7.43-7.42 (m, 2H), 2.38-7.29 (m, 3H), 7.23-7.14 (m, 4H), 5.56 (d, 1H), 5.29 (s, 2H), 4.82-4.74 (m, 3H), 3.68-3.62 (m, 6H), 3.55-3.54 (m, 2H), 3.39 (dd, 2H), 2.88 (dd, 2H)

[Example 10-5] Preparation of 2-(4-{2-[(2,3-di-hydro-1H-inden-2-yl)amino]pyrimidin-5-yl}-3-hydroxy-1H-pyrazol-1-yl)-1-{1H,4H,5H,6H,7H-[1,2,3]triazolo[4,5-c]pyridin-5-yl}ethan-1-one (Compound 65)

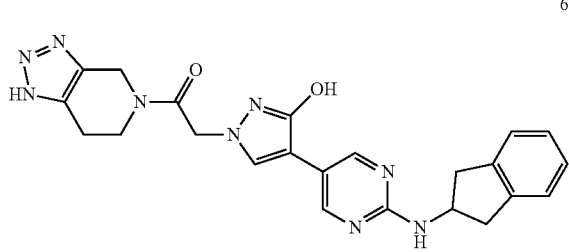

65

To a solution of the compound 63 (60 mg, 0.11 mmol) in a mixture solvent of methanol (3 mL) and ethyl acetate (0.5 mL) was added Pd/C (10% by weight, 75 mg), and the mixture was stirred for 15 hours under hydrogen pressure (1 atm). Upon the completion of the reaction, the catalyst was removed by filtering through a Celite pad, and the filtrate was concentrated under reduced pressure. The residue was then purified by silica gel column chromatography (methanol:methylene chloride=7:93) to obtain the title compound 65 as a dark brown solid (1.6 mg, 3.2%)

MS m/z: 458 [M+1]$^+$ $^1$H NMR (DMSO-d$_6$, 400 MHz), δ ppm: 10.34 (bs, 1H), 8.59 (s, 2H), 7.84-7.81 (m, 1H), 7.64 (br, 1H), h), 7.92 (s, 1H), 7.65 (br, 1H), 7.23-7.13 (m, 4H), 5.04-5.01 (m, 2H), 4.75-4.66 (m, 2H), 4.64-4.60 (m, 1H), 3.83-3.79 (m, 2H), 3.26 (dd, 2H), 2.90 (dd, 2H), 2.86-2.69 (m, 2H)

[Example 10-6] Preparation of 2-(4-{2-[(2,3-di-hydro-1H-inden-2-yl)amino]pyrimidin-5-yl}-3-[2-(morpholin-4-yl)ethoxy]-1H-pyrazol-1-yl)-1-{1H,4H,5H,6H,7H-[1,2,3]triazolo[4,5-c]pyridin-5-yl}ethan-1-one (Compound 66)

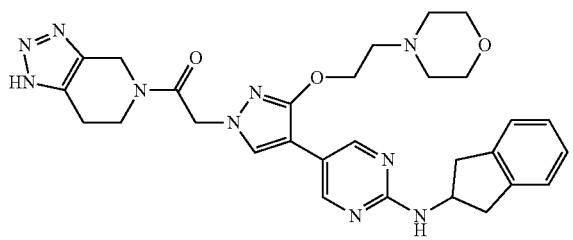

66

By using 4-(2-chloroethyl)morpholine instead of bromoethane, the reaction was carried out in the same manner as Example 10-1 to obtain the title compound 66.

MS m/z: 571 [M+1]$^+$ $^1$H NMR (CDCl$_3$, 400 MHz), δ ppm: 8.51 (s, 2H), 7.50 (d, 1H), 7.26-7.18 (m, 4H), 5.36-5.30 (m, 1H), 4.93 (d, 2H), 4.86-4.76 (m, 3H), 4.35 (m, 2H), 3.92 (m, 2H), 3.74-3.68 (m, 4H), 3.41 (dd, 2H), 2.94-2.78 (m, 6H), 2.61-2.54 (m, 4H)

[Example 10-7] Preparation of 2-(4-{2-[(2,3-di-hydro-1H-inden-2-yl)amino]pyrimidin-5-yl}-3-[2-(piperazin-1-yl)ethoxy]-1H-pyrazol-1-yl)-1-{1H,4H,5H,6H,7H-[1,2,3]triazolo[4,5-c]pyridin-5-yl}ethan-1-one (Compound 67)

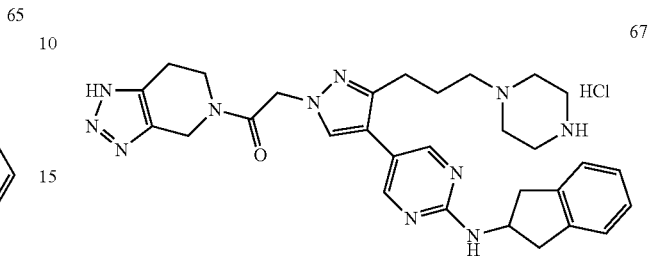

67

By using tert-butyl 4-(2-chloroethyl)piperazine-1-carboxylate instead of bromoethane, the reaction was carried out in the same manner as Example 10-1 and the Step 7 of Example 10-2 to obtain the title compound 67.

MS m/z: 570 [M+1]$^+$ $^1$H NMR (DMSO-d$_6$, 400 MHz), δ ppm: 9.49 (brs, 2H), 8.61 (s, 2H), 7.96 (d, 1H), 7.62 (s, 1H), 7.24-7.14 (m, 4H), 5.18 (d, 2H), 4.77-4.62 (m, 3H), 4.53 (s, 2H), 3.82-3.37 (m, 8H), 3.27 (dd, 2H), 2.94-2.67 (m, 4H)

[Example 10-8] Preparation of 2-(4-{2-[(2,3-di-hydro-1H-inden-2-yl)amino]pyrimidin-5-yl}-3-[(1-ethylazetidin-3-yl)oxy]-1H-pyrazol-1-yl)-1-{1H,4H,5H,6H,7H-[1,2,3]triazolo[4,5-c]pyridin-5-yl}ethan-1-one (Compound 68)

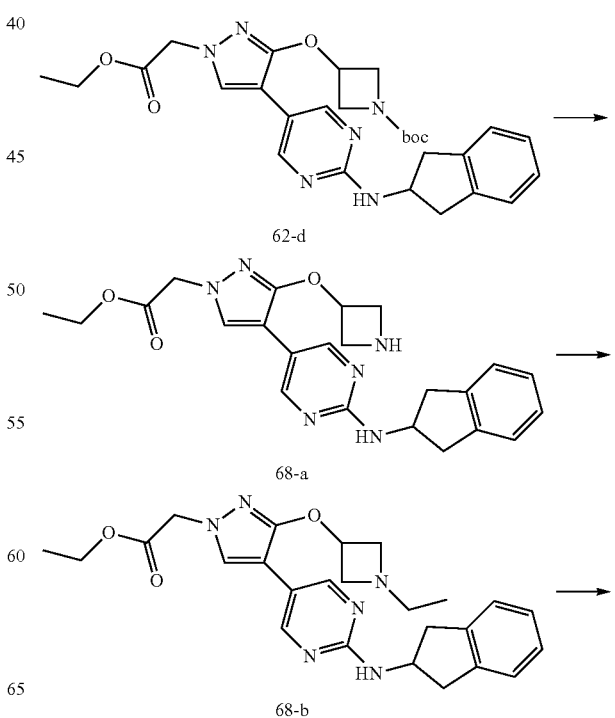

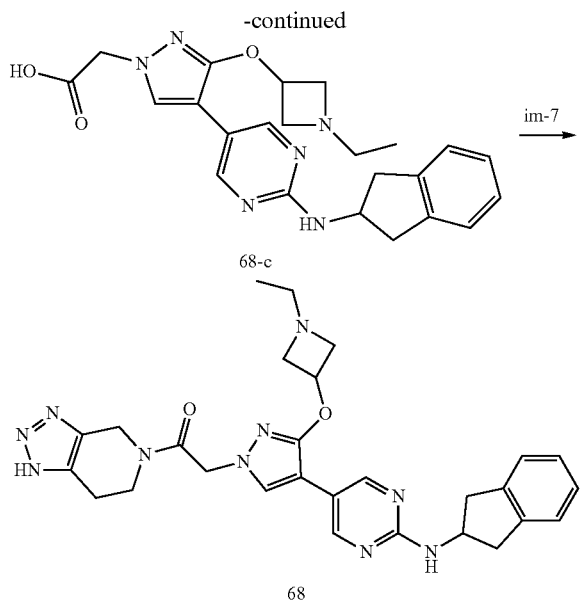

(Step 1) Preparation of ethyl 2-[3-(azetidin-3-yloxy)-4-{2-[(2,3-dihydro-1H-inden-2-yl)amino]pyrimidin-5-yl}-1H-pyrazol-1-yl]acetate hydrochloride (Compound 68-a)

To a solution of the compound 62-d (0.10 g, 0.19 mmol) in methylene chloride (2 mL) was added 4 N hydrogen chloride dioxane solution (2 mL), and the mixture was stirred for 15 hours at room. Upon the completion of the reaction, the solvent was removed, and the residue was then filtered, washed with diethyl ether, and dried to obtain the title compound 68-a as a light brown solid quantitatively (90 mg).

MS m/z 435 [M+1]$^+$ $^1$H NMR (DMSO-d$_6$, 400 MHz), δ ppm: 9.03-9.24 (m, 1H), 8.65 (s, 2H), 8.05 (s, 1H), 7.24-7.13 (m, 4H), 5.24-5.18 (m, 1H), 4.94 (s, 2H), 4.68-4.61 (m, 1H), 4.36-4.19 (m, 2H), 4.34-4.13 (m, 2H), 4.10-4.02 (m, 2H), 3.28 (dd, 2H), 2.93 (dd, 2H), 1.24-1.20 (m, 3H)

(Step 2) Preparation of ethyl 2-(4-{2-[(2,3-dihydro-1H-inden-2-yl)amino]pyrimidin-5-yl}-3-[(1-ethylazetidin-3-yl)oxy]-1H-pyrazol-1-yl)acetate (Compound 68-b)

To a solution of the compound 68-a (90 mg, 0.19 mmol) in N,N-dimethylformamide (1 mL) was added N,N-diisopropylethylamine (0.1 mL, 0.44 mmol) and bromoethane (16 μL, 0.21 mmol) in order, and the mixture was stirred for 1 hour at room temperature under nitrogen atmosphere. Upon the completion of the reaction, the mixture was cooled to room temperature, diluted with distilled water (25 mL), and extracted with ethyl acetate. The organic layer was washed with distilled water and saturated brine, dried over anhydrous sodium sulfate, and concentrated. The residue was purified by silica gel column chromatography (methanol:methylene chloride=1:9) to obtain the title compound 68-b as a white solid (40 mg, 45%).

MS m/z: 463 [M+1]$^+$ $^1$H NMR (CDCl$_3$, 400 MHz), δ ppm: 8.54 (s, 2H), 7.44 (s, 1H), 7.16-7.15 (m, 4H), 5.40 (d, 1H), 5.14-5.11 (m, 1H), 4.83-4.79 (m, 1H), 4.70 (s, 2H), 4.28-4.22 (m, 2H), 3.90 (t, 2H), 3.41 (dd, 2H), 3.18-3.14 (m, 2H), 2.91 (dd, 2H), 2.63-2.57 (m, 2H). 1.30 (t, 3H), 1.02 (t, 3H)

(Step 3) Preparation of 2-(4-{2-[(2,3-dihydro-1H-inden-2-yl)amino]pyrimidin-5-yl}-3-[(1-ethylazetidin-3-yl)oxy]-1H-pyrazol-1-yl)acetic Acid (Compound 68-c)

By using the compound 68-b (0.10 g, 0.19 mmol) instead of the compound 62-d, the reaction was carried out in the same manner as the Step 5 of Example 10-2 to obtain a crude product of the title compound 68-c as a yellow solid (37 mg), which was then used for the next reaction without further purification.

MS m/z: 435 [M+1]$^+$ $^1$H NMR (DMSO-d$_6$, 400 MHz), δ ppm: 8.53 (s, 2H), 7.79 (s, 1H), 7.35 (d, 1H), 7.23-7.13 (m, 4H), 4.92-4.88 (m, 1H), 4.64-4.58 (m, 2H), 4.13 (s, 3H), 3.64-3.60 (m, 2H), 3.28-3.23 (m, 2H), 2.97-2.86 (m, 4H), 2.46-2.40 (m, 2H), 0.89 (t, 3H)

(Step 4) Preparation of 2-(4-{2-[(2,3-dihydro-1H-inden-2-yl)amino]pyrimidin-5-yl}-3-[(1-ethylazetidin-3-yl)oxy]-1H-pyrazol-1-yl)-1-{1H,4H,5H,6H,7H-[1,2,3]triazolo[4,5-c]pyridin-5-yl}ethan-1-one (Compound 68)

By using the compound 68-c (37 mg, 0.086 mmol) instead of the compound 62-e, the reaction was carried out in the same manner as the Step 6 of Example 10-2 to obtain the title compound 68 as a white solid (12 mg, 26%).

MS m/z: 541 [M+1]$^+$ $^1$H NMR (DMSO-d$_6$, 400 MHz), δ ppm: 8.54 (s, 2H), 7.90 (d, 1H), 7.43 (d, 1H), 7.23-7.13 (m, 4H), 5.11 (d, 2H), 4.93-4.89 (m, 1H), 4.75-4.59 (m, 3H), 4.12-4.08 (m, 2H), 3.82-3.79 (m, 2H), 3.61 (s, 2H), 3.28-3.23 (m, 2H), 2.98 (s, 2H), 2.93-2.73 (m, 4H), 2.50-2.44 (m, 2H), 0.87 (t, 3H)

[Example 10-9] Preparation of 2-(4-{2-[(2,3-dihydro-1H-inden-2-yl)amino]pyrimidin-5-yl}-3-(piperidin-4-yloxy)-1H-pyrazol-1-yl)-1-{1H,4H,5H,6H,7H-[1,2,3]triazolo[4,5-c]pyridin-5-yl}ethan-1-one (Compound 69)

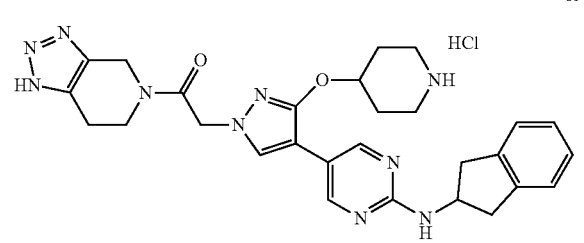

69

By using tert-butyl 4-hydroxypiperidine-1-carboxylate instead of 1-N-tert-butoxycarbonyl-3-hydroxyazetidine, the reaction was carried out in the same manner as Example 10-2 to obtain the title compound 69.

MS m/z: 541 [M+1]$^+$ $^1$H NMR (DMSO-d$_6$, 400 MHz), δ ppm: 8.89 (br 1H), 8.76 (br, 1H), 8.60 (s, 2H), 7.98-7.68 (m, 2H), 7.26-7.12 (m, 4H), 5.34 (d, 2H), 4.88-4.61 (m, 4H), 3.81 (s, 2H), 3.44 (dd, 2H), 3.04-3.22 (m, 4H), 2.96-2.71 (m, 4H), 2.18-2.10 (m, 2H), 2.00-1.88 (m, 2H)

[Example 10-10] Preparation of 2-(4-{2-[(2,3-dihydro-1H-inden-2-yl)amino]pyrimidin-5-yl}-3-[(1-ethylpiperidin-4-yl)oxy]-1H-pyrazol-1-yl)-1-{1H,4H,5H,6H,7H-[1,2,3]triazolo[4,5-c]pyridin-5-yl}ethan-1-one (Compound 70)

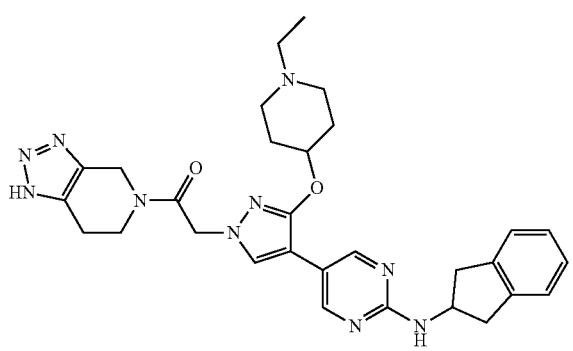

70

By using the compound 69 instead of the compound 68-a, the reaction was carried out in the same manner as the Step 2 of Example 10-8 to obtain the title compound 70.

MS m/z: 569 [M+1]+

¹H NMR (DMSO-d₆, 400 MHz), δ ppm: 8.55 (s, 2H), 7.88 (d, 1H), 7.41 (d, 1H), 7.28-7.12 (m, 4H), 5.11 (d, 2H), 4.79-4.58 (m, 4H), 3.84-3.78 (m, 2H), 3.34-3.22 (m, 6H), 2.94-2.71 (m, 6H), 2.06 (m, 2H), 1.96-1.78 (m, 2H), 1.24 (m, 3H)

[Example 10-11] Preparation of 2-(3-{[1-(2,2-difluoroethyl)piperidin-4-yl]oxy}-4-{2-[(2,3-dihydro-1H-inden-2-yl)amino]pyrimidin-5-yl}-1H-pyrazol-1-yl)-1-{1H,4H,5H,6H,7H-[1,2,3]triazolo[4,5-c]pyridin-5-yl}ethan-1-one (Compound 71)

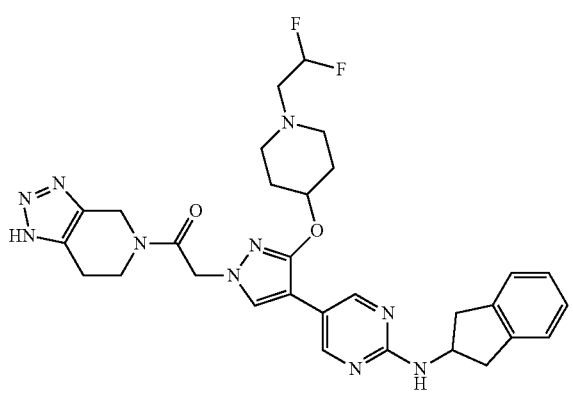

71

By using 2,2-difluoroethyl trifluoromethanesulfonate instead of bromoethane, the reaction was carried out in the same manner as Example 10-10 to obtain the title compound 71.

MS m/z: 605 [M+1]+

¹H NMR (CDCl₃, 400 MHz), δ ppm: 8.543 (s, 2H), 7.514 (d, 1H), 7.245-7.160 (m, 4H), 6.033-5.732 (m, 1H), 5.483 (d, 1H), 4.933 (d, 2H), 4.847-4.694 (m, 4H), 3.962-3.832 (m, 2H), 3.435-3.379 (m, 2H), 2.926-2.842 (m, 4H), 2.787-2.702 (m, 4H), 2.536-2.490 (m, 2H), 2.040-1.888 (m, 4H).

[Example 10-12] Preparation of 4-{[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)oxy]methyl}benzoic Acid (Compound 72)

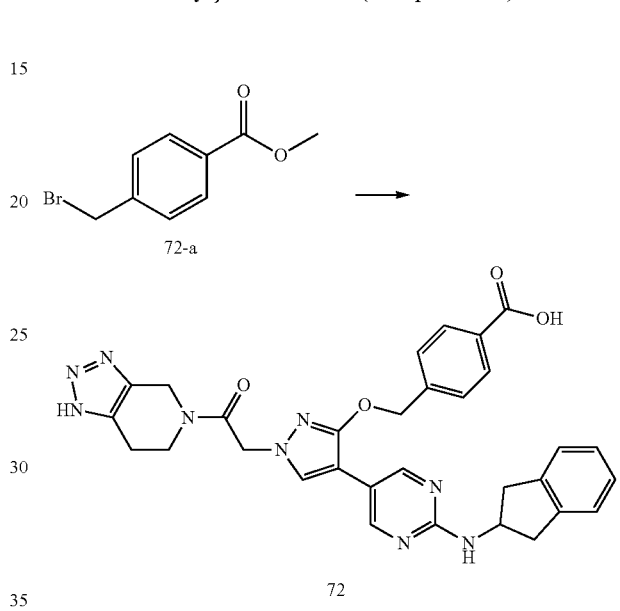

(Step 1) Preparation of Methyl 4-(bromomethyl)benzoate (Compound 72-a)

To a solution of methyl 4-(hydroxymethyl)benzoate (1.0 g, 6.0 mmol) in benzene (40 mL) was added triphenylphosphine (3.2 g, 12.0 mmol) and carbon tetrabromide (4.0 g, 12.0 mmol) in order at 0° C., and the mixture was stirred for 2 hours. Upon the completion of the reaction, n-hexane (60 mL) was added, and insoluble mass was removed by filtration. The filtrate was then concentrated under reduced pressure, and the residue was then purified by silica gel column chromatography (ethyl acetate:n-hexane=1:9) to obtain the title compound 72-a as a white solid (1.07 g, 78%).

MS m/z: 230 [M+1]+

¹H NMR (CDCl₃, 400 MHz), δ ppm: 8.02 (d, 2H), 7.46 (d, 2H), 4.50 (s, 2H), 3.92 (s, 3H)

(Step 2) Preparation of 4-{[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-H-pyrazol-3-yl)oxy]methyl}benzoic Acid (Compound 72)

By using the compound 72-a instead of bromoethane, the reaction was carried out in the same manner as Example 10-1 and the Step 5 of Example 10-2 to obtain the title compound 72.

MS m/z: 592 [M+1]+

¹H NMR (DMSO-d₆, 400 MHz), δ ppm: 8.64-8.59 (m, 2H), 8.05-7.93 (m, 3H), 7.59 (t, 2H), 7.25-7.12 (m, 4H), 5.38-5.30 (m, 2H), 5.18-5.13 (m, 1H), 4.83-4.77 (m, 1H), 4.69-4.60 (m, 2H), 2.82 (m, 2H), 3.30-3.24 (m, 2H), 2.94-2.84 (m, 4H)

[Example 10-13] Preparation of 2-[(4-{2-[(2,3-di-hydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)oxy]acetic Acid (Compound 73)

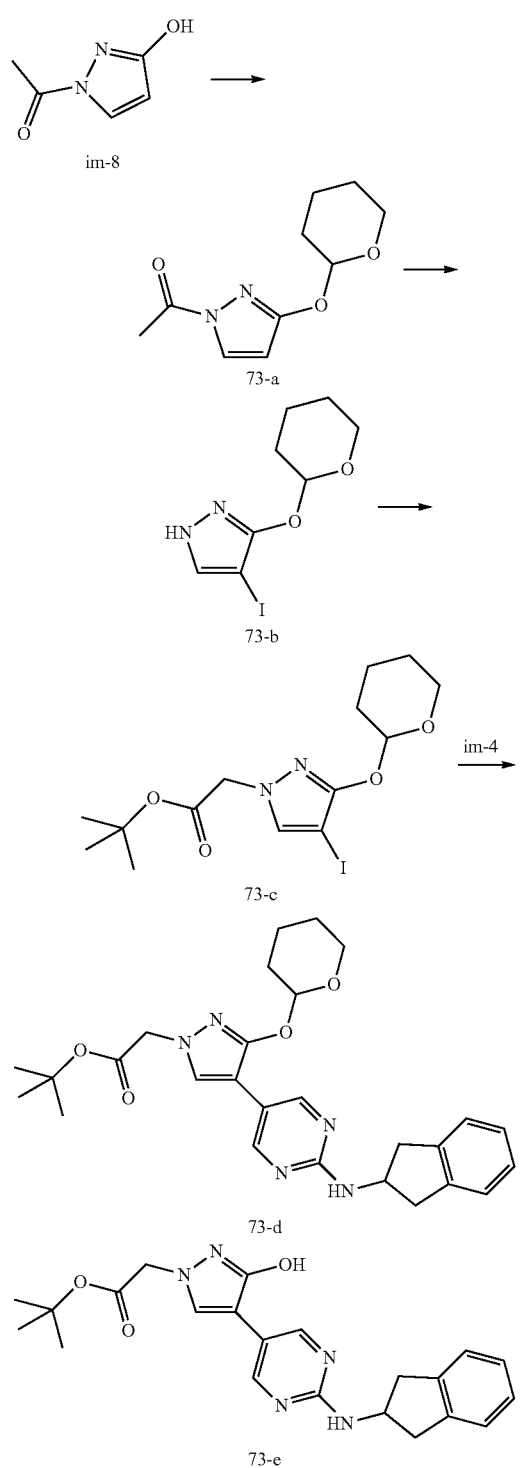

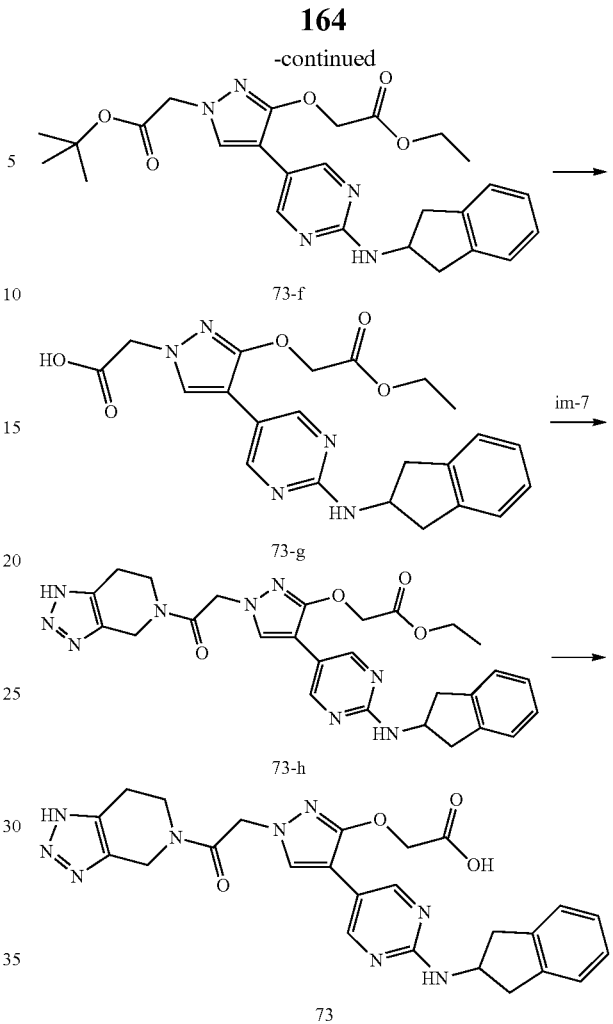

(Step 1) Preparation of 1-[3-(oxan-2-yloxy)-1H-pyrazol-1-yl]ethan-1-one (Compound 73-a)

To a solution of the compound im-8 (1.0 g, 7.9 mmol) in methylene chloride (20 mL) was added p-toluenesulfonic acid (0.4 g, 1.6 mmol) and 2',4'-dihydroxyacetophenone (2.2 mL, 23.8 mmol) in order, and the mixture was stirred for 2 hours at room temperature. Then, the mixture was heated to 40° C. and stirred for 4 hours. Upon the completion of the reaction, the mixture was cooled to room temperature, diluted with distilled (50 mL), and extracted with ethyl acetate. The organic layer was washed with distilled water and saturated brine, dried over anhydrous sodium sulfate, and concentrated. The obtained residue was purified by silica gel column chromatography (ethyl acetate:n-hexane=2:8) to obtain the title compound 73-a as a light brown liquid (0.5 g, 30%).

MS m/z: 211 [M+1]$^+$ $^1$H NMR (CDCl$_3$, 400 MHz), δ ppm: 8.10 (d, 1H), 6.12 (d, 1H), 5.74 (t, 1H), 3.97-3.49 (m, 3H), 2.61 (s, 2H), 2.03-1.51 (m, 6H)

(Step 2) Preparation of 4-iodo-3-(oxan-2-yloxy)-1H-pyrazole (Compound 73-b)

By using the compound 73-a (0.5 g, 2.4 mmol) instead of the compound 61-a, the reaction was carried out in the same manner as the Step 2 of Example 10-1 to obtain the title compound 73-b as a light brown liquid (0.68 g, 96%).
MS m/z: 295 [M+1]$^+$
$^1$H NMR (CDCl$_3$, 400 MHz), δ ppm: 10.07 (bs, 1H), 7.43 (s, 1H), 5.82-5.81 (m, 1H) 4.06-3.50 (m, 2H), 2.01-1.52 (m, 6H)

(Step 3) Preparation of tert-butyl 2-[4-iodo-3-(oxan-2-yloxy)-1H-pyrazol-1-yl]acetate (Compound 73-c)

By using the compound 73-b (0.68 g, 2.41 mmol) instead of the compound 61-b, the reaction was carried out in the same manner as the Step 3 of Example 10-1 to obtain the title compound 73-c as a white solid (0.29 g, 29%).
MS m/z: 409 [M+1]$^+$
$^1$H NMR (CDCl$_3$, 400 MHz), δ ppm: 7.32 (s, 1H), 5.85 (s, 1H), 4.71-4.57 (m, 2H), 4.05-3.99 (m, 1H), 3.66-3.64 (m, 1H), 2.66-2.05 (m, 6H), 1.46 (s, 9H)

(Step 4) Preparation of tert-butyl 2-(4-{2-[(2,3-dihydro-1H-inden-2-yl)amino]pyrimidin-5-yl}-3-(oxan-2-yloxy)-1H-pyrazol-1-yl)acetate (Compound 73-d)

By using the compound 73-c (0.29 g, 0.70 mmol) instead of the compound 61-c, the reaction was carried out in the same manner as the Step 4 of Example 10-1 to obtain the title compound 73-d as a yellow solid (0.28 g, 81%).
MS m/z: 492 [M+1]$^+$
$^1$H NMR (CDCl$_3$, 400 MHz), δ ppm: 8.58 (s, 2H), 7.47 (s, 1H), 7.24-7.17 (m, 4H), 5.97 (s, 1H), 0.5.51 (d, 1H), 4.89-4.84 (m, 1H), 4.83-4.49 (m, 2H), 3.90-3.79 (m, 1H), 3.79-3.66 (m, 1H), 3.55-3.35 (m, 3H), 2.93-2.83 (m, 3H), 1.97-1.63 (m, 6H), 1.48 (s, 9H)

(Step 5) Preparation of tert-butyl 2-(4-{2-[(2,3-dihydro-1H-inden-2-yl)amino]pyrimidin-5-yl}-3-hydroxy-1H-pyrazol-1-yl)acetate (Compound 73-e)

To a solution of the compound 73-d (0.28 g, 0.57 mmol) in methanol (1 mL) was added p-toluenesulfonic acid (0.4 g, 1.6 mmol), and the mixture was stirred for 2 hours at room temperature. Upon the completion of the reaction, the solvent was removed, the resulting solid was filtered, washed with diethyl ether, and dried to afford the title compound 73-e as a white solid (0.18 g, 78%).
MS m/z: 408 [M+1]$^+$
$^1$H NMR (DMSO-d$_6$, 400 MHz), δ ppm: 8.54 (s, 2H), 7.82 (s, 1H), 7.37 (d, 1H), 7.23-7.12 (m, 4H), 4.69-4.58 (m, 3H), 4.12-4.08 (m, 2H), 3.31-3.22 (m, 2H), 2.94-2.86 (m, 2H), 1.43 (s, 9H)

(Step 6) Preparation of ethyl 2-({1-[2-(tert-butoxy)-2-oxoethyl]-4-{2-[(2,3-dihydro-1H-inden-2-yl)amino]pyrimidin-5-yl}-1H-pyrazol-3-yl}oxy)acetate (Compound 73-f)

To a solution of the compound 73-e (0.14 g, 0.35 mmol) in N,N-dimethylformamide (1 mL) was added ethyl bromoacetate (0.04 mL, 0.35 mol) and potassium carbonate (72 mg, 0.53 mmol), and the mixture was stirred for 1 hour at room temperature. Upon the completion of the reaction, the mixture was diluted with distilled water (50 mL) was added and extracted with ethyl acetate. The organic layer was washed with distilled water and saturated brine, dried over anhydrous sodium sulfate, and concentrated. The obtained residue was purified by silica gel column chromatography (ethyl acetate:n-hexane=1:1) to obtain the title compound 73-f as a dark brown solid (92 mg, 53%).
MS m/z: 494 [M+1]$^+$
$^1$H NMR (CDCl$_3$, 400 MHz), δ ppm: 8.58 (s, 2H), 7.45 (s, 1H), 7.25-7.16 (m, 4H), 5.43 (d, 1H), 4.84-4.80 (m, 3H), 4.60 (s, 2H), 4.27-4.21 (m, 2H), 3.41 (dd, 2H), 2.89 (dd, 2H), 1.48 (s, 9H), 1.27 (t, 3H)

(Step 7) Preparation of 2-(4-{2-[(2,3-dihydro-1H-inden-2-yl)amino]pyrimidin-5-yl}-3-(2-ethoxy-2-oxoethoxy)-1H-pyrazol-1-yl)acetic Acid (Compound 73-g)

By using the compound 73-f (92 mg, 0.19 mmol) instead of the compound 61-d, the reaction was carried out in the same manner as the Step 5 of Example 10-1 to obtain the title compound 73-g as a yellow solid (72 mg, 90%).
MS m/z: 438 [M+1]$^+$
$^1$H NMR (DMSO-d$_6$, 400 MHz), δ ppm: 8.60 (s, 2H), 7.97 (s, 1H), 7.66 (brs, 1H), 7.23-7.13 (m, 4H), 4.85 (s, 2H), 4.77 (s, 2H), 4.65-4.65 (m, 1H), 3.27 (dd, 2H), 2.59 (dd, 2H), 1.20 (t, 3H)

(Step 8) Preparation of ethyl 2-[(4-{2-[(2,3-dihydro-1H-inden-2-yl)amino]pyrimidin-5-yl}-1-(2-oxo-2-{1H,4H,5H,6H,7H-(1,2,3]triazolo[4,5-c]pyridin-5-yl}ethyl)-1H-pyrazol-3-yl)oxy]acetate (Compound 73-h)

By using the compound 73-g (72 mg, 0.16 mmol) instead of the compound 61-e, the reaction was carried out in the same manner as the Step 6 of Example 10-1 to obtain the title compound 73-h as a yellow solid quantitatively (95 mg).
MS m/z: 544 [M+1]$^+$
$^1$H NMR (CDCl$_3$, 400 MHz), δ ppm: 8.56 (s, 2H), 7.53 (d, 1H), 7.24-7.15 (m, 4H), 5.54 (d, 1H), 4.90 (d, 2H), 4.82-4.72 (m, 5H), 4.25-4.20 (m, 2H), 3.95-3.81 (m, 2H), 3.48 (s, 2H), 3.40 (dd, 2H), 2.88 (m, 4H), 1.27 (t, 3H)

(Step 9) Preparation of 2-[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)oxy]acetic Acid (Compound 73)

By using the compound 73-h (95 mg, 0.18 mmol) instead of the compound 62-d, the reaction was carried out in the same manner as the Step 5 of Example 10-2 to obtain the title compound 73 as a light yellow solid (20 mg, 22%).
MS m/z: 516 [M+1]$^+$
$^1$H NMR (DMSO-d$_6$, 400 MHz), δ ppm: 8.67-8.58 (m, 2H), 7.85 (s, 1H), 7.37 (d, 1H), 7.22-7.13 (m, 4H), 5.09 (d, 1H), 4.73-4.58 (m, 2H), 4.43-4.29 (m, 4H), 4.11-3.81 (m, 2H), 3.28-3.22 (m, 2H), 2.92-2.73 (m, 4H)

[Example 10-14] Preparation of 2-(4-{2-[(2,3-dihydro-1H-inden-2-yl)amino]pyrimidin-5-yl}-3-(dimethylamino)-1H-pyrazol-1-yl)-1-{1H,4H,5H,6H,7H-[1,2,3]triazolo[4,5-c]pyridin-5-yl}ethan-1-one (Compound 74)

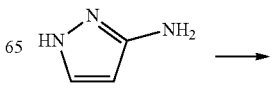

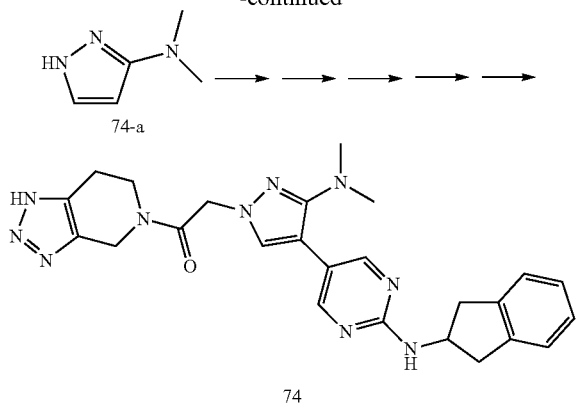

74-a

74

(Step 1) Preparation of N,N-dimethyl-1H-pyrazol-3-amine (Compound 74-a)

To a solution of 3-aminopyrazole (1.57 g, 0.019 mol) in methanol (50 mL) was added paraformaldehyde (1.70 g, 0.057 mol) at 0° C., and the mixture was stirred for 2 hours at room temperature. After cooling to 0° C. again, sodium cyanoborohydride (3.56 g, 0.057 mol) was added and stirred for 2 hours at room temperature. Upon the completion of the reaction, the mixture was cooled to room temperature, diluted with distilled water (10 mL), and extracted with ethyl acetate. The organic layer was washed with distilled water and saturated brine, dried over anhydrous sodium sulfate, and concentrated. The obtained residue was purified by silica gel column chromatography (ethyl acetate:n-hexane=6:4) to obtain the title compound 74-a as a light brown liquid (0.64 g, 30%).

MS m/z: 112 [M+1]$^+$ $^1$H NMR (CDCl$_3$, 400 MHz), δ ppm: 8.72 (bs, 1H), 7.37 (d, 1H), 5.66 (d, 1H), 2.88 (s, 6H)

(Step 2) Preparation of 2-(4-{2-[(2,3-dihydro-1H-inden-2-yl)amino]pyrimidin-5-yl}-3-(dimethylamino)-1H-pyrazol-1-yl)-1-{3H,4H,5H,6H,7H-[1,2,3]triazolo[4,5-c]pyridin-5-yl}ethan-1-one (Compound 74)

By using the compound 74-a (0.37 g, 3.36 mmol) instead of the compound 61-a, the reaction was carried out in the same manner as the Step 2 to Step 6 of Example 10-1 to obtain the title compound 74 as a white solid (23 mg, 5-step yield of 3%).

MS m/z: 485 [M+1]$^+$ $^1$H NMR (CDCl$_3$, 400 MHz), δ ppm: 8.46 (s, 2H), 7.44 (d, 1H), 7.25-7.16 (m, 4H), 5.57 (d, 1H), 5.08 (d, 2H), 4.84-4.71 (m, 3H), 3.94-3.91 (m, 1H), 3.83-3.80 (m, 1H), 3.41 (dd, 2H), 2.91 (dd, 2H), 2.81 (s, 2H), 2.72 (s, 6H)

[Example 10-15] Preparation of 4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazole-3-carboxylic Acid (Compound 75)

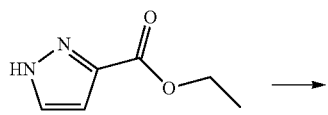

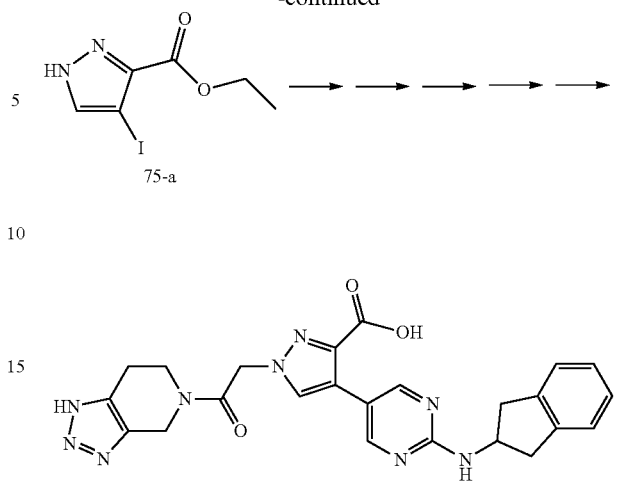

75-a

75

(Step 1) Preparation of ethyl 4-iodo-1H-pyrazole-3-carboxylate (Compound 75-a)

To a solution of ethyl pyrazole-3-carboxylate (1.00 g, 7.14 mmol) in acetonitrile (28 mL) was added N-iodosuccinimide (1.77 g, 7.85 mmol) and trifluoroacetic acid (0.16 mL, 2.14 mmol) in order, and the mixture was stirred for 3 hours at room temperature. Upon the completion of the reaction, the mixture was extracted with ethyl acetate. And the organic layer was washed with 5% aqueous sodium hydrogen carbonate and distilled water. The organic layer was dried over anhydrous sodium sulfate, and concentrated. The obtained residue was purified by silica gel column chromatography (ethyl acetate:n-hexane=4:6) to obtain the title compound 75-a as a yellow solid (1.69 g, 89%).

MS m/z: 26.7 [M+1]$^+$ $^1$H NMR (CDCl$_3$, 400 MHz), δ ppm: 12.067 (s, 1H), 7.805 (s, 1H), 4.477-4.424 (q, 2H), 1.468-1.431 (t, 3H) ppm (Step 2) Preparation of 4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazole-3-carboxylic Acid (Compound 75)

By using the compound 75-a (1.69 g, 6.35 mmol) instead of the compound 61-b, the reaction was carried out in the same manner as the Step 3 to Step 6 of Example 10-1 and the Step 5 of Example 10-2 to obtain the title compound 75.

MS m/z: 592 [M+1]$^+$ $^1$H NMR (DMSO-d$_6$, 400 MHz), δ ppm: 8.381 (s, 2H), 7.921 (d, 1H), 7.518 (d, 1H), 7.225-7.124 (m, 4H), 5.394 (d, 2H), 4.773 (s, 1H), 4.679-4.588 (m, 2H), 3.828 (m, 2H), 3.283-3.225 (m, 2H), 2.930-2.746 (m, 6H) ppm

[Example 10-16] Preparation of 2-(4-{2-[(2,3-dihydro-1H-inden-2-yl)amino]pyrimidin-5-yl}-3-(piperidine-1-carbonyl)-1H-pyrazol-1-yl)-1-{1H,4H,5H,6H,7H-[1,2,3]triazolo[4,5-c]pyridin-5-yl}ethan-1-one (Compound 76)

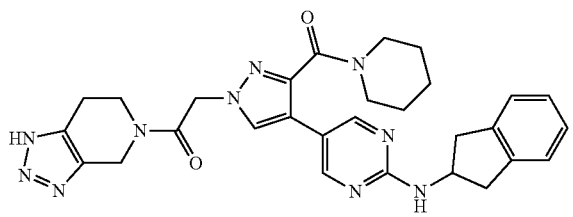

To a solution of the compound 73 (26 mg, 0.054 mmol) in N,N-dimethylformamide (2 mL) was added piperidine (11.0 µL, 0.11 mmol), followed by benzotriazol-1-yl oxytripyrrolidinophosphonium hexafluorophosphate (42 mg, 0.081 mmol) and N,N-diisopropylethylamine (47.0 µL, 0.27 mmol) in order at 0° C., and the mixture was stirred for 1 hour at room temperature. Upon the completion of the reaction, the mixture was diluted with distilled water (50 mL) and extracted with ethyl acetate. The organic layer was washed with distilled water and saturated brine, dried over anhydrous sodium sulfate, and concentrated. The obtained residue was purified by silica gel column chromatography (methanol:methylene chloride=5:95) to obtain the title compound 76 as a white solid (15 mg, 51%).

MS m/z: 553 [M+1]$^+$ $^1$H NMR (DMSO-d$_6$, 400 MHz), δ ppm: 8.354 (s, 2H), 8.029 (d, 1H), 7.556 (d, 1H), 7.225-7.128 (m, 4H), 5.338 (d, 2H), 4.729 (d, 2H), 4.641-4.570 (m, 1H), 3.830 (m, 2H), 3.583 (m, 2H), 3.312-3.222 (m, 4H), 2.920-2.731 (m, 4H), 1.564-1.492 (m, 4H), 1.308-1.235 (m, 2H) ppm

[Example 10-17] Preparation of 2-(4-{2-[(2,3-dihydro-1H-inden-2-yl)amino]pyrimidin-5-yl}-3-(piperazine-1-carbonyl)-1H-pyrazol-1-yl)-1-{1H,4H,5H,6H,7H-[1,2,3]triazolo[4,5-c]pyridin-5-yl}ethan-1-one hydrochloride (Compound 77)

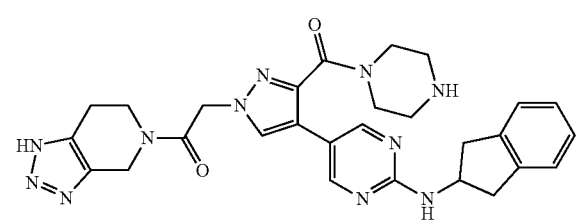

By using 1-(tert-butoxycarbonyl)piperazine instead of piperidine, the reaction was carried out in the same manner as Example 10-16 and the Step 7 of Example 10-2 to obtain the title compound 77.

MS m/z: 554 [M+1]$^+$ $^1$H NMR (DMSO-d$_6$, 400 MHz), δ ppm: 8.954 (m, 2H), 8.408 (s, 2H), 8.056 (d, 1H), 7.614 (d, 1H), 7.229-7.132 (m, 4H), 5.372 (d, 2H), 4.779 (s, 1H), 4.682-4.614 (m, 2H), 3.829-3.783 (m, 6H), 3.284-3.226 (m, 2H), 3.164-3.085 (m, 4H), 2.936-2.748 (m, 6H) ppm

[Example 11-1] Preparation of 2-(4-{2-[(2,3-dihydro-1H-inden-2-yl)amino]pyrimidin-5-yl}-5-ethyl-1H-pyrazol-1-yl)-1-{1H,4H,5H,6H,7H-[1,2,3]triazolo[4,5-c]pyridin-5-yl}ethan-1-one (Compound 78)

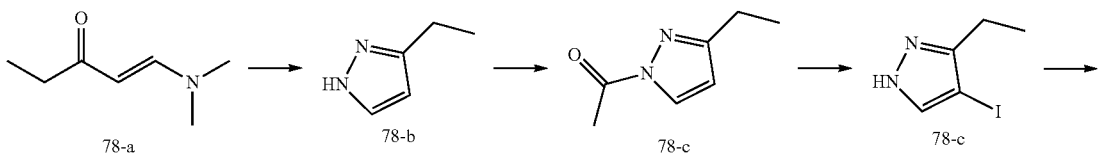

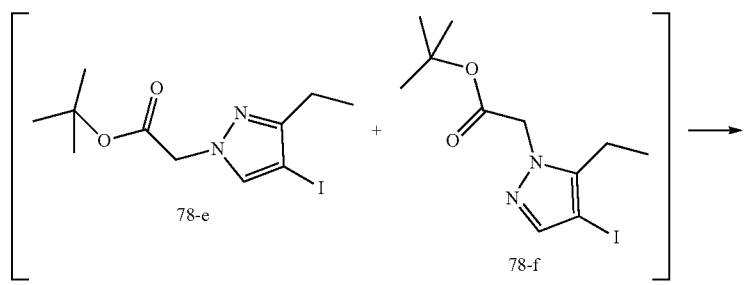

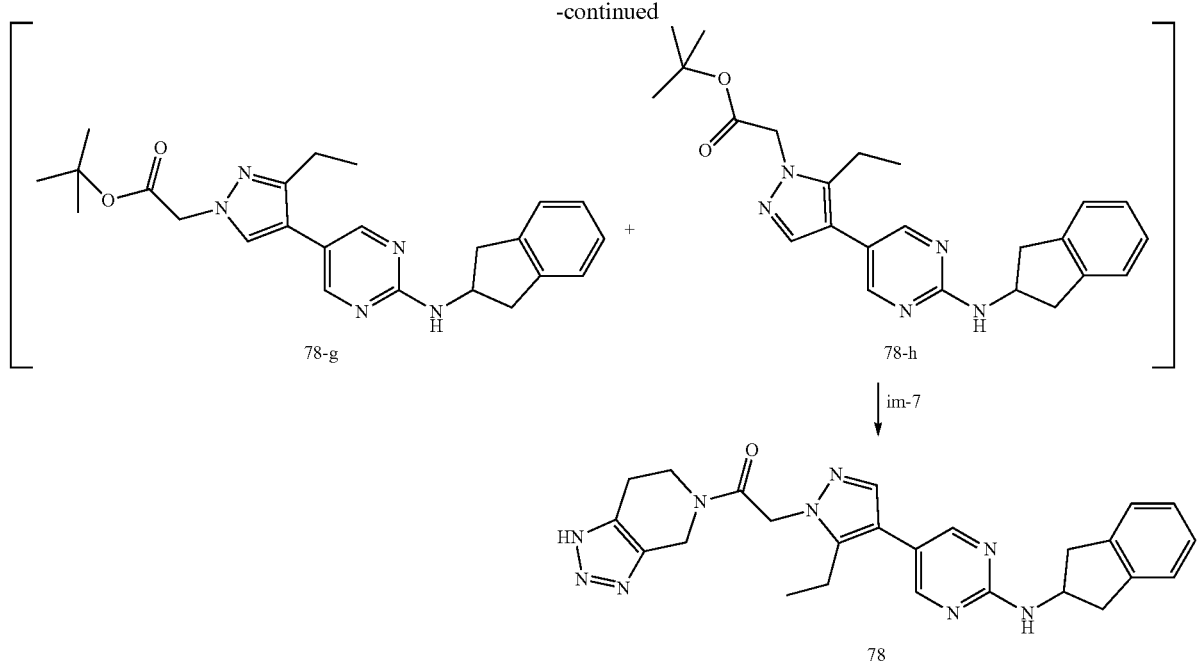

(Step 1) Preparation of (1E)-1-(dimethylamino) pent-1-en-3-one (Compound 78-a)

A mixture of 2-butanone (10 mL, 0.11 mol) and N,N-dimethylformamide dimethyl acetal (10 mL, 0.075 mol) was stirred for 9 hours at 110° C. Upon the completion of the reaction, the mixture was cooled to room temperature, and the solvent was removed to obtain the title compound 78-a (8.3 g, 86p).

MS m/z: 128 [M+1]$^+$
$^1$H NMR (DMSO-d$_6$, 400 MHz), δ ppm: 7.47 (d, 1H), 4.94 (d, 1H), 3.33 (s, 3H), 3.04 (s, 3H), 2.25 (m, 2H), 0.95 (t, 3H)

(Step 2) Preparation of 3-ethyl-1H-pyrazole (Compound 78-b)

To a solution of the compound 78-a (8.3 g, 0.065 mol) in ethanol (20 mL) was added hydrazine hydrate (4.9 mL, 0.098 mol) under stirring, and the mixture was stirred under reflux for 15 hours. Upon the completion of the reaction, the mixture was cooled to room temperature, and the solvent was removed to obtain the title compound 78-b as a yellow liquid quantitatively (6.2 g).

MS m/z: 97 [M+1]$^+$
$^1$H NMR (CDCl$_3$, 400 MHz), δ ppm: 7.50 (d, 1H), 6.09 (d, 1H), 2.72 (m, 2H), 1.29 (t, 3H)

(Step 3) Preparation of 1-(3-ethyl-1H-pyrazol-1-yl) ethan-1-one (Compound 78-c)

By using the compound 78-b (6.2 g, 0.065 mol) instead of the compound im-8-a, the reaction was carried out in the same manner as the Step 2 of Preparation example 8 to obtain the title compound 78-c as a yellow liquid (1.8 g, 20%).

MS m/z: 139 [M+1]$^+$
$^1$H NMR (CDCl$_3$, 400 MHz), δ ppm: 8.15 (d, 1H), 6.28 (d, 1H), 2.73-2.65 (m, 5H), 1.27 (t, 3H)

(Step 4) Preparation of 3-ethyl-4-iodo-1H-pyrazole (Compound 78-d)

By using the compound 78-c (1.8 g, 0.013 mol) instead of the compound 61-a, the reaction was carried out in the same manner as the Step 2 of Example 10-1 to obtain the title compound 78-d quantitatively (2.9 g).

MS m/z: 223 [M+1]$^+$
$^1$H NMR (CDCl$_3$, 400 MHz), δ ppm: 7.55 (s, 1H), 2.70 (m, 2H), 1.29 (t, 3H)

(Step 5) Preparation of tert-butyl 2-(3-ethyl-4-iodo-1H-pyrazol-1-yl)acetate (Compound 78-e) and tert-butyl 2-(5-ethyl-4-iodo-1H-pyrazol-1-yl)acetate (Compound 78-f)

By using the compound 78-d (2.9 g, 0.013 mol) instead of the compound 61-b, the reaction was carried out in the same manner as the Step 3 of Example 10-1 to obtain a mixture of the title compounds 78-e and 78-f as a yellow liquid (3.5 g, 80%), which was then used for the next reaction without further purification.

(Step 6) Preparation of tert-butyl 2-(4-{2-[(2,3-dihydro-1H-inden-2-yl)amino]pyrimidin-5-yl}-3-ethyl-1H-pyrazol-1-yl)acetate (Compound 78-g) and tert-butyl 2-(4-{2-[(2,3-dihydro-1H-inden-2-yl) amino]pyrimidin-5-yl}-5-ethyl-1H-pyrazol-1-yl) acetate (Compound 78-h)

By using the mixture of the compounds 78-e and 78-f (0.65 g, 1.93 mmol) instead of the compound 61-c, the reaction was carried out in the same manner as the Step 4 of Example 10-1, and then purified by silica gel column chromatography (ethyl acetate:n-hexane=2:8) to obtain the title compounds as a brown solid of each.

The compound 78-g: tert-butyl 2-(4-{2-[(2,3-dihydro-1H-inden-2-yl)amino]pyrimidin-5-yl}-3-ethyl-1H-pyrazol-1-yl)acetate (0.36 g)

MS m/z: 420 [M+1]+

¹H NMR (CDCl₃, 400 MHz), δ ppm: 8.32 (s, 2H), 7.44 (s, 1H), 7.24-7.16 (m, 4H), 5.35 (d, 1H), 4.83 (m, 1H), 4.79 (s, 2H), 3.42 (dd, 2H), 2.92 (dd, 2H), 2.72 (m, 2H), 1.49 (s, 9H), 1.24 (t, 3H)

The compound 78-h: tert-butyl 2-(4-{2-[(2,3-dihydro-1H-inden-2-yl)amino]pyrimidin-5-yl}-5-ethyl-1H-pyrazol-1-yl)acetate (0.094 g)

MS m/z: 420 [M+1]+

¹H NMR (CDCl₃, 400 MHz), δ ppm: 8.41 (s, 2H), 7.56 (s, 1H), 7.25-7.17 (m, 4H), 5.35 (d, 1H), 4.86-4.78 (m, 3H), 3.43 (dd, 2H), 2.92 (dd, 2H), 2.67 (m, 2H), 1.49 (s, 9H), 1.19 (t, 3H)

(Step 7) Preparation of 2-(4-{2-[(2,3-dihydro-1H-inden-2-yl)amino]pyrimidin-5-yl}-5-ethyl-1H-pyrazol-1-yl)-1-{1H,4H,5H,6H,7H-[1,2,3]triazolo[4,5-c]pyridin-5-yl}ethan-1-one (Compound 78)

By using the compound 78-h (0.094 g, 0.22 mmol), the reaction was carried out in the same manner as the Step 5 and Step 6 of Example 10-1 to obtain the title compound 78 as a beige solid (45 mg, 43%).

MS m/z: 470 [M+1]+

¹H NMR (DMSO-d₆, 400 MHz), δ ppm: 8.36 (s, 2H), 7.58-7.57 (m, 1H), 7.50 (d, 1H), 7.25-7.13 (m, 4H), 5.28-5.26 (m, 2H), 4.83-4.60 (m, 3H), 3.89-3.80 (m, 2H), 3.26 (dd, 2H), 2.76-2.61 (m, 6H), 1.08 (t, 3H)

[Example 11-2] Preparation of 2-(4-{2-[(2,3-dihydro-1H-inden-2-yl)amino]pyrimidin-5-yl}-3-ethyl-1H-pyrazol-1-yl)-1-{1H,4H,5H,6H,7H-[1,2,3]triazolo[4,5-c]pyridin-5-yl}ethan-1-one (Compound 79)

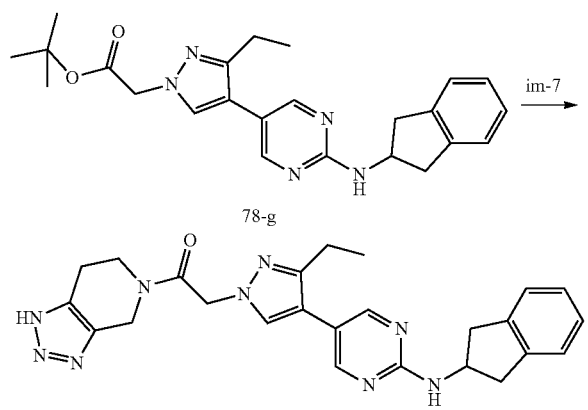

By using the compound 78-g (0.36 g, 0.86 mmol) instead of the compound 78-h, the reaction was carried out in the same manner as the Step 7 of Example 11 to synthesize the title compound 79 (24 mg, 38%).

MS m/z: 470 [M+1]+

¹H NMR (DMSO-d₆, 400 MHz), δ ppm: 8.35 (s, 2H), 7.79-7.76 (m, 2H), 7.49 (d, 1H), 7.23-7.13 (m, 4H), 5.23-5.19 (m, 2H), 4.77-4.60 (m, 3H), 3.85-3.79 (m, 2H), 3.26 (dd, 2H), 3.94-2.71 (m, 4H), 2.68-2.61 (m, 2H), 1.18-1.11 (m, 3H)

[Example 12-1] Preparation of 2-(4-{2-[(2,3-dihydro-1H-inden-2-yl)amino]pyrimidin-5-yl}-3-(morpholin-4-ylmethyl)-1H-pyrazol-1-yl)-1-{1H,4H,5H,6H,7H-[1,2,3]triazolo[4,5-c]pyridin-5-yl}ethan-1-one (Compound 80)

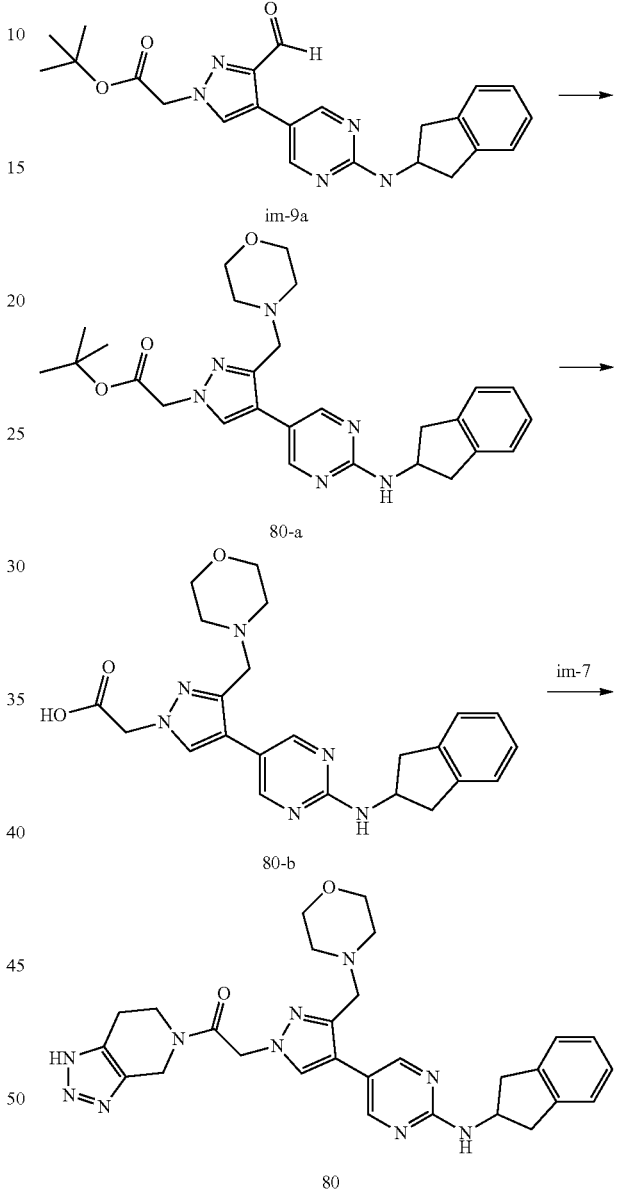

(Step 1) Preparation of tert-butyl 2-(4-{2-[(2,3-dihydro-1H-inden-2-yl)amino]pyrimidin-5-yl}-3-(morpholin-4-ylmethyl)-1H-pyrazol-1-yl)acetate (Compound 80-a)

To a solution of the compound im-9a (0.19 g, 0.44 mmol) in methanol (4 mL) was added morpholine (0.07 mL, 0.66 mmol), sodium cyanoborohydride (50 mg, 0.79 mmol), and acetic acid (0.03 mL, 0.44 mmol) in order, and the mixture was stirred for 1 hour at room temperature. After removing the solvent, the mixture wad diluted with ethyl acetate, washed with saturated aqueous solution of sodium hydrogen carbonate and distilled water. The organic layer was dried over anhydrous sodium sulfate, and concentrated. The obtained residue was purified by silica gel column chromatography (methanol:methylene chloride=1:99) to obtain the title compound 80-a as a white solid (0.14 g, 64%).

MS m/z: 491 [M+1]$^+$ $^1$H NMR (CDCl$_3$, 400 MHz), δ ppm: 8.55 (s, 2H), 7.53 (s, 1H), 7.25-7.17 (m, 4H), 5.35 (d, 1H), 4.85 (m, 1H), 4.80 (s, 2H), 3.69 (t, 4H), 3.51 (s, 2H), 3.42 (dd, 2H), 2.91 (dd, 2H), 2.50 (m, 4H), 1.48 (s, 9H)

(Step 2) Preparation of 2-(4-{2-[(2,3-dihydro-1H-inden-2-yl)amino]pyrimidin-5-yl}-3-(morpholin-4-ylmethyl)-1H-pyrazol-1-yl)acetic Acid (Compound 80-b)

By using the compound 80-a (0.14 g, 0.28 mmol) instead of the compound 61-d, the reaction was carried out in the same manner as the Step 5 of Example 10-1 to obtain the title compound 80-b as a white solid (90 mg, 73%).

MS m/z: 435 [M+1]$^+$ $^1$H NMR (DMSO-d$_6$, 400 MHz), δ ppm: 10.56 (br, 1H), 8.40 (s, 2H), 8.06 (s, 1H), 7.69 (br, 1H), 7.22-7.13 (m, 4H), 5.05 (s, 2H), 4.64 (m, 1H), 4.43 (m, 2H), 3.96-3.64 (m, 4H), 3.28-3.08 (m, 6H), 2.92 (dd, 2H)

(Step 3) Preparation of 2-(4-{2-[(2,3-dihydro-1H-inden-2-yl)amino]pyrimidin-5-yl}-3-(morpholin-4-ylmethyl)-1H-pyrazol-1-yl)-1-{1H,4H,5H,6H,7H-[1,2,3]triazolo[4,5-c]pyridin-5-yl}ethan-1-one (Compound 80)

By using the compound 80-b (230 mg, 0.28 mmol) instead of the compound 61-e, the reaction was carried out in the same manner as the Step 6 of Example 10-1 to obtain the title compound 80 as a white solid (80 mg, 53%).

MS m/z: 541 [M+1]$^+$ $^1$H NMR (DMSO-d$_6$, 400 MHz), δ ppm: 8.56 (s, 2H), 7.90 (d, 1H), 7.43 (d, 1H), 7.23-7.13 (m, 4H), 5.25 (d, 2H), 4.79-4.61 (m, 3H), 3.86-3.78 (m, 2H), 3.52 (m, 2H), 3.26 (dd, 2H), 2.94-2.71 (m, 4H), 2.36 (m, 4H)

[Example 12-2] Preparation of 2-(4-{2-[(2,3-dihydro-1H-inden-2-yl)amino]pyrimidin-5-yl}-3-(piperidin-1-ylmethyl)-1H-pyrazol-1-yl)-1-{1H,4H,5H,6H,7H-[1,2,3]triazolo[4,5-c]pyridin-5-yl}ethan-1-one (Compound 81)

81

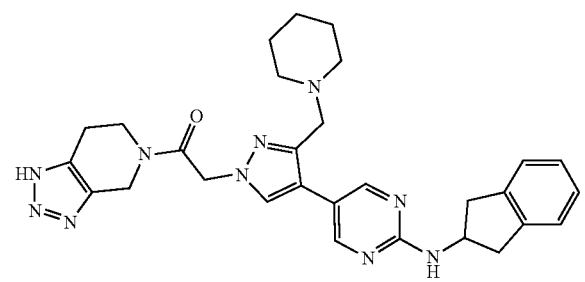

By using piperidine instead of morpholine, the reaction was carried out in the same manner as Example 12-1 to obtain the title compound 81 as a white solid.

MS m/z: 539 [M+1]$^+$ $^1$H NMR (CDCl$_3$, 400 MHz), δ ppm: 8.47 (br, 2H), 7.59 (d, 2H), 7.27-7.15 (m, 4H), 5.44 (dd, 1H), 5.13 (s, 2H), 4.89-4.72 (m, 3H), 3.91 (dt, 2H), 3.55 (br, 2H), 3.42 (dd, 2H), 2.94-2.81 (m, 4H), 2.49 (br, 4H), 1.59 (br, 4H), 1.25 (br, 2H)

[Example 12-3] Preparation of 4-[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)methyl]piperazin-2-one (Compound 82)

82

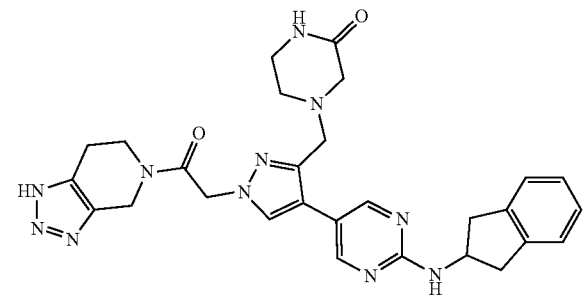

By using 2-piperazinone instead of morpholine, the reaction was carried out in the same manner as Example 12-1 to obtain the title compound 82 as a white solid.

MS m/z: 554 [M+1]$^+$ $^1$H NMR (DMSO-d$_6$, 400 MHz), δ ppm: 8.53 (s, 2H), 7.92 (d, 1H), 7.46 (s, 1H), 7.34 (d, 1H), 7.28-7.13 (m, 4H), 5.27 (d, 2H), 4.79-4.58 (m, 3H), 3.86-3.79 (m, 2H), 3.52 (s, 2H), 3.280 (dd, 2H), 3.12-3.06 (m, 2H), 2.96-2.41 (m, 6H), 2.59-2.52 (m, 2H)

[Example 12-4] Preparation of 2-(4-{2-[(2,3-dihydro-1H-inden-2-yl)amino]pyrimidin-5-yl}-3-(2,3-dihydro-1H-indol-1-ylmethyl)-1H-pyrazol-1-yl)-1-{1H,4H,5H,6H,7H-[1,2,3]triazolo[4,5-c]pyridin-5-yl}ethan-1-one (Compound 83)

83

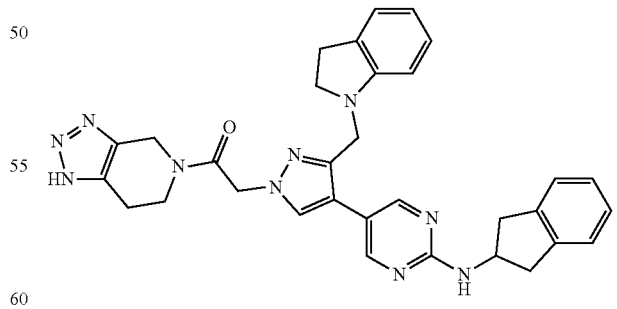

By using 2,3-dihydro-1H-indole instead of morpholine, the reaction was carried out in the same manner as Example 12-1 to obtain the title compound 83 as a white solid.

MS m/z: 57-3 [M+1]$^+$ $^1$H NMR (CDCl$_3$, 400 MHz), δ ppm: 13.12 (br, 1H), 8.41 (s, 2H), 7.61 (d, 1H), 7.24-7.14 (m, 2H), 7.08-7.02 (m, 2H), 6.67 (t, 1H), 6.59-6.56 (m, 1H), 5.53 (d, 1H), 5.18-5.12 (m, 2H), 4.82-4.68 (m, 3H), 4.22 (d, 2H), 3.94-3.79 (m, 2H), 3.49 (dd, 2H), 3.28-3.22 (m, 2H), 3.92-3.78 (m, 6H)

[Example 12-5] Preparation of 2-(4-{2-[(2,3-di-hydro-1H-inden-2-yl)amino]pyrimidin-5-yl}-3-(1,2,3,4-tetrahydroisoquinolin-2-ylmethyl)-1H-pyrazol-1-yl)-1-{1H,4H,5H,6H,7H-[1,2,3]triazolo[4,5-c]pyridin-5-yl}ethan-1-one (Compound 84)

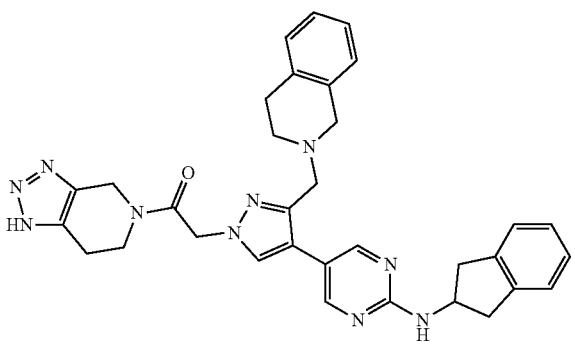

84

By using 1,2,3,4-tetrahydroisoquinoline instead of morpholine, the reaction was carried out in the same manner as Example 12-1 to obtain the title compound 84 as a white solid.

MS m/z: 587 [M+1]$^+$ $^1$H NMR (CDCl$_3$, 400 MHz), δ ppm: 8.548 (s, 2H), 7.609 (s, 1H), 7.236-7.154 (m, 4H), 7.097-6.982 (m, 4H), 5.387 (d, 1H), 5.134 (d, 2H), 4.864-4.780 (m, 3H), 3.995-3.893 (m, 2H), 3.678-3.661 (m, 4H), 3.420-3.361 (m, 2H), 2.915-2.781 (m, 8H) ppm

[Example 12-6] Preparation of 2-{3-[(4,4-difluoropiperidin-1-yl)methyl]-4-{2-[(2,3-dihydro-1H-inden-2-yl)amino]pyrimidin-5-yl}-1H-pyrazol-1-yl}-1-{1H,4H,5H,6H,7H-[1,2,3]triazolo[4,5-c]pyridin-5-yl}ethan-1-one hydrofluoride (Compound 85)

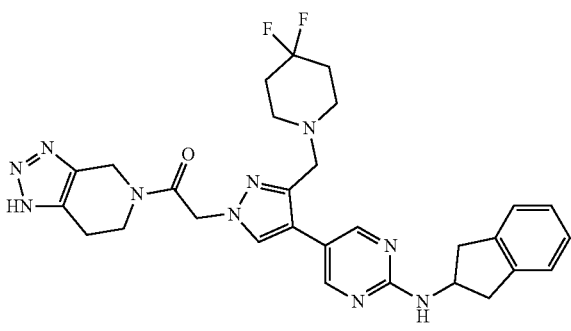

85

By using 4,4-difluoropiperidine instead of morpholine, the reaction was carried out in the same manner as Example 12-1 to obtain the title compound 85 as a white solid.

MS m/z: 575 [M+1]$^+$ $^1$H NMR (CDCl$_3$, 400 MHz), δ ppm: 8.50 (d, 2H), 7.61 (d, 1H), 7.26-7.17 (m, 4H), 5.49 (d, 1H), 5.15 (d, 2H), 4.86-4.74 (m, 3H), 3.98-3.84 (m, 2H), 3.45-3.39 (dd, 2H), 2.94-2.85 (m, 4H), 2.59 (s, 4H), 1.99-1.82 (m, 4H)

[Example 12-7] Preparation of 2-(4-{2-[(2,3-di-hydro-1H-inden-2-yl)amino]pyrimidin-5-yl}-3-[(4-phenyl-1,2,3,6-tetrahydropyridin-1-yl)methyl]-1H-pyrazol-1-yl)-1-{3H,4H,5H,6H,7H-[1,2,3]triazolo[4,5-c]pyridin-5-yl}ethan-1-one (Compound 86)

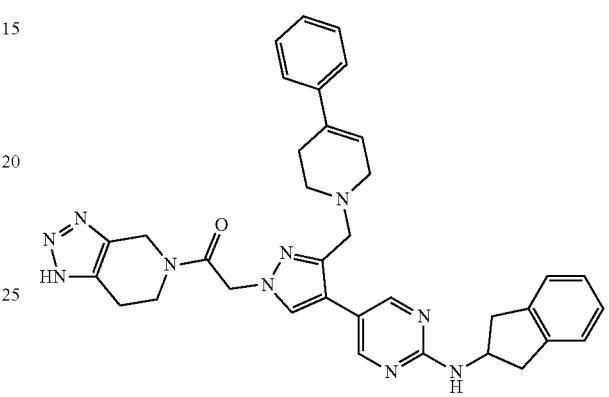

86

By using 4-phenyl-1,2,3,6-tetrahydropyridine instead of morpholine, the reaction was carried out in the same manner as Example 12-1 to obtain the title compound 86 as a white solid.

MS m/z: 613 [M+1]$^+$ $^1$H NMR (DMSO-d$_6$, 400 MHz), δ ppm: 8.578 (s, 2H), 7.944 (d, 1H), 7.436-7.118 (m, 9H), 6.161 (s, 1H), 5.278 (d, 2H), 4.793 (s, 1H), 4.685-4.549 (m, 3H), 3.832 (m, 2H), 3.543 (s, 2H), 3.269-3.211 (m, 2H), 3.096 (m, 2H), 2.887-2.869 (m, 2H), 2.743 (m, 2H), 2.668 (m, 2H), 2.426 (m, 2H) ppm

[Example 12-8] Preparation of 4-[(4-{2-[(2,3-di-hydro-1H-inden-2-yl)amino]pyrimidin-5-yl}-1-(2-oxo-2-{1H,2H,3H,4H,5H,6H,7H-[1,2,3]triazolo[4,5-c]pyridin-5-yl}ethyl)-1H-pyrazol-3-yl)methyl]-1-methylpiperazin-2-one (Compound 87)

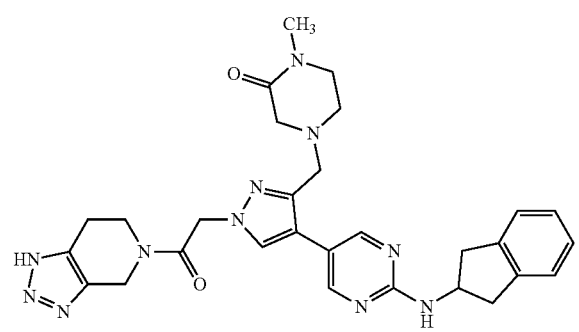

87

By using 1-methylpiperazin-2-one instead of morpholine, the reaction was carried out in the same manner as Example 12-1 to obtain the title compound 87 as a white solid.

MS m/z: 568 [M+1]⁺

¹H NMR (CDCl₃, 400 MHz), δ ppm: 8.454 (s, 2H), 7.606 (d, 1H), 7.223-7.173 (m, 4H), 5.702 (m, 1H), 5.140 (s, 2H), 4.796-4.746 (m, 3H), 3.916-3.813 (m, 2H), 3.565 (s, 2H), 3.428-3.376 (m, 2H), 3.301 (s, 2H), 3.184-3.146 (m, 2H), 2.919-2.748 (m, 5H) ppm

[Example 12-9] Preparation of 1-[(4-{2-[(2,3-di-hydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)methyl]piperazin-2-one (Compound 88)

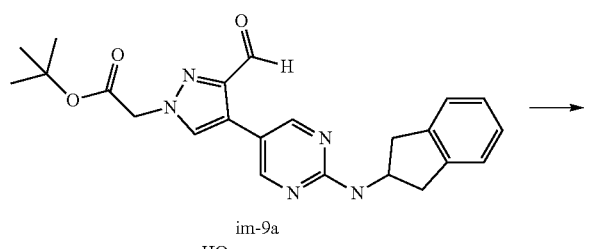

im-9a

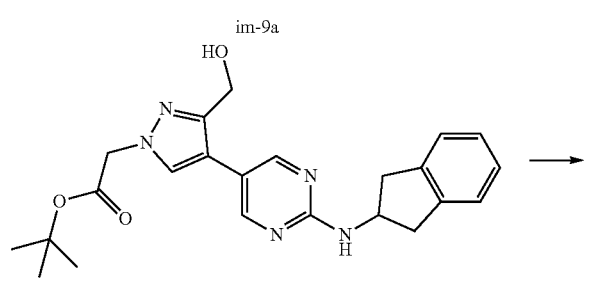

88-a

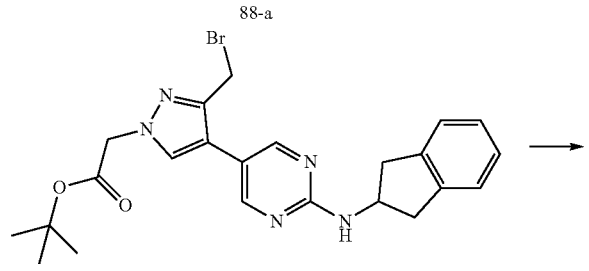

88-b

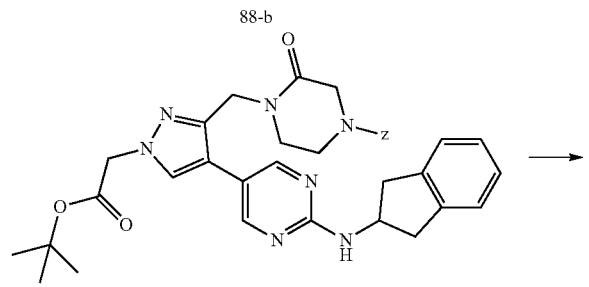

88-c

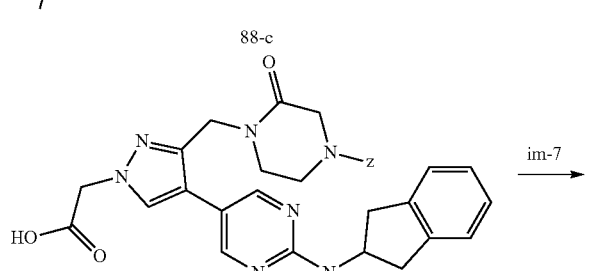

88-d

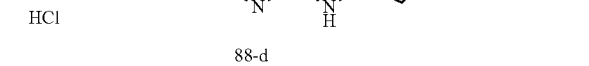

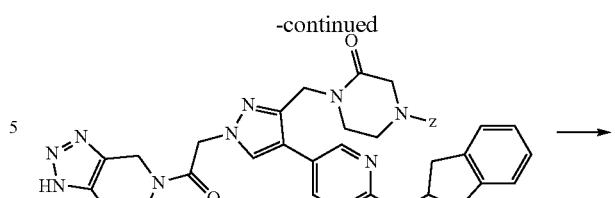

88-e

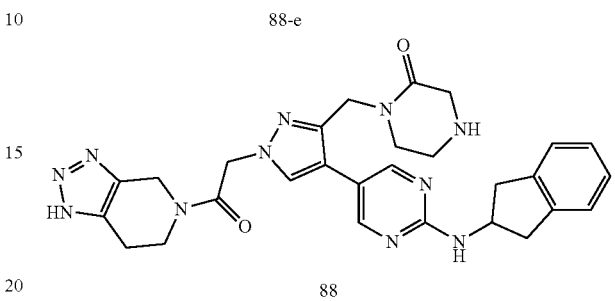

88

(Step 1) Preparation of tert-butyl 2-(4-{2-[(2,3-dihydro-1H-inden-2-yl)amino]pyrimidin-5-yl}-3-(hydroxymethyl)-1H-pyrazol-1-yl)acetate (Compound 88-a)

To a solution of the compound im-9a (0.30 g, 0.72 mmol) in methanol (5 mL) was added sodium borohydride (40 mg, 1.07 mmol) at 0° C., and the mixture was stirred for 3 hours at room temperature. By adding ice water, the reaction was terminated, and the reaction mixture was diluted with ethyl acetate, and washed with distilled water. The organic layer was dried over anhydrous sodium sulfate and concentrated to give the title compound 88-a as a brown solid (0.30 g, 99%).

MS m/z: 422 [M+1]⁺

¹H NMR (CDCl₃, 400 MHz), δ ppm: 8.44 (s, 2H), 7.53 (s, 1H), 7.24-7.16 (N, 4H), 5.75 (d, 1H), 4.91-4.80 (m, 3H), 4.70 (s 2H), 3.41 (dd, 2H), 2.91 (dd, 2H), 1.49 (s, 9H)

(Step 2) Preparation of tert-butyl 2-[3-(bromomethyl)-4-{2-[(2,3-dihydro-1H-inden-2-yl)amino]pyrimidin-5-yl}-1H-pyrazol-1-yl]acetate (Compound 88-b)

To a solution of the compound 88-a (0.30 g, 0.72 mmol) in methylene chloride (5 mL) was added carbon tetrabromide (0.33 g, 0.98 mmol) and triphenylphosphine (0.26 g, 0.98 mol) in order at 0° C., and the mixture was stirred for 18 hours at room temperature. Upon the completion of the reaction, the solvent was removed, and the residue was purified by silica gel column chromatography (ethyl acetate: n-hexane=3:7→4:6) to obtain the title compound 88-b as a yellow solid (0.24 g, 69%).

MS m/z: 485 [M+1]⁺

¹H NMR (CDCl₃, 400 MHz), δ ppm: 8.44 (s, 2H), 4.49 (s, 1H), 7.23-7.17 (m, 4H), 5.60 (d, 1H), 4.85-4.82 (m, 3H), 4.52 (s, 2H), 3.43 (dd, 2H), 2.92 (dd, 2H), 1.49 (s, 9H)

(Step 3) Preparation of benzyl 4-({1-[2-(tert-butoxy)-2-oxoethyl]-4-{2-[(2,3-dihydro-1H-inden-2-yl)amino]pyrimidin-5-yl}-1H-pyrazol-3-yl}methyl)-3-oxopiperazine-1-carboxylate (Compound 88-c)

To a solution of 4-benzyloxycarbonylpiperazin-2-one (63 mg, 0.27 mmol) in N,N-dimethylformamide (1 mL) was added sodium hydride (11 mg, 0.48 mmol) at 0° C., and the mixture was stirred for 1 hour at room temperature. After cooling again to 0° C., a solution of the compound 88-b (0.12 g, 0.25 mmol) in N,N-dimethylformamide (2 mL) was dropwise added thereto, and the mixture was stirred for 1 hour at room temperature. The reaction was terminated by adding distilled water (25 mL), and the mixture was extracted with ethyl acetate. The organic layer was washed with distilled water and saturated brine, dried over anhydrous sodium sulfate, and concentrated. The residue was purified by silica gel column chromatography (ethyl acetate:n-hexane=1:1→ethyl acetate) to obtain the title compound 88-c as a yellow liquid (20 mg, 13%).

MS m/z: 638 [M+1]$^+$ $^1$H NMR (CDCl$_3$, 400 MHz), δ ppm: 8.28 (s, 2H), 7.48 (s, 1H), 7.34-7.31 (m, 5H), 7.23-7.16 (m, 4H), 5.43 (d, 1H), 5.13 (s, 2H), 4.83-4.75 (m, 5H), 4.12 (s, 2H), 3.62-3.59 (m, 2H), 3.43-3.33 (m, 4H), 2.89 (dd, 2H), 1.49 (s, 9H)

(Step 4) Preparation of 2-[3-({4-[(benzyloxy)carbonyl]-2-oxopiperazin-1-yl}methyl)-4-{2-[(2,3-dihydro-1H-inden-2-yl)amino]pyrimidin-5-yl}-1H-pyrazol-1-yl]acetic Acid (Compound 88-d)

By using the compound 88-c (35 mg, 0.055 mmol) instead of the compound 61-d, the reaction was carried out in the same manner as the Step 5 of Example 10-1 to obtain the title compound 88-d as a brown liquid (38 mg).

MS m/z: 582[M+1]$^+$ $^1$H NMR (CDCl$_3$, 400 MHz), δ ppm: 7.34 (s, 5H), 7.21-7.19 (m, 4H), 5.13 (s, 2H), 4.90 (s, 3H), 4.60 (s, 2H), 4.13 (s, 2H), 3.63-3.38 (m, 6H), 3.09-3.03 (m, 2H)

(Step 5) Preparation of benzyl 4-[(4-{2-[(2,3-dihydro-1H-inden-2-yl amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)methyl]-3-oxopiperazine-1-carboxylate (Compound 88-e)

By using the compound 88-d (38 mg, 0.067 mmol) instead of the compound 61-e, the reaction was carried out in the same manner as the Step 6 of Example 10-1 to obtain the title compound 88-e as a yellow solid (25 mg, 54%).

MS m/z: 688[M+1]$^+$ $^1$H NMR (CDCl$_3$, 400 MHz), δ ppm: 8.27 (d, 2H), 7.57-7.51 (m, 1H), 7.34 (bs, 5H), 7.24-7.16 (m, 4H), 5.49 (s, 1H), 5.14-5.08 (m, 4H), 4.81-4.68 (m, 5H), 4.03-3.82 (m, 4H), 3.61 (s, 2H), 3.39 (dd, 2H), 3.30-3.25 (m, 2H), 2.90-2.86 (m, 4H)

(Step 6) Preparation of 1-[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)methyl]piperazin-2-one (Compound 88)

To a solution of the compound 88-e (25 mg, 0.036 mmol) in ethyl acetate (5 mL) was added Pd/C (10% by weight, 20 mg), and the mixture was stirred for 8 hours at room temperature under hydrogen pressure (1 atm). Upon the completion of the reaction, the catalyst was removed by filtration through a Celite pad, and the filtrate was concentrated under reduced pressure. The residue was then purified by silica gel column chromatography (methanol:methylene chloride=2:8) to obtain the title compound 88 as a white solid (4 mg, 20%).

MS m/z: 554 [M+1]$^+$ $^1$H NMR (DMSO-d$_6$, 400 MHz), δ ppm: 8.33 (s, 2H), 7.86 (d, 1H), 7.52 (d, 1H), 7.22-7.14 (m, 4H), 5.29 (d, 2H), 4.77-4.59 (m, 5H), 3.83 (d, 2H), 3.29-3.23 (m, 2H), 3.16-3.10 (m, 2H), 2.97-2.87 (m, 4H), 2.73-2.67 (m, 2H)

[Example 12-10] Preparation of 2-(4-{2-[(2,3-dihydro-1H-inden-2-yl)amino]pyrimidin-5-yl}-3-(piperazin-1-ylmethyl)-1H-pyrazol-1-yl)-1-{1H,4H,5H,6H,7H-[1,2,3]triazolo[4,5-c]pyridin-5-yl}ethan-1-one (Compound 89)

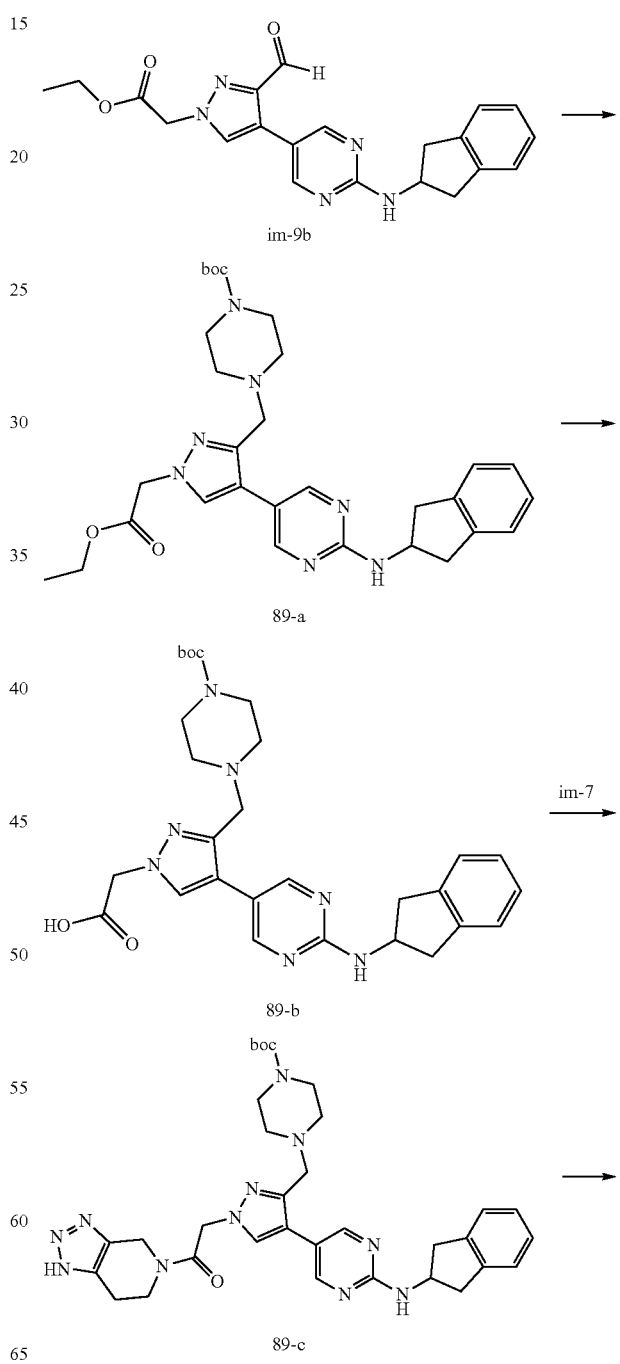

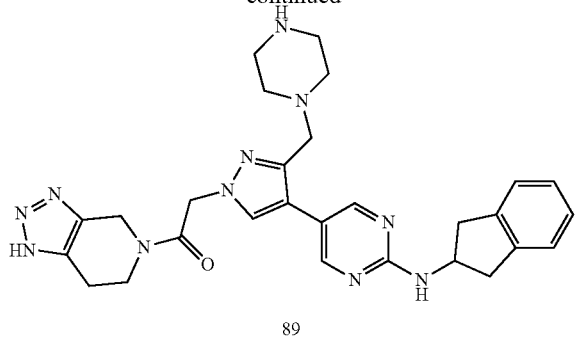

89

(Step 1) Preparation of tert-butyl 4-[(4-{2-[(2,3-dihydro-1H-inden-2-yl)amino]pyrimidin-5-yl}-1-(2-ethoxy-2-oxoethyl)-1H-pyrazol-3-yl)methyl]piperazine-1-carboxylate (Compound 89-a)

By using 1-(tert-butoxycarbonyl)piperazine (0.29 g, 1.53 mmol) instead of morpholine and using the compound im-9b (0.40 g, 1.02 mmol) instead of the compound im-9a, the reaction was carried out in the same manner as the Step 1 of Example 12-1 to obtain the title compound 89-a as a white solid (0.37 g, 65%).

MS m/z: 562 [M+1]$^+$ $^1$H NMR (CDCl$_3$, 400 MHz), δ ppm: 8.53 (s, 2H), 7.55 (s, 1H), 7.21-7.16 (m, 4H), 5.41 (d, 1H), 4.90 (s, 2H), 4.86-4.81 (m, 1H), 4.28-4.23 (m, 2H), 3.51 (s, 2H), 3.45-3.37 (m, 6H), 2.91 (dd, 2H), 2.43 (s, 4H), 1.45 (s, 9H), 1.29-1.24 (m, 3H)

(Step 2) Preparation of 2-[3-({4-[(tert-butoxy)carbonyl]piperazin-1-yl}methyl)-4-{2-[(2,3-dihydro-1H-inden-2-yl)amino]pyrimidin-5-yl}-1H-pyrazol-1-yl]acetic Acid (Compound 89-b)

By using the compound 89-a (45 mg, 0.08 mmol) instead of the compound 61-d, the reaction was carried out in the same manner as the Step 5 of Example 10-2 to obtain the title compound 89-b quantitatively (46 mg).

MS m/z: 534 [M+1]$^+$ $^1$H NMR (CD$_3$OD, 400 MHz), δ ppm: 8.63 (s, 2H), 7.82 (s, 1H), 7.23-7.13 (m, 4H), 4.76-4.73 (m, 3H), 3.52 (s, 2H), 3.41-3.33 (m, 6H), 2.94 (dd, 2H), 2.46-2.41 (m, 4H), 1.46 (s, 8H)

(Step 3) Preparation of tert-butyl 4-[(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)methyl]piperazine-1-carboxylate (Compound 89-c)

By using the compound 89-b (46 mg, 0.08 mmol) instead of the compound 61-e, the reaction was carried out in the same manner as the Step 6 of Example 10-1 to obtain the title compound 89-c as a white solid (28 mg, 55%).

MS m/z: 640 [M+1]$^+$ $^1$H NMR (CDCl$_3$, 400 MHz), δ ppm: 8.51 (d, 2H), 7.60 (s, 1H), 7.24-7.17 (m, 4H), 5.44 (d, 1H), 5.13 (s, 2H), 4.84-4.79 (m, 3H), 3.97-3.86 (m, 2H), 3.52-3.49 (m, 3H), 3.45-3.39 (m, 6H), 2.93-2.85 (m, 4H), 2.43-2.39 (m, 4H), 1.45 (s, 9H)

(Step 4) Preparation of 2-(4-{2-[(2,3-dihydro-1H-inden-2-yl)amino]pyrimidin-5-yl}-3-(piperazin-1-ylmethyl)-1H-pyrazol-1-yl)-1-{1H,4H,5H,6H,7H-[1,2,3]triazolo[4,5-c]pyridin-5-yl}ethan-1-one (Compound 89)

By using the compound 89-c (28 mg, 0.044 mmol) instead of the compound 62-f, the reaction was carried out in the same manner as the Step 7 of Example 10-e to obtain the title compound 89 as a white solid (21 mg, 83%).

MS m/z: 540 [M+1]$^+$ $^1$H NMR (DMSO-d$_6$, 400 MHz), δ ppm: 9.64 (s, 2H), 8.54 (s, 2H), 8.05-8.03 (m, 2H), 7.25-7.15 (m, 4H), 5.40-5.36 (m, 2H), 4.80-4.69 (m, 3H), 3.85-3.83 (m, 2H), 3.41-3.17 (m, 10H), 2.98-2.74 (m, 4H)

[Example 12-11] Preparation of 2-[3-(1,4-diazepan-1-ylmethyl)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one. HCl (Compound 90)

90

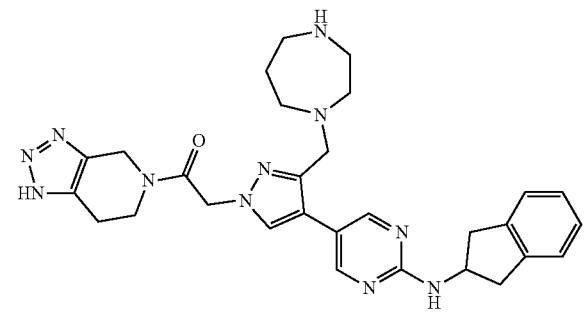

By using 1-tert-butoxycarbonyl homopiperazine instead of 1-(tert-butoxycarbonyl)piperazine, the reaction was carried out in the same manner as Example 12-10 to obtain the title compound 90 as a white solid.

MS m/z: 554 [M+1]$^+$ $^1$H NMR (DMSO-d$_6$, 400 MHz), δ ppm: 11.06 (br, 1H), 9.53-9.49 (m, 2H), 8.48 (s, 2H), 8.09-7.88 (m, 2H), 7.25-7.15 (m, 4H), 5.76-5.37 (m, 2H), 4.81-4.62 (m, 3H), 4.45 (br, 2H), 3.88-3.80 (m, 2H), 3.79-3.48 (m, 8H), 3.31-3.12 (m, 4H), 2.99-2.73 (m, 4H), 2.12 (br, 2H)

[Example 12-12] Preparation of 2-(4-{2-[(2,3-dihydro-1H-inden-2-yl)amino]pyrimidin-5-yl}-3-[(4-ethylpiperazin-1-yl)methyl]-1H-pyrazol-1-yl)-1-{1H,4H,5H,6H,7H-[1,2,3]triazolo[4,5-c]pyridin-5-yl}ethan-1-one (Compound 91)

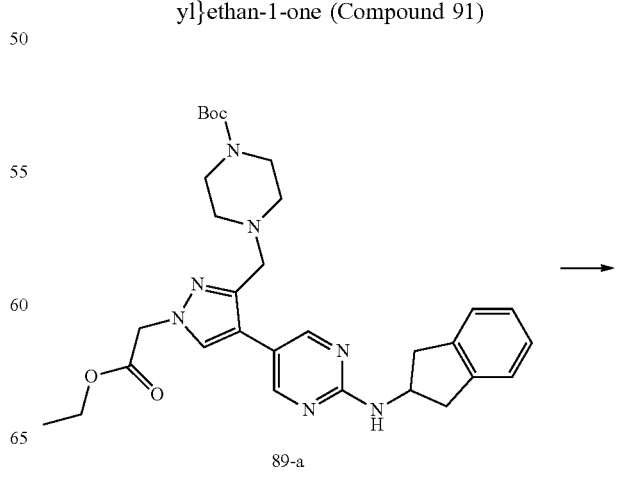

89-a

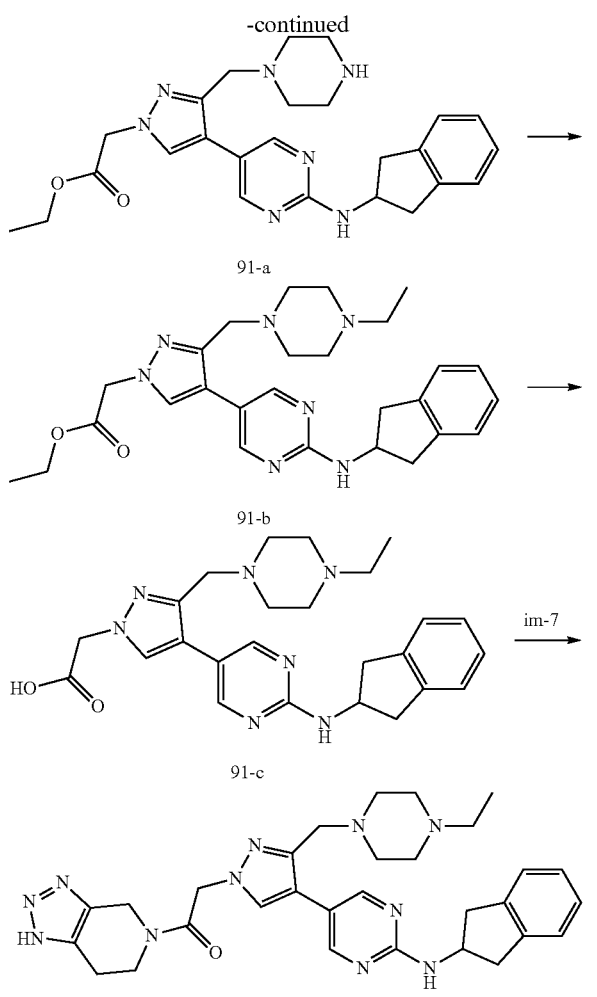

(Step 3) Preparation of 2-(4-{2-[(2,3-dihydro-1H-inden-2-yl)amino]pyrimidin-5-yl}-3-[(4-ethylpiperazin-1-yl)methyl]-1H-pyrazol-1-yl)acetic Acid (Compound 91-c)

By using the compound 91-b (0.10 g, 0.21 mmol) instead of the compound 62-d, the reaction was carried out in the same manner as the Step 5 of Example 10-2 to obtain the title compound 91-c quantitatively (0.13 g).

MS m/z: 462 [M+1]$^+$ (Step 4) Preparation of 2-(4-{2-[(2,3-dihydro-1H-inden-2-yl)amino]pyrimidin-5-yl}-3-[(4-ethylpiperazin-1-yl)methyl]-1H-pyrazol-1-yl)-1-{1H,4H,5H, 6H,7H-[1,2,3]triazolo[4,5-c]pyridin-5-yl}ethan-1-one (Compound 0.91)

By using the compound 91-c (0.13 g, 0.21 mmol) instead of the compound 61-e, the reaction was carried out in the same manner as the Step 6 of Example 10-1 to obtain the title compound 91 as a white solid (36 mg, 30%).

MS m/z: 568 [M+1]$^+$ $^1$H NMR (CDCl$_3$, 400 MHz), δ ppm: 8.54 (d, 2H), 7.59 (d, 2H), 7.25-7.14 (m, 4H), 5.39-5.32 (m, 1H), 5.10 (d, 2H), 4.83-4.79 (m, 3H), 3.91 (m, 2H), 3.50 (d, 2H), 3.42 (dd, 2H), 2.94-2.84 (m, 4H), 2.71-2.32 (m, 10H), 1.14-1.05 (m, 3H)

[Example 12-13] Preparation of 2-(3-{[4-(2,2-difluoroethyl)piperazin-1-yl]methyl}-4-{2-[(2,3-dihydro-1H-inden-2-yl)amino]pyrimidin-5-yl}-1H-pyrazol-1-yl)-1-{1H,4H,5H,6H,7H-[1,2,3]triazolo[4,5-c]pyridin-5-yl}ethan-1-one (Compound 92)

(Step 1) Preparation of ethyl 2-(4-{2-[(2,3-dihydro-1H-inden-2-yl)amino]pyrimidin-5-yl}-3-(piperazin-1-ylmethyl)-1H-pyrazol-1-yl)acetate (Compound 91-a)

By using the compound 89-a (0.18 g, 0.32 mmol) instead of the compound 62-f, the reaction was carried out in the same manner as the Step 7 of Example 10-2 to obtain the title compound 91-a as a beige solid quantitatively (0.20 g).

MS m/z: 462 [M+1]$^+$ $^1$H NMR (DMSO-d$_6$, 400 MHz), δ ppm: 9.65 (br, 2H), 8.53 (s, 2H), 8.11 (s, 1H), 8.03 (br, 1H), 7.25-7.15 (m, 4H), 5.17 (s, 2H), 4.69 (m, 1H), 4.58-4.22 (m, 2H), 4.18 (m, 2H), 3.54-3.24 (m, 11H), 2.61 (dd, 2H), 1.23 (t, 3H)

(Step 2) Preparation of ethyl 2-(4-{2-[(2,3-dihydro-1H-inden-2-yl)amino]pyrimidin-5-yl}-3-[(4-ethylpiperazin-1-yl)methyl]-1H-pyrazol-1-yl)acetate (Compound 91-b)

By using the compound 91-a (0.20 g, 0.32 mmol) instead of the compound 68-a, the reaction was carried out in the same manner as the Step 2 of Example 10-8 to obtain the title compound 91-b as a yellow solid (0.10 g, 66%).

MS m/z: 490 [M+1]$^+$

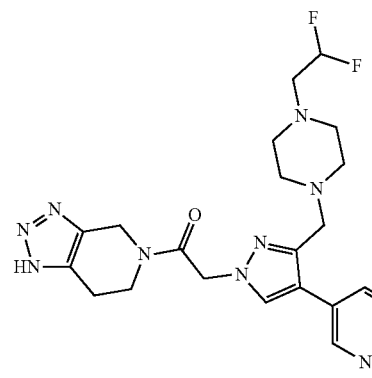

By using 2,2-difluoroethyl trifluoromethanesulfonate instead of bromoethane, the reaction was carried out in the same manner as the Step 2 to Step 4 of Example 12-12 to obtain the title compound 92.

MS m/z: 604 [M+1]$^+$ $^1$H NMR (CDCl$_3$, 400 MHz), δ ppm: 8.51 (s, 2H), 7.61 (d, 1H), 7.25-7.17 (m, 4H), 6.02-5.72 (m, 1H), 5.55-5.52 (m, 1H), 5.14 (d, 2H), 4.91-4.74 (m, 3H), 3.95 (t, 1H), 3.84 (t, 1H), 3.52 (s, 2H), 3.42 (dd, 2H), 2.94-2.84 (m, 4H), 2.76-2.67 (m, 2H), 2.58 (bs, 8H)

[Example 12-14] 2-(4-{2-[(2,3-dihydro-1H-inden-2-yl)amino]pyrimidin-5-yl}-3-[2-(morpholin-4-yl)ethyl]-1H-pyrazol-1-yl)-1-{1H,4H,5H,6H,7H-[1,2,3]triazolo[4,5-c]pyridin-5-yl}ethan-1-one (Compound 93)

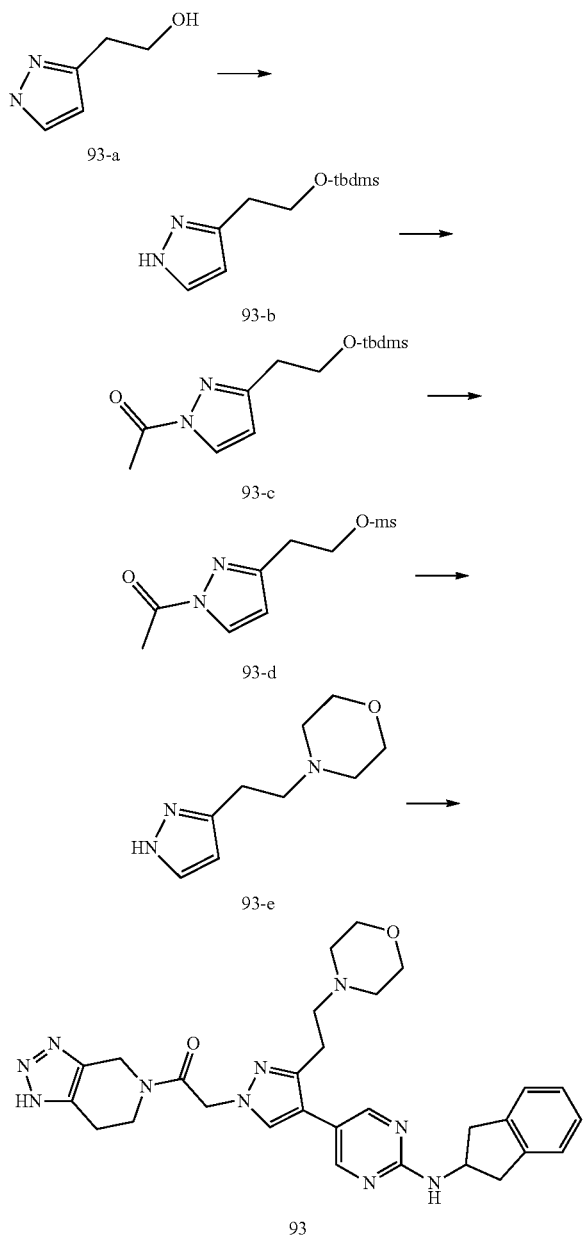

(Step 1) Preparation of 2-(1H-Pyrazol-3-yl)ethanol (Compound 93-a)

According to a well-known method (WO 2013164321, WO 2007034277), the title compound 93-a was synthesized.

MS m/z: 113 [M+1]+

1H NMR (CDCl3, 400 MHz), δ ppm: 7.49 (d, 1H), 6.15 (d, 1H), 3.91 (t, 2H), 2.92 (t, 2H)

(Step 2) Preparation of 3-{2-[(tert-butyldimethylsilyl)oxy]ethyl}-1H-pyrazole (Compound 93-b)

To a solution of the compound 93-a (0.60 g, 5.37 mmol) in N,N-dimethylformamide (10 mL) was added tert-butyldimethylsilyl chloride (2.43 g, 16.0 mmol) and imidazole (1.83 g, 26.8 mmol) in order, the mixture was stirred for 13 hours at room temperature. The reaction was terminated by adding distilled water (20 mL), and the mixture was extracted with ethyl acetate. The organic layer was washed with distilled water and saturated brine, dried over anhydrous sodium sulfate, and concentrated. The obtained residue was purified by silica gel column chromatography (ethyl acetate:n-hexane=1:9) to obtain the title compound 93-b as a colorless liquid quantitatively (1.2 g).

MS m/z: 227 [M+1]+

1H NMR (CDCl3, 400 MHz), δ ppm: 7.47 (d, 1H), 6.09 (d, 1H), 3.87 (t, 2H), 2.88 (t, 2H), 0.90 (s, 9H), 0.04 (s, 6H)

(Step 3) Preparation of 1-(3-{2-[(tert-butyldimethylsilyl)oxy]ethyl}-1H-pyrazol-1-yl)ethan-1-one (Compound 93-c)

To solution of the compound 93-b (1.2 g, 5.5 mmol) in pyridine (3 mL) was slowly added a solution of acetic anhydride (0.63 mL, 6.62 mmol) in pyridine (3 mL), and the mixture was stirred for 3 hours at room temperature. Upon the completion of the reaction, the solvent was removed, and the residue was purified by silica gel column chromatography (ethyl acetate:n-hexane=5:95) to obtain the title compound 93-c as a yellow liquid (0.76 g, 51%).

MS m/z: 269 [M+1]+

1H NMR (CDCl3, 400 MHz), δ ppm: 8.15 (d, 1H), 6.34 (d, 1H), 3.90 (t, 2H), 2.87 (t, 2H), 2.67 (s, 3H), 0.88 (s, 9H), 0.03 (s, 6H)

(Step 4) Preparation of 2-(1-acetyl-1H-pyrazol-3-yl)ethyl methanesulfonate (Compound 93-d)

To a solution of the compound 93-c (0.76 g, 2.83 mmol) in methylene chloride (5 mL) was added 4 N hydrogen chloride dioxane solution (2 mL), and the mixture was stirred for 1 hour at room temperature. Then, the solvent was removed, and the residue was dissolved again in methylene chloride (5 mL). To reaction mixture was added triethylamine (1.2 mL, 8.5 mmol) and methanesulfonyl chloride (0.33 mL, 4.24 mmol) at 0° C., and the mixture was stirred for 1 hour at room temperature. The mixture was diluted with distilled water (50 mL) and extracted with methylene chloride. The organic layer was washed with distilled water and saturated brine, dried over anhydrous sodium sulfate, and concentrated. The obtained residue was purified by silica gel column chromatography (methanol:methylene chloride=3:7) to obtain the title compound 93-d as a yellow liquid (0.29 g, 44%).

MS m/z: 233 [M+1]+

1H NMR (CDCl3, 400 MHz), δ ppm: 8.19 (d, 1H), 6.35 (d, 1H), 4.56 (t, 2H), 3.14 (t, 2H), 3.00 (s, 3H), 2.67 (s, 3H)

(Step 5) Preparation of 4-[2-(1H-pyrazol-3-yl)ethyl]morpholine (Compound 93-e)

To a solution of the compound 93-d (0.29 g, 1.25 mmol) in N,N-dimethylformamide (2 mL) was added triethylamine (0.35 mL, 2.5 mmol) and morpholine (0.16 g, 1.87 mmol), and the mixture was stirred at 95° C. for 2 hours. Upon the completion of the reaction, the mixture was cooled to room temperature, and concentrated to obtain the title compound 93-e quantitatively (0.50 g).

MS m/z: 182 [M+1]$^+$ (Step 6) Preparation of 2-(4-{2-[(2,3-dihydro-1H-inden-2-yl)amino]pyrimidin-5-yl}-3-[2-(morpholin-4-yl)ethyl]-1H-pyrazol-1-yl)-1-{1H,4H,5H,6H,7H-[1,2,3]triazolo[4,5-c]pyridin-5-yl}ethan-1-one (Compound 93)

By using the compound 93-e instead of the compound 61-a, the reaction was carried out in the same manner as the Step 2 to Step 6 of Example 10-1 to obtain the title compound 93 as a white solid.

MS m/z: 555 [M+1]$^+$ $^1$H NMR (DMSO-d$_6$, 400 MHz), δ ppm: 8.36 (s, 2H), 7.79-7.77 (m, 1H), 7.50 (d, 1H), 7.22-7.14 (m, 4H), 5.23-5.19 (m, 2H), 4.76-4.62 (m, 3H), 3.86-3.78 (m, 2H), 3.54 (br, 4H), 3.30-3.21 (m, 2H), 2.94-2.70 (m, 6H), 2.36 (br, 4H)

[Example 13] Preparation of 1-{4-[2-(4-{2-[(2,3-dihydro-1H-inden-2-yl)amino]pyrimidin-5-yl}-3-ethyl-1H-pyrazol-1-yl)acetyl]piperazin-1-yl}-2-hydroxyethan-1-one (Compound 94)

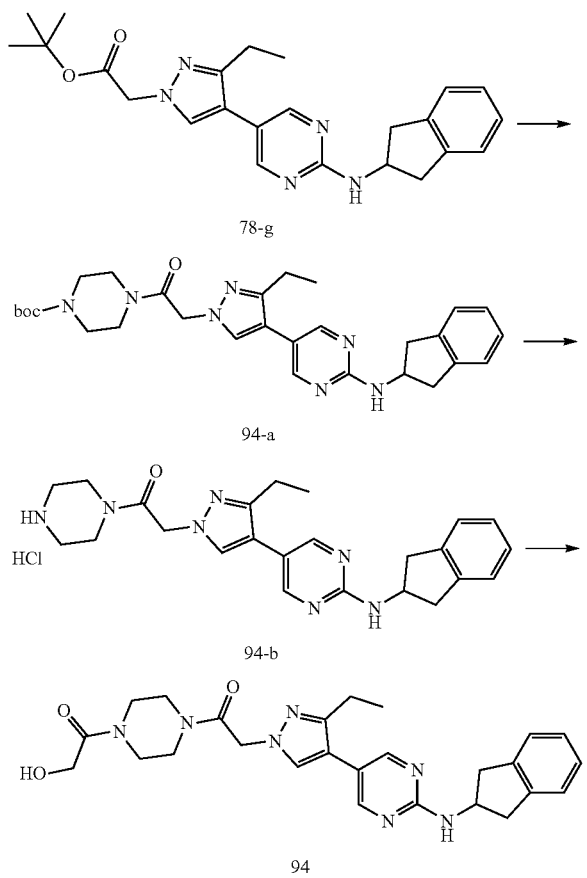

(Step 1) Preparation of tert-butyl 4-[2-(4-{2-[(2,3-dihydro-1H-inden-2-yl)amino]pyrimidin-5-yl}-3-ethyl-1H-pyrazol-1-yl)acetyl]piperazine-1-carboxylate (Compound 94-a)

Except that 1-(tert-butoxycarbonyl)piperazine (205 mg, 1.10 mmol) is used instead of im-7 by using the compound 78-g (0.23 g, 0.55 mmol), the reaction was carried out in the same manner as Example 11-2 to obtain the title compound 94-a as a beige solid (237 mg, 81%).

(Step 2) Preparation of 2-(4-{2-[(2,3-dihydro-1H-inden-2-yl)amino]pyrimidin-5-yl}-3-ethyl-H-pyrazol-1-yl)-1-(piperazin-1-yl)ethan-1-one hydrochloride (Compound 94-b)

To a solution of the compound 94-a (237 mg, 0.44 mmol) in methylene chloride (2 mL) was added 4 N hydrogen chloride dioxane solution (6 mL), and the mixture was stirred for 15 hours at room temperature. Upon the completion of the reaction, the solvent was removed followed by drying to obtain the title compound 94-b as an ivory-colored solid quantitatively (255 mg).

(Step 3) Preparation of 1-{4-[2-(4-{2-[(2,3-dihydro-1H-inden-2-yl)amino]pyrimidin-5-yl}-3-ethyl-1H-pyrazol-1-yl)acetyl]piperazin-1-yl}-2-hydroxyethan-1-one (Compound 94)

To a solution of glycolic acid (67 mg, 0.88 mmol) and the compound 94-b (255 mg, 0.44 mmol) in N,N-dimethylformamide (5 mL) was slowly added N,N-diisopropylethylamine (0.38 mL, 2.20 mmol) and benzotriazol-1-yl oxy-tripyrrolidinophosphonium hexafluorophosphate (343 mg, 0.66 mmol) in order at 0° C., and the reaction mixture was stirred for 3 hours at room temperature under nitrogen atmosphere. Upon the completion of the reaction, the mixture was diluted with distilled water (50 mL) and extracted with ethyl acetate. The organic layer was washed with distilled water and saturated brine, dried over anhydrous sodium sulfate, and concentrated. The residue was purified by silica gel column chromatography (methanol:methylene chloride=6:94) to obtain the title compound 94 as a white solid (123 mg, 57%).

MS m/z: 490 [M+1]$^+$ $^1$H NMR (CDCl$_3$, 400 MHz) δ 8.31 (s, 2H), 7.50 (s, 1H), 7.15-7.25 (m, 4H), 5.36 (d, 1H), 4.98 (s, 2H), 4.82 (m, 1H), 4.20 (s, 2H), 3.69 (m, 6H), 3.50 (br, 1H), 3.42 (dd, 2H), 3.30 (t, 2H), 2.91 (dd, 2H), 2.70 (m, 2H), 1.23 (t, 3H)

Examples 14 to 33

According to the methods of the above Examples 1 to 13, the compounds 95 to 114 of the following Table 1 were prepared. Structures of the compounds 1 to 114 that are prepared in Examples 1 to 33 are shown in the following Table 1.

TABLE 1

| Example | Compound No. | A | L | Q | X | Y | R |
|---|---|---|---|---|---|---|---|
| 1-1 | 1 | triazolo-tetrahydropyridine | -C(O)CH₂CH₂NH- | C(O) | CH | N | indanyl |
| 1-2 | 2 | triazolo-tetrahydropyridine | -C(O)CH₂CH₂NH- | C(O) | CH | N | 3-(OCF₃)benzyl |
| 1-3 | 3 | triazolo-tetrahydropyridine | -CH₂C(O)NH- | C(O) | CH | N | 3-(OCF₃)benzyl |
| 1-4 | 4 | triazolo-tetrahydropyridine | -CH(–)C(O)NH- | C(O) | CH | N | 3-(OCF₃)benzyl |
| 1-5 | 5 | HOOC-(CH₂)₃-NH- | Single bond | C(O) | CH | N | 3-(OCF₃)benzyl |
| 1-6 | 6 | triazolo-tetrahydropyridine | propyl-piperazinyl | C(O) | CH | N | 3-(OCF₃)benzyl |
| 1-7 | 7 | carboxy-oxa-azaspiro isoxazoline | Single bond | C(O) | CH | N | 3-(OCF₃)benzyl |
| 1-8 | 8 | triazolo-tetrahydropyridine | oxa-azaspiro isoxazoline linker | C(O) | CH | N | 3-(OCF₃)benzyl |
| 1-9 | 9 | benzotriazolyl | N-methyl diazaspiro dione piperidinyl | C(O) | CH | N | 3-(OCF₃)benzyl |

TABLE 1-continued

| Example | Compound No. | A | L | Q | X | Y | R |
|---|---|---|---|---|---|---|---|
| 1-10 | 10 | benzoxazol-2(3H)-one-6-yl | (S)-5-(aminomethyl)oxazolidin-2-one-3-yl | C=O | CH | N | 3-(trifluoromethoxy)benzyl |
| 1-11 | 11 | 3-carboxyphenyl | (S)-5-(aminomethyl)oxazolidin-2-one-3-yl | C=O | CH | N | 3-(trifluoromethoxy)benzyl |
| 2-1 | 12 | 4,5,6,7-tetrahydro-1H-[1,2,3]triazolo[4,5-c]pyridin-5-yl | propan-2-one-1,3-diyl | piperazin-1,4-diyl | CH | N | indan-2-yl |
| 2-2 | 13 | 4,5,6,7-tetrahydro-1H-[1,2,3]triazolo[4,5-c]pyridin-5-yl | propan-2-one-1,3-diyl | piperazin-1,4-diyl | CH | N | 3-(trifluoromethoxy)benzyl |
| 2-3 | 14 | 4,5,6,7-tetrahydro-1H-[1,2,3]triazolo[4,5-c]pyridin-5-yl | propan-2-one-1,3-diyl | piperidin-1,4-diyl | CH | N | indan-2-yl |
| 2-4 | 15 | 4-sulfamoylpiperazin-1-yl | propan-2-one-1,3-diyl | piperazin-1,4-diyl | CH | N | indan-2-yl |
| 2-5 | 16 | benzoxazol-2(3H)-one-6-yl | propan-2-one-1,3-diyl | piperidin-1,4-diyl | CH | N | indan-2-yl |
| 3-1 | 17 | 4,5,6,7-tetrahydro-1H-[1,2,3]triazolo[4,5-c]pyridin-5-yl | ethan-1-one-1,2-diyl | piperazin-1,4-diyl | CH | N | indan-2-yl |
| 3-2 | 18 | 4,5,6,7-tetrahydro-1H-[1,2,3]triazolo[4,5-c]pyridin-5-yl | ethan-1-one-1,2-diyl | piperazin-1,4-diyl | CH | N | 3-(trifluoromethoxy)benzyl |

TABLE 1-continued

| Example | Compound No. | A | L | Q | X | Y | R |
|---|---|---|---|---|---|---|---|
| 3-3 | 19 | 4,5,6,7-tetrahydro-triazolo-pyridine | -CH2-C(CH3)2-C(O)- | piperazine | CH | N | indan-2-yl |
| 4-1 | 20 | 4,5,6,7-tetrahydro-triazolo-pyridine | -CH2-C(O)-CH2- | piperazine | CH | N | indan-2-yl |
| 4-2 | 21 | 4,5,6,7-tetrahydro-triazolo-pyridine | -CH2-C(O)-CH2- | piperazine | CH | N | 3-(OCF3)benzyl |
| 4-3 | 22 | 4,5,6,7-tetrahydro-triazolo-pyridine | -CH2-C(O)-CH2- | piperidine | CH | N | indan-2-yl |
| 4-4 | 23 | 4,5,6,7-tetrahydro-triazolo-pyridine | -C(O)-CH2CH2- | piperazine | CH | N | indan-2-yl |
| 4-5 | 24 | 3-hydroxypyrrolidine | -CH2-C(O)-CH2- | piperazine | CH | N | 3-(OCF3)benzyl |
| 4-6 | 25 | 4-carboxypiperidine | -CH2-C(O)-CH2- | piperazine | CH | N | 3-(OCF3)benzyl |
| 5-1 | 26 | 2-oxo-2,3-dihydro-benzoxazol-6-yl | oxazolidin-2-one | piperazine | CH | N | indan-2-yl |
| 5-2 | 27 | 2-oxo-2,3-dihydro-benzoxazol-6-yl | -NH-C(O)-CH2- | piperazine | CH | N | indan-2-yl |
| 5-3 | 28 | 2-oxo-2,3-dihydro-benzoxazol-6-yl | -CH2-C(O)-CH2- | piperazine | CH | N | indan-2-yl |

TABLE 1-continued

| Example | Compound No. | A | L | Q | X | Y | R |
|---|---|---|---|---|---|---|---|
| 5-4 | 29 | benzoxazolone | =N-OH ketoxime | piperazine | CH | N | indanyl |
| 5-5 | 30 | benzoxazolone | =N-OH ketoxime (longer) | piperazine | CH | N | indanyl |
| 5-6 | 31 | benzoxazolone | isoxazoline | piperazine | CH | N | indanyl |
| 5-7 | 32 | benzoxazolone | -C(O)NH-CH2- | piperazine | CH | N | indanyl |
| 6-1 | 33 | triazolo-tetrahydropyridine | -CH2C(O)CH2- | 1,3,4-oxadiazole | CH | N | indanyl |
| 6-2 | 34 | triazolo-tetrahydropyridine | -CH2C(O)CH2- | 1,3,4-oxadiazole | CH | N | 3-(OCF3)benzyl |
| 6-3 | 35 | triazolo-tetrahydropyridine | -CH2C(O)CH2- | 1,3,4-oxadiazole | CH | N | 3-Cl-phenyl-cyclohexyl |
| 6-4 | 36 | triazolo-tetrahydropyridine | -CH2C(O)CH2- | 1,3,4-oxadiazole | CH | CH | indanyl |
| 6-5 | 37 | imidazo-tetrahydropyridine | -CH2C(O)CH2- | 1,3,4-oxadiazole | CH | N | indanyl |
| 6-6 | 38 | imidazo-tetrahydropyridine | -CH2C(O)CH2- | 1,3,4-oxadiazole | CH | N | indanyl |

TABLE 1-continued

| Example | Compound No. | A | L | Q | X | Y | R |
|---|---|---|---|---|---|---|---|
| 6-7 | 39 | 5,6,7,8-tetrahydro-1,6-naphthyridin-2(1H)-one | -C(=O)CH2- | 1,3,4-oxadiazole | CH | N | indan-2-yl |
| 6-8 | 40 | 2-oxo-2,3,4,5,6,7-hexahydro-1H-imidazo[4,5-c]pyridine | -C(=O)CH2- | 1,3,4-oxadiazole | CH | N | indan-2-yl |
| 6-9 | 41 | 5,6,7,8-tetrahydro-[1,2,4]triazolo[4,3-a]pyrazine | -C(=O)CH2- | 1,3,4-oxadiazole | CH | N | indan-2-yl |
| 6-10 | 42 | 4,5,6,7-tetrahydro-2H-pyrazolo[3,4-c]pyridine | -C(=O)CH2- | 1,3,4-oxadiazole | CH | N | indan-2-yl |
| 6-11 | 43 | 2-amino-4,5,6,7-tetrahydrothiazolo[5,4-c]pyridine | -C(=O)CH2- | 1,3,4-oxadiazole | CH | N | indan-2-yl |
| 6-12 | 44 | 4,5,6,7-tetrahydro-1H-pyrazolo[4,3-c]pyridine | -C(=O)CH2- | 1,3,4-oxadiazole | CH | N | indan-2-yl |
| 6-12 | 45 | 4,5,6,7-tetrahydro-1H-pyrazolo[3,4-b]pyridine | -C(=O)CH2- | 1,3,4-oxadiazole | CH | N | indan-2-yl |
| 6-13 | 46 | 3-(sulfamoylamino)pyrrolidine | -C(=O)CH2- | 1,3,4-oxadiazole | CH | N | indan-2-yl |
| 6-14 | 47 | 3-(sulfamoylamino)pyrrolidine | -C(=O)CH2- | 1,3,4-oxadiazole | CH | N | indan-2-yl |
| 6-15 | 48 | 1,2,3,6-tetrahydropyridine-4-carboxylic acid | -C(=O)CH2- | 1,3,4-oxadiazole | CH | N | indan-2-yl |
| 6-16 | 49 | 1,2,3,6-tetrahydropyridine-4-carboxamide | -C(=O)CH2- | 1,3,4-oxadiazole | CH | N | indan-2-yl |

TABLE 1-continued
| Example | Compound No. | A | L | Q | X | Y | R |
|---|---|---|---|---|---|---|---|
| 6-17 | 50 | 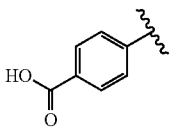 [SMILES: *c1ccc(C(=O)O)cc1] | 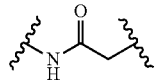 | 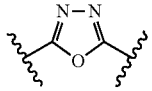 | CH | N | 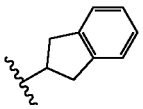 [SMILES: *C1Cc2ccccc2C1] |
| 7-1 | 51 | 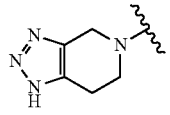 | 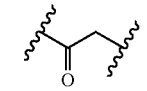 | 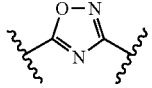 [SMILES: *c1noc(*)n1] | CH | N | 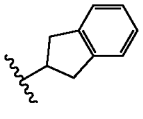 [SMILES: *C1Cc2ccccc2C1] |
| 7-2 | 52 | 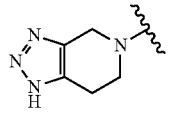 | 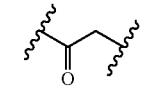 [SMILES: *CC(*)=O] | 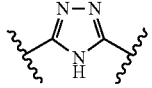 [SMILES: *c1nnc(*)[nH]1] | CH | N | 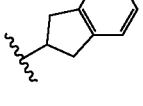 |
| 7-3 | 53 | 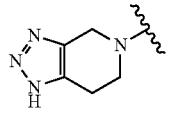 | 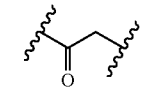 | 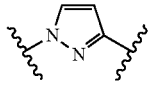 | CH | N | 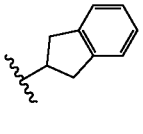 [SMILES: *C1Cc2ccccc2C1] |
| 7-4 | 54 | 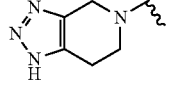 | 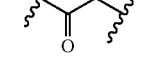 | 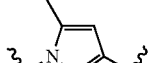 | CH | N | 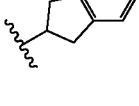 |
| 7-5 | 55 | 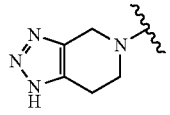 | 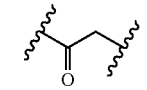 [SMILES: *CC(*)=O] | 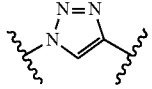 | CH | N | 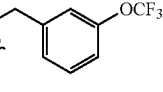 |
| 8-1 | 56 | 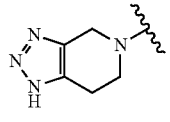 | 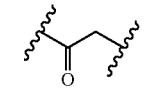 [SMILES: *CC(*)=O] | 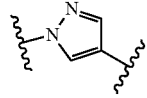 | CH | N | 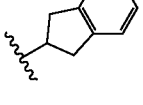 |
| 8-2 | 57 | 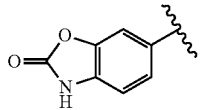 [SMILES: *c1ccc2[nH]c(=O)oc2c1] | 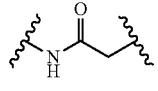 | 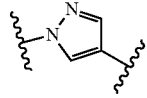 | CH | N | 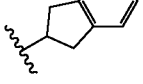 |
| 8-3 | 58 | 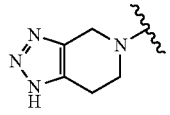 | 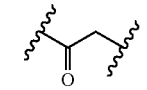 [SMILES: *CC(*)=O] | 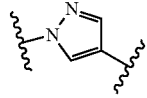 | CH | CH | 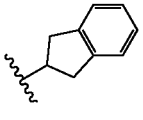 [SMILES: *C1Cc2ccccc2C1] |
| 8-4 | 59 | 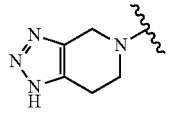 | 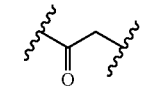 [SMILES: *CC(*)=O] | 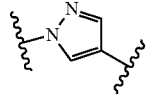 | N | CH | 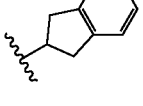 |

TABLE 1-continued

| Example | Compound No. | A | L | Q | X | Y | R |
|---|---|---|---|---|---|---|---|
| 9 | 60 | triazolo-tetrahydropyridine | C(=O)CH2 | imidazole | CH | N | indanyl |
| 10-1 | 61 | triazolo-tetrahydropyridine | C(=O)CH2 | pyrazole-OEt | CH | N | indanyl |
| 10-2 | 62 | triazolo-tetrahydropyridine | C(=O)CH2 | pyrazole-O-azetidine-NH | CH | N | indanyl |
| 10-3 | 63 | triazolo-tetrahydropyridine | C(=O)CH2 | pyrazole-OBn | CH | N | indanyl |
| 10-4 | 64 | morpholine | C(=O)CH2 | pyrazole-OBn | CH | N | indanyl |
| 10-5 | 65 | triazolo-tetrahydropyridine | C(=O)CH2 | pyrazole-OH | CH | N | indanyl |
| 10-6 | 66 | triazolo-tetrahydropyridine | C(=O)CH2 | pyrazole-OCH2CH2-morpholine | CH | N | indanyl |
| 10-7 | 67 | triazolo-tetrahydropyridine | C(=O)CH2 | pyrazole-OCH2CH2-piperazine | CH | N | indanyl |
| 10-8 | 68 | triazolo-tetrahydropyridine | C(=O)CH2 | pyrazole-O-azetidine-Et | CH | N | indanyl |
| 10-9 | 69 | triazolo-tetrahydropyridine | C(=O)CH2 | pyrazole-O-piperidine-NH | CH | N | indanyl |

TABLE 1-continued
| Example | Compound No. | A | L | Q | X | Y | R |
|---|---|---|---|---|---|---|---|
| 10-10 | 70 | 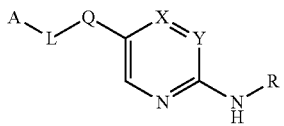 | 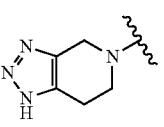 | 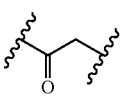 [SMILES: *CC(*)=O] | CH | N | 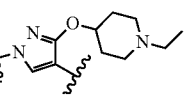 |
| 10-11 | 71 | 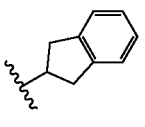 | 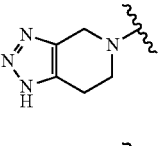 | 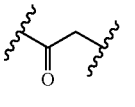 [SMILES: *CC(*)=O] | CH | N | 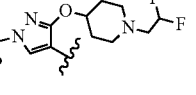 |
| 10-12 | 72 | 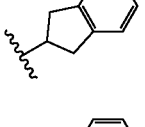 | 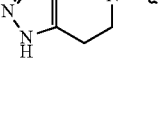 | 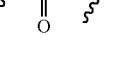 | CH | N | 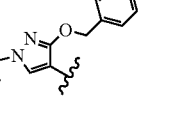 |
| 10-13 | 73 | 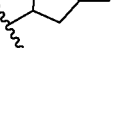 | 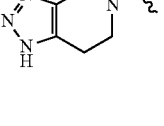 | 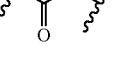 | CH | N | 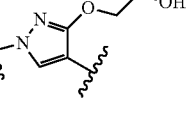 |
| 10-14 | 74 | 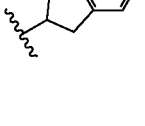 | 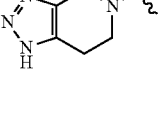 | 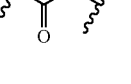 | CH | N | 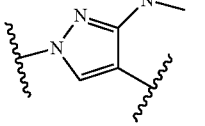 |
| 10-15 | 75 | 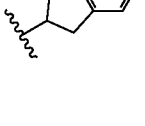 | 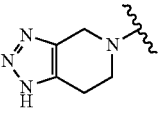 | 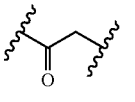 | CH | N | 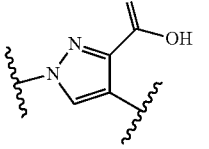 |
| 10-16 | 76 | 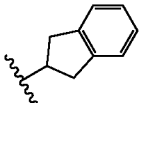 [SMILES: *C1Cc2ccccc2C1] | 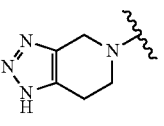 | 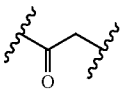 | CH | N | 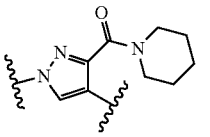 [SMILES: *c1cn(*)nc1C(=O)N1CCCCC1] |
| 10-17 | 77 | 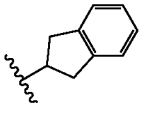 [SMILES: *C1Cc2ccccc2C1] | 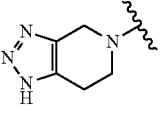 | 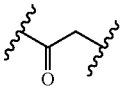 [SMILES: *CC(*)=O] | CH | N | 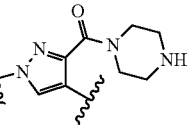 |
| 11-1 | 78 | 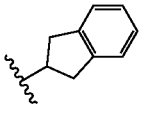 [SMILES: *C1Cc2ccccc2C1] | 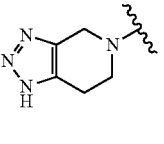 | 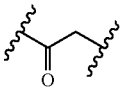 | CH | N | 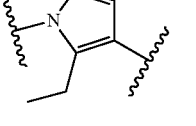 |

TABLE 1-continued

| Example | Compound No. | A | L | Q | X | Y | R |
|---|---|---|---|---|---|---|---|
| 11-2 | 79 | triazole-tetrahydropyridine | C(=O)CH2 | ethyl-pyrazole | CH | N | indanyl |
| 12-1 | 80 | triazole-tetrahydropyridine | C(=O)CH2 | pyrazole-CH2-morpholine | CH | N | indanyl |
| 12-2 | 81 | triazole-tetrahydropyridine | C(=O)CH2 | pyrazole-CH2-piperidine | CH | N | indanyl |
| 12-3 | 82 | triazole-tetrahydropyridine | C(=O)CH2 | pyrazole-CH2-(3-oxopiperazine) | CH | N | indanyl |
| 12-4 | 83 | triazole-tetrahydropyridine | C(=O)CH2 | pyrazole-CH2-indoline | CH | N | indanyl |
| 12-5 | 84 | triazole-tetrahydropyridine | C(=O)CH2 | pyrazole-CH2-tetrahydroisoquinoline | CH | N | indanyl |
| 12-6 | 85 | triazole-tetrahydropyridine | C(=O)CH2 | pyrazole-CH2-(4,4-difluoropiperidine) | CH | N | indanyl |
| 12-7 | 86 | triazole-tetrahydropyridine | C(=O)CH2 | pyrazole-CH2-(4-phenylpiperidine) | CH | N | indanyl |
| 12-8 | 87 | triazole-tetrahydropyridine | C(=O)CH2 | pyrazole-CH2-(4-methyl-3-oxopiperazine) | CH | N | indanyl |
| 12-9 | 88 | triazole-tetrahydropyridine | C(=O)CH2 | pyrazole-CH2-(2-oxopiperazine) | CH | N | indanyl |

TABLE 1-continued
| Example | Compound No. | A | L | Q | X | Y | R |
|---|---|---|---|---|---|---|---|
| 12-10 | 89 | 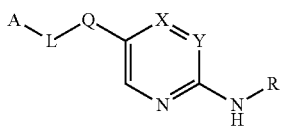 | 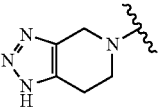 | 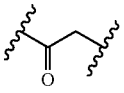 [SMILES: *CC(*)=O] | CH | N | 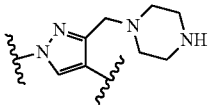 [SMILES: *c1cn(*)nc1CN1CCNCC1] |
| 12-11 | 90 | 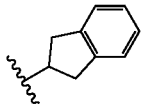 [SMILES: *C1Cc2ccccc2C1] | 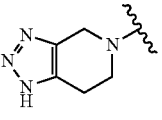 | 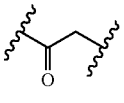 [SMILES: *CC(*)=O] | CH | N | 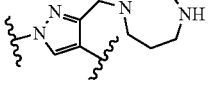 |
| 12-12 | 91 | 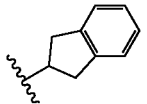 [SMILES: *C1Cc2ccccc2C1] | 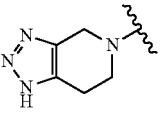 | 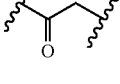 | CH | N | 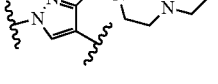 |
| 12-13 | 92 | 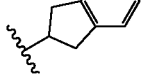 | 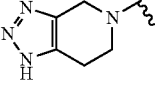 | 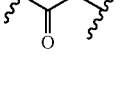 | CH | N | 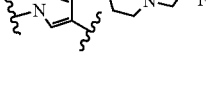 |
| 12-14 | 93 | 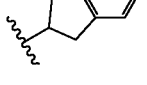 | 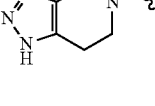 | 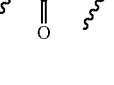 | CH | N | 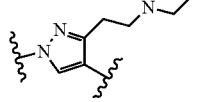 |
| 13 | 94 | 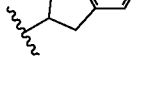 | 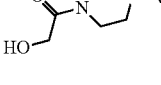 | 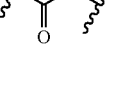 | CH | N | 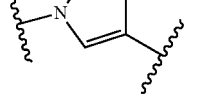 |
| 14 | 95 | 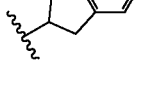 | 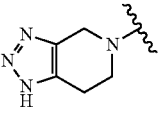 | 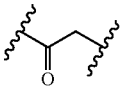 [SMILES: *CC(*)=O] | CH | N | 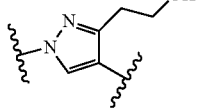 |
| 15 | 96 | 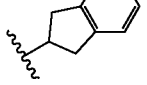 | 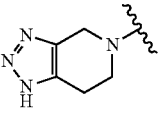 | 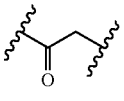 [SMILES: *CC(*)=O] | CH | N | 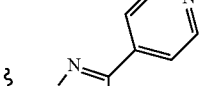 |
| 16 | 97 | 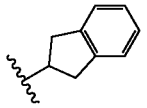 [SMILES: *C1Cc2ccccc2C1] | 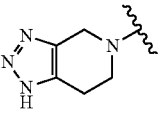 | 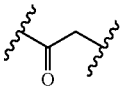 [SMILES: *CC(*)=O] | CH | N | 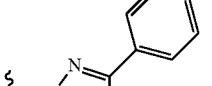 |

TABLE 1-continued

| Example | Compound No. | A | L | Q | X | Y | R |
|---|---|---|---|---|---|---|---|
| 17 | 98 | triazolo-tetrahydropyridine | -C(O)CH2- | pyrazole-piperidine(NH) | CH | N | indanyl |
| 18 | 99 | triazolo-tetrahydropyridine | -C(O)CH2- | pyrazole-cyclohexyl-NH2 | CH | N | indanyl |
| 19 | 100 | triazolo-tetrahydropyridine | -C(O)CH2- | pyrazole-NH-cyclobutyl | CH | N | indanyl |
| 20 | 101 | triazolo-tetrahydropyridine | -C(O)CH2- | pyrazole-NH-pyridyl | CH | N | indanyl |
| 21 | 102 | triazolo-tetrahydropyridine | -C(O)CH2- | pyrazole-NH-thiazolyl | CH | N | indanyl |
| 22 | 103 | triazolo-tetrahydropyridine | -C(O)CH2- | pyrazole-morpholinyl | CH | N | indanyl |

TABLE 1-continued

| Example | Compound No. | A | L | Q | X | Y | R |
|---|---|---|---|---|---|---|---|
| 23 | 104 | triazole-tetrahydropyridine | -C(=O)CH₂- | pyrazole-pyrrolidine | CH | N | indanyl |
| 24 | 105 | triazole-tetrahydropyridine | -C(=O)CH₂- | pyrazole-piperazine-C(=O)CH₂OH | CH | N | indanyl |
| 25 | 106 | triazole-tetrahydropyridine | -C(=O)CH₂- | pyrazole-N(Et)₂ | CH | N | indanyl |
| 26 | 107 | triazole-tetrahydropyridine | -C(=O)CH₂- | 2-methylimidazole | CH | N | indanyl |
| 27 | 108 | triazole-tetrahydropyridine | -C(=O)CH₂- | 2-ethylimidazole | CH | N | indanyl |
| 28 | 109 | triazole-tetrahydropyridine | -C(=O)CH₂- | 2-cyclopropylimidazole | CH | N | indanyl |
| 29 | 110 | triazole-tetrahydropyridine | -C(=O)CH₂- | 2-phenylimidazole | CH | N | indanyl |

TABLE 1-continued

| Example | Compound No. | A | L | Q | X | Y | R |
|---|---|---|---|---|---|---|---|
| 30 | 111 | triazolopyridine | C(=O)CH2 | N-methyl imidazole | CH | N | indanyl |
| 31 | 112 | triazolopyridine | C(=O)CH2 | N-ethyl imidazole | CH | N | indanyl |
| 32 | 113 | triazolopyridine | C(=O)CH2 | N-cyclopropyl imidazole | CH | N | indanyl |
| 33 | 114 | triazolopyridine | C(=O)CH2 | N-phenyl imidazole | CH | N | indanyl |

[Example 15] Preparation of 2-(4-{2-[(2,3-dihydro-1H-inden-2-yl)amino]pyrimidin-5-yl}-3-(pyridin-4-yl)-1H-pyrazol-1-yl)-1-{1H,4H,5H,6H-7H-[1,2,3]triazolo[4,5-c]pyridin-5-yl}ethan-1-one (Compound 96)

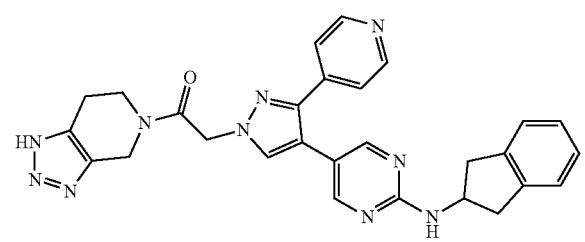

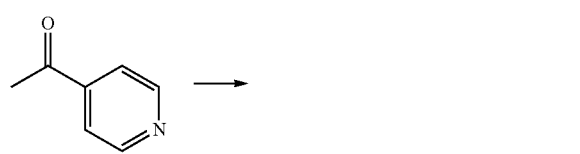

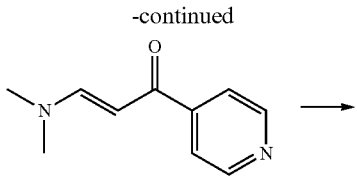

-continued

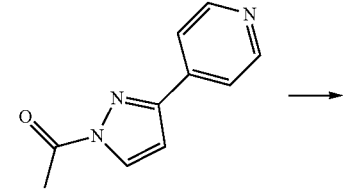

217
-continued

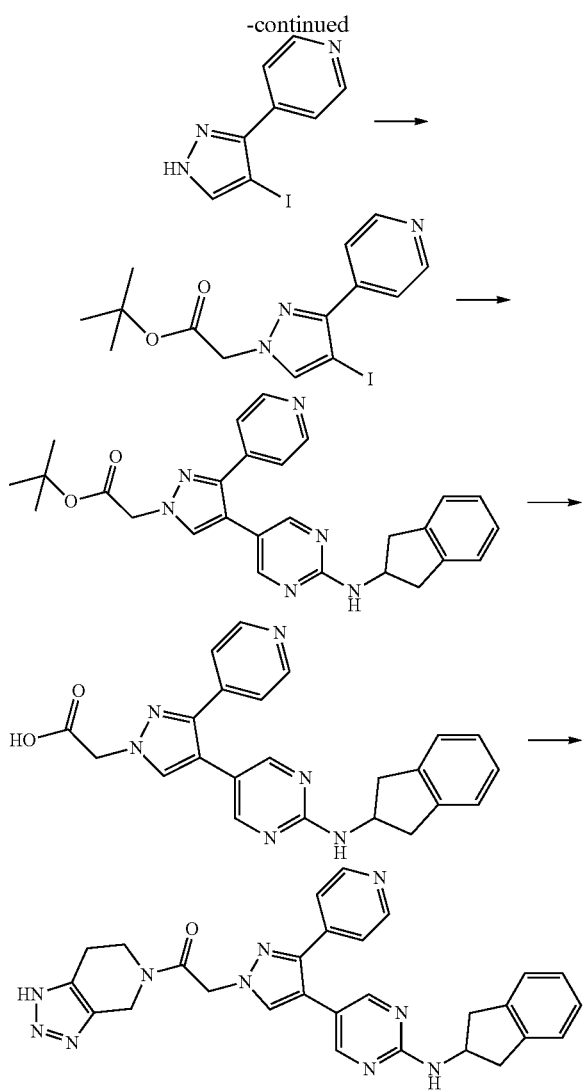

(Step 1) Preparation of 4-(1H-Pyrazol-3-yl)pyridine

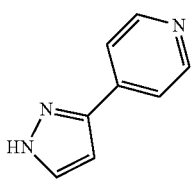

A mixture of 4-acetylpyridine (3 mL, 27 mmol) and DMF-DMA (6 mL, 45.15 mmol) was stirred at 110° C. for 2 h. After completion, the reaction mixture was cooled to room temperature and concentrated under reduced pressure. The remained residue was dissolved in ethanol (12 mL) and hydrazine hydrate (1.6 mL, 32.40 mmol) was added thereto. The reaction mixture was stirred at reflux for 15 h. After completion, the reaction mixture was cooled to room temperature and the solvent was removed under reduced pressure. The residue was diluted with dichloromethane (20 mL) and washed with water. The organic layer was dried over

218 anhydrous sodium sulfate, filtered, and concentrated under reduced pressure to afford the title compound as yellow solid (3.66 g, 93 in 2 steps).

MS m/z: 272 [M+1]$^+$.

$^1$H NMR (DMSO-d6, 400 MHz), δ ppm: 13.18 (bs, 1H), 8.57 (d, 2H), 7.87 (s, 1H), 7.78 (d, 2H), 6.91 (s, 1H)

(Step 2) Preparation of 1-[3-(Pyridin-4-yl)-1H-pyrazol-1-yl]ethan-1-one

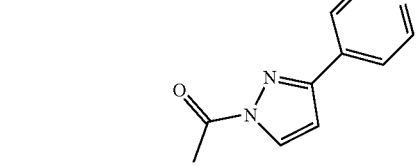

To a solution of 4-(1H-pyrazol-3-yl)pyridine (2.0 g, 13.78 mmol) in pyridine (10 mL) was added slowly acetic anhydride (1.56 mL, 16.53 mmol) which was dissolved in pyridine (5 mL), and the reaction mixture was stirred at room temperature for 4 h. After completion, the solvent was removed under reduced pressure. The remained residue was diluted with water (50 mL) and extracted with ethyl acetate. The organic layer was washed with brine, dried over anhydrous sodium sulfate, filtered, and concentrated under reduced pressure. The resulting residue was purified by column chromatography (40% ethyl acetate/n-hexane) to afford the title compound as white solid (2.02 g, 78%).

MS m/z: 188 [M+1]$^+$.

1H NMR (CDCl$_3$, 400 MHz), δ ppm: 8.71 (d, 2H), 8.34 (d, 1H), 7.76 (d, 2H), 6.84 (d, 1H), 2.79 (s, 3H).

(Step 3) Preparation of 4-(4-Iodo-1H-pyrazol-3-yl)pyridine

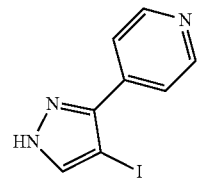 [SMILES: Ic1c[nH]nc1-c1ccncc1]

To a solution of 1-[3-(pyridin-4-yl)-1H-pyrazol-1-yl] ethan-1-one (1 g, 5.34 mmol) in a mixed solvent of ethanol/water (1/2, 15 mL) were added sodium iodide (0.88 g, 5.87 mmol), idodine (2.03 g, 8.01 mmol), potassium carbonate (2.94 g, 21.24 mmol) successively, and the reaction mixture was stirred at room temperature for 1.5 h. After completion, the reaction mixture was diluted with ethyl acetate and washed with saturated sodium thiosulfate aqueous solution. The organic layer was dried over anhydrous sodium sulfate, filtered, and concentrated under reduced pressure. The residue was triturated with dichloromethane to afford the title compound as light orange solid (1.17 g, 81%)

MS m/z: 272 [M+1]$^+$.

1H NMR (CDCl3, 400 MHz), δ ppm: 13.62 (bs, 1H), 8.66 (bs, 2H), 7.84 (bs, 2H)

(Step 4) Preparation of Tert-butyl 2-[4-iodo-3-(pyridin-4-yl)-1H-pyrazol-1-yl]acetate

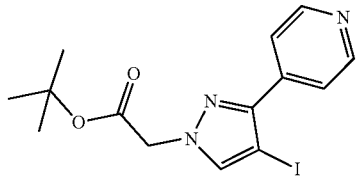 [SMILES: CC(C)(C)OC(=O)Cn1cc(I)c(-c2ccncc2)n1]

To a solution of 4-(4-iodo-1H-pyrazol-3-yl)pyridine (1.17 g, 4.32 mmol) in DMF (10 mL) were added cesium carbonate (2.1 g, 6.48 mmol) and tert-butyl bromoacetate (0.76 mL, 5.18 mmol) successively, and the reaction mixture was stirred at room temperature for 15 h. After completion, the reaction mixture was diluted with water (30 mL) and extracted with ethyl acetate. The organic layer was washed with brine, dried over anhydrous sodium sulfate, filtered, and concentrated under reduced pressure. The resulting residue was purified by column chromatography (30% ethyl acetate/n-hexane) to afford the title compound as orange oil (1.39 g, 83%).

MS m/z: 386 [M+1]$^+$.

$^1$H NMR (CDCl$_3$, 400 MHz), δ ppm: 8.67 (d, 2H), 7.84 (d, 2H), 7.65 (s, 1H), 4.86 (s, 2H), 1.50 (s, 9H)

(Step 5) Preparation of Tert-butyl 2-(4-{2-[(2,3-dihydro-1H-inden-2-yl)amino]pyrimidin-5-yl}-3-(pyridin-4-yl)-1H-pyrazol-1-yl)acetate

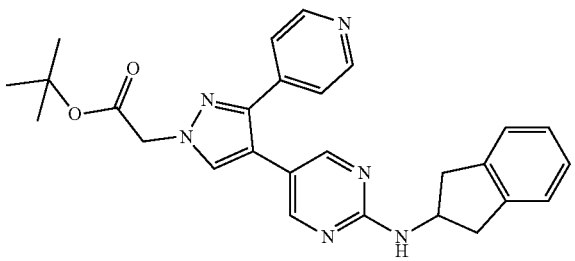 [SMILES: CC(C)(C)OC(=O)Cn1cc(-c2cnc(NC3Cc4ccccc4C3)nc2)c(-c2ccncc2)n1]

A mixture of tert-butyl 2-[4-iodo-3-(pyridin-4-yl)-1H-pyrazol-1-yl]acetate (0.50 g, 1.30 mmol), the compound im-2a (0.48 g, 1.43 mmol), tetrakis(triphenylphosphin)palladium(0) (150 mg, 0.13 mmol), 2N sodium carbonate solution (2 mL, 4.0 mmol) was dissolved in 1.4-dioxane (10 mL) and stirred at 100° C. for 6 h under nitrogen atmosphere. After completion, the reaction mixture was cooled to room temperature and water (50 mL) was added thereto, and then extracted with ethyl acetate (50 mL×3). The organic layer was washed with brine, dried over anhydrous sodium sulfate, filtered, and concentrated under reduced pressure. The resulting residue was purified by column chromatography (80% ethyl acetate/n-hexane) to afford the title compound as yellow oil (486 mg, 76%).

MS m/z: 469 [M+1]$^+$.

$^1$H NMR (CDCl$_3$, 400 MHz), δ ppm: 8.58 (d, 2H), 8.22 (s, 2H), 7.57 (s, 1H), 7.45 (d, 2H), 7.17-7.24 (m, 4H), 5.46 (d, 1H), 4.90 (s, 2H), 4.82 (m, 1H), 3.42 (dd, 2H), 2.91 (dd, 2H), 1.52 (s, 9H)

(Step 6) Preparation of 2-(4-{2-[(2,3-Dihydro-1H-inden-2-yl)amino]pyrimidin-5-yl}-3-(pyridin-4-yl)-1H-pyrazol-1-yl) Acetic Acid

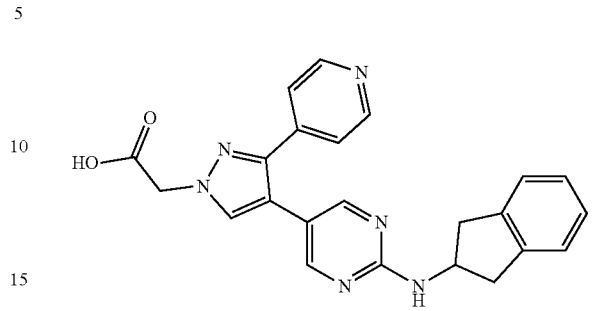

To a solution of tert-butyl 2-(4-{2-[(2,3-dihydro-1H-inden-2-yl)amino]pyrimidin-5-yl}-3-(pyridin-4-yl)-1H-pyrazol-1-yl)acetate (0.46 g, 1.00 mmol) in dichloromethane (2 mL) was added trifluoroacetic acid (6 mL), and the reaction mixture was stirred at room temperature for 3 h. After completion, the solvent was removed under reduced pressure to afford the title compound quantitatively as yellow solid (456 mg, 69%), which was used for the next step without further purification.

MS m/z: 413 [M+1]$^+$.

1H NMR (DMSO-d6, 400 MHz), δ ppm: 13.34 (bs, 1H), 8.71 (d, 2H), 8.26 (bs, 2H), 8.08 (s, 1H), 7.77 (d, 2H), 7.73 (d, 1H), 7.16-7.24 (m, 4H), 5.13 (s, 2H), 4.64 (m, 1H), 3.26 (dd, 2H), 2.93 (dd, 2H)

(Step 7) Preparation of 2-(4-{2-[(2,3-dihydro-1H-inden-2-yl)amino]pyrimidin-5-yl}-3-(pyridin-4-yl)-1H-pyrazol-1-yl)-1-{1H,4H,5H,6H,7H-[1,2,3]triazolo[4,5-c]pyridin-5-yl}ethan-1-one To an ice-cooled solution of 2-(4-{2-[(2,3-dihydro-1H-inden-2-yl)amino]pyrimidin-5-yl}-3-(pyridin-4-yl)-1H-pyrazol-1-yl)acetic acid (100 mg, 0.24 mmol) and the compound im-7 (58 mg, 0.36 mmol) in DMF (3 mL) were added DIPEA (0.21 mL, 1.20 mmol) and PyBOP (187 mg, 0.36 mmol), and the mixture was stirred at room temperature for 15 h under nitrogen atmosphere. After completion, water (50 mL) was added to the reaction mixture and it was extracted with ethyl acetate (50 mL×3). The organic layer was washed with brine, dried over anhydrous sodium sulfate, filtered, and concentrated under reduced pressure. The resulting residue was purified by column chromatography (5% methanol/dichloromethane) to afford the title compound as beige solid (71 mg, 57%)

MS m/z: 519 [M+1]$^+$.

1H NMR (DMSO-d6, 400 MHz), δ ppm: 8.55 (d, 1H), 8.20 (s, 2H), 7.94 (d, 1H), 7.62 (d, 1H), 7.41 (t, 2H), 7.11-7.25 (m, 4H), 5.41 (d, 2H), 4.75 (d, 2H), 4.61 (m, 1H), 3.81-3.85 (m, 2H), 3.26 (dd, 2H), 2.72-2.96 (m, 4H).

[Example 17] Preparation of 2-(4-{2-[(2,3-dihydro-1H-inden-2-yl)amino]pyrimidin-5-yl}-3-(piperidin-4-yl)-1H-pyrazol-1-yl)-1-{1H,4H,5H,6H,7H-[1,2,3]triazolo[4,5-c]pyridin-5-yl}ethan-1-one (Compound 98)

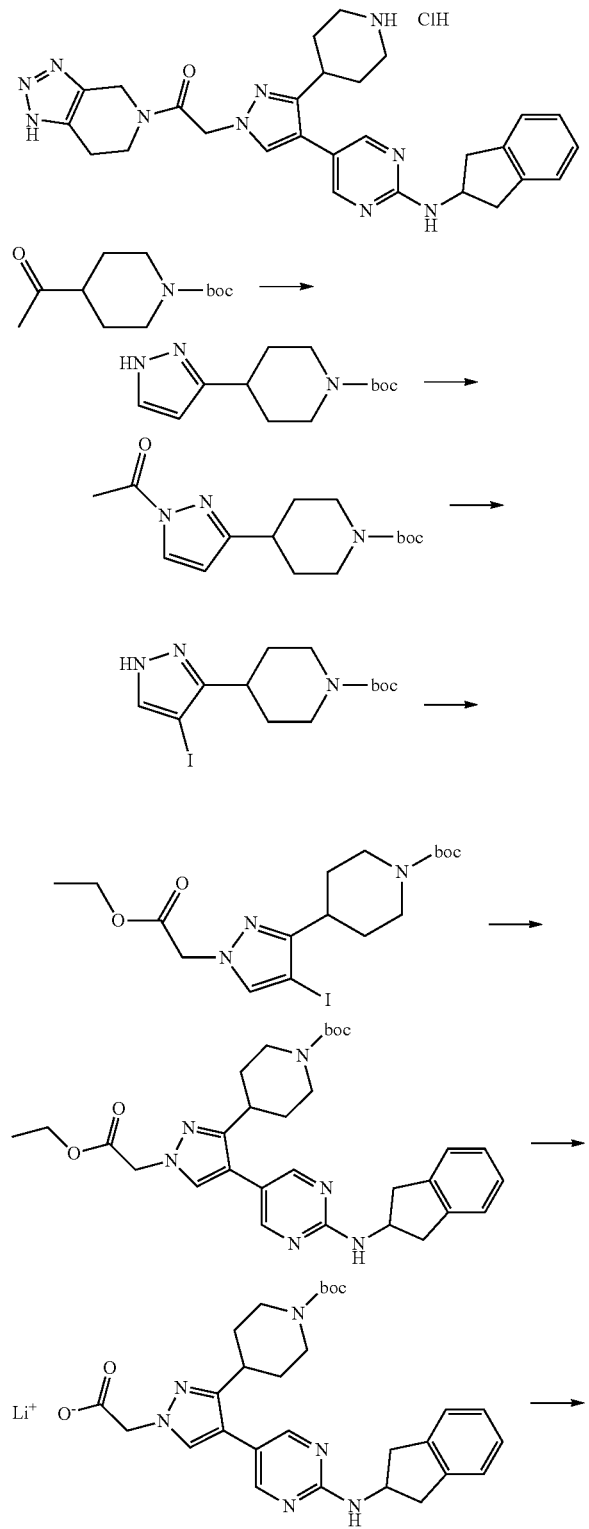

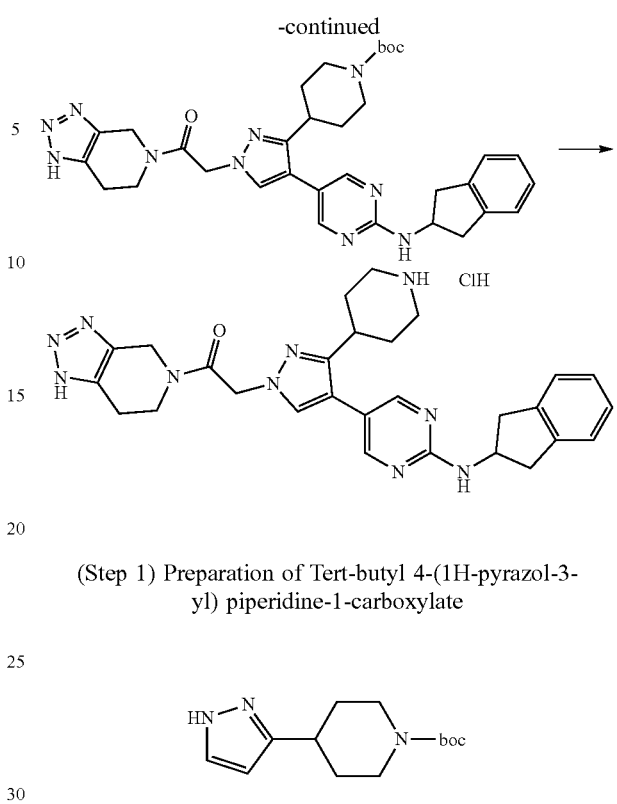

(Step 1) Preparation of Tert-butyl 4-(1H-pyrazol-3-yl) piperidine-1-carboxylate

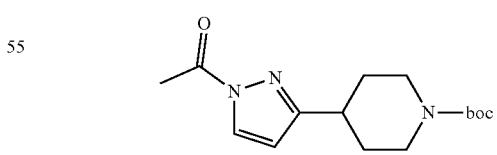

A mixture of tert-butyl 4-acetylpiperidine-1-carboxylate (Prepared according to the known procedure (Bioorganic & Medicinal Chemistry Letters, 21(5), 1299-1305; 2011)) (3.7 g, 16.277 mmol) and DMF-DMA (10 mL) was stirred at 140° C. for 48 h. After completion, the reaction mixture was cooled to room temperature and concentrated under reduced pressure. The remained residue was dissolved in ethanol (12 mL) and hydrazine hydrate (1.2 mL, 24.42 mmol) was added thereto. The reaction mixture was stirred at reflux for 18 h. After completion, the reaction mixture was cooled to room temperature and the solvent was removed under reduced pressure to afford the title compound quantitatively as brown oil (4.4 g).

MS m/z: 252 [M+1]$^+$.

1H NMR (CDCl3, 400 MHz), δ ppm: 7.50 (d, 1H), 6.12 (d, 1H), 4.02-4.24 (m, 2H), 2.76-2.92 (m, 3H), 1.90-2.01 (m, 2H), 1.58-1.68 (m, 2H), 1.47 (s, 9H)

(Step 2) Preparation of Tert-butyl 4-(1-acetyl-1H-pyrazol-3-yl)piperidine-1-carboxylate To a solution of tert-butyl 4-(1H-pyrazol-3-yl)piperidine-1-carboxylate (4.4 g, 16.28 mmol) in pyridine (10 mL) was added slowly acetic anhydride (2.3 mL, 24.42 mmol) which was dissolved in pyridine (10 mL), and the reaction mixture was stirred at room temperature for 15 h. After completion, the solvent was removed under reduced pressure. The remained residue was diluted with water (50 mL) and extracted with ethyl acetate. The organic layer was washed with brine, dried over anhydrous sodium sulfate, filtered, and concentrated under reduced pressure. The resulting residue was purified by column chromatography (20% ethyl acetate/n=hexane) to afford the title compound as white solid (4.5 g, 94%).

MS m/z: 294 [M+1]$^+$.

1H NMR (CDCl3, 400 MHz), δ ppm: 8.16 (d, 1H), 6.28 (d, 1H), 4.08-4.25 (m, 2H), 2.79-2.94 (m, 3H), 2.66 (s, 3H), 1.90-1.98 (m, 2H), 1.59-1.70 (m, 2H), 1.48 (s, 9H).

(Step 3) Preparation of Tert-butyl 4-(4-iodo-1H-pyrazol-3-yl)piperidine-1-carboxylate

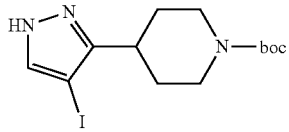

To a solution of tert-butyl 4-(1-acetyl-1H-pyrazol-3-yl)piperidine-1-carboxylate (1 g, 3.41 mmol) in a mixed solvent of ethanol/water (1/2, 15 mL) were added sodium iodide (0.56 g, 3.75 mmol), iodine (1.3 g, 5.11 mmol), potassium carbonate (1.9 g, 13.63 mmol) successively, and the reaction mixture was stirred at room temperature for 2 h. After completion, the reaction mixture was diluted with ethyl acetate and washed with saturated sodium thiosulfate aqueous solution. The organic layer was dried over anhydrous sodium sulfate, filtered, and concentrated under reduced pressure to afford the title compound quantitatively as yellow solid (1.42 g).

MS m/z: 378 [M+1]$^+$.

1H NMR (CDCl3, 400 MHz), δ ppm: 10.52 (bs, 1H), 7.55 (s, 1H), 4.12-4.34 (m, 2H), 2.78-2.92 (m, 3H), 1.86-1.94 (m, 2H), 1.62-1.75 (m, 2H), 1.48 (s, 9H)

(Step 4) Preparation of Tert-butyl 4-[1-(2-ethoxy-2-oxoethyl)-4-iodo-1H-pyrazol-3-yl]piperidine-1-carboxylate

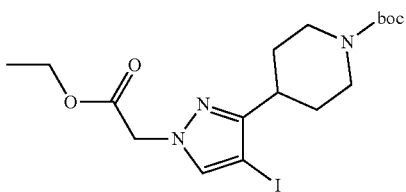

To a solution of tert-butyl 4-(4-iodo-1H-pyrazol-3-yl)piperidine-1-carboxylate (1.42 g, 3.41 mmol) in DMF (15 mL) were added cesium carbonate (1.67 g, 5.11 mmol) and ethyl bromoacetate (0.49 mL, 4.43 mmol) successively, and the reaction mixture was stirred at room temperature for 2 h. After completion, the reaction mixture was diluted with water (50 mL) and extracted with ethyl acetate. The organic layer was washed with brine, dried over anhydrous sodium sulfate, filtered, and concentrated under reduced pressure. The resulting residue was purified by column chromatography (30% ethyl acetate/n-hexane) to afford the title compound as yellow oil (1.3 g, 83%).

MS m/z: 464 [M+1]$^+$.

$^1$H NMR (CDCl3, 400 MHz), δ ppm: 7.46 (s, 1H), 4.83 (s, 2H), 4.09-4.28 (m, 4H), 2.72-2.94 (m, 3H), 1.82-1.92 (m, 2H), 1.65-1.79 (m, 2H), 1.46 (s, 9H), 1.28 (t, 3H)

(Step 5) Preparation of Tert-butyl 4-(4-{2-[(2,3-dihydro-1H-inden-2-yl)amino]pyrimidin-5-yl}-1-(2-ethoxy-2-oxoethyl)-1H-pyrazol-3-yl)piperidine-1-carboxylate

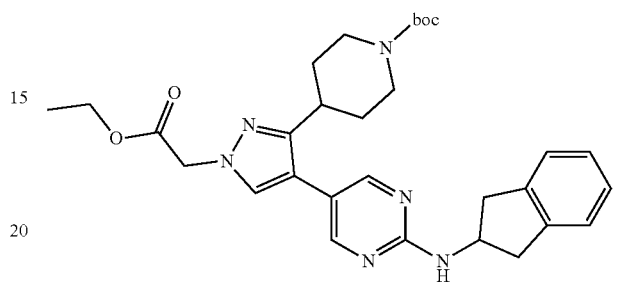

A mixture of tert-butyl 4-[1-(2-ethoxy-2-oxoethyl)-4-iodo-1H-pyrazol-3-yl]piperidine-1-carboxylate (0.40 g, 0.86 mmol), the compound im-2a (0.32 g, 0.95 mmol), tetrakis(triphenylphosphin)palladium(0) (100 mg, 0.086 mmol), 2N sodium carbonate solution (1.3 mL, 2.6 mmol) was dissolved in 1.4-dioxane (7 mL) and stirred at 100° C. for 1 h under nitrogen atmosphere. After completion, the reaction mixture was cooled to room temperature and water (50 mL) was added thereto, and then extracted with ethyl acetate (50 mL×3). The organic layer was washed with brine, dried over anhydrous sodium sulfate, filtered, and concentrated under reduced pressure. The resulting residue was purified by column chromatography (30% ethyl acetate/n-hexane) to afford the title compound as yellow solid (253 mg, 54%).

MS m/z: 547 [M+1]$^+$.

1H NMR (CDCl3, 400 MHz), δ ppm: 8.28 (s, 2H), 7.42 (s, 1H), 7.14-7.24 (m, 4H), 5.41 (d, 1H), 4.87 (s, 2H), 4.82 (m, 1H), 4.08-4.30 (m, 4H), 3.43 (dd, 2H), 2.92 (dd, 2H), 2.68-2.86 (m, 3H), 1.69-1.84 (m, 4H), 1.45 (s, 9H), 1.30 (t, 3H)

(Step 6) Preparation of 2-(3-{1-[(tert-butoxy)carbonyl]piperidin-4-yl}-4-{2-[(2,3-dihydro-1H-inden-2-yl)amino] pyrimidin-5-yl}-1H-pyrazol-1-yl)acetic Acid Lithium Salt

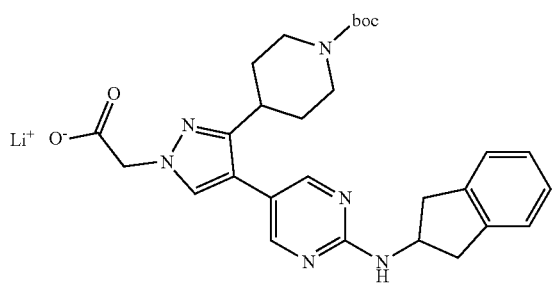

To a solution of tert-butyl 4-(4-{2-[(2,3-dihydro-1H-inden-2-yl)amino]pyrimidin-5-yl}-1-(2-ethoxy-2-oxoethyl)-1H-pyrazol-3-yl)piperidine-1-carboxylate (0.253 g, 0.46 mmol) in THF (3 mL) was added 1N lithium hydroxide aqueous solution (0.9 mL, 0.9 mmol), and the reaction mixture was stirred at room temperature for 1.5 h. After completion, the solvent was removed under reduced pressure to afford the title compound quantitatively as yellow solid (255 mg), which was used for the next step without further purification.

MS m/z: 519 [M+1]$^+$.

(Step 7) Tert-butyl 4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)piperidine-1-carboxylate

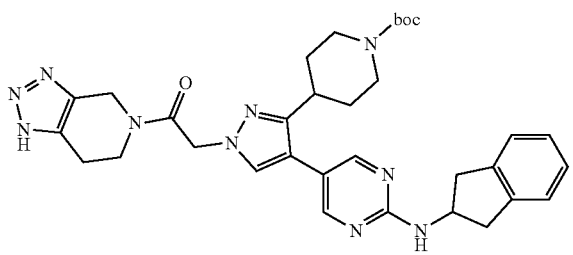

To an ice-cooled solution of 2-(3-{1-[(tert-butoxy)carbonyl]piperidin-4-yl}-4-{2-[(2,3-dihydro-1H-inden-2-yl)amino]pyrimidin-5-yl}-1H-pyrazol-1-yl)acetic acid lithium salt (255 mg, 0.46 mmol) and the compound im-7 (89 mg, 0.55 mmol) in DMF (5 mL) were added DIPEA (0.24 mL, 1.38 mmol) and PyBOP (359 mg, 0.69 mmol), and the mixture was stirred at room temperature for 15 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (3% methanol/dichloromethane) to afford the title compound as white solid (258 mg, 90%)

MS m/z: 625 [M+1]$^+$.

$^1$H NMR (CDCl$_3$, 400 MHz), δ ppm: 13.34 (bs, 1H), 8.24 (s, 2H), 7.47 (d, 1H), 7.14-7.25 (m, 4H), 5.61 (t, 1H), 4.61-5.14 (m, 5H), 3.81-4.24 (m, 4H), 3.41 (dd, 2H), 2.92 (dd, 2H), 2.61-2.86 (m, 5H), 1.60-1.86 (m, 4H), 1.41-1.51 (m, 9H)

(Step 8) Preparation of 2-(4-{2-[(2,3-Dihydro-1H-inden-2-yl)amino]pyrimidin-5-yl}-3-(piperidin-4-yl)-1H-pyrazol-1-yl)-1-{1H,4H,5H,6H,7H-[1,2,3]triazolo[4,5-c]pyridin-5-yl}ethan-1-one To a solution of tert-butyl 4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)piperidine-1-carboxylate (258 mg, 0.41 mmol) in dichloromethane (3 mL) was added 4N HCl in dioxane solution, and the reaction mixture was stirred at room temperature for 3 h. After completion, the solvent was removed under reduced pressure to afford the title compound as ivory solid (142 mg, 62%)

MS m/z: 525 [M+1]$^+$.

1H NMR (DMSO-d6, 400 MHz), δ ppm: 8.71-9.32 (m, 2H), 8.45 (s, 2H), 8.11 (bs, 1H), 7.83 (d, 1H), 7.12-7.26 (m, 4H), 5.26 (d, 2H), 4.63-4.79 (m, 3H), 3.76-3.86 (m, 2H), 3.21-3.34 (m, 4H), 2.91-3.14 (m, 5H), 2.71-2.86 (m, 2H), 1.79-1.98 (m, 4H).

[Example 18] Preparation of 2-[3-(4-aminocyclohexyl)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one (Compound 99)

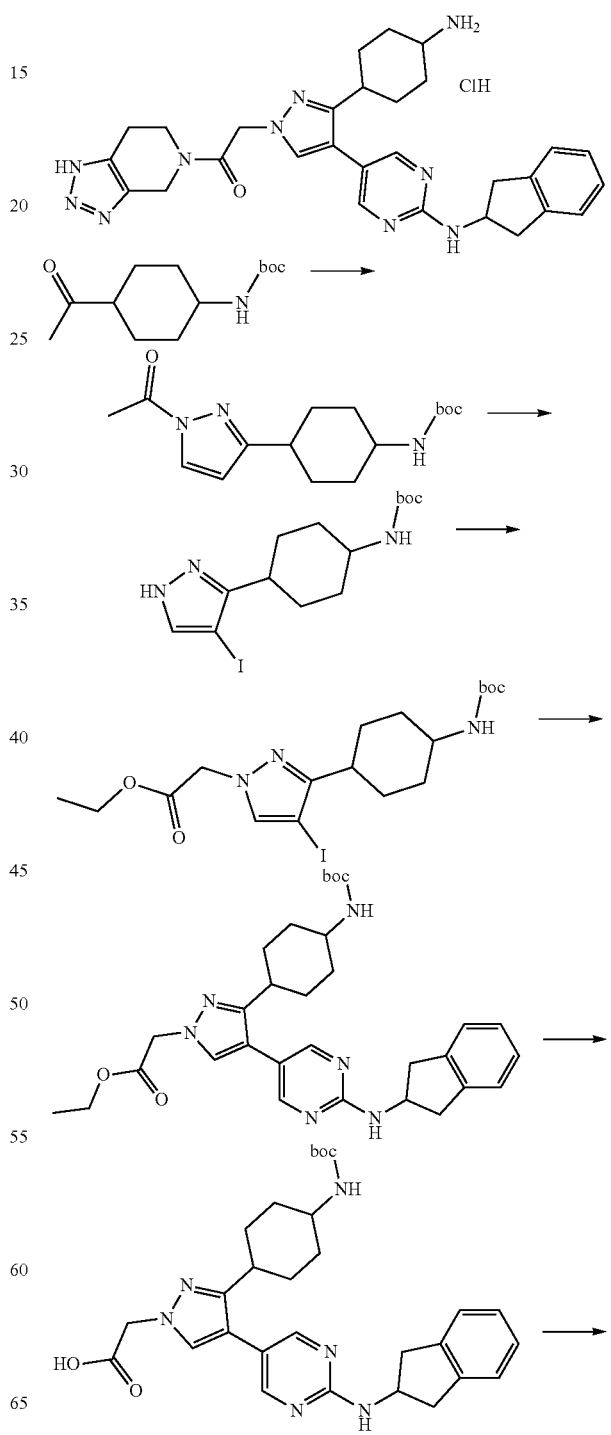

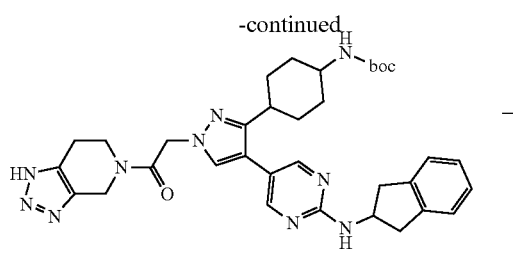

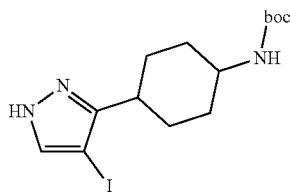

(Step 2) Preparation of Tert-butyl N-[4-(4-iodo-1H-pyrazol-3-yl)cyclohexyl]carbamate

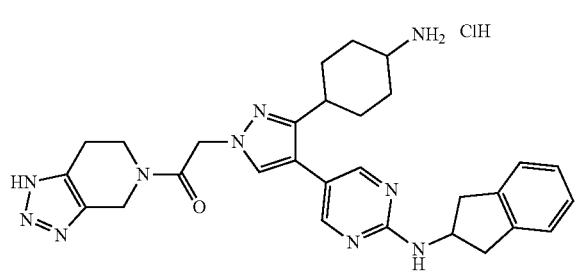

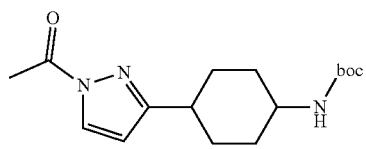

(Step 1) Preparation of Tert-butyl N-[4-(1-acetyl-1H-pyrazol-3-yl)cyclohexyl]carbamate A mixture of tert-butyl N-(4-acetylcyclohexyl)carbamate (Prepared according to the known procedure (WO 2012018668)) (1.20 g, 4.99 mmol) and DMF-DMA (3 mL) was stirred at 110° C. for 26 h. After completion, the reaction mixture was cooled to room temperature and concentrated under reduced pressure. The remained residue was dissolved in ethanol (10 mL) and hydrazine hydrate (0.36 mL, 7.48 mmol) was added thereto. The reaction mixture was stirred at reflux for 4 h. After completion, the reaction mixture was cooled to room temperature and the solvent was removed under reduced pressure. The resulting residue was dissolved in pyridine (3 mL), and acetic anhydride (0.7 mL, 7.48 mmol) was added slowly thereto. The reaction mixture was stirred at room temperature for 3 h. After completion, the solvent was removed under reduced pressure. The remained residue was diluted with water (50 mL) and extracted with ethyl acetate. The organic layer was washed with brine, dried over anhydrous sodium sulfate, filtered, and concentrated under reduced pressure. The resulting residue was further purified by column chromatography (30% ethyl acetate/n-hexane) to afford the title compound as white solid (628 mg, 40% in 3 steps), of which NMR spectra was unable to be assigned due to complexity.

MS m/z: 308 [M+1]$^+$.

To a solution of tert-butyl N-[4-(1-acetyl-1H-pyrazol-3-yl)cyclohexyl]carbamate (628 mg, 2.04 mmol) in a mixed solvent of ethanol/water (1/1, 8 mL) were added sodium iodide (337 mg, 2.25 mmol), iodine (778 mg, 3.07 mmol), potassium carbonate (1.1 g, 8.17 mmol) successively, and the reaction mixture was stirred at room temperature for 3 h. After completion, the reaction mixture was diluted with ethyl acetate and washed with saturated sodium thiosulfate aqueous solution. The organic layer was dried over anhydrous sodium sulfate, filtered, and concentrated under reduced pressure to afford the title compound quantitatively as yellow oil (814 mg), which was used without further purification.

MS m/z: 392 [M+1]$^+$.

(Step 3) Preparation of Ethyl 2-[3-(4-{[(tert-butoxy)carbonyl]amino}cyclohexyl)-4-iodo-1H-pyrazol-1-yl]acetate

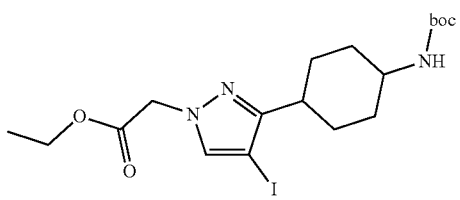

To a solution of tert-butyl N-[4-(4-iodo-1H-pyrazol-3-yl)cyclohexyl]carbamate (814 mg, 2.04 mmol) in DMF (5 mL) were added cesium carbonate (1.0 g, 3.12 mmol) and ethyl bromoacetate (0.25 mL, 2.29 mmol) successively, and the reaction mixture was stirred at room temperature overnight. After completion, the reaction mixture was diluted with water (30 mL) and extracted with ethyl acetate. The organic layer was washed with brine, dried over anhydrous sodium sulfate, filtered, and concentrated under reduced pressure. The resulting residue was purified by column chromatography (30% ethyl acetate/n-hexane) to afford the title compound as yellow oil (488 mg, 50%), of which NMR spectra was unable to be assigned due to complexity.

MS m/z: 478 [M+1]$^+$.

(Step 4) Preparation of Ethyl 2-[3-(4-{[(tert-butoxy)carbonyl]amino}cyclohexyl)-4-{2-[(2,3-dihydro-1H-inden-2-yl)amino]pyrimidin-5-yl}-1H-pyrazol-1-yl]acetate

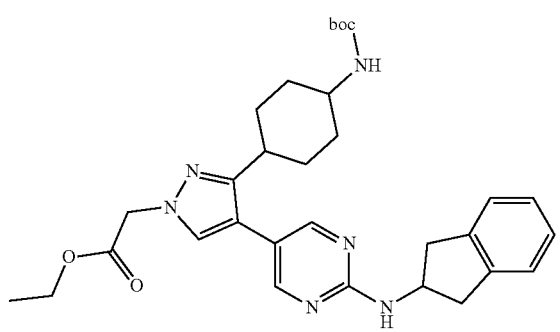

A mixture of ethyl 2-[3-(4-{[(tert-butoxy)carbonyl]amino}cyclohexyl)-4-iodo-1H-pyrazol-1-yl]acetate (271 mg, 0.57 mmol), the compound im-2a (249 mg, 0.74 mmol), tetrakis(triphenylphosphin)palladium(0) (66 mg, 0.057 mmol), 2N sodium carbonate solution (0.85 mL, 1.7 mmol) was dissolved in 1.4-dioxane (3 mL) and stirred at 80° C. for 1 h under nitrogen atmosphere. After completion, the reaction mixture was cooled to room temperature and water (50 mL) was added thereto, and then extracted with ethyl acetate (50 mL×3). The organic layer was washed with brine, dried over anhydrous sodium sulfate, filtered, and concentrated under reduced pressure. The resulting residue was purified by column chromatography (40% ethyl acetate/n-hexane) to afford the title compound as white solid (20 mg, 6%).

MS m/z: 562 [M+1]$^+$.

1HNMR (CDCl3, 400 MHz), δ ppm: 8.39 (s, 1H), 8.26 (s, 2H), 7.41 (s, 1H), 7.19 (m, 4H), 5.55 (d, 1H), 4.84 (m, 4H), 4.27 (m, 2H), 3.84 (s, 1H), 3.42 (dd, 2H), 2.88 (dd, 2H), 1.69 (m, 9H), 1.44 (s, 9H)

(Step 5) Preparation of 2-[3-(4-{[(Tert-butoxy)carbonyl]amino}cyclohexyl)-4-{²-[(2,3-dihydro-1H-inden-2-yl)amino]pyrimidin-5-yl}-1H-pyrazol-1-yl]acetic

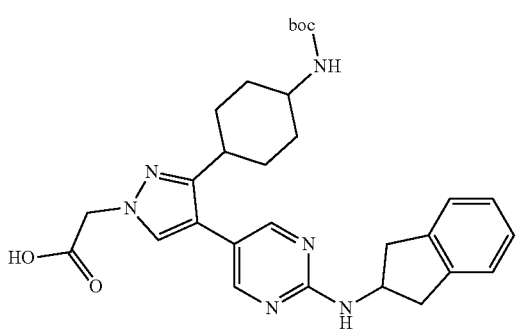

To a solution of ethyl 2-[3-(4-{[(tert-butoxy)carbonyl]amino}cyclohexyl)-4-{²-[(2,3-dihydro-1H-inden-2-yl)amino]pyrimidin-5-yl}-1H-pyrazol-1-yl]acetate (40 mg, 0.072 mmol) in THF (1 mL) was added 1N lithium hydroxide aqueous solution (0.2 mL, 0.2 mmol), and the reaction mixture was stirred at room temperature for 2 h.

After completion, the solvent was removed under reduced pressure to afford the title compound quantitatively as yellow solid (34 mg, 88%), which was used for the next step without further purification.

MS m/z: 533 [M+1]$^+$.

1HNMR (DMSO-d6, 400 MHz), δ ppm: 8.65 (s, 1H), 8.35 (s, 2H), 7.81 (m, 2H), 7.18 (m, 4H), 6.72 (s, 1H), 4.89 (s, 2H), 4.65 (m, 1H), 3.25 (dd, 2H), 2.88 (dd, 2H), 2.50 (s, 1H), 1.75 (m, 4H), 1.48 (m, 4H), 1.38 (s, 9H)

(Step 6) Preparation of tert-butyl N-[4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)cyclohexyl]carbamate

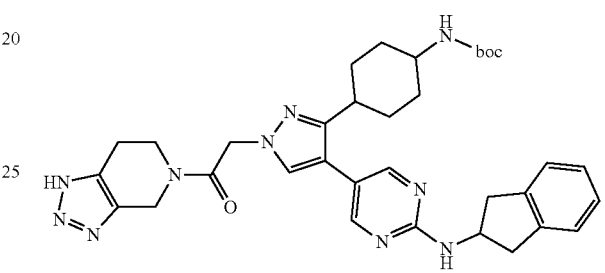

To an ice-cooled solution of 2-[3-(4-{[(tert-butoxy)carbonyl]amino}cyclohexyl)-4-{2-[(2,3-dihydro-1H-inden-2-yl)amino]pyrimidin-5-yl}-1H-pyrazol-1-yl]acetic acid (34 mg, 0.064 mmol) and the compound im-7 (15 mg, 0.095 mmol) in DMF (1 mL) were added DIPEA (0.04 mL, 0.256 mmol) and PyBOP (49 mg, 0.095 mmol), and the mixture was stirred at room temperature for 4 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (3% methanol/dichloromethane) to afford the title compound as white solid (22 mg, 54%).

MS m/z: 639 [M+1]$^+$.

1HNMR (DMSO-d6, 400 MHz), δ ppm: 8.28 (s, 2H), 7.72 (m, 1H), 7.46 (d, 1H), 7.15 (m, 4H), 6.65 (s, 1H), 5.20 (m, 2H), 4.64 (m, 4H), 3.83 (m, 2H), 3.39 (m, 1H), 3.25 (m, 2H), 3.00 (m, 1H), 2.90 (dd, 2H), 2.80 (m, 2H), 1.76 (m, 4H), 1.47 (m, 4H), 1.37 (s, 9H)

(Step 7) Preparation of 2-[3-(4-aminocyclohexyl)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one To a solution of tert-butyl N-[4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)cyclohexyl]carbamate (22 mg, 0.034 mmol) in dichloromethane (1 mL) was added 4N HCl in dioxane solution, and the reaction mixture was stirred at room temperature for 2 h. After completion, the solvent was removed under reduced pressure to afford the title compound as ivory solid (18.6 mg, 94%).

MS m/z: 539 [M+1]$^+$.

1HNMR (DMSO-d6, 400 MHz), δ ppm: 8.37 (s, 2H), 7.80 (m, 5H), 7.19 (m, 4H), 5.75 (s, 1H), 5.22 (m, 2H), 4.70 (m, 3H), 3.82 (m, 2H), 3.27 (m, 3H), 2.90 (m, 5H), 1.76 (m, 8H)

[Example 19] Preparation of 2-[3-(cyclobutylamino)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one (Compound 100)

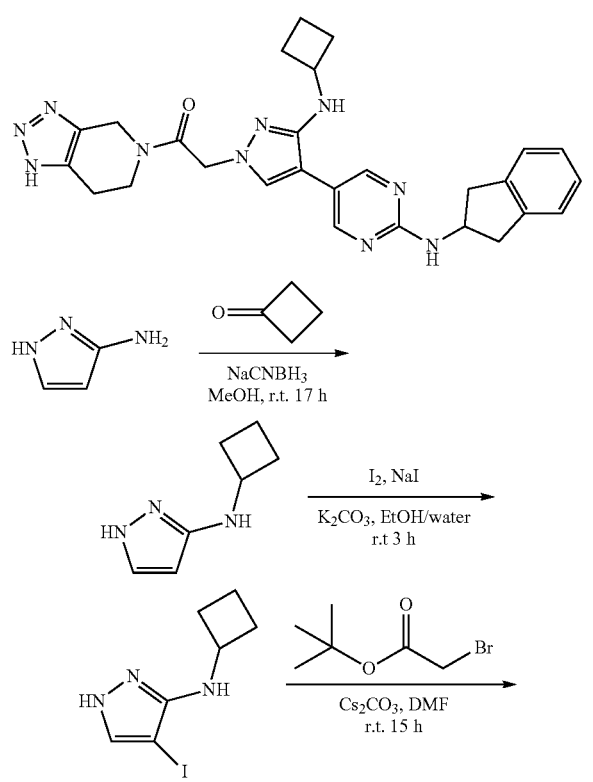

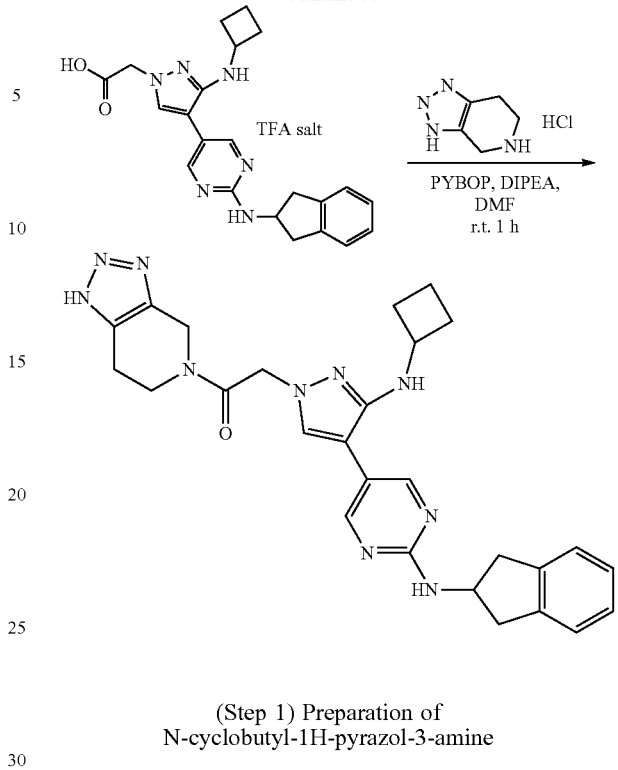

(Step 1) Preparation of N-cyclobutyl-1H-pyrazol-3-amine

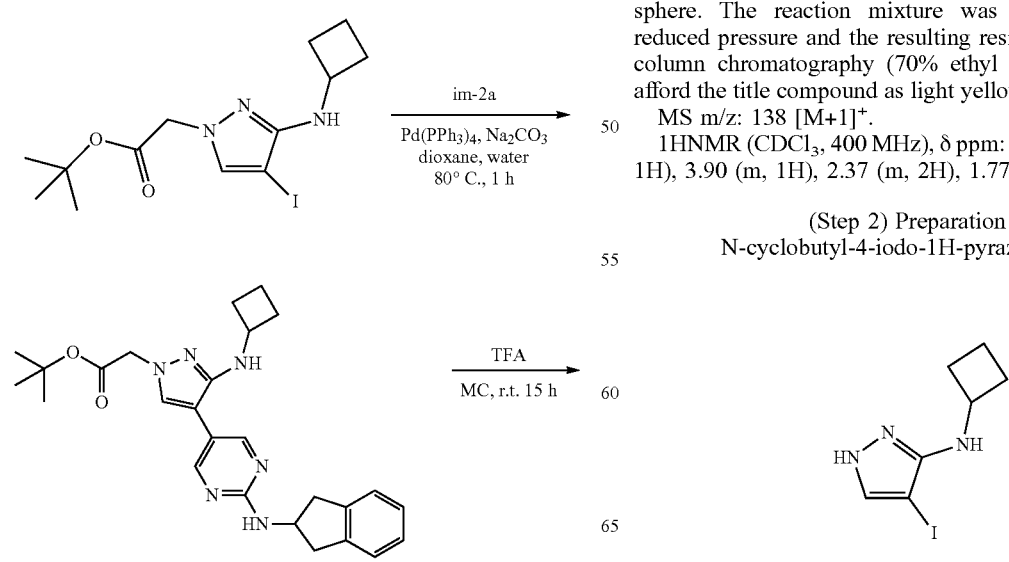

To an ice-cooled solution of 3-aminopyrazole (1.0 g, 12.04 mmol) in methanol (20 mL) were added cyclobutanone (0.99 mL, 13.24 mmol) and sodium cyanoborohydride (1.5 g, 24.07 mmol), and the reaction mixture was stirred at room temperature for 18 h under nitrogen atmosphere. The reaction mixture was concentrated under reduced pressure and the resulting residue was purified by column chromatography (70% ethyl acetate/n-hexane) to afford the title compound as light yellow oil (320 mg, 19%)

MS m/z: 138 [M+1]$^+$.

1HNMR (CDCl$_3$, 400 MHz), δ ppm: 7.32 (d, 1H), 8.59 (d, 1H), 3.90 (m, 1H), 2.37 (m, 2H), 1.77 (m, 4H)

(Step 2) Preparation of N-cyclobutyl-4-iodo-1H-pyrazol-3-amine

To a solution of N-cyclobutyl-1H-pyrazol-3-amine (320 mg, 2.33 mmol) in a mixed solvent of ethanol/water (1/1, 10 mL) were added sodium iodide (384 mg, 2.56 mmol), iodine (887 mg, 3.5 mmol), potassium carbonate (1.3 g, 9.32 mmol) successively, and the reaction mixture was stirred at room temperature for 3 h. After completion, the reaction mixture was diluted with ethyl acetate and washed with saturated sodium thiosulfate aqueous solution. The organic layer was dried over anhydrous sodium sulfate, filtered, and concentrated under reduced pressure. The residue was purified by column chromatography (30% ethyl acetate/n-hexne) to afford the title compound as brown oil (70 mg, 11%).

MS m/z: 264 [M+1]$^+$.

1HNMR (CDCl$_3$, 400 MHz), δ ppm: 10.24 (s, 1H), 7.48 (s, 1H), 4.00 (s, 1H), 2.80 (m, 2H0, 2.43 (m, 2H), 2.21 (m, 2H)

(Step 3) Preparation of tert-butyl 2-[3-(cyclobutylamino)-4-iodo-1H-pyrazol-1-yl]acetate

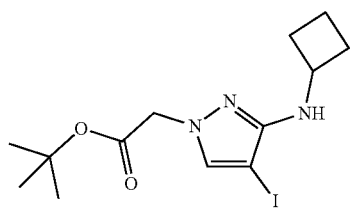 [SMILES: CC(C)(C)OC(=O)Cn1cc(I)c(NC2CCC2)n1]

To a solution of N-cyclobutyl-4-iodo-1H-pyrazol-3-amine (70 mg, 0.27 mmol) in DMF (1 mL) were added cesium carbonate (130 mg, 0.40 mmol) and tert-butyl bromoacetate (0.04 mL, 0.27 mmol) successively, and the reaction mixture was stirred at room temperature for 15 h. After completion, the reaction mixture was diluted with water (30 mL) and extracted with ethyl acetate. The organic layer was washed with brine, dried over anhydrous sodium sulfate, filtered, and concentrated under reduced pressure. The resulting residue was purified by column chromatography (15% ethyl acetate/n-hexne) to afford the title compound as light brown oil (53 mg, 52%).

MS m/z: 378 [M+1]$^+$.

1H NMR (CDCl$_3$, 400 MHz), δ ppm: 7.25 (d, 1H), 4.54 (s, 2H), 4.12 (m, 1H), 3.62 (d, 1H), 2.40 (m, 2H), 1.85 (m, 2H), 1.69 (m, 2H), 1.45 (s, 9H)

(Step 4) Preparation of tert-butyl 2-[3-(cyclobutylamino)-4-{2-[(2,3-dihydro-1H-inden-2-yl)amino]pyrimidin-5-yl}-1H-pyrazol-1-yl]acetate

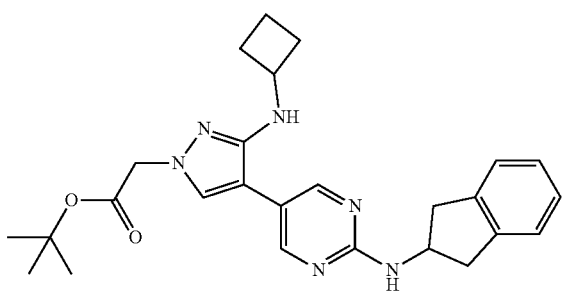 [SMILES: CC(C)(C)OC(=O)Cn1cc(-c2cnc(NC3Cc4ccccc4C3)nc2)c(NC2CCC2)n1]

A mixture of tert-butyl 2-[3-(cyclobutylamino)-4-iodo-1H-pyrazol-1-yl]acetate (53 mg, 0.14 mmol), the compound im-2a (61 mg, 0.18 mmol), tetrakis(triphenylphosphin)palladium(0) (16 mg, 0.014 mmol), 2N sodium carbonate solution (0.21 mL, 0.42 mmol) was dissolved in 1.4-dioxane (2 mL) and stirred at 80° C. for 1 h under nitrogen atmosphere. After completion, the reaction mixture was cooled to room temperature and water (10 mL) was added thereto, and then extracted with ethyl acetate (20 mL×3). The organic layer was washed with brine, dried over anhydrous sodium sulfate, filtered, and concentrated under reduced pressure. The resulting residue was passed through silica pad (40% ethyl acetate/n-hexane) to afford a crude mixture as brown solid containing the title compound (38 mg), which was used for the next step without further purification.

MS m/z: 462 [M+1]$^+$.

$^1$H NMR (CDCl$_3$, 400 MHz), δ ppm: 8.40 (s, 2H), 8.02 (s, 1H), 7.27 (s, 1H), 7.19 (m, 4H), 5.40 (d, 1H), 4.81 (m, 1H), 4.62 (s, 2H), 4.12 (m, 1H), 3.59 (s, 1H), 2.90 (dd, 2H), 2.38 (m, 2H), 1.70 (m, 4H), 1.47 (s, 9H)

(Step 5) Preparation of 2-[3-(cyclobutylamino)-4-{2-[(2,3-dihydro-1H-inden-2-yl)amino]pyrimidin-5-yl}-1H-pyrazol-1-yl]acetic Acid

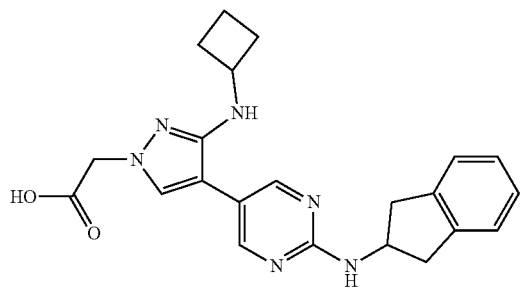 [SMILES: O=C(O)Cn1cc(-c2cnc(NC3Cc4ccccc4C3)nc2)c(NC2CCC2)n1]

To a solution of the residue obtained (38 mg) in dichloromethane (2 mL) was added trifluoroacetic acid (1 mL), and the reaction mixture was stirred at room temperature overnight. After completion, the solvent was removed under reduced pressure to afford a crude mixture as yellow oil containing the title compound (40 mg), which was used for the next step without further purification.

MS m/z: 405 [M+1]$^+$.

1H NMR (CD$_3$OD, 400 MHz), δ ppm: 8.37 (s, 2H), 7.52 (s, 1H), 7.16 (m, 4H), 4.70 (m, 2H), 2.91 (m, 2H), 2.32 (m, 2H), 2.02 (m, 2H), 1.87 (m, 2H)

(Step 6) Preparation of 2-[3-(cyclobutylamino)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one To an ice-tooled solution of the residue obtained (40 mg) and the compound im-7 (20 mg, 0.12 mmol) in DMF (1 mL) were added DIPEA (0.07 mL, 0.42 mmol) and PyBOP (64 mg, 0.12 mmol), and the mixture was stirred at room temperature for 3 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by preparative TLC (5% methanol/dichloromethane) to afford the title compound as beige solid (5 mg, 7% in 3 steps).

MS m/z: 512 [M+1]$^+$.

1HNMR (CDCl$_3$, 400 MHz), δ ppm: 8.35 (s, 1H), 7.34 (s, 1H), 7.21 (m, 4H), 5.42 (d, 1H), 4.96 (d, 2H), 4.80 (m, 3H), 4.07 (m, 1H), 3.90 (m, 2H), 3.41 (dd, 2H), 2.85 (m, 4H), 2.35 (m, 2H), 2.02 (m, 2H), 1.74 (m, 2H)

[Example 25] Preparation of 2-[3-(diethylamino)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one (Compound 106)

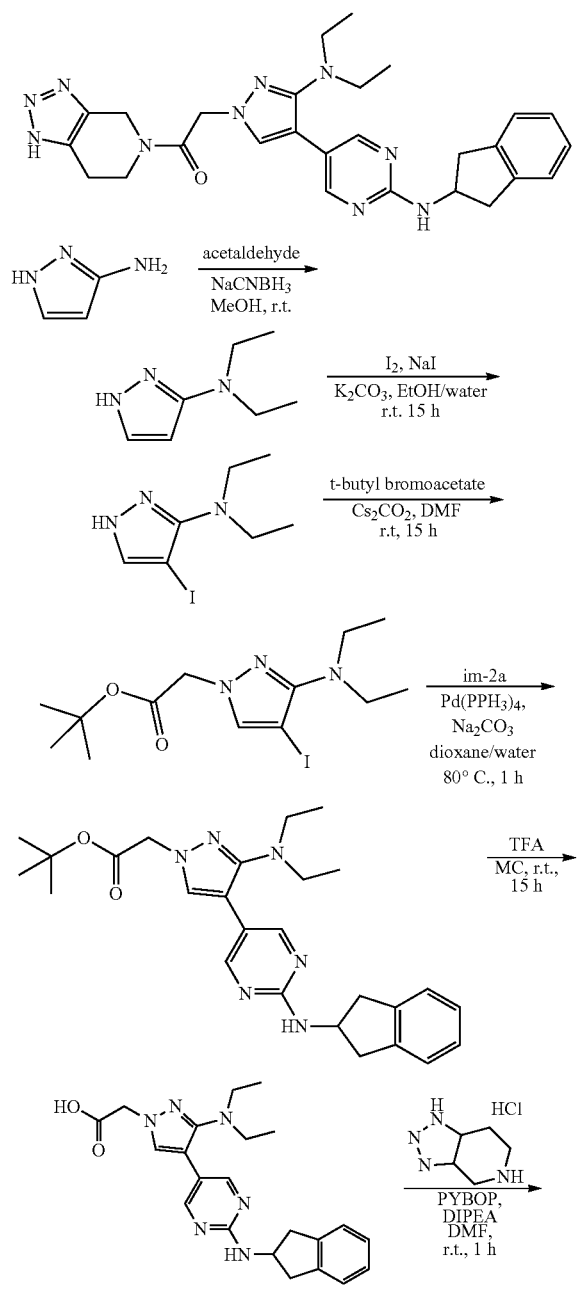

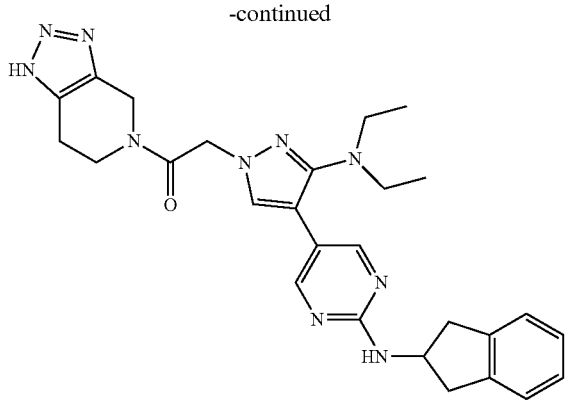

(Step 1) Preparation of N,N-diethyl-1H-pyrazol-3-amine

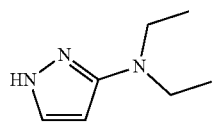

To an ice-cooled solution of 3-aminopyrazole (2.0 g, 24.07 mmol) in methanol (50 mL) were added acetaldehyde (3.4 mL, 60.18 mmol) and sodium cyanoborohydride (15 g, 72.21 mmol), and the reaction mixture was stirred at room temperature for 17 h under nitrogen atmosphere. The reaction mixture was concentrated under reduced pressure and the resulting residue was purified by column chromatography (30% ethyl acetate/n-hexane) to afford the title compound as colorless oil (1.87 g, 50%)

MS m/z: 140 [M+1]$^+$.

$^1$H NMR (DMSO-d$_6$, 400 MHz), δ ppm: 11.55 (s, 1H), 7.37 (s, 1H), 5.51 (s, 1H). 3.14 (m, 4H), 0.96 (m, 6H)

(Step 2) Preparation of N,N-diethyl-4-iodo-1H-pyrazol-3-amine

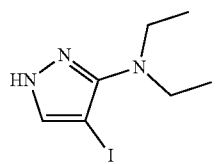

To a solution of N,N-diethyl-1H-pyrazol-3-amine (1.87 g, 13.43 mmol) in a mixed solvent of ethanol/water (1/1, 20 mL) were added sodium iodide (2.2 g, 14.78 mmol), idodine (5.1 g, 20.15 mmol), potassium carbonate (7.4 g, 53.7 mmol) successively, and the reaction mixture was stirred at room temperature for 15 h. After completion, the reaction mixture was diluted with ethyl acetate and washed with saturated sodium thiosulfate aqueous solution. The organic layer was dried over anhydrous sodium sulfate, filtered, and concentrated under reduced pressure. The residue was purified by column chromatography (30% ethyl acetate/n-hexne) to afford the title compound as brown oil (1.22 g, 34%).

MS m/z: 266 [M+1]$^+$.

1HNMR (CDCl$_3$, 400 MHz), δ ppm: 7.46 (s, 1H), 3.26 (m, 4H), 1.10 (m, 6H)

(Step 3) Preparation of tert-butyl 2-[3-(diethylamino)-4-iodo-1H-pyrazol-1-yl]acetate

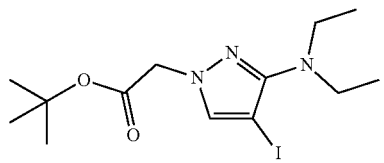 [SMILES: CCN(CC)c1nn(CC(=O)OC(C)(C)C)cc1I]

To a solution of N,N-diethyl-4-iodo-1H-pyrazol-3-amine (1.22 g, 4.60 mmol) in DMF (10 mL) were added cesium carbonate (2.2 g, 6.9 mmol) and tert-butyl bromoacetate (0.8 mL, 5.52 mmol) successively, and the reaction mixture was stirred at room temperature for 15 h. After completion, the reaction mixture was diluted with water (30 mL) and extracted with ethyl acetate. The organic layer was washed with brine, dried over anhydrous sodium sulfate, filtered, and concentrated under reduced pressure to afford the title compound quantitatively as brown oil (1.79 g), which was used for the next step without further purification.

MS m/z: 380 [M+1]$^+$.

1HNMR (DMSO-d$_6$, 400 MHz), δ ppm: 7.67 (s, 1H), 4.74 (s, 2H), 3.33 (s, 6H). 3.13 (m, 4H), 1.41 (s, 9H), 0.98 (m, 6H)

(Step 4) Preparation of tert-butyl 2-[3-(diethylamino)-4-{2-[(2,3-dihydro-1H-inden-2-yl)amino]pyrimidin-5-yl}-1H-pyrazol-1-yl]acetate

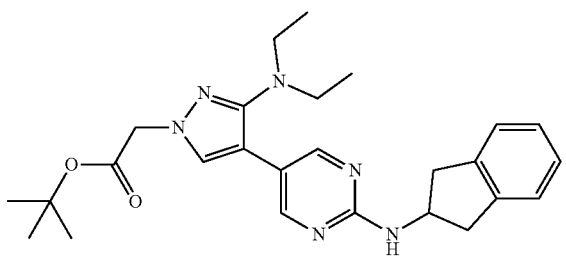 [SMILES: CCN(CC)c1nn(CC(=O)OC(C)(C)C)cc1-c1cnc(NC2Cc3ccccc3C2)nc1]

A mixture of tert-butyl 2-[3-(diethylamino)-4-iodo-1H-pyrazol-1-yl]acetate (0.50 g, 1.32 mmol), the compound im-2a (0.53 g, 1.58 mmol), tetrakis(triphenylphosphin)palladium(0) (152 mg, 0.13 mmol), 2N sodium carbonate solution (2 mL, 4.0 mmol) was dissolved in 1.4-dioxane (10 mL) and stirred at 80° C. for 3 h under nitrogen atmosphere. After completion, the reaction mixture was cooled to room temperature and water (40 mL) was added thereto, and then extracted with ethyl acetate (30 mL×3). The organic layer was washed with brine, dried over anhydrous sodium sulfate, filtered, and concentrated under reduced pressure. The resulting residue was passed through silica pad (40% ethyl acetate/n-hexane) to afford a mixture of title compound and deboronated byproduct (200 mg), which was used for the next step without further purification.

MS m/z: 463 [M+1]$^+$.

1HNMR (CDCl$_3$, 400 MHz), δ ppm: 8.52 (s, 2H), 7.36 (s, 1H), 7.19 (m, 4H), 5.55 (m, 1H), 4.82 (m, 1H), 4.55 (s, 2H), 3.39 (m, 2H), 3.07 (m, 4H), 2.88 (m, 2H), 1.23 (s, 9H), 1.02 (m, 6H)

(Step 5) Preparation of 2-[3-(diethylamino)-4-{2-[(2,3-dihydro-1H-inden-2-yl)amino]pyrimidin-5-yl}-1H-pyrazol-1-yl]acetic Acid

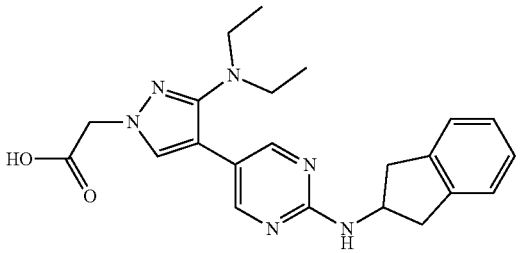 [SMILES: CCN(CC)c1nn(CC(=O)O)cc1-c1cnc(NC2Cc3ccccc3C2)nc1]

To a solution of the residue obtained (200 mg) in dichloromethane (2 mL) was added trifluoroacetic acid (6 mL), and the reaction mixture was stirred at room temperature overnight. After completion, the solvent was removed under reduced pressure. The residue was purified by column chromatography (20% methanol/dichloromethane) to afford the title compound as light brown solid (58 mg, 11% in 2 steps).

MS m/z: 407 [M+1]$^+$.

1HNMR (DMSO-d$_6$, 400 MHz), δ ppm: 8.50 (s, 2H), 7.80 (s, 1H), 7.23 (s, 1H), 7.16 (m, 4H), 5.75 (s, 1H), 4.80 (s, 2H), 4.61 (m, 1H), 3.26 (m, 2H), 3.00 (m, 4H), 2.90 (m, 2H), 0.94 (m, 6H)

(Step 6) Preparation of 2-[3-(diethylamino)-4-{2-[(2,3-dihydro-1H-inden-2-yl)amino]pyrimidin-5-yl}-1H-pyrazol-1-yl]-1-{1H,4H,5H,6H,7H-[1,2,3]triazolo[4,5-c]pyridin-5-yl}ethan-1-one To an ice-cooled solution of 2-[3-(diethylamino)-4-{2-[(2,3-dihydro-1H-inden-2-yl)amino]pyrimidin-5-yl}-1H-pyrazol-1-yl]acetic acid (57 mg, 0.14 mmol) and the compound im-7 (34 mg, 0.21 mmol) in DMF (1 mL) were added DIPEA (0.07 mL, 0.42 mmol) and PyBOP (109 mg, 0.21 mmol), and the mixture was stirred at room temperature for 15 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (5% methanol/dichloromethane) to afford the title compound as light yellow solid (21 mg, 29%).

MS m/z: 513 [M+1]$^+$.

1HNMR (DMSO-do, 400 MHz), δ ppm: 8.50 (s, 2H), 7.73 (d, 1H), 7.41 (d, 1H), 7.17 (m, 4H), 5.12 (m, 2H), 4.64 (m, 3H), 3.81 (s, 2H), 3.23 (m, 2H), 2.92 (m, 7H), 2.82 (m, 1H), 0.87 (m, 6H)

[Example 26] Preparation of 2-(4-{2-[(2,3-dihydro-1H-inden-2-yl)amino]pyrimidin-5-yl}-2-methyl-1H-imidazol-1-yl)-1-{1H,4H,5H,6H,7H-[1,2,3]triazolo[4,5-c]pyridin-5-yl}ethan-1-one (Compound 107)

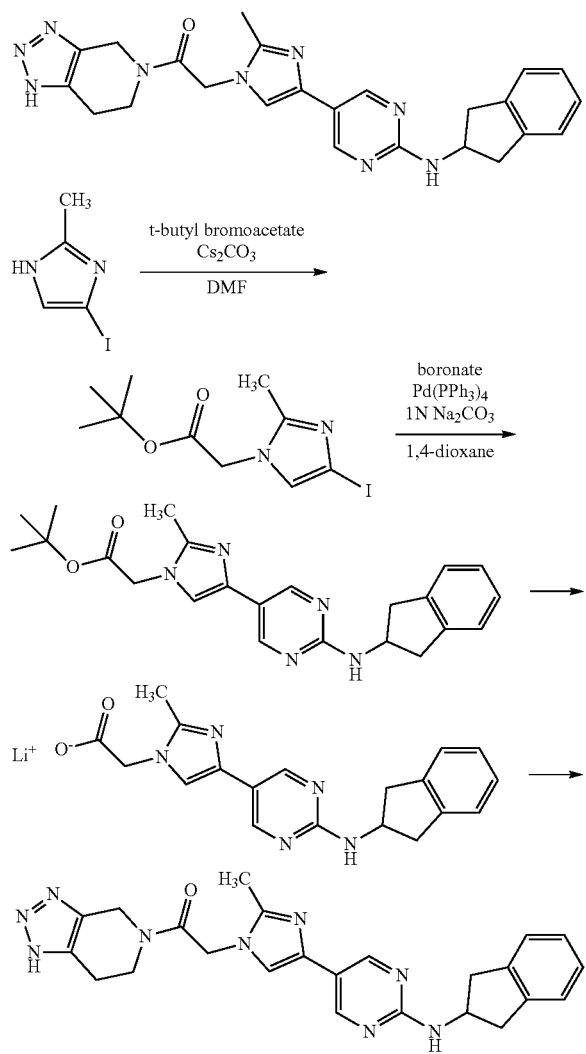

(Step 1) Preparation of tert-butyl 2-(4-iodo-2-methyl-1H-imidazol-1-yl)acetate

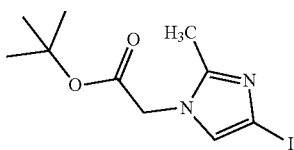

To a solution of 5-Iodo-2-methyl-1H-imidazole (300 mg, 1.44 mmol) in DMF (7.2 mL) were added cesium carbonate (704.7 mg, 2.16 mmol) and tert-butyl bromoacetate (0.21 mL, 1.44 mmol) successively, and the reaction mixture was stirred at room temperature for 18 h. After completion, the reaction mixture was diluted with water (20 mL) and extracted with ethyl acetate. The organic layer was washed with brine, dried over anhydrous sodium sulfate, filtered, and concentrated under reduced pressure. The resulting residue was purified by column chromatography (80% ethyl acetate/n-hexane) to afford the title compound as yellow oil (326.8 mg, 70%).

1H NMR (CDCl₃, 400 MHz), δ ppm: 6.91 (s, 1H), 4.45 (s, 2H), 2.34 (s, 3H), 1.47 (s, 9H)

(Step 2) tert-butyl 2-(4-{2-[(2,3-dihydro-1H-inden-2-yl)amino]pyrimidin-5-yl}-2-methyl-1H-imidazol-1-yl)acetate

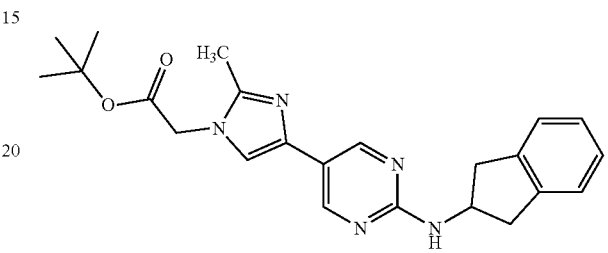

A mixture of tert-butyl 2-(4-iodo-2-methyl-1H-imidazol-1-yl)acetate (326.8 mg, 1.01 mmol), the compound im-2a (263 mg, 0.78 mmol), tetrakis(triphenylphosphin)palladium (0) (270.4 mg, 0.23 mmol), 1N sodium carbonate solution (2.6 mL, 2.34 mmol) was dissolved in 1.4-dioxane (12.5 mL) and stirred at 80° C. for 4 h under nitrogen atmosphere. After completion, the reaction mixture was cooled to room temperature and water (10 mL) was added thereto, and then extracted with ethyl acetate (10 mL×3). The organic layer was washed with brine, dried over anhydrous sodium sulfate, filtered, and concentrated under reduced pressure. The resulting residue was purified by column chromatography (80% ethyl acetate/n-hexane) first, and then impurities were separated by preparative-TLC (100% ethyl acetate) to afford the title compound as white solid (95.1 mg, 30%). 1H NMR (CDCl₃, 400 MHz), δ ppm: 8.64 (s, 2H), 7.24-7.15 (m, 4H), 7.00 (s, 1H), 5.44 (d, 1H), 4.87-4.79 (m, 1H), 4.51 (s, 2H), 3.43-3.37 (m, 2H), 2.91-2.86 (m, 2H), 2.38 (s, 3H), 1.49 (s, 9H).

(Step 3) Preparation of 2-(4-{2-[(2,3-dihydro-1H-inden-2-yl)amino]pyrimidin-5-yl}-2-methyl-1H-imidazol-1-yl)acetic Acid Lithium Salt

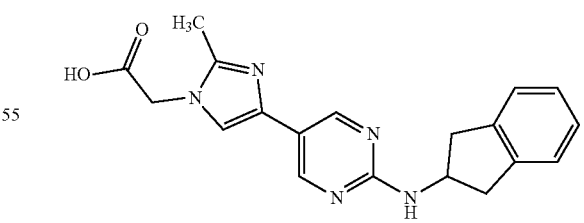

To a solution of tert-butyl 2-(4-{2-[(2,3-dihydro-1H-inden-2-yl)amino]pyrimidin-5-yl}-2-methyl-1H-imidazol-1-yl)acetate (65.1 mg, 0.16 mmol) in THF (1 mL) were added lithium hydroxide monohydrate (33.8 mg, 0.81 mmol) in water (1 mL) and the reaction mixture was stirred at room temperature for 2 h. After completion, the solvent was removed under reduced pressure, and the resulting residue was triturated with diethyl ether to afford light yellow solid (122.8 mg), which was used for the next step without further purification.

1H NMR (DMSO-d$_6$, 400 MHz), δ ppm: 8.57 (s, 2H), 7.32 (d, 1H), 7.24-7.12 (m, 5H), 4.65-4.59 (m, 1H), 4.08 (s, 2H), 3.28-3.22 (m, 2H), 2.91-2.86 (m, 2H), 2.19 (s, 3H).

(Step 4) Preparation of 2-(4-{2-[(2,3-dihydro-1H-inden-2-yl)amino]pyrimidin-5-yl}-2-methyl-1H-imidazol-1-yl)-1-{1H,4H,5H,6H,7H-[1,2,3]triazolo[4,5-c]pyridin-5-yl}ethan-1-one To an ice-cooled solution of the reside obtained in step 3 (122.8 mg) and the compound im-7 (112.7 mg, 0.70 mmol) in DMF (7 mL) were added DIPEA (0.31 mL, 1.76 mmol) and PyBOP (274.2 mg, 0.53 mmol), and the reaction mixture was stirred at room temperature for 4 h under nitrogen atmosphere. After completion, water (20 mL) was added to the reaction mixture and it was extracted with ethyl acetate (20 mL×3). The organic layer was washed with brine, dried over anhydrous sodium sulfate, filtered, and concentrated under reduced pressure. The resulting residue was purified by column chromatography (5% methanol/dichloromethane) to afford the title compound as white solid (35.4 mg, 48% in 2 steps).

1H NMR (DMSO-d$_6$, 400 MHz), δ ppm: 8.59 (s, 2H), 7.39 (d, 1H), 7.29 (d, 1H), 7.22-7.12 (m, 4H), 5.10 (d, 2H), 4.77 (s, 1H), 4.69 (s, 1H), 4.65-4.60 (m, 1H), 3.83-3.82 (m, 2H), 3.28-3.22 (m, 2H), 2.92-2.75 (m, 4H), 2.20 (s, 3H).

[Example 31] Preparation of 2-(2-{2-[(2,3-dihydro-1H-inden-2-yl)amino]pyrimidin-5-yl}-1-ethyl-1H-imidazol-4-yl)-1-{3H,4H,5H,6H,7H-[1,2,3]triazolo[4,5-c]pyridin-5-yl}ethan-1-one (Compound 112)

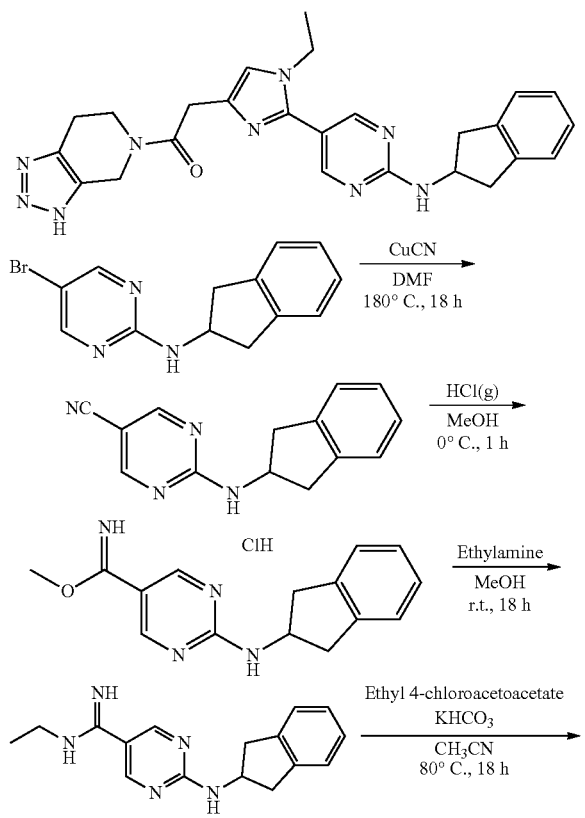

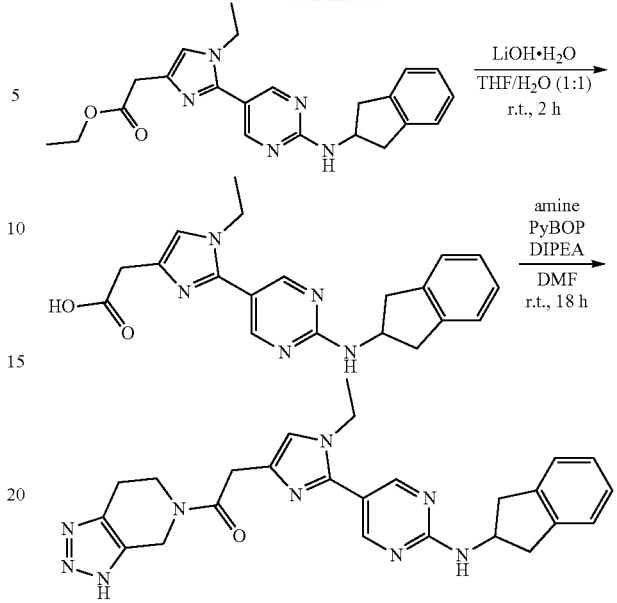

(Step 1) Preparation of 2-[(2,3-dihydro-1H-inden-2-yl)amino]pyrimidine-5-carbonitrile

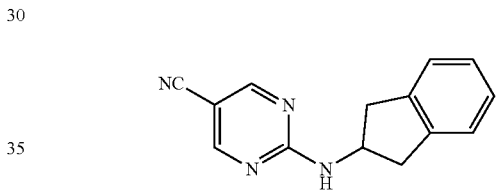

A mixture of the compound im-1a (2.5 g, 8.62 mmol) and copper cyanide (1.0 g, 11.2 mmol) in DMF (41 mL) was stirred at 180° C. for 18 h. After completion, the reaction mixture was diluted with ethyl acetate (50 mL) and washed with 10% Sodium cyanide solution (50 mL×2). The organic layer was dried over anhydrous sodium sulfate, filtered, and concentrated under reduced pressure. The residue was purified by column chromatography (15% ethyl acetate/n-hexane) to afford the title compound as beige solid (1.48 g, 73%).

1H NMR (CDCl$_3$, 400 MHz), δ ppm: 8.56 (s, 1H), 8.55 (s, 1H), 7.25-7.18 (m, 4H), 6.19 (d, 1H), 4.90-4.82 (m, 1H), 3.43-3.38 (m, 2H), 2.92-2.87 (m, 2H).

(Step 2) Preparation of methyl 2-[(2,3-dihydro-1H-inden-2-yl)amino]pyrimidine-5-carboximidate Hydrochloride

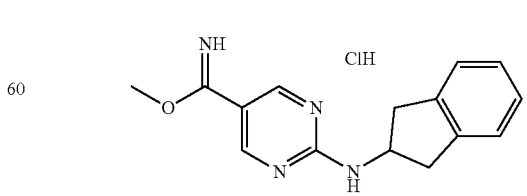

An ice-cooled solution of 2-[(2,3-dihydro-1H-inden-2-yl)amino]pyrimidine-5-carbonitrile (544 mg, 2.30 mmol) in methanol (20 mL) was stirred at room temperature while HCl gas was bubbled. After completion, ther solvent was removed under reduced pressure to afford the title compound as beige solid (701 mg, 2.30 mmol).

1H NMR (DMSO-d$_6$, 400 MHz), δ ppm: 9.08 (d, 1H), 8.99-8.95 (m, 2H), 7.24-7.13 (m, 4H), 4.79-4.70 (m, 1H), 4.22 (s, 3H), 3.31-3.25 (m, 2H), 2.97-2.92 (m, 2H).

(Step 3) Preparation of 2-[(2,3-dihydro-1H-inden-2-yl)amino]-N-ethylpyrimidine-5-carboximidamide

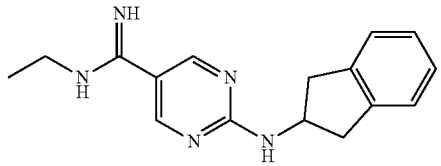 [SMILES: CCNC(=N)c1cnc(NC2Cc3ccccc3C2)nc1]

To an ice-cooled solution of methyl 2-[(2,3-dihydro-1H-inden-2-yl)amino]pyrimidine-5-carboximidate hydrochloride (701 mg, 2.30 mmol) in methanol (5 mL) was added ethyamine (6 mL, 11.5 mmol) slowly. After completion, the solvent was removed under reduced pressure, and the resulting residue was purified by column chromatography (20% methanol/dichloromethane) to afford the title compound as beige solid (184.5 mg, 0.66 mmol).

1H NMR (DMSO-d$_6$, 400 MHz), δ ppm: 9.28 (bs, 2H), 8.67 (d, 2H), 8.56 (d, 1H), 7.24-7.14 (m, 4H), 4.72-4.66 (m, 1H), 3.41-3.38 (m, 2H), 3.30-3.24 (m, 2H), 2.95-2.89 (m, 2H), 1.23 (t, 3H).

(Step 4) Preparation of ethyl 2-(2-{2-[(2,3-dihydro-1H-inden-2-yl)amino]pyrimidin-5-yl}-1-ethyl-1H-imidazol-4-yl)acetate

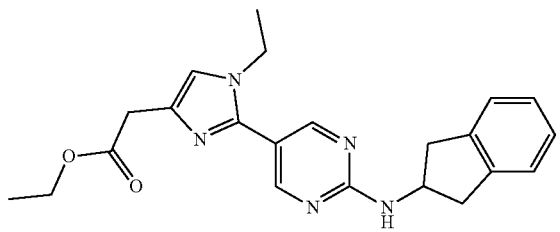 [SMILES: CCOC(=O)Cc1cn(CC)c(-c2cnc(NC3Cc4ccccc4C3)nc2)n1]

A mixture of 2-[(2,3-dihydro-1H-inden-2-yl)amino]-N-ethylpyrimidine-5-carboximidamide (184.5 mg, 0.66 mmol) and potassium bicarbonate (197 mg, 1.97 mmol) in acetonitrile (2 mL) was stirred at 50° C., and a solution of ethyl 4-chloroacetate (0.12 mL, 0.92 mmol) in acetonitrile (1 mL) was slowly added thereto. The reaction mixture was stirred at 80° C. for 18 h under nitrogen atmosphere. After completion, the reaction mixture was cooled to room temperature, and extracted with ethyl acetate and water. The organic layer was dried over anhydrous sodium sulfate, filtered, and concentrated under reduced pressure. The residue was purified by column chromatography (1% methanol/ethyl acetate) to afford the title compound as brown oil (66.9 mg), which was used without further purification.

MS m/z: 392 [M+1]$^+$.

1H NMR (CDCl$_3$, 400 MHz), δ ppm: 8.50 (s, 2H), 7.28-7.05 (m, 5H), 5.73-5.68 (m, 1H), 4.85 (m, 1H), 4.64 (s, 2H), 4.52-4.45 (m, 2H), 4.23-4.15 (m, 2H), 3.45-3.29 (m, 2H), 2.94-2.90 (m, 2H), 1.41 (t, 3H), 1.35-1.31 (m, 3H).

(Step 5) Preparation of 2-(2-{2-[(2,3-dihydro-1H-inden-2-yl)amino]pyrimidin-5-yl}-1-ethyl-1H-imidazol-4-yl)acetic Acid

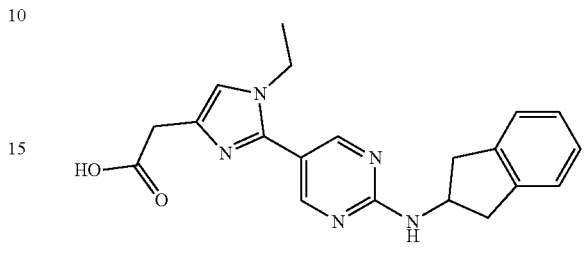

A mixture of ethyl 2-(2-{2-[(2,3-dihydro-1H-inden-2-yl)amino]pyrimidin-5-yl}-1-ethyl-1H-imidazol-4-yl)acetate (66.9 mg, 0.17 mmol) and lithium hydroxide monohydrate (35.7 mg, 0.85 mmol) was dissolved in THF (2 mL) and water (2 mL), and stirred at room temperature for 2 h. The solvent was removed under reduced pressure to afford the title compound as brown solid (109.6 mg), which was used for the next step without further purification.

MS m/z: 364 [M+1]$^+$.

(Step 6) Preparation of 2-(2-{2-[(2,3-dihydro-1H-inden-2-yl)amino]pyrimidin-5-yl}-1-ethyl-H-imidazol-4-yl)-1-{3H,4H,5H,6H,7H-[1,2,3]triazolo[4,5-c]pyridin-5-yl}ethan-1-one

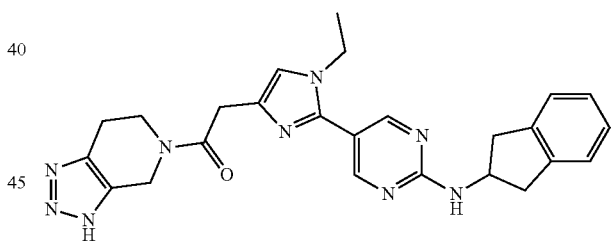

To an ice-cooled solution of 2-(2-{2-[(2,3-dihydro-1H-inden-2-yl)amino]pyrimidin-5-yl}-1-ethyl-1H-imidazol-4-yl)acetic acid (109.6 mg, 0.30 mmol) and the compound im-7 (97 mg, 0.60 mmol) in DMF (5 mL) was added PyBOP (235.7 mg, 0.45 mmol), followed by DIPEA (0.26 mL, 1.5 mmol). The reaction mixture was warmed to room temperature and stirred for 18 h. After completion of the reaction, the reaction mixture was diluted by ethyl acetate (20 mL), washed with water twice. The organic layer was dried over anhydrous sodium sulfate, filtered, and concentrated under reduced pressure. The resulting residue was purified by column chromatography (10% methanol/dichloromethane) to afford the title compound as pale reddish solid (3.0 mg, 4%).

1H NMR (CDCl$_3$, 400 MHz), δ ppm: 8.50 (s, 2H), 7.23-7.18 (m, 4H), 6.98 (d, 1H), 5.70 (d, 1H), 4.84-4.80 (m, 3H), 4.11-4.05 (m, 2H), 3.96-3.83 (m, 4H), 3.44-3.39 (m, 2H), 2.94-2.86 (m, 4H).

[Example 34] Preparation of 1-{4-[2-(4-(2-[(2,3-dihydro-1H-inden-2-yl)amino]pyrimidin-5-yl}-3-(pyridin-4-yl)-1H-pyrazol-1-yl)acetyl]piperazin-1-yl}-2-hydroxyethan-1-one (Compound 115)

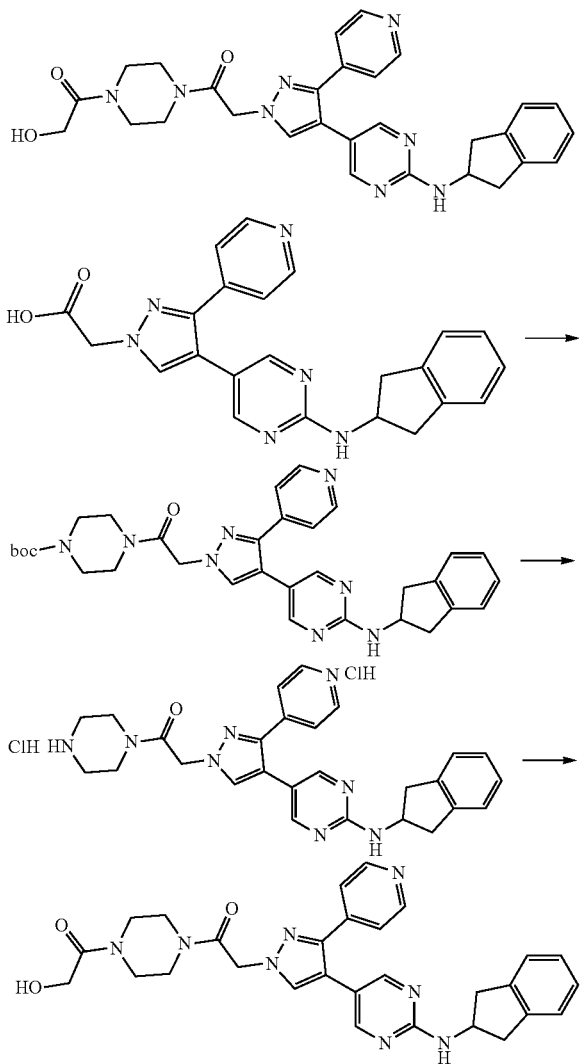

(Step 1) Preparation of tert-butyl 4-[2-(4-{2-[(2,3-dihydro-1H-inden-2-yl)amino]pyrimidin-5-yl}-3-(pyridin-4-yl)-1H-pyrazol-1-yl)acetyl]piperazine-1-carboxylate

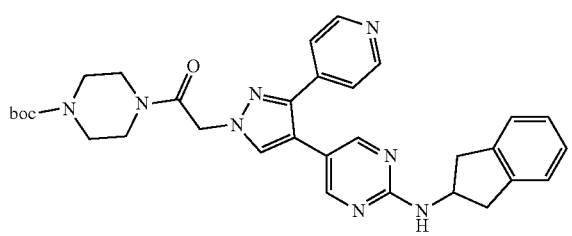

To an ice-cooled solution of 2-(4-{2-[(2,3-Dihydro-1H-inden-2-yl)amino]pyrimidin-5-yl}-3-(pyridin-4-yl)-1H-pyrazol-1-yl) acetic acid (described in example 36, step 6) (100 mg, 0.242 mmol) and 1-boc-piperazine (54 mg, 0.29 mmol) in DMF (1 mL) were added DIPEA (0.13 mL, 0.73 mmol) and PyBOP (188 mg, 0.36 mmol), and the mixture was stirred at room temperature for 15 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was passed through a silica pad (5% methanol/dichloromethane) to afford a mixture as beige solid containing the title compound (130 mg), which was used for the next reaction without further purification.

MS m/z: 581 [M+1]⁺.

1HNMR (CDCl₃, 400 MHz), δ ppm: 8.57 (d, 2H), 8.22 (s, 2H0, 7.61 (s, 1H), 7.43 (d, 2H), 7.20 (m, 4H), 5.41 (d, 1H), 5.08 (s, 1H), 4.81 (m, 1H), 3.48 (m, 10H), 2.90 (dd, 2H), 1.47 (s, 9H)

(Step 2) Preparation of 2-(4-{2-[(2,3-dihydro-1H-inden-2-yl)amino]pyrimidin-5-yl}-3-(pyridin-4-yl)-1H-pyrazol-1-yl)-1-(piperazin-1-yl) ethan-1-one Dihydrochloride

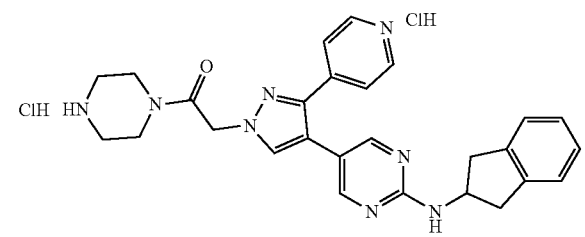 [SMILES: Cl ; O=C(Cn1cc(-c2cnc(NC3Cc4ccccc4C3)nc2)c(-c2ccncc2)n1)N1CCNCC1 ; Cl]

To an ice-cooled solution of the residue obtained (130 mg) in dichloromethane (2 mL) was added 4N HCl in dioxane solution (2 mL), then the reaction mixture was stirred at room temperature for 4 h. The solvent was removed under reduced pressure to afford the title compound as light yellow solid (100 mg, 75% in 2 steps), which was used for the next step without further purification.

MS m/z: 481 [M+1]⁺.

1HNMR (DMSO-do, 400 MHz), δ ppm: 9.46 (s, 2H), 8.82 (d, 2H), 8.33 (s, 2H0, 8.02 (m, 3H), 7.26 (s 1H), 7.19 (m, 4H), 5.43 (s, 2H0, 4.67 (m, 1H), 3.75 (m, 4H), 3.27 (dd, 2H), 3.16 (m, 4H), 2.94 (dd, 2H)

(Step 3) 1-{4-[2-(4-{2-[(2,3-dihydro-1H-inden-2-yl)amino]pyrimidin-5-yl}-3-(pyridin-4-yl)-1H-pyrazol-1-yl)acetyl]piperazin-1-yl}-2-hydroxyethan-1-one To an ice-cooled solution of 2-(4-{2-[(2,3-dihydro-1H-inden-2-yl)amino]pyrimidin-5-yl}-3-(pyridin-4-yl)-1H-pyrazol-1-yl)-1-(piperazin-1-yl)ethan-1-one dihydrochloride (100 mg, 0.18 mmol) and glycolic acid (20 mg, 0.27 mmol) in DMF (1 mL) were added DIPEA (0.24 mL, 1.35 mmol) and PyBOP (140 mg, 0.27 mmol), and the mixture was stirred at room temperature for 18 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (5%→10% methanol/dichloromethane) to afford the title compound as beige solid (52 mg, 54%)

MS m/z: 539 [M+1]⁺.

1HNMR (DMSO-do, 400 MHz), δ ppm: 8.55 (d, 2H), 8.20 (s, 2H), 7.92 (s, 1H), 7.62 (d, 1H), 7.43 (d, 2H), 7.18 (m, 4H), 5.30 (s, 2H), 4.64 (m, 2H), 4.13 (s, 2H), 3.52 (m, 7H), 3.26 (dd, 2H), 2.91 (dd, 2H)

[Example 35] Preparation of 2-(4-{2-[(2,3-dihydro-1H-inden-2-yl)amino]pyrimidin-5-yl}-3-(pyridin-2-yl)-1H-pyrazol-1-yl)-1-{1H,4H,5H,6H,7H-[1,2,3]triazolo[4,5-c]pyridin-5-yl}ethan-1-one (Compound 116)

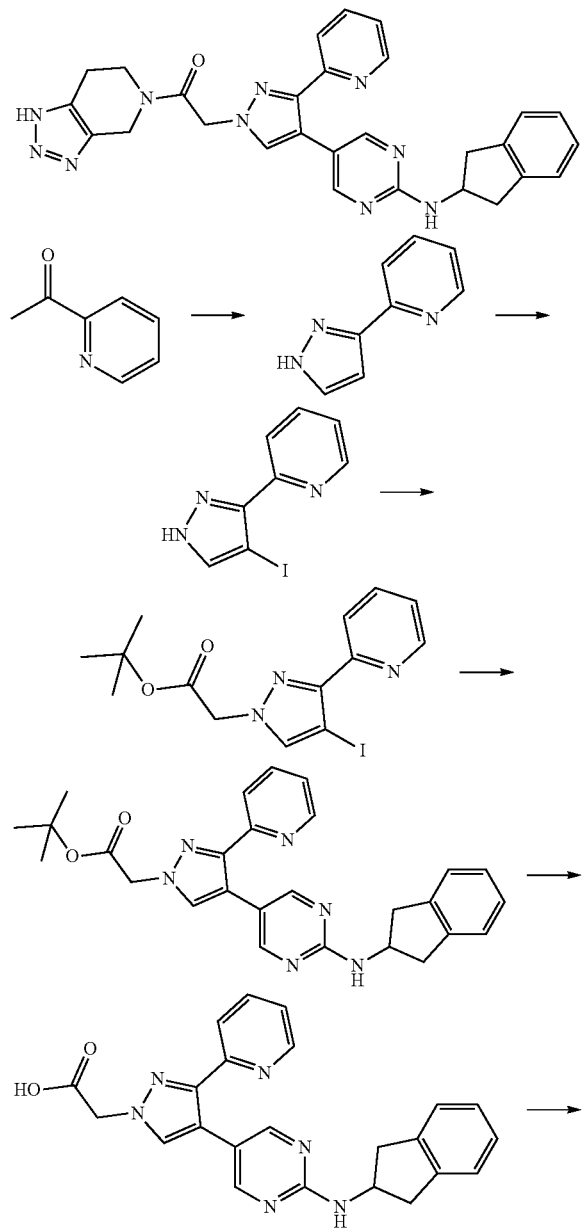

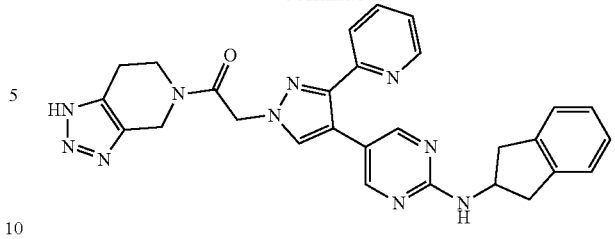

(Step 1) Preparation of 2-(1H-Pyrazol-3-yl)pyridine

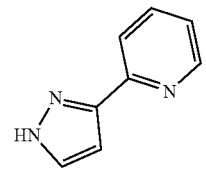 [SMILES: c1ccc(-c2cc[nH]n2)nc1]

A mixture of 2-acetylpyridine (3 mL, 27 mmol) and DMF-DMA (6 mL, 45.15 mmol) was stirred at 110° C. for 4 h. After completion, the reaction mixture was cooled to room temperature and concentrated under reduced pressure. The remained residue was dissolved in ethanol (12 mL) and hydrazine hydrate (1.6 mL, 32.40 mmol) was added thereto. The reaction mixture was stirred at reflux for 15 h. After completion, the reaction mixture was cooled to room temperature and the solvent was removed under reduced pressure. The residue was diluted with dichloromethane (20 mL) and washed with water. The organic layer was dried over anhydrous sodium sulfate, filtered, and concentrated under reduced pressure to afford the title compound as yellow solid (3.87 g, 99% in 2 steps).

MS m/z: 146 [M+1]⁺.

1H NMR (CDCl₃, 400 MHz), δ ppm: 11.35 (bs, 1H), 8.64 (d, 1H), 7.69-7.79 (m, 2H), 7.66 (d, 1H), 7.21-7.28 (m, 1H), 6.80 (s, 1H)

(Step 2) Preparation of 2-(4-Iodo-1H-pyrazol-3-yl)pyridine

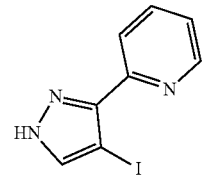 [SMILES: Ic1c[nH]nc1-c1ccccn1]

To a solution of 2-(1H-pyrazol-3-yl)pyridine (1 g, 6.89 mmol) in a mixed solvent of ethanol/water (1/2, 18 mL) were added sodium iodide (1.14 g, 7.87 mmol), iodine (2.62 g, 10.34 mmol), potassium carbonate (3.81 g, 27.56 mmol) successively, and the reaction mixture was stirred at room temperature for 3 h. After completion, the reaction mixture was diluted with ethyl acetate and washed with saturated sodium thiosulfate aqueous solution. The organic layer was dried over anhydrous sodium sulfate, filtered, and concentrated under reduced pressure to afford the title compound as light orange solid (1.32 g, 71%).

MS m/z: 272 [M+1]+.

1H NMR (CDCl3, 400 MHz), δ ppm: 11.53 (bs, 1H), 8.65 (d, 1H), 8.39 (d, 1H), 7.78-7.85 (m, 1H), 7.69 (s, 1H), 7.28-7.33 (m, 1H).

(Step 3) Preparation of Tert-butyl 2-[4-iodo-3-(pyridin-2-yl)-1H-pyrazol-1-yl]acetate

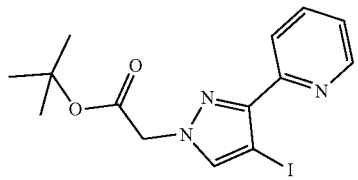 [SMILES: CC(C)(C)OC(=O)Cn1cc(I)c(-c2ccccn2)n1]

To a solution of 2-(4-Iodo-1H-pyrazol-3-yl)pyridine (1.70 g, 6.27 mmol) in DMF (12 mL) were added cesium carbonate (4.07 g, 12.50 mmol) and tert-butyl bromoacetate (1.39 mL, 9.41 mmol) successively, and the reaction mixture was stirred at room temperature for 2 h. After completion, the reaction mixture was diluted with water (40 mL) and extracted with ethyl acetate. The organic layer was washed with brine, dried over anhydrous sodium sulfate, filtered, and concentrated under reduced pressure. The resulting residue was purified by column chromatography (20% ethyl acetate/n-hexane) to afford the title compound as yellow oil (1.15 g, 48%).

MS m/z: 386 [M+1]+.

1H NMR (CDCl3, 400 MHz), δ ppm: 8.72 (d, 1H), 7.99 (d, 1H), 7.71-7.78 (m, 1H), 7.66 (s, 1H), 7.24-7.28 (m, 1H), 4.89 (s, 2H), 1.48 (s, 9H)

(Step 4) Preparation of Tert-butyl 2-(4-{2-[(2,3-dihydro-1H-inden-2-yl)amino]pyrimidin-5-yl}-3-(pyridin-2-yl)-1H-pyrazol-1-yl)acetate

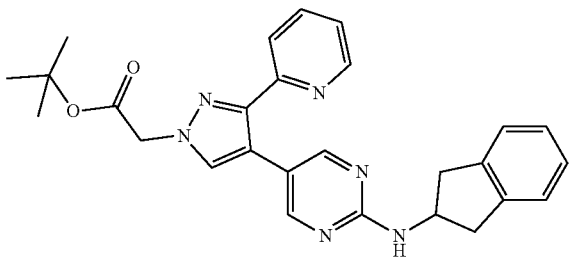 [SMILES: CC(C)(C)OC(=O)Cn1cc(-c2cnc(NC3Cc4ccccc4C3)nc2)c(-c2ccccn2)n1]

A mixture of tert-butyl 2-[4-iodo-3-(pyridin-2-yl)-1H-pyrazol-1-yl]acetate (0.31 g, 0.80 mmol), the compound im-2a (0.3 g, 0.89 mmol), tetrakis(triphenylphosphin)palladium(0) (92 mg, 0.08 mmol), 2N sodium carbonate solution (1.2 mL, 2.4 mmol) was dissolved in 1.4-dioxane (7 mL) and stirred at 100° C. for 15 h under nitrogen atmosphere. After completion, the reaction mixture was cooled to room temperature and water (50 mL) was added thereto, and then extracted with ethyl acetate (50 mL×3). The organic layer was washed with brine, dried over anhydrous sodium sulfate, filtered, and concentrated under reduced pressure. The resulting residue was purified by column chromatography (60% ethyl acetate/n-hexane) to afford the title compound as yellow oil (82 mg, 22%).

MS m/z: 469 [M+1]+.

1H NMR (CDCl3, 400 MHz), δ ppm: 8.59 (d, 1H), 8.38 (s, 2H), 7.64-7.71 (m, 2H), 7.58 (s, 1H), 7.14-7.24 (m, 4H), 5.40 (d, 1H), 4.91 (s, 2H), 4.81 (m, 1H), 3.41 (dd, 2H), 2.91 (dd, 2H), 1.50 (s, 9H)

(Step 5) Preparation of 2-(4-{2-[(2,3-Dihydro-1H-inden-2-yl)amino]pyrimidin-5-yl}-3-(pyridin-2-yl)-1H-pyrazol-1-yl)acetic Acid

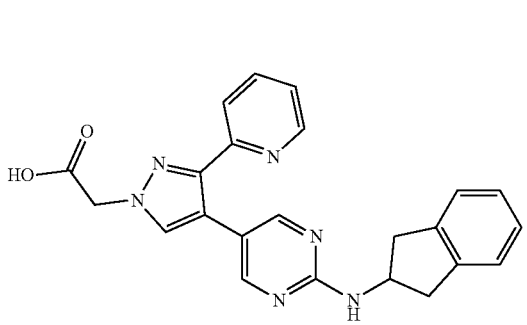 [SMILES: O=C(O)Cn1cc(-c2cnc(NC3Cc4ccccc4C3)nc2)c(-c2ccccn2)n1]

To a solution of tert-butyl 2-(4-{2-[(2,3-dihydro-1H-inden-2-yl)amino]pyrimidin-5-yl}-3-(pyridin-2-yl)-1H-pyrazol-1-yl)acetate. (82 mg, 0.175 mmol) in dichloromethane (1 mL) was added trifluoroacetic acid (3 mL), and the reaction mixture was stirred at room temperature for 3 h. After completion, the solvent was removed under reduced pressure to afford the title compound as white solid (50 mg, 69%), which was used for the next step without further purification.

MS m/z: 413 [M+1]+.

(Step 6) Preparation of 2-(4-{2-[(2,3-Dihydro-1H-inden-2-yl)amino]pyrimidin-5-yl}-3-(pyridin-2-yl)-1H-pyrazol-1-yl)-1-{1H,4H,5H,6H,7H-[1,2,3]triazolo[4,5-c]pyridin-5-yl}ethan-1-one To an ice-cooled solution of 2-(4-{2-[(2,3-dihydro-1H-inden-2-yl)amino]pyrimidin-5-yl}-3-(pyridin-2-yl)-1H-pyrazol-1-yl)acetic acid (50 mg, 0.12 mmol) and the compound im-7 (29 mg, 0.18 mmol) in DMF (2 mL) were added DIPEA (0.1 mL, 0.60 mmol) and PyBOP (94 mg, 0.18 mmol), and the mixture was stirred at room temperature for 5 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (3% methanol/dichloromethane) to afford the title compound as beige solid (42 mg, 67%).

MS m/z: 519 [M+1]+.

1H NMR (DMSO-d6, 400 MHz), δ ppm: 8.48 (d, 1H), 8.34 (s, 2H), 7.93 (d, 1H), 7.73-7.85 (m, 2H), 7.43 (d, 1H), 7.30 (t, 1H), 7.11-7.25 (m, 4H), 5.39 (d, 2H), 4.76 (d, 2H), 4.62 (m, 1H), 3.81-3.86 (m, 2H), 3.26 (dd, 2H), 2.72-2.94 (m, 4H)

[Example 36] Preparation of 2-[1-(4-chlorophenyl)-2-{2-[(2,3-dihydro-1H-inden-2-yl)amino]pyrimidin-5-yl}-1H-imidazol-4-yl]-1-{1H,4H,5H,6H,7H-[1,2,3]triazolo[4,5-c]pyridin-5-yl}ethan-1-one
(Compound 117)

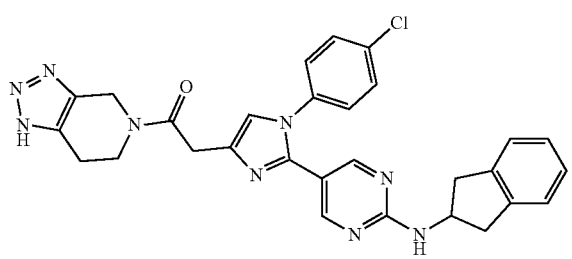

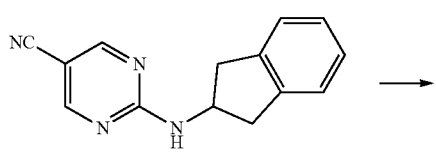

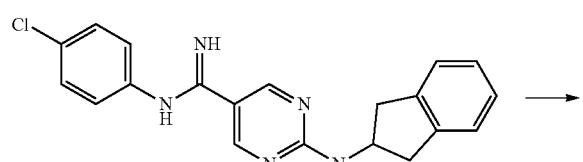

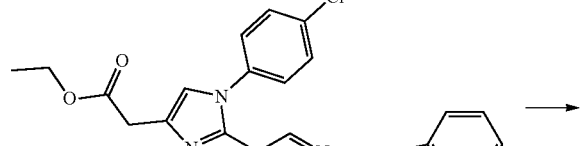

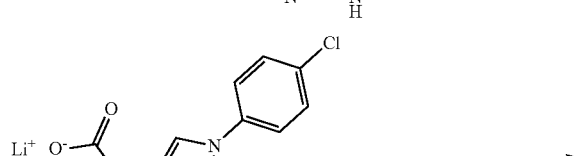

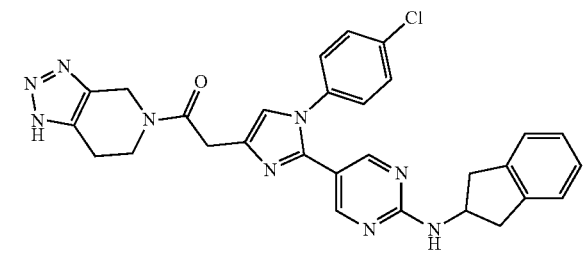

(Step 1) Preparation of N-(4-chlorophenyl)-2-[(2,3-dihydro-1H-inden-2-yl)amino]pyrimidine-5-carboximidamide

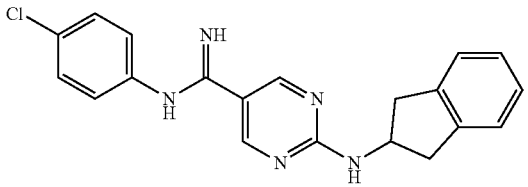 [SMILES: N=C(Nc1ccc(Cl)cc1)c1cnc(NC2Cc3ccccc3C2)nc1]

A mixture of the compound 51-a (100 mg, 0.42 mmol), 4-chloroaniline (59.3 mg, 0.47 mmol), aluminum chloride (62 mg, 0.47 mmol) was stirred at 130° C. for 1 h. After completion, 2M sodium hydroxide aqueous solution (1.7 mL) was added to the reaction mixture, and then slowly added ice water (4.2 mL). After stirring for 15 min, the reaction mixture was extracted with ethyl acetate (10 mL×3). The organic layer was washed with brine, dried over anhydrous sodium sulfate, filtered, and concentrated under reduced pressure. The resulting residue was purified by column chromatography (5% methanol/dichloromethane) to afford the title compound as light yellow solid (77.2 mg, 50%).

1H NMR (DMSO-$d_6$, 400 MHz), δ ppm: 8.82 (s, 2H), 7.91 (d, 1H), 7.31 (d, 2H), 7.23-7.13 (m, 4H), 6.84 (d, 2H), 6.38 (bs, 2H), 0.4.69-4.65 (m, 1H), 3.30-3.24 (m, 2H), 2.94-2.88 (m, 2H).

(Step 2) Preparation of ethyl 2-[1-(4-chlorophenyl)-2-{2-[(2,3-dihydro-1H-inden-2-yl)amino]pyrimidin-5-yl}-1H-imidazol-4-yl]acetate

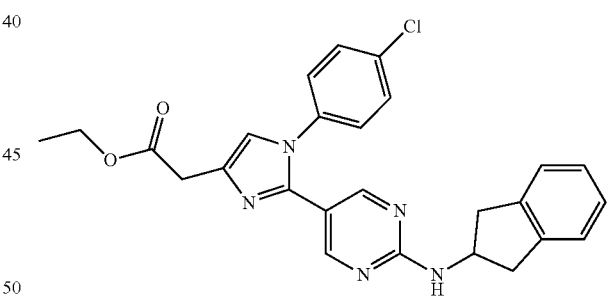

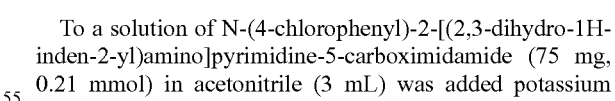

To a solution of N-(4-chlorophenyl)-2-[(2,3-dihydro-1H-inden-2-yl)amino]pyrimidine-5-carboximidamide (75 mg, 0.21 mmol) in acetonitrile (3 mL) was added potassium bicarbonate (62 mg, 0.62 mmol). The solution of ethyl-4-chloroacetoacetate (40 μL, 0.29 mmol) in acetonitrile (0.5 mL) was added to the reaction mixture while it was stirred at 50° C. The reaction mixture was allowed to stir at 90° C. for 18 h. After competion, the precipitate was filtered off, washed with ethyl acetate. The filtrate was concentrated under reduced pressure, and the resulting residue was purified by column chromatography (5% methanol/dichloromethane) to afford the title compound as brown solid (73.7 mg, 76%).

1H NMR (CDCl$_3$, 400 MHz), δ ppm: 8.28 (s, 2H), 7.42 (d, 2H), 7.23-7.15 (m, 6H), 7.12 (s, 1H), 5.47 (d, 1H), 4.80-4.72 (m, 1H), 4.25-4.19 (q, 2H), 3.74 (s, 2H), 3.39-3.34 (m, 2H), 2.88-2.38 (m, 2H), 1.31 (t, 3H).

(Step 3) Preparation of 2-[1-(4-chlorophenyl)-2-{2-[(2,3-dihydro-1H-inden-2-yl)amino]pyrimidin-5-yl}-1H-imidazol-4-yl]acetic Acid Lithium Salt

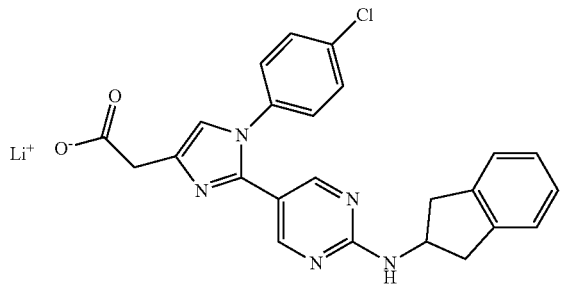 [SMILES: [Li+] ; O=C([O-])Cc1cn(-c2ccc(Cl)cc2)c(-c2cnc(NC3Cc4ccccc4C3)nc2)n1]

To a solution of ethyl 2-[1-(4-chlorophenyl)-2-{2-[(2,3-dihydro-1H-inden-2-yl)amino]pyrimidin-5-yl}-1H-imidazol-4-yl]acetate (73.7 mg, 0.16 mmol) in THF (0.8 mL) were added lithium hydroxide monohydrate (32.5 mg, 0.78 mmol) in water (0.8 mL), and the reaction mixture was stirred at room temperature for 3 h. After completion, the solvent was removed under reduced pressure and the resulting residue was triturated with diethyl ether to afford the title compound quantitatively as brown solid (73.7 mg), which was used for the next step without further purification.

1H NMR (DMSO-d6, 400 MHz), δ ppm: 8.17 (s, 2H), 7.78 (d, 1H), 7.56 (d, 2H), 7.37 (d, 2H), 7.20-7.12 (m, 5H), 4.61-4.56 (m, 1H), 3.23-3.15 (m, 4H), 2.90-2.84 (m, 2H).

(Step 4) Preparation of 2-[1-(4-chlorophenyl)-2-{2-[(2,3-dihydro-1H-inden-2-yl)amino] pyrimidin-5-yl}-1H-imidazol-4-yl]-1-{1H,4H,5H,6H,7H-[1,2,3]triazolo[4,5-c]pyridin-5-yl}ethan-1-one To an ice-cooled solution of 2-[1-(4-chlorophenyl)-2-{2-[(2,3-dihydro-1H-inden-2-yl)amino]pyrimidin-5-yl}-1H-imidazol-4-yl]acetic acid lithium salt (73.7 mg, 0.16 mmol) and the compound im-7 (53 mg, 0.33 mmol) in DMF (3.3 mL) were added DIPEA (0.14 mL, 0.83 mmol) and PyBOP (129 mg, 0.25 mmol), and the reaction mixture was stirred at room temperature for 18 h under nitrogen atmosphere. After completion, water (20 mL) was added to the reaction mixture and it was extracted with ethyl acetate (30 mL×3). The organic layer was washed with brine, dried over anhydrous sodium sulfate, filtered, and concentrated under reduced pressure. The resulting residue was purified by column chromatography (3% methanol/dichloromethane) to afford the title compound as light brown solid (40 mg, 44%).

1HNMR (CDCl3, 400 MHz), δ ppm: 8.23 (s, 2H), 7.42-7.40 (m, 2H), 7.22-7.16 (m, 6H), 7.10 (d, 1H), 5.59-5.47 (m, 1H), 4.91 (d, 2H), 4.79-4.74 (m, 1H), 4.05-3.97 (m, 2H), 3.89 (d, 2H), 3.40-3.33 (m, 2H), 2.95-2.84 (m, 4H)

[Example 37] Preparation of 1-[4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)piperidin-1-yl]-2-hydroxyethan-1-one (Compound 118)

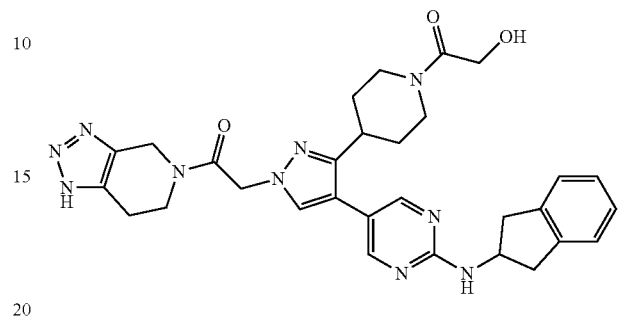

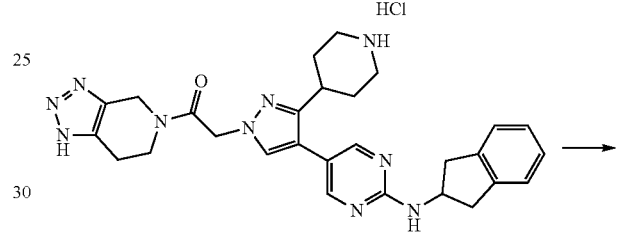

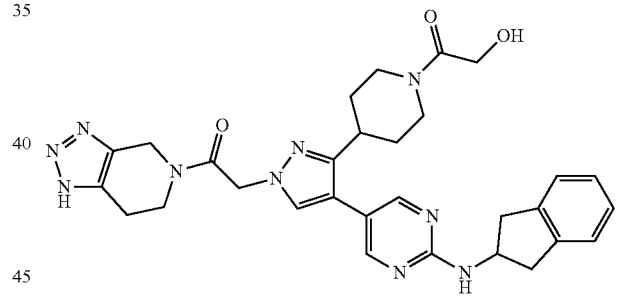

To an ice-cooled solution glycolic acid (26 mg, 0.34 mmol) and the compound 121 (60 mg, 0.107 mmol) in DMF (3 mL) were added DIPEA (0.1 mL, 0.535 mmol) and PyBOP (84 mg, 0.16 mmol), and the mixture was stirred at room temperature for 3 h under nitrogen atmosphere. After completion, water (50 mL) was added to the reaction mixture and it was extracted with ethyl acetate (50 mL×3). The organic layer was washed with brine, dried over anhydrous sodium sulfate, filtered, and concentrated under reduced pressure. The resulting residue was purified by column chromatography (3% methanol/dichloromethane) to afford the title compound as beige solid (25 mg, 40%)

MS m/z: 583 [M+1]+.

1H NMR (DMSO-d6, 400 MHz), δ ppm: 8.33 (s, 2H), 7.74 (d, 1H), 7.50 (s, 1H), 7.13-7.24 (m, 4H), 5.21 (d, 2H), 4.60-4.78 9m, 3H), 4.44 (t, 1H), 4.33 (m, 1H), 4.07 (t, 2H), 3.82 (m, 2H), 3.67 (m, 1H), 3.26 (dd, 2H), 2.96-3.08 (m, 2H), 2.92 (dd, 2H), 2.70-2.84 (m, 3H), 1.74-1.84 (m, 2H), 1.42-1.68 (m, 2H)

[Example 38] Preparation of 4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)benzoic Acid (Compound 119)

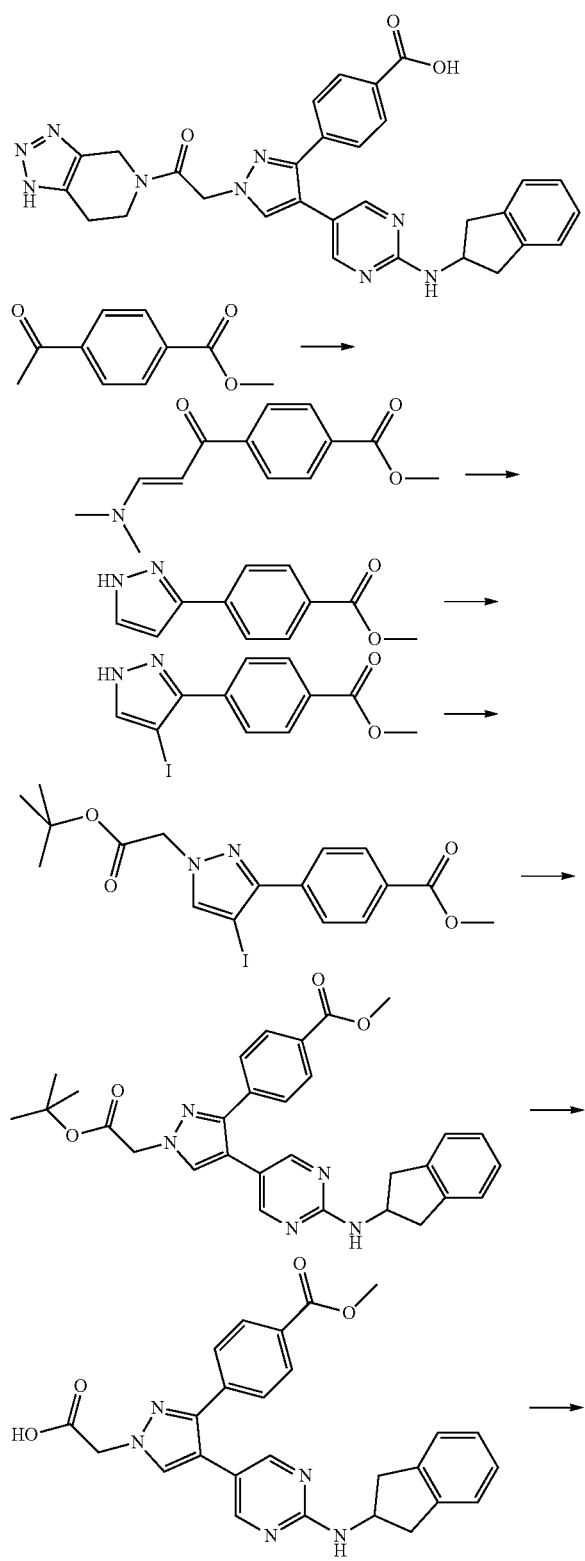

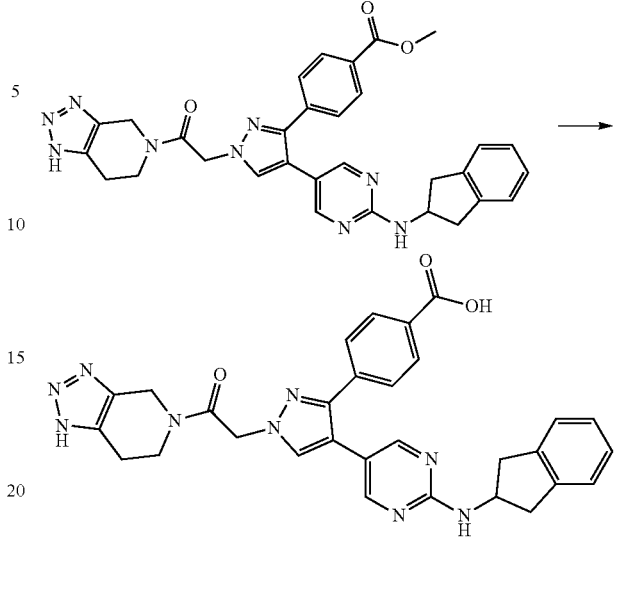

(Step 1) Preparation of Methyl 4-[(2E)-3-(dimethylamino) prop-2-enoyl]benzoate

A mixture of methyl 4-acetylbenzoate (1 g, 5.61 mmol) and DMF-DMA (5 mL, 45.15 mmol) was stirred at 130° C. for 15 h. After completion, the reaction mixture was cooled to room temperature and concentrated under reduced pressure. The remained residue was triturated with diethyl ether to afford the title compound as yellow solid (1.2 g, 92%)

MS m/z: 234 [M+1]$^+$.

1H NMR (CDCl$_3$, 400 MHz), δ ppm: 8.07 (d, 2H), 7.93 (d, 2H), 7.83 (d, 1H), 5.70 (d, 1H), 3.93 (s, 3H), 3.17 (bs, 3H), 2.95 (bs, 3H)

Step 2) Preparation of Methyl 4-(1H-pyrazol-3-yl)benzoate

To a solution of methyl 4-[(2E)-3-(dimethylamino)prop-2-enoyl]benzoate (1.2 g, 5.187 mmol) in ethanol (10 mL) was added hydrazine hydrate (0.39 mL, 7.781 mmol), and the reaction mixture was stirred at reflux for 4 h. After completion, the reaction mixture was cooled to room temperature and concentrated under reduced pressure to afford the title compound quantitatively as beige solid (1.1 g).

MS m/z: 205 [M+1]$^+$.

$^1$H NMR (CDCl$_3$, 400 MHz), δ ppm: 8.09 (d, 2H), 7.87 (d, 2H), 7.65 (d, 1H), 6.71 (d, 1H), 3.94 (s, 3H)

(Step 3) Preparation of Methyl 4-(4-iodo-1H-pyrazol-3-yl)benzoate

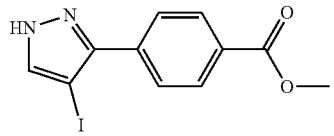 [SMILES: COC(=O)c1ccc(-c2n[nH]cc2I)cc1]

To a solution of methyl 4-(1H-pyrazol-3-yl)benzoate (0.65 g, 3.21 mmol) in a mixed solvent of ethanol/water (1/2, 15 mL) were added sodium iodide (0.57 g, 3.80 mmol), idodine (1.32 g, 5.19 mmol), and potassium carbonate (1.91 g, 13.84 mmol) successively, and the reaction mixture was stirred at room temperature for 1 h. After completion, the reaction mixture was diluted with ethyl acetate and washed with saturated sodium thiosulfate aqueous solution. The organic layer was dried over anhydrous sodium sulfate, filtered, and concentrated under reduced pressure to afford the title compound quantitatively as beige solid (1.09 g).

MS m/z: 329 [M+1]+.

1H NMR (CDCl$_3$, 400 MHz), δ ppm: 8.13 (d, 2H), 7.88 (d, 2H), 7.21 (s, 1H), 3.95 (s, 3H)

(Step 4) Preparation of Methyl 4-{1-[2-(tert-butoxy)-2-oxoethyl]-4-iodo-1H-pyrazol-3-yl}benzoate

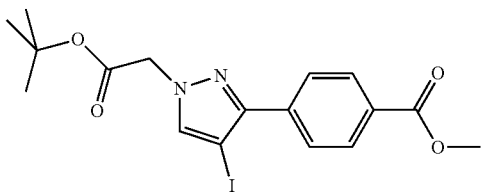 [SMILES: COC(=O)c1ccc(-c2nn(CC(=O)OC(C)(C)C)cc2I)cc1]

To a solution of methyl 4-(4-iodo-1H-pyrazol-3-yl)benzoate (1.09 g, 3.21 mmol) in DMF (10 mL) were added cesium carbonate (1.57 g, 4.82 mmol) and tert-butyl bromoacetate (0.57 mL, 3.85 mmol) successively, and the reaction mixture was stirred at room temperature for 1 h. After completion, the reaction mixture was diluted with water (40 mL) and extracted with ethyl acetate. The organic layer was washed with brine, dried over anhydrous sodium sulfate, filtered, and concentrated under reduced pressure. The resulting residue was purified by column chromatography (10% ethyl acetate/n-hexane) to afford the title compound as yellow oil (1.28 g, 90%).

MS m/z: 443 [M+1]+.

1HNMR (CDCl$_3$, 400 MHz), δ ppm: 8.10 (d, 2H), 7.95 (d, 2H), 7.64 (s, 1H), 4.85 (s, 2H), 3.93 (s, 3H), 1.49 (s, 9H).

(Step 5) Preparation of Methyl 4-{1-[2-(tert-butoxy)-2-oxoethyl]-4-{2-[(2,3-dihydro-1H-inden-2-yl)amino]pyrimidin-5-yl}-1H-pyrazol-3-yl}benzoate

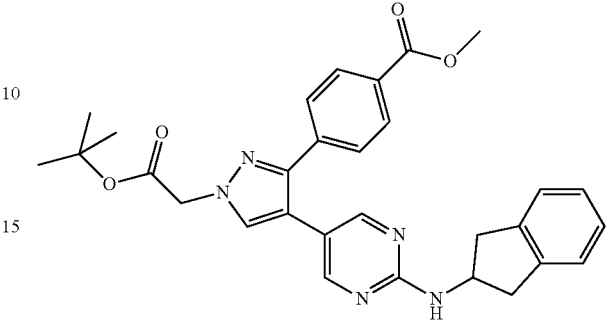

A mixture of methyl 4-{1-[2-(tert-butoxy)-2-oxoethyl]-4-iodo-1H-pyrazol-3-yl}benzoate (1.28 g, 2.89 mmol), the compound im-2a (1.07 g, 3.18 mmol), tetrakis(triphenylphosphin)palladium(0) (333 mg, 0.29 mmol), 2N sodium carbonate solution (4.3 mL, 8.6 mmol) was dissolved in 1.4-dioxane (15 mL) and stirred at 100° C. for 2 h under nitrogen atmosphere. After completion, the reaction mixture was cooled to room temperature and water (50 mL) was added thereto, and then extracted with ethyl acetate (50 mL×3). The organic layer was washed with brine, dried over anhydrous sodium sulfate, filtered, and concentrated under reduced pressure. The resulting residue was purified by column chromatography (10% ethyl acetate/n-hexane) to afford the title compound as beige solid (773 mg, 51%).

MS m/z: 526 [M+1]$^+$.

$^1$H NMR (CDCl$_3$, 400 MHz), δ ppm: 8.21 (s, 2H), 8.03 (d, 2H), 7.61 (d, 2H), 7.58 (s, 1H), 7.16-7.24 (m, 4H), 5.40 (d, 1H), 4.91 (s, 2H), 4.81 (m, 1H), 3.93 (s, 3H), 3.42 (dd, 2H), 2.92 (dd, 2H), 1.53 (s, 9H))

(Step 6) Preparation of 2-(4-{2-[(2,3-Dihydro-1H-inden-2-yl)amino]pyrimidin-5-yl}-3-[4-(methoxycarbonyl)phenyl]-1H-pyrazol-1-yl)acetic Acid

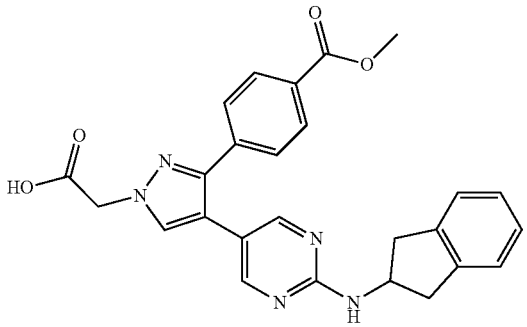 [SMILES: COC(=O)c1ccc(-c2nn(CC(=O)O)cc2-c2cnc(NC3Cc4ccccc4C3)nc2)cc1]

To a solution of methyl 4-{1-[2-(tert-butoxy)-2-oxoethyl]-4-{2-[(2,3-dihydro-1H-inden-2-yl)amino] pyrimidin-5-yl}-1H-pyrazol-3-yl}benzoate (0.77 g, 1.47 mmol) in dichloromethane (3 mL) was added trifluoroacetic acid (8 mL), and the reaction mixture was stirred at room temperature for 4 h. After completion, the solvent was removed under reduced pressure to afford the title compound quantitatively as yellow solid (941 mg).

MS m/z: 470 [M+1]+.

1H NMR (DMSO-d6, 400 MHz), δ ppm: 8.19 (s, 2H), 8.01 (s, 1H), 7.96 (d, 2H), 7.65 (bs, 1H), 7.61 (d, 2H), 7.13-7.23 (m, 4H), 5.06 (s, 2H), 4.62 (m, 1H), 3.85 (s, 3H), 3.25 (dd, 2H), 2.91 (m, 2H).

(Step 7) Preparation of Methyl 4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)benzoate

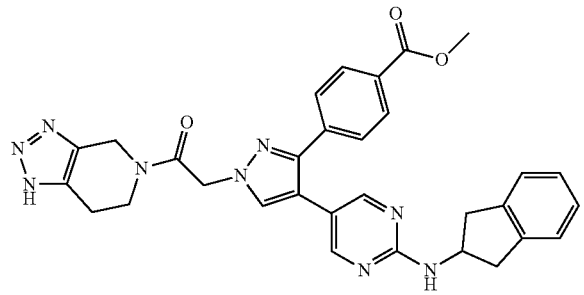 [SMILES: COC(=O)c1ccc(-c2nn(CC(=O)N3CCc4[nH]nnc4C3)cc2-c2cnc(NC3Cc4ccccc4C3)nc2)cc1]

To an ice-cooled solution of 2-(4-{2-[(2,3-dihydro-1H-inden-2-yl)amino]pyrimidin-5-yl}-3-[4-(methoxycarbonyl)phenyl]-1H-pyrazol-1-yl)acetic acid (116 mg, 0.35 mmol) and the compound im-7 (307 mg, 1.91 mmol) in DMF (10 mL) were added DIPEA (1.3 mL, 7.35 mmol) and PyBOP (1.15 g, 2.21 mmol), and the mixture was stirred at room temperature for 2 h under nitrogen atmosphere. After completion, water (50 mL) was added to the reaction mixture and it was extracted with ethyl acetate (50 mL×3). The organic layer was washed with brine, dried over anhydrous sodium sulfate, filtered, and concentrated under reduced pressure. The resulting residue was purified by column chromatography (3% methanol/dichloromethane) to afford the title compound as white solid (589 mg, 70%).

MS m/z: 576 [M+1]+.

1H NMR (CDCl3, 400 MHz), δ ppm: 11.78 (bs, 1H), 8.19 (s, 2H), 8.00 (m 2H), 7.52-8.02 (m, 3H), 7.17-7.24 (m, 4H), 5.41 (d, 1H), 5.19 (d, 2H), 4.86 (m, 2H), 4.79 (m, 1H), 5.47 (dt, 2H), 3.92 (s, 3H), 3.40 (dd, 2H), 2.86-2.96 (m, 4H)

(Step 8) Preparation of 4-(4-{2-[(2,3-Dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)benzoic Acid

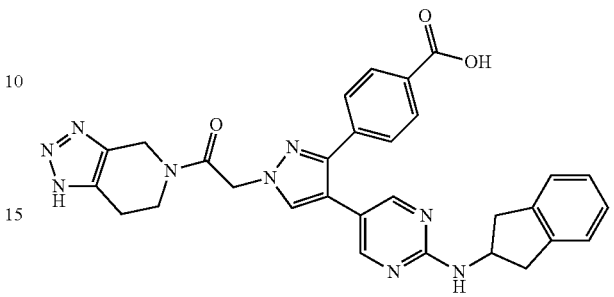

A solution of methyl 4-(4-{2-[(2,3-dihydro-1H-inden-2-yl)amino]pyrimidin-5-yl}-1-(2-oxo-2-{1H,4H,5H,6H,7H-[1,2,3]triazolo[4,5-c]pyridin-5-yl}ethyl)-1H-pyrazol-3-yl)benzoate (0.1 g, 0.17 mmol) in THF (2 mL) and 1N lithium hydroxide solution (0.52 mL, 0.52 mmol) was stirred at room temperature for 4 h. After completion of the reaction, 2N HCl aqueous solution was added to adjust pH to 2 and extracted with dichloromethane. The organic layer was separated, dried over anhydrous sodium sulfate, filtered, and concentrated under reduced pressure. The resulting residue was purified by column chromatography (15% methanol/dichloromethane) to afford the title compound as white solid (20 mg, 21%).

MS m/z: 562 [M+1]+.

1H NMR (DMSO-d6, 400 MHz), δ ppm: 8.17 (s, 2H), 7.86-7.94 (m, 3H), 7.45-7.57 (m, 3H), 7.11-7.24 (m, 4H), 5.37 (d, 2H), 4.75 (d, 2H), 4.61 (m, 1H), 3.81-3.84 (m, 2H), 3.21-3.24 (m, 2H), 2.72-2.94 (m, 4H)

[Example 39] Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carbohydrazide Hydrochloride (Compound 120)

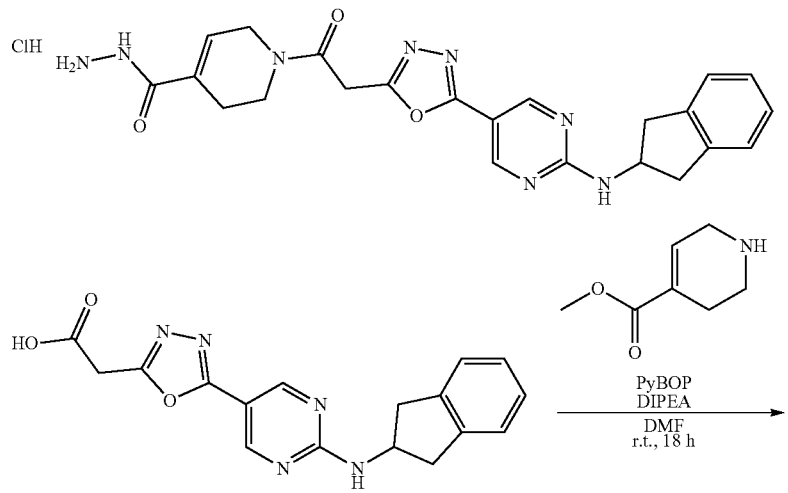

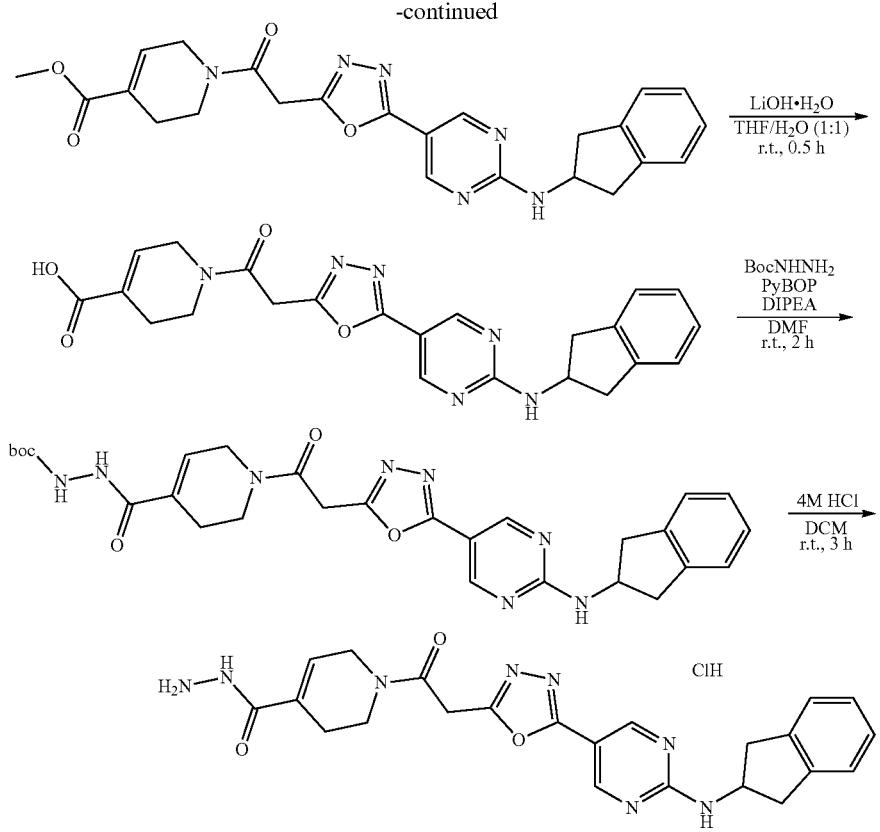

(Step 1) Preparation of Methyl 1-[2-(5-{2-[(2,3-dihydro-1H-inden-2-yl)amino]pyrimidin-5-yl}-1,3,4-oxadiazol-2-yl) acetyl]-1,2,3,6-tetrahydropyridine-4-carboxylate

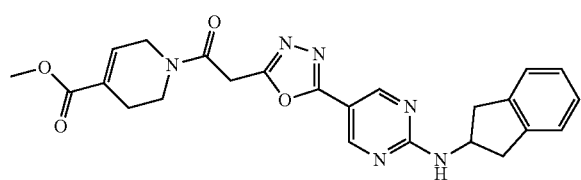 [SMILES: COC(=O)C1=CCN(C(=O)Cc2nnc(-c3cnc(NC4Cc5ccccc5C4)nc3)o2)CC1]

To an ice-cooled solution of the compound 33-d (98.9 mg, 0.29 mmol) and the compound im-10 (83 mg, 0.59 mmol) in DMF (8 mL) were added PyBOP (229 mg, 0.44 mmol) and DIPEA (0.26 mL, 1.47 mmol). The reaction mixture was warmed to room temperature and stirred for 18 h. After completion of the reaction, the reaction mixture was diluted by ethyl acetate (20 mL), washed with water three times. The organic layer was dried over anhydrous sodium sulfate, filtered, and concentrated under reduced pressure. The resulting residue was purified by column chromatography (80% ethyl acetate/n-hexane) to afford the title compound quantitatively as white solid (135 mg).

1H NMR (CDCl$_3$, 400 MHz), δ ppm: 8.89 (d, 2H), 7.24-7.18 (m, 4H), 6.93-6.88 (m, 1H), 5.82 (d, 1H), 4.92-4.87 (m, 1H), 4.28 (bs, 2H), 4.11-4.07 (m, 2H), 3.78-3.68 (m, 5H), 3.45-3.40 (m, 2H), 2.94-2.89 (m, 2H), 2.52-2.47 (m, 2H)

(Step 2) Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxylic Acid Lithium Salt

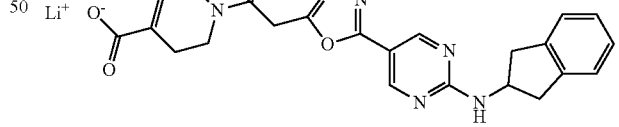

A mixture of methyl 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxylate (135 mg, 0.29 mmol) and lithium hydroxide monohydrate (61.7 mg, 1.47 mmol) was dissolved in THF (1 mL) and water (1 mL), and stirred at room temperature for 0.5 h. The solvent was removed under reduced pressure and the resulting residue was triturated with diethyl ether to afford the title compound as pale yellow solid (141 mg), which was used for the next step without further purification.

MS m/z: 44. [M+1]$^+$.

(Step 3) Preparation of N'-[(tert-butoxy)carbonyl]-1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carbohydrazide

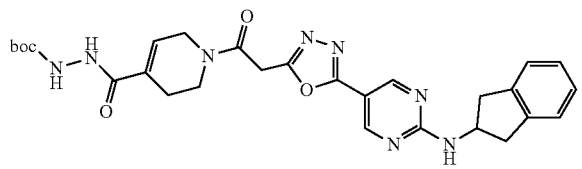

To an ice-cooled solution of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carboxylic acid (50 mg, 0.11 mmol) and tert-Butyl carbazate (29.6 mg, 0.22 mmol) in DMF (3 mL) were added PyBOP (87.4 mg, 0.17 mmol) and DIPEA (0.10 ml, 0.56 mmol). The reaction mixture was warmed to room temperature and stirred for 2 h. After completion of the reaction, the reaction mixture was diluted by EA (20 mL), washed with water three times. The organic layer was dried over anhydrous sodium sulfate, filtered, and concentrated under reduced pressure. The resulting residue was purified by column chromatography (ethyl acetate) to afford the title compound as pale yellow solid (14.3 mg, 23%).

1H NMR (CDCl$_3$, 400 MHz), δ ppm: 8.88 (d, 2H), 7.77 (d, 1H), 7.25-7.20 (m, 4H), 6.72 (d, 1H), 6.11 (d, 1H), 5.20-5.13 (m, 1H), 4.89-4.88 (m, 1H), 4.22-4.10 (m, 3H), 3.96-3.66 (m, 2H), 3.49-3.39 (m, 2H), 3.14 (s, 1H), 2.96-2.89 (m, 2H), 2.33-2.22 (m, 2H), 1.46 (s, 9H).

(Step 4) Preparation of 1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carbohydrazide Hydrochloride To an ice-cooled solution of N'-[(tert-butoxy)carbonyl]-1-[2-(5-{2-[(2,3-dihydro-1H-inden-2-yl)amino]pyrimidin-5-yl}-1,3,4-oxadiazol-2-yl)acetyl]-1,2,3,6-tetrahydropyridine-4-carbohydrazide (14.3 mg, 0.03 mmol) in dichloromethane (1 mL) was added 4N HCl in dioxane solution (1 mL), and the reaction mixture was stirred at room temperature for 3 h. After completion, the solvent was removed under reduced pressure. The resulting residue was triturated with diethyl ether to afford the title compound as beige solid (6.3 mg, 50%).

1H NMR (DMSO-d$_6$, 400 MHz), δ ppm: 8.82-8.76 (m, 2H), 8.42-8.34 (m, 1H), 7.22-7.16 (m, 5H), 4.72-4.69 (m, 1H), 3.70-3.67 (m, 2H), 3.30-3.26 (m, 2H), 2.95-2.91 (m, 6H), 2.33-2.28 (m, 2H).

[Test Example 1] Measurement of Inhibitory Activity on Human ENPP2

Two-fold dilution of each test compound solution (10 μM, 100% dimethyl sulfoxide) is carried out on 96-well V bottom plate (Costar 3363). After ten-fold dilution of each the test compound solution (100% dimethyl sulfoxide) with deionized distilled water, 10 μL of the diluted each mpound solution (10% dimethyl sulfoxide) was aliquoted to a black flat bottom 96-well plate (Costar 3915). 50 μL of 1.6× Assay solution (224 mM NaCl, 80 mM Tris-HCl (pH 8.0), 8 mM KCl, 1.6 mM CaCl$_2$, 1.6 mM MgCl$_2$, and 1.6 mg/mL fatty acid free BSA) was added thereto, and subsequently 20 μL of 20 nM human ENPP2 solution (buffer solution: 140 mM NaCl, 50 mM Tris-HCl (pH 8.0), 5 mM KCl, 1 mM CaCl$_2$, 1 mM MgCl$_2$, and 1 mg/mL fatty acid free BSA) and 20 μL of 5 μM FS-3 solution (buffer solution:deionized distilled water) were added thereto, respectively, followed by mixing. Under reaction for 30 minutes at 37° C., fluorescence intensity measurement (Ex: 485 mm, Em: 528 mm) was carried out at every 5 minutes by Envision Xcite Multilabel Reader. ΔCFU$_{30\ min}$ value (CFU value measured at 30 minutes–CFU value measured at 0 minute) is obtained for each test solution and based on the equation of 100–(ΔCFU$_{30\ min}$ of test solution/Mean value of ΔCFU$_{30\ min}$ of control group)×100, the inhibitory activity percentage ratio (i.e., % inhibition) is obtained. Furthermore, IC$_{50}$ values that are shown in Table 2 were calculated using Grafit5 Software based on the inhibitory activity percentage ratio.

TABLE 2

| Example | Compound No. | IC$_{50}$ (nM) |
|---|---|---|
| 1-1 | 1 | 3.3 |
| 1-2 | 2 | 2.1 |
| 1-3 | 3 | 14.3 |
| 1-4 | 4 | 18.9 |
| 1-8 | 8 | 3.5 |
| 1-9 | 9 | 9.0 |
| 1-10 | 10 | 2.8 |
| 2-1 | 12 | 3.2 |
| 2-2 | 13 | 3.7 |
| 2-3 | 14 | 2.4 |
| 2-5 | 16 | 2.2 |
| 3-1 | 17 | 3.4 |
| 3-2 | 18 | 3.6 |
| 3-3 | 19 | 3.1 |
| 4-1 | 20 | 2.6 |
| 4-2 | 21 | 4.1 |
| 4-3 | 22 | 2.9 |
| 4-4 | 23 | 6.8 |
| 5-1 | 26 | 13.1 |
| 5-2 | 27 | 2.4 |
| 5-3 | 28 | 3.1 |
| 5-4 | 29 | 3.9 |
| 5-6 | 31 | 11.8 |
| 5-7 | 32 | 2.9 |
| 6-1 | 33 | 2.4 |
| 6-2 | 34 | 2.0 |
| 6-3 | 35 | 2.4 |
| 6-4 | 36 | 2.9 |
| 6-6 | 38 | 4.0 |
| 6-7 | 39 | 10.6 |
| 6-8 | 40 | 10.1 |
| 6-10 | 42 | 8.1 |
| 6-11 | 43 | 11.2 |
| 6-12 | 44 | 16.6 |
| 6-13 | 46 | 4.6 |
| 6-15 | 48 | 13.3 |
| 6-17 | 50 | 4.5 |
| 7-1 | 51 | 2.5 |
| 7-2 | 52 | 3.6 |
| 7-3 | 53 | 3.1 |
| 7-4 | 54 | 15.8 |
| 7-5 | 55 | 2.9 |
| 8-1 | 56 | 2.2 |
| 8-2 | 57 | 2.0 |
| 8-3 | 58 | 3.5 |
| 8-4 | 59 | 11.1 |
| 9 | 60 | 1.8 |
| 10-1 | 61 | 1.5 |
| 10-2 | 62 | 2.4 |
| 10-3 | 63 | 2.0 |
| 10-4 | 64 | 3.0 |
| 10-5 | 65 | <1.56 |
| 10-6 | 66 | 1.9 |
| 10-7 | 67 | 6.1 |

TABLE 2-continued

| Example | Compound No. | IC$_{50}$ (nM) |
|---------|--------------|----------------|
| 10-8    | 68           | 1.8            |
| 10-9    | 69           | 4.0            |
| 10-10   | 70           | 2.3            |
| 10-11   | 71           | 3.6            |
| 10-12   | 72           | 3.4            |
| 10-13   | 73           | 3.7            |
| 10-14   | 74           | 1.7            |
| 10-15   | 75           | 1.5            |
| 10-16   | 76           | 3.0            |
| 10-17   | 77           | 6.5            |
| 11-1    | 78           | 2.4            |
| 11-2    | 79           | 1.6            |
| 12-1    | 80           | <1.56          |
| 12-2    | 81           | <1.56          |
| 12-3    | 82           | <1.56          |
| 12-4    | 83           | 2.1            |
| 12-5    | 84           | 2.8            |
| 12-6    | 85           | 2.2            |
| 12-7    | 86           | 3.0            |
| 12-8    | 87           | 3.1            |
| 12-9    | 88           | 4.1            |
| 12-10   | 89           | 4.2            |
| 12-11   | 90           | 2.6            |
| 12-12   | 91           | 2.4            |
| 12-13   | 92           | 2.3            |
| 12-14   | 93           | 2.1            |
| 13      | 94           | 2.3            |

From the results of above Table 2, it was confirmed that the compounds of the present invention have an inhibitory activity on ENPP in significant sense.

[Test Example 2] Measurement of Inhibitory Activity on LPA Production in Blood Serum After 100-fold dilution of each test compound solution (5 μL) (10 mM, 100%, dimethyl sulfoxide) with 495 μL of methanol, 3 μL of the diluted methanol solution (1% dimethyl sulfoxide) was mixed with 57 μL of human or mouse blood serum solution in a 1.5 mL tube. The mixed test compound solution was serially diluted, 12 μL for each, with 48 μL of 100% blood serum to have 5 different concentrations, and each tube was kept for 15 minutes in a water bath with constant temperature of 37° C. Subsequently, a solution prepared by diluting 10 mg/mL 18:1 LPC solution (50% ethanol) with blood serum to have concentration of 375 μg/mL was aliquoted in an amount of 2 μL to each tube so as to have 50 μL. Each tube was kept for 3 hours in a water bath at 37° C. to allow a reaction. To the tube obtained after the reaction, 100 μL of 0.5 μM 17:0 LPA solution (chloroform/methanol/water=65/35/8) was aliquoted and mixed therein. Centrifuge was carried out for 10 minutes using a centrifuge at conditions of 14,000 rpm and 4° C. 100 μL of 50% methanol solution is aliquoted first to a 96-well polypropylene plate (Agilent Technology 5042-1385), and the supernatant (50 μL) in a tube after the centrifuge was carefully transferred to the plate followed by mixing. After covering it with Well cap (Thermo 276011), analysis was carried out by LC-MS/MS (Agilent 1260). Based on the equation 100−(Blood serum at 3 hours+Test solution/Blood serum at 3 hours+Control group)×100, the percentage ratio (i.e., % inhibition) was obtained, and then IC$_{50}$ values that are shown in Table 3 were calculated using Grafit5 Software.

In the following Table 3, the mouse blood serum was described as (m) and human blood serum was described as (h).

TABLE 3

| Example | Compound No. | IC$_{50}$ (nM) |
|---------|--------------|----------------|
| 1-2     | 2            | 23 (m)         |
| 1-10    | 10           | 10 (m)         |
| 2-1     | 12           | 11 (m)         |
| 2-2     | 13           | 13 (m)         |
| 2-3     | 14           | 8 (m)          |
| 3-3     | 19           | 25 (m)         |
| 4-1     | 20           | 29 (m)         |
| 4-3     | 22           | 57 (m)         |
| 5-2     | 27           | 10 (m)         |
| 6-1     | 33           | 9 (m)          |
|         |              | 6 (h)          |
| 6-2     | 34           | 52 (m)         |
| 6-3     | 35           | 46 (m)         |
|         |              | 99 (h)         |
| 8-1     | 56           | 13 (m)         |
| 9       | 60           | 11 (m)         |
| 10-1    | 61           | 25 (m)         |
| 10-2    | 62           | 22 (m)         |
| 10-3    | 63           | 12 (m)         |
|         |              | 10 (h)         |
| 10-5    | 65           | 30 (m)         |
| 10-6    | 66           | 12 (m)         |
| 10-8    | 68           | 32 (m)         |
| 10-10   | 70           | 11 (m)         |
| 10-12   | 72           | 42 (m)         |
| 10-13   | 73           | 69 (m)         |
| 10-14   | 74           | 15 (m)         |
| 11-2    | 79           | 5 (h)          |
| 12-1    | 80           | 6 (m)          |
| 12-2    | 81           | 5 (m)          |
| 12-3    | 82           | 8 (m)          |
| 12-5    | 84           | 8 (m)          |
| 12-10   | 89           | 21 (m)         |

From the results of above Table 3, it was confirmed that the compounds of the present invention can reduce LPA in the presence of mouse or human blood serum, and also can inhibit the LPA production caused by autotoxin.

[Test Example 3] Assay/ADME Data

FS-3 Assay

The test was carried out in the same process as Test example 1 to obtain the IC$_{50}$ values in the following table 4.

Bis-pNPP Assay

Eight-fold dilution of each test compound solution (10 μM, 100% dimethyl sulfoxide) is carried out on 96-well V bottom plate (Costar 3363). After eight-fold dilution of each test compound solution (100% dimethyl sulfoxide) with deionized distilled water, 10 μL of the diluted each test compound solution (10% dimethyl sulfoxide) was aliquoted to a black flat bottom 96-well plate (Costar 3915). 50 μL of 60 mM Tris-HCl (pH9.0) buffer was added thereto, and subsequently 20 μL of 3.75 nM human ATX solution (buffer solution: 50 mM Tris-HCl (pH8.5), 5 mM CaCl$_2$, 2.5 mM MgCl$_2$, 0.01% Brij35) and 20 μL of 25 mM Bis-pNPP (bis(p-Nitrophenyl)-phosphate sodium salt) solution (buffer solution: 50 mM Tris-HCl (pH9.0)) were added thereto, respectively, followed by mixing. Fluorescence intensity measurement (measurement condition—Wavelengths: 405, Time: 35 min, Interval: 10 s, reads: 211, Minimum Interval: 0:09, Template: 370) was carried out by Molecular Devices Spectramax 190 Microplate Reader. ΔOD$_{10\ min}$ value (OD value measured at 10 minutes−OD value measured at 0 minute) is obtained for each test solution and based on the equation of 100−(ΔOD$_{10\ min}$ of test solution/Mean value of ΔOD$_{10\ min}$ of control group)×100, the inhibitory activity percentage ratio (i.e., % inhibition) is obtained. Furthermore, IC$_{50}$ values that are shown in Table 3 were calculated using Grafit5 Software based on the inhibitory activity percentage ratio.

Ex-Vivo Assay (LPC Assay)

The test was carried out in the same process as Test example 2 to obtain the IC$_{50}$ values in the following table 4.

Microsomal Stability

A 2.5 mM stock solution of test compound in DMSO is diluted to 25 uM with 100 mM potassium phosphate buffer (pH 7.4) containing 5 mM EDTA. This solution was mixed with reaction mixtures (final concentration 1 μM). The incubation mixtures (final volume 700 μL) of test compound with liver microsomes [Xenotech; rat (male SD), human (mixed gender)] consisted of liver microsomes (0.5 mg/mL), substrate (Compound 4, 5 μM), NADPH regenerating system (1.3 mM NADP+, 3.3 mM Glucose-6-phosphate, 3.3 mM MgCl$_2$, 0.4 U/ml Glucose-6-phosphate dehydrogenase) in 81.3 mM potassium phosphate buffer (pH 7.4) containing 1 mM EDTA in duplicates. The reaction was initiated by addition of the NADPH regenerating system after preincubation at 37° C. for 10 min with test compounds. 100 uL of aliquot of the sample was removed at 0, 5, 10, 20, 30 and 60 min. The reaction was stopped by addition of 200 uL of acetonitrile containing internal standard (0.3 uM of Dextromethorphan). Each sample was mixed and centrifuged at 14000 rpm for 10 min. The resulting supernatant was analyzed by the LC-MS/MS method for determination of loss of parent compound. % parent remaining was calculated at 6 point time testing was done for T½ determination.

The invention claimed is:

1. A compound represented by the chemical formula 1, or a pharmaceutically acceptable salt thereof:

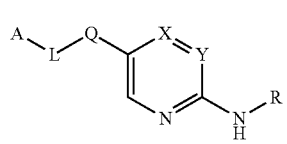

[Chemical formula 1]

wherein:

X is CH and Y is N;

R is indanyl;

A is

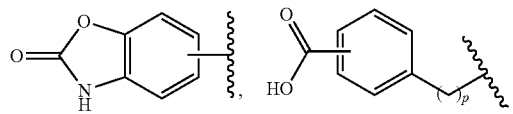

or a ring selected from:

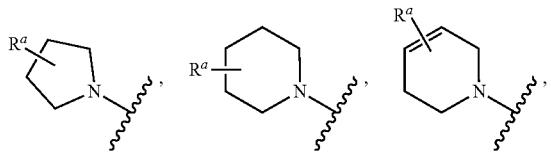

TABLE 4

| Example | Compound No. | Enzymatic assay (IC50) FS-3 | Enzymatic assay (IC50) bis-pNPP | Ex-vivo assay[1] (IC50) | Additional assay[2] |
|---|---|---|---|---|---|
| 15 | 96 | 2.02 nM | <1.56 nM | 3.65 nM[3] | MS: t1/2 = 22.2 ± 0.70 min (h); 30.0 ± 1.57 min(r) |
| 17 | 98 | 9.39 | <1.56 nM | | MS: t1/2 > 60 min (h, r); Rat PK |
| 18 | 99 | 2.8 nM | 5.59 nM | | |
| 19 | 100 | 1.74 nM | 3.6 nM | | MS: t1/2 = 16.4 ± 0.45 min (h); 10.3 ± 0.72 min (r) |
| 25 | 106 | 2.57 nM | 2.27 nM | | MS: t1/2 = 4.2 ± 0.19 min (h); 3.9 ± 0.03 min (r) |
| 26 | 107 | 1.56 nM | 4.87 nM | | |
| 34 | 115 | 3.04 nM | 66.8 nM | 125 nM[4] | MS: t1/2 > 60 min (h, r); Rat PK |
| 35 | 116 | <1.56 nM | <1.56 nM | 7.10 nM[5] | MS: t1/2 = 33.0 ± 0.41 min (h); 25.2 ± 0.69 min (r); Rat PK |
| 36 | 117 | 1.84 nM | >100 nM | | |
| 37 | 118 | <1.56 nM | 5.3 nM | | |
| 38 | 119 | <1.56 nM | 9.19 nM | | |
| 39 | 120 | 25.9 nM | 380 nM | | |

[1] In mouse plasma, LPA 18:1
[2] MS = microsomal stability
[3] For the other LPA isoforms: 3.26 nM (16:0), 14.9 nM (18:0), 3.39 nM (18:2), 2.77 nM (20:4)
[4] For the other LPA isoforms: 31.7 nM (16:0), 323 nM (18:0), 107 nM (18:2), 78.2 nM (20:4)
[5] For the other LPA isoforms: 2.72 nM (16:0), 30.0 nM (18:0), 5.30 nM (18:2), 4.46 nM (20:4)

-continued

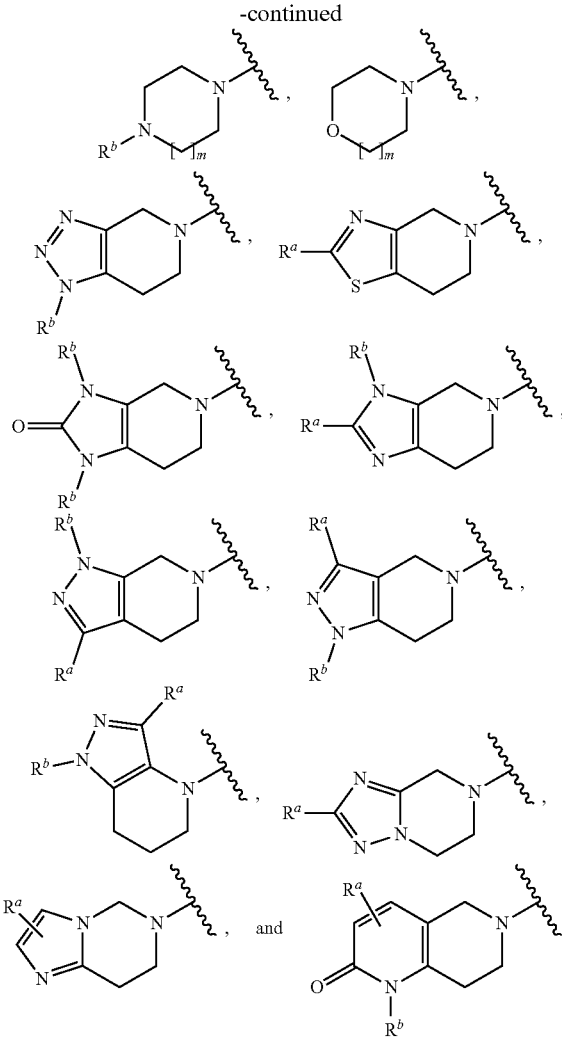

wherein
$R^a$ is hydrogen, carboxyl, carbamoyl, C1-C10 alkylsulfonylamino, aminosulfonylamino (—NHSO$_2$NH$_2$), or amino;
$R^b$ is hydrogen, carboxyl, or aminosulfonyl;
m is an integer of 0, 1, or 2;
p is 0;
L is —(CR$_3$R$_4$)$_a$C(=O)—, —C(=O)—(CR$_3$R$_4$)$_a$—, —C(=O)—(CR$_5$R$_6$)$_b$—NH—(CR$_7$R$_8$)$_c$—, —NH—(CR$_7$R$_8$)$_c$—C(=O)—(CR$_5$R$_6$)$_b$—, or —C(=NR$_9$)—(CR$_3$R$_4$)$_a$—;
$R_3$ to $R_8$ are each independently hydrogen or C1-C10 alkyl;
$R_9$ is hydroxy;
a is an integer of from 1 to 5;
b and c are each independently an integer of from 0 to 5;
Q is a five-membered heteroarylene having 2 or 3 heteroatoms selected from nitrogen, oxygen and sulfur;
said heteroarylene of above Q may be further substituted with one or more substituents that are selected from C1-C10 alkyl, halo-substituted C1-C10 alkyl, hydroxy C1-C10 alkyl, C3-C10 cycloalkyl, C6-C12 aryl, C2-C12 heterocycloalkyl, carboxyl, NR$_{11}$R$_{12}$, —O(CH$_2$)$_e$R$_{13}$, —(CH$_2$)$_f$R$_{14}$, and —C(=O)R$_{15}$, in which said alkyl, cycloalkyl, aryl, and heteroaryl may be further substituted with NR$_{11}$R$_{12}$ or carboxyl;

$R_{11}$ and $R_{12}$ are each independently hydrogen, C1-C10 alkyl, C6-C12 aryl, C2-C12 heteroaryl, or C3-C10 cycloalkyl;
e and f are each independently an integer of from 0 to 5;
$R_{13}$ is hydrogen, C1-C10 alkyl, C6-C12 aryl, C2-C12 heterocycloalkyl, or carboxyl, in which said aryl and heterocycloalkyl of above $R_{13}$ may be further substituted with one or more substituents that are selected from C1-C10 alkyl, halo-substituted C1-C10 alkyl, and carboxyl;
$R_{14}$ and $R_{15}$ are each independently C2-C12 heterocycloalkyl, in which said heterocycloalkyl of $R_{14}$ and $R_{15}$ may be a single ring, a fused ring, or a spiro ring that is either saturated or unsaturated, in which a CH$_2$ in the ring may be substituted with oxo and also in which said heterocycloalkyl of $R_{14}$ and $R_{15}$ may be substituted with or further substituted with one or more substituents that are selected from halogen, C1-C10 alkyl, halo-substituted C1-C10 alkyl, and C6-C12 aryl; and
said heteroaryl and heterocycloalkyl contain at least one heteroatom that is selected from nitrogen, oxygen, and sulfur.

2. The compound of claim 1, or a pharmaceutically acceptable salt thereof, wherein A is selected from the following structures:

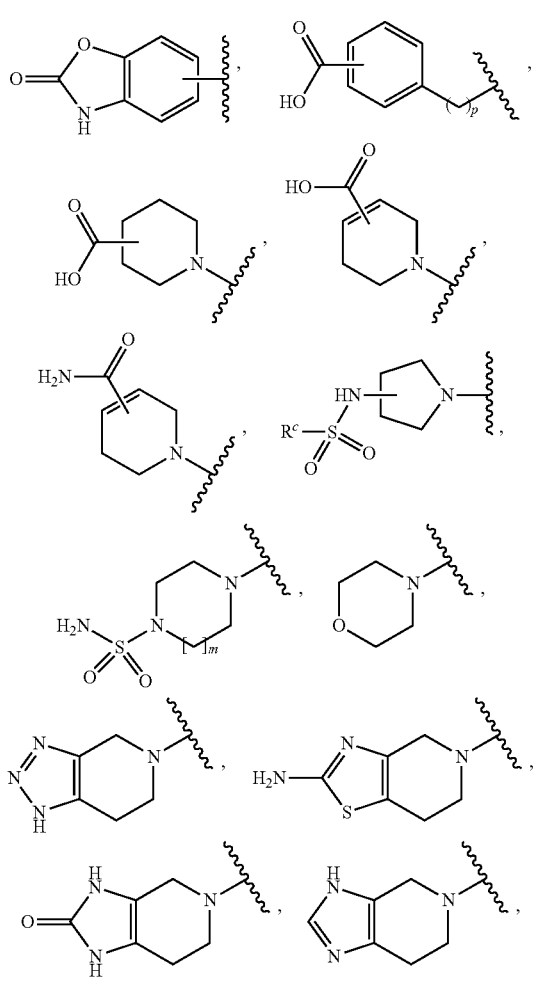

-continued

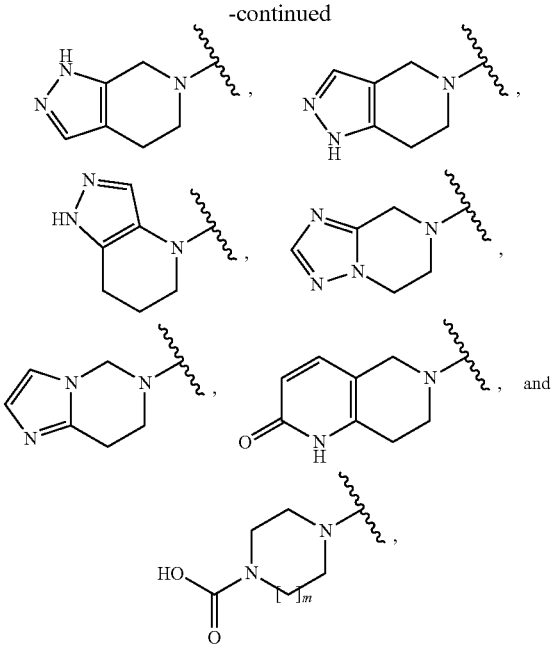

wherein

R$^c$ is C1-C7 alkyl, or amino;

p is 0; and m is an integer of 0, 1, or 2.

3. The compound according to claim 1, or a pharmaceutically acceptable salt thereof, wherein L is selected from:

wherein

R$_d$ and R$_e$ are each independently hydrogen or C1-C7 alkyl;

R$_f$ is hydroxy;

s is an integer of from 0 to 3; and t is an integer of from 1 to 3.

4. The compound according to claim 1, or a pharmaceutically acceptable salt thereof, wherein the Q is selected from:

wherein

R$^g$ is hydrogen or C1-C7 alkyl;

R$^h$ is hydrogen, hydroxy, NR$_{11}$R$_{12}$, C1-C7 alkoxy, C1-C7 alkyl, hydroxy C1-C7 alkyl, C3-C7 cycloalkyl, C6-C12 aryl, C2-C12 heteroaryl, carboxyl, —O(CH$_2$)$_e$R$_{13}$, —(CH2)$_f$R$_{14}$, or —C(=O)R$_{15}$, in which said alkyl, cycloalkyl, aryl, and heteroaryl of R$^h$ may be further substituted with NR$_{11}$R$_{12}$ or carboxyl;

R$_{11}$ and R$_{12}$ are each independently hydrogen, C1-C7 alkyl, C6-C12 aryl, C2-C12 heteroaryl, or C3-C7 cycloalkyl;

R$_{13}$ is C6-C12 aryl, C3-C9 heterocycloalkyl, or carboxyl, in which said aryl and heterocycloalkyl of R$_{13}$ may be further substituted with one or more substituents that are selected from C1-C7 alkyl, halo-substituted C1-C7 alkyl, and carboxyl;

R$_{14}$ and R$_{15}$ are each independently C3-C9 heterocycloalkyl, in which said heterocycloalkyl of R$_{14}$ and R$_{15}$ may be a single ring, a fused ring, or a spiro ring that is either saturated or unsaturated, in which a CH$_2$ in the ring may be substituted with oxo, and also in which said heterocycloalkyl of R$_{14}$ and R$_{15}$ may be substituted with or further substituted with one or more substituents that are selected from halogen, C1-C7 alkyl, halo-substituted C1-C7 alkyl, and C6-C12 aryl;

R$^i$ is hydrogen, C1-C7 alkyl, or halo-substituted C1-C7 alkyl;

R$^j$ is hydrogen, C1-C7 alkyl, halo-substituted C1-C7 alkyl, C3-C7 cycloalkyl, or C6-C12 aryl;

e is an integer of from 0 to 3; and f is an integer of from 0 to 3.

5. The compound according to claim 4, or a pharmaceutically acceptable salt thereof, wherein the R$^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from:

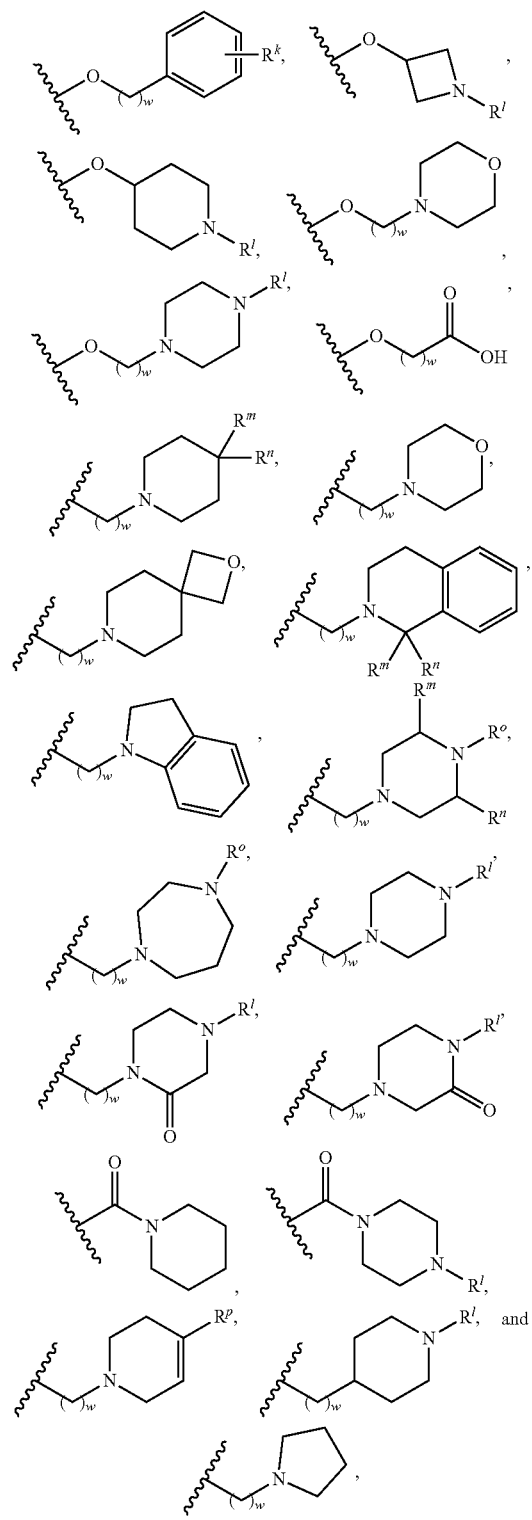

wherein
$R_{11}$ and $R_{12}$ are each independently hydrogen, C1-C7 alkyl, C6-C12 aryl, or C3-C7 cycloalkyl;
$R^k$ is hydrogen or carboxyl;

$R^l$ is hydrogen, C1-C7 alkyl, or halo-substituted C1-C7 alkyl;

$R^m$ and $R^n$ are each independently hydrogen, C1-C7 alkyl, or halogen;

$R^o$ is hydrogen or C1-C7 alkyl;

$R^p$ is C6-C12 aryl; and w is an integer of from 0 to 3.

6. The compound according to claim 1, or a pharmaceutically acceptable salt thereof, wherein the compound is a compound represented by the following chemical formula 2;

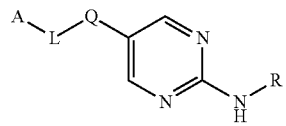

wherein

R is indanyl;

A is selected from the following structures;

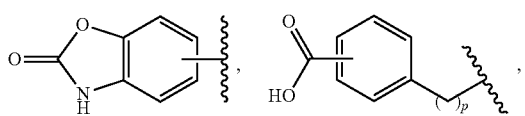

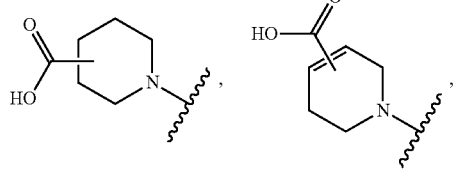

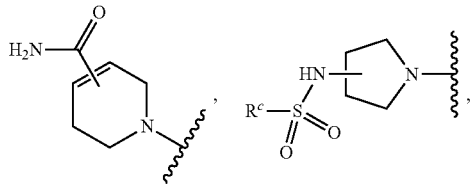

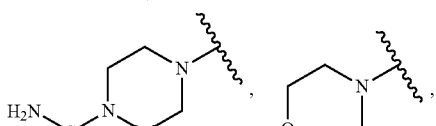

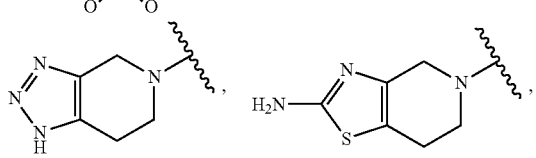

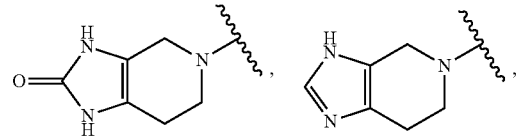

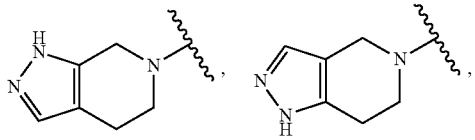

-continued

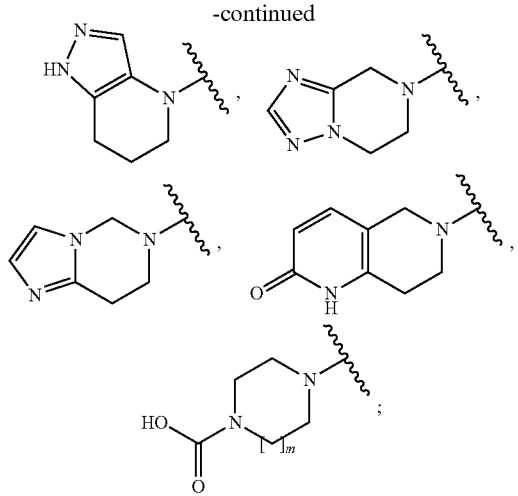

$R^c$ is C1-C7 alkyl or amino;
p is 0;
m is an integer of 0, 1, or 2;
L is selected from:

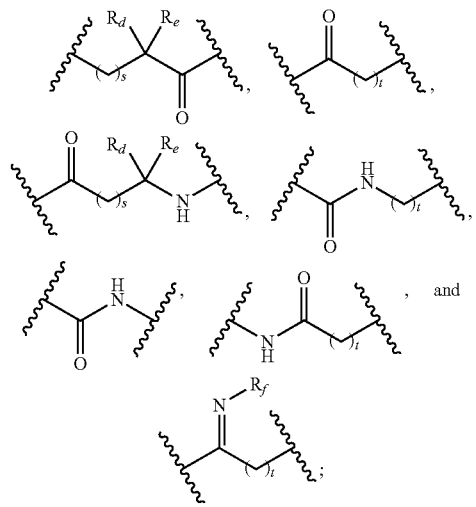

$R_d$ and $R_e$ are each independently hydrogen or C1-C7 alkyl;
$R_f$ is hydroxy;
s is an integer of from 0 to 3;
t is an integer of from 1 to 3;
Q is selected from the following structures:

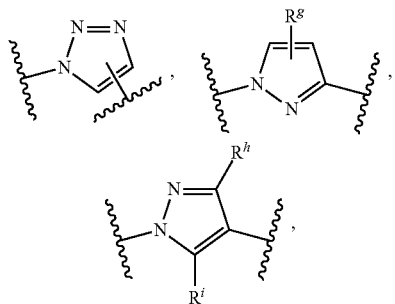

-continued

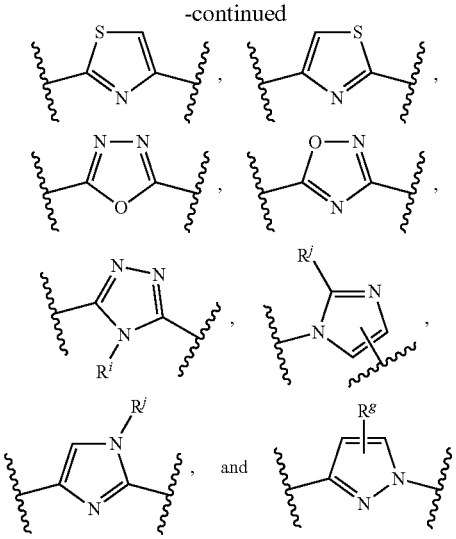

$R^g$ is hydrogen or C1-C7 alkyl;
$R^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from:

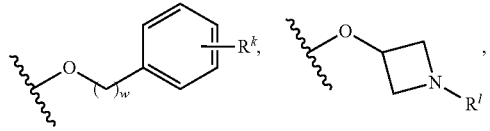
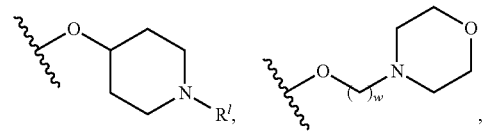
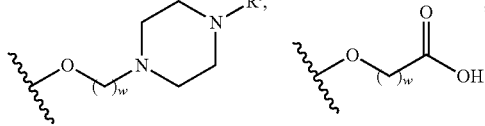
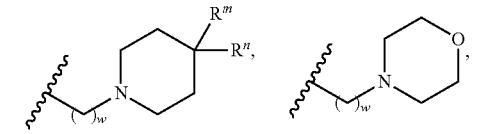
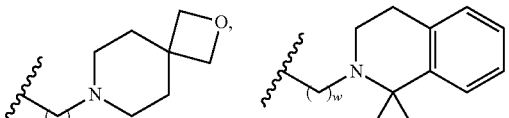
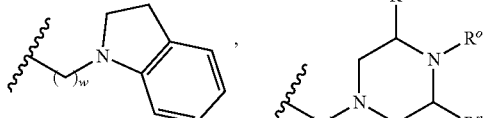
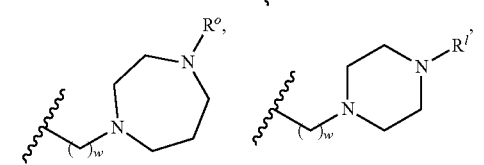

-continued

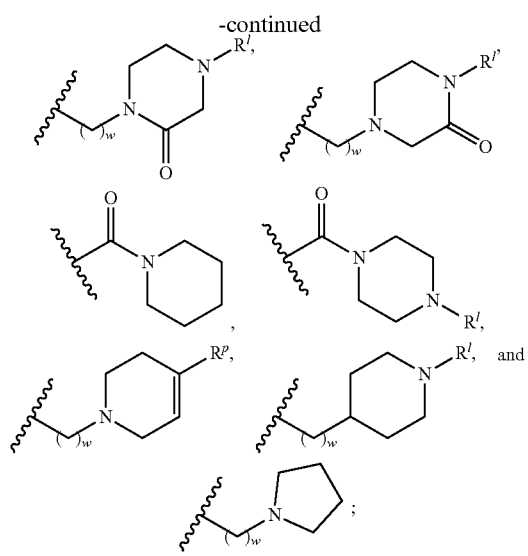

said alkyl, cycloalkyl, aryl, and heteroaryl of $R^h$ may be further substituted with $NR_{11}R_{12}$ or carboxyl;
$R^i$ is hydrogen, C1-C7 alkyl, or halo-substituted C1-C7 alkyl;
$R^j$ is hydrogen, C1-C7 alkyl, halo-substituted C1-C7 alkyl, C3-C7 cycloalkyl, or C6-C12 aryl;
$R_{11}$ and $R_{12}$ are each independently hydrogen, C1-C7 alkyl, C6-C12 aryl, or C3-C7 cycloalkyl;
$R^k$ is hydrogen or carboxyl;
$R^l$ is hydrogen, C1-C7 alkyl, or halo-substituted C1-C7 alkyl;
$R^m$ and $R^n$ are each independently hydrogen, C1-C7 alkyl, or halogen;
$R^o$ is hydrogen or C1-C7 alkyl;
$R^p$ is C6-C12 aryl; and
w is an integer of from 0 to 3.

7. The compound according to claim 6, or a pharmaceutically acceptable salt thereof, wherein
R is indanyl;
A is selected from:

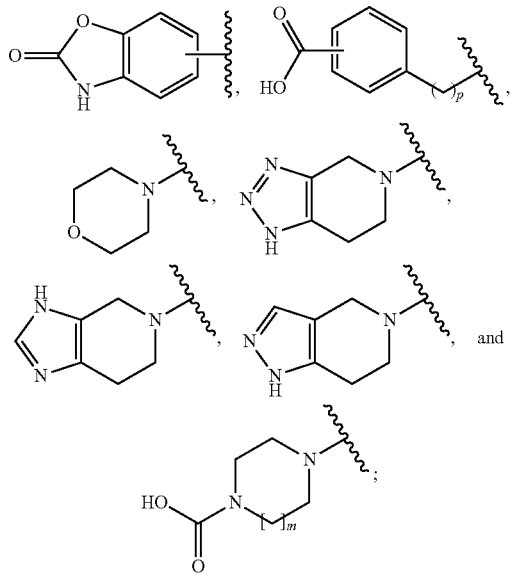

p is 0;
m is an integer of 0, 1, or 2;
L is selected from:

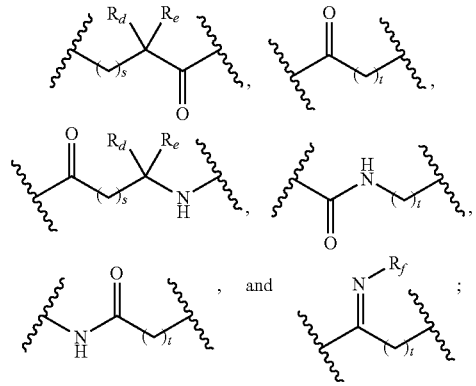

$R^d$ and $R^e$ are each independently hydrogen or C1-C7 alkyl;
s is an integer of from 0 to 3;
t is an integer of from 1 to 3;
Q is selected from the following structures;

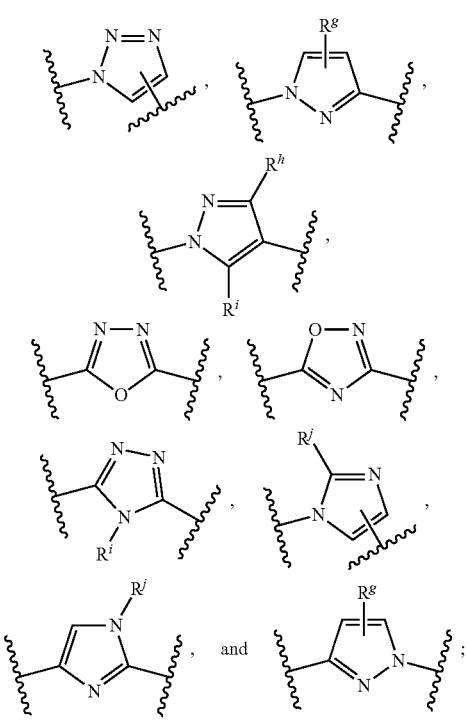

$R^g$ is hydrogen or C1-C7 alkyl;
$R^i$ is hydrogen, C1-C7 alkyl, or halo-substituted C1-C7 alkyl;
$R^j$ is hydrogen, C1-C7 alkyl, halo-substituted C1-C7 alkyl, C3-C7 cycloalkyl, or C6-C12 aryl;
$R^h$ is hydrogen, hydroxy, $NR_{11}R_{12}$, C1-C7 alkoxy, C1-C7 alkyl, hydroxy C1-C7 alkyl, C3-C7 cycloalkyl, C6-C12 aryl, C2-C12 heteroaryl, or carboxyl, or selected from:

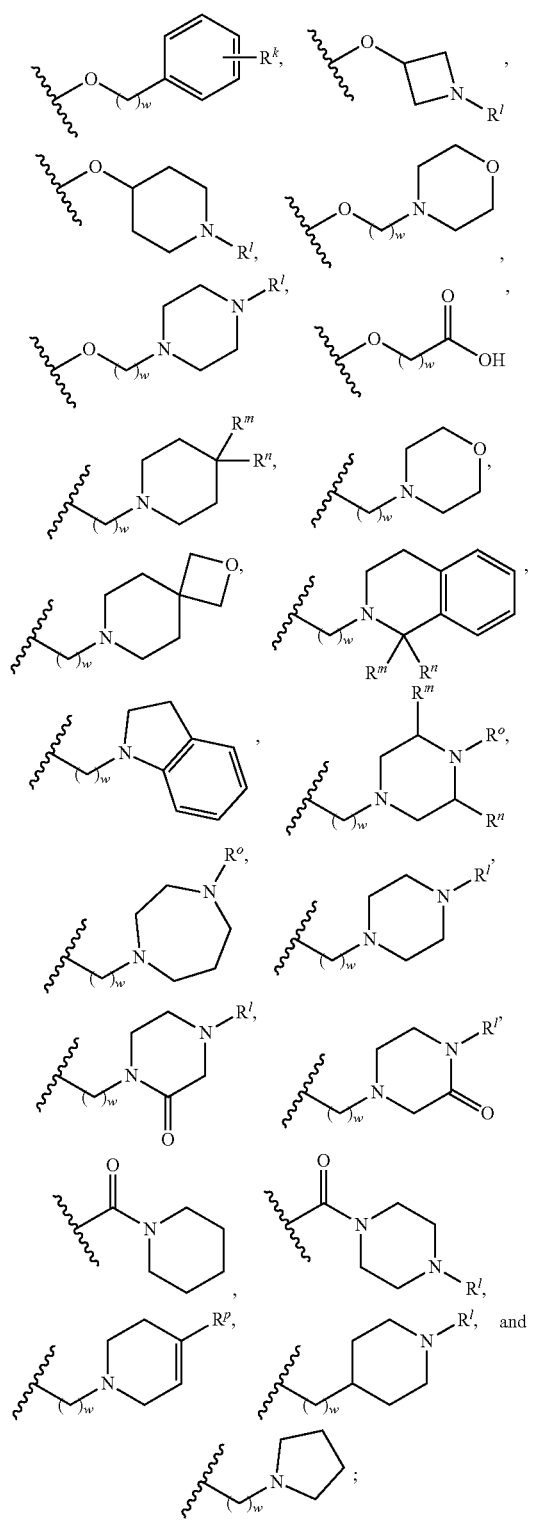

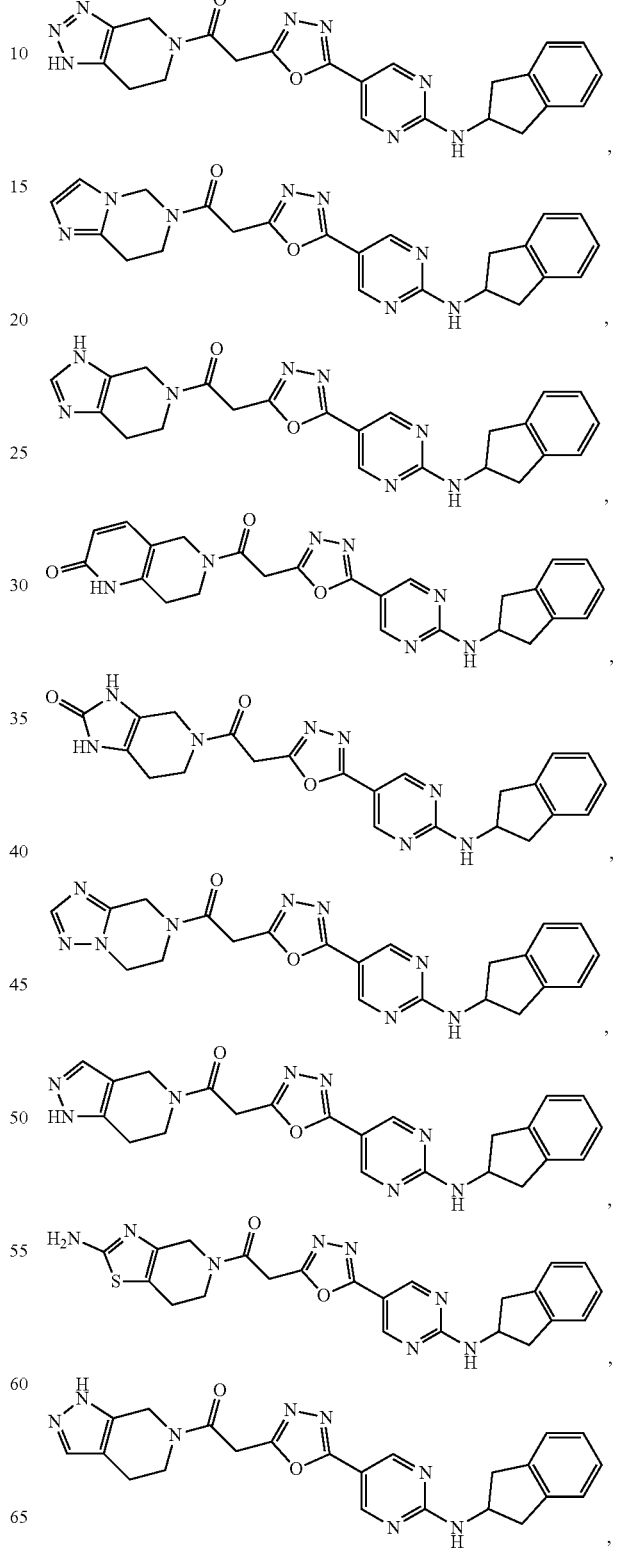

$R_{11}$ and $R_{12}$ are each independently hydrogen C1-C7 alkyl, C6-C12 aryl, or C3-C7 cycloalkyl;
$R^k$ is hydrogen or carboxyl;
$R^l$ is hydrogen, C1-C7 alkyl, or halo-substituted C1-C7 alkyl;
$R^m$ and $R^n$ are each independently hydrogen, C1-C7 alkyl, or halogen;
$R^o$ is hydrogen or C1-C7 alkyl;

$R^p$ is C6-C12 aryl; and
w is an integer of from 0 to 3.

8. The compound according to claim 1, or a pharmaceutically acceptable salt thereof, wherein the compound is selected from:

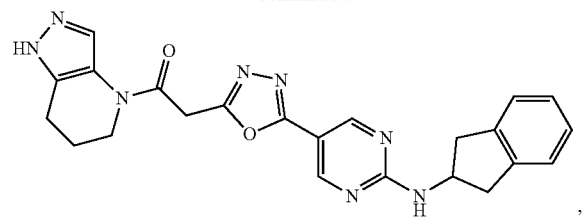
,
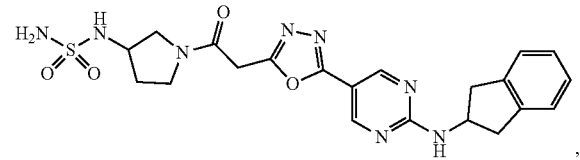
,
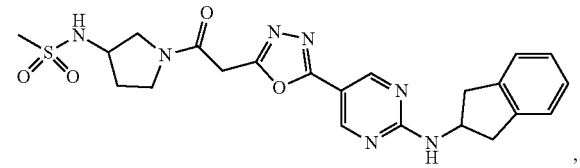
,
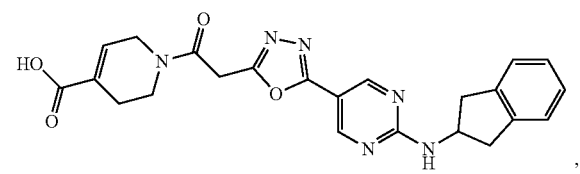
,
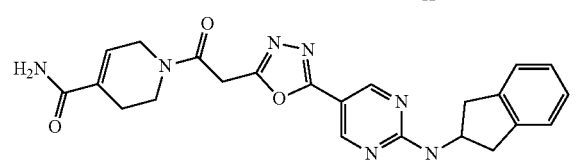
,
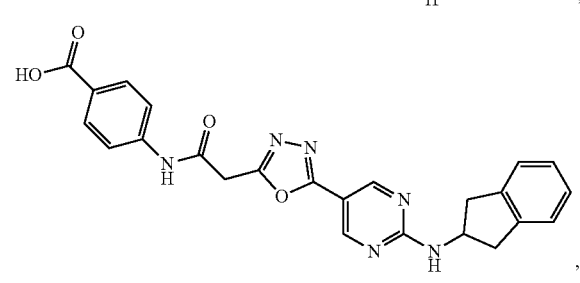
,
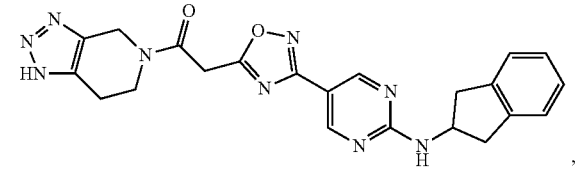
,
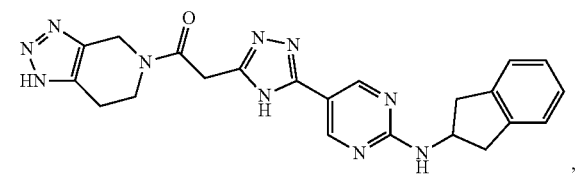
,
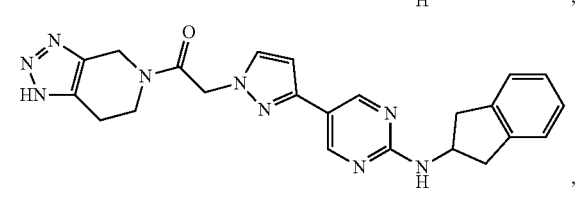
,
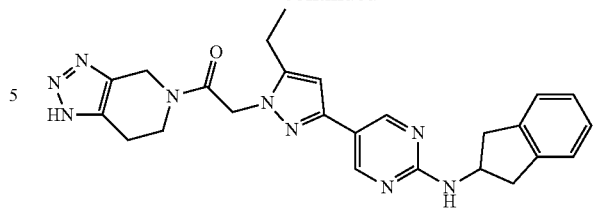
,
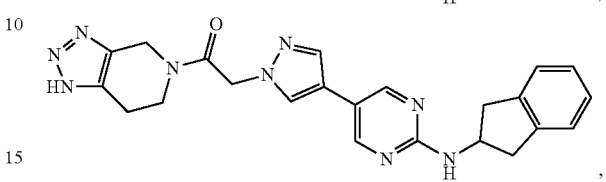
,
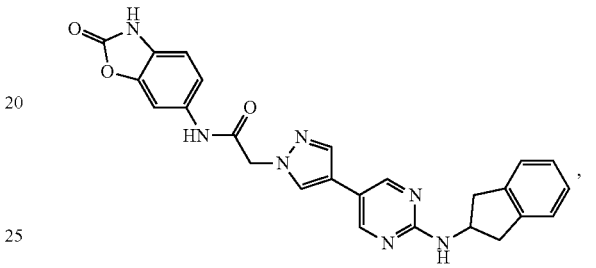
,
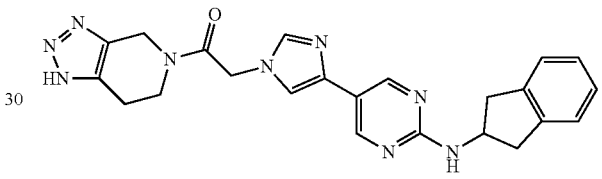
,
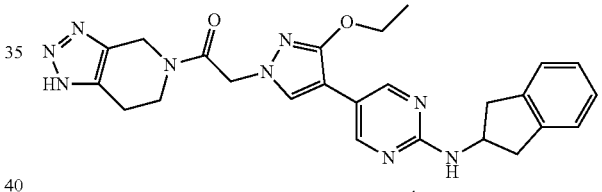
,
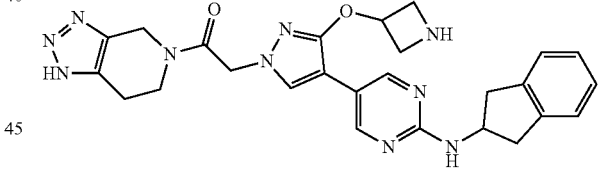
,
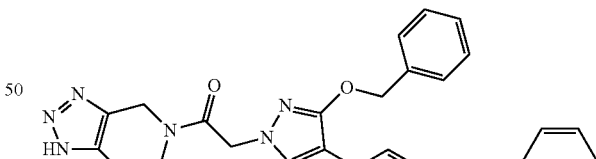
,
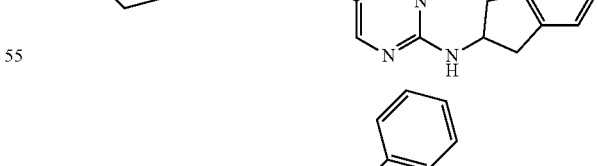
,
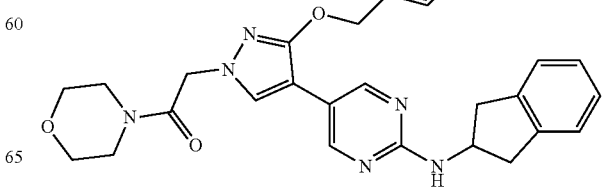
, 283
-continued
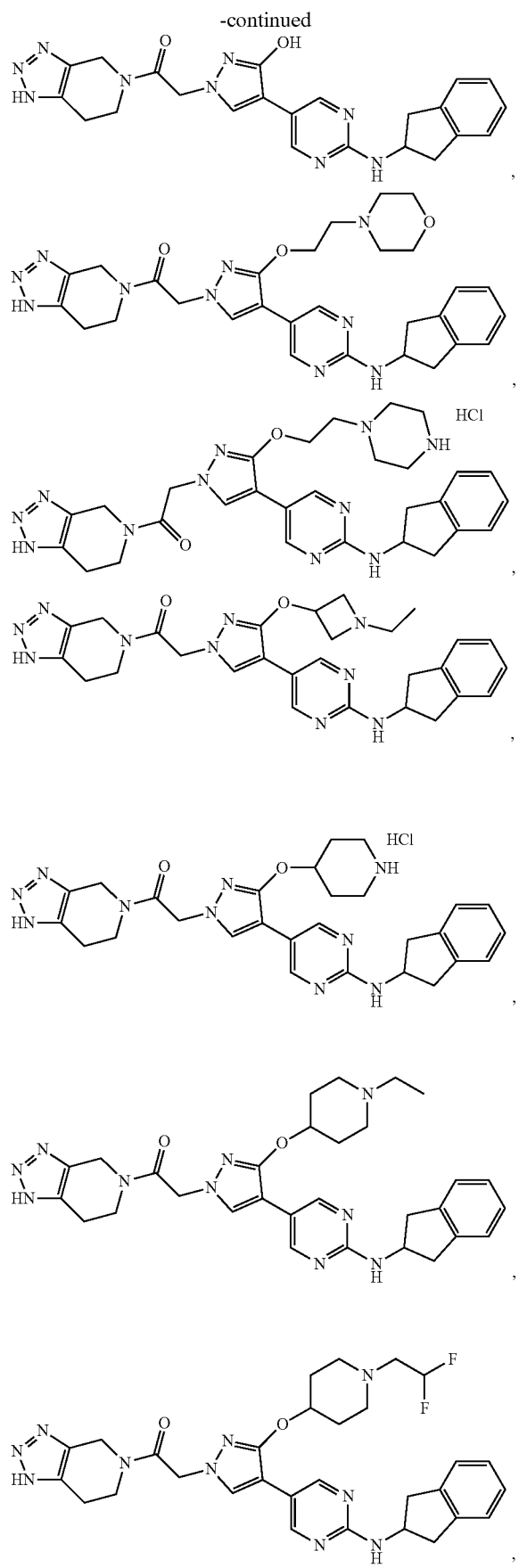
284
-continued
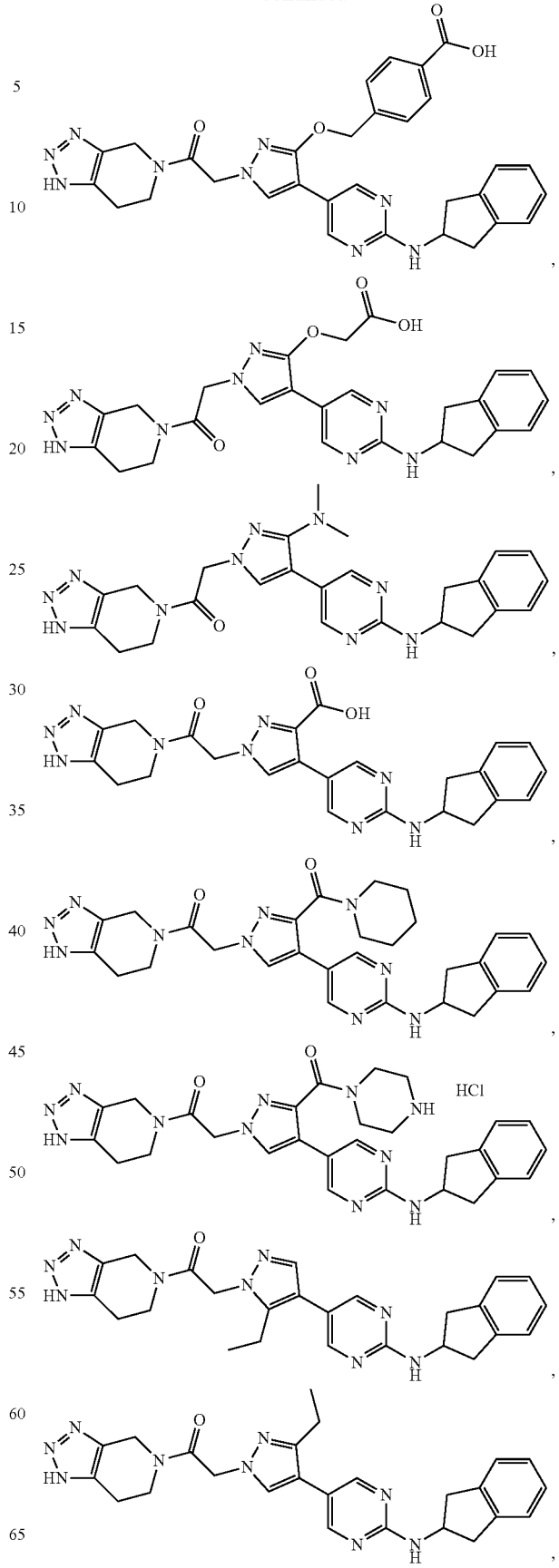

285
-continued
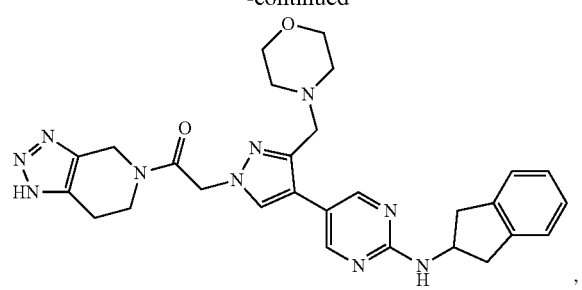
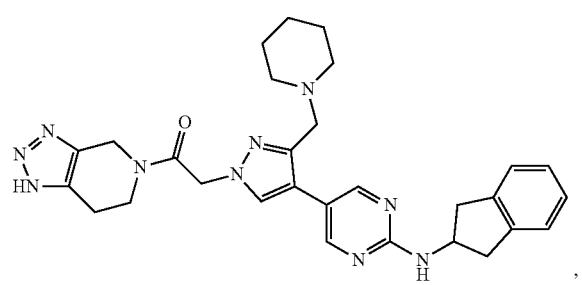
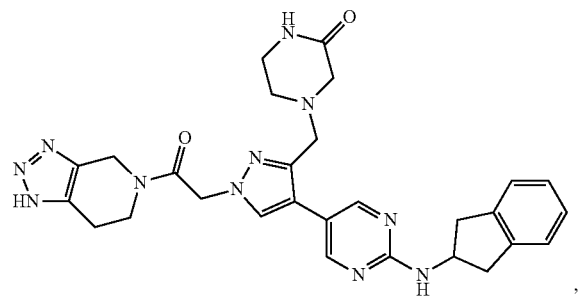
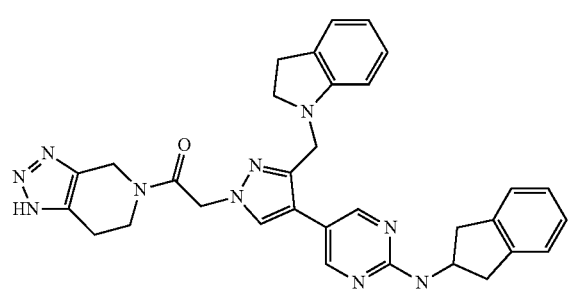
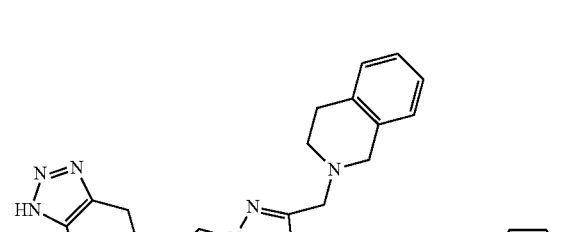
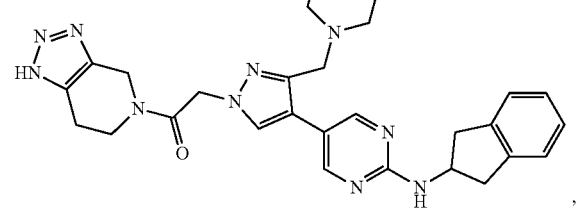
286
-continued
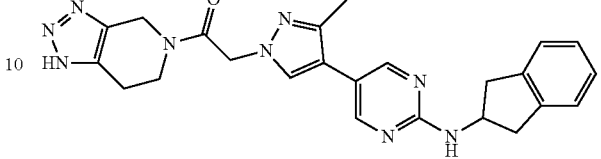
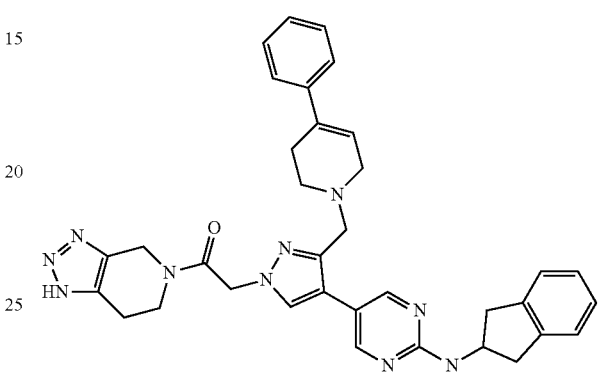
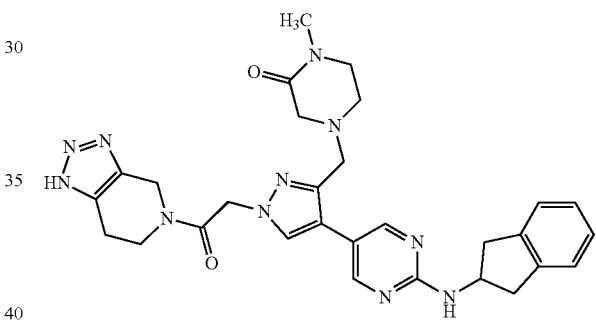
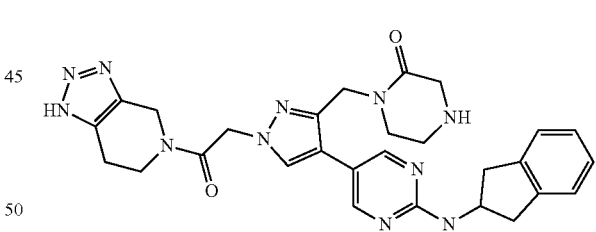
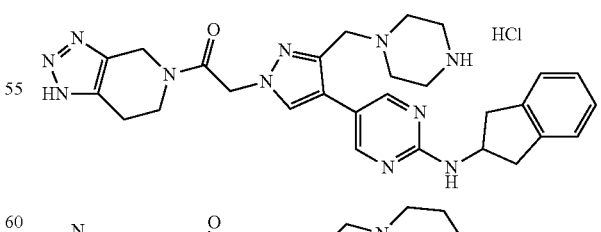
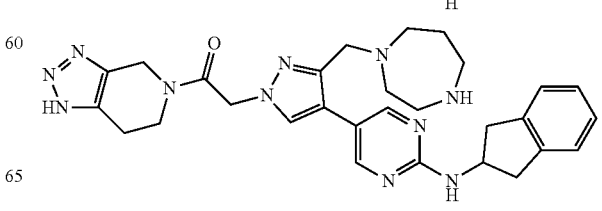

287
-continued
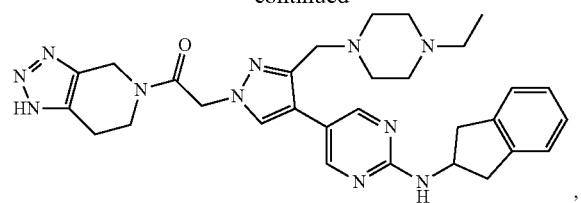
,
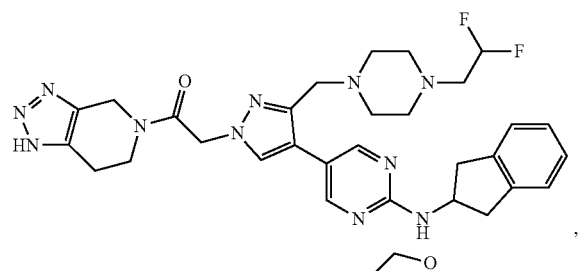
,
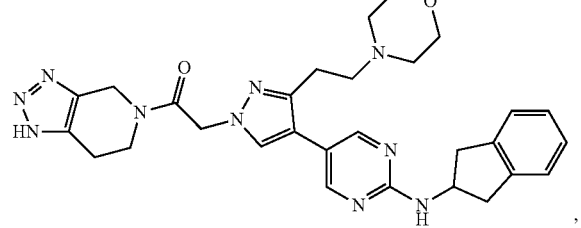
,
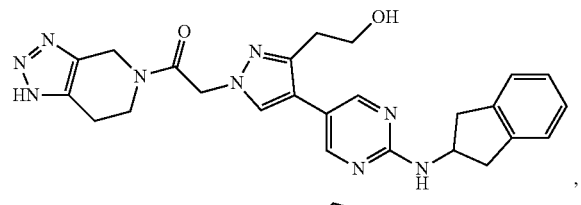
,
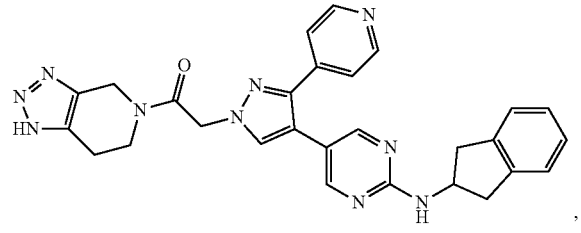
,
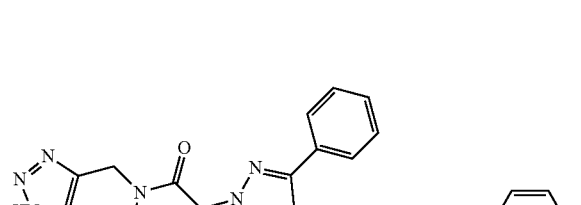
,
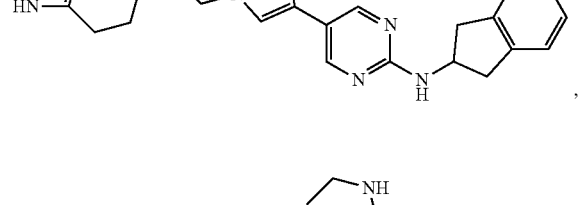
,
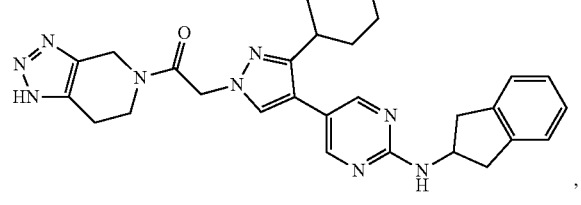
,
288
-continued
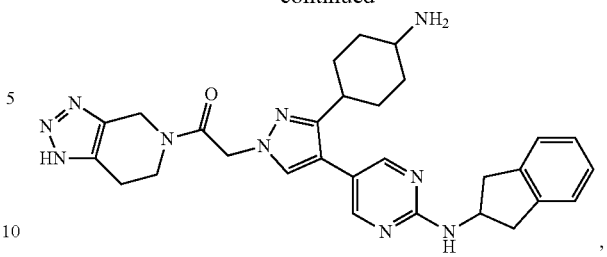
,
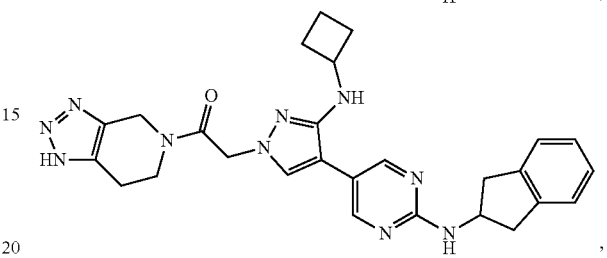
,
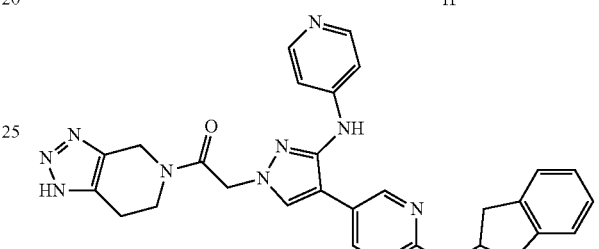
,
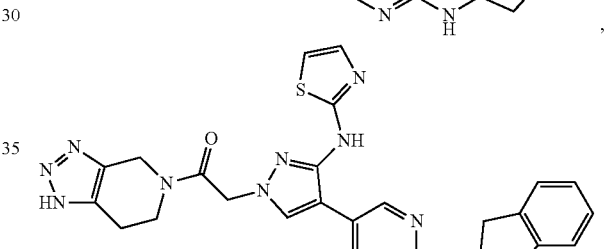
,
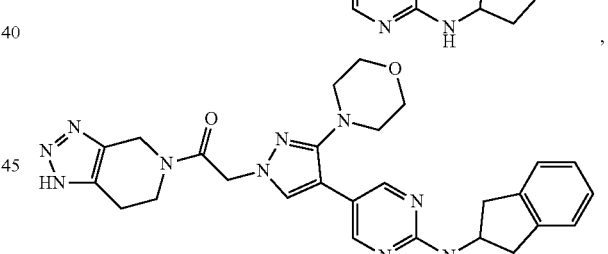
,
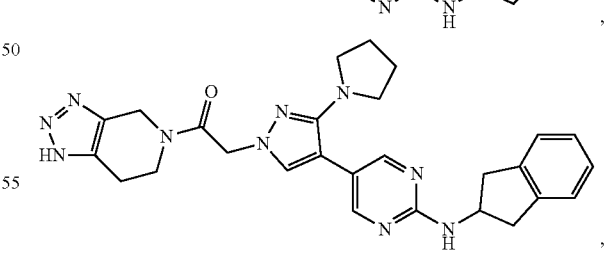
,
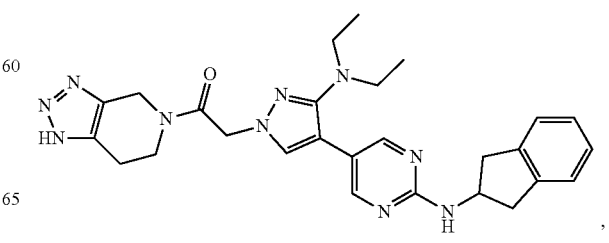
, -continued
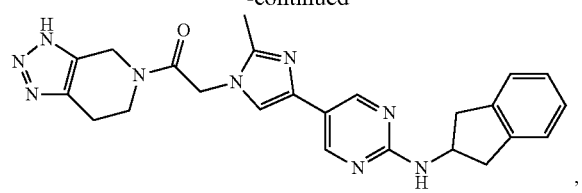
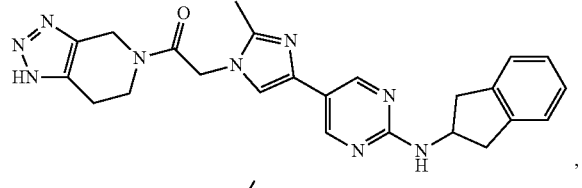
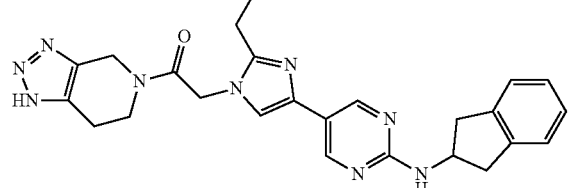
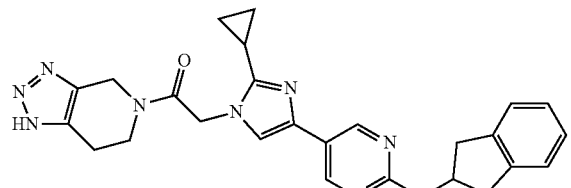
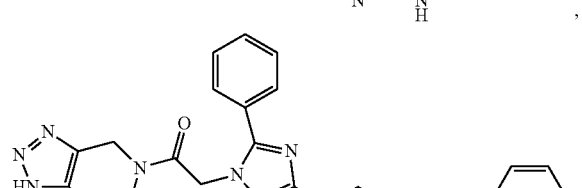
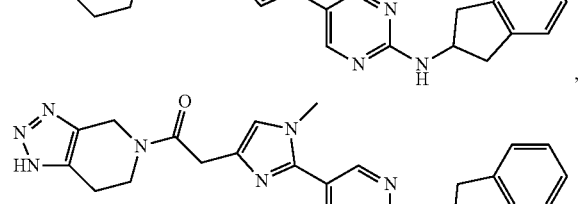
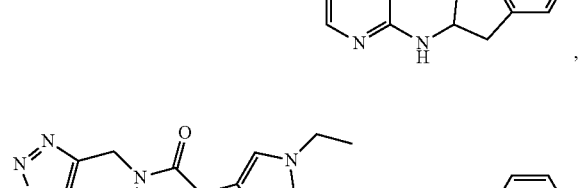
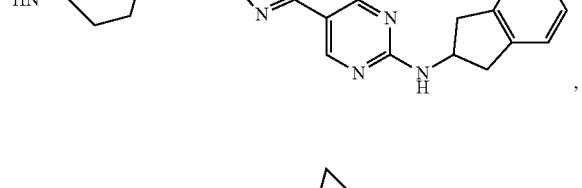
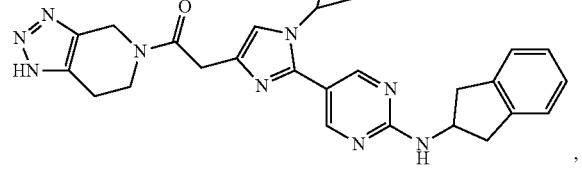
-continued
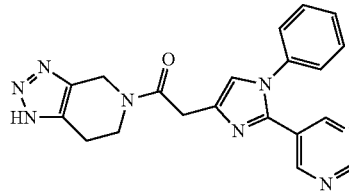
, and
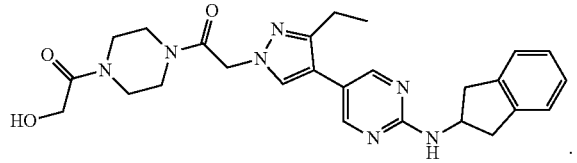
.
9. A compound selected from:
(2.1)
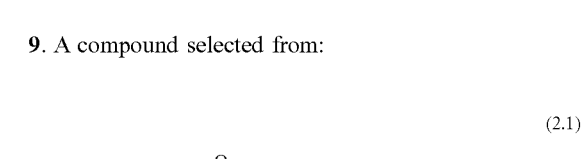
,
(2.3)
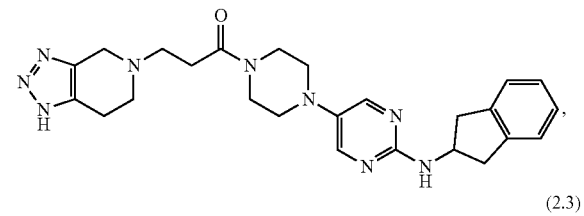
,
(3.3)
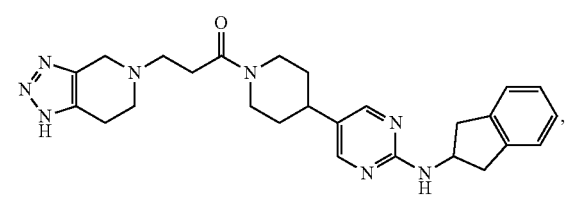
,
(4.1)
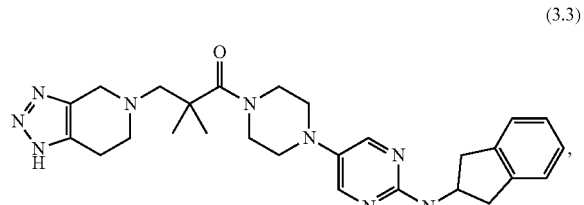
,
(4.3)
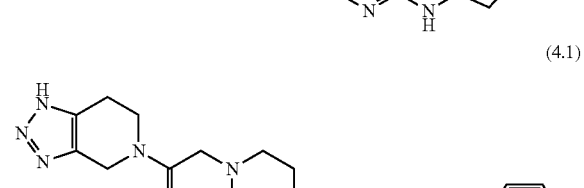
, -continued (5.2)
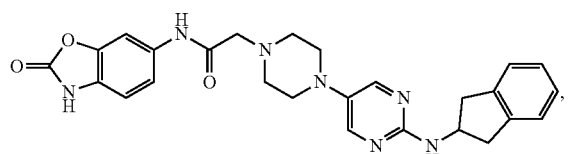
and (6.1)
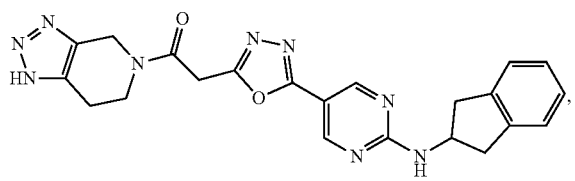

or a pharmaceutically acceptable salt thereof.
10. A compound of formula 2.1

2.1
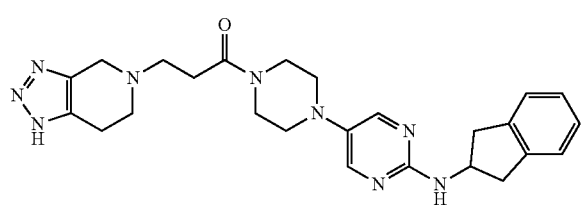

or a pharmaceutically acceptable salt thereof.
11. A compound of formula 2.3

2.3
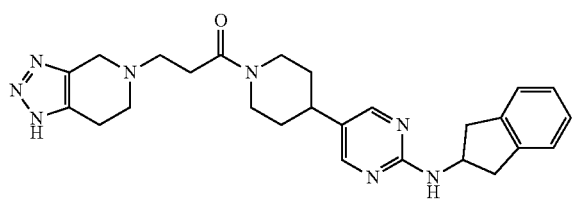

or a pharmaceutically acceptable salt thereof.
12. A compound of formula 3.3

3.3
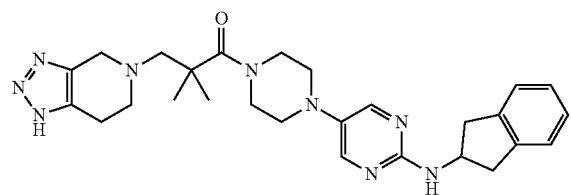

or a pharmaceutically acceptable salt thereof.

13. A compound of formula 4.1

4.1
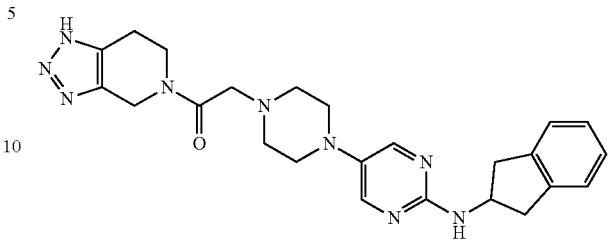

or a pharmaceutically acceptable salt thereof.
14. A compound of formula 4.3

4.3
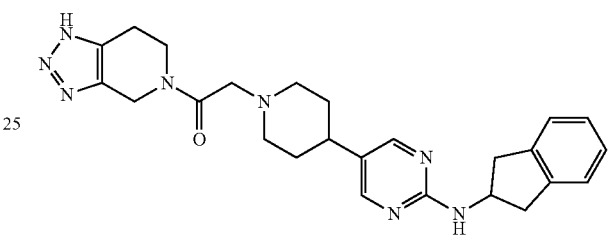

or a pharmaceutically acceptable salt thereof.
15. A compound of formula 5.2

5.2
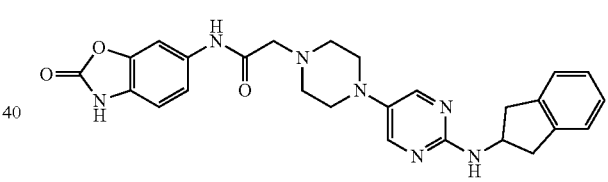

or a pharmaceutically acceptable salt thereof.
16. A compound of formula 6.1

6.1
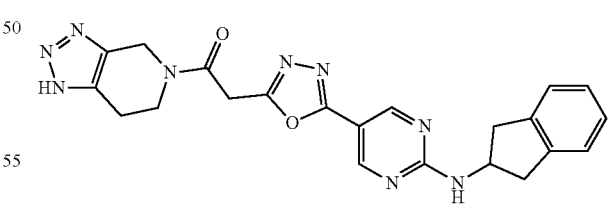

or a pharmaceutically acceptable salt thereof.

17. A pharmaceutical composition comprising a compound of claim 1, or a hydrate, solvate, or pharmaceutically acceptable salt thereof, and a pharmaceutically acceptable carrier.

18. A method of prophylaxis or treatment of a disorder, the method comprising administering to a subject in need thereof a therapeutically effective amount of a compound according to claim 1, or a pharmaceutically acceptable salt thereof, wherein the disorder is selected from the group consisting of cardiovascular disorder, cancer, obesity, diabetes mellitus, acute kidney failure, chronic kidney disease, diabetic nephropathy, acute kidney transplant rejection, chronic allograft nephropathy, liver cirrhosis, hepatic congestion, pruritus, nonalcoholic steatohepatitis, acute and chronic liver transplant rejection, arthritis, atopic dermatitis, asthma, neuropathic pain, schizophrenia, neuro-inflammation, peripheral neuropathy, autonomic neuropathy, systemic disease, vasculitides, sarcoidosis, hypersensitivity pneumonia, alveolar proteinosis, langerhans cell granulomatosis, lymphangioleiomyomatosis, radiation induced fibrosis, silicosis, asbestos induced pulmonary fibrosis, acute respiratory distress syndrome (ARDS), myocardial and vascular fibrosis, kidney fibrosis, liver fibrosis, pulmonary fibrosis, skin fibrosis, scleroderma, encapsulating peritonitis, renal tubulo-interstitial fibrosis, glomerulosclerosis, non-alcoholic liver steatosis, idiopathic pulmonary fibrosis, proliferative and non-proliferative retinopathy, dry and wet age-related macular degeneration (AMD), macular edema, central arterial/venous occlusion, traumatic injury, glaucoma, chronic pruritus of cholestatic form, and acute or chronic organ transplant rejection.

19. A pharmaceutical composition comprising a compound of claim 9, or a hydrate, solvate, or pharmaceutically acceptable salt thereof, and a pharmaceutically acceptable carrier.

20. A method of prophylaxis or treatment of a disorder, the method comprising administering to a subject in need thereof a therapeutically effective amount of a compound according to claim 9, or a pharmaceutically acceptable salt thereof, wherein the disorder is selected from the group consisting of cardiovascular disorder, cancer, obesity, diabetes mellitus, acute kidney failure, chronic kidney disease, diabetic nephropathy, acute kidney transplant rejection, chronic allograft nephropathy, liver cirrhosis, hepatic congestion, pruritus, nonalcoholic steatohepatitis, acute and chronic liver transplant rejection, arthritis, atopic dermatitis, asthma, neuropathic pain, schizophrenia, neuro-inflammation, peripheral neuropathy, autonomic neuropathy, systemic disease, vasculitides, sarcoidosis, hypersensitivity pneumonia, alveolar proteinosis, langerhans cell granulomatosis, lymphangioleiomyomatosis, radiation induced fibrosis, silicosis, asbestos induced pulmonary fibrosis, acute respiratory distress syndrome (ARDS), myocardial and vascular fibrosis, kidney fibrosis, liver fibrosis, pulmonary fibrosis, skin fibrosis, scleroderma, encapsulating peritonitis, renal tubulo-interstitial fibrosis, glomerulosclerosis, non-alcoholic liver steatosis, idiopathic pulmonary fibrosis, proliferative and non-proliferative retinopathy, dry and wet age-related macular degeneration (AMD), macular edema, central arterial/venous occlusion, traumatic injury, glaucoma, chronic pruritus of cholestatic form, and acute or chronic organ transplant rejection.

21. A compound selected from:

(2.1)
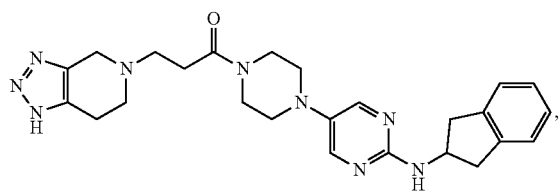

(2.3)
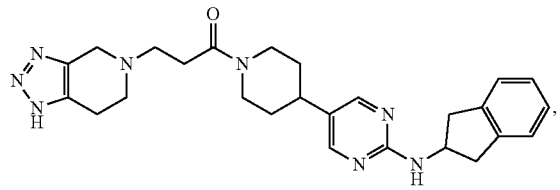

(3.3)
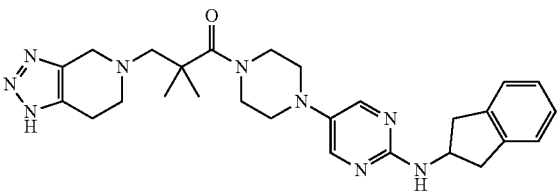

(4.1)
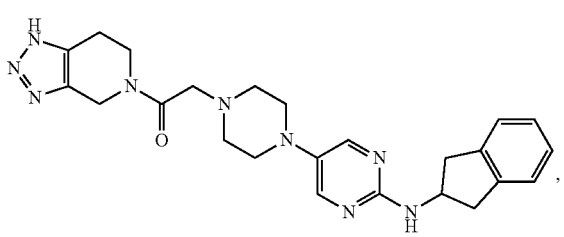

(4.3)
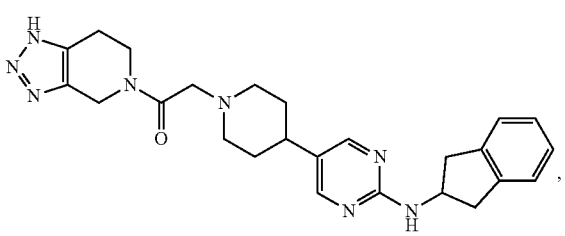

(5.2)
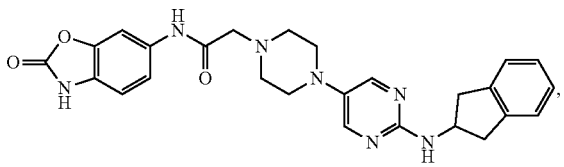

and (6.1)
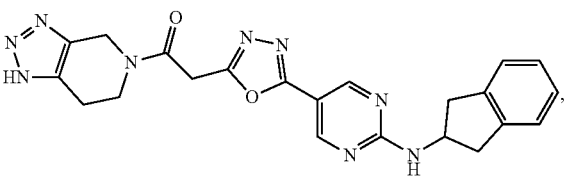

or a hydrate, solvate, or pharmaceutically acceptable salt thereof.

22. A compound of formula 2.1

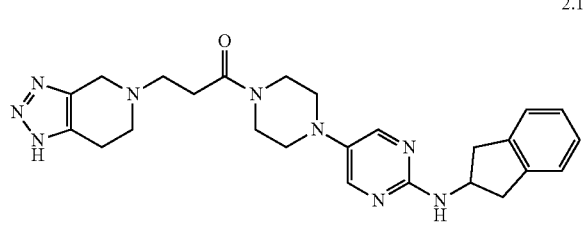

2.1 or a hydrate, solvate, or pharmaceutically acceptable salt thereof.

23. A compound of formula 2.3

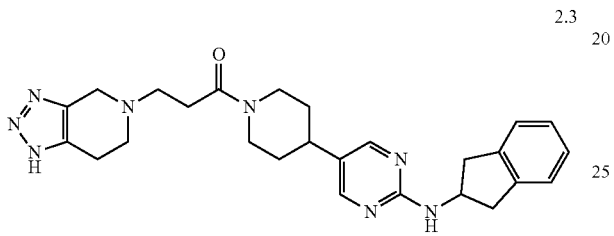

2.3 or a hydrate, solvate, or pharmaceutically acceptable salt thereof.

24. A compound of formula 3.3

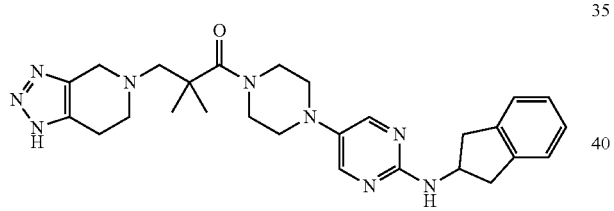

3.3 or a hydrate, solvate, or pharmaceutically acceptable salt thereof.

25. A compound of formula 4.1

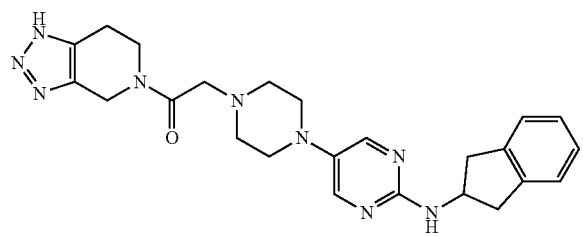

4.1 or a hydrate, solvate, or pharmaceutically acceptable salt thereof.

26. A compound of formula 4.3

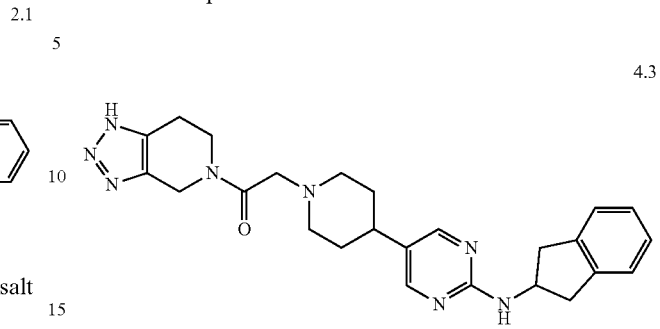

4.3 or a hydrate, solvate, or pharmaceutically acceptable salt thereof.

27. A compound of formula 5.2

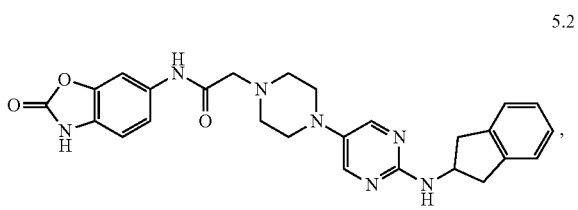 [SMILES: O=C(CN1CCN(c2cnc(NC3Cc4ccccc4C3)nc2)CC1)Nc1ccc2[nH]c(=O)oc2c1]

5.2 or a hydrate, solvate, or pharmaceutically acceptable salt thereof.

28. A compound of formula 6.1

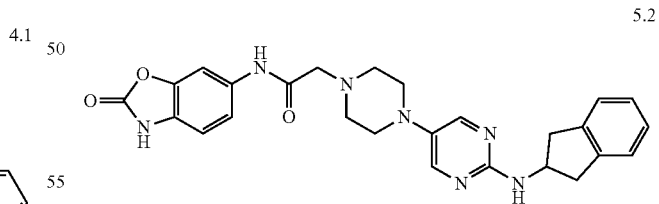

5.2 or a hydrate, solvate, or pharmaceutically acceptable salt thereof.

* * * * *

UNITED STATES PATENT AND TRADEMARK OFFICE
CERTIFICATE OF CORRECTION

PATENT NO. : 10,961,242 B2  
APPLICATION NO. : 16/783893  
DATED : March 30, 2021  
INVENTOR(S) : Dae Yon Lee et al.

Page 1 of 1

It is certified that error appears in the above-identified patent and that said Letters Patent is hereby corrected as shown below:

In the Claims

At Claim 28, Column 296, Line number 50, please replace:

"
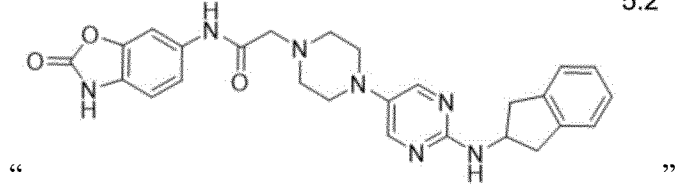
"

With:

--
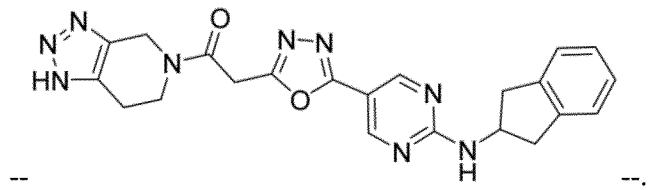
--.

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*